US011965182B2

(12) United States Patent
Malik et al.

(10) Patent No.: US 11,965,182 B2
(45) **Date of Patent: *Apr. 23, 2024**

(54) PLANTS WITH ENHANCED YIELD AND METHODS OF CONSTRUCTION

(71) Applicant: YIELD10 BIOSCIENCE, INC., Woburn, MA (US)

(72) Inventors: Meghna Malik, Saskatoon (CA); Jihong Tang, West Roxbury, MA (US); Kristi D. Snell, Belmont, MA (US)

(73) Assignee: YIELD10 BIOSCIENCE, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/498,240

(22) Filed: Oct. 11, 2021

(65) Prior Publication Data

US 2022/0025340 A1 Jan. 27, 2022

Related U.S. Application Data

(63) Continuation of application No. 15/565,086, filed as application No. PCT/US2016/026767 on Apr. 8, 2016, now Pat. No. 11,174,467.

(60) Provisional application No. 62/190,281, filed on Jul. 9, 2015, provisional application No. 62/145,757, filed on Apr. 10, 2015, provisional application No. 62/144,727, filed on Apr. 8, 2015.

(51) Int. Cl.

| | |
|---|---|
| ***C12N 15/82*** | (2006.01) |
| ***C07K 14/415*** | (2006.01) |
| ***C12N 9/04*** | (2006.01) |
| ***C12N 15/52*** | (2006.01) |

(52) U.S. Cl.

CPC .......... *C12N 9/0006* (2013.01); *C07K 14/415* (2013.01); *C12N 15/52* (2013.01); *C12N 15/8243* (2013.01); *C12N 15/8247* (2013.01); *C12N 15/8261* (2013.01); *C12Y 101/01082* (2013.01); *Y02A 40/146* (2018.01)

(58) Field of Classification Search

None

See application file for complete search history.

(56) References Cited

U.S. PATENT DOCUMENTS 6,624,342 B1 * 9/2003 Grimm .................... C12N 9/00
800/278

FOREIGN PATENT DOCUMENTS

| | | | | |
|---|---|---|---|---|
| WO | 0000619 A2 | | 1/2000 | |
| WO | 2009103782 A1 | | 8/2009 | |
| WO | 2010108836 A1 | | 9/2010 | |
| WO | 2011099006 A2 | | 8/2011 | |
| WO | 2014085261 A1 | | 6/2014 | |
| WO | 2014210587 A1 | | 12/2014 | |
| WO | WO-2014210587 A1 | * | 12/2014 | ......... C12N 15/8247 |
| WO | 2016164810 A1 | | 10/2016 | |

OTHER PUBLICATIONS

Wang, Yingying, et al. "Pyruvate: ferredoxin oxidoreductase and low abundant ferredoxins support aerobic photomixotrophic growth in cyanobacteria." Elife 11 (2022): e71339. (Year: 2022).*

Brysch et al., "Lithautotrophic growth of sulfate-reducing bacteria, and description of *Desulfobacterium autotrophicum* gen. nov., sp. nov.", Archives of Microbioogy, vol. 148, pp. 264-274, Jul. 2, 1987.

Chabriere et al., "Crystal structures of the key anaerobic enzyme pyruvate ferredoxin oxidoreductase, free and in complex with pyruvate", Nature Structural Biology, vol. 6, No. 2, pp. 182-190, Feb. 1999.

Ma et al., "Pyruvate ferredoxin oxidoreductase from the hyperthermophilic archaeon, Pyrococcus furiosus, functions as a CoA-dependent pyruvate decarboxylase", Biochemistry, Proc. Natl. Acad. Sci, USA, vol. 94, pp. 9608-9613, Sep. 1997.

Noth et al., "Pyruvate:Ferrodoxin Oxidoreductase Is Coupled to Light-Independent Hydrogen Production in Chlamydomonas reinhardtii", The Journal of Biological Chemistry, vol. 288, No. 6, pp. 4368-4377, Feb. 8, 2013.

Postgate et al., "Classification of *Desulfovibrio* Species, the Nonsporulating Sulfate-Reducing Bacteria", Bacteriological Reviews, vol. 30, No. 4, pp. 732-738, Dec. 1966.

Thorgersen et al., "Mechanism of oxygen detoxification by the surprisingly oxygen-tolerant hyperthermophilic archaeon, Pyrococcus furiosus", Proc. Natl. Acad. Sci, USA, vol. 109, No. 45, pp. 18547-18552, Nov. 6, 2012.

Van Lis et al., "Chlamydomonas reinhardtii Chloroplasts Contain a Homodimeric Pyruvate: Ferredoxin Oxidoreductase That Functions with FDX1", Plant Physiology, vol. 161, pp. 57-71, Jan. 2013.

Vita et al., "Disulfide Bond-Dependent Mechanism of Protection against Oxidative Stress in Phyuvate-Ferredoxin Oxidoreductase of Anaerobic Desulfovibrio Bacteria", Biochemistry, vol. 47, No. 3, pp. 957-964, 2008.

Vuorijoki et al., "Inactivation of iron-sulfur cluster biogenesis regulator SufR in *Synechocystis* sp. PCC 6803 induces unique iron-dependent protein-level responses", Biochimica et Biophysica Acta, vol. 1861, pp. 1085-1098, 2017.

(Continued)

*Primary Examiner* — Weihua Fan

(74) *Attorney, Agent, or Firm* — Pearne & Gordon LLP

(57) ABSTRACT

Transgenic plants having enhanced yield and having enhanced seed yield are disclosed. The transgenic plants are transformed with a transgenic polynucleotide encoding one or more metabolic enzymes. The metabolic enzymes can be from any biological source. The transgenic polynucleotide(s) comprises a nucleic acid sequences encoding the metabolic enzymes under the control of functional plant promoters, the one or more metabolic enzymes are targeted to the plastids by the addition of plastid targeting signals. Optionally the functional plant promoters are seed specific promoters and the metabolic enzymes are targeted to the plastids by the addition of plastid targeting peptide heterologous to the metabolic enzymes. Methods of making the transgenic plants and transgenic polynucleotides are disclosed. The magnitude of the increases in seed yield achieved with these transgenic plants are unprecedented.

16 Claims, 85 Drawing Sheets

Specification includes a Sequence Listing.

(56) References Cited

OTHER PUBLICATIONS

Yu et al., "Development of *Synechocystis* sp. PCC 6803 as a Phototrophic Cell Factory", Marine Drugs, vol. 11, pp. 2894-2916, 2013.

NCBI, "D.africanus por gene for pyruvate-ferredoxin oxidoreductase", pp. 1-3, available at https://www.ncbi.nlm.nih.gov/nuccore/y09702, last accessed Jun. 24, 2020.

NCBI, "Pyruvate:ferredoxin (flavodoxin) oxidoreductase [Desulfomicrobium baculatum]", pp. 1-2, available at https://www.ncbi.nlm.nih.gov/protein/wp_015773255, last accessed Jun. 24, 2020.

NCBI, "Pyruvate:ferredoxin (flavodoxin) oxidoreductase [Desulfovibrio vulgaris]", pp. 1-2, available at https://www.ncbi.nlm.nih.gov/protein/WP_012612979, last accessed Jun. 24, 2020.

NCBI, "Pyruvate ferredoxin oxidoreductase [Clostridium acetobutylicum DSM 1731]", pp. 1-2, available at https://www.ncbi.nlm.nih.gov/protein/aei34679, last accessed Jun. 24, 2020.

NCBI, "Putative pyruvate-flavodoxin oxidoreductase [*Escherichia coli* str. K-12 substr. MG1655]", pp. 1-3, available at https://www.ncbi.nlm.nih.gov/protein/np_415896, last accessed Jun. 26, 2020.

NCBI, "Pyruvate oxidoreductase [*Synechocystis* sp. PCC 6803]", pp. 1-2, available at https://www.ncbi.nlm.nih.gov/protein/BAA10774.1, last accessed Jun. 26, 2020.

Bar-Even, et al., "Daring metabolic designs for enhanced plant carbon fixation," Plant Science, vol. 273, pp. 71-83, doi:https://doi.org/10.1016/j.plantsci.2017.12.007 (2018).

Schwender et al., "Rubisco without the Calvin cycle improves the carbon efficiency of developing green seeds," Nature, vol. 432, pp. 779-782 (2004).

Lonien et al., "Analysis of metabolic flux phenotypes for two *Arabidopsis* mutants with severe impairment in seed storage lipid synthesis," Plant Physiol., vol. 151, pp. 1617-1634, doi:10.1104/pp.109.144121 (2009).

Rubisco large subunit (RBCL) gene results from *Arabidopsis* eFP Browser 2.0, available at http://bar.utoronto.ca/efp2/Arabidopsis/Arabidopsis_eFPBrowser2.html, last accessed Apr. 11, 2021, 1 page.

Carey et al. "High Flux Through the Oxidative Pentose Phosphate Pathway Lowers Efficiency in Developing Camelina Seeds," Plant Physiology, vol. 182, pp. 493-506, doi: 10.1104/pp.19.00740 (2020).

Kegg, Enzyme: 1.2.7.1; https://www.genome.jp/dbget-bin/www_bget?ec:1.2.7.1, 2013.

Backhausen et al., "Transgenic potato plants with altered expression levels of chloroplast NADP-malate dehydrogenase: interactions between photosynthetic electron transport and malate metabolism in leaves and in isolated intact chloroplasts", Planta, 207; 105-114, 1998.

Bar-Even et al., "Design and Analysis of Synthetic Carbon Fixation Pathways", Proc Natl Acad Sci USA, vol. 107, No. 19, pp. 8889-8894, May 11, 2010.

Beaujean et al., "Integration and expression of Sorghum C4 phosphoenolpyruvate carboxylase and choloroplastic NADP+-malate dehydrogenase sparately or together in C3 potato plants", Plant Science, vol. 160, pp. 1199-1210, 2001.

International Search Report on Patentability for International Patent Application No. PCT/2016/026767 dated Oct. 10, 2017.

International Search Report and Written Opinion for International Application No. PCT/2016/026767 dated Jul. 28, 2016.

Olsen et al., "Targeting of Glyoxysomal Proteins of Peroxisomes in Leaves and Roots of a Higher Plant", Plant Cell, vol. 5, pp. 941-952, Aug. 1993.

Raines, "Increasing Photosynthetic Carbon Assimilation in C3 Plants to Improve Crop Yield: Current and Future Strategies", Plant Physiology, vol. 155, pp. 36-42, 2011.

Jitrapakdee et al., "Structure, Mechanism and Regulation of Pyruvate Carboxylase," Biochem J. Author manuscript, available in PMC Apr. 25, 2010, pp. 1-42, published in final form as Biochem J. Aug. 1, 2008; 413(3): 369-387.

* cited by examiner (a)

(b)

(a)

(b)

(a)

(b)

FIG. 19A DNA sequence of pMBXS918 (SEQ ID NO: 1)

```
1     CTAGGGTACG TAGTGTTTAT CTTTGTTGCT TTTCTGAACA ATTTATTTAC
51    TATGTAAATA TATTATCAAT GTTTAATCTA TTTTAATTTG CACATGAATT
101   TTCATTTTAT TTTTACTTTA CAAAACAAAT AAATATATAT GCAAAAAAAT
151   TTACAAACGA TGCACGGGTT ACAAACTAAT TTCATTAAAT GCTAATGCAG
201   ATTTTGTGAA GTAAAACTCC AATTATGATG AAAAATACCA CCAACACCAC
251   CTGCGAAACT GTATCCCAAC TGTCCTTAAT AAAAATGTTA AAAAGTATAT
301   TATTCTCATT TGTCTGTCAT AATTTATGTA CCCCACTTTA ATTTTTCTGA
351   TGTACTAAAC CGAGGGCAAA CTGAAACCTG TTCCTCATGC AAAGCCCCTA
401   CTCACCATGT ATCATGTACG TGTCATCACC CAACAACTCC ACTTTTGCTA
451   TATAACAACA CCCCCGTCAC ACTCTCCCTC TCTAACACAC ACCCCACTAA
501   CAATTCCTTC ACTTGCAGCA CTGTTGCATC ATCATCTTCA TTGCAAAACC
551   CTAAACTTCA CCTTCAACCG GATCCAAAAT GGCTTCTATG ATATCCTCTT
601   CCGCTGTGAC AACAGTCAGC CGTGCCTCTA GGGGGCAATC CGCCGCAGTG
651   GCTCCATTCG GCGGCCTCAA ATCCATGACT GGATTCCCAG TGAAGAAGGT
701   CAACACTGAC ATTACTTCCA TTACAAGCAA TGGTGGAAGA GTAAAGTGCA
751   TGCAGGTGTG GCCTCCAATT GGAAAGAAGA AGTTTGAGAC TCTTTCCTAT
801   TTGCCACCAT TGACGAGAGA TTCTAGAGTT TCGAGCACAC TGAGAGAAGC
851   ATCAAAAGAT ACGTTGCAAG CAAAGGATAA AACATATCAT TACTACTCTT
901   TACCTCTCGC TGCTAAGTCT CTAGGAGACA TAACTCGTTT GCCGAAGTCC
951   TTGAAGGTAT TACTCGAAAA CCTATTAAGG TGGCAAGACG GAAATAGCGT
1001  TACAGAAGAA GATATTCACG CTCTTGCGGG ATGGTTGAAG AATGCACACG
1051  CAGATCGAGA GATTGCATAT AGACCTGCTA GAGTGTTGAT GCAAGATTTC
1101  ACCGGTGTTC CGGCTGTCGT TGATTTAGCG GCTATGAGGG AAGCAGTGAA
1151  GAGGTTGGGT GGGGATACTG CCAAAGTGAA CCCTCTTAGT CCCGTTGATC
1201  TTGTTATAGA TCATTCAGTC ACTGTTGACA GGTTTGGAGA TGATGAGGCA
1251  TTTGAAGAGA ACGTGCGTCT GGAAATGGAA CGTAACCATG AGAGATATGT
1301  CTTTCTTAAG TGGGGGAAAC AAGCGTTTTC TCGTTTCTCC GTTGTTCCGC
1351  CTGGTACCGG AATCTGTCAT CAGGTCAATC TTGAGTATCT CGGAAAAGCA
1401  GTCTGGTCCG AGCTTCAGGA TGGTGAGTGG ATTGCCTACC CAGATACACT
1451  TGTTGGCACG GATTCCCATA CTACAATGAT CAATGGACTG GGGGTTTTGG
1501  GCTGGGGAGT AGGTGGGATC GAGGCTGAAG CTGCTATGCT AGGGCAACCG
1551  GTGTCAATGC TCATTCCTGA TGTCGTGGGT TTTAAGCTCA CTGGAAAACT
1601  TCGAGAGGGA ATTACCGCTA CCGATCTGGT ACTCACAGTT ACCCAAATGC
1651  TTAGAAAACA TGGTGTAGTG GGGAAATTTG TTGAATTCTA CGGTGACGGA
1701  CTTGATAGTC TGCCGCTCGC CGACCGTGCT ACTATTGCCA ATATGTCGCC
1751  AGAGTATGGT GCGACATGTG GCTTCTTCCC AATTGATGCG GTTACGCTGG
1801  ATTACATGCG TTTATCTGGT CGATCTGAGG ATCAAGTTGA GTTGGTTGAG
1851  AAGTATGCGA AGGCACAGGG TATGTGGAGA AATCCAGGAG ATGAACCTAT
1901  CTTTACTTCT ACTTTGGAGT TAGACATGAA TGATGTTGAG GCTAGCTTGG
1951  CTGGGCCTAA GCGTCCACAA GATAGGGTTG CTCTTCCAGA TGTGCCGAAA
2001  GCCTTTGCAG CTTCAAACGA ATTAGAAGTC AACGCGACCC ATAAAGACAG
2051  ACAACCAGTT GACTATGTAA TGAACGGTCA TCAATACCAG CTTCCTGATG
2101  GCGCTGTTGT TATCGCGGCA ATAACTTCTT GCACCAATAC GAGTAATCCA
2151  AGTGTACTAA TGGCCGCTGG ACTCCTGGCC AAGAAGGCTG TGACTCTTGG
2201  TCTTAAGCGA CAGCCTTGGG TTAAGGCATC ACTGGCTCCC GGTAGCAAAG
2251  TCGTGAGCGA TTATCTTGCT AAAGCGAAAC TCACGCCATA CTTGGACGAA
2301  CTGGGTTTCA ATCTCGTTGG ATATGGATGC ACAACCTGTA TCGGAAACTC
2351  TGGCCCTTTA CCTGATCCCA TTGAAACAGC TATAAAGAAG AGTGATCTTA
2401  CTGTGGGCGC TGTCCTAAGT GGAAACAGAA ATTTCGAGGG AAGAATACAC
2451  CCTCTCGTTA AAACAAATTG GTTAGCTTCT CCCCCATTAG TTGTGGCCTA
2501  TGCTTTGGCC GGGAATATGA ACATTAACCT TGCTTCAGAG CCGATTGGAC
2551  ACGATCGTAA AGGGGACCCT GTGTATTTGA AAGACATCTG GCCATCCGCA
2601  CAAGAAATAG CTCGTGCGGT TGAACAAGTG TCTACAGAAA TGTTCCGAAA
2651  AGAGTATGCC GAGGTTTTTG AAGGTACTGC TGAGTGGAAG GGTATAAACG
2701  TTACAAGGTC TGACACGTAT GGTTGGCAAG AAGATTCTAC TTACATCAGG
2751  CTTAGTCCAT TCTTTGATGA GATGCAGGCA ACTCCTGCCC CAGTAGAGGA
```

FIG. 19B DNA sequence of pMBXS918 (Cont'd)

```
2801  CATCCACGGA GCTAGAATTC TGGCAATGCT AGGAGATTCT GTTACTACCG
2851  ATCACATTTC CCCAGCTGGC TCGATTAAGC CCGATTCACC AGCTGGAAGG
2901  TACTTGCAAG GTAGGGGCGT TGAGAGAAAG GACTTTAACT CATACGGTTC
2951  GCGTAGAGGC AACCACGAAG TAATGATGAG GGGCACGTTC GCAAATATCC
3001  GAATCAGAAA TGAAATGGTG CCAGGCGTGG AAGGGGGAAT GACAAGACAT
3051  TTGCCTGACT CAGATGTCGT TTCGATTTAC GATGCTGCAA TGAGATACAA
3101  ACAGGAGCAG ACACCTCTAG CAGTCATAGC TGGTAAAGAA TATGGAAGTG
3151  GTAGCTCTAG GGATTGGGCG GCTAAAGGAC CGAGACTTCT CGGTATCAGG
3201  GTGGTGATTG CGGAATCATT CGAGAGAATC CATAGAAGCA ATCTCATAGG
3251  GATGGGAATA TTGCCTTTAG AGTTTCCACA GGGAGTGACG CGAAAGACTT
3301  TGGGACTTAC CGGTGAAGAA AAGATTGACA TTGGTGATCT CCAGAATTTA
3351  CAGCCTGGTG CAACTGTCCC TGTTACCCTC ACAAGAGCCG ACGGGTCCCA
3401  AGAGGTGGTC CCGTGTCGAT GCAGAATCGA CACAGCAACG GAATTGACTT
3451  ACTATCAGAA CGATGGAATA CTGCATTACG TGATCCGTAA CATGCTTAAA
3501  TGAGGCGCGC CTGAGTAATT CTGATATTAG AGGGAGCATT AATGTGTTGT
3551  TGTGATGTGG TTTATATGGG GAAATTAAAT AAATGATGTA TGTACCTCTT
3601  GCCTATGTAG GTTTGTGTGT TTTGTTTTGT TGTCTAGCTT TGGTTATTAA
3651  GTAGTAGGGA CGTTCGTTCG TGTCTCAAAA AAAGGGGTAC TACCACTCTG
3701  TAGTGTATAT GGATGCTGGA AATCAATGTG TTTTGTATTT GTTCACCTCC
3751  ATTGTTGAAT TCAATGTCAA ATGTGTTTTG CGTTGGTTAT GTGTAAAATT
3801  ACTATCTTTC TCGTCCGATG ATCAAAGTTT TAAGCAACAA AACCAAGGGT
3851  GAAATTTAAA CTGTGCTTTG TTGAAGATTC TTTTATCATA TTGAAAATCA
3901  AATTACTAGC AGCAGATTTT ACCTAGCATG AAATTTTATC AACAGTACAG
3951  CACTCACTAA CCAAGTTCCA AACTAAGATG CGCCATTAAC ATCAGCCAAT
4001  AGGCATTTTC AGCAAAAGCT TGTACGTAGT GTTTATCTTT GTTGCTTTTC
4051  TGAACAATTT ATTTACTATG TAAATATATT ATCAATGTTT AATCTATTTT
4101  AATTTGCACA TGAATTTTCA TTTTATTTTT ACTTTACAAA ACAAATAAAT
4151  ATATATGCAA AAAAATTTAC AAACGATGCA CGGGTTACAA ACTAATTTCA
4201  TTAAATGCTA ATGCAGATTT TGTGAAGTAA AACTCCAATT ATGATGAAAA
4251  ATACCACCAA CACCACCTGC GAAACTGTAT CCCAACTGTC CTTAATAAAA
4301  ATGTTAAAAA GTATATTATT CTCATTTGTC TGTCATAATT TATGTACCCC
4351  ACTTTAATTT TTCTGATGTA CTAAACCGAG GGCAAACTGA AACCTGTTCC
4401  TCATGCAAAG CCCCTACTCA CCATGTATCA TGTACGTGTC ATCACCCAAC
4451  AACTCCACTT TTGCTATATA ACAACACCCC CGTCACACTC TCCCTCTCTA
4501  ACACACACCC CACTAACAAT TCCTTCACTT GCAGCACTGT TGCATCATCA
4551  TCTTCATTGC AAAACCCTAA ACTTCACCTT CAACCGCGGC CGCAGATCTA
4601  AAATGGCTTC TATGATATCC TCTTCCGCTG TGACAACAGT CAGCCGTGCC
4651  TCTAGGGGGC AATCCGCCGC AGTGGCTCCA TTCGGCGGCC TCAAATCCAT
4701  GACTGGATTC CCAGTGAAGA AGGTCAACAC TGACATTACT TCCATTACAA
4751  GCAATGGTGG AAGAGTAAAG TGCATGCAGG TGTGGCCTCC AATTGGAAAG
4801  AAGAAGTTTG AGACTCTTTC CTATTTGCCA CCATTGACGA GAGATTCTAG
4851  AGTGGTTGAC GGAAGGTCAT CAGCTTCGAT CGTGGCAGTC GATCCTGAAA
4901  GGGCTGCAAG GGAGAGAGAT GCTGCAGCCA GGGCGCTTCT CCAAGATTCC
4951  CCTTTGCATA CTACGATGCA GTATGCAACT TCTGGACTTG AACTTACCGT
5001  ACCGTATGCT CTTAAGGTTG TGGCATCTGC GGATACGTTT GACCGTGCTA
5051  AAGAAGTCGC AGACGAGGTT CTGAGATGTG CTTGGCAGCT TGCTGATACT
5101  GTTCTAAATT CGTTTAATCC TAACTCAGAA GTCAGTCTTG TTGGGAGACT
5151  TCCAGTGGGG CAGAAACACC AAATGTCTGC GCCTCTCAAA AGAGTGATGG
5201  CTTGTTGTCA GAGGGTATAC AACTCTTCAG CAGGATGCTT CGATCCTTCC
5251  ACTGCTCCAG TTGCAAAGGC CTTAAGAGAG ATTGCCTTGG GTAAAGAGAG
5301  AAATAACGCA TGTTTGGAAG CCCTCACCCA AGCGTGCACT CTTCCAAACT
5351  CATTTGTCAT TGATTTTGAA GCTGGTACCA TTAGTAGAAA GCATGAACAT
5401  GCGAGTTTAG ACCTTGGTGG AGTATCTAAG GGTTACATAG TAGATTACGT
5451  TATAGATAAC ATAAACGCAG CTGGTTTCCA GAACGTTTTC TTCGACTGGG
5501  GCGGTGATTG CAGGGCTTCT GGGATGAACG CAAGAAATAC ACCGTGGGTT
5551  GTTGGGATCA CTAGACCGCC ATCTCTTGAC ATGCTTCCTA ACCCACCCAA
5601  AGAGGCTTCA TATATCTCGG TTATTTCCCT CGACAATGAA GCATTAGCGA
5651  CATCTGGTGA TTACGAGAAT TTGATTTACA CCGCAGACGA TAAGCCGTTG
5701  ACGTGCACAT ATGACTGGAA AGGTAAAGAA CTAATGAAGC CTAGCCAAAG
```

FIG. 19C DNA sequence of pMBXS918 (Cont'd)

```
5751  TAACATAGCC CAAGTGTCTG TAAAATGCTA CTCTGCTATG TATGCTGACG
5801  CCCTCGCAAC CGCTTGTTTT ATCAAGCGAG ATCCAGCTAA GGTAAGACAA
5851  CTTCTAGACG GATGGCGTTA TGTTCGTGAT ACTGTGCGAG ATTATCGAGT
5901  CTATGTAAGA GAGAATGAAA GAGTGGCAAA AATGTTTGAG ATCGCCACGG
5951  AAGATGCTGA GATGAGAAAG AGAAGAATAA GTAATACGCT TCCAGCCCGA
6001  GTGATCGTTG TTGGTGGCGG CTTGGCAGGG CTATCTGCGG CGATCGAGGC
6051  GGCTGGTTGT GGGGCACAGG TTGTTCTAAT GGAGAAAGAA GCCAAGTTAG
6101  GCGGTAACAG TGCTAAGGCA ACCAGCGGGA TAAATGGATG GGGTACTAGA
6151  GCACAGGCAA AAGCCTCAAT CGTTGATGGT GGTAAATACT TTGAACGAGA
6201  TACATATAAG TCAGGAATTG GCGGAAATAC TGATCCAGCA CTTGTTAAGA
6251  CACTCAGCAT GAAGAGTGCG GATGCCATTG GGTGGCTGAC TTCGCTCGGT
6301  GTGCCTCTTA CTGTCTTATC TCAATTAGGT GGACACTCAC GTAAGAGAAC
6351  ACACAGGGCA CCTGATAAGA AGGATGGAAC GCCACTACCT ATTGGATTCA
6401  CTATTATGAA AACTCTCGAA GATCATGTTC GTGGAAACTT ATCTGGACGA
6451  ATTACAATTA TGGAAAATTG TTCGGTTACA TCACTGCTTT CCGAAACTAA
6501  AGAGCGTCCT GATGGGACCA AACAAATTCG TGTCACGGGT GTTGAGTTCA
6551  CCCAGGCTGG TAGCGGGAAA ACTACAATCT TAGCTGATGC CGTTATCTTA
6601  GCTACAGGTG GGTTTTCTAA TGACAAAACC GCGGATTCCC TTTTGAGGGA
6651  ACACGCACCG CATTTGGTCA ACTTCCCCAC CACAAACGGG CCTTGGGCTA
6701  CTGGAGATGG AGTTAAACTT GCACAGAGAC TTGGTGCTCA ACTTGTAGAT
6751  ATGGATAAAG TTCAGTTACA TCCGACAGGA CTCATAAACC CTAAAGATCC
6801  AGCAAACCCG ACAAAGTTCT TAGGACCTGA GGCCTTGCGT GGCAGCGGTG
6851  GTGTGCTGCT GAACAAGCAA GGCAAGAGAT TTGTGAATGA ACTAGACCTA
6901  CGTTCTGTTG TGAGTAAGGC TATTATGGAA CAAGGTGCTG AGTACCCAGG
6951  TTCTGGCGGC TCGATGTTCG CTTACTGCGT TCTTAACGCC GCAGCTCAAA
7001  AGCTATTTGG AGTATCATCC CATGAGTTCT ACTGGAAAAA GATGGGTCTT
7051  TTCGTCAAAG CTGACACTAT GAGGGATCTG GCTGCTCTTA TCGGTTGTCC
7101  TGTCGAGTCT GTGCAACAGA CATTGGAAGA ATATGAGAGA CTGTCTATTT
7151  CCCAGAGATC ATGCCCAATA ACCAGGAAGT CGGTTTACCC TTGTGTCTTA
7201  GGAACTAAGG GTCCGTATTA CGTTGCTTTT GTGACACCTT CAATCCACTA
7251  TACTATGGGT GGTTGCTTGA TTTCCCCTAG TGCAGAAATT CAAATGAAAA
7301  ACACCTCATC GAGAGCACCT TTATCACATT CCAATCCCAT CCTGGGTTTA
7351  TTCGGAGCTG GTGAGGTAAC TGGCGGTGTC CACGGTGGCA ATAGGCTTGG
7401  GGGCAATTCC CTTCTGGAAT GTGTGGTTTT CGGAAGGATT GCAGGTGACC
7451  GAGCTTCCAC TATATTGCAA AGAAAAATCCA GTGCGCTGTC TTTCAAGGTG
7501  TGGACTACAG TTGTTCTTAG AGAGGTGCGT GAGGGCGGAG TGTACGGCGC
7551  TGGTTCTAGG GTTCTAAGAT TTAACCTTCC TGGAGCACTT CAACGTTCCG
7601  GGCTATCTTT AGGACAGTTT ATCGCTATAC GAGGGGATTG GGATGGACAG
7651  CAACTTATTG GTTACTATTC TCCAATTACT CTCCCAGATG ACCTCGGAAT
7701  GATAGACATT CTTGCTAGAT CAGACAAAGG CACACTCAGG GAGTGGATTT
7751  CTGCTCTGGA GCCAGGTGAT GCCGTGGAAA TGAAAGCGTG CGGCGGTCTT
7801  GTAATTGAAC GTAGACTTTC AGATAAGCAT TTTGTGTTTA TGGGGCACAT
7851  CATCAATAAG CTATGTTTGA TCGCCGGTGG GACTGGCGTT GCGCCCATGT
7901  TGCAGATTAT CAAGGCGGCA TTTATGAAGC CCTTTATAGA TACGCTGGAG
7951  AGTGTGCATT TGATCTATGC TGCAGAGGAT GTAACGGAGC TTACATATCG
8001  TGAAGTTCTG GAAGAACGAC GAAGGGAATC GAGAGGTAAA TTCAAGAAAA
8051  CTTTCGTTCT TAATAGGCCA CCCCCTTTGT GGACTGACGG CGTCGGGTTC
8101  ATAGATCGAG GGATACTTAC AAATCATGTC CAACCCCCAT CCGATAATCT
8151  TTTGGTGGCC ATTTGTGGAC CGCCCGTTAT GCAGCGTATA GTGAAGGCTA
8201  CACTGAAAAC TTTGGGATAT AACATGAACT TGGTTAGAAC GGTAGACGAG
8251  ACTGAACCTT CAGGTAGCAG TAAGATTTGA GCGATCGCGC GGCCGCTGAG
8301  TAATTCTGAT ATTAGAGGGA GCATTAATGT GTTGTTGTGA TGTGGTTTAT
8351  ATGGGGAAAT TAAATAAATG ATGTATGTAC CTCTTGCCTA TGTAGGTTTG
8401  TGTGTTTTGT TTTGTTGTCT AGCTTTGGTT ATTAAGTAGT AGGGACGTTC
8451  GTTCGTGTCT CAAAAAAAGG GGTACTACCA CTCTGTAGTG TATATGGATG
8501  CTGGAAATCA ATGTGTTTTG TATTTGTTCA CCTCCATTGT TGAATTCAAT
8551  GTCAAATGTG TTTTGCGTTG GTTATGTGTA AAATTACTAT CTTTCTCGTC
8601  CGATGATCAA AGTTTTAAGC AACAAAACCA AGGGTGAAAT TTAAACTGTG
8651  CTTTGTTGAA GATTCTTTTA TCATATTGAA AATCAAATTA CTAGCAGCAG
```

FIG. 19D DNA sequence of pMBXS918 (Cont'd)

```
8701  ATTTTACCTA GCATGAAATT TTATCAACAG TACAGCACTC ACTAACCAAG
8751  TTCCAAACTA AGATGCGCCA TTAACATCAG CCAATAGGCA TTTTCAGCAA
8801  GTTTAAACTA CGTAGTGTTT ATCTTTGTTG CTTTTCTGAA CAATTTATTT
8851  ACTATGTAAA TATATTATCA ATGTTTAATC TATTTTAATT TGCACATGAA
8901  TTTTCATTTT ATTTTTACTT TACAAAACAA ATAAATATAT ATGCAAAAAA
8951  ATTTACAAAC GATGCACGGG TTACAAACTA ATTTCATTAA ATGCTAATGC
9001  AGATTTTGTG AAGTAAAACT CCAATTATGA TGAAAAATAC CACCAACACC
9051  ACCTGCGAAA CTGTATCCCA ACTGTCCTTA ATAAAAATGT TAAAAAGTAT
9101  ATTATTCTCA TTTGTCTGTC ATAATTTATG TACCCCACTT TAATTTTTCT
9151  GATGTACTAA ACCGAGGGCA AACTGAAACC TGTTCCTCAT GCAAAGCCCC
9201  TACTCACCAT GTATCATGTA CGTGTCATCA CCCAACAACT CCACTTTTGC
9251  TATATAACAA CACCCCCGTC ACACTCTCCC TCTCTAACAC ACACCCCACT
9301  AACAATTCCT TCACTTGCAG CACTGTTGCA TCATCATCTT CATTGCAAAA
9351  CCCTAAACTT CACCTTCAAC CGCGGCCGCT CGCGAAAAAT GGCTTCTATG
9401  ATATCCTCTT CCGCTGTGAC AACAGTCAGC CGTGCCTCTA GGGGGCAATC
9451  CGCCGCAGTG GCTCCATTCG GCGGCCTCAA ATCCATGACT GGATTCCCAG
9501  TGAAGAAGGT CAACACTGAC ATTACTTCCA TTACAAGCAA TGGTGGAAGA
9551  GTAAAGTGCA TGCAGGTGTG GCCTCCAATT GGAAAGAAGA AGTTTGAGAC
9601  TCTTTCCTAT TTGCCACCAT TGACGAGAGA TTCTAGAGTG GCTAGGAAGA
9651  AGATCCGTGA ATATGACTCT AAAAGGCTTG TCAAAGAACA TTTCAAGAGG
9701  CTTAGTGGAA AAGAACTCCC TATTAGGTCT GTGCAGATTA ACGAAACAAC
9751  TGATCTTAAC GAATTGGTTG AGAAAGAGCC TTGGTTGAGC AGTGAAAAGT
9801  TAGTCGTGAA GCCAGACATG TTGTTTGGAA AACGTGGAAA ATCAGGACTT
9851  GTCGCTCTCA AACTGGACTT TGCTGATGTC GCAACGTTTG TTAAAGAGAG
9901  ACTAGGTAAA GAGGTTGAGA TGTCAGGATG TAAAGGACCC ATAACGACCT
9951  TTATTGTTGA ACCATTCGTT CCACATAACG AAGAATACTA CCTTAATGTA
10001 GTGTCGGATA GATTAGGATG CTCCATATCA TTCTCCGAGT GTGGCGGGAT
10051 CGAGATTGAA GAGAACTGGG ATAAGGTCAA AACAATCTTT TTGCCAACCG
10101 GTGCTTCGCT GACACCTGAG ATTTGTGCTC CCCTTGTTGC TACACTTCCA
10151 CTTGAGATTA AGGCAGAAAT AGAAGAGTTC ATCAAGGTTA TCTTTACTCT
10201 GTTCCAAGAT TTAGATTTCA CTTTTCTCGA AATGAATCCG TTTACTTTAG
10251 TCGATGGTTC TCCGTATCCT TTGGATATGC GAGGTGAGCT GGATGACACA
10301 GCGGCTTTTA AGAACTTCAA GAAGTGGGGA GATATTGAGT TCCCATTGCC
10351 GTTTGGCCGT GTTATGTCTC CAACTGAATC CTTCATACAC GGACTCGATG
10401 AAAAGACCAG TGCATCTCTC AAGTTTACCG TTCTAAATCC TAAGGGTAGA
10451 ATCTGGACTA TGGTAGCTGG GGGTGGAGCC TCTGTAATCT ACGCTGATAC
10501 TGTTGGTGAT CTTGGCTATG CTAGCGAATT AGGGAACTAT GCGGAGTACA
10551 GCGGTGCACC TAAAGAGGAC GAGGTACTCC AATATGCCCG AGTGGTGATT
10601 GATTGTGCTA CGGCAAATCC TGACGGAAAG TCAAGAGCCC TTGTGATTGG
10651 GGGTGGTATA GCAAATTTCA CAGACGTTGC AGCGACTTTC AATGGTATCA
10701 TTAGAGCCTT GAAAGAGAAA GAGGCCAAAC TAAAGGCTGC GAGAATGCAC
10751 ATTTTTGTTC GTAGAGGTGG CCCTAATTAC CAGAAGGGTT TGGCTAAAAT
10801 GCGAGCTTTG GGAGATGATA TAGGCGTGCC TATCGAAGTT TATGGACCTG
10851 AAGCAACGAT GACCGGGATC TGCAAAGAAG CAATACAATA CATTACAGCT
10901 GCAGCGTGAA CGCGTTGAGT AATTCTGATA TTAGAGGGAG CATTAATGTG
10951 TTGTTGTGAT GTGGTTTATA TGGGGAAATT AAATAAATGA TGTATGTACC
11001 TCTTGCCTAT GTAGGTTTGT GTGTTTTGTT TTGTTGTCTA GCTTTGGTTA
11051 TTAAGTAGTA GGGACGTTCG TTCGTGTCTC AAAAAAAGGG GTACTACCAC
11101 TCTGTAGTGT ATATGGATGC TGGAAATCAA TGTGTTTTGT ATTTGTTCAC
11151 CTCCATTGTT GAATTCAATG TCAAATGTGT TTTGCGTTGG TTATGTGTAA
11201 AATTACTATC TTTCTCGTCC GATGATCAAA GTTTTAAGCA ACAAAACCAA
11251 GGGTGAAATT TAAACTGTGC TTTGTTGAAG ATTCTTTTAT CATATTGAAA
11301 ATCAAATTAC TAGCAGCAGA TTTTACCTAG CATGAAATTT TATCAACAGT
11351 ACAGCACTCA CTAACCAAGT TCCAAACTAA GATGCGCCAT TAACATCAGC
11401 CAATAGGCAT TTTCAGCAAT GTACATACGT AGTGTTTATC TTTGTTGCTT
11451 TTCTGAACAA TTTATTTACT ATGTAAATAT ATTATCAATG TTTAATCTAT
11501 TTTAATTTGC ACATGAATTT TCATTTTATT TTTACTTTAC AAAACAAATA
11551 AATATATATG CAAAAAAATT TACAAACGAT GCACGGGTTA CAAACTAATT
11601 TCATTAAATG CTAATGCAGA TTTTGTGAAG TAAAACTCCA ATTATGATGA
```

FIG. 19E DNA sequence of pMBXS918 (Cont'd)

```
11651 AAAATACCAC CAACACCACC TGCGAAACTG TATCCCAACT GTCCTTAATA
11701 AAAATGTTAA AAAGTATATT ATTCTCATTT GTCTGTCATA ATTTATGTAC
11751 CCCACTTTAA TTTTTCTGAT GTACTAAACC GAGGGCAAAC TGAAACCTGT
11801 TCCTCATGCA AAGCCCCTAC TCACCATGTA TCATGTACGT GTCATCACCC
11851 AACAACTCCA CTTTTGCTAT ATAACAACAC CCCCGTCACA CTCTCCCTCT
11901 CTAACACACA CCCCACTAAC AATTCCTTCA CTTGCAGCAC TGTTGCATCA
11951 TCATCTTCAT TGCAAAACCC TAAACTTCAC CTTCAACCGC GGCCGCGACG
12001 TCAAAATGGC TTCTATGATA TCCTCTTCCG CTGTGACAAC AGTCAGCCGT
12051 GCCTCTAGGG GGCAATCCGC CGCAGTGGCT CCATTCGGCG GCCTCAAATC
12101 CATGACTGGA TTCCCAGTGA AGAAGGTCAA CACTGACATT ACTTCCATTA
12151 CAAGCAATGG TGGAAGAGTA AAGTGCATGC AGGTGTGGCC TCCAATTGGA
12201 AAGAAGAAGT TTGAGACTCT TTCCTATTTG CCACCATTGA CGAGAGATTC
12251 TAGAGTTGCT ACCGGCCAAC TCTTTTCCCG AACAACGCAA GCTCTATTCT
12301 ACAACTATAA ACAACTTCCA GTTCAAAGAA TGTTAGATTT CGATTTCTTA
12351 TGCGGAAGAG AAACACCATC AGTGGCTGGA ATTATCAATC CAGGGTCCGA
12401 GGGATTTCAG AAATTGTTTT TCGGTCAAGA AGAGATAGCT ATTCCAGTCC
12451 ATGCGGCCAT AGAAGCAGCT TGTGCCGCCC ACCCCACTGC TGATGTTTTC
12501 ATCAACTTTG CTTCGTTCAG GAGTGCGGCT GCAAGTTCGA TGGCAGCTCT
12551 CAAGCAACCT ACAATCAAGG TCGTAGCAAT AATCGCAGAG GGAGTCCCAG
12601 AATCTGACAC CAAGCAACTC ATCGCTTATG CCCGAGCGAA CAATAAAGTG
12651 GTTATAGGTC CTGCTACTGT GGGCGGAATT CAGGCTGGAG CTTTTAAGAT
12701 TGGTGACACT GCGGGGACCA TTGATAACAT TATCCAATGC AAGCTGTATC
12751 GTCCGGGTAG TGTCGGATTT GTTTCCAAGT CTGGTGGGAT GTCTAATGAG
12801 ATGTATAACA CTGTAGCAAG AGTAACTGAT GGCATTTATG AGGGGATAGC
12851 AATTGGGGGT GACGTTTTCC CCGGTTCAAC TTTATCCGAT CATATCCTGA
12901 GATTTAACAA TATCCCGCAA ATCAAGATGA TGGTTGTACT AGGAGAGCTT
12951 GGGGGACGTG ACGAGTATTC ACTTGTTGAA GCTCTGAAAG AGGGTAAAGT
13001 CAATAAACCT GTTGTCGCTT GGGTGTCAGG CACCTGTGCA AGACTCTTCA
13051 AAAGCGAGGT CCAGTTTGGT CACGCAGGAG CGAAGAGCGG TGGAGAGATG
13101 GAGTCTGCAC AAGCTAAAAA CCAGGCGTTG ATAGATGCAG GCGCAATTGT
13151 TCCAACATCT TTTGAAGCCT TGGAGAGCGC GATCAAAGAA ACTTTTGAGA
13201 AACTTGTCGA AGAAGGTAAG GTTTCGCCGA TTAAAGAAGT AATCCCACCT
13251 CAGATCCCTG AGGATCTAAA TTCCGCAATT AAGTCTGGAA AGGTGAGGGC
13301 TCCAACGCAT ATCATATCGA CGATTTCTGA TGATAGAGGG GAAGAGCCGT
13351 GCTACGCAGG TGTTCCTATG TCTAGCATAA TTGAGCAAGG TTACGGAGTG
13401 GGAGATGTCA TTTCATTGTT ATGGTTCAAA CGTAGTCTCC CGAGGTATTG
13451 TACCAAATTC ATTGAGATTT GCATAATGCT TTGTGCGGAT CATGGACCCT
13501 GTGTATCTGG TGCTCATAAT ACTATCGTTA CTGCCAGAGC TGGAAAAGAT
13551 TTGGTGTCTA GTCTCGTTTC AGGCTTATTG ACAATAGGTC CTCGATTCGG
13601 TGGGGCCATC GACGACGCTG CCAGGTACTT TAAGGATGCA TGTGACAGAA
13651 ACCTCACACC ATATGAATTT GTGGAAGGCA TGAAAAAGAA GGGCATTAGA
13701 GTGCCTGGAA TTGGTCATCG TATTAAGTCA AGGGATAATA GAGACAAGAG
13751 AGTTGAACTT TTACAGAAGT TTGCTCGAAG TAATTTCCCT AGCGTTAAGT
13801 ACATGGAATA CGCGGTTACT GTTGAAACGT ACACATTGTC TAAGGCTAAT
13851 AACTTGGTGC TTAATGTTGA TGGTGCTATA GGTTCATTAT TCTTGGATCT
13901 ACTTGCAGGT TCTGGAATGT TCACAAAGCA GGAAATCGAC GAGATAGTGC
13951 AAATTGGATA CCTGAACGGA CTATTTGTGT TGGCTAGGTC AATAGGGCTT
14001 ATCGGACACA CGTTTGATCA GAAACGTCTT AAACAGCCTC TCTACCGACA
14051 CCCTTGGGAA GATGTTCTGT ATACCAAATG AGTTAACTGA GTAATTCTGA
14101 TATTAGAGGG AGCATTAATG TGTTGTTGTG ATGTGGTTTA TATGGGGAAA
14151 TTAAATAAAT GATGTATGTA CCTCTTGCCT ATGTAGGTTT GTGTGTTTTG
14201 TTTTGTTGTC TAGCTTTGGT TATTAAGTAG TAGGGACGTT CGTTCGTGTC
14251 TCAAAAAAAG GGGTACTACC ACTCTGTAGT GTATATGGAT GCTGGAAATC
14301 AATGTGTTTT GTATTTGTTC ACCTCCATTG TTGAATTCAA TGTCAAATGT
14351 GTTTTGCGTT GGTTATGTGT AAAATTACTA TCTTTCTCGT CCGATGATCA
14401 AAGTTTTAAG CAACAAAACC AAGGGTGAAA TTTAAACTGT GCTTTGTTGA
14451 AGATTCTTTT ATCATATTGA AAATCAAATT ACTAGCAGCA GATTTTACCT
14501 AGCATGAAAT TTTATCAACA GTACAGCACT CACTAACCAA GTTCCAAACT
14551 AAGATGCGCC ATTAACATCA GCCAATAGGC ATTTTCAGCA AGTTTAAACC
```

FIG. 19F DNA sequence of pMBXS918 (Cont'd)

```
14601  GGACCGTACG TAGTGTTTAT CTTTGTTGCT TTTCTGAACA ATTTATTTAC
14651  TATGTAAATA TATTATCAAT GTTTAATCTA TTTTAATTTG CACATGAATT
14701  TTCATTTTAT TTTTACTTTA CAAAACAAAT AAATATATAT GCAAAAAAAT
14751  TTACAAACGA TGCACGGGTT ACAAACTAAT TTCATTAAAT GCTAATGCAG
14801  ATTTTGTGAA GTAAAACTCC AATTATGATG AAAAATACCA CCAACACCAC
14851  CTGCGAAACT GTATCCCAAC TGTCCTTAAT AAAAATGTTA AAAAGTATAT
14901  TATTCTCATT TGTCTGTCAT AATTTATGTA CCCCACTTTA ATTTTTCTGA
14951  TGTACTAAAC CGAGGGCAAA CTGAAACCTG TTCCTCATGC AAAGCCCCTA
15001  CTCACCATGT ATCATGTACG TGTCATCACC CAACAACTCC ACTTTTGCTA
15051  TATAACAACA CCCCCGTCAC ACTCTCCCTC TCTAACACAC ACCCCACTAA
15101  CAATTCCTTC ACTTGCAGCA CTGTTGCATC ATCATCTTCA TTGCAAAACC
15151  CTAAACTTCA CCTTCAACCG CGGCCGCCAC GTGAAAATGG CTTCTATGAT
15201  ATCCTCTTCC GCTGTGACAA CAGTCAGCCG TGCCTCTAGG GGGCAATCCG
15251  CCGCAGTGGC TCCATTCGGC GGCCTCAAAT CCATGACTGG ATTCCCAGTG
15301  AAGAAGGTCA ACACTGACAT TACTTCCATT ACAAGCAATG GTGGAAGAGT
15351  AAAGTGCATG CAGGTGTGGC CTCCAATTGG AAAGAAGAAG TTTGAGACTC
15401  TTTCCTATTT GCCACCATTG ACGAGAGATT CTAGAGTGAA TACTGTTCGT
15451  TCAGAGAAAG ACTCTATGGG GGCTATAGAC GTGCCTGCTG ATAAGTTATG
15501  GGGAGCCCAG ACTCAACGTA GCCTGGAGCA CTTTAGGATA TCGACTGAGA
15551  AGATGCCTAC GTCCTTGATT CATGCCCTTG CTCTCACTAA GAGAGCAGCA
15601  GCAAAAGTTA ATGAGGATCT CGGCCTTTTA TCCGAAGAGA AAGCATCTGC
15651  CATACGACAG GCCGCTGATG AAGTGTTGGC GGGTCAGCAT GATGATGAGT
15701  TCCCATTAGC TATCTGGCAG ACAGGCTCTG GTACTCAATC CAACATGAAC
15751  ATGAATGAGG TGCTAGCAAA CAGGGCCTCA GAGCTTTTAG GTGGGGTCAG
15801  GGGAATGGAA CGAAAGGTTC ATCCCAACGA TGACGTAAAC AAGTCACAAT
15851  CGAGTAATGA TGTGTTCCCA ACTGCTATGC ACGTTGCAGC TCTGCTTGCG
15901  TTGAGAAAGC AACTTATTCC ACAACTCAAA ACTCTCACCC AAACATTGAA
15951  TGAAAAGTCA AGGGCCTTTG CAGATATCGT GAAGATCGGA CGAACACATC
16001  TTCAGGACGC TACACCACTG ACGTTGGGAC AAGAGATTTC TGGATGGGTT
16051  GCTATGTTGG AACATAACTT GAAACATATC GAGTATAGTT TACCTCATGT
16101  TGCAGAACTA GCATTGGGTG GTACAGCAGT CGGTACCGGC CTCAACACAC
16151  ATCCTGAATA CGCTAGACGT GTAGCTGATG AACTTGCCGT TATTACCTGC
16201  GCTCCGTTCG TTACGGCTCC TAATAAGTTT GAAGCTCTTG CTACTTGTGA
16251  TGCTCTAGTC CAAGCTCATG GTGCACTAAA GGGACTTGCG GCATCTTTAA
16301  TGAAGATTGC AAATGATGTC CGTTGGCTAG CAAGCGGACC AAGATGTGGA
16351  ATAGGCGAAA TTTCCATCCC TGAGAACGAG CCCGGATCAT CTATTATGCC
16401  GGGTAAAGTT AATCCAACGC AGTGTGAAGC CTTGACCATG CTTTGCTGCC
16451  AGGTAATGGG AAACGATGTG GCCATCAATA TGGGTGGTGC GAGTGGAAAC
16501  TTTGAGCTGA ATGTCTTTAG ACCGATGGTT ATCCACAACT TTCTTCAGAG
16551  TGTAAGGCTT CTCGCCGACG GGATGGAGTC ATTCAATAAA CACTGTGCGG
16601  TTGGCATAGA GCCAAACAGA GAACGTATCA ATCAACTTCT CAATGAATCT
16651  CTAATGTTGG TTACTGCTCT CAACACCCAC ATTGGGTACG ACAAAGCTGC
16701  TGAAATTGCT AAAAAGGCGC ACAAAGAAGG TTTAACACTG AAAGCGGCAG
16751  CTCTCGCTCT CGGTTATCTG TCTGAAGCTG AGTTCGATTC GTGGGTCAGA
16801  CCTGAACAAA TGGTGGGAAG CATGAAGGCT GGGAGATGAA CTAGTTGAGT
16851  AATTCTGATA TTAGAGGGAG CATTAATGTG TTGTTGTGAT GTGGTTTATA
16901  TGGGGAAATT AAATAAATGA TGTATGTACC TCTTGCCTAT GTAGGTTTGT
16951  GTGTTTTGTT TTGTTGTCTA GCTTTGGTTA TTAAGTAGTA GGGACGTTCG
17001  TTCGTGTCTC AAAAAAAGGG GTACTACCAC TCTGTAGTGT ATATGGATGC
17051  TGGAAATCAA TGTGTTTTGT ATTTGTTCAC CTCCATTGTT GAATTCAATG
17101  TCAAATGTGT TTTGCGTTGG TTATGTGTAA AATTACTATC TTTCTCGTCC
17151  GATGATCAAA GTTTTAAGCA ACAAAACCAA GGGTGAAATT TAAACTGTGC
17201  TTTGTTGAAG ATTCTTTTAT CATATTGAAA ATCAAATTAC TAGCAGCAGA
17251  TTTTACCTAG CATGAAATTT TATCAACAGT ACAGCACTCA CTAACCAAGT
17301  TCCAAACTAA GATGCGCCAT TAACATCAGC CAATAGGCAT TTTCAGCAAG
17351  TTTAAACTCC GGATTAATTA AGTCGACGGG CCCGTTTAAA CCACGTAGTG
17401  CCTCAGCGTT TAAACGTACG TAGTGTTTAT CTTTGTTGCT TTTCTGAACA
17451  ATTTATTTAC TATGTAAATA TATTATCAAT GTTTAATCTA TTTTAATTTG
17501  CACATGAATT TTCATTTTAT TTTTACTTTA CAAAACAAAT AAATATATAT
```

FIG. 19G DNA sequence of pMBXS918 (Cont'd)

```
17551   GCAAAAAAAT TTACAAACGA TGCACGGGTT ACAAACTAAT TTCATTAAAT
17601   GCTAATGCAG ATTTTGTGAA GTAAAACTCC AATTATGATG AAAAATACCA
17651   CCAACACCAC CTGCGAAACT GTATCCCAAC TGTCCTTAAT AAAAATGTTA
17701   AAAAGTATAT TATTCTCATT TGTCTGTCAT AATTTATGTA CCCCACTTTA
17751   ATTTTTCTGA TGTACTAAAC CGAGGGCAAA CTGAAACCTG TTCCTCATGC
17801   AAAGCCCCTA CTCACCATGT ATCATGTACG TGTCATCACC CAACAACTCC
17851   ACTTTTGCTA TATAACAACA CCCCCGTCAC ACTCTCCCTC TCTAACACAC
17901   ACCCCACTAA CAATTCCTTC ACTTGCAGCA CTGTTGCATC ATCATCTTCA
17951   TTGCAAAACC CTAAACTTCA CCTTCAACCG CGGCCGCTTC GAAAAAATGG
18001   CTTCTATGAT ATCCTCTTCC GCTGTGACAA CAGTCAGCCG TGCCTCTAGG
18051   GGGCAATCCG CCGCAGTGGC TCCATTCGGC GGCCTCAAAT CCATGACTGG
18101   ATTCCCAGTG AAGAAGGTCA ACACTGACAT TACTTCCATT ACAAGCAATG
18151   GTGGAAGAGT AAAGTGCATG CAGGTGTGGC CTCCAATTGG AAAGAAGAAG
18201   TTTGAGACTC TTTCCTATTT GCCACCATTG ACGAGAGATT CTAGAGTGAA
18251   AGTTGCAGTT CTTGGAGCAG CAGGTGGAAT TGGACAGGCT TTGGCTCTCT
18301   TGCTTAAAAC TCAACTACCC AGTGGATCTG AGTTATCATT GTACGATATT
18351   GCCCCAGTAA CCCCTGGGGT GGCAGTTGAT CTCTCCCATA TCCCCACAGC
18401   TGTTAAGATT AAGGGATTCA GCGGTGAGGA TGCTACACCT GCTTTGGAAG
18451   GCGCAGATGT GGTTCTCATT TCGGCAGGCG TGGCAAGAAA GCCAGGTATG
18501   GATAGGTCTG ATCTCTTTAA CGTCAATGCT GGGATAGTCA AGAACTTGGT
18551   ACAACAAGTC GCTAAGACCT GCCCTAAGGC CTGTATTGGT ATCATAACGA
18601   ATCCGGTTAA TACAACAGTT GCTATTGCGG CAGAGGTTCT CAAAAAGGCG
18651   GGAGTTTACG ACAAGAATAA ACTATTTGGC GTAACTACTC TTGATATCAT
18701   ACGTAGTAAT ACGTTCGTAG CCGAACTCAA AGGGAAGCAA CCTGGTGAGG
18751   TAGAAGTGCC AGTTATTGGT GGGCACTCAG GAGTCACTAT CCTGCCTCTT
18801   CTTAGTCAGG TTCCAGGTGT GAGCTTTACC GAGCAAGAAG TCGCGGATCT
18851   TACAAAGAGA ATCCAAAACG CGGGAACTGA AGTTGTTGAG GCTAAAGCTG
18901   GTGGTGGGTC GGCCACGCTG TCTATGGGAC AAGCCGCAGC CCGTTTTGGC
18951   CTTTCACTTG TGCGAGCTTT GCAGGGAGAG CAAGGGGTTG TCGAATGTGC
19001   ATATGTGGAA GGTGACGGTC AGTATGCTAG GTTCTTCTCT CAGCCGTTGT
19051   TACTTGGCAA AAATGGAGTT GAAGAGAGAA AATCTATCGG TACCTTATCC
19101   GCGTTTGAGC AGAACGCTCT AGAGGGAATG CTGGACACTT TAAAGAAAGA
19151   CATAGCTCTG GGAGAAGAAT TCGTGAACAA ATGAATTTAA ATGCGGCCGC
19201   TGAGTAATTC TGATATTAGA GGGAGCATTA ATGTGTTGTT GTGATGTGGT
19251   TTATATGGGG AAATTAAATA AATGATGTAT GTACCTCTTG CCTATGTAGG
19301   TTTGTGTGTT TTGTTTTGTT GTCTAGCTTT GGTTATTAAG TAGTAGGGAC
19351   GTTCGTTCGT GTCTCAAAAA AAGGGGTACT ACCACTCTGT AGTGTATATG
19401   GATGCTGGAA ATCAATGTGT TTTGTATTTG TTCACCTCCA TTGTTGAATT
19451   CAATGTCAAA TGTGTTTTGC GTTGGTTATG TGTAAAATTA CTATCTTTCT
19501   CGTCCGATGA TCAAAGTTTT AAGCAACAAA ACCAAGGGTG AAATTTAAAC
19551   TGTGCTTTGT TGAAGATTCT TTTATCATAT TGAAAATCAA ATTACTAGCA
19601   GCAGATTTTA CCTAGCATGA AATTTTATCA ACAGTACAGC ACTCACTAAC
19651   CAAGTTCCAA ACTAAGATGC GCCATTAACA TCAGCCAATA GGCATTTTCA
19701   GCAAAGCAAA TGAATTCGTA ATCATGTCAT AGCTGTTTCC TGTGTGAAAT
19751   TGTTATCCGC TCACAATTCC ACACAACATA CGAGCCGGAA GCATAAAGTG
19801   TAAAGCCTGG GGTGCCTAAT GAGTGAGCTA ACTCACATTA ATTGCGTTGC
19851   GCTCACTGCC CGCTTTCCAG TCGGGAAACC TGTCGTGCCA GCTGCATTAA
19901   TGAATCGGCC AACGCGCGGG GAGAGGCGGT TTGCGTATTG GCTAGAGCAG
19951   CTTGCCAACA TGGTGGAGCA CGACACTCTC GTCTACTCCA AGAATATCAA
20001   AGATACAGTC TCAGAAGACC AAAGGGCTAT TGAGACTTTT CAACAAAGGG
20051   TAATATCGGG AAACCTCCTC GGATTCCATT GCCCAGCTAT CTGTCACTTC
20101   ATCAAAAGGA CAGTAGAAAA GGAAGGTGGC ACCTACAAAT GCCATCATTG
20151   CGATAAAGGA AAGGCTATCG TTCAAGATGC CTCTGCCGAC AGTGGTCCCA
20201   AAGATGGACC CCCACCCACG AGGAGCATCG TGGAAAAAGA AGACGTTCCA
20251   ACCACGTCTT CAAAGCAAGT GGATTGATGT GAACATGGTG GAGCACGACA
20301   CTCTCGTCTA CTCCAAGAAT ATCAAAGATA CAGTCTCAGA AGACCAAAGG
20351   GCTATTGAGA CTTTTCAACA AAGGGTAATA TCGGGAAACC TCCTCGGATT
20401   CCATTGCCCA GCTATCTGTC ACTTCATCAA AAGGACAGTA GAAAAGGAAG
20451   GTGGCACCTA CAAATGCCAT CATTGCGATA AAGGAAAGGC TATCGTTCAA
```

FIG. 19H DNA sequence of pMBXS918 (Cont'd)

```
20501     GATGCCTCTG CCGACAGTGG TCCCAAAGAT GGACCCCCAC CCACGAGGAG
20551     CATCGTGGAA AAAGAAGACG TTCCAACCAC GTCTTCAAAG CAAGTGGATT
20601     GATGTGATAT CTCCACTGAC GTAAGGGATG ACGCACAATC CCACTATCCT
20651     TCGCAAGACC CTTCCTCTAT ATAAGGAAGT TCATTTCATT TGGAGAGGAC
20701     ACGCTGAAAT CACCAGTCTC TCTCTACAAA TCTATCTCTC TCGAGATGAG
20751     CCCAGAACGA CGCCCGGCCG ACATCCGCCG TGCCACCGAG GCGGACATGC
20801     CGGCGGTCTG CACCATCGTC AACCACTACA TCGAGACAAG CACGGTCAAC
20851     TTCCGTACCG AGCCGCAGGA ACCGCAGGAG TGGACGGACG ACCTCGTCCG
20901     TCTGCGGGAG CGCTATCCCT GGCTCGTCGC CGAGGTGGAC GGCGAGGTCG
20951     CCGGCATCGC CTACGCGGGC CCCTGGAAGG CACGCAACGC CTACGACTGG
21001     ACGGCCGAGT CGACCGTGTA CGTCTCCCCC CGCCACCAGC GGACGGGACT
21051     GGGCTCCACG CTCTACACCC ACCTGCTGAA GTCCCTGGAG GCACAGGGCT
21101     TCAAGAGCGT GGTCGCTGTC ATCGGGCTGC CCAACGACCC GAGCGTGCGC
21151     ATGCACGAGG CGCTCGGATA TGCCCCCCGC GGCATGCTGC GGGCGGCCGG
21201     CTTCAAGCAC GGGAACTGGC ATGACGTGGG TTTCTGGCAG CTGGACTTCA
21251     GCCTGCCGGT ACCGCCCCGT CCGGTCCTGC CCGTCACCGA GATTTGAGAG
21301     CTCGGTCACC TGTCCAACAG TCTCAGGGTT AATGTCTATG TATCTTAAAT
21351     AATGTTGTCG GCGATCGTTC AAACATTTGG CAATAAAGTT TCTTAAGATT
21401     GAATCCTGTT GCCGGTCTTG CGATGATTAT CATATAATTT CTGTTGAATT
21451     ACGTTAAGCA TGTAATAATT AACATGTAAT GCATGACGTT ATTTATGAGA
21501     TGGGTTTTTA TGATTAGAGT CCCGCAATTA TACATTTAAT ACGCGATAGA
21551     AAACAAAATA TAGCGCGCAA ACTAGGATAA ATTATCGCGC GCGGTGTCAT
21601     CTATGTTACT AGATCGGGAA TTAAACTATC AGTGTTTGAC AGGATATATT
21651     GGCGGGTAAA CCTAAGAGAA AAGAGCGTTT ATTAGAATAA TCGGATATTT
21701     AAAAGGGCGT GAAAAGGTTT ATCCGTTCGT CCATTTGTAT GTGCATGCCA
21751     ACCACAGGGT TCCCCTCGGG ATCAAAGTAC TTTGATCCAA CCCCTCCGCT
21801     GCTATAGTGC AGTCGGCTTC TGACGTTCAG TGCAGCCGTC TTCTGAAAAC
21851     GACATGTCGC ACAAGTCCTA AGTTACGCGA CAGGCTGCCG CCCTGCCCTT
21901     TTCCTGGCGT TTTCTTGTCG CGTGTTTTAG TCGCATAAAG TAGAATACTT
21951     GCGACTAGAA CCGGAGACAT TACGCCATGA ACAAGAGCGC CGCCGCTGGC
22001     CTGCTGGGCT ATGCCCGCGT CAGCACCGAC GACCAGGACT TGACCAACCA
22051     ACGGGCCGAA CTGCACGCGG CCGGCTGCAC CAAGCTGTTT TCCGAGAAGA
22101     TCACCGGCAC CAGGCGCGAC CGCCCGGAGC TGGCCAGGAT GCTTGACCAC
22151     CTACGCCCTG GCGACGTTGT GACAGTGACC AGGCTAGACC GCCTGGCCCG
22201     CAGCACCCGC GACCTACTGG ACATTGCCGA GCGCATCCAG GAGGCCGGCG
22251     CGGGCCTGCG TAGCCTGGCA GAGCCGTGGG CCGACACCAC CACGCCGGCC
22301     GGCCGCATGG TGTTGACCGT GTTCGCCGGC ATTGCCGAGT TCGAGCGTTC
22351     CCTAATCATC GACCGCACCC GGAGCGGGCG CGAGGCCGCC AAGGCCCGAG
22401     GCGTGAAGTT TGGCCCCCGC CCTACCCTCA CCCCGGCACA GATCGCGCAC
22451     GCCCGCGAGC TGATCGACCA GGAAGGCCGC ACCGTGAAAG AGGCGGCTGC
22501     ACTGCTTGGC GTGCATCGCT CGACCCTGTA CCGCGCACTT GAGCGCAGCG
22551     AGGAAGTGAC GCCCACCGAG GCCAGGCGGC GCGGTGCCTT CCGTGAGGAC
22601     GCATTGACCG AGGCCGACGC CCTGGCGGCC GCCGAGAATG AACGCCAAGA
22651     GGAACAAGCA TGAAACCGCA CCAGGACGGC CAGGACGAAC CGTTTTTCAT
22701     TACCGAAGAG ATCGAGGCGG AGATGATCGC GGCCGGGTAC GTGTTCGAGC
22751     CGCCCGCGCA CGTCTCAACC GTGCGGCTGC ATGAAATCCT GGCCGGTTTG
22801     TCTGATGCCA AGCTGGCGGC CTGGCCGGCC AGCTTGGCCG CTGAAGAAAC
22851     CGAGCGCCGC CGTCTAAAAA GGTGATGTGT ATTTGAGTAA AACAGCTTGC
22901     GTCATGCGGT CGCTGCGTAT ATGATGCGAT GAGTAAATAA ACAAATACGC
22951     AAGGGGAACG CATGAAGGTT ATCGCTGTAC TTAACCAGAA AGGCGGGTCA
23001     GGCAAGACGA CCATCGCAAC CCATCTAGCC CGCGCCCTGC AACTCGCCGG
23051     GGCCGATGTT CTGTTAGTCG ATTCCGATCC CCAGGGCAGT GCCCGCGATT
23101     GGGCGGCCGT GCGGGAAGAT CAACCGCTAA CCGTTGTCGG CATCGACCGC
23151     CCGACGATTG ACCGCGACGT GAAGGCCATC GGCCGGCGCG ACTTCGTAGT
23201     GATCGACGGA GCGCCCCAGG CGGCGGACTT GGCTGTGTCC GCGATCAAGG
23251     CAGCCGACTT CGTGCTGATT CCGGTGCAGC CAAGCCCTTA CGACATATGG
23301     GCCACCGCCG ACCTGGTGGA GCTGGTTAAG CAGCGCATTG AGGTCACGGA
23351     TGGAAGGCTA CAAGCGGCCT TTGTCGTGTC GCGGGCGATC AAAGGCACGC
23401     GCATCGGCGG TGAGGTTGCC GAGGCGCTGG CCGGGTACGA GCTGCCCATT
```

FIG. 19I DNA sequence of pMBXS918 (Cont'd)

```
23451     CTTGAGTCCC GTATCACGCA GCGCGTGAGC TACCCAGGCA CTGCCGCCGC
23501     CGGCACAACC GTTCTTGAAT CAGAACCCGA GGGCGACGCT GCCCGCGAGG
23551     TCCAGGCGCT GGCCGCTGAA ATTAAATCAA AACTCATTTG AGTTAATGAG
23601     GTAAAGAGAA AATGAGCAAA AGCACAAACA CGCTAAGTGC CGGCCGTCCG
23651     AGCGCACGCA GCAGCAAGGC TGCAACGTTG GCCAGCCTGG CAGACACGCC
23701     AGCCATGAAG CGGGTCAACT TTCAGTTGCC GGCGGAGGAT CACACCAAGC
23751     TGAAGATGTA CGCGGTACGC CAAGGCAAGA CCATTACCGA GCTGCTATCT
23801     GAATACATCG CGCAGCTACC AGAGTAAATG AGCAAATGAA TAAATGAGTA
23851     GATGAATTTT AGCGGCTAAA GGAGGCGGCA TGGAAAATCA AGAACAACCA
23901     GGCACCGACG CCGTGGAATG CCCCATGTGT GGAGGAACGG GCGGTTGGCC
23951     AGGCGTAAGC GGCTGGGTTG CCTGCCGGCC CTGCAATGGC ACTGGAACCC
24001     CCAAGCCCGA GGAATCGGCG TGAGCGGTCG CAAACCATCC GGCCCGGTAC
24051     AAATCGGCGC GGCGCTGGGT GATGACCTGG TGGAGAAGTT GAAGGCCGCG
24101     CAGGCCGCCC AGCGGCAACG CATCGAGGCA GAAGCACGCC CCGGTGAATC
24151     GTGGCAAGCG GCCGCTGATC GAATCCGCAA AGAATCCCGG CAACCGCCGG
24201     CAGCCGGTGC GCCGTCGATT AGGAAGCCGC CCAAGGGCGA CGAGCAACCA
24251     GATTTTTTCG TTCCGATGCT CTATGACGTG GGCACCCGCG ATAGTCGCAG
24301     CATCATGGAC GTGGCCGTTT TCCGTCTGTC GAAGCGTGAC CGACGAGCTG
24351     GCGAGGTGAT CCGCTACGAG CTTCCAGACG GGCACGTAGA GGTTTCCGCA
24401     GGGCCGGCCG GCATGGCCAG TGTGTGGGAT TACGACCTGG TACTGATGGC
24451     GGTTTCCCAT CTAACCGAAT CCATGAACCG ATACCGGGAA GGGAAGGGAG
24501     ACAAGCCCGG CCGCGTGTTC CGTCCACACG TTGCGGACGT ACTCAAGTTC
24551     TGCCGGCGAG CCGATGGCGG AAAGCAGAAA GACGACCTGG TAGAAACCTG
24601     CATTCGGTTA AACACCACGC ACGTTGCCAT GCAGCGTACG AAGAAGGCCA
24651     AGAACGGCCG CCTGGTGACG GTATCCGAGG GTGAAGCCTT GATTAGCCGC
24701     TACAAGATCG TAAAGAGCGA AACCGGGCGG CCGGAGTACA TCGAGATCGA
24751     GCTAGCTGAT TGGATGTACC GCGAGATCAC AGAAGGCAAG AACCCGGACG
24801     TGCTGACGGT TCACCCCGAT TACTTTTTGA TCGATCCCGG CATCGGCCGT
24851     TTTCTCTACC GCCTGGCACG CCGCGCCGCA GGCAAGGCAG AAGCCAGATG
24901     GTTGTTCAAG ACGATCTACG AACGCAGTGG CAGCGCCGGA GAGTTCAAGA
24951     AGTTCTGTTT CACCGTGCGC AAGCTGATCG GGTCAAATGA CCTGCCGGAG
25001     TACGATTTGA AGGAGGAGGC GGGGCAGGCT GGCCCGATCC TAGTCATGCG
25051     CTACCGCAAC CTGATCGAGG GCGAAGCATC CGCCGGTTCC TAATGTACGG
25101     AGCAGATGCT AGGGCAAATT GCCCTAGCAG GGGAAAAAGG TCGAAAAGGT
25151     CTCTTTCCTG TGGATAGCAC GTACATTGGG AACCCAAAGC CGTACATTGG
25201     GAACCGGAAC CCGTACATTG GGAACCCAAA GCCGTACATT GGGAACCGGT
25251     CACACATGTA AGTGACTGAT ATAAAAGAGA AAAAAGGCGA TTTTTCCGCC
25301     TAAAACTCTT TAAAACTTAT TAAAACTCTT AAAACCCGCC TGGCCTGTGC
25351     ATAACTGTCT GGCCAGCGCA CAGCCGAAGA GCTGCAAAAA GCGCCTACCC
25401     TTCGGTCGCT GCGCTCCCTA CGCCCCGCCG CTTCGCGTCG GCCTATCGCG
25451     GCCGCTGGCC GCTCAAAAAT GGCTGGCCTA CGGCCAGGCA ATCTACCAGG
25501     GCGCGGACAA GCCGCGCCGT CGCCACTCGA CCGCCGGCGC CCACATCAAG
25551     GCACCCTGCC TCGCGCGTTT CGGTGATGAC GGTGAAAACC TCTGACACAT
25601     GCAGCTCCCG GAGACGGTCA CAGCTTGTCT GTAAGCGGAT GCCGGGAGCA
25651     GACAAGCCCG TCAGGGCGCG TCAGCGGGTG TTGGCGGGTG TCGGGGCGCA
25701     GCCATGACCC AGTCACGTAG CGATAGCGGA GTGTATACTG GCTTAACTAT
25751     GCGGCATCAG AGCAGATTGT ACTGAGAGTG CACCATATGC GGTGTGAAAT
25801     ACCGCACAGA TGCGTAAGGA GAAAATACCG CATCAGGCGC TCTTCCGCTT
25851     CCTCGCTCAC TGACTCGCTG CGCTCGGTCG TTCGGCTGCG GCGAGCGGTA
25901     TCAGCTCACT CAAAGGCGGT AATACGGTTA TCCACAGAAT CAGGGGATAA
25951     CGCAGGAAAG AACATGTGAG CAAAAGGCCA GCAAAAGGCC AGGAACCGTA
26001     AAAAGGCCGC GTTGCTGGCG TTTTTCCATA GGCTCCGCCC CCCTGACGAG
26051     CATCACAAAA ATCGACGCTC AAGTCAGAGG TGGCGAAACC CGACAGGACT
26101     ATAAAGATAC CAGGCGTTTC CCCCTGGAAG CTCCCTCGTG CGCTCTCCTG
26151     TTCCGACCCT GCCGCTTACC GGATACCTGT CCGCCTTTCT CCCTTCGGGA
26201     AGCGTGGCGC TTTCTCATAG CTCACGCTGT AGGTATCTCA GTTCGGTGTA
26251     GGTCGTTCGC TCCAAGCTGG GCTGTGTGCA CGAACCCCCC GTTCAGCCCG
26301     ACCGCTGCGC CTTATCCGGT AACTATCGTC TTGAGTCCAA CCCGGTAAGA
26351     CACGACTTAT CGCCACTGGC AGCAGCCACT GGTAACAGGA TTAGCAGAGC
```

FIG. 19J DNA sequence of pMBXS918 (Cont'd)

```
26401GAGGTATGTA GGCGGTGCTA CAGAGTTCTT GAAGTGGTGG CCTAACTACG
26451GCTACACTAG AAGGACAGTA TTTGGTATCT GCGCTCTGCT GAAGCCAGTT
26501ACCTTCGGAA AAAGAGTTGG TAGCTCTTGA TCCGGCAAAC AAACCACCGC
26551TGGTAGCGGT GGTTTTTTTG TTTGCAAGCA GCAGATTACG CGCAGAAAAA
26601AAGGATCTCA AGAAGATCCT TTGATCTTTT CTACGGGGTC TGACGCTCAG
26651TGGAACGAAA ACTCACGTTA AGGGATTTTG GTCATGCATT CTAGGTACTA
26701AAACAATTCA TCCAGTAAAA TATAATATTT TATTTTCTCC CAATCAGGCT
26751TGATCCCCAG TAAGTCAAAA AATAGCTCGA CATACTGTTC TTCCCCGATA
26801TCCTCCCTGA TCGACCGGAC GCAGAAGGCA ATGTCATACC ACTTGTCCGC
26851CCTGCCGCTT CTCCCAAGAT CAATAAAGCC ACTTACTTTG CCATCTTTCA
26901CAAAGATGTT GCTGTCTCCC AGGTCGCCGT GGGAAAAGAC AAGTTCCTCT
26951TCGGGCTTTT CCGTCTTTAA AAAATCATAC AGCTCGCGCG GATCTTTAAA
27001TGGAGTGTCT TCTTCCCAGT TTTCGCAATC CACATCGGCC AGATCGTTAT
27051TCAGTAAGTA ATCCAATTCG GCTAAGCGGC TGTCTAAGCT ATTCGTATAG
27101GGACAATCCG ATATGTCGAT GGAGTGAAAG AGCCTGATGC ACTCCGCATA
27151CAGCTCGATA ATCTTTTCAG GGCTTTGTTC ATCTTCATAC TCTTCCGAGC
27201AAAGGACGCC ATCGGCCTCA CTCATGAGCA GATTGCTCCA GCCATCATGC
27251CGTTCAAAGT GCAGGACCTT TGGAACAGGC AGCTTTCCTT CCAGCCATAG
27301CATCATGTCC TTTTCCCGTT CCACATCATA GGTGGTCCCT TTATACCGGC
27351TGTCCGTCAT TTTTAAATAT AGGTTTTCAT TTTCTCCCAC CAGCTTATAT
27401ACCTTAGCAG GAGACATTCC TTCCGTATCT TTTACGCAGC GGTATTTTTC
27451GATCAGTTTT TTCAATTCCG GTGATATTCT CATTTTAGCC ATTTATTATT
27501TCCTTCCTCT TTTCTACAGT ATTTAAAGAT ACCCCAAGAA GCTAATTATA
27551ACAAGACGAA CTCCAATTCA CTGTTCCTTG CATTCTAAAA CCTTAAATAC
27601CAGAAAACAG CTTTTTCAAA GTTGTTTTCA AAGTTGGCGT ATAACATAGT
27651ATCGACGGAG CCGATTTTGA AACCGCGGTG ATCACAGGCA GCAACGCTCT
27701GTCATCGTTA CAATCAACAT GCTACCCTCC GCGAGATCAT CCGTGTTTCA
27751AACCCGGCAG CTTAGTTGCC GTTCTTCCGA ATAGCATCGG TAACATGAGC
27801AAAGTCTGCC GCCTTACAAC GGCTCTCCCG CTGACGCCGT CCCGGACTGA
27851TGGGCTGCCT GTATCGAGTG GTGATTTTGT GCCGAGCTGC CGGTCGGGGA
27901GCTGTTGGCT GGCTGGTGGC AGGATATATT GTGGTGTAAA CAAATTGACG
27951CTTAGACAAC TTAATAACAC ATTGCGGACG TTTTTAATGT ACTGAATTAA
28001CGCCGAATTA ATTC
```

FIG. 20A DNA sequence of pMBXS919 (SEQ ID NO:2)

```
   1 CTAGGGTACG TAGTGTTTAT CTTTGTTGCT TTTCTGAACA ATTTATTTAC
  51 TATGTAAATA TATTATCAAT GTTTAATCTA TTTTAATTTG CACATGAATT
 101 TTCATTTTAT TTTTACTTTA CAAAACAAAT AAATATATAT GCAAAAAAAT
 151 TTACAAACGA TGCACGGGTT ACAAACTAAT TTCATTAAAT GCTAATGCAG
 201 ATTTTGTGAA GTAAAACTCC AATTATGATG AAAAATACCA CCAACACCAC
 251 CTGCGAAACT GTATCCCAAC TGTCCTTAAT AAAAATGTTA AAAAGTATAT
 301 TATTCTCATT TGTCTGTCAT AATTTATGTA CCCCACTTTA ATTTTTCTGA
 351 TGTACTAAAC CGAGGGCAAA CTGAAACCTG TTCCTCATGC AAAGCCCCTA
 401 CTCACCATGT ATCATGTACG TGTCATCACC CAACAACTCC ACTTTTGCTA
 451 TATAACAACA CCCCCGTCAC ACTCTCCCTC TCTAACACAC ACCCCACTAA
 501 CAATTCCTTC ACTTGCAGCA CTGTTGCATC ATCATCTTCA TTGCAAAACC
 551 CTAAACTTCA CCTTCAACCG GATCCAAAAT GGCTTCTATG ATATCCTCTT
 601 CCGCTGTGAC AACAGTCAGC CGTGCCTCTA GGGGGCAATC CGCCGCAGTG
 651 GCTCCATTCG GCGGCCTCAA ATCCATGACT GGATTCCCAG TGAAGAAGGT
 701 CAACACTGAC ATTACTTCCA TTACAAGCAA TGGTGGAAGA GTAAAGTGCA
 751 TGCAGGTGTG GCCTCCAATT GGAAAGAAGA AGTTTGAGAC TCTTTCCTAT
 801 TTGCCACCAT TGACGAGAGA TTCTAGAGTT TCGAGCACAC TGAGAGAAGC
 851 ATCAAAAGAT ACGTTGCAAG CAAAGGATAA AACATATCAT TACTACTCTT
 901 TACCTCTCGC TGCTAAGTCT CTAGGAGACA TAACTCGTTT GCCGAAGTCC
 951 TTGAAGGTAT TACTCGAAAA CCTATTAAGG TGGCAAGACG GAAATAGCGT
1001 TACAGAAGAA GATATTCACG CTCTTGCGGG ATGGTTGAAG AATGCACACG
1051 CAGATCGAGA GATTGCATAT AGACCTGCTA GAGTGTTGAT GCAAGATTTC
1101 ACCGGTGTTC CGGCTGTCGT TGATTTAGCG GCTATGAGGG AAGCAGTGAA
1151 GAGGTTGGGT GGGGATACTG CCAAAGTGAA CCCTCTTAGT CCCGTTGATC
1201 TTGTTATAGA TCATTCAGTC ACTGTTGACA GGTTTGGAGA TGATGAGGCA
1251 TTTGAAGAGA ACGTGCGTCT GGAAATGGAA CGTAACCATG AGAGATATGT
1301 CTTTCTTAAG TGGGGGAAAC AAGCGTTTTC TCGTTTCTCC GTTGTTCCGC
1351 CTGGTACCGG AATCTGTCAT CAGGTCAATC TTGAGTATCT CGGAAAAGCA
1401 GTCTGGTCCG AGCTTCAGGA TGGTGAGTGG ATTGCCTACC CAGATACACT
1451 TGTTGGCACG GATTCCCATA CTACAATGAT CAATGGACTG GGGGTTTTGG
1501 GCTGGGGAGT AGGTGGGATC GAGGCTGAAG CTGCTATGCT AGGGCAACCG
1551 GTGTCAATGC TCATTCCTGA TGTCGTGGGT TTTAAGCTCA CTGGAAAACT
1601 TCGAGAGGGA ATTACCGCTA CCGATCTGGT ACTCACAGTT ACCCAAATGC
1651 TTAGAAAACA TGGTGTAGTG GGGAAATTTG TTGAATTCTA CGGTGACGGA
1701 CTTGATAGTC TGCCGCTCGC CGACCGTGCT ACTATTGCCA ATATGTCGCC
1751 AGAGTATGGT GCGACATGTG GCTTCTTCCC AATTGATGCG GTTACGCTGG
1801 ATTACATGCG TTTATCTGGT CGATCTGAGG ATCAAGTTGA GTTGGTTGAG
1851 AAGTATGCGA AGGCACAGGG TATGTGGAGA AATCCAGGAG ATGAACCTAT
1901 CTTTACTTCT ACTTTGGAGT TAGACATGAA TGATGTTGAG GCTAGCTTGG
1951 CTGGGCCTAA GCGTCCACAA GATAGGGTTG CTCTTCCAGA TGTGCCGAAA
2001 GCCTTTGCAG CTTCAAACGA ATTAGAAGTC AACGCGACCC ATAAAGACAG
2051 ACAACCAGTT GACTATGTAA TGAACGGTCA TCAATACCAG CTTCCTGATG
2101 GCGCTGTTGT TATCGCGGCA ATAACTTCTT GCACCAATAC GAGTAATCCA
2151 AGTGTACTAA TGGCCGCTGG ACTCCTGGCC AAGAAGGCTG TGACTCTTGG
2201 TCTTAAGCGA CAGCCTTGGG TTAAGGCATC ACTGGCTCCC GGTAGCAAAG
2251 TCGTGAGCGA TTATCTTGCT AAAGCGAAAC TCACGCCATA CTTGGACGAA
2301 CTGGGTTTCA ATCTCGTTGG ATATGGATGC ACAACCTGTA TCGGAAACTC
2351 TGGCCCTTTA CCTGATCCCA TTGAAACAGC TATAAAGAAG AGTGATCTTA
2401 CTGTGGGCGC TGTCCTAAGT GGAAACAGAA ATTTCGAGGG AAGAATACAC
2451 CCTCTCGTTA AAACAAATTG GTTAGCTTCT CCCCCATTAG TTGTGGCCTA
2501 TGCTTTGGCC GGGAATATGA ACATTAACCT TGCTTCAGAG CCGATTGGAC
2551 ACGATCGTAA AGGGGACCCT GTGTATTTGA AAGACATCTG GCCATCCGCA
2601 CAAGAAATAG CTCGTGCGGT TGAACAAGTG TCTACAGAAA TGTTCCGAAA
2651 AGAGTATGCC GAGGTTTTTG AAGGTACTGC TGAGTGGAAG GGTATAAACG
2701 TTACAAGGTC TGACACGTAT GGTTGGCAAG AAGATTCTAC TTACATCAGG
2751 CTTAGTCCAT TCTTTGATGA GATGCAGGCA ACTCCTGCCC CAGTAGAGGA
2801 CATCCACGGA GCTAGAATTC TGGCAATGCT AGGAGATTCT GTTACTACCG
```

FIG. 20B DNA sequence of pMBXS919 (Cont'd)

```
2851   ATCACATTTC CCCAGCTGGC TCGATTAAGC CCGATTCACC AGCTGGAAGG
2901   TACTTGCAAG GTAGGGGCGT TGAGAGAAAG GACTTTAACT CATACGGTTC
2951   GCGTAGAGGC AACCACGAAG TAATGATGAG GGGCACGTTC GCAAATATCC
3001   GAATCAGAAA TGAAATGGTG CCAGGCGTGG AAGGGGGAAT GACAAGACAT
3051   TTGCCTGACT CAGATGTCGT TTCGATTTAC GATGCTGCAA TGAGATACAA
3101   ACAGGAGCAG ACACCTCTAG CAGTCATAGC TGGTAAAGAA TATGGAAGTG
3151   GTAGCTCTAG GGATTGGGCG GCTAAAGGAC CGAGACTTCT CGGTATCAGG
3201   GTGGTGATTG CGGAATCATT CGAGAGAATC CATAGAAGCA ATCTCATAGG
3251   GATGGGAATA TTGCCTTTAG AGTTTCCACA GGGAGTGACG CGAAAGACTT
3301   TGGGACTTAC CGGTGAAGAA AAGATTGACA TTGGTGATCT CCAGAATTTA
3351   CAGCCTGGTG CAACTGTCCC TGTTACCCTC ACAAGAGCCG ACGGGTCCCA
3401   AGAGGTGGTC CCGTGTCGAT GCAGAATCGA CACAGCAACG GAATTGACTT
3451   ACTATCAGAA CGATGGAATA CTGCATTACG TGATCCGTAA CATGCTTAAA
3501   TGAGGCGCGC CTGAGTAATT CTGATATTAG AGGGAGCATT AATGTGTTGT
3551   TGTGATGTGG TTTATATGGG GAAATTAAAT AAATGATGTA TGTACCTCTT
3601   GCCTATGTAG GTTTGTGTGT TTTGTTTTGT TGTCTAGCTT TGGTTATTAA
3651   GTAGTAGGGA CGTTCGTTCG TGTCTCAAAA AAAGGGGTAC TACCACTCTG
3701   TAGTGTATAT GGATGCTGGA AATCAATGTG TTTTGTATTT GTTCACCTCC
3751   ATTGTTGAAT TCAATGTCAA ATGTGTTTTG CGTTGGTTAT GTGTAAAATT
3801   ACTATCTTTC TCGTCCGATG ATCAAAGTTT TAAGCAACAA AACCAAGGGT
3851   GAAATTTAAA CTGTGCTTTG TTGAAGATTC TTTTATCATA TTGAAAATCA
3901   AATTACTAGC AGCAGATTTT ACCTAGCATG AAATTTTATC AACAGTACAG
3951   CACTCACTAA CCAAGTTCCA AACTAAGATG CGCCATTAAC ATCAGCCAAT
4001   AGGCATTTTC AGCAAAAGCT TGTACGTAGT GTTTATCTTT GTTGCTTTTC
4051   TGAACAATTT ATTTACTATG TAAATATATT ATCAATGTTT AATCTATTTT
4101   AATTTGCACA TGAATTTTCA TTTTATTTTT ACTTTACAAA ACAAATAAAT
4151   ATATATGCAA AAAAATTTAC AAACGATGCA CGGGTTACAA ACTAATTTCA
4201   TTAAATGCTA ATGCAGATTT TGTGAAGTAA AACTCCAATT ATGATGAAAA
4251   ATACCACCAA CACCACCTGC GAAACTGTAT CCCAACTGTC CTTAATAAAA
4301   ATGTTAAAAA GTATATTATT CTCATTTGTC TGTCATAATT TATGTACCCC
4351   ACTTTAATTT TTCTGATGTA CTAAACCGAG GGCAAACTGA AACCTGTTCC
4401   TCATGCAAAG CCCCTACTCA CCATGTATCA TGTACGTGTC ATCACCCAAC
4451   AACTCCACTT TTGCTATATA ACAACACCCC CGTCACACTC TCCCTCTCTA
4501   ACACACACCC CACTAACAAT TCCTTCACTT GCAGCACTGT TGCATCATCA
4551   TCTTCATTGC AAAACCCTAA ACTTCACCTT CAACCGCGGC CGCAGATCTA
4601   AAATGGCTTC TATGATATCC TCTTCCGCTG TGACAACAGT CAGCCGTGCC
4651   TCTAGGGGGC AATCCGCCGC AGTGGCTCCA TTCGGCGGCC TCAAATCCAT
4701   GACTGGATTC CCAGTGAAGA AGGTCAACAC TGACATTACT TCCATTACAA
4751   GCAATGGTGG AAGAGTAAAG TGCATGCAGG TGTGGCCTCC AATTGGAAAG
4801   AAGAAGTTTG AGACTCTTTC CTATTTGCCA CCATTGACGA GAGATTCTAG
4851   AGTGGTTGAC GGAAGGTCAT CAGCTTCGAT CGTGGCAGTC GATCCTGAAA
4901   GGGCTGCAAG GGAGAGAGAT GCTGCAGCCA GGGCGCTTCT CCAAGATTCC
4951   CCTTTGCATA CTACGATGCA GTATGCAACT TCTGGACTTG AACTTACCGT
5001   ACCGTATGCT CTTAAGGTTG TGGCATCTGC GGATACGTTT GACCGTGCTA
5051   AAGAAGTCGC AGACGAGGTT CTGAGATGTG CTTGGCAGCT TGCTGATACT
5101   GTTCTAAATT CGTTTAATCC TAACTCAGAA GTCAGTCTTG TTGGGAGACT
5151   TCCAGTGGGG CAGAAACACC AAATGTCTGC GCCTCTCAAA AGAGTGATGG
5201   CTTGTTGTCA GAGGGTATAC AACTCTTCAG CAGGATGCTT CGATCCTTCC
5251   ACTGCTCCAG TTGCAAAGGC CTTAAGAGAG ATTGCCTTGG GTAAAGAGAG
5301   AAATAACGCA TGTTTGGAAG CCCTCACCCA AGCGTGCACT CTTCCAAACT
5351   CATTTGTCAT TGATTTTGAA GCTGGTACCA TTAGTAGAAA GCATGAACAT
5401   GCGAGTTTAG ACCTTGGTGG AGTATCTAAG GGTTACATAG TAGATTACGT
5451   TATAGATAAC ATAAACGCAG CTGGTTTCCA GAACGTTTTC TTCGACTGGG
5501   GCGGTGATTG CAGGGCTTCT GGGATGAACG CAAGAAATAC ACCGTGGGTT
5551   GTTGGGATCA CTAGACCGCC ATCTCTTGAC ATGCTTCCTA ACCCACCCAA
5601   AGAGGCTTCA TATATCTCGG TTATTTCCCT CGACAATGAA GCATTAGCGA
5651   CATCTGGTGA TTACGAGAAT TTGATTTACA CCGCAGACGA TAAGCCGTTG
5701   ACGTGCACAT ATGACTGGAA AGGTAAAGAA CTAATGAAGC CTAGCCAAAG
```

FIG. 20C DNA sequence of pMBXS919 (Cont'd)

```
5751   TAACATAGCC CAAGTGTCTG TAAAATGCTA CTCTGCTATG TATGCTGACG
5801   CCCTCGCAAC CGCTTGTTTT ATCAAGCGAG ATCCAGCTAA GGTAAGACAA
5851   CTTCTAGACG GATGGCGTTA TGTTCGTGAT ACTGTGCGAG ATTATCGAGT
5901   CTATGTAAGA GAGAATGAAA GAGTGGCAAA AATGTTTGAG ATCGCCACGG
5951   AAGATGCTGA GATGAGAAAG AGAAGAATAA GTAATACGCT TCCAGCCCGA
6001   GTGATCGTTG TTGGTGGCGG CTTGGCAGGG CTATCTGCGG CGATCGAGGC
6051   GGCTGGTTGT GGGGCACAGG TTGTTCTAAT GGAGAAAGAA GCCAAGTTAG
6101   GCGGTAACAG TGCTAAGGCA ACCAGCGGGA TAAATGGATG GGGTACTAGA
6151   GCACAGGCAA AAGCCTCAAT CGTTGATGGT GGTAAATACT TTGAACGAGA
6201   TACATATAAG TCAGGAATTG GCGGAAATAC TGATCCAGCA CTTGTTAAGA
6251   CACTCAGCAT GAAGAGTGCG GATGCCATTG GGTGGCTGAC TTCGCTCGGT
6301   GTGCCTCTTA CTGTCTTATC TCAATTAGGT GGACACTCAC GTAAGAGAAC
6351   ACACAGGGCA CCTGATAAGA AGGATGGAAC GCCACTACCT ATTGGATTCA
6401   CTATTATGAA AACTCTCGAA GATCATGTTC GTGGAAACTT ATCTGGACGA
6451   ATTACAATTA TGGAAAATTG TTCGGTTACA TCACTGCTTT CCGAAACTAA
6501   AGAGCGTCCT GATGGGACCA AACAAATTCG TGTCACGGGT GTTGAGTTCA
6551   CCCAGGCTGG TAGCGGGAAA ACTACAATCT TAGCTGATGC CGTTATCTTA
6601   GCTACAGGTG GGTTTTCTAA TGACAAAACC GCGGATTCCC TTTTGAGGGA
6651   ACACGCACCG CATTTGGTCA ACTTCCCCAC CACAAACGGG CCTTGGGCTA
6701   CTGGAGATGG AGTTAAACTT GCACAGAGAC TTGGTGCTCA ACTTGTAGAT
6751   ATGGATAAAG TTCAGTTACA TCCGACAGGA CTCATAAACC CTAAAGATCC
6801   AGCAAACCCG ACAAAGTTCT TAGGACCTGA GGCCTTGCGT GGCAGCGGTG
6851   GTGTGCTGCT GAACAAGCAA GGCAAGAGAT TTGTGAATGA ACTAGACCTA
6901   CGTTCTGTTG TGAGTAAGGC TATTATGGAA CAAGGTGCTG AGTACCCAGG
6951   TTCTGGCGGC TCGATGTTCG CTTACTGCGT TCTTAACGCC GCAGCTCAAA
7001   AGCTATTTGG AGTATCATCC CATGAGTTCT ACTGGAAAAA GATGGGTCTT
7051   TTCGTCAAAG CTGACACTAT GAGGGATCTG GCTGCTCTTA TCGGTTGTCC
7101   TGTCGAGTCT GTGCAACAGA CATTGGAAGA ATATGAGAGA CTGTCTATTT
7151   CCCAGAGATC ATGCCCAATA ACCAGGAAGT CGGTTTACCC TTGTGTCTTA
7201   GGAACTAAGG GTCCGTATTA CGTTGCTTTT GTGACACCTT CAATCCACTA
7251   TACTATGGGT GGTTGCTTGA TTTCCCCTAG TGCAGAAATT CAAATGAAAA
7301   ACACCTCATC GAGAGCACCT TTATCACATT CCAATCCCAT CCTGGGTTTA
7351   TTCGGAGCTG GTGAGGTAAC TGGCGGTGTC CACGGTGGCA ATAGGCTTGG
7401   GGGCAATTCC CTTCTGGAAT GTGTGGTTTT CGGAAGGATT GCAGGTGACC
7451   GAGCTTCCAC TATATTGCAA AGAAAATCCA GTGCGCTGTC TTTCAAGGTG
7501   TGGACTACAG TTGTTCTTAG AGAGGTGCGT GAGGGCGGAG TGTACGGCGC
7551   TGGTTCTAGG GTTCTAAGAT TTAACCTTCC TGGAGCACTT CAACGTTCCG
7601   GGCTATCTTT AGGACAGTTT ATCGCTATAC GAGGGGATTG GGATGGACAG
7651   CAACTTATTG GTTACTATTC TCCAATTACT CTCCCAGATG ACCTCGGAAT
7701   GATAGACATT CTTGCTAGAT CAGACAAAGG CACACTCAGG GAGTGGATTT
7751   CTGCTCTGGA GCCAGGTGAT GCCGTGGAAA TGAAAGCGTG CGGCGGTCTT
7801   GTAATTGAAC GTAGACTTTC AGATAAGCAT TTTGTGTTTA TGGGGCACAT
7851   CATCAATAAG CTATGTTTGA TCGCCGGTGG GACTGGCGTT GCGCCCATGT
7901   TGCAGATTAT CAAGGCGGCA TTTATGAAGC CCTTTATAGA TACGCTGGAG
7951   AGTGTGCATT TGATCTATGC TGCAGAGGAT GTAACGGAGC TTACATATCG
8001   TGAAGTTCTG GAAGAACGAC GAAGGGAATC GAGAGGTAAA TTCAAGAAAA
8051   CTTTCGTTCT TAATAGGCCA CCCCCTTTGT GGACTGACGG CGTCGGGTTC
8101   ATAGATCGAG GGATACTTAC AAATCATGTC CAACCCCCAT CCGATAATCT
8151   TTTGGTGGCC ATTTGTGGAC CGCCCGTTAT GCAGCGTATA GTGAAGGCTA
8201   CACTGAAAAC TTTGGGATAT AACATGAACT TGGTTAGAAC GGTAGACGAG
8251   ACTGAACCTT CAGGTAGCAG TAAGATTTGA GCGATCGCGC GGCCGCTGAG
8301   TAATTCTGAT ATTAGAGGGA GCATTAATGT GTTGTTGTGA TGTGGTTTAT
8351   ATGGGGAAAT TAAATAAATG ATGTATGTAC CTCTTGCCTA TGTAGGTTTG
8401   TGTGTTTTGT TTTGTTGTCT AGCTTTGGTT ATTAAGTAGT AGGGACGTTC
8451   GTTCGTGTCT CAAAAAAAGG GGTACTACCA CTCTGTAGTG TATATGGATG
8501   CTGGAAATCA ATGTGTTTTG TATTTGTTCA CCTCCATTGT TGAATTCAAT
8551   GTCAAATGTG TTTTGCGTTG GTTATGTGTA AAATTACTAT CTTTCTCGTC
8601   CGATGATCAA AGTTTTAAGC AACAAAACCA AGGGTGAAAT TTAAACTGTG
```

FIG. 20D DNA sequence of pMBXS919 (Cont'd)

```
 8651    CTTTGTTGAA GATTCTTTTA TCATATTGAA AATCAAATTA CTAGCAGCAG
 8701    ATTTTACCTA GCATGAAATT TTATCAACAG TACAGCACTC ACTAACCAAG
 8751    TTCCAAACTA AGATGCGCCA TTAACATCAG CCAATAGGCA TTTTCAGCAA
 8801    GTTTAAACTA CGTAGTGTTT ATCTTTGTTG CTTTTCTGAA CAATTTATTT
 8851    ACTATGTAAA TATATTATCA ATGTTTAATC TATTTTAATT TGCACATGAA
 8901    TTTTCATTTT ATTTTTACTT TACAAAACAA ATAAATATAT ATGCAAAAAA
 8951    ATTTACAAAC GATGCACGGG TTACAAACTA ATTTCATTAA ATGCTAATGC
 9001    AGATTTTGTG AAGTAAAACT CCAATTATGA TGAAAAATAC CACCAACACC
 9051    ACCTGCGAAA CTGTATCCCA ACTGTCCTTA ATAAAAATGT TAAAAAGTAT
 9101    ATTATTCTCA TTTGTCTGTC ATAATTTATG TACCCCACTT TAATTTTTCT
 9151    GATGTACTAA ACCGAGGGCA AACTGAAACC TGTTCCTCAT GCAAAGCCCC
 9201    TACTCACCAT GTATCATGTA CGTGTCATCA CCCAACAACT CCACTTTTGC
 9251    TATATAACAA CACCCCCGTC ACACTCTCCC TCTCTAACAC ACACCCCACT
 9301    AACAATTCCT TCACTTGCAG CACTGTTGCA TCATCATCTT CATTGCAAAA
 9351    CCCTAAACTT CACCTTCAAC CGCGGCCGCT CGCGAAAAAT GGCTTCTATG
 9401    ATATCCTCTT CCGCTGTGAC AACAGTCAGC CGTGCCTCTA GGGGGCAATC
 9451    CGCCGCAGTG GCTCCATTCG GCGGCCTCAA ATCCATGACT GGATTCCCAG
 9501    TGAAGAAGGT CAACACTGAC ATTACTTCCA TTACAAGCAA TGGTGGAAGA
 9551    GTAAAGTGCA TGCAGGTGTG GCCTCCAATT GGAAAGAAGA AGTTTGAGAC
 9601    TCTTTCCTAT TTGCCACCAT TGACGAGAGA TTCTAGAGTG GCTAGGAAGA
 9651    AGATCCGTGA ATATGACTCT AAAAGGCTTG TCAAAGAACA TTTCAAGAGG
 9701    CTTAGTGGAA AAGAACTCCC TATTAGGTCT GTGCAGATTA ACGAAACAAC
 9751    TGATCTTAAC GAATTGGTTG AGAAAGAGCC TTGGTTGAGC AGTGAAAAGT
 9801    TAGTCGTGAA GCCAGACATG TTGTTTGGAA AACGTGGAAA ATCAGGACTT
 9851    GTCGCTCTCA AACTGGACTT TGCTGATGTC GCAACGTTTG TTAAAGAGAG
 9901    ACTAGGTAAA GAGGTTGAGA TGTCAGGATG TAAAGGACCC ATAACGACCT
 9951    TTATTGTTGA ACCATTCGTT CCACATAACG AAGAATACTA CCTTAATGTA
10001    GTGTCGGATA GATTAGGATG CTCCATATCA TTCTCCGAGT GTGGCGGGAT
10051    CGAGATTGAA GAGAACTGGG ATAAGGTCAA AACAATCTTT TTGCCAACCG
10101    GTGCTTCGCT GACACCTGAG ATTTGTGCTC CCCTTGTTGC TACACTTCCA
10151    CTTGAGATTA AGGCAGAAAT AGAAGAGTTC ATCAAGGTTA TCTTTACTCT
10201    GTTCCAAGAT TTAGATTTCA CTTTTCTCGA AATGAATCCG TTTACTTTAG
10251    TCGATGGTTC TCCGTATCCT TTGGATATGC GAGGTGAGCT GGATGACACA
10301    GCGGCTTTTA AGAACTTCAA GAAGTGGGGA GATATTGAGT TCCCATTGCC
10351    GTTTGGCCGT GTTATGTCTC CAACTGAATC CTTCATACAC GGACTCGATG
10401    AAAAGACCAG TGCATCTCTC AAGTTTACCG TTCTAAATCC TAAGGGTAGA
10451    ATCTGGACTA TGGTAGCTGG GGGTGGAGCC TCTGTAATCT ACGCTGATAC
10501    TGTTGGTGAT CTTGGCTATG CTAGCGAATT AGGGAACTAT GCGGAGTACA
10551    GCGGTGCACC TAAAGAGGAC GAGGTACTCC AATATGCCCG AGTGGTGATT
10601    GATTGTGCTA CGGCAAATCC TGACGGAAAG TCAAGAGCCC TTGTGATTGG
10651    GGGTGGTATA GCAAATTTCA CAGACGTTGC AGCGACTTTC AATGGTATCA
10701    TTAGAGCCTT GAAAGAGAAA GAGGCCAAAC TAAAGGCTGC GAGAATGCAC
10751    ATTTTTGTTC GTAGAGGTGG CCCTAATTAC CAGAAGGGTT TGGCTAAAAT
10801    GCGAGCTTTG GGAGATGATA TAGGCGTGCC TATCGAAGTT TATGGACCTG
10851    AAGCAACGAT GACCGGGATC TGCAAAGAAG CAATACAATA CATTACAGCT
10901    GCAGCGTGAA CGCGTTGAGT AATTCTGATA TTAGAGGGAG CATTAATGTG
10951    TTGTTGTGAT GTGGTTTATA TGGGGAAATT AAATAAATGA TGTATGTACC
11001    TCTTGCCTAT GTAGGTTTGT GTGTTTTGTT TTGTTGTCTA GCTTTGGTTA
11051    TTAAGTAGTA GGGACGTTCG TTCGTGTCTC AAAAAAAGGG GTACTACCAC
11101    TCTGTAGTGT ATATGGATGC TGGAAATCAA TGTGTTTTGT ATTTGTTCAC
11151    CTCCATTGTT GAATTCAATG TCAAATGTGT TTTGCGTTGG TTATGTGTAA
11201    AATTACTATC TTTCTCGTCC GATGATCAAA GTTTTAAGCA ACAAAACCAA
11251    GGGTGAAATT TAAACTGTGC TTTGTTGAAG ATTCTTTTAT CATATTGAAA
11301    ATCAAATTAC TAGCAGCAGA TTTTACCTAG CATGAAATTT TATCAACAGT
11351    ACAGCACTCA CTAACCAAGT TCCAAACTAA GATGCGCCAT TAACATCAGC
11401    CAATAGGCAT TTTCAGCAAT GTACATACGT AGTGTTTATC TTTGTTGCTT
11451    TTCTGAACAA TTTATTTACT ATGTAAATAT ATTATCAATG TTTAATCTAT
11501    TTTAATTTGC ACATGAATTT TCATTTTATT TTTACTTTAC AAAACAAATA
```

FIG. 20E DNA sequence of pMBXS919 (Cont'd)

```
11551     AATATATATG CAAAAAAATT TACAAACGAT GCACGGGTTA CAAACTAATT
11601     TCATTAAATG CTAATGCAGA TTTTGTGAAG TAAAACTCCA ATTATGATGA
11651     AAAATACCAC CAACACCACC TGCGAAACTG TATCCCAACT GTCCTTAATA
11701     AAAATGTTAA AAAGTATATT ATTCTCATTT GTCTGTCATA ATTTATGTAC
11751     CCCACTTTAA TTTTTCTGAT GTACTAAACC GAGGGCAAAC TGAAACCTGT
11801     TCCTCATGCA AAGCCCCTAC TCACCATGTA TCATGTACGT GTCATCACCC
11851     AACAACTCCA CTTTTGCTAT ATAACAACAC CCCCGTCACA CTCTCCCTCT
11901     CTAACACACA CCCCACTAAC AATTCCTTCA CTTGCAGCAC TGTTGCATCA
11951     TCATCTTCAT TGCAAAACCC TAAACTTCAC CTTCAACCGC GGCCGCGACG
12001     TCAAAATGGC TTCTATGATA TCCTCTTCCG CTGTGACAAC AGTCAGCCGT
12051     GCCTCTAGGG GGCAATCCGC CGCAGTGGCT CCATTCGGCG GCCTCAAATC
12101     CATGACTGGA TTCCCAGTGA AGAAGGTCAA CACTGACATT ACTTCCATTA
12151     CAAGCAATGG TGGAAGAGTA AAGTGCATGC AGGTGTGGCC TCCAATTGGA
12201     AAGAAGAAGT TTGAGACTCT TTCCTATTTG CCACCATTGA CGAGAGATTC
12251     TAGAGTTGCT ACCGGCCAAC TCTTTTCCCG AACAACGCAA GCTCTATTCT
12301     ACAACTATAA ACAACTTCCA GTTCAAAGAA TGTTAGATTT CGATTTCTTA
12351     TGCGGAAGAG AAACACCATC AGTGGCTGGA ATTATCAATC CAGGGTCCGA
12401     GGGATTTCAG AAATTGTTTT TCGGTCAAGA AGAGATAGCT ATTCCAGTCC
12451     ATGCGGCCAT AGAAGCAGCT TGTGCCGCCC ACCCCACTGC TGATGTTTTC
12501     ATCAACTTTG CTTCGTTCAG GAGTGCGGCT GCAAGTTCGA TGGCAGCTCT
12551     CAAGCAACCT ACAATCAAGG TCGTAGCAAT AATCGCAGAG GGAGTCCCAG
12601     AATCTGACAC CAAGCAACTC ATCGCTTATG CCCGAGCGAA CAATAAAGTG
12651     GTTATAGGTC CTGCTACTGT GGGCGGAATT CAGGCTGGAG CTTTTAAGAT
12701     TGGTGACACT GCGGGGACCA TTGATAACAT TATCCAATGC AAGCTGTATC
12751     GTCCGGGTAG TGTCGGATTT GTTTCCAAGT CTGGTGGGAT GTCTAATGAG
12801     ATGTATAACA CTGTAGCAAG AGTAACTGAT GGCATTTATG AGGGGATAGC
12851     AATTGGGGGT GACGTTTTCC CCGGTTCAAC TTTATCCGAT CATATCCTGA
12901     GATTTAACAA TATCCCGCAA ATCAAGATGA TGGTTGTACT AGGAGAGCTT
12951     GGGGGACGTG ACGAGTATTC ACTTGTTGAA GCTCTGAAAG AGGGTAAAGT
13001     CAATAAACCT GTTGTCGCTT GGGTGTCAGG CACCTGTGCA AGACTCTTCA
13051     AAAGCGAGGT CCAGTTTGGT CACGCAGGAG CGAAGAGCGG TGGAGAGATG
13101     GAGTCTGCAC AAGCTAAAAA CCAGGCGTTG ATAGATGCAG GCGCAATTGT
13151     TCCAACATCT TTTGAAGCCT TGGAGAGCGC GATCAAAGAA ACTTTTGAGA
13201     AACTTGTCGA AGAAGGTAAG GTTTCGCCGA TTAAAGAAGT AATCCCACCT
13251     CAGATCCCTG AGGATCTAAA TTCCGCAATT AAGTCTGGAA AGGTGAGGGC
13301     TCCAACGCAT ATCATATCGA CGATTTCTGA TGATAGAGGG GAAGAGCCGT
13351     GCTACGCAGG TGTTCCTATG TCTAGCATAA TTGAGCAAGG TTACGGAGTG
13401     GGAGATGTCA TTTCATTGTT ATGGTTCAAA CGTAGTCTCC CGAGGTATTG
13451     TACCAAATTC ATTGAGATTT GCATAATGCT TTGTGCGGAT CATGGACCCT
13501     GTGTATCTGG TGCTCATAAT ACTATCGTTA CTGCCAGAGC TGGAAAAGAT
13551     TTGGTGTCTA GTCTCGTTTC AGGCTTATTG ACAATAGGTC CTCGATTCGG
13601     TGGGGCCATC GACGACGCTG CCAGGTACTT TAAGGATGCA TGTGACAGAA
13651     ACCTCACACC ATATGAATTT GTGGAAGGCA TGAAAAAGAA GGGCATTAGA
13701     GTGCCTGGAA TTGGTCATCG TATTAAGTCA AGGGATAATA GAGACAAGAG
13751     AGTTGAACTT TTACAGAAGT TTGCTCGAAG TAATTTCCCT AGCGTTAAGT
13801     ACATGGAATA CGCGGTTACT GTTGAAACGT ACACATTGTC TAAGGCTAAT
13851     AACTTGGTGC TTAATGTTGA TGGTGCTATA GGTTCATTAT TCTTGGATCT
13901     ACTTGCAGGT TCTGGAATGT TCACAAAGCA GGAAATCGAC GAGATAGTGC
13951     AAATTGGATA CCTGAACGGA CTATTTGTGT TGGCTAGGTC AATAGGGCTT
14001     ATCGGACACA CGTTTGATCA GAAACGTCTT AAACAGCCTC TCTACCGACA
14051     CCCTTGGGAA GATGTTCTGT ATACCAAATG AGTTAACTGA GTAATTCTGA
14101     TATTAGAGGG AGCATTAATG TGTTGTTGTG ATGTGGTTTA TATGGGGAAA
14151     TTAAATAAAT GATGTATGTA CCTCTTGCCT ATGTAGGTTT GTGTGTTTTG
14201     TTTTGTTGTC TAGCTTTGGT TATTAAGTAG TAGGGACGTT CGTTCGTGTC
14251     TCAAAAAAAG GGGTACTACC ACTCTGTAGT GTATATGGAT GCTGGAAATC
14301     AATGTGTTTT GTATTTGTTC ACCTCCATTG TTGAATTCAA TGTCAAATGT
14351     GTTTTGCGTT GGTTATGTGT AAAATTACTA TCTTTCTCGT CCGATGATCA
14401     AAGTTTTAAG CAACAAAACC AAGGGTGAAA TTTAAACTGT GCTTTGTTGA
```

FIG. 20F DNA sequence of pMBXS919 (Cont'd)

```
14451    AGATTCTTTT ATCATATTGA AAATCAAATT ACTAGCAGCA GATTTTACCT
14501    AGCATGAAAT TTTATCAACA GTACAGCACT CACTAACCAA GTTCCAAACT
14551    AAGATGCGCC ATTAACATCA GCCAATAGGC ATTTTCAGCA AGTTTAAACC
14601    GGACCGTACG TAGTGTTTAT CTTTGTTGCT TTTCTGAACA ATTTATTTAC
14651    TATGTAAATA TATTATCAAT GTTTAATCTA TTTTAATTTG CACATGAATT
14701    TTCATTTTAT TTTTACTTTA CAAAACAAAT AAATATATAT GCAAAAAAAT
14751    TTACAAACGA TGCACGGGTT ACAAACTAAT TTCATTAAAT GCTAATGCAG
14801    ATTTTGTGAA GTAAAACTCC AATTATGATG AAAAATACCA CCAACACCAC
14851    CTGCGAAACT GTATCCCAAC TGTCCTTAAT AAAAATGTTA AAAAGTATAT
14901    TATTCTCATT TGTCTGTCAT AATTTATGTA CCCCACTTTA ATTTTTCTGA
14951    TGTACTAAAC CGAGGGCAAA CTGAAACCTG TTCCTCATGC AAAGCCCCTA
15001    CTCACCATGT ATCATGTACG TGTCATCACC CAACAACTCC ACTTTTGCTA
15051    TATAACAACA CCCCCGTCAC ACTCTCCCTC TCTAACACAC ACCCCACTAA
15101    CAATTCCTTC ACTTGCAGCA CTGTTGCATC ATCATCTTCA TTGCAAAACC
15151    CTAAACTTCA CCTTCAACCG CGGCCGCCAC GTGAAAATGG CTTCTATGAT
15201    ATCCTCTTCC GCTGTGACAA CAGTCAGCCG TGCCTCTAGG GGGCAATCCG
15251    CCGCAGTGGC TCCATTCGGC GGCCTCAAAT CCATGACTGG ATTCCCAGTG
15301    AAGAAGGTCA ACACTGACAT TACTTCCATT ACAAGCAATG GTGGAAGAGT
15351    AAAGTGCATG CAGGTGTGGC CTCCAATTGG AAAGAAGAAG TTTGAGACTC
15401    TTTCCTATTT GCCACCATTG ACGAGAGATT CTAGAGTGAA TACTGTTCGT
15451    TCAGAGAAAG ACTCTATGGG GGCTATAGAC GTGCCTGCTG ATAAGTTATG
15501    GGGAGCCCAG ACTCAACGTA GCCTGGAGCA CTTTAGGATA TCGACTGAGA
15551    AGATGCCTAC GTCCTTGATT CATGCCCTTG CTCTCACTAA GAGAGCAGCA
15601    GCAAAAGTTA ATGAGGATCT CGGCCTTTTA TCCGAAGAGA AAGCATCTGC
15651    CATACGACAG GCCGCTGATG AAGTGTTGGC GGGTCAGCAT GATGATGAGT
15701    TCCCATTAGC TATCTGGCAG ACAGGCTCTG GTACTCAATC CAACATGAAC
15751    ATGAATGAGG TGCTAGCAAA CAGGGCCTCA GAGCTTTTAG GTGGGGTCAG
15801    GGGAATGGAA CGAAAGGTTC ATCCCAACGA TGACGTAAAC AAGTCACAAT
15851    CGAGTAATGA TGTGTTCCCA ACTGCTATGC ACGTTGCAGC TCTGCTTGCG
15901    TTGAGAAAGC AACTTATTCC ACAACTCAAA ACTCTCACCC AAACATTGAA
15951    TGAAAAGTCA AGGGCCTTTG CAGATATCGT GAAGATCGGA CGAACACATC
16001    TTCAGGACGC TACACCACTG ACGTTGGGAC AAGAGATTTC TGGATGGGTT
16051    GCTATGTTGG AACATAACTT GAAACATATC GAGTATAGTT TACCTCATGT
16101    TGCAGAACTA GCATTGGGTG GTACAGCAGT CGGTACCGGC CTCAACACAC
16151    ATCCTGAATA CGCTAGACGT GTAGCTGATG AACTTGCCGT TATTACCTGC
16201    GCTCCGTTCG TTACGGCTCC TAATAAGTTT GAAGCTCTTG CTACTTGTGA
16251    TGCTCTAGTC CAAGCTCATG GTGCACTAAA GGGACTTGCG GCATCTTTAA
16301    TGAAGATTGC AAATGATGTC CGTTGGCTAG CAAGCGGACC AAGATGTGGA
16351    ATAGGCGAAA TTTCCATCCC TGAGAACGAG CCCGGATCAT CTATTATGCC
16401    GGGTAAAGTT AATCCAACGC AGTGTGAAGC CTTGACCATG CTTTGCTGCC
16451    AGGTAATGGG AAACGATGTG GCCATCAATA TGGGTGGTGC GAGTGGAAAC
16501    TTTGAGCTGA ATGTCTTTAG ACCGATGGTT ATCCACAACT TTCTTCAGAG
16551    TGTAAGGCTT CTCGCCGACG GGATGGAGTC ATTCAATAAA CACTGTGCGG
16601    TTGGCATAGA GCCAAACAGA GAACGTATCA ATCAACTTCT CAATGAATCT
16651    CTAATGTTGG TTACTGCTCT CAACACCCAC ATTGGGTACG ACAAAGCTGC
16701    TGAAATTGCT AAAAAGGCGC ACAAAGAAGG TTTAACACTG AAAGCGGCAG
16751    CTCTCGCTCT CGGTTATCTG TCTGAAGCTG AGTTCGATTC GTGGGTCAGA
16801    CCTGAACAAA TGGTGGGAAG CATGAAGGCT GGGAGATGAA CTAGTTGAGT
16851    AATTCTGATA TTAGAGGGAG CATTAATGTG TTGTTGTGAT GTGGTTTATA
16901    TGGGGAAATT AAATAAATGA TGTATGTACC TCTTGCCTAT GTAGGTTTGT
16951    GTGTTTTGTT TTGTTGTCTA GCTTTGGTTA TTAAGTAGTA GGGACGTTCG
17001    TTCGTGTCTC AAAAAAAGGG GTACTACCAC TCTGTAGTGT ATATGGATGC
17051    TGGAAATCAA TGTGTTTTGT ATTTGTTCAC CTCCATTGTT GAATTCAATG
17101    TCAAATGTGT TTTGCGTTGG TTATGTGTAA AATTACTATC TTTCTCGTCC
17151    GATGATCAAA GTTTTAAGCA ACAAAACCAA GGGTGAAATT TAAACTGTGC
17201    TTTGTTGAAG ATTCTTTTAT CATATTGAAA ATCAAATTAC TAGCAGCAGA
17251    TTTTACCTAG CATGAAATTT TATCAACAGT ACAGCACTCA CTAACCAAGT
17301    TCCAAACTAA GATGCGCCAT TAACATCAGC CAATAGGCAT TTTCAGCAAG
```

FIG. 20G DNA sequence of pMBXS919 (Cont'd)

```
17351    TTTAAACTCC GGATTAATTA AGTCGACGGG CCCGTTTAAA CCACGTAGTG
17401    CCTCAGCGTT TAAACGTACG TAGTGTTTAT CTTTGTTGCT TTTCTGAACA
17451    ATTTATTTAC TATGTAAATA TATTATCAAT GTTTAATCTA TTTTAATTTG
17501    CACATGAATT TTCATTTTAT TTTTACTTTA CAAAACAAAT AAATATATAT
17551    GCAAAAAAAT TTACAAACGA TGCACGGGTT ACAAACTAAT TTCATTAAAT
17601    GCTAATGCAG ATTTTGTGAA GTAAAACTCC AATTATGATG AAAAATACCA
17651    CCAACACCAC CTGCGAAACT GTATCCCAAC TGTCCTTAAT AAAAATGTTA
17701    AAAAGTATAT TATTCTCATT TGTCTGTCAT AATTTATGTA CCCCACTTTA
17751    ATTTTTCTGA TGTACTAAAC CGAGGGCAAA CTGAAACCTG TTCCTCATGC
17801    AAAGCCCCTA CTCACCATGT ATCATGTACG TGTCATCACC CAACAACTCC
17851    ACTTTTGCTA TATAACAACA CCCCCGTCAC ACTCTCCCTC TCTAACACAC
17901    ACCCCACTAA CAATTCCTTC ACTTGCAGCA CTGTTGCATC ATCATCTTCA
17951    TTGCAAAACC CTAAACTTCA CCTTCAACCG CGGCCGCTTC GAAAAAATGG
18001    CTTCTATGAT ATCCTCTTCC GCTGTGACAA CAGTCAGCCG TGCCTCTAGG
18051    GGGCAATCCG CCGCAGTGGC TCCATTCGGC GGCCTCAAAT CCATGACTGG
18101    ATTCCCAGTG AAGAAGGTCA ACACTGACAT TACTTCCATT ACAAGCAATG
18151    GTGGAAGAGT AAAGTGCATG CAGGTGTGGC CTCCAATTGG AAAGAAGAAG
18201    TTTGAGACTC TTTCCTATTT GCCACCATTG ACGAGAGATT CTAGAGTTGC
18251    ATTGAACATG AAACAGCAAC AAGCAGGTCT TTCCCGTAAA GCCGCTAGGT
18301    CTGTATCTTC TAGAGCACCT GTAGTTGTGC GTGCTGTTGC TGCTCCCGTC
18351    GCACCTGCGG CAGAGGCTGA AGCCAAAAAG GCTTATGGAG TTTTCAGACT
18401    CTCATATGAC ACGCAAAATG AAGATGCATC ACTTACAAGG TCATGGAAAA
18451    AGACTGTTAA GGTTGCTGTC ACTGGCGCAT CAGGTAATAT CGCCAACCAT
18501    CTCTTATTCA TGTTGGCATC CGGTGAAGTG TATGGAAAGG ATCAACCTAT
18551    CGCATTGCAA CTGCTCGGAT CGGAGAGGTC GAAAGAAGCT CTAGAGGGCG
18601    TAGCTATGGA GCTGGAAGAT AGCTTGTACC CACTTTTGCG TGAGGTCAGC
18651    ATTGGTACAG ACCCATACGA GGTTTTTGGC GATGCCGATT GGGCGCTAAT
18701    GATAGGAGCC AAGCCAAGAG GTCCAGGAAT GGAACGAGCT GACTTACTTC
18751    AGCAGAATGG TGAGATTTTT CAGGTGCAAG GGAGAGCACT AAATGAGTCA
18801    GCATCGAGAA ACTGCAAGGT GCTCGTAGTG GGAAATCCTT GTAATACGAA
18851    CGCTCTCATT GCTATGGAAA ATGCTCCAAA CATCCCACGA AAGAACTTTC
18901    ACGCCCTTAC TCGTTTAGAT GAAAACCGTG CTAAATGTCA ATTGGCTCTA
18951    AAATCTGGAA AGTTCTACAC CAGTGTCTCT CGAATGGCGA TATGGGGTAA
19001    CCATAGCACT ACACAGGTTC CTGACTTTGT GAATGCAAGG ATAGGTGGAC
19051    TTCCTGCGCC GGATGTTATT AGGGACATGA AATGGTTTAG GGAAGAGTTC
19101    ACACCTAAGG TCGCGCTGAG AGGTGGTGCC CTTATCAAAA AGTGGGGCAG
19151    ATCCAGTGCG GCATCCACAG CGGTTTCTGT GGCAGATGCT ATCAGAGCTT
19201    TAGTAGTGCC CACTGCGCCA GGGGATTGTT TTAGTACCGG AGTTATTAGC
19251    GATGGCAATC CTTACGGAGT TCGTGAAGGA TTGATTTTCA GTTTTCCGTG
19301    CAGAAGTAAG GGGGACGGAG ATTATGAGAT TTGTGATAAC TTCATTGTTG
19351    ACGAATGGCT TCGAGCTAAG ATCAGGGCCT CTGAAGATGA GTTACAGAAA
19401    GAAAAAGAGT GCGTGTCTCA CCTTATAGGG ATGATGGGTG GAAGTTGTGC
19451    TCTCAGAGGG GCAGAGGATA CCACGGTCCC TGGTGAAAAT TGAATTTAAA
19501    TGCGGCCGCT GAGTAATTCT GATATTAGAG GGAGCATTAA TGTGTTGTTG
19551    TGATGTGGTT TATATGGGGA AATTAAATAA ATGATGTATG TACCTCTTGC
19601    CTATGTAGGT TTGTGTGTTT TGTTTTGTTG TCTAGCTTTG GTTATTAAGT
19651    AGTAGGGACG TTCGTTCGTG TCTCAAAAAA AGGGGTACTA CCACTCTGTA
19701    GTGTATATGG ATGCTGGAAA TCAATGTGTT TTGTATTTGT TCACCTCCAT
19751    TGTTGAATTC AATGTCAAAT GTGTTTTGCG TTGGTTATGT GTAAAATTAC
19801    TATCTTTCTC GTCCGATGAT CAAAGTTTTA AGCAACAAAA CCAAGGGTGA
19851    AATTTAAACT GTGCTTTGTT GAAGATTCTT TTATCATATT GAAAATCAAA
19901    TTACTAGCAG CAGATTTTAC CTAGCATGAA ATTTTATCAA CAGTACAGCA
19951    CTCACTAACC AAGTTCCAAA CTAAGATGCG CCATTAACAT CAGCCAATAG
20001    GCATTTTCAG CAAAGCAAAT GAATTCGTAA TCATGTCATA GCTGTTTCCT
20051    GTGTGAAATT GTTATCCGCT CACAATTCCA CACAACATAC GAGCCGGAAG
20101    CATAAAGTGT AAAGCCTGGG GTGCCTAATG AGTGAGCTAA CTCACATTAA
20151    TTGCGTTGCG CTCACTGCCC GCTTTCCAGT CGGGAAACCT GTCGTGCCAG
20201    CTGCATTAAT GAATCGGCCA ACGCGCGGGG AGAGGCGGTT TGCGTATTGG
```

FIG. 20H DNA sequence of pMBXS919 (Cont'd)

```
20251     CTAGAGCAGC TTGCCAACAT GGTGGAGCAC GACACTCTCG TCTACTCCAA
20301     GAATATCAAA GATACAGTCT CAGAAGACCA AAGGGCTATT GAGACTTTTC
20351     AACAAAGGGT AATATCGGGA AACCTCCTCG GATTCCATTG CCCAGCTATC
20401     TGTCACTTCA TCAAAAGGAC AGTAGAAAAG GAAGGTGGCA CCTACAAATG
20451     CCATCATTGC GATAAAGGAA AGGCTATCGT TCAAGATGCC TCTGCCGACA
20501     GTGGTCCCAA AGATGGACCC CCACCCACGA GGAGCATCGT GGAAAAAGAA
20551     GACGTTCCAA CCACGTCTTC AAAGCAAGTG GATTGATGTG AACATGGTGG
20601     AGCACGACAC TCTCGTCTAC TCCAAGAATA TCAAAGATAC AGTCTCAGAA
20651     GACCAAAGGG CTATTGAGAC TTTTCAACAA AGGGTAATAT CGGGAAACCT
20701     CCTCGGATTC CATTGCCCAG CTATCTGTCA CTTCATCAAA AGGACAGTAG
20751     AAAAGGAAGG TGGCACCTAC AAATGCCATC ATTGCGATAA AGGAAAGGCT
20801     ATCGTTCAAG ATGCCTCTGC CGACAGTGGT CCCAAAGATG GACCCCCACC
20851     CACGAGGAGC ATCGTGGAAA AAGAAGACGT TCCAACCACG TCTTCAAAGC
20901     AAGTGGATTG ATGTGATATC TCCACTGACG TAAGGGATGA CGCACAATCC
20951     CACTATCCTT CGCAAGACCC TTCCTCTATA TAAGGAAGTT CATTTCATTT
21001     GGAGAGGACA CGCTGAAATC ACCAGTCTCT CTCTACAAAT CTATCTCTCT
21051     CGAGATGAGC CCAGAACGAC GCCCGGCCGA CATCCGCCGT GCCACCGAGG
21101     CGGACATGCC GGCGGTCTGC ACCATCGTCA ACCACTACAT CGAGACAAGC
21151     ACGGTCAACT TCCGTACCGA GCCGCAGGAA CCGCAGGAGT GGACGGACGA
21201     CCTCGTCCGT CTGCGGGAGC GCTATCCCTG GCTCGTCGCC GAGGTGGACG
21251     GCGAGGTCGC CGGCATCGCC TACGCGGGCC CCTGGAAGGC ACGCAACGCC
21301     TACGACTGGA CGGCCGAGTC GACCGTGTAC GTCTCCCCCC GCCACCAGCG
21351     GACGGGACTG GGCTCCACGC TCTACACCCA CCTGCTGAAG TCCCTGGAGG
21401     CACAGGGCTT CAAGAGCGTG GTCGCTGTCA TCGGGCTGCC CAACGACCCG
21451     AGCGTGCGCA TGCACGAGGC GCTCGGATAT GCCCCCCGCG GCATGCTGCG
21501     GGCGGCCGGC TTCAAGCACG GGAACTGGCA TGACGTGGGT TTCTGGCAGC
21551     TGGACTTCAG CCTGCCGGTA CCGCCCCGTC CGGTCCTGCC CGTCACCGAG
21601     ATTTGAGAGC TCGGTCACCT GTCCAACAGT CTCAGGGTTA ATGTCTATGT
21651     ATCTTAAATA ATGTTGTCGG CGATCGTTCA AACATTTGGC AATAAAGTTT
21701     CTTAAGATTG AATCCTGTTG CCGGTCTTGC GATGATTATC ATATAATTTC
21751     TGTTGAATTA CGTTAAGCAT GTAATAATTA ACATGTAATG CATGACGTTA
21801     TTTATGAGAT GGGTTTTTAT GATTAGAGTC CCGCAATTAT ACATTTAATA
21851     CGCGATAGAA AACAAAATAT AGCGCGCAAA CTAGGATAAA TTATCGCGCG
21901     CGGTGTCATC TATGTTACTA GATCGGGAAT TAAACTATCA GTGTTTGACA
21951     GGATATATTG GCGGGTAAAC CTAAGAGAAA AGAGCGTTTA TTAGAATAAT
22001     CGGATATTTA AAAGGGCGTG AAAAGGTTTA TCCGTTCGTC CATTTGTATG
22051     TGCATGCCAA CCACAGGGTT CCCCTCGGGA TCAAAGTACT TTGATCCAAC
22101     CCCTCCGCTG CTATAGTGCA GTCGGCTTCT GACGTTCAGT GCAGCCGTCT
22151     TCTGAAAACG ACATGTCGCA CAAGTCCTAA GTTACGCGAC AGGCTGCCGC
22201     CCTGCCCTTT TCCTGGCGTT TTCTTGTCGC GTGTTTTAGT CGCATAAAGT
22251     AGAATACTTG CGACTAGAAC CGGAGACATT ACGCCATGAA CAAGAGCGCC
22301     GCCGCTGGCC TGCTGGGCTA TGCCCGCGTC AGCACCGACG ACCAGGACTT
22351     GACCAACCAA CGGGCCGAAC TGCACGCGGC CGGCTGCACC AAGCTGTTTT
22401     CCGAGAAGAT CACCGGCACC AGGCGCGACC GCCCGGAGCT GGCCAGGATG
22451     CTTGACCACC TACGCCCTGG CGACGTTGTG ACAGTGACCA GGCTAGACCG
22501     CCTGGCCCGC AGCACCCGCG ACCTACTGGA CATTGCCGAG CGCATCCAGG
22551     AGGCCGGCGC GGGCCTGCGT AGCCTGGCAG AGCCGTGGGC CGACACCACC
22601     ACGCCGGCCG GCCGCATGGT GTTGACCGTG TTCGCCGGCA TTGCCGAGTT
22651     CGAGCGTTCC CTAATCATCG ACCGCACCCG GAGCGGGCGC GAGGCCGCCA
22701     AGGCCCGAGG CGTGAAGTTT GGCCCCCGCC CTACCCTCAC CCCGGCACAG
22751     ATCGCGCACG CCCGCGAGCT GATCGACCAG GAAGGCCGCA CCGTGAAAGA
22801     GGCGGCTGCA CTGCTTGGCG TGCATCGCTC GACCCTGTAC CGCGCACTTG
22851     AGCGCAGCGA GGAAGTGACG CCCACCGAGG CCAGGCGGCG CGGTGCCTTC
22901     CGTGAGGACG CATTGACCGA GGCCGACGCC CTGGCGGCCG CCGAGAATGA
22951     ACGCCAAGAG GAACAAGCAT GAAACCGCAC CAGGACGGCC AGGACGAACC
23001     GTTTTTCATT ACCGAAGAGA TCGAGGCGGA GATGATCGCG GCCGGGTACG
23051     TGTTCGAGCC GCCCGCGCAC GTCTCAACCG TGCGGCTGCA TGAAATCCTG
23101     GCCGGTTTGT CTGATGCCAA GCTGGCGGCC TGGCCGGCCA GCTTGGCCGC
```

FIG. 20I DNA sequence of pMBXS919 (Cont'd)

```
23151  TGAAGAAACC GAGCGCCGCC GTCTAAAAAG GTGATGTGTA TTTGAGTAAA
23201  ACAGCTTGCG TCATGCGGTC GCTGCGTATA TGATGCGATG AGTAAATAAA
23251  CAAATACGCA AGGGGAACGC ATGAAGGTTA TCGCTGTACT TAACCAGAAA
23301  GGCGGGTCAG GCAAGACGAC CATCGCAACC CATCTAGCCC GCGCCCTGCA
23351  ACTCGCCGGG GCCGATGTTC TGTTAGTCGA TTCCGATCCC CAGGGCAGTG
23401  CCCGCGATTG GGCGGCCGTG CGGGAAGATC AACCGCTAAC CGTTGTCGGC
23451  ATCGACCGCC CGACGATTGA CCGCGACGTG AAGGCCATCG GCCGGCGCGA
23501  CTTCGTAGTG ATCGACGGAG CGCCCCAGGC GGCGGACTTG GCTGTGTCCG
23551  CGATCAAGGC AGCCGACTTC GTGCTGATTC CGGTGCAGCC AAGCCCTTAC
23601  GACATATGGG CCACCGCCGA CCTGGTGGAG CTGGTTAAGC AGCGCATTGA
23651  GGTCACGGAT GGAAGGCTAC AAGCGGCCTT TGTCGTGTCG CGGGCGATCA
23701  AAGGCACGCG CATCGGCGGT GAGGTTGCCG AGGCGCTGGC CGGGTACGAG
23751  CTGCCCATTC TTGAGTCCCG TATCACGCAG CGCGTGAGCT ACCCAGGCAC
23801  TGCCGCCGCC GGCACAACCG TTCTTGAATC AGAACCCGAG GGCGACGCTG
23851  CCCGCGAGGT CCAGGCGCTG GCCGCTGAAA TTAAATCAAA ACTCATTTGA
23901  GTTAATGAGG TAAAGAGAAA ATGAGCAAAA GCACAAACAC GCTAAGTGCC
23951  GGCCGTCCGA GCGCACGCAG CAGCAAGGCT GCAACGTTGG CCAGCCTGGC
24001  AGACACGCCA GCCATGAAGC GGGTCAACTT TCAGTTGCCG GCGGAGGATC
24051  ACACCAAGCT GAAGATGTAC GCGGTACGCC AAGGCAAGAC CATTACCGAG
24101  CTGCTATCTG AATACATCGC GCAGCTACCA GAGTAAATGA GCAAATGAAT
24151  AAATGAGTAG ATGAATTTTA GCGGCTAAAG GAGGCGGCAT GGAAAATCAA
24201  GAACAACCAG GCACCGACGC CGTGGAATGC CCCATGTGTG GAGGAACGGG
24251  CGGTTGGCCA GGCGTAAGCG GCTGGGTTGC CTGCCGGCCC TGCAATGGCA
24301  CTGGAACCCC CAAGCCCGAG GAATCGGCGT GAGCGGTCGC AAACCATCCG
24351  GCCCGGTACA AATCGGCGCG GCGCTGGGTG ATGACCTGGT GGAGAAGTTG
24401  AAGGCCGCGC AGGCCGCCCA GCGGCAACGC ATCGAGGCAG AAGCACGCCC
24451  CGGTGAATCG TGGCAAGCGG CCGCTGATCG AATCCGCAAA GAATCCCGGC
24501  AACCGCCGGC AGCCGGTGCG CCGTCGATTA GGAAGCCGCC CAAGGGCGAC
24551  GAGCAACCAG ATTTTTTCGT TCCGATGCTC TATGACGTGG GCACCCGCGA
24601  TAGTCGCAGC ATCATGGACG TGGCCGTTTT CCGTCTGTCG AAGCGTGACC
24651  GACGAGCTGG CGAGGTGATC CGCTACGAGC TTCCAGACGG GCACGTAGAG
24701  GTTTCCGCAG GGCCGGCCGG CATGGCCAGT GTGTGGGATT ACGACCTGGT
24751  ACTGATGGCG GTTTCCCATC TAACCGAATC CATGAACCGA TACCGGGAAG
24801  GGAAGGGAGA CAAGCCCGGC CGCGTGTTCC GTCCACACGT TGCGGACGTA
24851  CTCAAGTTCT GCCGGCGAGC CGATGGCGGA AAGCAGAAAG ACGACCTGGT
24901  AGAAACCTGC ATTCGGTTAA ACACCACGCA CGTTGCCATG CAGCGTACGA
24951  AGAAGGCCAA GAACGGCCGC CTGGTGACGG TATCCGAGGG TGAAGCCTTG
25001  ATTAGCCGCT ACAAGATCGT AAAGAGCGAA ACCGGGCGGC CGGAGTACAT
25051  CGAGATCGAG CTAGCTGATT GGATGTACCG CGAGATCACA GAAGGCAAGA
25101  ACCCGGACGT GCTGACGGTT CACCCCGATT ACTTTTTGAT CGATCCCGGC
25151  ATCGGCCGTT TTCTCTACCG CCTGGCACGC CGCGCCGCAG GCAAGGCAGA
25201  AGCCAGATGG TTGTTCAAGA CGATCTACGA ACGCAGTGGC AGCGCCGGAG
25251  AGTTCAAGAA GTTCTGTTTC ACCGTGCGCA AGCTGATCGG GTCAAATGAC
25301  CTGCCGGAGT ACGATTTGAA GGAGGAGGCG GGGCAGGCTG GCCCGATCCT
25351  AGTCATGCGC TACCGCAACC TGATCGAGGG CGAAGCATCC GCCGGTTCCT
25401  AATGTACGGA GCAGATGCTA GGGCAAATTG CCCTAGCAGG GGAAAAAGGT
25451  CGAAAAGGTC TCTTTCCTGT GGATAGCACG TACATTGGGA ACCCAAAGCC
25501  GTACATTGGG AACCGGAACC CGTACATTGG GAACCCAAAG CCGTACATTG
25551  GGAACCGGTC ACACATGTAA GTGACTGATA TAAAAGAGAA AAAAGGCGAT
25601  TTTTCCGCCT AAAACTCTTT AAAACTTATT AAAACTCTTA AAACCCGCCT
25651  GGCCTGTGCA TAACTGTCTG GCCAGCGCAC AGCCGAAGAG CTGCAAAAAG
25701  CGCCTACCCT TCGGTCGCTG CGCTCCCTAC GCCCCGCCGC TTCGCGTCGG
25751  CCTATCGCGG CCGCTGGCCG CTCAAAAATG GCTGGCCTAC GGCCAGGCAA
25801  TCTACCAGGG CGCGGACAAG CCGCGCCGTC GCCACTCGAC CGCCGGCGCC
25851  CACATCAAGG CACCCTGCCT CGCGCGTTTC GGTGATGACG GTGAAAACCT
25901  CTGACACATG CAGCTCCCGG AGACGGTCAC AGCTTGTCTG TAAGCGGATG
25951  CCGGGAGCAG ACAAGCCCGT CAGGGCGCGT CAGCGGGTGT TGGCGGGTGT
26001  CGGGGCGCAG CCATGACCCA GTCACGTAGC GATAGCGGAG TGTATACTGG
```

FIG. 20J DNA sequence of pMBXS919 (Cont'd)

```
26051CTTAACTATG CGGCATCAGA GCAGATTGTA CTGAGAGTGC ACCATATGCG
26101GTGTGAAATA CCGCACAGAT GCGTAAGGAG AAAATACCGC ATCAGGCGCT
26151CTTCCGCTTC CTCGCTCACT GACTCGCTGC GCTCGGTCGT TCGGCTGCGG
26201CGAGCGGTAT CAGCTCACTC AAAGGCGGTA ATACGGTTAT CCACAGAATC
26251AGGGGATAAC GCAGGAAAGA ACATGTGAGC AAAAGGCCAG CAAAAGGCCA
26301GGAACCGTAA AAAGGCCGCG TTGCTGGCGT TTTTCCATAG GCTCCGCCCC
26351CCTGACGAGC ATCACAAAAA TCGACGCTCA AGTCAGAGGT GGCGAAACCC
26401GACAGGACTA TAAAGATACC AGGCGTTTCC CCCTGGAAGC TCCCTCGTGC
26451GCTCTCCTGT TCCGACCCTG CCGCTTACCG GATACCTGTC CGCCTTTCTC
26501CCTTCGGGAA GCGTGGCGCT TTCTCATAGC TCACGCTGTA GGTATCTCAG
26551TTCGGTGTAG GTCGTTCGCT CCAAGCTGGG CTGTGTGCAC GAACCCCCCG
26601TTCAGCCCGA CCGCTGCGCC TTATCCGGTA ACTATCGTCT TGAGTCCAAC
26651CCGGTAAGAC ACGACTTATC GCCACTGGCA GCAGCCACTG GTAACAGGAT
26701TAGCAGAGCG AGGTATGTAG GCGGTGCTAC AGAGTTCTTG AAGTGGTGGC
26751CTAACTACGG CTACACTAGA AGGACAGTAT TTGGTATCTG CGCTCTGCTG
26801AAGCCAGTTA CCTTCGGAAA AAGAGTTGGT AGCTCTTGAT CCGGCAAACA
26851AACCACCGCT GGTAGCGGTG GTTTTTTTGT TTGCAAGCAG CAGATTACGC
26901GCAGAAAAAA AGGATCTCAA GAAGATCCTT TGATCTTTTC TACGGGGTCT
26951GACGCTCAGT GGAACGAAAA CTCACGTTAA GGGATTTTGG TCATGCATTC
27001TAGGTACTAA AACAATTCAT CCAGTAAAAT ATAATATTTT ATTTTCTCCC
27051AATCAGGCTT GATCCCCAGT AAGTCAAAAA ATAGCTCGAC ATACTGTTCT
27101TCCCCGATAT CCTCCCTGAT CGACCGGACG CAGAAGGCAA TGTCATACCA
27151CTTGTCCGCC CTGCCGCTTC TCCCAAGATC AATAAAGCCA CTTACTTTGC
27201CATCTTTCAC AAAGATGTTG CTGTCTCCCA GGTCGCCGTG GGAAAAGACA
27251AGTTCCTCTT CGGGCTTTTC CGTCTTTAAA AAATCATACA GCTCGCGCGG
27301ATCTTTAAAT GGAGTGTCTT CTTCCCAGTT TTCGCAATCC ACATCGGCCA
27351GATCGTTATT CAGTAAGTAA TCCAATTCGG CTAAGCGGCT GTCTAAGCTA
27401TTCGTATAGG GACAATCCGA TATGTCGATG GAGTGAAAGA GCCTGATGCA
27451CTCCGCATAC AGCTCGATAA TCTTTTCAGG GCTTTGTTCA TCTTCATACT
27501CTTCCGAGCA AAGGACGCCA TCGGCCTCAC TCATGAGCAG ATTGCTCCAG
27551CCATCATGCC GTTCAAAGTG CAGGACCTTT GGAACAGGCA GCTTTCCTTC
27601CAGCCATAGC ATCATGTCCT TTTCCCGTTC CACATCATAG GTGGTCCCTT
27651TATACCGGCT GTCCGTCATT TTTAAATATA GGTTTTCATT TTCTCCCACC
27701AGCTTATATA CCTTAGCAGG AGACATTCCT TCCGTATCTT TTACGCAGCG
27751GTATTTTTCG ATCAGTTTTT TCAATTCCGG TGATATTCTC ATTTTAGCCA
27801TTTATTATTT CCTTCCTCTT TTCTACAGTA TTTAAAGATA CCCCAAGAAG
27851CTAATTATAA CAAGACGAAC TCCAATTCAC TGTTCCTTGC ATTCTAAAAC
27901CTTAAATACC AGAAAACAGC TTTTTCAAAG TTGTTTTCAA AGTTGGCGTA
27951TAACATAGTA TCGACGGAGC CGATTTTGAA ACCGCGGTGA TCACAGGCAG
28001CAACGCTCTG TCATCGTTAC AATCAACATG CTACCCTCCG CGAGATCATC
28051CGTGTTTCAA ACCCGGCAGC TTAGTTGCCG TTCTTCCGAA TAGCATCGGT
28101AACATGAGCA AAGTCTGCCG CCTTACAACG GCTCTCCCGC TGACGCCGTC
28151CCGGACTGAT GGGCTGCCTG TATCGAGTGG TGATTTTGTG CCGAGCTGCC
28201GGTCGGGGAG CTGTTGGCTG GCTGGTGGCA GGATATATTG TGGTGTAAAC
28251AAATTGACGC TTAGACAACT TAATAACACA TTGCGGACGT TTTTAATGTA
28301CTGAATTAAC GCCGAATTAA TTC
```

FIG. 21A DNA Sequence of pMBXS1022 (SEQ ID NO:3)

```
   1 AAGGTACGTA GTGTTTATCT TTGTTGCTTT TCTGAACAAT TTATTTACTA
  51 TGTAAATATA TTATCAATGT TTAATCTATT TTAATTTGCA CATGAATTTT
 101 CATTTTATTT TTACTTTACA AAACAAATAA ATATATATGC AAAAAAATTT
 151 ACAAACGATG CACGGGTTAC AAACTAATTT CATTAAATGC TAATGCAGAT
 201 TTTGTGAAGT AAAACTCCAA TTATGATGAA AAATACCACC AACACCACCT
 251 GCGAAACTGT ATCCCAACTG TCCTTAATAA AAATGTTAAA AAGTATATTA
 301 TTCTCATTTG TCTGTCATAA TTTATGTACC CCACTTTAAT TTTTCTGATG
 351 TACTAAACCG AGGGCAAACT GAAACCTGTT CCTCATGCAA AGCCCCTACT
 401 CACCATGTAT CATGTACGTG TCATCACCCA ACAACTCCAC TTTTGCTATA
 451 TAACAACACC CCCGTCACAC TCTCCCTCTC TAACACACAC CCCACTAACA
 501 ATTCCTTCAC TTGCAGCACT GTTGCATCAT CATCTTCATT GCAAAACCCT
 551 AAACTTCACC TTCAACCGGA TCCAAAATGG CTTCTATGAT ATCCTCTTCC
 601 GCTGTGACAA CAGTCAGCCG TGCCTCTAGG GGGCAATCCG CCGCAGTGGC
 651 TCCATTCGGC GGCCTCAAAT CCATGACTGG ATTCCCAGTG AAGAAGGTCA
 701 ACACTGACAT TACTTCCATT ACAAGCAATG GTGGAAGAGT AAAGTGCATG
 751 CAGGTGTGGC CTCCAATTGG AAAGAAGAAG TTTGAGACTC TTTCCTATTT
 801 GCCACCATTG ACGAGAGATT CTAGAGTTGG GAAAAAGATG ATGACTACTG
 851 ATGGGAATAC TGCAACCGCT CACGTAGCTT ATGCGATGTC AGAAGTTGCA
 901 GCTATCTACC CAATCACGCC GTCCAGTACA ATGGGAGAGG AAGCTGATGA
 951 CTGGGCAGCA CAGGGAAGAA AGAATATCTT CGGTCAAACG CTTACGATTA
1001 GGGAGATGCA ATCGGAAGCC GGAGCAGCGG GTGCCGTACA TGGAGCTCTT
1051 GCAGCTGGCG CCTTAACTAC CACCTTTACG GCTTCTCAAG GACTACTCTT
1101 GATGATCCCT AACATGTACA AGATATCAGG AGAATTGCTT CCTGGAGTCT
1151 TTCATGTCAC TGCTAGAGCT ATTGCCGCCC ACGCCCTTTC AATCTTTGGT
1201 GATCATCAGG ATATATATGC AGCGAGGCAG ACAGGGTTCG CTATGCTTGC
1251 TTCAAGCTCG GTGCAAGAAG CACATGACAT GGCTTTAGTT GCCCACCTTG
1301 CCGCCATCGA ATCTAACGTC CCTTTCATGC ATTTCTTCGA CGGGTTTCGC
1351 ACGTCACACG AAATTCAAAA GATTGAAGTT CTCGATTATG CAGATATGGC
1401 ATCCTTAGTG AATCAGAAAG CTCTCGCAGA GTTCCGTGCT AAATCTATGA
1451 ATCCAGAGCA TCCACATGTT CGTGGTACTG CTCAAAACCC TGACATATAT
1501 TTCCAGGGAA GAGAGGCAGC AAACCCGTAT TACTTGAAAG TTCCTGGGAT
1551 TGTAGCAGAG TATATGCAAA AAGTTGCAAG TCTAACAGGG AGATCGTACA
1601 AGCTGTTCGA CTATGTTGGA GCTCCTGATG CTGAGCGTGT CATTGTTTCT
1651 ATGGGTTCCA GTTGCGAGAC AATCGAAGAA GTGATCAATC ACCTCGCTGC
1701 TAAGGGAGAA AAGATTGGTT TGATTAAGGT CCGATTATAC CGTCCATTTG
1751 TATCTGAAGC TTTCTTTGCT GCGTTACCGG CATCTGCTAA GGTTATTACA
1801 GTTCTGGATA GAACTAAGGA GCCCGGAGCT CCTGGCGACC CTTTGTACCT
1851 TGATGTCTGT TCAGCATTCG TCGAAAGGGG AGAAGCTATG CCCAAAATCC
1901 TCGCAGGCCG CTATGGGCTC GGATCTAAGG AGTTTTCACC CGCTATGGTT
1951 AAATCTGTTT ATGATAACAT GAGTGGTGCT AAGAAGAACC ATTTTACCGT
2001 TGGTATAGAG GACGATGTCA CGGGAACATC TCTGCCGGTT GATAATGCGT
2051 TTGCTGATAC AACCCCTAAA GGAACTATCC AGTGTCAGTT CTGGGGTTTG
2101 GGTGCAGATG GTACTGTCGG GGCGAATAAG CAGGCTATCA AAATCATAGG
2151 AGATAACACT GATCTATTCG CTCAAGGTTA CTTTTCATAC GACTCTAAGA
2201 AAAGTGGTGG TATAACTATC AGTCACTTGC GATTTGGAGA AAAGCCAATA
2251 CAATCTACCT ATTTGGTGAA CCGGGCTGAC TACGTTGCTT GTCATAACCC
2301 TGCCTATGTT GGTATATACG ATATTTTAGA GGGTATCAAA GATGGGGGCA
2351 CATTTGTCCT CAATTCTCCC TGGTCGAGTC TTGAAGATAT GGATAAACAT
2401 CTTCCAAGCG GGATTAAGAG AACCATAGCG AATAAGAAGC TTAAGTTTTA
2451 CAACATTGAT GCGGTGAAAA TAGCAACAGA TGTTGGTTTG GGCGGCAGAA
2501 TTAACATGAT AATGCAGACC GCATTCTTCA AACTAGCTGG TGTACTCCCT
```

FIG. 21B DNA Sequence of pMBXS1022 (Cont'd)

```
2551   TTCGAGAAGG CAGTGGATCT CCTCAAAAAG TCTATTCATA AAGCCTATGG
2601   AAAGAAGGGA GAGAAGATCG TGAAAATGAA TACTGACGCA GTAGATCAAG
2651   CAGTTACGAG CCTTCAAGAG TTCAAGTACC CAGACTCATG GAAGGATGCT
2701   CCAGCAGAGA CAAAAGCTGA GCCAATGACA AACGAGTTCT TCAAAAATGT
2751   TGTCAAGCCT ATCCTCACTC AACAAGGCGA TAAATTACCG GTTTCCGCTT
2801   TTGAAGCCGA TGGACGTTTT CCACTGGGAA CTTCTCAGTT TGAGAAACGC
2851   GGAGTGGCTA TTAACGTTCC TCAGTGGGTA CCTGAAAATT GCATCCAATG
2901   CAATCAATGC GCTTTTGTGT GCCCGCATTC CGCGATACTT CCTGTTTTGG
2951   CTAAAGAGGA AGAGTTAGTC GGAGCGCCTG CCAACTTCAC CGCTTTGGAA
3001   GCGAAAGGAA AAGAATTGAA AGGTTACAAA TTCAGAATTC AGATTAACAC
3051   TCTCGACTGC ATGGGCTGCG GAAATTGTGC CGACATATGT CCTCCCAAAG
3101   AAAAGGCTTT AGTGATGCAG CCACTGGACA CTCAGAGGGA TGCCCAAGTG
3151   CCAAATTTGG AGTATGCAGC CAGAATTCCA GTGAAGTCCG AGGTTCTTCC
3201   GCGGGATTCT CTCAAAGGAT CACAATTCCA AGAACCACTG ATGGAGTTTT
3251   CAGGCGCATG TAGTGGATGT GGTGAAACAC CTTACGTACG TGTGATTACT
3301   CAGTTATTTG GAGAACGGAT GTTTATCGCT AATGCAACAG GTTGTAGCTC
3351   GATCTGGGGT GCCAGCGCTC CGTCGATGCC ATACAAGACC AACAGGCTGG
3401   GACAGGGTCC AGCTTGGGGG AATTCCCTAT TCGAGGATGC TGCAGAGTAC
3451   GGGTTCGGAA TGAACATGAG TATGTTTGCG CGTAGAACTC ATCTCGCGGA
3501   TCTTGCTGCT AAAGCTCTCG AGTCTGATGC TTCTGGAGAT GTCAAGGAAG
3551   CATTGCAGGG TTGGCTCGCT GGGAAAAACG ACCCGATTAA GTCTAAAGAA
3601   TACGGGGATA AGTTGAAGAA ACTTCTAGCT GGTCAAAAGG ACGGGTTGTT
3651   GGGACAAATT GCAGCAATGT CAGACCTTTA CACGAAGAAA AGTGTTTGGA
3701   TCTTTGGTGG CGATGGATGG GCGTATGATA TTGGTTATGG TGGCCTTGAT
3751   CACGTCCTCG CAAGCGGCGA AGATGTGAAC GTGTTTGTGA TGGATACTGA
3801   AGTTTACTCC AACACCGGTG GACAATCCTC AAAAGCAACA CCAACCGGGG
3851   CCGTGGCTAA ATTCGCGGCT GCCGGCAAAA GGACTGGAAA AAAGGATCTG
3901   GCCAGAATGG TTATGACTTA TGGATACGTA TATGTAGCTA CAGTATCAAT
3951   GGGCTATAGC AAACAGCAAT TTCTTAAAGT CCTCAAGGAA GCTGAGAGCT
4001   TCCCAGGTCC TTCACTTGTT ATCGCCTACG CGACATGTAT CAATCAAGGT
4051   TTACGAAAGG GAATGGGGAA AAGCCAAGAT GTGATGAACA CCGCTGTTAA
4101   AAGCGGTTAT TGGCCTTTGT TCCGCTATGA TCCTCGTCTT GCGGCCCAAG
4151   GAAAGAATCC GTTTCAGCTA GACTCTAAGG CACCAGACGG TAGTGTTGAG
4201   GAATTTTTGA TGGCTCAGAA TCGATTTGCG GTCCTTGATC GATCGTTCCC
4251   AGAAGATGCC AAGAGGTTGA GGGCGCAAGT TGCACATGAA TTGGATGTTA
4301   GGTTTAAGGA GTTAGAACAC ATGGCGGCTA CAAATATCTT CGAGTCCTTC
4351   GCTCCTGCTG GAGGCAAAGC TGACGGTTCA GTAGATTTTG GAGAAGGCGC
4401   AGAGTTTTGT ACTAGAGATG ACACACCGAT GATGGCCAGA CCAGATAGTG
4451   GCGAAGCATG CGACCAAAAT AGAGCAGGAA CGTCTGAGCA GCAAGGAGAT
4501   TTGTCGAAGA GGACCAAGAA ATGAGGCGCG CCTGAGTAAT TCTGATATTA
4551   GAGGGAGCAT TAATGTGTTG TTGTGATGTG GTTTATATGG GGAAATTAAA
4601   TAAATGATGT ATGTACCTCT TGCCTATGTA GGTTTGTGTG TTTTGTTTTG
4651   TTGTCTAGCT TTGGTTATTA AGTAGTAGGG ACGTTCGTTC GTGTCTCAAA
4701   AAAAGGGGTA CTACCACTCT GTAGTGTATA TGGATGCTGG AAATCAATGT
4751   GTTTTGTATT TGTTCACCTC CATTGTTGAA TTCAATGTCA AATGTGTTTT
4801   GCGTTGGTTA TGTGTAAAAT TACTATCTTT CTCGTCCGAT GATCAAAGTT
4851   TTAAGCAACA AAACCAAGGG TGAAATTTAA ACTGTGCTTT GTTGAAGATT
4901   CTTTTATCAT ATTGAAAATC AAATTACTAG CAGCAGATTT TACCTAGCAT
4951   GAAATTTTAT CAACAGTACA GCACTCACTA ACCAAGTTCC AAACTAAGAT
5001   GCGCCATTAA CATCAGCCAA TAGGCATTTT CAGCAAAAGC TTGTACGTAG
5051   TGTTTATCTT TGTTGCTTTT CTGAACAATT TATTTACTAT GTAAATATAT
5101   TATCAATGTT TAATCTATTT TAATTTGCAC ATGAATTTTC ATTTTATTTT
5151   TACTTTACAA AACAAATAAA TATATATGCA AAAAAATTTA CAAACGATGC
5201   ACGGGTTACA AACTAATTTC ATTAAATGCT AATGCAGATT TTGTGAAGTA
```

FIG. 21C DNA Sequence of pMBXS1022 (Cont'd)

```
5251  AAACTCCAAT TATGATGAAA AATACCACCA ACACCACCTG CGAAACTGTA
5301  TCCCAACTGT CCTTAATAAA AATGTTAAAA AGTATATTAT TCTCATTTGT
5351  CTGTCATAAT TTATGTACCC CACTTTAATT TTTCTGATGT ACTAAACCGA
5401  GGGCAAACTG AAACCTGTTC CTCATGCAAA GCCCCTACTC ACCATGTATC
5451  ATGTACGTGT CATCACCCAA CAACTCCACT TTTGCTATAT AACAACACCC
5501  CCGTCACACT CTCCCTCTCT AACACACACC CCACTAACAA TTCCTTCACT
5551  TGCAGCACTG TTGCATCATC ATCTTCATTG CAAAACCCTA AACTTCACCT
5601  TCAACCGCGG CCGCAGATCT AAAATGGCTT CTATGATATC CTCTTCCGCT
5651  GTGACAACAG TCAGCCGTGC CTCTAGGGGG CAATCCGCCG CAGTGGCTCC
5701  ATTCGGCGGC CTCAAATCCA TGACTGGATT CCCAGTGAAG AAGGTCAACA
5751  CTGACATTAC TTCCATTACA AGCAATGGTG GAAGAGTAAA GTGCATGCAG
5801  GTGTGGCCTC CAATTGGAAA GAAGAAGTTT GAGACTCTTT CCTATTTGCC
5851  ACCATTGACG AGAGATTCTA GAGTGCTCAG CCAGCAATCC ATCCAGAAGG
5901  TTCTCGTGGC TAACCGTGGT GAGATTGCTA TTCGTATCTT TAGAGCGTGT
5951  ACCGAGTTGA ACATCCGAAC TGTCGCTGTT TATAGTAAAG AAGATTCTGG
6001  ATCATACCAC AGATACAAAG CTGACGAGGC CTACTTGGTT GGTGAAGGTA
6051  AGAAGCCTAT TGACGCTTAT CTTGATATAG AGGGCATCAT TGATATTGCC
6101  AAGAGAAACA AAGTTGATGC AATTCATCCG GGATACGGTT TTCTATCAGA
6151  AAACATTCAC TTTGCACGAC GATGTGAAGA AGAGGGAATC GTGTTCATCG
6201  GACCTAAAAG CGAACACTTG GATATGTTTG GGGACAAGGT TAAGGCAAGG
6251  GAACAAGCAG AGAAGGCAGG AATTCCAGTG ATACCTGGAT CGGATGGGCC
6301  TGCTGAAACT CTTGAAGCTG TCGAACAATT CGGCCAGGCT AACGGATACC
6351  CAATCATCAT TAAGGCTTCT TTAGGTGGTG GGGGAAGGGG GATGAGAATC
6401  GTGCGATCCG AATCTGAGGT AAAAGAGGCT TATGAACGTG CTAAATCGGA
6451  AGCTAAAGCG GCCTTTGGGA ACGATGAAGT CTATGTCGAG AAACTAATCG
6501  AGAATCCCAA GCACATCGAG GTTCAAGTGA TTGGTGATAA GCAAGGTAAC
6551  GTTGTTCACC TTTTCGAGAG AGATTGTTCT GTTCAACGTA GACACCAAAA
6601  AGTGATAGAA GTAGCTCCAT CGGTATCGTT GAGCCCAGAA CTAAGGGACC
6651  AGATATGCGA GGCTGCTGTC GCGCTTGCAA AGAATGTCAA CTATATCAAT
6701  GCAGGCACTG TCGAATTCTT GGTAGCCAAT AATGAGTTTT ACTTCATTGA
6751  GGTCAACCCT AGAGTTCAAG TTGAGCATAC CATTACCGAA ATGATCACTG
6801  GGGTGGATAT CGTACAGACT CAGATCCTCG TTGCTCAAGG CCATTCCCTT
6851  CATTCCAAGA AGGTGAATAT TCCAGAGCAA AAGGATATCT TTACAATTGG
6901  TTATGCGATT CAATCACGAG TTACCACAGA AGATCCACAA AATGACTTCA
6951  TGCCAGATAC GGGAAAGATA ATGGCATACC GTTCTGGTGG CGGATTTGGT
7001  GTTCGATTAG ACACAGGTAA TAGTTTTCAG GGAGCTGTGA TAACGCCATA
7051  CTATGATTCT TTATTGGTTA AGTTGAGTAC TTGGGCTCTC ACTTTCGAGC
7101  AAGCCGCAGC GAAAATGGTC AGAAACCTTC AGGAGTTCAG AATTAGAGGT
7151  ATTAAGACGA ACATTCCATT CTTAGAGAAC GTTGCTAAAC ATGAGAAGTT
7201  TCTGACAGGA CAATATGATA CAAGTTTCAT AGACACTACA CCTGAACTCT
7251  TTAACTTCCC TAAACAAAAA GACAGAGGTA CGAAAATGTT GACATATATC
7301  GGAAACGTGA CAGTTAATGG GTTCCCAGGT ATCGGTAAGA AAGAAAAGCC
7351  GGCCTTTGAT AAACCCCTTG GTGTTAAAGT GGATGTGGAT CAACAACCTG
7401  CTAGGGGCAC TAAGCAAATC CTTGATGAAA AGGGTGCAGA GGGACTGGCA
7451  AATTGGGTTA AAGAGCAGAA ATCAGTTCTT CTGACAGATA CCACATTTCG
7501  TGATGCTCAT CAATCATTAC TAGCAACAAG AATTAGATCA CACGATCTGA
7551  AAAAGATCGC TAATCCAACC GCTGCTCTTT GGCCGGAACT CTTCTCTATG
7601  GAAATGTGGG GTGGGGCCAC ATTCGATGTC GCGTACCGTT TTCTAAAAGA
7651  AGATCCTTGG AAGCGTCTGG AAGATTTGAG AAAAGAGGTG CCCAATACCC
7701  TGTTCCAGAT GCTTTTGCGT TCTAGCAATG CCGTCGGATA TACCAATTAT
7751  CCTGACAATG TGATCAAAGA ATTCGTAAAA CAGTCCGCTC AATCTGGTAT
7801  CGACGTTTTT AGGATTTTCG ATTCACTTAA TTGGGTAAAA GGTATGACGT
7851  TAGCGATTGA TGCTGTACGT GATACTGGAA AGGTTGCAGA GGCCGCCATT
7901  TGCTACACTG GAGACATTTT GGATAAGAAT AGAACTAAAT ACGACTTGGC
```

FIG. 21D DNA Sequence of pMBXS1022 (Cont'd)

```
7951   TTATTACACT TCCATGGCAA AAGAACTTGA GGCTGCCGGT GCACATATTC
8001   TGGGGATAAA GGATATGGCC GGTTTGCTCA AACCGCAGGC AGCATATGAG
8051   TTGGTTTCAG CCCTTAAAGA AACTATTGAC ATACCCGTTC ATCTGCACAC
8101   GCATGACACG TCGGGCAATG GAATCTATAT GTATGCAAAG GCTGTCGAGG
8151   CTGGCGTGGA TATCATTGAT GTCGCTGTAA GCTCTATGGC TGGACTTACA
8201   TCCCAGCCAT CAGCCTCTGG ATTCTATCAT GCTATGGAAG GTAACGATCG
8251   TAGACCCGAA ATGAATGTCC AAGGGGTCGA ATTACTGTCA CAGTACTGGG
8301   AGAGTGTGCG TAAGTATTAC TCAGAGTTTG AGAGCGGTAT GAAGAGTCCC
8351   CATACCGAGA TTTATGAGCA CGAGATGCCT GGTGGACAAT ACTCTAACTT
8401   GCAACAGCAA GCGAAGGGGG TTGGTTTGGG AGATAGGTGG AACGAAGTGA
8451   AAGAAATGTA TAGACGTGTC AACGACATGT TTGGTGATAT TGTGAAAGTA
8501   ACTCCTAGTT CTAAGGTAGT TGGAGACATG GCACTGTACA TGGTTCAGAA
8551   TAACCTTACT GAAAAGGATG TTTACGAGAA GGGGGAGTCA CTTGACTTCC
8601   CTGATTCAGT GGTTGAACTG TTCAAGGGAA ATATCGGTCA ACCGCATGGG
8651   GGATTTCCAG AAAAACTACA GAAACTGATA CTAAAGGGAC AGGAGCCAAT
8701   TACTGTTCGA CCAGGAGAGC TCTTGGAGCC GGTTTCTTTT GAGGCTATCA
8751   AGCAAGAATT CAAAGAACAA CATAACCTTG AAATTTCTGA TCAGGACGCG
8801   GTTGCTTACG CACTTTATCC AAAGGTCTTT ACTGATTACG TGAAAACCAC
8851   AGAGTCTTAT GGTGATATAA GTGTGCTAGA TACACCAACA TTTTTCTATG
8901   GCATGACTCT TGGAGAAGAG ATTGAAGTGG AAATAGAAAG GGGAAAAACA
8951   CTCATTGTTA AACTGATATC TATCGGAGAG CCTCAACCTG ATGCTACAAG
9001   GGTAGTGTAC TTTGAATTGA ATGGACAACC TAGAGAAGTA GTGATTAAAG
9051   ATGAGTCAAT AAAGTCAAGC GTGCAGGAGA GGCTAAAGGC AGATAGAACC
9101   AATCCGTCGC ACATTGCAGC TTCTATGCCT GGCACCGTCA TAAAAGTCCT
9151   CGCTGAAGCT GGTACTAAAG TCAACAAAGG TGACCATCTT ATGATCAACG
9201   AAGCAATGAA GATGGAAACT ACGGTTCAGG CACCTTTCAG TGGAACAATC
9251   AAGCAGGTTC ATGTTAAGAA TGGCGAGCCT ATCCAGACTG GTGACTTGCT
9301   TTTGGAGATT GAAAAGGCCT GAGTCGACGC GATCGCGCGG CCGCTGAGTA
9351   ATTCTGATAT TAGAGGGAGC ATTAATGTGT TGTTGTGATG TGGTTTATAT
9401   GGGGAAATTA AATAAATGAT GTATGTACCT CTTGCCTATG TAGGTTTGTG
9451   TGTTTTGTTT TGTTGTCTAG CTTTGGTTAT TAAGTAGTAG GGACGTTCGT
9501   TCGTGTCTCA AAAAAAGGGG TACTACCACT CTGTAGTGTA TATGGATGCT
9551   GGAAATCAAT GTGTTTTGTA TTTGTTCACC TCCATTGTTG AATTCAATGT
9601   CAAATGTGTT TTGCGTTGGT TATGTGTAAA ATTACTATCT TTCTCGTCCG
9651   ATGATCAAAG TTTTAAGCAA CAAAACCAAG GGTGAAATTT AAACTGTGCT
9701   TTGTTGAAGA TTCTTTTATC ATATTGAAAA TCAAATTACT AGCAGCAGAT
9751   TTTACCTAGC ATGAAATTTT ATCAACAGTA CAGCACTCAC TAACCAAGTT
9801   CCAAACTAAG ATGCGCCATT AACATCAGCC AATAGGCATT TTCAGCAAGT
9851   TTAAACTACG TAGTGTTTAT CTTTGTTGCT TTTCTGAACA ATTTATTTAC
9901   TATGTAAATA TATTATCAAT GTTTAATCTA TTTTAATTTG CACATGAATT
9951   TTCATTTTAT TTTTACTTTA CAAAACAAAT AAATATATAT GCAAAAAAAT
10001  TTACAAACGA TGCACGGGTT ACAAACTAAT TTCATTAAAT GCTAATGCAG
10051  ATTTTGTGAA GTAAAACTCC AATTATGATG AAAAATACCA CCAACACCAC
10101  CTGCGAAACT GTATCCCAAC TGTCCTTAAT AAAAATGTTA AAAAGTATAT
10151  TATTCTCATT TGTCTGTCAT AATTTATGTA CCCCACTTTA ATTTTTCTGA
10201  TGTACTAAAC CGAGGGCAAA CTGAAACCTG TTCCTCATGC AAAGCCCCTA
10251  CTCACCATGT ATCATGTACG TGTCATCACC CAACAACTCC ACTTTTGCTA
10301  TATAACAACA CCCCCGTCAC ACTCTCCCTC TCTAACACAC ACCCCACTAA
10351  CAATTCCTTC ACTTGCAGCA CTGTTGCATC ATCATCTTCA TTGCAAAACC
10401  CTAAACTTCA CCTTCAACCG CGGCCGCTCG CGAAAAATGG CTTCTATGAT
10451  ATCCTCTTCC GCTGTGACAA CAGTCAGCCG TGCCTCTAGG GGGCAATCCG
10501  CCGCAGTGGC TCCATTCGGC GGCCTCAAAT CCATGACTGG ATTCCCAGTG
10551  AAGAAGGTCA ACACTGACAT TACTTCCATT ACAAGCAATG GTGGAAGAGT
10601  AAAGTGCATG CAGGTGTGGC CTCCAATTGG AAAGAAGAAG TTTGAGACTC
```

FIG. 21E DNA Sequence of pMBXS1022 (Cont'd)

```
10651  TTTCCTATTT GCCACCATTG ACGAGAGATT CTAGAGTGAA CATACACGAG
10701  TACCAAGCAA AAGAGTTGCT CAAGACCTAT GGAGTGCCGG TCCCAGACGG
10751  AGCGGTAGCT TATAGTGATG CTCAAGCGGC TTCCGTCGCT GAAGAGATTG
10801  GTGGCTCTAG ATGGGTTGTA AAGGCGCAGA TACACGCTGG TGGAAGGGGA
10851  AAGGCAGGTG GTGTGAAGGT GGCCCATAGC ATTGAAGAGG TTCGTCAGTA
10901  CGCTGATGCG ATGCTTGGGT CCCATCTCGT TACACATCAA ACAGGGCCTG
10951  GTGGTTCATT AGTTCAACGT TTGTGGGTGG AGCAAGCATC ACATATCAAG
11001  AAAGAGTATT ATCTGGGATT TGTTATTGAT AGAGGTAACC AAAGAATTAC
11051  CTTAATTGCT TCTTCTGAAG GGGGAATGGA GATAGAAGAG GTTGCTAAAG
11101  AGACACCAGA AAAGATCGTC AAAGAGGTTG TAGACCCTGC AATCGGATTG
11151  CTTGATTTTC AGTGTAGAAA GGTTGCAACT GCAATAGGAC TTAAGGGAAA
11201  GCTTATGCCC CAGGCAGTTA GACTTATGAA GGCTATCTAT AGGTGTATGC
11251  GAGATAAGGA TGCTCTCCAG GCAGAGATCA ATCCTTTGGC AATAGTAGGT
11301  GAAAGTGACG AGTCGCTCAT GGTTCTTGAT GCTAAATTCA ATTTTGATGA
11351  CAATGCTCTT TACAGACAAC GAACAATTAC TGAAATGAGG GATCTCGCAG
11401  AAGAAGATCC TAAAGAAGTC GAAGCTTCTG GACACGGATT GAATTACATC
11451  GCCCTCGATG GGAACATCGG TTGTATTGTG AATGGAGCTG GTCTTGCTAT
11501  GGCCAGCCTG GATGCCATCA CTCTACATGG CGGTCGTCCA GCTAACTTCT
11551  TAGATGTCGG CGGTGGGGCT TCTCCTGAAA AGGTTACGAA TGCGTGCAGA
11601  ATTGTTTTGG AAGATCCGAA CGTCCGTTGT ATACTGGTGA ACATTTTTGC
11651  CGGAATTAAC AGGTGCGATT GGATTGCAAA AGGACTTATT CAAGCCTGCG
11701  ACTCACTACA GATTAAAGTT CCACTGATCG TTCGATTGGC AGGCACTAAT
11751  GTAGATGAAG GCAGGAAAAT CCTAGCGGAG TCGGGTTTAA GTTTCATAAC
11801  GGCAGAGAAT TTGGACGACG CGGCTGCTAA AGCCGTGGCT ATCGTGAAAG
11851  GGTGAACGCG TTGAGTAATT CTGATATTAG AGGGAGCATT AATGTGTTGT
11901  TGTGATGTGG TTTATATGGG GAAATTAAAT AAATGATGTA TGTACCTCTT
11951  GCCTATGTAG GTTTGTGTGT TTTGTTTTGT TGTCTAGCTT TGGTTATTAA
12001  GTAGTAGGGA CGTTCGTTCG TGTCTCAAAA AAAGGGGTAC TACCACTCTG
12051  TAGTGTATAT GGATGCTGGA AATCAATGTG TTTTGTATTT GTTCACCTCC
12101  ATTGTTGAAT TCAATGTCAA ATGTGTTTTG CGTTGGTTAT GTGTAAAATT
12151  ACTATCTTTC TCGTCCGATG ATCAAAGTTT TAAGCAACAA AACCAAGGGT
12201  GAAATTTAAA CTGTGCTTTG TTGAAGATTC TTTTATCATA TTGAAAATCA
12251  AATTACTAGC AGCAGATTTT ACCTAGCATG AAATTTTATC AACAGTACAG
12301  CACTCACTAA CCAAGTTCCA AACTAAGATG CGCCATTAAC ATCAGCCAAT
12351  AGGCATTTTC AGCAATGTAC ATACGTAGTG TTTATCTTTG TTGCTTTTCT
12401  GAACAATTTA TTTACTATGT AAATATATTA TCAATGTTTA ATCTATTTTA
12451  ATTTGCACAT GAATTTTCAT TTTATTTTTA CTTTACAAAA CAAATAAATA
12501  TATATGCAAA AAAATTTACA AACGATGCAC GGGTTACAAA CTAATTTCAT
12551  TAAATGCTAA TGCAGATTTT GTGAAGTAAA ACTCCAATTA TGATGAAAAA
12601  TACCACCAAC ACCACCTGCG AAACTGTATC CCAACTGTCC TTAATAAAAA
12651  TGTTAAAAAG TATATTATTC TCATTTGTCT GTCATAATTT ATGTACCCCA
12701  CTTTAATTTT TCTGATGTAC TAAACCGAGG GCAAACTGAA ACCTGTTCCT
12751  CATGCAAAGC CCCTACTCAC CATGTATCAT GTACGTGTCA TCACCCAACA
12801  ACTCCACTTT TGCTATATAA CAACACCCCC GTCACACTCT CCCTCTCTAA
12851  CACACACCCC ACTAACAATT CCTTCACTTG CAGCACTGTT GCATCATCAT
12901  CTTCATTGCA AAACCCTAAA CTTCACCTTC AACCGCGGCC GCGACGTCAA
12951  AATGGCTTCT ATGATATCCT CTTCCGCTGT GACAACAGTC AGCCGTGCCT
13001  CTAGGGGGCA ATCCGCCGCA GTGGCTCCAT TCGGCGGCCT CAAATCCATG
13051  ACTGGATTCC CAGTGAAGAA GGTCAACACT GACATTACTT CCATTACAAG
13101  CAATGGTGGA AGAGTAAAGT GCATGCAGGT GTGGCCTCCA ATTGGAAAGA
13151  AGAAGTTTGA GACTCTTTCC TATTTGCCAC CATTGACGAG AGATTCTAGA
13201  GTCTCGGTTT TCGTGAATAA ACATTCCAAG GTCATCTTTC AAGGCTTTAC
13251  CGGGGAGCAT GCTACATTTC ACGCAAAAGA TGCAATGCGA ATGGGCACAA
13301  GGGTTGTCGG TGGCGTTACT CCTGGAAAGG GTGGGACTAG ACATCCAGAT
```

FIG. 21F DNA Sequence of pMBXS1022 (Cont'd)

```
13351   CCTGAGCTCG CTCATCTTCC GGTATTCGAT ACCGTTGCCG AAGCCGTTGC
13401   TGCTACAGGA GCTGATGTAT CAGCTGTGTT TGTCCCACCC CCTTTCAATG
13451   CAGACGCACT TATGGAAGCA ATTGATGCCG GTATTAGAGT GGCTGTCACT
13501   ATAGCGGATG GAATTCCTGT GCATGACATG ATCAGATTGC AAAGGTATAG
13551   AGTAGGAAAG GACTCTATTG TTATCGGGCC TAACACACCA GGAATCATAA
13601   CGCCTGGTGA GTGTAAAGTG GGTATCATGC CGAGTCACAT ATACAAGAAG
13651   GGAAACGTGG GTATAGTGAG TCGATCAGGA ACATTGAATT ACGAGGCGAC
13701   GGAACAAATG GCTGCGCTAG GCTTAGGGAT TACTACTTCT GTTGGAATTG
13751   GTGGTGATCC TATAAACGGC ACTGACTTTG TGACTGTTCT CCGTGCATTC
13801   GAGGCTGATC CAGAAACGGA AATTGTAGTT ATGATCGGAG AAATAGGTGG
13851   ACCGCAGGAA GTTGCCGCAG CTAGATGGGC AAAAGAGAAT ATGACCAAAC
13901   CAGTTATTGG GTTCGTAGCT GGTTTAGCAG CCCCCACAGG GCGTAGGATG
13951   GGACACGCAG GTGCTATTAT CAGCTCTGAG GCTGATACCG CTGGAGCTAA
14001   GATGGATGCC ATGGAAGCTC TTGGTCTGTA TGTCGCTAGG AACCCAGCGC
14051   AAATCGGACA GACAGTTTTG CGTGCGGCAC AGGAGCATGG AATTAGATTT
14101   TGAGGGCCCG TTAACTGAGT AATTCTGATA TTAGAGGGAG CATTAATGTG
14151   TTGTTGTGAT GTGGTTTATA TGGGGAAATT AAATAAATGA TGTATGTACC
14201   TCTTGCCTAT GTAGGTTTGT GTGTTTTGTT TTGTTGTCTA GCTTTGGTTA
14251   TTAAGTAGTA GGGACGTTCG TTCGTGTCTC AAAAAAAGGG GTACTACCAC
14301   TCTGTAGTGT ATATGGATGC TGGAAATCAA TGTGTTTTGT ATTTGTTCAC
14351   CTCCATTGTT GAATTCAATG TCAAATGTGT TTTGCGTTGG TTATGTGTAA
14401   AATTACTATC TTTCTCGTCC GATGATCAAA GTTTTAAGCA ACAAAACCAA
14451   GGGTGAAATT TAAACTGTGC TTTGTTGAAG ATTCTTTTAT CATATTGAAA
14501   ATCAAATTAC TAGCAGCAGA TTTTACCTAG CATGAAATTT TATCAACAGT
14551   ACAGCACTCA CTAACCAAGT TCCAAACTAA GATGCGCCAT TAACATCAGC
14601   CAATAGGCAT TTTCAGCAAG TTTAAACCGG ACCGTACGTA GTGTTTATCT
14651   TTGTTGCTTT TCTGAACAAT TTATTTACTA TGTAAATATA TTATCAATGT
14701   TTAATCTATT TTAATTTGCA CATGAATTTT CATTTTATTT TTACTTTACA
14751   AAACAAATAA ATATATATGC AAAAAAATTT ACAAACGATG CACGGGTTAC
14801   AAACTAATTT CATTAAATGC TAATGCAGAT TTTGTGAAGT AAAACTCCAA
14851   TTATGATGAA AAATACCACC AACACCACCT GCGAAACTGT ATCCCAACTG
14901   TCCTTAATAA AAATGTTAAA AAGTATATTA TTCTCATTTG TCTGTCATAA
14951   TTTATGTACC CCACTTTAAT TTTTCTGATG TACTAAACCG AGGGCAAACT
15001   GAAACCTGTT CCTCATGCAA AGCCCCTACT CACCATGTAT CATGTACGTG
15051   TCATCACCCA ACAACTCCAC TTTTGCTATA TAACAACACC CCCGTCACAC
15101   TCTCCCTCTC TAACACACAC CCCACTAACA ATTCCTTCAC TTGCAGCACT
15151   GTTGCATCAT CATCTTCATT GCAAAACCCT AAACTTCACC TTCAACCGCG
15201   GCCGCCACGT GAAAATGGCT TCTATGATAT CCTCTTCCGC TGTGACAACA
15251   GTCAGCCGTG CCTCTAGGGG GCAATCCGCC GCAGTGGCTC CATTCGGCGG
15301   CCTCAAATCC ATGACTGGAT TCCCAGTGAA GAAGGTCAAC ACTGACATTA
15351   CTTCCATTAC AAGCAATGGT GGAAGAGTAA AGTGCATGCA GGTGTGGCCT
15401   CCAATTGGAA AGAAGAAGTT TGAGACTCTT TCCTATTTGC CACCATTGAC
15451   GAGAGATTCT AGAGTGAGCT TCCGTTTGCA ACCAGCTCCG CCAGCAAGGC
15501   CCAATAGATG TCAACTTTTT GGGCCTGGAT CTCGACCGGC TTTGTTTGAG
15551   AAAATGGCCG CTTCAGCCGC GGACGTTATC AATCTGGATT TAGAGGATAG
15601   TGTTGCCCCA GATGATAAAG CTCAGGCTAG AGCAAATATC ATTGAGGCTA
15651   TAAACGGTCT AGACTGGGGT AGAAAGTATC TCAGTGTTAG AATTAACGGA
15701   CTTGATACGC CTTTCTGGTA TCGAGATGTC GTTGACTTGC TTGAGCAGGC
15751   AGGAGATAGA CTTGATCAAA TCATGATCCC TAAGGTTGGC TGTGCTGCGG
15801   ATGTTTACGC CGTCGATGCT TTGGTAACAG CAATTGAACG TGCTAAAGGG
15851   CGTACTAAGC CTCTATCATT TGAAGTGATA ATAGAGTCTG CAGCTGGTAT
15901   CGCACATGTT GAAGAAATAG CCGCTTCGTC ACCAAGACTC CAAGCCATGT
15951   CTTTGGGTGC AGCCGATTTT GCAGCTTCTA TGGGAATGCA GACTACAGGG
16001   ATTGGTGGAA CGCAAGAGAA CTACTATATG CTCCACGACG GACAAAAGCA
```

FIG. 21G DNA Sequence of pMBXS1022 (Cont'd)

```
16051   CTGGTCCGAT CCTTGGCATT GGGCTCAGGC TGCAATCGTC GCAGCGTGCA
16101   GAACACATGG GATTTTACCC GTTGACGGCC CGTTCGGTGA CTTCTCTGAT
16151   GACGAAGGAT TCAGGGCACA AGCTCGAAGG TCCGCTACTC TTGGAATGGT
16201   GGGAAAATGG GCCATACATC CAAAGCAAGT GGCTCTCGCT AATGAAGTGT
16251   TTACACCTAG CGAGACTGCA GTAACCGAAG CGAGGGAGAT TTTAGCGGCT
16301   ATGGATGCTG CTAAGGCGAG AGGCGAAGGT GCTACCGTGT ACAAAGGTAG
16351   GCTGGTAGAT ATCGCGTCGA TTAAACAGGC AGAAGTCATT GTTCGTCAGG
16401   CTGAGATGAT TAGTGCATGA ACTAGTTGAG TAATTCTGAT ATTAGAGGGA
16451   GCATTAATGT GTTGTTGTGA TGTGGTTTAT ATGGGGAAAT TAAATAAATG
16501   ATGTATGTAC CTCTTGCCTA TGTAGGTTTG TGTGTTTTGT TTTGTTGTCT
16551   AGCTTTGGTT ATTAAGTAGT AGGGACGTTC GTTCGTGTCT CAAAAAAAGG
16601   GGTACTACCA CTCTGTAGTG TATATGGATG CTGGAAATCA ATGTGTTTTG
16651   TATTTGTTCA CCTCCATTGT TGAATTCAAT GTCAAATGTG TTTTGCGTTG
16701   GTTATGTGTA AAATTACTAT CTTTCTCGTC CGATGATCAA AGTTTTAAGC
16751   AACAAAACCA AGGGTGAAAT TTAAACTGTG CTTTGTTGAA GATTCTTTTA
16801   TCATATTGAA AATCAAATTA CTAGCAGCAG ATTTTACCTA GCATGAAATT
16851   TTATCAACAG TACAGCACTC ACTAACCAAG TTCCAAACTA AGATGCGCCA
16901   TTAACATCAG CCAATAGGCA TTTTCAGCAA GTTTAAACTC CGGATACGTA
16951   GTGTTTATCT TTGTTGCTTT TCTGAACAAT TTATTTACTA TGTAAATATA
17001   TTATCAATGT TTAATCTATT TTAATTTGCA CATGAATTTT CATTTTATTT
17051   TTACTTTACA AAACAAATAA ATATATATGC AAAAAAATTT ACAAACGATG
17101   CACGGGTTAC AAACTAATTT CATTAAATGC TAATGCAGAT TTTGTGAAGT
17151   AAAACTCCAA TTATGATGAA AAATACCACC AACACCACCT GCGAAACTGT
17201   ATCCCAACTG TCCTTAATAA AAATGTTAAA AAGTATATTA TTCTCATTTG
17251   TCTGTCATAA TTTATGTACC CCACTTTAAT TTTTCTGATG TACTAAACCG
17301   AGGGCAAACT GAAACCTGTT CCTCATGCAA AGCCCCTACT CACCATGTAT
17351   CATGTACGTG TCATCACCCA ACAACTCCAC TTTTGCTATA TAACAACACC
17401   CCCGTCACAC TCTCCCTCTC TAACACACAC CCCACTAACA ATTCCTTCAC
17451   TTGCAGCACT GTTGCATCAT CATCTTCATT GCAAAACCCT AAACTTCACC
17501   TTCAACCGCG GCCGCCCTAG GAAAATGGCT TCTATGATAT CCTCTTCCGC
17551   TGTGACAACA GTCAGCCGTG CCTCTAGGGG GCAATCCGCC GCAGTGGCTC
17601   CATTCGGCGG CCTCAAATCC ATGACTGGAT TCCCAGTGAA GAAGGTCAAC
17651   ACTGACATTA CTTCCATTAC AAGCAATGGT GGAAGAGTAA AGTGCATGCA
17701   GGTGTGGCCT CCAATTGGAA AGAAGAAGTT TGAGACTCTT TCCTATTTGC
17751   CACCATTGAC GAGAGATTCT AGAGTTGCAC AGTACCAAGA CGATATCAAG
17801   GCGGTTGCAG GGCTTAAGGA GAATCACGGC TCCGCATGGA ATGCCATCAA
17851   CCCGGAGTAT GCCGCCAGGA TGAGGGCGCA GAACAAGTTC AAGACGGGCC
17901   TTGACATTGC AAAGTATACG GCTAAGATTA TGCGGGCCGA TATGGCAGCC
17951   TACGACGCCG ACAGCTCGAA GTACACACAG AGCCTCGGTT GTTGGCATGG
18001   TTTCATTGGT CAGCAGAAGA TGATCTCAAT CAAGAAACAT TTCAACAGCA
18051   CGGAACGCCG TTACCTCTAC CTTTCTGGCT GGATGGTAGC CGCGCTTAGA
18101   TCCGAGTTTG GCCCCCTACC GGATCAGTCC ATGCACGAAA AGACGAGTGT
18151   CTCCGCACTC ATTCGGGAAC TCTACACTTT TCTGCGCCAA GCGGACGCTA
18201   GGGAGTTGGG GGGCCTGTTT CGGGAGCTTG ACGCGGCCCA AGGCCCAGCT
18251   AAGGCGGCCA TTCAAGCGAA GATCGACAAC CACGTCACTC ATGTGGTCCC
18301   AATCATAGCT GATATCGACG CTGGCTTCGG CAATGCGGAA GCAACATACC
18351   TGTTGGCCAA GCAGTTCATC GAGGCCGGGG CTTGCTGCAT ACAGATAGAG
18401   AACCAGGTTT CTGACGAAAA GCAATGTGGA CATCAAGACG GAAAGGTTAC
18451   CGTGCCCCAC GAGGATTTTC TTGCAAAAAT CCGAGCGATT CGTTATGCGT
18501   TTTTAGAGTT GGGCGTGGAT GACGGTATCA TCGTGGCCAG GACCGATAGT
18551   CTCGGTGCTG GTCTGACAAA GCAAATCGCA GTGACCAATA CGCCTGGAGA
18601   CTTAGGGGAT CAGTACAACA GCTTCCTCGA TTGCGAGGAG CTTAGCGCAG
18651   ATCAGCTCGG AAATGGCGAC GTTATCATCA AGCGTGATGG AAAGCTACTC
18701   CGCCCCAAGC GCCTCCCGTC TAACTTGTTC CAGTTCCGGG CTGGAACTGG
```

FIG. 21H DNA Sequence of pMBXS1022 (Cont'd)

```
18751   CGAAGCGCGA TGCGTCCTGG ACTGCGTGAC CGCGCTCCAG AACGGCGCCG
18801   ACCTACTCTG GATTGAGACA GAAAAGCCTC ACATAGCTCA AATCGGCGGA
18851   ATGGTATCGG AGATAAGGAA AGTCATACCC AACGCCAAAC TGGTGTACAA
18901   CAACTCTCCG TCGTTCAATT GGACCCTGAA CTTTAGACAG CAAGCATACG
18951   ATGCTATGAA AGCCGCTGGG AAAGACGTGT CAGCATACGA CCGCGCCCAG
19001   CTTATGTCCG TGGAGTACGA CCAAACGGAA CTGGCTAAGC TGGCTGATGA
19051   GAAAATCAGA ACATTCCAGG CCGACGCCTC AAGGGAGGCC GGGATCTTCC
19101   ATCACTTGAT TACCTTACCA ACATATCACA CTGCGGCCCT GTCAACCGAC
19151   AATTTGGCTA AGGAGTACTT CGGAGATCAG GGGATGCTCG GTTATGTCGC
19201   GGGCGTTCAG AGGAAGGAGA TCCGACAGGG CATCGCATGT GTCAAGCACC
19251   AAAACATGAG CGGGAGTGAC ATCGGGGATG ATCATAAAGA GTATTTCTCC
19301   GGCGAAGCCG CGCTGAAGGC CGCCGGCAAA GACAACACTA TGAATCAATT
19351   CTGACCCGGG TGAGTAATTC TGATATTAGA GGGAGCATTA ATGTGTTGTT
19401   GTGATGTGGT TTATATGGGG AAATTAAATA AATGATGTAT GTACCTCTTG
19451   CCTATGTAGG TTTGTGTGTT TTGTTTTGTT GTCTAGCTTT GGTTATTAAG
19501   TAGTAGGGAC GTTCGTTCGT GTCTCAAAAA AAGGGGTACT ACCACTCTGT
19551   AGTGTATATG GATGCTGGAA ATCAATGTGT TTTGTATTTG TTCACCTCCA
19601   TTGTTGAATT CAATGTCAAA TGTGTTTTGC GTTGGTTATG TGTAAAATTA
19651   CTATCTTTCT CGTCCGATGA TCAAAGTTTT AAGCAACAAA ACCAAGGGTG
19701   AAATTTAAAC TGTGCTTTGT TGAAGATTCT TTTATCATAT TGAAAATCAA
19751   ATTACTAGCA GCAGATTTTA CCTAGCATGA AATTTTATCA ACAGTACAGC
19801   ACTCACTAAC CAAGTTCCAA ACTAAGATGC GCCATTAACA TCAGCCAATA
19851   GGCATTTTCA GCAAGCTCGA GTCACGTAGT GGTACGTAGT GTTTATCTTT
19901   GTTGCTTTTC TGAACAATTT ATTTACTATG TAAATATATT ATCAATGTTT
19951   AATCTATTTT AATTTGCACA TGAATTTTCA TTTTATTTTT ACTTTACAAA
20001   ACAAATAAAT ATATATGCAA AAAAATTTAC AAACGATGCA CGGGTTACAA
20051   ACTAATTTCA TTAAATGCTA ATGCAGATTT TGTGAAGTAA AACTCCAATT
20101   ATGATGAAAA ATACCACCAA CACCACCTGC GAAACTGTAT CCCAACTGTC
20151   CTTAATAAAA ATGTTAAAAA GTATATTATT CTCATTTGTC TGTCATAATT
20201   TATGTACCCC ACTTTAATTT TTCTGATGTA CTAAACCGAG GGCAAACTGA
20251   AACCTGTTCC TCATGCAAAG CCCCTACTCA CCATGTATCA TGTACGTGTC
20301   ATCACCCAAC AACTCCACTT TTGCTATATA ACAACACCCC CGTCACACTC
20351   TCCCTCTCTA ACACACACCC CACTAACAAT TCCTTCACTT GCAGCACTGT
20401   TGCATCATCA TCTTCATTGC AAAACCCTAA ACTTCACCTT CAACCGCGGC
20451   CGCTTCGAAG GATCCAAAAT GGTGAGCAAG GGCGAGGAGC TGTTCACCGG
20501   GGTGGTGCCC ATCCTGGTCG AGCTGGACGG CGACGTAAAC GGCCACAAGT
20551   TCAGCGTGTC CGGCGAGGGC GAGGGCGATG CCACCTACGG CAAGCTGACC
20601   CTGAAGTTCA TCTGCACCAC CGGCAAGCTG CCCGTGCCCT GGCCCACCCT
20651   CGTGACCACC TTCACCTACG GCGTGCAGTG CTTCAGCCGC TACCCCGACC
20701   ACATGAAGCA GCACGACTTC TTCAAGTCCG CCATGCCCGA AGGCTACGTC
20751   CAGGAGCGCA CCATCTTCTT CAAGGACGAC GGCAACTACA AGACCCGCGC
20801   CGAGGTGAAG TTCGAGGGCG ACACCCTGGT GAACCGCATC GAGCTGAAGG
20851   GCATCGACTT CAAGGAGGAC GGCAACATCC TGGGGCACAA GCTGGAGTAC
20901   AACTACAACA GCCACAACGT CTATATCATG GCCGACAAGC AGAAGAACGG
20951   CATCAAGGTG AACTTCAAGA TCCGCCACAA CATCGAGGAC GGCAGCGTGC
21001   AGCTCGCCGA CCACTACCAG CAGAACACCC CCATCGGCGA CGGCCCCGTG
21051   CTGCTGCCCG ACAACCACTA CCTGAGCACC CAGTCCGCCC TGAGCAAAGA
21101   CCCCAACGAG AAGCGCGATC ACATGGTCCT GCTGGAGTTC GTGACCGCCG
21151   CCGGGATCAC TCACGGCATG GACGAGCTGT ACAAGTAAAG CGGCCGCCCG
21201   GGCTGCAGTT CGAAATTTAA ATGCGGCCGC TGAGTAATTC TGATATTAGA
21251   GGGAGCATTA ATGTGTTGTT GTGATGTGGT TTATATGGGG AAATTAAATA
21301   AATGATGTAT GTACCTCTTG CCTATGTAGG TTTGTGTGTT TTGTTTTGTT
21351   GTCTAGCTTT GGTTATTAAG TAGTAGGGAC GTTCGTTCGT GTCTCAAAAA
21401   AAGGGGTACT ACCACTCTGT AGTGTATATG GATGCTGGAA ATCAATGTGT
```

FIG. 21I DNA Sequence of pMBXS1022 (Cont'd)

```
21451   TTTGTATTTG TTCACCTCCA TTGTTGAATT CAATGTCAAA TGTGTTTTGC
21501   GTTGGTTATG TGTAAAATTA CTATCTTTCT CGTCCGATGA TCAAAGTTTT
21551   AAGCAACAAA ACCAAGGGTG AAATTTAAAC TGTGCTTTGT TGAAGATTCT
21601   TTTATCATAT TGAAAATCAA ATTACTAGCA GCAGATTTTA CCTAGCATGA
21651   AATTTTATCA ACAGTACAGC ACTCACTAAC CAAGTTCCAA ACTAAGATGC
21701   GCCATTAACA TCAGCCAATA GGCATTTTCA GCAACCTCAG CGTTTAAACG
21751   TACGTAGTGT TTATCTTTGT TGCTTTTCTG AACAATTTAT TTACTATGTA
21801   AATATATTAT CAATGTTTAA TCTATTTTAA TTTGCACATG AATTTTCATT
21851   TTATTTTTAC TTTACAAAAC AAATAAATAT ATATGCAAAA AAATTTACAA
21901   ACGATGCACG GGTTACAAAC TAATTTCATT AAATGCTAAT GCAGATTTTG
21951   TGAAGTAAAA CTCCAATTAT GATGAAAAAT ACCACCAACA CCACCTGCGA
22001   AACTGTATCC CAACTGTCCT TAATAAAAAT GTTAAAAAGT ATATTATTCT
22051   CATTTGTCTG TCATAATTTA TGTACCCCAC TTTAATTTTT CTGATGTACT
22101   AAACCGAGGG CAAACTGAAA CCTGTTCCTC ATGCAAAGCC CCTACTCACC
22151   ATGTATCATG TACGTGTCAT CACCCAACAA CTCCACTTTT GCTATATAAC
22201   AACACCCCCG TCACACTCTC CCTCTCTAAC ACACACCCCA CTAACAATTC
22251   CTTCACTTGC AGCACTGTTG CATCATCATC TTCATTGCAA AACCCTAAAC
22301   TTCACCTTCA ACCGCGGCCG CTTCGAAAAA ATGGCTTCTA TGATATCCTC
22351   TTCCGCTGTG ACAACAGTCA GCCGTGCCTC TAGGGGGCAA TCCGCCGCAG
22401   TGGCTCCATT CGGCGGCCTC AAATCCATGA CTGGATTCCC AGTGAAGAAG
22451   GTCAACACTG ACATTACTTC CATTACAAGC AATGGTGGAA GAGTAAAGTG
22501   CATGCAGGTG TGGCCTCCAA TTGGAAAGAA GAAGTTTGAG ACTCTTTCCT
22551   ATTTGCCACC ATTGACGAGA GATTCTAGAG TCACCGAGCA AGCCACAACG
22601   ACAGATGAAC TCGCTTTTAC TAGGCCATAT GGTGAACAGG AAAAGCAAAT
22651   TCTTACAGCA GAAGCTGTTG AGTTTTTGAC CGAGTTGGTT ACTCACTTTA
22701   CACCTCAAAG AAACAAGTTA CTCGCAGCAC GTATCCAGCA GCAACAAGAC
22751   ATAGATAATG GTACACTTCC AGATTTCATT TCGGAGACTG CATCTATTCG
22801   AGATGCCGAT TGGAAAATCA GGGGTATCCC CGCAGATTTA GAAGATAGGA
22851   GAGTTGAAAT AACCGGACCT GTAGAAAGAA AAATGGTCAT CAACGCTCTA
22901   AACGCCAACG TCAAAGTGTT TATGGCTGAT TTTGAGGACT CGCTAGCACC
22951   TGATTGGAAC AAGGTGATAG ATGGCCAGAT CAATTTGAGA GATGCTGTCA
23001   ATGGGACAAT CTCCTATACT AATGAGGCTG GAAAGATTTA TCAACTCAAA
23051   CCTAATCCGG CAGTGCTGAT TTGTAGGGTT CGTGGATTAC ACCTGCCTGA
23101   AAAGCATGTT ACGTGGCGTG GGGAAGCAAT TCCTGGCAGC CTTTTTGACT
23151   TCGCTCTTTA CTTTTTCCAT AACTACCAGG CGCTGTTGGC TAAGGGGTCA
23201   GGTCCATATT TCTATCTTCC GAAAACTCAA AGTTGGCAAG AAGCTGCCTG
23251   GTGGTCTGAG GTGTTCTCCT ATGCAGAGGA TCGTTTCAAT TTACCACGAG
23301   GTACGATCAA AGCAACTCTG TTAATTGAGA CACTCCCGGC TGTGTTTCAA
23351   ATGGACGAGA TACTACACGC TCTCAGGGAC CACATTGTTG GTCTTAATTG
23401   CGGAAGATGG GACTATATCT TCTCCTACAT CAAGACTCTA AAGAACTACC
23451   CGGATAGAGT TCTGCCTGAC CGTCAAGCTG TTACTATGGA TAAACCATTT
23501   CTTAATGCTT ACTCTAGACT CTTGATTAAG ACCTGTCATA AGCGTGGAGC
23551   CTTCGCAATG GGCGGAATGG CCGCTTTTAT CCCGTCAAAA GATGAAGAGC
23601   ACAACAATCA GGTTTTGAAC AAGGTAAAAG CGGATAAATC TCTTGAAGCC
23651   AATAATGGGC ATGATGGCAC TTGGATTGCT CATCCAGGTC TAGCTGATAC
23701   AGCGATGGCT GTATTCAACG ACATCTTGGG TTCAAGAAAG AATCAACTTG
23751   AAGTGATGAG AGAGCAAGAC GCGCCAATAA CAGCTGATCA ACTTTTGGCG
23801   CCATGCGATG GTGAACGAAC GGAAGAAGGT ATGAGAGCCA ATATCCGAGT
23851   TGCTGTGCAG TACATAGAGG CTTGGATTTC AGGAAACGGG TGTGTCCCCA
23901   TTTATGGACT CATGGAAGAT GCGGCTACTG CTGAAATTAG CAGGACCTCT
23951   ATTTGGCAGT GGATACATCA TCAAAAGACA TTAAGCAACG GAAAACCTGT
24001   TACTAAGGCC CTCTTCAGGC AGATGCTTGG GGAAGAGATG AAAGTAATTG
24051   CGAGTGAGTT GGGAGAAGAG AGATTTTCTC AGGGTAGATT TGATGACGCA
24101   GCGAGGTTGA TGGAGCAGAT CACCACCAGT GACGAGCTCA TAGATTTCTT
```

FIG. 21J DNA Sequence of pMBXS1022 (Cont'd)

```
24151   AACGTTGCCT GGATACCGAC TACTTGCTTG AATTTAAATG CGGCCGCTGA
24201   GTAATTCTGA TATTAGAGGG AGCATTAATG TGTTGTTGTG ATGTGGTTTA
24251   TATGGGGAAA TTAAATAAAT GATGTATGTA CCTCTTGCCT ATGTAGGTTT
24301   GTGTGTTTTG TTTTGTTGTC TAGCTTTGGT TATTAAGTAG TAGGGACGTT
24351   CGTTCGTGTC TCAAAAAAAG GGGTACTACC ACTCTGTAGT GTATATGGAT
24401   GCTGGAAATC AATGTGTTTT GTATTTGTTC ACCTCCATTG TTGAATTCAA
24451   TGTCAAATGT GTTTTGCGTT GGTTATGTGT AAAATTACTA TCTTTCTCGT
24501   CCGATGATCA AAGTTTTAAG CAACAAAACC AAGGGTGAAA TTTAAACTGT
24551   GCTTTGTTGA AGATTCTTTT ATCATATTGA AAATCAAATT ACTAGCAGCA
24601   GATTTTACCT AGCATGAAAT TTTATCAACA GTACAGCACT CACTAACCAA
24651   GTTCCAAACT AAGATGCGCC ATTAACATCA GCCAATAGGC ATTTTCAGCA
24701   AAGCAAATGA ATTCGTAATC ATGTCATAGC TGTTTCCTGT GTGAAATTGT
24751   TATCCGCTCA CAATTCCACA CAACATACGA GCCGGAAGCA TAAAGTGTAA
24801   AGCCTGGGGT GCCTAATGAG TGAGCTAACT CACATTAATT GCGTTGCGCT
24851   CACTGCCCGC TTTCCAGTCG GGAAACCTGT CGTGCCAGCT GCATTAATGA
24901   ATCGGCCAAC GCGCGGGGAG AGGCGGTTTG CGTATTGGCT AGAGCAGCTT
24951   GCCAACATGG TGGAGCACGA CACTCTCGTC TACTCCAAGA ATATCAAAGA
25001   TACAGTCTCA GAAGACCAAA GGGCTATTGA GACTTTTCAA CAAAGGGTAA
25051   TATCGGGAAA CCTCCTCGGA TTCCATTGCC CAGCTATCTG TCACTTCATC
25101   AAAAGGACAG TAGAAAAGGA AGGTGGCACC TACAAATGCC ATCATTGCGA
25151   TAAAGGAAAG GCTATCGTTC AAGATGCCTC TGCCGACAGT GGTCCCAAAG
25201   ATGGACCCCC ACCCACGAGG AGCATCGTGG AAAAAGAAGA CGTTCCAACC
25251   ACGTCTTCAA AGCAAGTGGA TTGATGTGAA CATGGTGGAG CACGACACTC
25301   TCGTCTACTC CAAGAATATC AAAGATACAG TCTCAGAAGA CCAAAGGGCT
25351   ATTGAGACTT TTCAACAAAG GGTAATATCG GGAAACCTCC TCGGATTCCA
25401   TTGCCCAGCT ATCTGTCACT TCATCAAAAG GACAGTAGAA AAGGAAGGTG
25451   GCACCTACAA ATGCCATCAT TGCGATAAAG GAAAGGCTAT CGTTCAAGAT
25501   GCCTCTGCCG ACAGTGGTCC CAAAGATGGA CCCCCACCCA CGAGGAGCAT
25551   CGTGGAAAAA GAAGACGTTC CAACCACGTC TTCAAAGCAA GTGGATTGAT
25601   GTGATATCTC CACTGACGTA AGGGATGACG CACAATCCCA CTATCCTTCG
25651   CAAGACCCTT CCTCTATATA AGGAAGTTCA TTTCATTTGG AGAGGACACG
25701   CTGAAATCAC CAGTCTCTCT CTACAAATCT ATCTCTCTCG AGAAAATGGT
25751   GAGCAAGGGC GAGGAGCTGT TCACCGGGGT GGTGCCCATC CTGGTCGAGC
25801   TGGACGGCGA CGTAAACGGC CACAAGTTCA GCGTGTCCGG CGAGGGCGAG
25851   GGCGATGCCA CCTACGGCAA GCTGACCCTG AAGTTCATCT GCACCACCGG
25901   CAAGCTGCCC GTGCCCTGGC CCACCCTCGT GACCACCTTC ACCTACGGCG
25951   TGCAGTGCTT CAGCCGCTAC CCCGACCACA TGAAGCAGCA CGACTTCTTC
26001   AAGTCCGCCA TGCCCGAAGG CTACGTCCAG GAGCGCACCA TCTTCTTCAA
26051   GGACGACGGC AACTACAAGA CCCGCGCCGA GGTGAAGTTC GAGGGCGACA
26101   CCCTGGTGAA CCGCATCGAG CTGAAGGGCA TCGACTTCAA GGAGGACGGC
26151   AACATCCTGG GGCACAAGCT GGAGTACAAC TACAACAGCC ACAACGTCTA
26201   TATCATGGCC GACAAGCAGA AGAACGGCAT CAAGGTGAAC TTCAAGATCC
26251   GCCACAACAT CGAGGACGGC AGCGTGCAGC TCGCCGACCA CTACCAGCAG
26301   AACACCCCCA TCGGCGACGG CCCCGTGCTG CTGCCCGACA ACCACTACCT
26351   GAGCACCCAG TCCGCCCTGA GCAAAGACCC CAACGAGAAG CGCGATCACA
26401   TGGTCCTGCT GGAGTTCGTG ACCGCCGCCG GGATCACTCA CGGCATGGAC
26451   GAGCTGTACA AGTAAGAGCT CGGTCACCTG TCCAACAGTC TCAGGGTTAA
26501   TGTCTATGTA TCTTAAATAA TGTTGTCGGC GATCGTTCAA ACATTTGGCA
26551   ATAAAGTTTC TTAAGATTGA ATCCTGTTGC CGGTCTTGCG ATGATTATCA
26601   TATAATTTCT GTTGAATTAC GTTAAGCATG TAATAATTAA CATGTAATGC
26651   ATGACGTTAT TTATGAGATG GGTTTTTATG ATTAGAGTCC CGCAATTATA
26701   CATTTAATAC GCGATAGAAA ACAAAATATA GCGCGCAAAC TAGGATAAAT
26751   TATCGCGCGC GGTGTCATCT ATGTTACTAG ATCGGGAATT AAACTATCAG
26801   TGTTTGACAG GATATATTGG CGGGTAAACC TAAGAGAAAA GAGCGTTTAT
```

FIG. 21K DNA Sequence of pMBXS1022 (Cont'd)

```
26851   TAGAATAATC GGATATTTAA AAGGGCGTGA AAAGGTTTAT CCGTTCGTCC
26901   ATTTGTATGT GCATGCCAAC CACAGGGTTC CCCTCGGGAT CAAAGTACTT
26951   TGATCCAACC CCTCCGCTGC TATAGTGCAG TCGGCTTCTG ACGTTCAGTG
27001   CAGCCGTCTT CTGAAAACGA CATGTCGCAC AAGTCCTAAG TTACGCGACA
27051   GGCTGCCGCC CTGCCCTTTT CCTGGCGTTT TCTTGTCGCG TGTTTTAGTC
27101   GCATAAAGTA GAATACTTGC GACTAGAACC GGAGACATTA CGCCATGAAC
27151   AAGAGCGCCG CCGCTGGCCT GCTGGGCTAT GCCCGCGTCA GCACCGACGA
27201   CCAGGACTTG ACCAACCAAC GGGCCGAACT GCACGCGGCC GGCTGCACCA
27251   AGCTGTTTTC CGAGAAGATC ACCGGCACCA GGCGCGACCG CCCGGAGCTG
27301   GCCAGGATGC TTGACCACCT ACGCCCTGGC GACGTTGTGA CAGTGACCAG
27351   GCTAGACCGC CTGGCCCGCA GCACCCGCGA CCTACTGGAC ATTGCCGAGC
27401   GCATCCAGGA GGCCGGCGCG GGCCTGCGTA GCCTGGCAGA GCCGTGGGCC
27451   GACACCACCA CGCCGGCCGG CCGCATGGTG TTGACCGTGT TCGCCGGCAT
27501   TGCCGAGTTC GAGCGTTCCC TAATCATCGA CCGCACCCGG AGCGGGCGCG
27551   AGGCCGCCAA GGCCCGAGGC GTGAAGTTTG GCCCCCGCCC TACCCTCACC
27601   CCGGCACAGA TCGCGCACGC CCGCGAGCTG ATCGACCAGG AAGGCCGCAC
27651   CGTGAAAGAG GCGGCTGCAC TGCTTGGCGT GCATCGCTCG ACCCTGTACC
27701   GCGCACTTGA GCGCAGCGAG GAAGTGACGC CCACCGAGGC CAGGCGGCGC
27751   GGTGCCTTCC GTGAGGACGC ATTGACCGAG GCCGACGCCC TGGCGGCCGC
27801   CGAGAATGAA CGCCAAGAGG AACAAGCATG AAACCGCACC AGGACGGCCA
27851   GGACGAACCG TTTTTCATTA CCGAAGAGAT CGAGGCGGAG ATGATCGCGG
27901   CCGGGTACGT GTTCGAGCCG CCCGCGCACG TCTCAACCGT GCGGCTGCAT
27951   GAAATCCTGG CCGGTTTGTC TGATGCCAAG CTGGCGGCCT GGCCGGCCAG
28001   CTTGGCCGCT GAAGAAACCG AGCGCCGCCG TCTAAAAAGG TGATGTGTAT
28051   TTGAGTAAAA CAGCTTGCGT CATGCGGTCG CTGCGTATAT GATGCGATGA
28101   GTAAATAAAC AAATACGCAA GGGGAACGCA TGAAGGTTAT CGCTGTACTT
28151   AACCAGAAAG GCGGGTCAGG CAAGACGACC ATCGCAACCC ATCTAGCCCG
28201   CGCCCTGCAA CTCGCCGGGG CCGATGTTCT GTTAGTCGAT TCCGATCCCC
28251   AGGGCAGTGC CCGCGATTGG GCGGCCGTGC GGGAAGATCA ACCGCTAACC
28301   GTTGTCGGCA TCGACCGCCC GACGATTGAC CGCGACGTGA AGGCCATCGG
28351   CCGGCGCGAC TTCGTAGTGA TCGACGGAGC GCCCCAGGCG GCGGACTTGG
28401   CTGTGTCCGC GATCAAGGCA GCCGACTTCG TGCTGATTCC GGTGCAGCCA
28451   AGCCCTTACG ACATATGGGC CACCGCCGAC CTGGTGGAGC TGGTTAAGCA
28501   GCGCATTGAG GTCACGGATG GAAGGCTACA AGCGGCCTTT GTCGTGTCGC
28551   GGGCGATCAA AGGCACGCGC ATCGGCGGTG AGGTTGCCGA GGCGCTGGCC
28601   GGGTACGAGC TGCCCATTCT TGAGTCCCGT ATCACGCAGC GCGTGAGCTA
28651   CCCAGGCACT GCCGCCGCCG GCACAACCGT TCTTGAATCA GAACCCGAGG
28701   GCGACGCTGC CCGCGAGGTC CAGGCGCTGG CCGCTGAAAT TAAATCAAAA
28751   CTCATTTGAG TTAATGAGGT AAAGAGAAAA TGAGCAAAAG CACAAACACG
28801   CTAAGTGCCG GCCGTCCGAG CGCACGCAGC AGCAAGGCTG CAACGTTGGC
28851   CAGCCTGGCA GACACGCCAG CCATGAAGCG GGTCAACTTT CAGTTGCCGG
28901   CGGAGGATCA CACCAAGCTG AAGATGTACG CGGTACGCCA AGGCAAGACC
28951   ATTACCGAGC TGCTATCTGA ATACATCGCG CAGCTACCAG AGTAAATGAG
29001   CAAATGAATA AATGAGTAGA TGAATTTTAG CGGCTAAAGG AGGCGGCATG
29051   GAAAATCAAG AACAACCAGG CACCGACGCC GTGGAATGCC CCATGTGTGG
29101   AGGAACGGGC GGTTGGCCAG GCGTAAGCGG CTGGGTTGCC TGCCGGCCCT
29151   GCAATGGCAC TGGAACCCCC AAGCCCGAGG AATCGGCGTG AGCGGTCGCA
29201   AACCATCCGG CCCGGTACAA ATCGGCGCGG CGCTGGGTGA TGACCTGGTG
29251   GAGAAGTTGA AGGCCGCGCA GGCCGCCCAG CGGCAACGCA TCGAGGCAGA
29301   AGCACGCCCC GGTGAATCGT GGCAAGCGGC CGCTGATCGA ATCCGCAAAG
29351   AATCCCGGCA ACCGCCGGCA GCCGGTGCGC CGTCGATTAG GAAGCCGCCC
29401   AAGGGCGACG AGCAACCAGA TTTTTTCGTT CCGATGCTCT ATGACGTGGG
29451   CACCCGCGAT AGTCGCAGCA TCATGGACGT GGCCGTTTTC CGTCTGTCGA
29501   AGCGTGACCG ACGAGCTGGC GAGGTGATCC GCTACGAGCT TCCAGACGGG
```

FIG. 21L DNA Sequence of pMBXS1022 (Cont'd)

```
29551  CACGTAGAGG TTTCCGCAGG GCCGGCCGGC ATGGCCAGTG TGTGGGATTA
29601  CGACCTGGTA CTGATGGCGG TTTCCCATCT AACCGAATCC ATGAACCGAT
29651  ACCGGGAAGG GAAGGGAGAC AAGCCCGGCC GCGTGTTCCG TCCACACGTT
29701  GCGGACGTAC TCAAGTTCTG CCGGCGAGCC GATGGCGGAA AGCAGAAAGA
29751  CGACCTGGTA GAAACCTGCA TTCGGTTAAA CACCACGCAC GTTGCCATGC
29801  AGCGTACGAA GAAGGCCAAG AACGGCCGCC TGGTGACGGT ATCCGAGGGT
29851  GAAGCCTTGA TTAGCCGCTA CAAGATCGTA AAGAGCGAAA CCGGGCGGCC
29901  GGAGTACATC GAGATCGAGC TAGCTGATTG GATGTACCGC GAGATCACAG
29951  AAGGCAAGAA CCCGGACGTG CTGACGGTTC ACCCCGATTA CTTTTTGATC
30001  GATCCCGGCA TCGGCCGTTT TCTCTACCGC CTGGCACGCC GCGCCGCAGG
30051  CAAGGCAGAA GCCAGATGGT TGTTCAAGAC GATCTACGAA CGCAGTGGCA
30101  GCGCCGGAGA GTTCAAGAAG TTCTGTTTCA CCGTGCGCAA GCTGATCGGG
30151  TCAAATGACC TGCCGGAGTA CGATTTGAAG GAGGAGGCGG GGCAGGCTGG
30201  CCCGATCCTA GTCATGCGCT ACCGCAACCT GATCGAGGGC GAAGCATCCG
30251  CCGGTTCCTA ATGTACGGAG CAGATGCTAG GGCAAATTGC CCTAGCAGGG
30301  GAAAAAGGTC GAAAAGGTCT CTTTCCTGTG GATAGCACGT ACATTGGGAA
30351  CCCAAAGCCG TACATTGGGA ACCGGAACCC GTACATTGGG AACCCAAAGC
30401  CGTACATTGG GAACCGGTCA CACATGTAAG TGACTGATAT AAAAGAGAAA
30451  AAAGGCGATT TTTCCGCCTA AAACTCTTTA AAACTTATTA AAACTCTTAA
30501  AACCCGCCTG GCCTGTGCAT AACTGTCTGG CCAGCGCACA GCCGAAGAGC
30551  TGCAAAAAGC GCCTACCCTT CGGTCGCTGC GCTCCCTACG CCCCGCCGCT
30601  TCGCGTCGGC CTATCGCGGC CGCTGGCCGC TCAAAAATGG CTGGCCTACG
30651  GCCAGGCAAT CTACCAGGGC GCGGACAAGC CGCGCCGTCG CCACTCGACC
30701  GCCGGCGCCC ACATCAAGGC ACCCTGCCTC GCGCGTTTCG GTGATGACGG
30751  TGAAAACCTC TGACACATGC AGCTCCCGGA GACGGTCACA GCTTGTCTGT
30801  AAGCGGATGC CGGGAGCAGA CAAGCCCGTC AGGGCGCGTC AGCGGGTGTT
30851  GGCGGGTGTC GGGGCGCAGC CATGACCCAG TCACGTAGCG ATAGCGGAGT
30901  GTATACTGGC TTAACTATGC GGCATCAGAG CAGATTGTAC TGAGAGTGCA
30951  CCATATGCGG TGTGAAATAC CGCACAGATG CGTAAGGAGA AAATACCGCA
31001  TCAGGCGCTC TTCCGCTTCC TCGCTCACTG ACTCGCTGCG CTCGGTCGTT
31051  CGGCTGCGGC GAGCGGTATC AGCTCACTCA AAGGCGGTAA TACGGTTATC
31101  CACAGAATCA GGGGATAACG CAGGAAAGAA CATGTGAGCA AAAGGCCAGC
31151  AAAAGGCCAG GAACCGTAAA AAGGCCGCGT TGCTGGCGTT TTTCCATAGG
31201  CTCCGCCCCC CTGACGAGCA TCACAAAAAT CGACGCTCAA GTCAGAGGTG
31251  GCGAAACCCG ACAGGACTAT AAAGATACCA GGCGTTTCCC CCTGGAAGCT
31301  CCCTCGTGCG CTCTCCTGTT CCGACCCTGC CGCTTACCGG ATACCTGTCC
31351  GCCTTTCTCC CTTCGGGAAG CGTGGCGCTT TCTCATAGCT CACGCTGTAG
31401  GTATCTCAGT TCGGTGTAGG TCGTTCGCTC CAAGCTGGGC TGTGTGCACG
31451  AACCCCCCGT TCAGCCCGAC CGCTGCGCCT TATCCGGTAA CTATCGTCTT
31501  GAGTCCAACC CGGTAAGACA CGACTTATCG CCACTGGCAG CAGCCACTGG
31551  TAACAGGATT AGCAGAGCGA GGTATGTAGG CGGTGCTACA GAGTTCTTGA
31601  AGTGGTGGCC TAACTACGGC TACACTAGAA GGACAGTATT TGGTATCTGC
31651  GCTCTGCTGA AGCCAGTTAC CTTCGGAAAA AGAGTTGGTA GCTCTTGATC
31701  CGGCAAACAA ACCACCGCTG GTAGCGGTGG TTTTTTTGTT TGCAAGCAGC
31751  AGATTACGCG CAGAAAAAAA GGATCTCAAG AAGATCCTTT GATCTTTTCT
31801  ACGGGGTCTG ACGCTCAGTG GAACGAAAAC TCACGTTAAG GGATTTTGGT
31851  CATGCATTCT AGGTACTAAA ACAATTCATC CAGTAAAATA TAATATTTTA
31901  TTTTCTCCCA ATCAGGCTTG ATCCCCAGTA AGTCAAAAAA TAGCTCGACA
31951  TACTGTTCTT CCCCGATATC CTCCCTGATC GACCGGACGC AGAAGGCAAT
32001  GTCATACCAC TTGTCCGCCC TGCCGCTTCT CCCAAGATCA ATAAAGCCAC
32051  TTACTTTGCC ATCTTTCACA AAGATGTTGC TGTCTCCCAG GTCGCCGTGG
32101  GAAAAGACAA GTTCCTCTTC GGGCTTTTCC GTCTTTAAAA AATCATACAG
32151  CTCGCGCGGA TCTTTAAATG GAGTGTCTTC TTCCCAGTTT TCGCAATCCA
32201  CATCGGCCAG ATCGTTATTC AGTAAGTAAT CCAATTCGGC TAAGCGGCTG
```

FIG. 21M DNA Sequence of pMBXS1022 (Cont'd)

```
32251   TCTAAGCTAT TCGTATAGGG ACAATCCGAT ATGTCGATGG AGTGAAAGAG
32301   CCTGATGCAC TCCGCATACA GCTCGATAAT CTTTTCAGGG CTTTGTTCAT
32351   CTTCATACTC TTCCGAGCAA AGGACGCCAT CGGCCTCACT CATGAGCAGA
32401   TTGCTCCAGC CATCATGCCG TTCAAAGTGC AGGACCTTTG GAACAGGCAG
32451   CTTTCCTTCC AGCCATAGCA TCATGTCCTT TTCCCGTTCC ACATCATAGG
32501   TGGTCCCTTT ATACCGGCTG TCCGTCATTT TTAAATATAG GTTTTCATTT
32551   TCTCCCACCA GCTTATATAC CTTAGCAGGA GACATTCCTT CCGTATCTTT
32601   TACGCAGCGG TATTTTTCGA TCAGTTTTTT CAATTCCGGT GATATTCTCA
32651   TTTTAGCCAT TTATTATTTC CTTCCTCTTT TCTACAGTAT TTAAAGATAC
32701   CCCAAGAAGC TAATTATAAC AAGACGAACT CCAATTCACT GTTCCTTGCA
32751   TTCTAAAACC TTAAATACCA GAAAACAGCT TTTTCAAAGT TGTTTTCAAA
32801   GTTGGCGTAT AACATAGTAT CGACGGAGCC GATTTTGAAA CCGCGGTGAT
32851   CACAGGCAGC AACGCTCTGT CATCGTTACA ATCAACATGC TACCCTCCGC
32901   GAGATCATCC GTGTTTCAAA CCCGGCAGCT TAGTTGCCGT TCTTCCGAAT
32951   AGCATCGGTA ACATGAGCAA AGTCTGCCGC CTTACAACGG CTCTCCCGCT
33001   GACGCCGTCC CGGACTGATG GGCTGCCTGT ATCGAGTGGT GATTTTGTGC
33051   CGAGCTGCCG GTCGGGGAGC TGTTGGCTGG CTGGTGGCAG GATATATTGT
33101   GGTGTAAACA AATTGACGCT TAGACAACTT AATAACACAT TGCGGACGTT
33151   TTTAATGTAC TGAATTAACG CCGAATTAAT T
```

FIG. 22A DNA Sequence of pMBXS1023 (SEQ ID NO:4)

```
   1 AAGGTACGTA GTGTTTATCT TTGTTGCTTT TCTGAACAAT TTATTTACTA
  51 TGTAAATATA TTATCAATGT TTAATCTATT TTAATTTGCA CATGAATTTT
 101 CATTTTATTT TTACTTTACA AAACAAATAA ATATATATGC AAAAAAATTT
 151 ACAAACGATG CACGGGTTAC AAACTAATTT CATTAAATGC TAATGCAGAT
 201 TTTGTGAAGT AAAACTCCAA TTATGATGAA AAATACCACC AACACCACCT
 251 GCGAAACTGT ATCCCAACTG TCCTTAATAA AAATGTTAAA AAGTATATTA
 301 TTCTCATTTG TCTGTCATAA TTTATGTACC CCACTTTAAT TTTTCTGATG
 351 TACTAAACCG AGGGCAAACT GAAACCTGTT CCTCATGCAA AGCCCCTACT
 401 CACCATGTAT CATGTACGTG TCATCACCCA ACAACTCCAC TTTTGCTATA
 451 TAACAACACC CCCGTCACAC TCTCCCTCTC TAACACACAC CCCACTAACA
 501 ATTCCTTCAC TTGCAGCACT GTTGCATCAT CATCTTCATT GCAAAACCCT
 551 AAACTTCACC TTCAACCGGA TCCAAAATGG CTTCTATGAT ATCCTCTTCC
 601 GCTGTGACAA CAGTCAGCCG TGCCTCTAGG GGGCAATCCG CCGCAGTGGC
 651 TCCATTCGGC GGCCTCAAAT CCATGACTGG ATTCCCAGTG AAGAAGGTCA
 701 ACACTGACAT TACTTCCATT ACAAGCAATG GTGGAAGAGT AAAGTGCATG
 751 CAGGTGTGGC CTCCAATTGG AAAGAAGAAG TTTGAGACTC TTTCCTATTT
 801 GCCACCATTG ACGAGAGATT CTAGAGTTGG GAAAAAGATG ATGACTACTG
 851 ATGGGAATAC TGCAACCGCT CACGTAGCTT ATGCGATGTC AGAAGTTGCA
 901 GCTATCTACC CAATCACGCC GTCCAGTACA ATGGGAGAGG AAGCTGATGA
 951 CTGGGCAGCA CAGGGAAGAA AGAATATCTT CGGTCAAACG CTTACGATTA
1001 GGGAGATGCA ATCGGAAGCC GGAGCAGCGG GTGCCGTACA TGGAGCTCTT
1051 GCAGCTGGCG CCTTAACTAC CACCTTTACG GCTTCTCAAG GACTACTCTT
1101 GATGATCCCT AACATGTACA AGATATCAGG AGAATTGCTT CCTGGAGTCT
1151 TTCATGTCAC TGCTAGAGCT ATTGCCGCCC ACGCCCTTTC AATCTTTGGT
1201 GATCATCAGG ATATATATGC AGCGAGGCAG ACAGGGTTCG CTATGCTTGC
1251 TTCAAGCTCG GTGCAAGAAG CACATGACAT GGCTTTAGTT GCCCACCTTG
1301 CCGCCATCGA ATCTAACGTC CCTTTCATGC ATTTCTTCGA CGGGTTTCGC
1351 ACGTCACACG AAATTCAAAA GATTGAAGTT CTCGATTATG CAGATATGGC
1401 ATCCTTAGTG AATCAGAAAG CTCTCGCAGA GTTCCGTGCT AAATCTATGA
1451 ATCCAGAGCA TCCACATGTT CGTGGTACTG CTCAAAACCC TGACATATAT
1501 TTCCAGGGAA GAGAGGCAGC AAACCCGTAT TACTTGAAAG TTCCTGGGAT
1551 TGTAGCAGAG TATATGCAAA AAGTTGCAAG TCTAACAGGG AGATCGTACA
1601 AGCTGTTCGA CTATGTTGGA GCTCCTGATG CTGAGCGTGT CATTGTTTCT
1651 ATGGGTTCCA GTTGCGAGAC AATCGAAGAA GTGATCAATC ACCTCGCTGC
1701 TAAGGGAGAA AAGATTGGTT TGATTAAGGT CCGATTATAC CGTCCATTTG
1751 TATCTGAAGC TTTCTTTGCT GCGTTACCGG CATCTGCTAA GGTTATTACA
1801 GTTCTGGATA GAACTAAGGA GCCCGGAGCT CCTGGCGACC CTTTGTACCT
1851 TGATGTCTGT TCAGCATTCG TCGAAAGGGG AGAAGCTATG CCCAAAATCC
1901 TCGCAGGCCG CTATGGGCTC GGATCTAAGG AGTTTTCACC CGCTATGGTT
1951 AAATCTGTTT ATGATAACAT GAGTGGTGCT AAGAAGAACC ATTTTACCGT
2001 TGGTATAGAG GACGATGTCA CGGGAACATC TCTGCCGGTT GATAATGCGT
2051 TTGCTGATAC AACCCCTAAA GGAACTATCC AGTGTCAGTT CTGGGGTTTG
2101 GGTGCAGATG GTACTGTCGG GGCGAATAAG CAGGCTATCA AAATCATAGG
2151 AGATAACACT GATCTATTCG CTCAAGGTTA CTTTTCATAC GACTCTAAGA
2201 AAAGTGGTGG TATAACTATC AGTCACTTGC GATTTGGAGA AAAGCCAATA
2251 CAATCTACCT ATTTGGTGAA CCGGGCTGAC TACGTTGCTT GTCATAACCC
2301 TGCCTATGTT GGTATATACG ATATTTTAGA GGGTATCAAA GATGGGGGCA
2351 CATTTGTCCT CAATTCTCCC TGGTCGAGTC TTGAAGATAT GGATAAACAT
2401 CTTCCAAGCG GGATTAAGAG AACCATAGCG AATAAGAAGC TTAAGTTTTA
2451 CAACATTGAT GCGGTGAAAA TAGCAACAGA TGTTGGTTTG GGCGGCAGAA
2501 TTAACATGAT AATGCAGACC GCATTCTTCA AACTAGCTGG TGTACTCCCT
2551 TTCGAGAAGG CAGTGGATCT CCTCAAAAAG TCTATTCATA AAGCCTATGG
2601 AAAGAAGGGA GAGAAGATCG TGAAAATGAA TACTGACGCA GTAGATCAAG
2651 CAGTTACGAG CCTTCAAGAG TTCAAGTACC CAGACTCATG GAAGGATGCT
2701 CCAGCAGAGA CAAAAGCTGA GCCAATGACA AACGAGTTCT TCAAAAATGT
2751 TGTCAAGCCT ATCCTCACTC AACAAGGCGA TAAATTACCG GTTTCCGCTT
2801 TTGAAGCCGA TGGACGTTTT CCACTGGGAA CTTCTCAGTT TGAGAAACGC
```

FIG. 22B DNA Sequence of pMBXS1023 (Cont'd)

```
2851  GGAGTGGCTA TTAACGTTCC TCAGTGGGTA CCTGAAAATT GCATCCAATG
2901  CAATCAATGC GCTTTTGTGT GCCCGCATTC CGCGATACTT CCTGTTTTGG
2951  CTAAAGAGGA AGAGTTAGTC GGAGCGCCTG CCAACTTCAC CGCTTTGGAA
3001  GCGAAAGGAA AAGAATTGAA AGGTTACAAA TTCAGAATTC AGATTAACAC
3051  TCTCGACTGC ATGGGCTGCG GAAATTGTGC CGACATATGT CCTCCCAAAG
3101  AAAAGGCTTT AGTGATGCAG CCACTGGACA CTCAGAGGGA TGCCCAAGTG
3151  CCAAATTTGG AGTATGCAGC CAGAATTCCA GTGAAGTCCG AGGTTCTTCC
3201  GCGGGATTCT CTCAAAGGAT CACAATTCCA AGAACCACTG ATGGAGTTTT
3251  CAGGCGCATG TAGTGGATGT GGTGAAACAC CTTACGTACG TGTGATTACT
3301  CAGTTATTTG GAGAACGGAT GTTTATCGCT AATGCAACAG GTTGTAGCTC
3351  GATCTGGGGT GCCAGCGCTC CGTCGATGCC ATACAAGACC AACAGGCTGG
3401  GACAGGGTCC AGCTTGGGGG AATTCCCTAT TCGAGGATGC TGCAGAGTAC
3451  GGGTTCGGAA TGAACATGAG TATGTTTGCG CGTAGAACTC ATCTCGCGGA
3501  TCTTGCTGCT AAAGCTCTCG AGTCTGATGC TTCTGGAGAT GTCAAGGAAG
3551  CATTGCAGGG TTGGCTCGCT GGGAAAAACG ACCCGATTAA GTCTAAAGAA
3601  TACGGGGATA AGTTGAAGAA ACTTCTAGCT GGTCAAAAGG ACGGGTTGTT
3651  GGGACAAATT GCAGCAATGT CAGACCTTTA CACGAAGAAA AGTGTTTGGA
3701  TCTTTGGTGG CGATGGATGG GCGTATGATA TTGGTTATGG TGGCCTTGAT
3751  CACGTCCTCG CAAGCGGCGA AGATGTGAAC GTGTTTGTGA TGGATACTGA
3801  AGTTTACTCC AACACCGGTG GACAATCCTC AAAAGCAACA CCAACCGGGG
3851  CCGTGGCTAA ATTCGCGGCT GCCGGCAAAA GGACTGGAAA AAAGGATCTG
3901  GCCAGAATGG TTATGACTTA TGGATACGTA TATGTAGCTA CAGTATCAAT
3951  GGGCTATAGC AAACAGCAAT TTCTTAAAGT CCTCAAGGAA GCTGAGAGCT
4001  TCCCAGGTCC TTCACTTGTT ATCGCCTACG CGACATGTAT CAATCAAGGT
4051  TTACGAAAGG GAATGGGGAA AAGCCAAGAT GTGATGAACA CCGCTGTTAA
4101  AAGCGGTTAT TGGCCTTTGT TCCGCTATGA TCCTCGTCTT GCGGCCCAAG
4151  GAAAGAATCC GTTTCAGCTA GACTCTAAGG CACCAGACGG TAGTGTTGAG
4201  GAATTTTTGA TGGCTCAGAA TCGATTTGCG GTCCTTGATC GATCGTTCCC
4251  AGAAGATGCC AAGAGGTTGA GGGCGCAAGT TGCACATGAA TTGGATGTTA
4301  GGTTTAAGGA GTTAGAACAC ATGGCGGCTA CAAATATCTT CGAGTCCTTC
4351  GCTCCTGCTG GAGGCAAAGC TGACGGTTCA GTAGATTTTG GAGAAGGCGC
4401  AGAGTTTTGT ACTAGAGATG ACACACCGAT GATGGCCAGA CCAGATAGTG
4451  GCGAAGCATG CGACCAAAAT AGAGCAGGAA CGTCTGAGCA GCAAGGAGAT
4501  TTGTCGAAGA GGACCAAGAA ATGAGGCGCG CCTGAGTAAT TCTGATATTA
4551  GAGGGAGCAT TAATGTGTTG TTGTGATGTG GTTTATATGG GGAAATTAAA
4601  TAAATGATGT ATGTACCTCT TGCCTATGTA GGTTTGTGTG TTTTGTTTTG
4651  TTGTCTAGCT TTGGTTATTA AGTAGTAGGG ACGTTCGTTC GTGTCTCAAA
4701  AAAAGGGGTA CTACCACTCT GTAGTGTATA TGGATGCTGG AAATCAATGT
4751  GTTTTGTATT TGTTCACCTC CATTGTTGAA TTCAATGTCA AATGTGTTTT
4801  GCGTTGGTTA TGTGTAAAAT TACTATCTTT CTCGTCCGAT GATCAAAGTT
4851  TTAAGCAACA AAACCAAGGG TGAAATTTAA ACTGTGCTTT GTTGAAGATT
4901  CTTTTATCAT ATTGAAAATC AAATTACTAG CAGCAGATTT TACCTAGCAT
4951  GAAATTTTAT CAACAGTACA GCACTCACTA ACCAAGTTCC AAACTAAGAT
5001  GCGCCATTAA CATCAGCCAA TAGGCATTTT CAGCAAAAGC TTGTACGTAG
5051  TGTTTATCTT TGTTGCTTTT CTGAACAATT TATTTACTAT GTAAATATAT
5101  TATCAATGTT TAATCTATTT TAATTTGCAC ATGAATTTTC ATTTTATTTT
5151  TACTTTACAA AACAAATAAA TATATATGCA AAAAAATTTA CAAACGATGC
5201  ACGGGTTACA AACTAATTTC ATTAAATGCT AATGCAGATT TTGTGAAGTA
5251  AAACTCCAAT TATGATGAAA AATACCACCA ACACCACCTG CGAAACTGTA
5301  TCCCAACTGT CCTTAATAAA AATGTTAAAA AGTATATTAT TCTCATTTGT
5351  CTGTCATAAT TTATGTACCC CACTTTAATT TTTCTGATGT ACTAAACCGA
5401  GGGCAAACTG AAACCTGTTC CTCATGCAAA GCCCCTACTC ACCATGTATC
5451  ATGTACGTGT CATCACCCAA CAACTCCACT TTTGCTATAT AACAACACCC
5501  CCGTCACACT CTCCCTCTCT AACACACACC CCACTAACAA TTCCTTCACT
5551  TGCAGCACTG TTGCATCATC ATCTTCATTG CAAAACCCTA AACTTCACCT
5601  TCAACCGCGG CCGCAGATCT AAAATGGCTT CTATGATATC CTCTTCCGCT
5651  GTGACAACAG TCAGCCGTGC CTCTAGGGGG CAATCCGCCG CAGTGGCTCC
5701  ATTCGGCGGC CTCAAATCCA TGACTGGATT CCCAGTGAAG AAGGTCAACA
5751  CTGACATTAC TTCCATTACA AGCAATGGTG GAAGAGTAAA GTGCATGCAG
```

FIG. 22C DNA Sequence of pMBXS1023 (Cont'd)

```
5801    GTGTGGCCTC CAATTGGAAA GAAGAAGTTT GAGACTCTTT CCTATTTGCC
5851    ACCATTGACG AGAGATTCTA GAGTGCTCAG CCAGCAATCC ATCCAGAAGG
5901    TTCTCGTGGC TAACCGTGGT GAGATTGCTA TTCGTATCTT TAGAGCGTGT
5951    ACCGAGTTGA ACATCCGAAC TGTCGCTGTT TATAGTAAAG AAGATTCTGG
6001    ATCATACCAC AGATACAAAG CTGACGAGGC CTACTTGGTT GGTGAAGGTA
6051    AGAAGCCTAT TGACGCTTAT CTTGATATAG AGGGCATCAT TGATATTGCC
6101    AAGAGAAACA AAGTTGATGC AATTCATCCG GGATACGGTT TTCTATCAGA
6151    AAACATTCAC TTTGCACGAC GATGTGAAGA AGAGGGAATC GTGTTCATCG
6201    GACCTAAAAG CGAACACTTG GATATGTTTG GGGACAAGGT TAAGGCAAGG
6251    GAACAAGCAG AGAAGGCAGG AATTCCAGTG ATACCTGGAT CGGATGGGCC
6301    TGCTGAAACT CTTGAAGCTG TCGAACAATT CGGCCAGGCT AACGGATACC
6351    CAATCATCAT TAAGGCTTCT TTAGGTGGTG GGGGAAGGGG GATGAGAATC
6401    GTGCGATCCG AATCTGAGGT AAAAGAGGCT TATGAACGTG CTAAATCGGA
6451    AGCTAAAGCG GCCTTTGGGA ACGATGAAGT CTATGTCGAG AAACTAATCG
6501    AGAATCCCAA GCACATCGAG GTTCAAGTGA TTGGTGATAA GCAAGGTAAC
6551    GTTGTTCACC TTTTCGAGAG AGATTGTTCT GTTCAACGTA GACACCAAAA
6601    AGTGATAGAA GTAGCTCCAT CGGTATCGTT GAGCCCAGAA CTAAGGGACC
6651    AGATATGCGA GGCTGCTGTC GCGCTTGCAA AGAATGTCAA CTATATCAAT
6701    GCAGGCACTG TCGAATTCTT GGTAGCCAAT AATGAGTTTT ACTTCATTGA
6751    GGTCAACCCT AGAGTTCAAG TTGAGCATAC CATTACCGAA ATGATCACTG
6801    GGGTGGATAT CGTACAGACT CAGATCCTCG TTGCTCAAGG CCATTCCCTT
6851    CATTCCAAGA AGGTGAATAT TCCAGAGCAA AAGGATATCT TTACAATTGG
6901    TTATGCGATT CAATCACGAG TTACCACAGA AGATCCACAA AATGACTTCA
6951    TGCCAGATAC GGGAAAGATA ATGGCATACC GTTCTGGTGG CGGATTTGGT
7001    GTTCGATTAG ACACAGGTAA TAGTTTTCAG GGAGCTGTGA TAACGCCATA
7051    CTATGATTCT TTATTGGTTA AGTTGAGTAC TTGGGCTCTC ACTTTCGAGC
7101    AAGCCGCAGC GAAAATGGTC AGAAACCTTC AGGAGTTCAG AATTAGAGGT
7151    ATTAAGACGA ACATTCCATT CTTAGAGAAC GTTGCTAAAC ATGAGAAGTT
7201    TCTGACAGGA CAATATGATA CAAGTTTCAT AGACACTACA CCTGAACTCT
7251    TTAACTTCCC TAAACAAAAA GACAGAGGTA CGAAAATGTT GACATATATC
7301    GGAAACGTGA CAGTTAATGG GTTCCCAGGT ATCGGTAAGA AAGAAAAGCC
7351    GGCCTTTGAT AAACCCCTTG GTGTTAAAGT GGATGTGGAT CAACAACCTG
7401    CTAGGGGCAC TAAGCAAATC CTTGATGAAA AGGGTGCAGA GGGACTGGCA
7451    AATTGGGTTA AAGAGCAGAA ATCAGTTCTT CTGACAGATA CCACATTTCG
7501    TGATGCTCAT CAATCATTAC TAGCAACAAG AATTAGATCA CACGATCTGA
7551    AAAAGATCGC TAATCCAACC GCTGCTCTTT GGCCGGAACT CTTCTCTATG
7601    GAAATGTGGG GTGGGGCCAC ATTCGATGTC GCGTACCGTT TTCTAAAAGA
7651    AGATCCTTGG AAGCGTCTGG AAGATTTGAG AAAAGAGGTG CCCAATACCC
7701    TGTTCCAGAT GCTTTTGCGT TCTAGCAATG CCGTCGGATA TACCAATTAT
7751    CCTGACAATG TGATCAAAGA ATTCGTAAAA CAGTCCGCTC AATCTGGTAT
7801    CGACGTTTTT AGGATTTTCG ATTCACTTAA TTGGGTAAAA GGTATGACGT
7851    TAGCGATTGA TGCTGTACGT GATACTGGAA AGGTTGCAGA GGCCGCCATT
7901    TGCTACACTG GAGACATTTT GGATAAGAAT AGAACTAAAT ACGACTTGGC
7951    TTATTACACT TCCATGGCAA AAGAACTTGA GGCTGCCGGT GCACATATTC
8001    TGGGGATAAA GGATATGGCC GGTTTGCTCA AACCGCAGGC AGCATATGAG
8051    TTGGTTTCAG CCCTTAAAGA AACTATTGAC ATACCCGTTC ATCTGCACAC
8101    GCATGACACG TCGGGCAATG GAATCTATAT GTATGCAAAG GCTGTCGAGG
8151    CTGGCGTGGA TATCATTGAT GTCGCTGTAA GCTCTATGGC TGGACTTACA
8201    TCCCAGCCAT CAGCCTCTGG ATTCTATCAT GCTATGGAAG GTAACGATCG
8251    TAGACCCGAA ATGAATGTCC AAGGGGTCGA ATTACTGTCA CAGTACTGGG
8301    AGAGTGTGCG TAAGTATTAC TCAGAGTTTG AGAGCGGTAT GAAGAGTCCC
8351    CATACCGAGA TTTATGAGCA CGAGATGCCT GGTGGACAAT ACTCTAACTT
8401    GCAACAGCAA GCGAAGGGGG TTGGTTTGGG AGATAGGTGG AACGAAGTGA
8451    AAGAAATGTA TAGACGTGTC AACGACATGT TTGGTGATAT TGTGAAAGTA
8501    ACTCCTAGTT CTAAGGTAGT TGGAGACATG GCACTGTACA TGGTTCAGAA
8551    TAACCTTACT GAAAAGGATG TTTACGAGAA GGGGGAGTCA CTTGACTTCC
8601    CTGATTCAGT GGTTGAACTG TTCAAGGGAA ATATCGGTCA ACCGCATGGG
8651    GGATTTCCAG AAAAACTACA GAAACTGATA CTAAAGGGAC AGGAGCCAAT
8701    TACTGTTCGA CCAGGAGAGC TCTTGGAGCC GGTTTCTTTT GAGGCTATCA
```

FIG. 22D DNA Sequence of pMBXS1023 (Cont'd)

```
 8751   AGCAAGAATT CAAAGAACAA CATAACCTTG AAATTTCTGA TCAGGACGCG
 8801   GTTGCTTACG CACTTTATCC AAAGGTCTTT ACTGATTACG TGAAAACCAC
 8851   AGAGTCTTAT GGTGATATAA GTGTGCTAGA TACACCAACA TTTTTCTATG
 8901   GCATGACTCT TGGAGAAGAG ATTGAAGTGG AAATAGAAAG GGGAAAAACA
 8951   CTCATTGTTA AACTGATATC TATCGGAGAG CCTCAACCTG ATGCTACAAG
 9001   GGTAGTGTAC TTTGAATTGA ATGGACAACC TAGAGAAGTA GTGATTAAAG
 9051   ATGAGTCAAT AAAGTCAAGC GTGCAGGAGA GGCTAAAGGC AGATAGAACC
 9101   AATCCGTCGC ACATTGCAGC TTCTATGCCT GGCACCGTCA TAAAAGTCCT
 9151   CGCTGAAGCT GGTACTAAAG TCAACAAAGG TGACCATCTT ATGATCAACG
 9201   AAGCAATGAA GATGGAAACT ACGGTTCAGG CACCTTTCAG TGGAACAATC
 9251   AAGCAGGTTC ATGTTAAGAA TGGCGAGCCT ATCCAGACTG GTGACTTGCT
 9301   TTTGGAGATT GAAAAGGCCT GAGTCGACGC GATCGCGCGG CCGCTGAGTA
 9351   ATTCTGATAT TAGAGGGAGC ATTAATGTGT TGTTGTGATG TGGTTTATAT
 9401   GGGGAAATTA AATAAATGAT GTATGTACCT CTTGCCTATG TAGGTTTGTG
 9451   TGTTTTGTTT TGTTGTCTAG CTTTGGTTAT TAAGTAGTAG GGACGTTCGT
 9501   TCGTGTCTCA AAAAAAGGGG TACTACCACT CTGTAGTGTA TATGGATGCT
 9551   GGAAATCAAT GTGTTTTGTA TTTGTTCACC TCCATTGTTG AATTCAATGT
 9601   CAAATGTGTT TTGCGTTGGT TATGTGTAAA ATTACTATCT TTCTCGTCCG
 9651   ATGATCAAAG TTTTAAGCAA CAAAACCAAG GGTGAAATTT AAACTGTGCT
 9701   TTGTTGAAGA TTCTTTTATC ATATTGAAAA TCAAATTACT AGCAGCAGAT
 9751   TTTACCTAGC ATGAAATTTT ATCAACAGTA CAGCACTCAC TAACCAAGTT
 9801   CCAAACTAAG ATGCGCCATT AACATCAGCC AATAGGCATT TTCAGCAAGT
 9851   TTAAACTACG TAGTGTTTAT CTTTGTTGCT TTTCTGAACA ATTTATTTAC
 9901   TATGTAAATA TATTATCAAT GTTTAATCTA TTTTAATTTG CACATGAATT
 9951   TTCATTTTAT TTTTACTTTA CAAAACAAAT AAATATATAT GCAAAAAAAT
10001   TTACAAACGA TGCACGGGTT ACAAACTAAT TTCATTAAAT GCTAATGCAG
10051   ATTTTGTGAA GTAAAACTCC AATTATGATG AAAAATACCA CCAACACCAC
10101   CTGCGAAACT GTATCCCAAC TGTCCTTAAT AAAAATGTTA AAAAGTATAT
10151   TATTCTCATT TGTCTGTCAT AATTTATGTA CCCCACTTTA ATTTTTCTGA
10201   TGTACTAAAC CGAGGGCAAA CTGAAACCTG TTCCTCATGC AAAGCCCCTA
10251   CTCACCATGT ATCATGTACG TGTCATCACC CAACAACTCC ACTTTTGCTA
10301   TATAACAACA CCCCCGTCAC ACTCTCCCTC TCTAACACAC ACCCCACTAA
10351   CAATTCCTTC ACTTGCAGCA CTGTTGCATC ATCATCTTCA TTGCAAAACC
10401   CTAAACTTCA CCTTCAACCG CGGCCGCTCG CGAAAAATGG CTTCTATGAT
10451   ATCCTCTTCC GCTGTGACAA CAGTCAGCCG TGCCTCTAGG GGGCAATCCG
10501   CCGCAGTGGC TCCATTCGGC GGCCTCAAAT CCATGACTGG ATTCCCAGTG
10551   AAGAAGGTCA ACACTGACAT TACTTCCATT ACAAGCAATG GTGGAAGAGT
10601   AAAGTGCATG CAGGTGTGGC CTCCAATTGG AAAGAAGAAG TTTGAGACTC
10651   TTTCCTATTT GCCACCATTG ACGAGAGATT CTAGAGTGAA CATACACGAG
10701   TACCAAGCAA AAGAGTTGCT CAAGACCTAT GGAGTGCCGG TCCCAGACGG
10751   AGCGGTAGCT TATAGTGATG CTCAAGCGGC TTCCGTCGCT GAAGAGATTG
10801   GTGGCTCTAG ATGGGTTGTA AAGGCGCAGA TACACGCTGG TGGAAGGGGA
10851   AAGGCAGGTG GTGTGAAGGT GGCCCATAGC ATTGAAGAGG TTCGTCAGTA
10901   CGCTGATGCG ATGCTTGGGT CCCATCTCGT TACACATCAA ACAGGGCCTG
10951   GTGGTTCATT AGTTCAACGT TTGTGGGTGG AGCAAGCATC ACATATCAAG
11001   AAAGAGTATT ATCTGGGATT TGTTATTGAT AGAGGTAACC AAAGAATTAC
11051   CTTAATTGCT TCTTCTGAAG GGGGAATGGA GATAGAAGAG GTTGCTAAAG
11101   AGACACCAGA AAAGATCGTC AAAGAGGTTG TAGACCCTGC AATCGGATTG
11151   CTTGATTTTC AGTGTAGAAA GGTTGCAACT GCAATAGGAC TTAAGGGAAA
11201   GCTTATGCCC CAGGCAGTTA GACTTATGAA GGCTATCTAT AGGTGTATGC
11251   GAGATAAGGA TGCTCTCCAG GCAGAGATCA ATCCTTTGGC AATAGTAGGT
11301   GAAAGTGACG AGTCGCTCAT GGTTCTTGAT GCTAAATTCA ATTTTGATGA
11351   CAATGCTCTT TACAGACAAC GAACAATTAC TGAAATGAGG GATCTCGCAG
11401   AAGAAGATCC TAAAGAAGTC GAAGCTTCTG GACACGGATT GAATTACATC
11451   GCCCTCGATG GGAACATCGG TTGTATTGTG AATGGAGCTG GTCTTGCTAT
11501   GGCCAGCCTG GATGCCATCA CTCTACATGG CGGTCGTCCA GCTAACTTCT
11551   TAGATGTCGG CGGTGGGGCT TCTCCTGAAA AGGTTACGAA TGCGTGCAGA
11601   ATTGTTTTGG AAGATCCGAA CGTCCGTTGT ATACTGGTGA ACATTTTTGC
11651   CGGAATTAAC AGGTGCGATT GGATTGCAAA AGGACTTATT CAAGCCTGCG
```

FIG. 22E DNA Sequence of pMBXS1023 (Cont'd)

```
11701  ACTCACTACA GATTAAAGTT CCACTGATCG TTCGATTGGC AGGCACTAAT
11751  GTAGATGAAG GCAGGAAAAT CCTAGCGGAG TCGGGTTTAA GTTTCATAAC
11801  GGCAGAGAAT TTGGACGACG CGGCTGCTAA AGCCGTGGCT ATCGTGAAAG
11851  GGTGAACGCG TTGAGTAATT CTGATATTAG AGGGAGCATT AATGTGTTGT
11901  TGTGATGTGG TTTATATGGG GAAATTAAAT AAATGATGTA TGTACCTCTT
11951  GCCTATGTAG GTTTGTGTGT TTTGTTTTGT TGTCTAGCTT TGGTTATTAA
12001  GTAGTAGGGA CGTTCGTTCG TGTCTCAAAA AAAGGGGTAC TACCACTCTG
12051  TAGTGTATAT GGATGCTGGA AATCAATGTG TTTTGTATTT GTTCACCTCC
12101  ATTGTTGAAT TCAATGTCAA ATGTGTTTTG CGTTGGTTAT GTGTAAAATT
12151  ACTATCTTTC TCGTCCGATG ATCAAAGTTT TAAGCAACAA AACCAAGGGT
12201  GAAATTTAAA CTGTGCTTTG TTGAAGATTC TTTTATCATA TTGAAAATCA
12251  AATTACTAGC AGCAGATTTT ACCTAGCATG AAATTTTATC AACAGTACAG
12301  CACTCACTAA CCAAGTTCCA AACTAAGATG CGCCATTAAC ATCAGCCAAT
12351  AGGCATTTTC AGCAATGTAC ATACGTAGTG TTTATCTTTG TTGCTTTTCT
12401  GAACAATTTA TTTACTATGT AAATATATTA TCAATGTTTA ATCTATTTTA
12451  ATTTGCACAT GAATTTTCAT TTTATTTTTA CTTTACAAAA CAAATAAATA
12501  TATATGCAAA AAAATTTACA AACGATGCAC GGGTTACAAA CTAATTTCAT
12551  TAAATGCTAA TGCAGATTTT GTGAAGTAAA ACTCCAATTA TGATGAAAAA
12601  TACCACCAAC ACCACCTGCG AAACTGTATC CCAACTGTCC TTAATAAAAA
12651  TGTTAAAAAG TATATTATTC TCATTTGTCT GTCATAATTT ATGTACCCCA
12701  CTTTAATTTT TCTGATGTAC TAAACCGAGG GCAAACTGAA ACCTGTTCCT
12751  CATGCAAAGC CCCTACTCAC CATGTATCAT GTACGTGTCA TCACCCAACA
12801  ACTCCACTTT TGCTATATAA CAACACCCCC GTCACACTCT CCCTCTCTAA
12851  CACACACCCC ACTAACAATT CCTTCACTTG CAGCACTGTT GCATCATCAT
12901  CTTCATTGCA AAACCCTAAA CTTCACCTTC AACCGCGGCC GCGACGTCAA
12951  AATGGCTTCT ATGATATCCT CTTCCGCTGT GACAACAGTC AGCCGTGCCT
13001  CTAGGGGGCA ATCCGCCGCA GTGGCTCCAT TCGGCGGCCT CAAATCCATG
13051  ACTGGATTCC CAGTGAAGAA GGTCAACACT GACATTACTT CCATTACAAG
13101  CAATGGTGGA AGAGTAAAGT GCATGCAGGT GTGGCCTCCA ATTGGAAAGA
13151  AGAAGTTTGA GACTCTTTCC TATTTGCCAC CATTGACGAG AGATTCTAGA
13201  GTCTCGGTTT TCGTGAATAA ACATTCCAAG GTCATCTTTC AAGGCTTTAC
13251  CGGGGAGCAT GCTACATTTC ACGCAAAAGA TGCAATGCGA ATGGGCACAA
13301  GGGTTGTCGG TGGCGTTACT CCTGGAAAGG GTGGGACTAG ACATCCAGAT
13351  CCTGAGCTCG CTCATCTTCC GGTATTCGAT ACCGTTGCCG AAGCCGTTGC
13401  TGCTACAGGA GCTGATGTAT CAGCTGTGTT TGTCCCACCC CCTTTCAATG
13451  CAGACGCACT TATGGAAGCA ATTGATGCCG GTATTAGAGT GGCTGTCACT
13501  ATAGCGGATG GAATTCCTGT GCATGACATG ATCAGATTGC AAAGGTATAG
13551  AGTAGGAAAG GACTCTATTG TTATCGGGCC TAACACACCA GGAATCATAA
13601  CGCCTGGTGA GTGTAAAGTG GGTATCATGC CGAGTCACAT ATACAAGAAG
13651  GGAAACGTGG GTATAGTGAG TCGATCAGGA ACATTGAATT ACGAGGCGAC
13701  GGAACAAATG GCTGCGCTAG GCTTAGGGAT TACTACTTCT GTTGGAATTG
13751  GTGGTGATCC TATAAACGGC ACTGACTTTG TGACTGTTCT CCGTGCATTC
13801  GAGGCTGATC CAGAAACGGA AATTGTAGTT ATGATCGGAG AAATAGGTGG
13851  ACCGCAGGAA GTTGCCGCAG CTAGATGGGC AAAAGAGAAT ATGACCAAAC
13901  CAGTTATTGG GTTCGTAGCT GGTTTAGCAG CCCCCACAGG GCGTAGGATG
13951  GGACACGCAG GTGCTATTAT CAGCTCTGAG GCTGATACCG CTGGAGCTAA
14001  GATGGATGCC ATGGAAGCTC TTGGTCTGTA TGTCGCTAGG AACCCAGCGC
14051  AAATCGGACA GACAGTTTTG CGTGCGGCAC AGGAGCATGG AATTAGATTT
14101  TGAGGGCCCG TTAACTGAGT AATTCTGATA TTAGAGGGAG CATTAATGTG
14151  TTGTTGTGAT GTGGTTTATA TGGGGAAATT AAATAAATGA TGTATGTACC
14201  TCTTGCCTAT GTAGGTTTGT GTGTTTTGTT TTGTTGTCTA GCTTTGGTTA
14251  TTAAGTAGTA GGGACGTTCG TTCGTGTCTC AAAAAAAGGG GTACTACCAC
14301  TCTGTAGTGT ATATGGATGC TGGAAATCAA TGTGTTTTGT ATTTGTTCAC
14351  CTCCATTGTT GAATTCAATG TCAAATGTGT TTTGCGTTGG TTATGTGTAA
14401  AATTACTATC TTTCTCGTCC GATGATCAAA GTTTTAAGCA ACAAAACCAA
14451  GGGTGAAATT TAAACTGTGC TTTGTTGAAG ATTCTTTTAT CATATTGAAA
14501  ATCAAATTAC TAGCAGCAGA TTTTACCTAG CATGAAATTT TATCAACAGT
14551  ACAGCACTCA CTAACCAAGT TCCAAACTAA GATGCGCCAT TAACATCAGC
14601  CAATAGGCAT TTTCAGCAAG TTTAAACCGG ACCGTACGTA GTGTTTATCT
```

FIG. 22F DNA Sequence of pMBXS1023 (Cont'd)

```
14651   TTGTTGCTTT TCTGAACAAT TTATTTACTA TGTAAATATA TTATCAATGT
14701   TTAATCTATT TTAATTTGCA CATGAATTTT CATTTTATTT TTACTTTACA
14751   AAACAAATAA ATATATATGC AAAAAAATTT ACAAACGATG CACGGGTTAC
14801   AAACTAATTT CATTAAATGC TAATGCAGAT TTTGTGAAGT AAAACTCCAA
14851   TTATGATGAA AAATACCACC AACACCACCT GCGAAACTGT ATCCCAACTG
14901   TCCTTAATAA AAATGTTAAA AAGTATATTA TTCTCATTTG TCTGTCATAA
14951   TTTATGTACC CCACTTTAAT TTTTCTGATG TACTAAACCG AGGGCAAACT
15001   GAAACCTGTT CCTCATGCAA AGCCCCTACT CACCATGTAT CATGTACGTG
15051   TCATCACCCA ACAACTCCAC TTTTGCTATA TAACAACACC CCCGTCACAC
15101   TCTCCCTCTC TAACACACAC CCCACTAACA ATTCCTTCAC TTGCAGCACT
15151   GTTGCATCAT CATCTTCATT GCAAAACCCT AAACTTCACC TTCAACCGCG
15201   GCCGCCACGT GAAAATGGCT TCTATGATAT CCTCTTCCGC TGTGACAACA
15251   GTCAGCCGTG CCTCTAGGGG GCAATCCGCC GCAGTGGCTC CATTCGGCGG
15301   CCTCAAATCC ATGACTGGAT TCCCAGTGAA GAAGGTCAAC ACTGACATTA
15351   CTTCCATTAC AAGCAATGGT GGAAGAGTAA AGTGCATGCA GGTGTGGCCT
15401   CCAATTGGAA AGAAGAAGTT TGAGACTCTT TCCTATTTGC CACCATTGAC
15451   GAGAGATTCT AGAGTGAGCT TCCGTTTGCA ACCAGCTCCG CCAGCAAGGC
15501   CCAATAGATG TCAACTTTTT GGGCCTGGAT CTCGACCGGC TTTGTTTGAG
15551   AAAATGGCCG CTTCAGCCGC GGACGTTATC AATCTGGATT TAGAGGATAG
15601   TGTTGCCCCA GATGATAAAG CTCAGGCTAG AGCAAATATC ATTGAGGCTA
15651   TAAACGGTCT AGACTGGGGT AGAAAGTATC TCAGTGTTAG AATTAACGGA
15701   CTTGATACGC CTTTCTGGTA TCGAGATGTC GTTGACTTGC TTGAGCAGGC
15751   AGGAGATAGA CTTGATCAAA TCATGATCCC TAAGGTTGGC TGTGCTGCGG
15801   ATGTTTACGC CGTCGATGCT TTGGTAACAG CAATTGAACG TGCTAAAGGG
15851   CGTACTAAGC CTCTATCATT TGAAGTGATA ATAGAGTCTG CAGCTGGTAT
15901   CGCACATGTT GAAGAAATAG CCGCTTCGTC ACCAAGACTC CAAGCCATGT
15951   CTTTGGGTGC AGCCGATTTT GCAGCTTCTA TGGGAATGCA GACTACAGGG
16001   ATTGGTGGAA CGCAAGAGAA CTACTATATG CTCCACGACG GACAAAAGCA
16051   CTGGTCCGAT CCTTGGCATT GGGCTCAGGC TGCAATCGTC GCAGCGTGCA
16101   GAACACATGG GATTTTACCC GTTGACGGCC CGTTCGGTGA CTTCTCTGAT
16151   GACGAAGGAT TCAGGGCACA AGCTCGAAGG TCCGCTACTC TTGGAATGGT
16201   GGGAAAATGG GCCATACATC CAAAGCAAGT GGCTCTCGCT AATGAAGTGT
16251   TTACACCTAG CGAGACTGCA GTAACCGAAG CGAGGGAGAT TTTAGCGGCT
16301   ATGGATGCTG CTAAGGCGAG AGGCGAAGGT GCTACCGTGT ACAAAGGTAG
16351   GCTGGTAGAT ATCGCGTCGA TTAAACAGGC AGAAGTCATT GTTCGTCAGG
16401   CTGAGATGAT TAGTGCATGA ACTAGTTGAG TAATTCTGAT ATTAGAGGGA
16451   GCATTAATGT GTTGTTGTGA TGTGGTTTAT ATGGGGAAAT TAAATAAATG
16501   ATGTATGTAC CTCTTGCCTA TGTAGGTTTG TGTGTTTTGT TTTGTTGTCT
16551   AGCTTTGGTT ATTAAGTAGT AGGGACGTTC GTTCGTGTCT CAAAAAAAGG
16601   GGTACTACCA CTCTGTAGTG TATATGGATG CTGGAAATCA ATGTGTTTTG
16651   TATTTGTTCA CCTCCATTGT TGAATTCAAT GTCAAATGTG TTTTGCGTTG
16701   GTTATGTGTA AAATTACTAT CTTTCTCGTC CGATGATCAA AGTTTTAAGC
16751   AACAAAACCA AGGGTGAAAT TTAAACTGTG CTTTGTTGAA GATTCTTTTA
16801   TCATATTGAA AATCAAATTA CTAGCAGCAG ATTTTACCTA GCATGAAATT
16851   TTATCAACAG TACAGCACTC ACTAACCAAG TTCCAAACTA AGATGCGCCA
16901   TTAACATCAG CCAATAGGCA TTTTCAGCAA GTTTAAACTC CGGATACGTA
16951   GTGTTTATCT TTGTTGCTTT TCTGAACAAT TTATTTACTA TGTAAATATA
17001   TTATCAATGT TTAATCTATT TTAATTTGCA CATGAATTTT CATTTTATTT
17051   TTACTTTACA AAACAAATAA ATATATATGC AAAAAAATTT ACAAACGATG
17101   CACGGGTTAC AAACTAATTT CATTAAATGC TAATGCAGAT TTTGTGAAGT
17151   AAAACTCCAA TTATGATGAA AAATACCACC AACACCACCT GCGAAACTGT
17201   ATCCCAACTG TCCTTAATAA AAATGTTAAA AAGTATATTA TTCTCATTTG
17251   TCTGTCATAA TTTATGTACC CCACTTTAAT TTTTCTGATG TACTAAACCG
17301   AGGGCAAACT GAAACCTGTT CCTCATGCAA AGCCCCTACT CACCATGTAT
17351   CATGTACGTG TCATCACCCA ACAACTCCAC TTTTGCTATA TAACAACACC
17401   CCCGTCACAC TCTCCCTCTC TAACACACAC CCCACTAACA ATTCCTTCAC
17451   TTGCAGCACT GTTGCATCAT CATCTTCATT GCAAAACCCT AAACTTCACC
17501   TTCAACCGCG GCCGCCCTAG GAAAATGGCT TCTATGATAT CCTCTTCCGC
17551   TGTGACAACA GTCAGCCGTG CCTCTAGGGG GCAATCCGCC GCAGTGGCTC
```

FIG. 22G DNA Sequence of pMBXS1023 (Cont'd)

```
17601   CATTCGGCGG CCTCAAATCC ATGACTGGAT TCCCAGTGAA GAAGGTCAAC
17651   ACTGACATTA CTTCCATTAC AAGCAATGGT GGAAGAGTAA AGTGCATGCA
17701   GGTGTGGCCT CCAATTGGAA AGAAGAAGTT TGAGACTCTT TCCTATTTGC
17751   CACCATTGAC GAGAGATTCT AGAGTTGCAC AGTACCAAGA CGATATCAAG
17801   GCGGTTGCAG GGCTTAAGGA GAATCACGGC TCCGCATGGA ATGCCATCAA
17851   CCCGGAGTAT GCCGCCAGGA TGAGGGCGCA GAACAAGTTC AAGACGGGCC
17901   TTGACATTGC AAAGTATACG GCTAAGATTA TGCGGGCCGA TATGGCAGCC
17951   TACGACGCCG ACAGCTCGAA GTACACACAG AGCCTCGGTT GTTGGCATGG
18001   TTTCATTGGT CAGCAGAAGA TGATCTCAAT CAAGAAACAT TTCAACAGCA
18051   CGGAACGCCG TTACCTCTAC CTTTCTGGCT GGATGGTAGC CGCGCTTAGA
18101   TCCGAGTTTG GCCCCCTACC GGATCAGTCC ATGCACGAAA AGACGAGTGT
18151   CTCCGCACTC ATTCGGGAAC TCTACACTTT TCTGCGCCAA GCGGACGCTA
18201   GGGAGTTGGG GGGCCTGTTT CGGGAGCTTG ACGCGGCCCA AGGCCCAGCT
18251   AAGGCGGCCA TTCAAGCGAA GATCGACAAC CACGTCACTC ATGTGGTCCC
18301   AATCATAGCT GATATCGACG CTGGCTTCGG CAATGCGGAA GCAACATACC
18351   TGTTGGCCAA GCAGTTCATC GAGGCCGGGG CTTGCTGCAT ACAGATAGAG
18401   AACCAGGTTT CTGACGAAAA GCAATGTGGA CATCAAGACG GAAAGGTTAC
18451   CGTGCCCCAC GAGGATTTTC TTGCAAAAAT CCGAGCGATT CGTTATGCGT
18501   TTTTAGAGTT GGGCGTGGAT GACGGTATCA TCGTGGCCAG GACCGATAGT
18551   CTCGGTGCTG GTCTGACAAA GCAAATCGCA GTGACCAATA CGCCTGGAGA
18601   CTTAGGGGAT CAGTACAACA GCTTCCTCGA TTGCGAGGAG CTTAGCGCAG
18651   ATCAGCTCGG AAATGGCGAC GTTATCATCA AGCGTGATGG AAAGCTACTC
18701   CGCCCCAAGC GCCTCCCGTC TAACTTGTTC CAGTTCCGGG CTGGAACTGG
18751   CGAAGCGCGA TGCGTCCTGG ACTGCGTGAC CGCGCTCCAG AACGGCGCCG
18801   ACCTACTCTG GATTGAGACA GAAAAGCCTC ACATAGCTCA AATCGGCGGA
18851   ATGGTATCGG AGATAAGGAA AGTCATACCC AACGCCAAAC TGGTGTACAA
18901   CAACTCTCCG TCGTTCAATT GGACCCTGAA CTTTAGACAG CAAGCATACG
18951   ATGCTATGAA AGCCGCTGGG AAAGACGTGT CAGCATACGA CCGCGCCCAG
19001   CTTATGTCCG TGGAGTACGA CCAAACGGAA CTGGCTAAGC TGGCTGATGA
19051   GAAAATCAGA ACATTCCAGG CCGACGCCTC AAGGGAGGCC GGGATCTTCC
19101   ATCACTTGAT TACCTTACCA ACATATCACA CTGCGGCCCT GTCAACCGAC
19151   AATTTGGCTA AGGAGTACTT CGGAGATCAG GGGATGCTCG GTTATGTCGC
19201   GGGCGTTCAG AGGAAGGAGA TCCGACAGGG CATCGCATGT GTCAAGCACC
19251   AAAACATGAG CGGGAGTGAC ATCGGGGATG ATCATAAAGA GTATTTCTCC
19301   GGCGAAGCCG CGCTGAAGGC CGCCGGCAAA GACAACACTA TGAATCAATT
19351   CTGACCCGGG TGAGTAATTC TGATATTAGA GGGAGCATTA ATGTGTTGTT
19401   GTGATGTGGT TTATATGGGG AAATTAAATA AATGATGTAT GTACCTCTTG
19451   CCTATGTAGG TTTGTGTGTT TTGTTTTGTT GTCTAGCTTT GGTTATTAAG
19501   TAGTAGGGAC GTTCGTTCGT GTCTCAAAAA AAGGGGTACT ACCACTCTGT
19551   AGTGTATATG GATGCTGGAA ATCAATGTGT TTTGTATTTG TTCACCTCCA
19601   TTGTTGAATT CAATGTCAAA TGTGTTTTGC GTTGGTTATG TGTAAAATTA
19651   CTATCTTTCT CGTCCGATGA TCAAAGTTTT AAGCAACAAA ACCAAGGGTG
19701   AAATTTAAAC TGTGCTTTGT TGAAGATTCT TTTATCATAT TGAAAATCAA
19751   ATTACTAGCA GCAGATTTTA CCTAGCATGA AATTTTATCA ACAGTACAGC
19801   ACTCACTAAC CAAGTTCCAA ACTAAGATGC GCCATTAACA TCAGCCAATA
19851   GGCATTTTCA GCAAGCTCGA GTCACGTAGT GGTACGTAGT GTTTATCTTT
19901   GTTGCTTTTC TGAACAATTT ATTTACTATG TAAATATATT ATCAATGTTT
19951   AATCTATTTT AATTTGCACA TGAATTTTCA TTTTATTTTT ACTTTACAAA
20001   ACAAATAAAT ATATATGCAA AAAAATTTAC AAACGATGCA CGGGTTACAA
20051   ACTAATTTCA TTAAATGCTA ATGCAGATTT TGTGAAGTAA AACTCCAATT
20101   ATGATGAAAA ATACCACCAA CACCACCTGC GAAACTGTAT CCCAACTGTC
20151   CTTAATAAAA ATGTTAAAAA GTATATTATT CTCATTTGTC TGTCATAATT
20201   TATGTACCCC ACTTTAATTT TTCTGATGTA CTAAACCGAG GGCAAACTGA
20251   AACCTGTTCC TCATGCAAAG CCCCTACTCA CCATGTATCA TGTACGTGTC
20301   ATCACCCAAC AACTCCACTT TTGCTATATA ACAACACCCC CGTCACACTC
20351   TCCCTCTCTA ACACACACCC CACTAACAAT TCCTTCACTT GCAGCACTGT
20401   TGCATCATCA TCTTCATTGC AAAACCCTAA ACTTCACCTT CAACCGCGGC
20451   CGCTTCGAAG GATCCAAAAT GGTGAGCAAG GGCGAGGAGC TGTTCACCGG
20501   GGTGGTGCCC ATCCTGGTCG AGCTGGACGG CGACGTAAAC GGCCACAAGT
```

FIG. 22H DNA Sequence of pMBXS1023 (Cont'd)

```
20551    TCAGCGTGTC CGGCGAGGGC GAGGGCGATG CCACCTACGG CAAGCTGACC
20601    CTGAAGTTCA TCTGCACCAC CGGCAAGCTG CCCGTGCCCT GGCCCACCCT
20651    CGTGACCACC TTCACCTACG GCGTGCAGTG CTTCAGCCGC TACCCCGACC
20701    ACATGAAGCA GCACGACTTC TTCAAGTCCG CCATGCCCGA AGGCTACGTC
20751    CAGGAGCGCA CCATCTTCTT CAAGGACGAC GGCAACTACA AGACCCGCGC
20801    CGAGGTGAAG TTCGAGGGCG ACACCCTGGT GAACCGCATC GAGCTGAAGG
20851    GCATCGACTT CAAGGAGGAC GGCAACATCC TGGGGCACAA GCTGGAGTAC
20901    AACTACAACA GCCACAACGT CTATATCATG GCCGACAAGC AGAAGAACGG
20951    CATCAAGGTG AACTTCAAGA TCCGCCACAA CATCGAGGAC GGCAGCGTGC
21001    AGCTCGCCGA CCACTACCAG CAGAACACCC CCATCGGCGA CGGCCCCGTG
21051    CTGCTGCCCG ACAACCACTA CCTGAGCACC CAGTCCGCCC TGAGCAAAGA
21101    CCCCAACGAG AAGCGCGATC ACATGGTCCT GCTGGAGTTC GTGACCGCCG
21151    CCGGGATCAC TCACGGCATG GACGAGCTGT ACAAGTAAAG CGGCCGCCCG
21201    GGCTGCAGTT CGAAATTTAA ATGCGGCCGC TGAGTAATTC TGATATTAGA
21251    GGGAGCATTA ATGTGTTGTT GTGATGTGGT TTATATGGGG AAATTAAATA
21301    AATGATGTAT GTACCTCTTG CCTATGTAGG TTTGTGTGTT TTGTTTTGTT
21351    GTCTAGCTTT GGTTATTAAG TAGTAGGGAC GTTCGTTCGT GTCTCAAAAA
21401    AAGGGGTACT ACCACTCTGT AGTGTATATG GATGCTGGAA ATCAATGTGT
21451    TTTGTATTTG TTCACCTCCA TTGTTGAATT CAATGTCAAA TGTGTTTTGC
21501    GTTGGTTATG TGTAAAATTA CTATCTTTCT CGTCCGATGA TCAAAGTTTT
21551    AAGCAACAAA ACCAAGGGTG AAATTTAAAC TGTGCTTTGT TGAAGATTCT
21601    TTTATCATAT TGAAAATCAA ATTACTAGCA GCAGATTTTA CCTAGCATGA
21651    AATTTTATCA ACAGTACAGC ACTCACTAAC CAAGTTCCAA ACTAAGATGC
21701    GCCATTAACA TCAGCCAATA GGCATTTTCA GCAAAGCAAA TGAATTCGTA
21751    ATCATGTCAT AGCTGTTTCC TGTGTGAAAT TGTTATCCGC TCACAATTCC
21801    ACACAACATA CGAGCCGGAA GCATAAAGTG TAAAGCCTGG GGTGCCTAAT
21851    GAGTGAGCTA ACTCACATTA ATTGCGTTGC GCTCACTGCC CGCTTTCCAG
21901    TCGGGAAACC TGTCGTGCCA GCTGCATTAA TGAATCGGCC AACGCGCGGG
21951    GAGAGGCGGT TTGCGTATTG GCTAGAGCAG CTTGCCAACA TGGTGGAGCA
22001    CGACACTCTC GTCTACTCCA AGAATATCAA AGATACAGTC TCAGAAGACC
22051    AAAGGGCTAT TGAGACTTTT CAACAAAGGG TAATATCGGG AAACCTCCTC
22101    GGATTCCATT GCCCAGCTAT CTGTCACTTC ATCAAAAGGA CAGTAGAAAA
22151    GGAAGGTGGC ACCTACAAAT GCCATCATTG CGATAAAGGA AAGGCTATCG
22201    TTCAAGATGC CTCTGCCGAC AGTGGTCCCA AAGATGGACC CCCACCCACG
22251    AGGAGCATCG TGGAAAAAGA AGACGTTCCA ACCACGTCTT CAAAGCAAGT
22301    GGATTGATGT GAACATGGTG GAGCACGACA CTCTCGTCTA CTCCAAGAAT
22351    ATCAAAGATA CAGTCTCAGA AGACCAAAGG GCTATTGAGA CTTTTCAACA
22401    AAGGGTAATA TCGGGAAACC TCCTCGGATT CCATTGCCCA GCTATCTGTC
22451    ACTTCATCAA AAGGACAGTA GAAAAGGAAG GTGGCACCTA CAAATGCCAT
22501    CATTGCGATA AAGGAAAGGC TATCGTTCAA GATGCCTCTG CCGACAGTGG
22551    TCCCAAAGAT GGACCCCCAC CCACGAGGAG CATCGTGGAA AAAGAAGACG
22601    TTCCAACCAC GTCTTCAAAG CAAGTGGATT GATGTGATAT CTCCACTGAC
22651    GTAAGGGATG ACGCACAATC CCACTATCCT TCGCAAGACC CTTCCTCTAT
22701    ATAAGGAAGT TCATTTCATT TGGAGAGGAC ACGCTGAAAT CACCAGTCTC
22751    TCTCTACAAA TCTATCTCTC TCGAGAAAAT GGTGAGCAAG GGCGAGGAGC
22801    TGTTCACCGG GGTGGTGCCC ATCCTGGTCG AGCTGGACGG CGACGTAAAC
22851    GGCCACAAGT TCAGCGTGTC CGGCGAGGGC GAGGGCGATG CCACCTACGG
22901    CAAGCTGACC CTGAAGTTCA TCTGCACCAC CGGCAAGCTG CCCGTGCCCT
22951    GGCCCACCCT CGTGACCACC TTCACCTACG GCGTGCAGTG CTTCAGCCGC
23001    TACCCCGACC ACATGAAGCA GCACGACTTC TTCAAGTCCG CCATGCCCGA
23051    AGGCTACGTC CAGGAGCGCA CCATCTTCTT CAAGGACGAC GGCAACTACA
23101    AGACCCGCGC CGAGGTGAAG TTCGAGGGCG ACACCCTGGT GAACCGCATC
23151    GAGCTGAAGG GCATCGACTT CAAGGAGGAC GGCAACATCC TGGGGCACAA
23201    GCTGGAGTAC AACTACAACA GCCACAACGT CTATATCATG GCCGACAAGC
23251    AGAAGAACGG CATCAAGGTG AACTTCAAGA TCCGCCACAA CATCGAGGAC
23301    GGCAGCGTGC AGCTCGCCGA CCACTACCAG CAGAACACCC CCATCGGCGA
23351    CGGCCCCGTG CTGCTGCCCG ACAACCACTA CCTGAGCACC CAGTCCGCCC
23401    TGAGCAAAGA CCCCAACGAG AAGCGCGATC ACATGGTCCT GCTGGAGTTC
23451    GTGACCGCCG CCGGGATCAC TCACGGCATG GACGAGCTGT ACAAGTAAGA
```

FIG. 22I DNA Sequence of pMBXS1023 (Cont'd)

```
23501  GCTCGGTCAC CTGTCCAACA GTCTCAGGGT TAATGTCTAT GTATCTTAAA
23551  TAATGTTGTC GGCGATCGTT CAAACATTTG GCAATAAAGT TTCTTAAGAT
23601  TGAATCCTGT TGCCGGTCTT GCGATGATTA TCATATAATT TCTGTTGAAT
23651  TACGTTAAGC ATGTAATAAT TAACATGTAA TGCATGACGT TATTTATGAG
23701  ATGGGTTTTT ATGATTAGAG TCCCGCAATT ATACATTTAA TACGCGATAG
23751  AAAACAAAAT ATAGCGCGCA AACTAGGATA AATTATCGCG CGCGGTGTCA
23801  TCTATGTTAC TAGATCGGGA ATTAAACTAT CAGTGTTTGA CAGGATATAT
23851  TGGCGGGTAA ACCTAAGAGA AAAGAGCGTT TATTAGAATA ATCGGATATT
23901  TAAAAGGGCG TGAAAAGGTT TATCCGTTCG TCCATTTGTA TGTGCATGCC
23951  AACCACAGGG TTCCCCTCGG GATCAAAGTA CTTTGATCCA ACCCCTCCGC
24001  TGCTATAGTG CAGTCGGCTT CTGACGTTCA GTGCAGCCGT CTTCTGAAAA
24051  CGACATGTCG CACAAGTCCT AAGTTACGCG ACAGGCTGCC GCCCTGCCCT
24101  TTTCCTGGCG TTTTCTTGTC GCGTGTTTTA GTCGCATAAA GTAGAATACT
24151  TGCGACTAGA ACCGGAGACA TTACGCCATG AACAAGAGCG CCGCCGCTGG
24201  CCTGCTGGGC TATGCCCGCG TCAGCACCGA CGACCAGGAC TTGACCAACC
24251  AACGGGCCGA ACTGCACGCG GCCGGCTGCA CCAAGCTGTT TTCCGAGAAG
24301  ATCACCGGCA CCAGGCGCGA CCGCCCGGAG CTGGCCAGGA TGCTTGACCA
24351  CCTACGCCCT GGCGACGTTG TGACAGTGAC CAGGCTAGAC CGCCTGGCCC
24401  GCAGCACCCG CGACCTACTG GACATTGCCG AGCGCATCCA GGAGGCCGGC
24451  GCGGGCCTGC GTAGCCTGGC AGAGCCGTGG GCCGACACCA CCACGCCGGC
24501  CGGCCGCATG GTGTTGACCG TGTTCGCCGG CATTGCCGAG TTCGAGCGTT
24551  CCCTAATCAT CGACCGCACC CGGAGCGGGC GCGAGGCCGC CAAGGCCCGA
24601  GGCGTGAAGT TTGGCCCCCG CCCTACCCTC ACCCCGGCAC AGATCGCGCA
24651  CGCCCGCGAG CTGATCGACC AGGAAGGCCG CACCGTGAAA GAGGCGGCTG
24701  CACTGCTTGG CGTGCATCGC TCGACCCTGT ACCGCGCACT TGAGCGCAGC
24751  GAGGAAGTGA CGCCCACCGA GGCCAGGCGG CGCGGTGCCT TCCGTGAGGA
24801  CGCATTGACC GAGGCCGACG CCCTGGCGGC CGCCGAGAAT GAACGCCAAG
24851  AGGAACAAGC ATGAAACCGC ACCAGGACGG CCAGGACGAA CCGTTTTTCA
24901  TTACCGAAGA GATCGAGGCG GAGATGATCG CGGCCGGGTA CGTGTTCGAG
24951  CCGCCCGCGC ACGTCTCAAC CGTGCGGCTG CATGAAATCC TGGCCGGTTT
25001  GTCTGATGCC AAGCTGGCGG CCTGGCCGGC CAGCTTGGCC GCTGAAGAAA
25051  CCGAGCGCCG CCGTCTAAAA AGGTGATGTG TATTTGAGTA AAACAGCTTG
25101  CGTCATGCGG TCGCTGCGTA TATGATGCGA TGAGTAAATA AACAAATACG
25151  CAAGGGGAAC GCATGAAGGT TATCGCTGTA CTTAACCAGA AAGGCGGGTC
25201  AGGCAAGACG ACCATCGCAA CCCATCTAGC CCGCGCCCTG CAACTCGCCG
25251  GGGCCGATGT TCTGTTAGTC GATTCCGATC CCCAGGGCAG TGCCCGCGAT
25301  TGGGCGGCCG TGCGGGAAGA TCAACCGCTA ACCGTTGTCG GCATCGACCG
25351  CCCGACGATT GACCGCGACG TGAAGGCCAT CGGCCGGCGC GACTTCGTAG
25401  TGATCGACGG AGCGCCCCAG GCGGCGGACT TGGCTGTGTC CGCGATCAAG
25451  GCAGCCGACT TCGTGCTGAT TCCGGTGCAG CCAAGCCCTT ACGACATATG
25501  GGCCACCGCC GACCTGGTGG AGCTGGTTAA GCAGCGCATT GAGGTCACGG
25551  ATGGAAGGCT ACAAGCGGCC TTTGTCGTGT CGCGGGCGAT CAAAGGCACG
25601  CGCATCGGCG GTGAGGTTGC CGAGGCGCTG GCCGGGTACG AGCTGCCCAT
25651  TCTTGAGTCC CGTATCACGC AGCGCGTGAG CTACCCAGGC ACTGCCGCCG
25701  CCGGCACAAC CGTTCTTGAA TCAGAACCCG AGGGCGACGC TGCCCGCGAG
25751  GTCCAGGCGC TGGCCGCTGA AATTAAATCA AAACTCATTT GAGTTAATGA
25801  GGTAAAGAGA AAATGAGCAA AAGCACAAAC ACGCTAAGTG CCGGCCGTCC
25851  GAGCGCACGC AGCAGCAAGG CTGCAACGTT GGCCAGCCTG GCAGACACGC
25901  CAGCCATGAA GCGGGTCAAC TTTCAGTTGC CGGCGGAGGA TCACACCAAG
25951  CTGAAGATGT ACGCGGTACG CCAAGGCAAG ACCATTACCG AGCTGCTATC
26001  TGAATACATC GCGCAGCTAC CAGAGTAAAT GAGCAAATGA ATAAATGAGT
26051  AGATGAATTT TAGCGGCTAA AGGAGGCGGC ATGGAAAATC AAGAACAACC
26101  AGGCACCGAC GCCGTGGAAT GCCCCATGTG TGGAGGAACG GGCGGTTGGC
26151  CAGGCGTAAG CGGCTGGGTT GCCTGCCGGC CCTGCAATGG CACTGGAACC
26201  CCCAAGCCCG AGGAATCGGC GTGAGCGGTC GCAAACCATC CGGCCCGGTA
26251  CAAATCGGCG CGGCGCTGGG TGATGACCTG GTGGAGAAGT TGAAGGCCGC
26301  GCAGGCCGCC CAGCGGCAAC GCATCGAGGC AGAAGCACGC CCCGGTGAAT
26351  CGTGGCAAGC GGCCGCTGAT CGAATCCGCA AAGAATCCCG GCAACCGCCG
26401  GCAGCCGGTG CGCCGTCGAT TAGGAAGCCG CCCAAGGGCG ACGAGCAACC
```

FIG. 22J DNA Sequence of pMBXS1023 (Cont'd)

```
26451  AGATTTTTTC GTTCCGATGC TCTATGACGT GGGCACCCGC GATAGTCGCA
26501  GCATCATGGA CGTGGCCGTT TTCCGTCTGT CGAAGCGTGA CCGACGAGCT
26551  GGCGAGGTGA TCCGCTACGA GCTTCCAGAC GGGCACGTAG AGGTTTCCGC
26601  AGGGCCGGCC GGCATGGCCA GTGTGTGGGA TTACGACCTG GTACTGATGG
26651  CGGTTTCCCA TCTAACCGAA TCCATGAACC GATACCGGGA AGGGAAGGGA
26701  GACAAGCCCG GCCGCGTGTT CCGTCCACAC GTTGCGGACG TACTCAAGTT
26751  CTGCCGGCGA GCCGATGGCG GAAAGCAGAA AGACGACCTG GTAGAAACCT
26801  GCATTCGGTT AAACACCACG CACGTTGCCA TGCAGCGTAC GAAGAAGGCC
26851  AAGAACGGCC GCCTGGTGAC GGTATCCGAG GGTGAAGCCT TGATTAGCCG
26901  CTACAAGATC GTAAAGAGCG AAACCGGGCG GCCGGAGTAC ATCGAGATCG
26951  AGCTAGCTGA TTGGATGTAC CGCGAGATCA CAGAAGGCAA GAACCCGGAC
27001  GTGCTGACGG TTCACCCCGA TTACTTTTTG ATCGATCCCG GCATCGGCCG
27051  TTTTCTCTAC CGCCTGGCAC GCCGCGCCGC AGGCAAGGCA GAAGCCAGAT
27101  GGTTGTTCAA GACGATCTAC GAACGCAGTG GCAGCGCCGG AGAGTTCAAG
27151  AAGTTCTGTT TCACCGTGCG CAAGCTGATC GGGTCAAATG ACCTGCCGGA
27201  GTACGATTTG AAGGAGGAGG CGGGGCAGGC TGGCCCGATC CTAGTCATGC
27251  GCTACCGCAA CCTGATCGAG GGCGAAGCAT CCGCCGGTTC CTAATGTACG
27301  GAGCAGATGC TAGGGCAAAT TGCCCTAGCA GGGGAAAAAG GTCGAAAAGG
27351  TCTCTTTCCT GTGGATAGCA CGTACATTGG GAACCCAAAG CCGTACATTG
27401  GGAACCGGAA CCCGTACATT GGGAACCCAA AGCCGTACAT TGGGAACCGG
27451  TCACACATGT AAGTGACTGA TATAAAAGAG AAAAAAGGCG ATTTTTCCGC
27501  CTAAAACTCT TTAAAACTTA TTAAAACTCT TAAAACCCGC CTGGCCTGTG
27551  CATAACTGTC TGGCCAGCGC ACAGCCGAAG AGCTGCAAAA AGCGCCTACC
27601  CTTCGGTCGC TGCGCTCCCT ACGCCCCGCC GCTTCGCGTC GGCCTATCGC
27651  GGCCGCTGGC CGCTCAAAAA TGGCTGGCCT ACGGCCAGGC AATCTACCAG
27701  GGCGCGGACA AGCCGCGCCG TCGCCACTCG ACCGCCGGCG CCCACATCAA
27751  GGCACCCTGC CTCGCGCGTT TCGGTGATGA CGGTGAAAAC CTCTGACACA
27801  TGCAGCTCCC GGAGACGGTC ACAGCTTGTC TGTAAGCGGA TGCCGGGAGC
27851  AGACAAGCCC GTCAGGGCGC GTCAGCGGGT GTTGGCGGGT GTCGGGGCGC
27901  AGCCATGACC CAGTCACGTA GCGATAGCGG AGTGTATACT GGCTTAACTA
27951  TGCGGCATCA GAGCAGATTG TACTGAGAGT GCACCATATG CGGTGTGAAA
28001  TACCGCACAG ATGCGTAAGG AGAAAATACC GCATCAGGCG CTCTTCCGCT
28051  TCCTCGCTCA CTGACTCGCT GCGCTCGGTC GTTCGGCTGC GGCGAGCGGT
28101  ATCAGCTCAC TCAAAGGCGG TAATACGGTT ATCCACAGAA TCAGGGGATA
28151  ACGCAGGAAA GAACATGTGA GCAAAAGGCC AGCAAAAGGC CAGGAACCGT
28201  AAAAAGGCCG CGTTGCTGGC GTTTTTCCAT AGGCTCCGCC CCCCTGACGA
28251  GCATCACAAA AATCGACGCT CAAGTCAGAG GTGGCGAAAC CCGACAGGAC
28301  TATAAAGATA CCAGGCGTTT CCCCCTGGAA GCTCCCTCGT GCGCTCTCCT
28351  GTTCCGACCC TGCCGCTTAC CGGATACCTG TCCGCCTTTC TCCCTTCGGG
28401  AAGCGTGGCG CTTTCTCATA GCTCACGCTG TAGGTATCTC AGTTCGGTGT
28451  AGGTCGTTCG CTCCAAGCTG GGCTGTGTGC ACGAACCCCC CGTTCAGCCC
28501  GACCGCTGCG CCTTATCCGG TAACTATCGT CTTGAGTCCA ACCCGGTAAG
28551  ACACGACTTA TCGCCACTGG CAGCAGCCAC TGGTAACAGG ATTAGCAGAG
28601  CGAGGTATGT AGGCGGTGCT ACAGAGTTCT TGAAGTGGTG GCCTAACTAC
28651  GGCTACACTA GAAGGACAGT ATTTGGTATC TGCGCTCTGC TGAAGCCAGT
28701  TACCTTCGGA AAAAGAGTTG GTAGCTCTTG ATCCGGCAAA CAAACCACCG
28751  CTGGTAGCGG TGGTTTTTTT GTTTGCAAGC AGCAGATTAC GCGCAGAAAA
28801  AAAGGATCTC AAGAAGATCC TTTGATCTTT TCTACGGGGT CTGACGCTCA
28851  GTGGAACGAA AACTCACGTT AAGGGATTTT GGTCATGCAT TCTAGGTACT
28901  AAAACAATTC ATCCAGTAAA ATATAATATT TTATTTTCTC CCAATCAGGC
28951  TTGATCCCCA GTAAGTCAAA AAATAGCTCG ACATACTGTT CTTCCCCGAT
29001  ATCCTCCCTG ATCGACCGGA CGCAGAAGGC AATGTCATAC CACTTGTCCG
29051  CCCTGCCGCT TCTCCCAAGA TCAATAAAGC CACTTACTTT GCCATCTTTC
29101  ACAAAGATGT TGCTGTCTCC CAGGTCGCCG TGGGAAAAGA CAAGTTCCTC
29151  TTCGGGCTTT TCCGTCTTTA AAAAATCATA CAGCTCGCGC GGATCTTTAA
29201  ATGGAGTGTC TTCTTCCCAG TTTTCGCAAT CCACATCGGC CAGATCGTTA
29251  TTCAGTAAGT AATCCAATTC GGCTAAGCGG CTGTCTAAGC TATTCGTATA
29301  GGGACAATCC GATATGTCGA TGGAGTGAAA GAGCCTGATG CACTCCGCAT
29351  ACAGCTCGAT AATCTTTTCA GGGCTTTGTT CATCTTCATA CTCTTCCGAG
```

FIG. 22K DNA Sequence of pMBXS1023 (Cont'd)

```
29401CAAAGGACGC CATCGGCCTC ACTCATGAGC AGATTGCTCC AGCCATCATG
29451CCGTTCAAAG TGCAGGACCT TTGGAACAGG CAGCTTTCCT TCCAGCCATA
29501GCATCATGTC CTTTTCCCGT TCCACATCAT AGGTGGTCCC TTTATACCGG
29551CTGTCCGTCA TTTTTAAATA TAGGTTTTCA TTTTCTCCCA CCAGCTTATA
29601TACCTTAGCA GGAGACATTC CTTCCGTATC TTTTACGCAG CGGTATTTTT
29651CGATCAGTTT TTTCAATTCC GGTGATATTC TCATTTTAGC CATTTATTAT
29701TTCCTTCCTC TTTTCTACAG TATTTAAAGA TACCCCAAGA AGCTAATTAT
29751AACAAGACGA ACTCCAATTC ACTGTTCCTT GCATTCTAAA ACCTTAAATA
29801CCAGAAAACA GCTTTTTCAA AGTTGTTTTC AAAGTTGGCG TATAACATAG
29851TATCGACGGA GCCGATTTTG AAACCGCGGT GATCACAGGC AGCAACGCTC
29901TGTCATCGTT ACAATCAACA TGCTACCCTC CGCGAGATCA TCCGTGTTTC
29951AAACCCGGCA GCTTAGTTGC CGTTCTTCCG AATAGCATCG GTAACATGAG
30001CAAAGTCTGC CGCCTTACAA CGGCTCTCCC GCTGACGCCG TCCCGGACTG
30051ATGGGCTGCC TGTATCGAGT GGTGATTTTG TGCCGAGCTG CCGGTCGGGG
30101AGCTGTTGGC TGGCTGGTGG CAGGATATAT TGTGGTGTAA ACAAATTGAC
30151GCTTAGACAA CTTAATAACA CATTGCGGAC GTTTTTAATG TACTGAATTA
30201ACGCCGAATT AATT
```

FIG. 23A DNA sequence of pMBXS1024 (SEQ ID NO:5)

```
   1 GTAGTGTTTA TCTTTGTTGC TTTTCTGAAC AATTTATTTA CTATGTAAAT
  51 ATATTATCAA TGTTTAATCT ATTTTAATTT GCACATGAAT TTTCATTTTA
 101 TTTTTACTTT ACAAAACAAA TAAATATATA TGCAAAAAAA TTTACAAACG
 151 ATGCACGGGT TACAAACTAA TTTCATTAAA TGCTAATGCA GATTTTGTGA
 201 AGTAAAACTC CAATTATGAT GAAAAATACC ACCAACACCA CCTGCGAAAC
 251 TGTATCCCAA CTGTCCTTAA TAAAAATGTT AAAAAGTATA TTATTCTCAT
 301 TTGTCTGTCA TAATTTATGT ACCCCACTTT AATTTTTCTG ATGTACTAAA
 351 CCGAGGGCAA ACTGAAACCT GTTCCTCATG CAAAGCCCCT ACTCACCATG
 401 TATCATGTAC GTGTCATCAC CCAACAACTC CACTTTTGCT ATATAACAAC
 451 ACCCCCGTCA CACTCTCCCT CTCTAACACA CACCCCACTA ACAATTCCTT
 501 CACTTGCAGC ACTGTTGCAT CATCATCTTC ATTGCAAAAC CCTAAACTTC
 551 ACCTTCAACC GCGGCCGCAG ATCTAAAATG GCTTCTATGA TATCCTCTTC
 601 CGCTGTGACA ACAGTCAGCC GTGCCTCTAG GGGGCAATCC GCCGCAGTGG
 651 CTCCATTCGG CGGCCTCAAA TCCATGACTG GATTCCCAGT GAAGAAGGTC
 701 AACACTGACA TTACTTCCAT TACAAGCAAT GGTGGAAGAG TAAAGTGCAT
 751 GCAGGTGTGG CCTCCAATTG GAAAGAAGAA GTTTGAGACT CTTTCCTATT
 801 TGCCACCATT GACGAGAGAT TCTAGAGTGC TCAGCCAGCA ATCCATCCAG
 851 AAGGTTCTCG TGGCTAACCG TGGTGAGATT GCTATTCGTA TCTTTAGAGC
 901 GTGTACCGAG TTGAACATCC GAACTGTCGC TGTTTATAGT AAAGAAGATT
 951 CTGGATCATA CCACAGATAC AAAGCTGACG AGGCCTACTT GGTTGGTGAA
1001 GGTAAGAAGC CTATTGACGC TTATCTTGAT ATAGAGGGCA TCATTGATAT
1051 TGCCAAGAGA AACAAAGTTG ATGCAATTCA TCCGGGATAC GGTTTTCTAT
1101 CAGAAAACAT TCACTTTGCA CGACGATGTG AAGAAGAGGG AATCGTGTTC
1151 ATCGGACCTA AAAGCGAACA CTTGGATATG TTTGGGGACA AGGTTAAGGC
1201 AAGGGAACAA GCAGAGAAGG CAGGAATTCC AGTGATACCT GGATCGGATG
1251 GGCCTGCTGA AACTCTTGAA GCTGTCGAAC AATTCGGCCA GGCTAACGGA
1301 TACCCAATCA TCATTAAGGC TTCTTTAGGT GGTGGGGGAA GGGGGATGAG
1351 AATCGTGCGA TCCGAATCTG AGGTAAAAGA GGCTTATGAA CGTGCTAAAT
1401 CGGAAGCTAA AGCGGCCTTT GGGAACGATG AAGTCTATGT CGAGAAACTA
1451 ATCGAGAATC CCAAGCACAT CGAGGTTCAA GTGATTGGTG ATAAGCAAGG
1501 TAACGTTGTT CACCTTTTCG AGAGAGATTG TTCTGTTCAA CGTAGACACC
1551 AAAAAGTGAT AGAAGTAGCT CCATCGGTAT CGTTGAGCCC AGAACTAAGG
1601 GACCAGATAT GCGAGGCTGC TGTCGCGCTT GCAAAGAATG TCAACTATAT
1651 CAATGCAGGC ACTGTCGAAT TCTTGGTAGC CAATAATGAG TTTTACTTCA
1701 TTGAGGTCAA CCCTAGAGTT CAAGTTGAGC ATACCATTAC CGAAATGATC
1751 ACTGGGGTGG ATATCGTACA GACTCAGATC CTCGTTGCTC AAGGCCATTC
1801 CCTTCATTCC AAGAAGGTGA ATATTCCAGA GCAAAAGGAT ATCTTTACAA
1851 TTGGTTATGC GATTCAATCA CGAGTTACCA CAGAAGATCC ACAAAATGAC
1901 TTCATGCCAG ATACGGGAAA GATAATGGCA TACCGTTCTG GTGGCGGATT
1951 TGGTGTTCGA TTAGACACAG GTAATAGTTT TCAGGGAGCT GTGATAACGC
2001 CATACTATGA TTCTTTATTG GTTAAGTTGA GTACTTGGGC TCTCACTTTC
2051 GAGCAAGCCG CAGCGAAAAT GGTCAGAAAC CTTCAGGAGT TCAGAATTAG
2101 AGGTATTAAG ACGAACATTC CATTCTTAGA GAACGTTGCT AAACATGAGA
2151 AGTTTCTGAC AGGACAATAT GATACAAGTT TCATAGACAC TACACCTGAA
2201 CTCTTTAACT TCCCTAAACA AAAAGACAGA GGTACGAAAA TGTTGACATA
2251 TATCGGAAAC GTGACAGTTA ATGGGTTCCC AGGTATCGGT AAGAAAGAAA
2301 AGCCGGCCTT TGATAAACCC CTTGGTGTTA AAGTGGATGT GGATCAACAA
2351 CCTGCTAGGG GCACTAAGCA AATCCTTGAT GAAAAGGGTG CAGAGGGACT
2401 GGCAAATTGG GTTAAAGAGC AGAAATCAGT TCTTCTGACA GATACCACAT
2451 TTCGTGATGC TCATCAATCA TTACTAGCAA CAAGAATTAG ATCACACGAT
2501 CTGAAAAAGA TCGCTAATCC AACCGCTGCT CTTTGGCCGG AACTCTTCTC
2551 TATGGAAATG TGGGGTGGGG CCACATTCGA TGTCGCGTAC CGTTTTCTAA
2601 AAGAAGATCC TTGGAAGCGT CTGGAAGATT TGAGAAAAGA GGTGCCCAAT
2651 ACCCTGTTCC AGATGCTTTT GCGTTCTAGC AATGCCGTCG GATATACCAA
2701 TTATCCTGAC AATGTGATCA AAGAATTCGT AAAACAGTCC GCTCAATCTG
2751 GTATCGACGT TTTTAGGATT TTCGATTCAC TTAATTGGGT AAAAGGTATG
2801 ACGTTAGCGA TTGATGCTGT ACGTGATACT GGAAAGGTTG CAGAGGCCGC
```

FIG. 23B DNA sequence of pMBXS1024 (Cont'd)

```
2851  CATTTGCTAC ACTGGAGACA TTTTGGATAA GAATAGAACT AAATACGACT
2901  TGGCTTATTA CACTTCCATG GCAAAAGAAC TTGAGGCTGC CGGTGCACAT
2951  ATTCTGGGGA TAAAGGATAT GGCCGGTTTG CTCAAACCGC AGGCAGCATA
3001  TGAGTTGGTT TCAGCCCTTA AAGAAACTAT TGACATACCC GTTCATCTGC
3051  ACACGCATGA CACGTCGGGC AATGGAATCT ATATGTATGC AAAGGCTGTC
3101  GAGGCTGGCG TGGATATCAT TGATGTCGCT GTAAGCTCTA TGGCTGGACT
3151  TACATCCCAG CCATCAGCCT CTGGATTCTA TCATGCTATG GAAGGTAACG
3201  ATCGTAGACC CGAAATGAAT GTCCAAGGGG TCGAATTACT GTCACAGTAC
3251  TGGGAGAGTG TGCGTAAGTA TTACTCAGAG TTTGAGAGCG GTATGAAGAG
3301  TCCCCATACC GAGATTTATG AGCACGAGAT GCCTGGTGGA CAATACTCTA
3351  ACTTGCAACA GCAAGCGAAG GGGGTTGGTT TGGGAGATAG GTGGAACGAA
3401  GTGAAAGAAA TGTATAGACG TGTCAACGAC ATGTTTGGTG ATATTGTGAA
3451  AGTAACTCCT AGTTCTAAGG TAGTTGGAGA CATGGCACTG TACATGGTTC
3501  AGAATAACCT TACTGAAAAG GATGTTTACG AGAAGGGGGA GTCACTTGAC
3551  TTCCCTGATT CAGTGGTTGA ACTGTTCAAG GGAAATATCG GTCAACCGCA
3601  TGGGGGATTT CCAGAAAAAC TACAGAAACT GATACTAAAG GGACAGGAGC
3651  CAATTACTGT TCGACCAGGA GAGCTCTTGG AGCCGGTTTC TTTTGAGGCT
3701  ATCAAGCAAG AATTCAAAGA ACAACATAAC CTTGAAATTT CTGATCAGGA
3751  CGCGGTTGCT TACGCACTTT ATCCAAAGGT CTTTACTGAT TACGTGAAAA
3801  CCACAGAGTC TTATGGTGAT ATAAGTGTGC TAGATACACC AACATTTTTC
3851  TATGGCATGA CTCTTGGAGA AGAGATTGAA GTGGAAATAG AAAGGGGAAA
3901  AACACTCATT GTTAAACTGA TATCTATCGG AGAGCCTCAA CCTGATGCTA
3951  CAAGGGTAGT GTACTTTGAA TTGAATGGAC AACCTAGAGA AGTAGTGATT
4001  AAAGATGAGT CAATAAAGTC AAGCGTGCAG GAGAGGCTAA AGGCAGATAG
4051  AACCAATCCG TCGCACATTG CAGCTTCTAT GCCTGGCACC GTCATAAAAG
4101  TCCTCGCTGA AGCTGGTACT AAAGTCAACA AAGGTGACCA TCTTATGATC
4151  AACGAAGCAA TGAAGATGGA AACTACGGTT CAGGCACCTT TCAGTGGAAC
4201  AATCAAGCAG GTTCATGTTA AGAATGGCGA GCCTATCCAG ACTGGTGACT
4251  TGCTTTTGGA GATTGAAAAG GCCTGAGTCG ACGCGATCGC GCGGCCGCTG
4301  AGTAATTCTG ATATTAGAGG GAGCATTAAT GTGTTGTTGT GATGTGGTTT
4351  ATATGGGGAA ATTAAATAAA TGATGTATGT ACCTCTTGCC TATGTAGGTT
4401  TGTGTGTTTT GTTTTGTTGT CTAGCTTTGG TTATTAAGTA GTAGGGACGT
4451  TCGTTCGTGT CTCAAAAAAA GGGGTACTAC CACTCTGTAG TGTATATGGA
4501  TGCTGGAAAT CAATGTGTTT TGTATTTGTT CACCTCCATT GTTGAATTCA
4551  ATGTCAAATG TGTTTTGCGT TGGTTATGTG TAAAATTACT ATCTTTCTCG
4601  TCCGATGATC AAAGTTTTAA GCAACAAAAC CAAGGGTGAA ATTTAAACTG
4651  TGCTTTGTTG AAGATTCTTT TATCATATTG AAAATCAAAT TACTAGCAGC
4701  AGATTTTACC TAGCATGAAA TTTTATCAAC AGTACAGCAC TCACTAACCA
4751  AGTTCCAAAC TAAGATGCGC CATTAACATC AGCCAATAGG CATTTTCAGC
4801  AAGTTTAAAC TACGTAGTGT TTATCTTTGT TGCTTTTCTG AACAATTTAT
4851  TTACTATGTA AATATATTAT CAATGTTTAA TCTATTTTAA TTTGCACATG
4901  AATTTTCATT TTATTTTTAC TTTACAAAAC AAATAAATAT ATATGCAAAA
4951  AAATTTACAA ACGATGCACG GGTTACAAAC TAATTTCATT AAATGCTAAT
5001  GCAGATTTTG TGAAGTAAAA CTCCAATTAT GATGAAAAAT ACCACCAACA
5051  CCACCTGCGA AACTGTATCC CAACTGTCCT TAATAAAAAT GTTAAAAAGT
5101  ATATTATTCT CATTTGTCTG TCATAATTTA TGTACCCCAC TTTAATTTTT
5151  CTGATGTACT AAACCGAGGG CAAACTGAAA CCTGTTCCTC ATGCAAAGCC
5201  CCTACTCACC ATGTATCATG TACGTGTCAT CACCCAACAA CTCCACTTTT
5251  GCTATATAAC AACACCCCCG TCACACTCTC CCTCTCTAAC ACACACCCCA
5301  CTAACAATTC CTTCACTTGC AGCACTGTTG CATCATCATC TTCATTGCAA
5351  AACCCTAAAC TTCACCTTCA ACCGCGGCCG CTCGCGAAAA ATGGCTTCTA
5401  TGATATCCTC TTCCGCTGTG ACAACAGTCA GCCGTGCCTC TAGGGGGCAA
5451  TCCGCCGCAG TGGCTCCATT CGGCGGCCTC AAATCCATGA CTGGATTCCC
5501  AGTGAAGAAG GTCAACACTG ACATTACTTC CATTACAAGC AATGGTGGAA
5551  GAGTAAAGTG CATGCAGGTG TGGCCTCCAA TTGGAAAGAA GAAGTTTGAG
5601  ACTCTTTCCT ATTTGCCACC ATTGACGAGA GATTCTAGAG TGAACATACA
5651  CGAGTACCAA GCAAAAGAGT TGCTCAAGAC CTATGGAGTG CCGGTCCCAG
5701  ACGGAGCGGT AGCTTATAGT GATGCTCAAG CGGCTTCCGT CGCTGAAGAG
5751  ATTGGTGGCT CTAGATGGGT TGTAAAGGCG CAGATACACG CTGGTGGAAG
```

FIG. 23C DNA sequence of pMBXS1024 (Cont'd)

```
5801    GGGAAAGGCA GGTGGTGTGA AGGTGGCCCA TAGCATTGAA GAGGTTCGTC
5851    AGTACGCTGA TGCGATGCTT GGGTCCCATC TCGTTACACA TCAAACAGGG
5901    CCTGGTGGTT CATTAGTTCA ACGTTTGTGG GTGGAGCAAG CATCACATAT
5951    CAAGAAAGAG TATTATCTGG GATTTGTTAT TGATAGAGGT AACCAAAGAA
6001    TTACCTTAAT TGCTTCTTCT GAAGGGGGAA TGGAGATAGA AGAGGTTGCT
6051    AAAGAGACAC CAGAAAAGAT CGTCAAAGAG GTTGTAGACC CTGCAATCGG
6101    ATTGCTTGAT TTTCAGTGTA GAAAGGTTGC AACTGCAATA GGACTTAAGG
6151    GAAAGCTTAT GCCCCAGGCA GTTAGACTTA TGAAGGCTAT CTATAGGTGT
6201    ATGCGAGATA AGGATGCTCT CCAGGCAGAG ATCAATCCTT TGGCAATAGT
6251    AGGTGAAAGT GACGAGTCGC TCATGGTTCT TGATGCTAAA TTCAATTTTG
6301    ATGACAATGC TCTTTACAGA CAACGAACAA TTACTGAAAT GAGGGATCTC
6351    GCAGAAGAAG ATCCTAAAGA AGTCGAAGCT TCTGGACACG GATTGAATTA
6401    CATCGCCCTC GATGGGAACA TCGGTTGTAT TGTGAATGGA GCTGGTCTTG
6451    CTATGGCCAG CCTGGATGCC ATCACTCTAC ATGGCGGTCG TCCAGCTAAC
6501    TTCTTAGATG TCGGCGGTGG GGCTTCTCCT GAAAAGGTTA CGAATGCGTG
6551    CAGAATTGTT TTGGAAGATC CGAACGTCCG TTGTATACTG GTGAACATTT
6601    TTGCCGGAAT TAACAGGTGC GATTGGATTG CAAAAGGACT TATTCAAGCC
6651    TGCGACTCAC TACAGATTAA AGTTCCACTG ATCGTTCGAT TGGCAGGCAC
6701    TAATGTAGAT GAAGGCAGGA AAATCCTAGC GGAGTCGGGT TTAAGTTTCA
6751    TAACGGCAGA GAATTTGGAC GACGCGGCTG CTAAAGCCGT GGCTATCGTG
6801    AAAGGGTGAA CGCGTTGAGT AATTCTGATA TTAGAGGGAG CATTAATGTG
6851    TTGTTGTGAT GTGGTTTATA TGGGGAAATT AAATAAATGA TGTATGTACC
6901    TCTTGCCTAT GTAGGTTTGT GTGTTTTGTT TTGTTGTCTA GCTTTGGTTA
6951    TTAAGTAGTA GGGACGTTCG TTCGTGTCTC AAAAAAAGGG GTACTACCAC
7001    TCTGTAGTGT ATATGGATGC TGGAAATCAA TGTGTTTTGT ATTTGTTCAC
7051    CTCCATTGTT GAATTCAATG TCAAATGTGT TTTGCGTTGG TTATGTGTAA
7101    AATTACTATC TTTCTCGTCC GATGATCAAA GTTTTAAGCA ACAAAACCAA
7151    GGGTGAAATT TAAACTGTGC TTTGTTGAAG ATTCTTTTAT CATATTGAAA
7201    ATCAAATTAC TAGCAGCAGA TTTTACCTAG CATGAAATTT TATCAACAGT
7251    ACAGCACTCA CTAACCAAGT TCCAAACTAA GATGCGCCAT TAACATCAGC
7301    CAATAGGCAT TTTCAGCAAT GTACATACGT AGTGTTTATC TTTGTTGCTT
7351    TTCTGAACAA TTTATTTACT ATGTAAATAT ATTATCAATG TTTAATCTAT
7401    TTTAATTTGC ACATGAATTT TCATTTTATT TTTACTTTAC AAAACAAATA
7451    AATATATATG CAAAAAAATT TACAAACGAT GCACGGGTTA CAAACTAATT
7501    TCATTAAATG CTAATGCAGA TTTTGTGAAG TAAAACTCCA ATTATGATGA
7551    AAAATACCAC CAACACCACC TGCGAAACTG TATCCCAACT GTCCTTAATA
7601    AAAATGTTAA AAAGTATATT ATTCTCATTT GTCTGTCATA ATTTATGTAC
7651    CCCACTTTAA TTTTTCTGAT GTACTAAACC GAGGGCAAAC TGAAACCTGT
7701    TCCTCATGCA AAGCCCCTAC TCACCATGTA TCATGTACGT GTCATCACCC
7751    AACAACTCCA CTTTTGCTAT ATAACAACAC CCCCGTCACA CTCTCCCTCT
7801    CTAACACACA CCCCACTAAC AATTCCTTCA CTTGCAGCAC TGTTGCATCA
7851    TCATCTTCAT TGCAAAACCC TAAACTTCAC CTTCAACCGC GGCCGCGACG
7901    TCAAAATGGC TTCTATGATA TCCTCTTCCG CTGTGACAAC AGTCAGCCGT
7951    GCCTCTAGGG GGCAATCCGC CGCAGTGGCT CCATTCGGCG GCCTCAAATC
8001    CATGACTGGA TTCCCAGTGA AGAAGGTCAA CACTGACATT ACTTCCATTA
8051    CAAGCAATGG TGGAAGAGTA AAGTGCATGC AGGTGTGGCC TCCAATTGGA
8101    AAGAAGAAGT TTGAGACTCT TTCCTATTTG CCACCATTGA CGAGAGATTC
8151    TAGAGTCTCG GTTTTCGTGA ATAAACATTC CAAGGTCATC TTTCAAGGCT
8201    TTACCGGGGA GCATGCTACA TTTCACGCAA AAGATGCAAT GCGAATGGGC
8251    ACAAGGGTTG TCGGTGGCGT TACTCCTGGA AAGGGTGGGA CTAGACATCC
8301    AGATCCTGAG CTCGCTCATC TTCCGGTATT CGATACCGTT GCCGAAGCCG
8351    TTGCTGCTAC AGGAGCTGAT GTATCAGCTG TGTTTGTCCC ACCCCCTTTC
8401    AATGCAGACG CACTTATGGA AGCAATTGAT GCCGGTATTA GAGTGGCTGT
8451    CACTATAGCG GATGGAATTC CTGTGCATGA CATGATCAGA TTGCAAAGGT
8501    ATAGAGTAGG AAAGGACTCT ATTGTTATCG GGCCTAACAC ACCAGGAATC
8551    ATAACGCCTG GTGAGTGTAA AGTGGGTATC ATGCCGAGTC ACATATACAA
8601    GAAGGGAAAC GTGGGTATAG TGAGTCGATC AGGAACATTG AATTACGAGG
8651    CGACGGAACA AATGGCTGCG CTAGGCTTAG GGATTACTAC TTCTGTTGGA
8701    ATTGGTGGTG ATCCTATAAA CGGCACTGAC TTTGTGACTG TTCTCCGTGC
```

FIG. 23D DNA sequence of pMBXS1024 (Cont'd)

```
8751    ATTCGAGGCT GATCCAGAAA CGGAAATTGT AGTTATGATC GGAGAAATAG
8801    GTGGACCGCA GGAAGTTGCC GCAGCTAGAT GGGCAAAAGA GAATATGACC
8851    AAACCAGTTA TTGGGTTCGT AGCTGGTTTA GCAGCCCCCA CAGGGCGTAG
8901    GATGGGACAC GCAGGTGCTA TTATCAGCTC TGAGGCTGAT ACCGCTGGAG
8951    CTAAGATGGA TGCCATGGAA GCTCTTGGTC TGTATGTCGC TAGGAACCCA
9001    GCGCAAATCG GACAGACAGT TTTGCGTGCG GCACAGGAGC ATGGAATTAG
9051    ATTTTGAGGG CCCGTTAACT GAGTAATTCT GATATTAGAG GGAGCATTAA
9101    TGTGTTGTTG TGATGTGGTT TATATGGGGA AATTAAATAA ATGATGTATG
9151    TACCTCTTGC CTATGTAGGT TTGTGTGTTT TGTTTTGTTG TCTAGCTTTG
9201    GTTATTAAGT AGTAGGGACG TTCGTTCGTG TCTCAAAAAA AGGGGTACTA
9251    CCACTCTGTA GTGTATATGG ATGCTGGAAA TCAATGTGTT TTGTATTTGT
9301    TCACCTCCAT TGTTGAATTC AATGTCAAAT GTGTTTTGCG TTGGTTATGT
9351    GTAAAATTAC TATCTTTCTC GTCCGATGAT CAAAGTTTTA AGCAACAAAA
9401    CCAAGGGTGA AATTTAAACT GTGCTTTGTT GAAGATTCTT TTATCATATT
9451    GAAAATCAAA TTACTAGCAG CAGATTTTAC CTAGCATGAA ATTTTATCAA
9501    CAGTACAGCA CTCACTAACC AAGTTCCAAA CTAAGATGCG CCATTAACAT
9551    CAGCCAATAG GCATTTTCAG CAAGTTTAAA CCGGACCGTA CGTAGTGTTT
9601    ATCTTTGTTG CTTTTCTGAA CAATTTATTT ACTATGTAAA TATATTATCA
9651    ATGTTTAATC TATTTTAATT TGCACATGAA TTTTCATTTT ATTTTTACTT
9701    TACAAAACAA ATAAATATAT ATGCAAAAAA ATTTACAAAC GATGCACGGG
9751    TTACAAACTA ATTTCATTAA ATGCTAATGC AGATTTTGTG AAGTAAAACT
9801    CCAATTATGA TGAAAAATAC CACCAACACC ACCTGCGAAA CTGTATCCCA
9851    ACTGTCCTTA ATAAAAATGT TAAAAAGTAT ATTATTCTCA TTTGTCTGTC
9901    ATAATTTATG TACCCCACTT TAATTTTTCT GATGTACTAA ACCGAGGGCA
9951    AACTGAAACC TGTTCCTCAT GCAAAGCCCC TACTCACCAT GTATCATGTA
10001   CGTGTCATCA CCCAACAACT CCACTTTTGC TATATAACAA CACCCCCGTC
10051   ACACTCTCCC TCTCTAACAC ACACCCCACT AACAATTCCT TCACTTGCAG
10101   CACTGTTGCA TCATCATCTT CATTGCAAAA CCCTAAACTT CACCTTCAAC
10151   CGCGGCCGCC ACGTGAAAAT GGCTTCTATG ATATCCTCTT CCGCTGTGAC
10201   AACAGTCAGC CGTGCCTCTA GGGGGCAATC CGCCGCAGTG GCTCCATTCG
10251   GCGGCCTCAA ATCCATGACT GGATTCCCAG TGAAGAAGGT CAACACTGAC
10301   ATTACTTCCA TTACAAGCAA TGGTGGAAGA GTAAAGTGCA TGCAGGTGTG
10351   GCCTCCAATT GGAAAGAAGA AGTTTGAGAC TCTTTCCTAT TTGCCACCAT
10401   TGACGAGAGA TTCTAGAGTG AGCTTCCGTT TGCAACCAGC TCCGCCAGCA
10451   AGGCCCAATA GATGTCAACT TTTTGGGCCT GGATCTCGAC CGGCTTTGTT
10501   TGAGAAAATG GCCGCTTCAG CCGCGGACGT TATCAATCTG GATTTAGAGG
10551   ATAGTGTTGC CCCAGATGAT AAAGCTCAGG CTAGAGCAAA TATCATTGAG
10601   GCTATAAACG GTCTAGACTG GGGTAGAAAG TATCTCAGTG TTAGAATTAA
10651   CGGACTTGAT ACGCCTTTCT GGTATCGAGA TGTCGTTGAC TTGCTTGAGC
10701   AGGCAGGAGA TAGACTTGAT CAAATCATGA TCCCTAAGGT TGGCTGTGCT
10751   GCGGATGTTT ACGCCGTCGA TGCTTTGGTA ACAGCAATTG AACGTGCTAA
10801   AGGGCGTACT AAGCCTCTAT CATTTGAAGT GATAATAGAG TCTGCAGCTG
10851   GTATCGCACA TGTTGAAGAA ATAGCCGCTT CGTCACCAAG ACTCCAAGCC
10901   ATGTCTTTGG GTGCAGCCGA TTTTGCAGCT TCTATGGGAA TGCAGACTAC
10951   AGGGATTGGT GGAACGCAAG AGAACTACTA TATGCTCCAC GACGGACAAA
11001   AGCACTGGTC CGATCCTTGG CATTGGGCTC AGGCTGCAAT CGTCGCAGCG
11051   TGCAGAACAC ATGGGATTTT ACCCGTTGAC GGCCCGTTCG GTGACTTCTC
11101   TGATGACGAA GGATTCAGGG CACAAGCTCG AAGGTCCGCT ACTCTTGGAA
11151   TGGTGGGAAA ATGGGCCATA CATCCAAAGC AAGTGGCTCT CGCTAATGAA
11201   GTGTTTACAC CTAGCGAGAC TGCAGTAACC GAAGCGAGGG AGATTTTAGC
11251   GGCTATGGAT GCTGCTAAGG CGAGAGGCGA AGGTGCTACC GTGTACAAAG
11301   GTAGGCTGGT AGATATCGCG TCGATTAAAC AGGCAGAAGT CATTGTTCGT
11351   CAGGCTGAGA TGATTAGTGC ATGAACTAGT TGAGTAATTC TGATATTAGA
11401   GGGAGCATTA ATGTGTTGTT GTGATGTGGT TTATATGGGG AAATTAAATA
11451   AATGATGTAT GTACCTCTTG CCTATGTAGG TTTGTGTGTT TTGTTTTGTT
11501   GTCTAGCTTT GGTTATTAAG TAGTAGGGAC GTTCGTTCGT GTCTCAAAAA
11551   AAGGGGTACT ACCACTCTGT AGTGTATATG GATGCTGGAA ATCAATGTGT
11601   TTTGTATTTG TTCACCTCCA TTGTTGAATT CAATGTCAAA TGTGTTTTGC
11651   GTTGGTTATG TGTAAAATTA CTATCTTTCT CGTCCGATGA TCAAAGTTTT
```

FIG. 23E DNA sequence of pMBXS1024 (Cont'd)

```
11701  AAGCAACAAA ACCAAGGGTG AAATTTAAAC TGTGCTTTGT TGAAGATTCT
11751  TTTATCATAT TGAAAATCAA ATTACTAGCA GCAGATTTTA CCTAGCATGA
11801  AATTTTATCA ACAGTACAGC ACTCACTAAC CAAGTTCCAA ACTAAGATGC
11851  GCCATTAACA TCAGCCAATA GGCATTTTCA GCAAGTTTAA ACTCCGGATA
11901  CGTAGTGTTT ATCTTTGTTG CTTTTCTGAA CAATTTATTT ACTATGTAAA
11951  TATATTATCA ATGTTTAATC TATTTTAATT TGCACATGAA TTTTCATTTT
12001  ATTTTTACTT TACAAAACAA ATAAATATAT ATGCAAAAAA ATTTACAAAC
12051  GATGCACGGG TTACAAACTA ATTTCATTAA ATGCTAATGC AGATTTTGTG
12101  AAGTAAAACT CCAATTATGA TGAAAAATAC CACCAACACC ACCTGCGAAA
12151  CTGTATCCCA ACTGTCCTTA ATAAAAATGT TAAAAAGTAT ATTATTCTCA
12201  TTTGTCTGTC ATAATTTATG TACCCCACTT TAATTTTTCT GATGTACTAA
12251  ACCGAGGGCA AACTGAAACC TGTTCCTCAT GCAAAGCCCC TACTCACCAT
12301  GTATCATGTA CGTGTCATCA CCCAACAACT CCACTTTTGC TATATAACAA
12351  CACCCCCGTC ACACTCTCCC TCTCTAACAC ACACCCCACT AACAATTCCT
12401  TCACTTGCAG CACTGTTGCA TCATCATCTT CATTGCAAAA CCCTAAACTT
12451  CACCTTCAAC CGCGGCCGCC CTAGGAAAAT GGCTTCTATG ATATCCTCTT
12501  CCGCTGTGAC AACAGTCAGC CGTGCCTCTA GGGGGCAATC CGCCGCAGTG
12551  GCTCCATTCG GCGGCCTCAA ATCCATGACT GGATTCCCAG TGAAGAAGGT
12601  CAACACTGAC ATTACTTCCA TTACAAGCAA TGGTGGAAGA GTAAAGTGCA
12651  TGCAGGTGTG GCCTCCAATT GGAAAGAAGA AGTTTGAGAC TCTTTCCTAT
12701  TTGCCACCAT TGACGAGAGA TTCTAGAGTT GCACAGTACC AAGACGATAT
12751  CAAGGCGGTT GCAGGGCTTA AGGAGAATCA CGGCTCCGCA TGGAATGCCA
12801  TCAACCCGGA GTATGCCGCC AGGATGAGGG CGCAGAACAA GTTCAAGACG
12851  GGCCTTGACA TTGCAAAGTA TACGGCTAAG ATTATGCGGG CCGATATGGC
12901  AGCCTACGAC GCCGACAGCT CGAAGTACAC ACAGAGCCTC GGTTGTTGGC
12951  ATGGTTTCAT TGGTCAGCAG AAGATGATCT CAATCAAGAA ACATTTCAAC
13001  AGCACGGAAC GCCGTTACCT CTACCTTTCT GGCTGGATGG TAGCCGCGCT
13051  TAGATCCGAG TTTGGCCCCC TACCGGATCA GTCCATGCAC GAAAAGACGA
13101  GTGTCTCCGC ACTCATTCGG GAACTCTACA CTTTTCTGCG CCAAGCGGAC
13151  GCTAGGGAGT TGGGGGGCCT GTTTCGGGAG CTTGACGCGG CCCAAGGCCC
13201  AGCTAAGGCG GCCATTCAAG CGAAGATCGA CAACCACGTC ACTCATGTGG
13251  TCCCAATCAT AGCTGATATC GACGCTGGCT TCGGCAATGC GGAAGCAACA
13301  TACCTGTTGG CCAAGCAGTT CATCGAGGCC GGGGCTTGCT GCATACAGAT
13351  AGAGAACCAG GTTTCTGACG AAAAGCAATG TGGACATCAA GACGGAAAGG
13401  TTACCGTGCC CCACGAGGAT TTTCTTGCAA AAATCCGAGC GATTCGTTAT
13451  GCGTTTTTAG AGTTGGGCGT GGATGACGGT ATCATCGTGG CCAGGACCGA
13501  TAGTCTCGGT GCTGGTCTGA CAAAGCAAAT CGCAGTGACC AATACGCCTG
13551  GAGACTTAGG GGATCAGTAC AACAGCTTCC TCGATTGCGA GGAGCTTAGC
13601  GCAGATCAGC TCGGAAATGG CGACGTTATC ATCAAGCGTG ATGGAAAGCT
13651  ACTCCGCCCC AAGCGCCTCC CGTCTAACTT GTTCCAGTTC CGGGCTGGAA
13701  CTGGCGAAGC GCGATGCGTC CTGGACTGCG TGACCGCGCT CCAGAACGGC
13751  GCCGACCTAC TCTGGATTGA GACAGAAAAG CCTCACATAG CTCAAATCGG
13801  CGGAATGGTA TCGGAGATAA GGAAAGTCAT ACCCAACGCC AAACTGGTGT
13851  ACAACAACTC TCCGTCGTTC AATTGGACCC TGAACTTTAG ACAGCAAGCA
13901  TACGATGCTA TGAAAGCCGC TGGGAAAGAC GTGTCAGCAT ACGACCGCGC
13951  CCAGCTTATG TCCGTGGAGT ACGACCAAAC GGAACTGGCT AAGCTGGCTG
14001  ATGAGAAAAT CAGAACATTC CAGGCCGACG CCTCAAGGGA GGCCGGGATC
14051  TTCCATCACT TGATTACCTT ACCAACATAT CACACTGCGG CCCTGTCAAC
14101  CGACAATTTG GCTAAGGAGT ACTTCGGAGA TCAGGGGATG CTCGGTTATG
14151  TCGCGGGCGT TCAGAGGAAG GAGATCCGAC AGGGCATCGC ATGTGTCAAG
14201  CACCAAAACA TGAGCGGGAG TGACATCGGG GATGATCATA AAGAGTATTT
14251  CTCCGGCGAA GCCGCGCTGA AGGCCGCCGG CAAAGACAAC ACTATGAATC
14301  AATTCTGACC CGGGTGAGTA ATTCTGATAT TAGAGGGAGC ATTAATGTGT
14351  TGTTGTGATG TGGTTTATAT GGGGAAATTA AATAAATGAT GTATGTACCT
14401  CTTGCCTATG TAGGTTTGTG TGTTTTGTTT TGTTGTCTAG CTTTGGTTAT
14451  TAAGTAGTAG GGACGTTCGT TCGTGTCTCA AAAAAAGGGG TACTACCACT
14501  CTGTAGTGTA TATGGATGCT GGAAATCAAT GTGTTTTGTA TTTGTTCACC
14551  TCCATTGTTG AATTCAATGT CAAATGTGTT TTGCGTTGGT TATGTGTAAA
14601  ATTACTATCT TTCTCGTCCG ATGATCAAAG TTTTAAGCAA CAAAACCAAG
```

FIG. 23F DNA sequence of pMBXS1024 (Cont'd)

```
14651  GGTGAAATTT AAACTGTGCT TTGTTGAAGA TTCTTTTATC ATATTGAAAA
14701  TCAAATTACT AGCAGCAGAT TTTACCTAGC ATGAAATTTT ATCAACAGTA
14751  CAGCACTCAC TAACCAAGTT CCAAACTAAG ATGCGCCATT AACATCAGCC
14801  AATAGGCATT TTCAGCAAGC TCGAGTCACG TAGTGGTACG TAGTGTTTAT
14851  CTTTGTTGCT TTTCTGAACA ATTTATTTAC TATGTAAATA TATTATCAAT
14901  GTTTAATCTA TTTTAATTTG CACATGAATT TTCATTTTAT TTTTACTTTA
14951  CAAAACAAAT AAATATATAT GCAAAAAAAT TTACAAACGA TGCACGGGTT
15001  ACAAACTAAT TTCATTAAAT GCTAATGCAG ATTTTGTGAA GTAAAACTCC
15051  AATTATGATG AAAAATACCA CCAACACCAC CTGCGAAACT GTATCCCAAC
15101  TGTCCTTAAT AAAAATGTTA AAAAGTATAT TATTCTCATT TGTCTGTCAT
15151  AATTTATGTA CCCCACTTTA ATTTTTCTGA TGTACTAAAC CGAGGGCAAA
15201  CTGAAACCTG TTCCTCATGC AAAGCCCCTA CTCACCATGT ATCATGTACG
15251  TGTCATCACC CAACAACTCC ACTTTTGCTA TATAACAACA CCCCCGTCAC
15301  ACTCTCCCTC TCTAACACAC ACCCCACTAA CAATTCCTTC ACTTGCAGCA
15351  CTGTTGCATC ATCATCTTCA TTGCAAAACC CTAAACTTCA CCTTCAACCG
15401  CGGCCGCTTC GAAGGATCCA AAATGGTGAG CAAGGGCGAG GAGCTGTTCA
15451  CCGGGGTGGT GCCCATCCTG GTCGAGCTGG ACGGCGACGT AAACGGCCAC
15501  AAGTTCAGCG TGTCCGGCGA GGGCGAGGGC GATGCCACCT ACGGCAAGCT
15551  GACCCTGAAG TTCATCTGCA CCACCGGCAA GCTGCCCGTG CCCTGGCCCA
15601  CCCTCGTGAC CACCTTCACC TACGGCGTGC AGTGCTTCAG CCGCTACCCC
15651  GACCACATGA AGCAGCACGA CTTCTTCAAG TCCGCCATGC CCGAAGGCTA
15701  CGTCCAGGAG CGCACCATCT TCTTCAAGGA CGACGGCAAC TACAAGACCC
15751  GCGCCGAGGT GAAGTTCGAG GGCGACACCC TGGTGAACCG CATCGAGCTG
15801  AAGGGCATCG ACTTCAAGGA GGACGGCAAC ATCCTGGGGC ACAAGCTGGA
15851  GTACAACTAC AACAGCCACA ACGTCTATAT CATGGCCGAC AAGCAGAAGA
15901  ACGGCATCAA GGTGAACTTC AAGATCCGCC ACAACATCGA GGACGGCAGC
15951  GTGCAGCTCG CCGACCACTA CCAGCAGAAC ACCCCCATCG GCGACGGCCC
16001  CGTGCTGCTG CCCGACAACC ACTACCTGAG CACCCAGTCC GCCCTGAGCA
16051  AAGACCCCAA CGAGAAGCGC GATCACATGG TCCTGCTGGA GTTCGTGACC
16101  GCCGCCGGGA TCACTCACGG CATGGACGAG CTGTACAAGT AAAGCGGCCG
16151  CCCGGGCTGC AGTTCGAAAT TTAAATGCGG CCGCTGAGTA ATTCTGATAT
16201  TAGAGGGAGC ATTAATGTGT TGTTGTGATG TGGTTTATAT GGGGAAATTA
16251  AATAAATGAT GTATGTACCT CTTGCCTATG TAGGTTTGTG TGTTTTGTTT
16301  TGTTGTCTAG CTTTGGTTAT TAAGTAGTAG GGACGTTCGT TCGTGTCTCA
16351  AAAAAAGGGG TACTACCACT CTGTAGTGTA TATGGATGCT GGAAATCAAT
16401  GTGTTTTGTA TTTGTTCACC TCCATTGTTG AATTCAATGT CAAATGTGTT
16451  TTGCGTTGGT TATGTGTAAA ATTACTATCT TTCTCGTCCG ATGATCAAAG
16501  TTTTAAGCAA CAAAACCAAG GGTGAAATTT AAACTGTGCT TTGTTGAAGA
16551  TTCTTTTATC ATATTGAAAA TCAAATTACT AGCAGCAGAT TTTACCTAGC
16601  ATGAAATTTT ATCAACAGTA CAGCACTCAC TAACCAAGTT CCAAACTAAG
16651  ATGCGCCATT AACATCAGCC AATAGGCATT TTCAGCAACC TCAGCGTTTA
16701  AACGTACGTA GTGTTTATCT TTGTTGCTTT TCTGAACAAT TTATTTACTA
16751  TGTAAATATA TTATCAATGT TTAATCTATT TTAATTTGCA CATGAATTTT
16801  CATTTTATTT TTACTTTACA AAACAAATAA ATATATATGC AAAAAAATTT
16851  ACAAACGATG CACGGGTTAC AAACTAATTT CATTAAATGC TAATGCAGAT
16901  TTTGTGAAGT AAAACTCCAA TTATGATGAA AAATACCACC AACACCACCT
16951  GCGAAACTGT ATCCCAACTG TCCTTAATAA AAATGTTAAA AAGTATATTA
17001  TTCTCATTTG TCTGTCATAA TTTATGTACC CCACTTTAAT TTTTCTGATG
17051  TACTAAACCG AGGGCAAACT GAAACCTGTT CCTCATGCAA AGCCCCTACT
17101  CACCATGTAT CATGTACGTG TCATCACCCA ACAACTCCAC TTTTGCTATA
17151  TAACAACACC CCCGTCACAC TCTCCCTCTC TAACACACAC CCCACTAACA
17201  ATTCCTTCAC TTGCAGCACT GTTGCATCAT CATCTTCATT GCAAAACCCT
17251  AAACTTCACC TTCAACCGCG GCCGCTTCGA AAAAATGGCT TCTATGATAT
17301  CCTCTTCCGC TGTGACAACA GTCAGCCGTG CCTCTAGGGG GCAATCCGCC
17351  GCAGTGGCTC CATTCGGCGG CCTCAAATCC ATGACTGGAT TCCCAGTGAA
17401  GAAGGTCAAC ACTGACATTA CTTCCATTAC AAGCAATGGT GGAAGAGTAA
17451  AGTGCATGCA GGTGTGGCCT CCAATTGGAA AGAAGAAGTT TGAGACTCTT
17501  TCCTATTTGC CACCATTGAC GAGAGATTCT AGAGTCACCG AGCAAGCCAC
17551  AACGACAGAT GAACTCGCTT TTACTAGGCC ATATGGTGAA CAGGAAAAGC
```

FIG. 23G DNA sequence of pMBXS1024 (Cont'd)

```
17601   AAATTCTTAC AGCAGAAGCT GTTGAGTTTT TGACCGAGTT GGTTACTCAC
17651   TTTACACCTC AAAGAAACAA GTTACTCGCA GCACGTATCC AGCAGCAACA
17701   AGACATAGAT AATGGTACAC TTCCAGATTT CATTTCGGAG ACTGCATCTA
17751   TTCGAGATGC CGATTGGAAA ATCAGGGGTA TCCCCGCAGA TTTAGAAGAT
17801   AGGAGAGTTG AAATAACCGG ACCTGTAGAA AGAAAAATGG TCATCAACGC
17851   TCTAAACGCC AACGTCAAAG TGTTTATGGC TGATTTTGAG GACTCGCTAG
17901   CACCTGATTG GAACAAGGTG ATAGATGGCC AGATCAATTT GAGAGATGCT
17951   GTCAATGGGA CAATCTCCTA TACTAATGAG GCTGGAAAGA TTTATCAACT
18001   CAAACCTAAT CCGGCAGTGC TGATTTGTAG GGTTCGTGGA TTACACCTGC
18051   CTGAAAAGCA TGTTACGTGG CGTGGGGAAG CAATTCCTGG CAGCCTTTTT
18101   GACTTCGCTC TTTACTTTTT CCATAACTAC CAGGCGCTGT TGGCTAAGGG
18151   GTCAGGTCCA TATTTCTATC TTCCGAAAAC TCAAAGTTGG CAAGAAGCTG
18201   CCTGGTGGTC TGAGGTGTTC TCCTATGCAG AGGATCGTTT CAATTTACCA
18251   CGAGGTACGA TCAAAGCAAC TCTGTTAATT GAGACACTCC CGGCTGTGTT
18301   TCAAATGGAC GAGATACTAC ACGCTCTCAG GGACCACATT GTTGGTCTTA
18351   ATTGCGGAAG ATGGGACTAT ATCTTCTCCT ACATCAAGAC TCTAAAGAAC
18401   TACCCGGATA GAGTTCTGCC TGACCGTCAA GCTGTTACTA TGGATAAACC
18451   ATTTCTTAAT GCTTACTCTA GACTCTTGAT TAAGACCTGT CATAAGCGTG
18501   GAGCCTTCGC AATGGGCGGA ATGGCCGCTT TTATCCCGTC AAAAGATGAA
18551   GAGCACAACA ATCAGGTTTT GAACAAGGTA AAAGCGGATA AATCTCTTGA
18601   AGCCAATAAT GGGCATGATG GCACTTGGAT TGCTCATCCA GGTCTAGCTG
18651   ATACAGCGAT GGCTGTATTC AACGACATCT TGGGTTCAAG AAAGAATCAA
18701   CTTGAAGTGA TGAGAGAGCA AGACGCGCCA ATAACAGCTG ATCAACTTTT
18751   GGCGCCATGC GATGGTGAAC GAACGGAAGA AGGTATGAGA GCCAATATCC
18801   GAGTTGCTGT GCAGTACATA GAGGCTTGGA TTTCAGGAAA CGGGTGTGTC
18851   CCCATTTATG GACTCATGGA AGATGCGGCT ACTGCTGAAA TTAGCAGGAC
18901   CTCTATTTGG CAGTGGATAC ATCATCAAAA GACATTAAGC AACGGAAAAC
18951   CTGTTACTAA GGCCCTCTTC AGGCAGATGC TTGGGGAAGA GATGAAAGTA
19001   ATTGCGAGTG AGTTGGGAGA AGAGAGATTT TCTCAGGGTA GATTTGATGA
19051   CGCAGCGAGG TTGATGGAGC AGATCACCAC CAGTGACGAG CTCATAGATT
19101   TCTTAACGTT GCCTGGATAC CGACTACTTG CTTGAATTTA AATGCGGCCG
19151   CTGAGTAATT CTGATATTAG AGGGAGCATT AATGTGTTGT TGTGATGTGG
19201   TTTATATGGG GAAATTAAAT AAATGATGTA TGTACCTCTT GCCTATGTAG
19251   GTTTGTGTGT TTTGTTTTGT TGTCTAGCTT TGGTTATTAA GTAGTAGGGA
19301   CGTTCGTTCG TGTCTCAAAA AAAGGGGTAC TACCACTCTG TAGTGTATAT
19351   GGATGCTGGA AATCAATGTG TTTTGTATTT GTTCACCTCC ATTGTTGAAT
19401   TCAATGTCAA ATGTGTTTTG CGTTGGTTAT GTGTAAAATT ACTATCTTTC
19451   TCGTCCGATG ATCAAAGTTT TAAGCAACAA AACCAAGGGT GAAATTTAAA
19501   CTGTGCTTTG TTGAAGATTC TTTTATCATA TTGAAAATCA AATTACTAGC
19551   AGCAGATTTT ACCTAGCATG AAATTTTATC AACAGTACAG CACTCACTAA
19601   CCAAGTTCCA AACTAAGATG CGCCATTAAC ATCAGCCAAT AGGCATTTTC
19651   AGCAAAGCAA ATGAATTCGT AATCATGTCA TAGCTGTTTC CTGTGTGAAA
19701   TTGTTATCCG CTCACAATTC CACACAACAT ACGAGCCGGA AGCATAAAGT
19751   GTAAAGCCTG GGGTGCCTAA TGAGTGAGCT AACTCACATT AATTGCGTTG
19801   CGCTCACTGC CCGCTTTCCA GTCGGGAAAC CTGTCGTGCC AGCTGCATTA
19851   ATGAATCGGC CAACGCGCGG GGAGAGGCGG TTTGCGTATT GGCTAGAGCA
19901   GCTTGCCAAC ATGGTGGAGC ACGACACTCT CGTCTACTCC AAGAATATCA
19951   AAGATACAGT CTCAGAAGAC CAAAGGGCTA TTGAGACTTT TCAACAAAGG
20001   GTAATATCGG GAAACCTCCT CGGATTCCAT TGCCCAGCTA TCTGTCACTT
20051   CATCAAAAGG ACAGTAGAAA AGGAAGGTGG CACCTACAAA TGCCATCATT
20101   GCGATAAAGG AAAGGCTATC GTTCAAGATG CCTCTGCCGA CAGTGGTCCC
20151   AAAGATGGAC CCCCACCCAC GAGGAGCATC GTGGAAAAAG AAGACGTTCC
20201   AACCACGTCT TCAAAGCAAG TGGATTGATG TGAACATGGT GGAGCACGAC
20251   ACTCTCGTCT ACTCCAAGAA TATCAAAGAT ACAGTCTCAG AAGACCAAAG
20301   GGCTATTGAG ACTTTTCAAC AAAGGGTAAT ATCGGGAAAC CTCCTCGGAT
20351   TCCATTGCCC AGCTATCTGT CACTTCATCA AAAGGACAGT AGAAAAGGAA
20401   GGTGGCACCT ACAAATGCCA TCATTGCGAT AAAGGAAAGG CTATCGTTCA
20451   AGATGCCTCT GCCGACAGTG GTCCCAAAGA TGGACCCCCA CCCACGAGGA
20501   GCATCGTGGA AAAAGAAGAC GTTCCAACCA CGTCTTCAAA GCAAGTGGAT
```

FIG. 23H DNA sequence of pMBXS1024 (Cont'd)

```
20551    TGATGTGATA TCTCCACTGA CGTAAGGGAT GACGCACAAT CCCACTATCC
20601    TTCGCAAGAC CCTTCCTCTA TATAAGGAAG TTCATTTCAT TTGGAGAGGA
20651    CACGCTGAAA TCACCAGTCT CTCTCTACAA ATCTATCTCT CTCGAGAAAA
20701    TGGTGAGCAA GGGCGAGGAG CTGTTCACCG GGGTGGTGCC CATCCTGGTC
20751    GAGCTGGACG GCGACGTAAA CGGCCACAAG TTCAGCGTGT CCGGCGAGGG
20801    CGAGGGCGAT GCCACCTACG GCAAGCTGAC CCTGAAGTTC ATCTGCACCA
20851    CCGGCAAGCT GCCCGTGCCC TGGCCCACCC TCGTGACCAC CTTCACCTAC
20901    GGCGTGCAGT GCTTCAGCCG CTACCCCGAC CACATGAAGC AGCACGACTT
20951    CTTCAAGTCC GCCATGCCCG AAGGCTACGT CCAGGAGCGC ACCATCTTCT
21001    TCAAGGACGA CGGCAACTAC AAGACCCGCG CCGAGGTGAA GTTCGAGGGC
21051    GACACCCTGG TGAACCGCAT CGAGCTGAAG GGCATCGACT TCAAGGAGGA
21101    CGGCAACATC CTGGGGCACA AGCTGGAGTA CAACTACAAC AGCCACAACG
21151    TCTATATCAT GGCCGACAAG CAGAAGAACG GCATCAAGGT GAACTTCAAG
21201    ATCCGCCACA ACATCGAGGA CGGCAGCGTG CAGCTCGCCG ACCACTACCA
21251    GCAGAACACC CCCATCGGCG ACGGCCCCGT GCTGCTGCCC GACAACCACT
21301    ACCTGAGCAC CCAGTCCGCC CTGAGCAAAG ACCCCAACGA GAAGCGCGAT
21351    CACATGGTCC TGCTGGAGTT CGTGACCGCC GCCGGGATCA CTCACGGCAT
21401    GGACGAGCTG TACAAGTAAG AGCTCGGTCA CCTGTCCAAC AGTCTCAGGG
21451    TTAATGTCTA TGTATCTTAA ATAATGTTGT CGGCGATCGT TCAAACATTT
21501    GGCAATAAAG TTTCTTAAGA TTGAATCCTG TTGCCGGTCT TGCGATGATT
21551    ATCATATAAT TTCTGTTGAA TTACGTTAAG CATGTAATAA TTAACATGTA
21601    ATGCATGACG TTATTTATGA GATGGGTTTT TATGATTAGA GTCCCGCAAT
21651    TATACATTTA ATACGCGATA GAAAACAAAA TATAGCGCGC AAACTAGGAT
21701    AAATTATCGC GCGCGGTGTC ATCTATGTTA CTAGATCGGG AATTAAACTA
21751    TCAGTGTTTG ACAGGATATA TTGGCGGGTA AACCTAAGAG AAAAGAGCGT
21801    TTATTAGAAT AATCGGATAT TTAAAAGGGC GTGAAAAGGT TTATCCGTTC
21851    GTCCATTTGT ATGTGCATGC CAACCACAGG GTTCCCCTCG GGATCAAAGT
21901    ACTTTGATCC AACCCCTCCG CTGCTATAGT GCAGTCGGCT TCTGACGTTC
21951    AGTGCAGCCG TCTTCTGAAA ACGACATGTC GCACAAGTCC TAAGTTACGC
22001    GACAGGCTGC CGCCCTGCCC TTTTCCTGGC GTTTTCTTGT CGCGTGTTTT
22051    AGTCGCATAA AGTAGAATAC TTGCGACTAG AACCGGAGAC ATTACGCCAT
22101    GAACAAGAGC GCCGCCGCTG GCCTGCTGGG CTATGCCCGC GTCAGCACCG
22151    ACGACCAGGA CTTGACCAAC CAACGGGCCG AACTGCACGC GGCCGGCTGC
22201    ACCAAGCTGT TTTCCGAGAA GATCACCGGC ACCAGGCGCG ACCGCCCGGA
22251    GCTGGCCAGG ATGCTTGACC ACCTACGCCC TGGCGACGTT GTGACAGTGA
22301    CCAGGCTAGA CCGCCTGGCC CGCAGCACCC GCGACCTACT GGACATTGCC
22351    GAGCGCATCC AGGAGGCCGG CGCGGGCCTG CGTAGCCTGG CAGAGCCGTG
22401    GGCCGACACC ACCACGCCGG CCGGCCGCAT GGTGTTGACC GTGTTCGCCG
22451    GCATTGCCGA GTTCGAGCGT TCCCTAATCA TCGACCGCAC CCGGAGCGGG
22501    CGCGAGGCCG CCAAGGCCCG AGGCGTGAAG TTTGGCCCCC GCCCTACCCT
22551    CACCCCGGCA CAGATCGCGC ACGCCCGCGA GCTGATCGAC CAGGAAGGCC
22601    GCACCGTGAA AGAGGCGGCT GCACTGCTTG GCGTGCATCG CTCGACCCTG
22651    TACCGCGCAC TTGAGCGCAG CGAGGAAGTG ACGCCCACCG AGGCCAGGCG
22701    GCGCGGTGCC TTCCGTGAGG ACGCATTGAC CGAGGCCGAC GCCCTGGCGG
22751    CCGCCGAGAA TGAACGCCAA GAGGAACAAG CATGAAACCG CACCAGGACG
22801    GCCAGGACGA ACCGTTTTTC ATTACCGAAG AGATCGAGGC GGAGATGATC
22851    GCGGCCGGGT ACGTGTTCGA GCCGCCCGCG CACGTCTCAA CCGTGCGGCT
22901    GCATGAAATC CTGGCCGGTT TGTCTGATGC CAAGCTGGCG GCCTGGCCGG
22951    CCAGCTTGGC CGCTGAAGAA ACCGAGCGCC GCCGTCTAAA AAGGTGATGT
23001    GTATTTGAGT AAAACAGCTT GCGTCATGCG GTCGCTGCGT ATATGATGCG
23051    ATGAGTAAAT AAACAAATAC GCAAGGGGAA CGCATGAAGG TTATCGCTGT
23101    ACTTAACCAG AAAGGCGGGT CAGGCAAGAC GACCATCGCA ACCCATCTAG
23151    CCCGCGCCCT GCAACTCGCC GGGGCCGATG TTCTGTTAGT CGATTCCGAT
23201    CCCCAGGGCA GTGCCCGCGA TTGGGCGGCC GTGCGGGAAG ATCAACCGCT
23251    AACCGTTGTC GGCATCGACC GCCCGACGAT TGACCGCGAC GTGAAGGCCA
23301    TCGGCCGGCG CGACTTCGTA GTGATCGACG GAGCGCCCCA GGCGGCGGAC
23351    TTGGCTGTGT CCGCGATCAA GGCAGCCGAC TTCGTGCTGA TTCCGGTGCA
23401    GCCAAGCCCT TACGACATAT GGGCCACCGC CGACCTGGTG GAGCTGGTTA
23451    AGCAGCGCAT TGAGGTCACG GATGGAAGGC TACAAGCGGC CTTTGTCGTG
```

FIG. 23I DNA sequence of pMBXS1024 (Cont'd)

```
23501    TCGCGGGCGA TCAAAGGCAC GCGCATCGGC GGTGAGGTTG CCGAGGCGCT
23551    GGCCGGGTAC GAGCTGCCCA TTCTTGAGTC CCGTATCACG CAGCGCGTGA
23601    GCTACCCAGG CACTGCCGCC GCCGGCACAA CCGTTCTTGA ATCAGAACCC
23651    GAGGGCGACG CTGCCCGCGA GGTCCAGGCG CTGGCCGCTG AAATTAAATC
23701    AAAACTCATT TGAGTTAATG AGGTAAAGAG AAAATGAGCA AAAGCACAAA
23751    CACGCTAAGT GCCGGCCGTC CGAGCGCACG CAGCAGCAAG GCTGCAACGT
23801    TGGCCAGCCT GGCAGACACG CCAGCCATGA AGCGGGTCAA CTTTCAGTTG
23851    CCGGCGGAGG ATCACACCAA GCTGAAGATG TACGCGGTAC GCCAAGGCAA
23901    GACCATTACC GAGCTGCTAT CTGAATACAT CGCGCAGCTA CCAGAGTAAA
23951    TGAGCAAATG AATAAATGAG TAGATGAATT TTAGCGGCTA AAGGAGGCGG
24001    CATGGAAAAT CAAGAACAAC CAGGCACCGA CGCCGTGGAA TGCCCCATGT
24051    GTGGAGGAAC GGGCGGTTGG CCAGGCGTAA GCGGCTGGGT TGCCTGCCGG
24101    CCCTGCAATG GCACTGGAAC CCCCAAGCCC GAGGAATCGG CGTGAGCGGT
24151    CGCAAACCAT CCGGCCCGGT ACAAATCGGC GCGGCGCTGG GTGATGACCT
24201    GGTGGAGAAG TTGAAGGCCG CGCAGGCCGC CCAGCGGCAA CGCATCGAGG
24251    CAGAAGCACG CCCCGGTGAA TCGTGGCAAG CGGCCGCTGA TCGAATCCGC
24301    AAAGAATCCC GGCAACCGCC GGCAGCCGGT GCGCCGTCGA TTAGGAAGCC
24351    GCCCAAGGGC GACGAGCAAC CAGATTTTTT CGTTCCGATG CTCTATGACG
24401    TGGGCACCCG CGATAGTCGC AGCATCATGG ACGTGGCCGT TTTCCGTCTG
24451    TCGAAGCGTG ACCGACGAGC TGGCGAGGTG ATCCGCTACG AGCTTCCAGA
24501    CGGGCACGTA GAGGTTTCCG CAGGGCCGGC CGGCATGGCC AGTGTGTGGG
24551    ATTACGACCT GGTACTGATG GCGGTTTCCC ATCTAACCGA ATCCATGAAC
24601    CGATACCGGG AAGGGAAGGG AGACAAGCCC GGCCGCGTGT TCCGTCCACA
24651    CGTTGCGGAC GTACTCAAGT TCTGCCGGCG AGCCGATGGC GGAAAGCAGA
24701    AAGACGACCT GGTAGAAACC TGCATTCGGT TAAACACCAC GCACGTTGCC
24751    ATGCAGCGTA CGAAGAAGGC CAAGAACGGC CGCCTGGTGA CGGTATCCGA
24801    GGGTGAAGCC TTGATTAGCC GCTACAAGAT CGTAAAGAGC GAAACCGGGC
24851    GGCCGGAGTA CATCGAGATC GAGCTAGCTG ATTGGATGTA CCGCGAGATC
24901    ACAGAAGGCA AGAACCCGGA CGTGCTGACG GTTCACCCCG ATTACTTTTT
24951    GATCGATCCC GGCATCGGCC GTTTTCTCTA CCGCCTGGCA CGCCGCGCCG
25001    CAGGCAAGGC AGAAGCCAGA TGGTTGTTCA AGACGATCTA CGAACGCAGT
25051    GGCAGCGCCG GAGAGTTCAA GAAGTTCTGT TTCACCGTGC GCAAGCTGAT
25101    CGGGTCAAAT GACCTGCCGG AGTACGATTT GAAGGAGGAG GCGGGGCAGG
25151    CTGGCCCGAT CCTAGTCATG CGCTACCGCA ACCTGATCGA GGGCGAAGCA
25201    TCCGCCGGTT CCTAATGTAC GGAGCAGATG CTAGGGCAAA TTGCCCTAGC
25251    AGGGGAAAAA GGTCGAAAAG GTCTCTTTCC TGTGGATAGC ACGTACATTG
25301    GGAACCCAAA GCCGTACATT GGGAACCGGA ACCCGTACAT TGGGAACCCA
25351    AAGCCGTACA TTGGGAACCG GTCACACATG TAAGTGACTG ATATAAAAGA
25401    GAAAAAAGGC GATTTTTCCG CCTAAAACTC TTTAAAACTT ATTAAAACTC
25451    TTAAAACCCG CCTGGCCTGT GCATAACTGT CTGGCCAGCG CACAGCCGAA
25501    GAGCTGCAAA AAGCGCCTAC CCTTCGGTCG CTGCGCTCCC TACGCCCCGC
25551    CGCTTCGCGT CGGCCTATCG CGGCCGCTGG CCGCTCAAAA ATGGCTGGCC
25601    TACGGCCAGG CAATCTACCA GGGCGCGGAC AAGCCGCGCC GTCGCCACTC
25651    GACCGCCGGC GCCCACATCA AGGCACCCTG CCTCGCGCGT TTCGGTGATG
25701    ACGGTGAAAA CCTCTGACAC ATGCAGCTCC CGGAGACGGT CACAGCTTGT
25751    CTGTAAGCGG ATGCCGGGAG CAGACAAGCC CGTCAGGGCG CGTCAGCGGG
25801    TGTTGGCGGG TGTCGGGGCG CAGCCATGAC CCAGTCACGT AGCGATAGCG
25851    GAGTGTATAC TGGCTTAACT ATGCGGCATC AGAGCAGATT GTACTGAGAG
25901    TGCACCATAT GCGGTGTGAA ATACCGCACA GATGCGTAAG GAGAAAATAC
25951    CGCATCAGGC GCTCTTCCGC TTCCTCGCTC ACTGACTCGC TGCGCTCGGT
26001    CGTTCGGCTG CGGCGAGCGG TATCAGCTCA CTCAAAGGCG GTAATACGGT
26051    TATCCACAGA ATCAGGGGAT AACGCAGGAA AGAACATGTG AGCAAAAGGC
26101    CAGCAAAAGG CCAGGAACCG TAAAAAGGCC GCGTTGCTGG CGTTTTTCCA
26151    TAGGCTCCGC CCCCCTGACG AGCATCACAA AAATCGACGC TCAAGTCAGA
26201    GGTGGCGAAA CCCGACAGGA CTATAAAGAT ACCAGGCGTT TCCCCCTGGA
26251    AGCTCCCTCG TGCGCTCTCC TGTTCCGACC CTGCCGCTTA CCGGATACCT
26301    GTCCGCCTTT CTCCCTTCGG GAAGCGTGGC GCTTTCTCAT AGCTCACGCT
26351    GTAGGTATCT CAGTTCGGTG TAGGTCGTTC GCTCCAAGCT GGGCTGTGTG
26401    CACGAACCCC CCGTTCAGCC CGACCGCTGC GCCTTATCCG GTAACTATCG
```

FIG. 23J DNA sequence of pMBXS1024 (Cont'd)

```
26451    TCTTGAGTCC AACCCGGTAA GACACGACTT ATCGCCACTG GCAGCAGCCA
26501    CTGGTAACAG GATTAGCAGA GCGAGGTATG TAGGCGGTGC TACAGAGTTC
26551    TTGAAGTGGT GGCCTAACTA CGGCTACACT AGAAGGACAG TATTTGGTAT
26601    CTGCGCTCTG CTGAAGCCAG TTACCTTCGG AAAAAGAGTT GGTAGCTCTT
26651    GATCCGGCAA ACAAACCACC GCTGGTAGCG GTGGTTTTTT TGTTTGCAAG
26701    CAGCAGATTA CGCGCAGAAA AAAAGGATCT CAAGAAGATC CTTTGATCTT
26751    TTCTACGGGG TCTGACGCTC AGTGGAACGA AAACTCACGT TAAGGGATTT
26801    TGGTCATGCA TTCTAGGTAC TAAAACAATT CATCCAGTAA AATATAATAT
26851    TTTATTTTCT CCCAATCAGG CTTGATCCCC AGTAAGTCAA AAAATAGCTC
26901    GACATACTGT TCTTCCCCGA TATCCTCCCT GATCGACCGG ACGCAGAAGG
26951    CAATGTCATA CCACTTGTCC GCCCTGCCGC TTCTCCCAAG ATCAATAAAG
27001    CCACTTACTT TGCCATCTTT CACAAAGATG TTGCTGTCTC CCAGGTCGCC
27051    GTGGGAAAAG ACAAGTTCCT CTTCGGGCTT TTCCGTCTTT AAAAAATCAT
27101    ACAGCTCGCG CGGATCTTTA AATGGAGTGT CTTCTTCCCA GTTTTCGCAA
27151    TCCACATCGG CCAGATCGTT ATTCAGTAAG TAATCCAATT CGGCTAAGCG
27201    GCTGTCTAAG CTATTCGTAT AGGGACAATC CGATATGTCG ATGGAGTGAA
27251    AGAGCCTGAT GCACTCCGCA TACAGCTCGA TAATCTTTTC AGGGCTTTGT
27301    TCATCTTCAT ACTCTTCCGA GCAAAGGACG CCATCGGCCT CACTCATGAG
27351    CAGATTGCTC CAGCCATCAT GCCGTTCAAA GTGCAGGACC TTTGGAACAG
27401    GCAGCTTTCC TTCCAGCCAT AGCATCATGT CCTTTTCCCG TTCCACATCA
27451    TAGGTGGTCC CTTTATACCG GCTGTCCGTC ATTTTTAAAT ATAGGTTTTC
27501    ATTTTCTCCC ACCAGCTTAT ATACCTTAGC AGGAGACATT CCTTCCGTAT
27551    CTTTTACGCA GCGGTATTTT TCGATCAGTT TTTTCAATTC CGGTGATATT
27601    CTCATTTTAG CCATTTATTA TTTCCTTCCT CTTTTCTACA GTATTTAAAG
27651    ATACCCCAAG AAGCTAATTA TAACAAGACG AACTCCAATT CACTGTTCCT
27701    TGCATTCTAA AACCTTAAAT ACCAGAAAAC AGCTTTTTCA AAGTTGTTTT
27751    CAAAGTTGGC GTATAACATA GTATCGACGG AGCCGATTTT GAAACCGCGG
27801    TGATCACAGG CAGCAACGCT CTGTCATCGT TACAATCAAC ATGCTACCCT
27851    CCGCGAGATC ATCCGTGTTT CAAACCCGGC AGCTTAGTTG CCGTTCTTCC
27901    GAATAGCATC GGTAACATGA GCAAAGTCTG CCGCCTTACA ACGGCTCTCC
27951    CGCTGACGCC GTCCCGGACT GATGGGCTGC CTGTATCGAG TGGTGATTTT
28001    GTGCCGAGCT GCCGGTCGGG GAGCTGTTGG CTGGCTGGTG GCAGGATATA
28051    TTGTGGTGTA AACAAATTGA CGCTTAGACA ACTTAATAAC ACATTGCGGA
28101    CGTTTTTAAT GTACTGAATT AACGCCGAAT TA
```

FIG. 24 DNA Sequence of the bicarbonate transporter gene of Chlamydomonas reinhardtii strain CC-503 cw92 mt+, NCBI Reference Sequence: XM_001692145.1 (SEQ ID NO:6)

```
   1 cataacttca aagcctaaac gtctattcct cgtgccaagg cactttctcc ggaagcgcac
  61 ccacctctcc gcgccgctcg ccttcacgcg tgctctcagc tcaacaccac tgtaactcag
 121 gccttgacgg gcttgtttta tcaaaaccag caagaatgtc atccgacgct atgactatca
 181 acgagtcgct gatggaggtg gagcacactc ccgccgtcca caagcgcatt ctggatatcc
 241 tgcccggcat ttcaggcggt gtggcccgtg tcatgatcgg ccagcccttt gacaccatca
 301 aggtgcggct gcaagtgctg ggtcagggca ctgccctggc ggccaagctg ccgccgtcgg
 361 aggtgtacaa ggactcgatg gactgcatcc gcaagatgat caagagcgag ggcccgctgt
 421 ccttctacaa gggcaccgtc gcgcccctgg tcggcaacat ggtcctgctg ggcatccact
 481 tccccgtctt ctcggccgtg cgaaagcagc tggagggtga tgaccactac tccaacttct
 541 cccacgccaa cgtcctgctg tcgggcgcgg ctgccggtgc cgccggttct ctgatctctg
 601 cccccgtgga gctggtccgc accaagatgc agatgcagcg ccgcgccgct ctggctggca
 661 cggtggccgc cggcgccgcc gcctcggctg gcgccgagga gttctacaag ggctcgctgg
 721 actgcttcaa gcaggtcatg tccaagcacg gcatcaaggg cctgtaccgt ggtttcacct
 781 ccaccatcct gcgtgacatg cagggctacg cctggttctt cctgggctac gaggccactg
 841 tcaaccactt cctgcagaac gccggccccg gtgtgcacac caaggccgac ctcaactacc
 901 tgcaggtcat ggccgccggc gtggtggcgg gcttcggcct gtggggctcc atgttcccca
 961 tcgacaccat caagtccaag ctgcaggccg actccttcgc caagccccag tactcgtcca
1021 cgatggactg cctcaagaag gtgctggcga gcgagggcca ggcgggtctg tggcgcggct
1081 tctccgccgc catgtaccgc gccatccccg tcaacgccgg catcttcctg gcggtggagg
1141 gcacgcgcca gggcatcaag tggtacgagg agaacgtgga gcacatctac ggcggcgtga
1201 tcggccccgc cacgcccacc gccgcgcagt aaatgtggcc gcggctgcgg ctacgtgctt
1261 gagcgcccgc gtgtgctcta tctagctgct gcaacagctg ctgttgcgca cgcggcgcaa
1321 ggcgcaacct cctggcatga caacatggct caaaaggtgt cacgtgtgtg tgtgtgtgtg
1381 tatgtttgtg tgtgcgtgtg gagagtctgg cataggtaga tgtggtcgtt agctttctgc
1441 ttcgttcccc atcgtgaggc gcatacatgc ggcaacaagc cagtggatgc actctgggca
1501 gaacgtgcgt gtgtgctcgt ttttcctagc ttagtggtgg cagcagcggc aacagaaaga
1561 ggtaggcaga agcaggagcg gtcgagggaa caggacagct gctgaataca aaggcgtcag
1621 acctgaacgt aattttgtgc gggcaccata ccccgcttac ggtccaaggg catgatgcct
1681 ttttgatgca cacatcaccc ctccccgcgc atgtatgtta aatgatgatt ttgactgctg
1741 tttttgagag cggaacaagg ggaactgcag tactggctcg gacatgagag gagaggccgg
1801 cgagagaggc tcatgacaaa aagtggaatg ggcttgcaga tgtatatagc agggcaaact
1861 ggcaaaagga gcgatacctt tcgtaagcac agggctgagg tgcatggtcg tggaaggtca
1921 cgggagttga gccgctacac cggctgtcag tgctggtctg tttctccatc gggaaacgcg
1981 ggtcaatatg taatcgtgat gggtttca
```

FIG. 25

Protein sequence of Low-CO2-inducible chloroplast envelope protein CCP1 of *Chlamydomonas reinhardtii* (source: www.uniprot.org/uniprot/A8IT08) (SEQ ID NO:7)

```
                10         20         30         40         50
MSSDAMTINE SLMEVEHTPA VHKRILDILP GISGGVARVM IGQPFDTIKV
                60         70         80         90        100
RLQVLGQGTA LAAKLPPSEV YKDSMDCIRK MIKSEGPLSF YKGTVAPLVG
               110        120        130        140        150
NMVLLGIHFP VFSAVRKQLE GDDHYSNFSH ANVLLSGAAA GAAGSLISAP
               160        170        180        190        200
VELVRTKMQM QRRAALAGTV AAGAAASAGA EEFYKGSLDC FKQVMSKHGI
               210        220        230        240        250
KGLYRGFTST ILRDMQGYAW FFLGYEATVN HFLQNAGPGV HTKADLNYLQ
               260        270        280        290        300
VMAAGVVAGF GLWGSMFPID TIKSKLQADS FAKPQYSSTM DCLKKVLASE
               310        320        330        340        350
GQAGLWRGFS AAMYRAIPVN AGIFLAVEGT RQGIKWYEEN VEHIYGGVIG

PATPTAAQ
```

FIG. 26A DNA sequence of pMBXS994 (SEQ ID NO:8)

```
1     AAGGTACGTA GTGTTTATCT TTGTTGCTTT TCTGAACAAT TTATTTACTA
51    TGTAAATATA TTATCAATGT TTAATCTATT TTAATTTGCA CATGAATTTT
101   CATTTTATTT TTACTTTACA AAACAAATAA ATATATATGC AAAAAAATTT
151   ACAAACGATG CACGGGTTAC AAACTAATTT CATTAAATGC TAATGCAGAT
201   TTTGTGAAGT AAAACTCCAA TTATGATGAA AAATACCACC AACACCACCT
251   GCGAAACTGT ATCCCAACTG TCCTTAATAA AAATGTTAAA AAGTATATTA
301   TTCTCATTTG TCTGTCATAA TTTATGTACC CCACTTTAAT TTTTCTGATG
351   TACTAAACCG AGGGCAAACT GAAACCTGTT CCTCATGCAA AGCCCCTACT
401   CACCATGTAT CATGTACGTG TCATCACCCA ACAACTCCAC TTTTGCTATA
451   TAACAACACC CCCGTCACAC TCTCCCTCTC TAACACACAC CCCACTAACA
501   ATTCCTTCAC TTGCAGCACT GTTGCATCAT CATCTTCATT GCAAAACCCT
551   AAACTTCACC TTCAACCGGA TCCAAAATGG CTTCTATGAT ATCCTCTTCC
601   GCTGTGACAA CAGTCAGCCG TGCCTCTAGG GGGCAATCCG CCGCAGTGGC
651   TCCATTCGGC GGCCTCAAAT CCATGACTGG ATTCCCAGTG AAGAAGGTCA
701   ACACTGACAT TACTTCCATT ACAAGCAATG GTGGAAGAGT AAAGTGCATG
751   CAGGTGTGGC CTCCAATTGG AAAGAAGAAG TTTGAGACTC TTTCCTATTT
801   GCCACCATTG ACGAGAGATT CTAGAGTTGG GAAAAAGATG ATGACTACTG
851   ATGGGAATAC TGCAACCGCT CACGTAGCTT ATGCGATGTC AGAAGTTGCA
901   GCTATCTACC CAATCACGCC GTCCAGTACA ATGGGAGAGG AAGCTGATGA
951   CTGGGCAGCA CAGGGAAGAA AGAATATCTT CGGTCAAACG CTTACGATTA
1001  GGGAGATGCA ATCGGAAGCC GGAGCAGCGG GTGCCGTACA TGGAGCTCTT
1051  GCAGCTGGCG CCTTAACTAC CACCTTTACG GCTTCTCAAG GACTACTCTT
1101  GATGATCCCT AACATGTACA AGATATCAGG AGAATTGCTT CCTGGAGTCT
1151  TTCATGTCAC TGCTAGAGCT ATTGCCGCCC ACGCCCTTTC AATCTTTGGT
1201  GATCATCAGG ATATATATGC AGCGAGGCAG ACAGGGTTCG CTATGCTTGC
1251  TTCAAGCTCG GTGCAAGAAG CACATGACAT GGCTTTAGTT GCCCACCTTG
1301  CCGCCATCGA ATCTAACGTC CCTTTCATGC ATTTCTTCGA CGGGTTTCGC
1351  ACGTCACACG AAATTCAAAA GATTGAAGTT CTCGATTATG CAGATATGGC
1401  ATCCTTAGTG AATCAGAAAG CTCTCGCAGA GTTCCGTGCT AAATCTATGA
1451  ATCCAGAGCA TCCACATGTT CGTGGTACTG CTCAAAACCC TGACATATAT
1501  TTCCAGGGAA GAGAGGCAGC AAACCCGTAT TACTTGAAAG TTCCTGGGAT
1551  TGTAGCAGAG TATATGCAAA AAGTTGCAAG TCTAACAGGG AGATCGTACA
1601  AGCTGTTCGA CTATGTTGGA GCTCCTGATG CTGAGCGTGT CATTGTTTCT
1651  ATGGGTTCCA GTTGCGAGAC AATCGAAGAA GTGATCAATC ACCTCGCTGC
1701  TAAGGGAGAA AAGATTGGTT TGATTAAGGT CCGATTATAC CGTCCATTTG
1751  TATCTGAAGC TTTCTTTGCT GCGTTACCGG CATCTGCTAA GGTTATTACA
1801  GTTCTGGATA GAACTAAGGA GCCCGGAGCT CCTGGCGACC CTTTGTACCT
1851  TGATGTCTGT TCAGCATTCG TCGAAAGGGG AGAAGCTATG CCCAAAATCC
1901  TCGCAGGCCG CTATGGGCTC GGATCTAAGG AGTTTTCACC CGCTATGGTT
1951  AAATCTGTTT ATGATAACAT GAGTGGTGCT AAGAAGAACC ATTTTACCGT
2001  TGGTATAGAG GACGATGTCA CGGGAACATC TCTGCCGGTT GATAATGCGT
2051  TTGCTGATAC AACCCCTAAA GGAACTATCC AGTGTCAGTT CTGGGGTTTG
2101  GGTGCAGATG GTACTGTCGG GGCGAATAAG CAGGCTATCA AAATCATAGG
2151  AGATAACACT GATCTATTCG CTCAAGGTTA CTTTTCATAC GACTCTAAGA
2201  AAAGTGGTGG TATAACTATC AGTCACTTGC GATTTGGAGA AAAGCCAATA
2251  CAATCTACCT ATTTGGTGAA CCGGGCTGAC TACGTTGCTT GTCATAACCC
2301  TGCCTATGTT GGTATATACG ATATTTTAGA GGGTATCAAA GATGGGGGCA
2351  CATTTGTCCT CAATTCTCCC TGGTCGAGTC TTGAAGATAT GGATAAACAT
2401  CTTCCAAGCG GGATTAAGAG AACCATAGCG AATAAGAAGC TTAAGTTTTA
2451  CAACATTGAT GCGGTGAAAA TAGCAACAGA TGTTGGTTTG GGCGGCAGAA
2501  TTAACATGAT AATGCAGACC GCATTCTTCA AACTAGCTGG TGTACTCCCT
2551  TTCGAGAAGG CAGTGGATCT CCTCAAAAAG TCTATTCATA AAGCCTATGG
2601  AAAGAAGGGA GAGAAGATCG TGAAAATGAA TACTGACGCA GTAGATCAAG
2651  CAGTTACGAG CCTTCAAGAG TTCAAGTACC CAGACTCATG GAAGGATGCT
2701  CCAGCAGAGA CAAAAGCTGA GCCAATGACA AACGAGTTCT TCAAAAATGT
2751  TGTCAAGCCT ATCCTCACTC AACAAGGCGA TAAATTACCG GTTTCCGCTT
2801  TTGAAGCCGA TGGACGTTTT CCACTGGGAA CTTCTCAGTT TGAGAAACGC
2851  GGAGTGGCTA TTAACGTTCC TCAGTGGGTA CCTGAAAATT GCATCCAATG
2901  CAATCAATGC GCTTTTGTGT GCCCGCATTC CGCGATACTT CCTGTTTTGG
```

FIG. 26B DNA sequence of pMBXS994 (Cont'd)

```
2951    CTAAAGAGGA AGAGTTAGTC GGAGCGCCTG CCAACTTCAC CGCTTTGGAA
3001    GCGAAAGGAA AAGAATTGAA AGGTTACAAA TTCAGAATTC AGATTAACAC
3051    TCTCGACTGC ATGGGCTGCG GAAATTGTGC CGACATATGT CCTCCCAAAG
3101    AAAAGGCTTT AGTGATGCAG CCACTGGACA CTCAGAGGGA TGCCCAAGTG
3151    CCAAATTTGG AGTATGCAGC CAGAATTCCA GTGAAGTCCG AGGTTCTTCC
3201    GCGGGATTCT CTCAAAGGAT CACAATTCCA AGAACCACTG ATGGAGTTTT
3251    CAGGCGCATG TAGTGGATGT GGTGAAACAC CTTACGTACG TGTGATTACT
3301    CAGTTATTTG GAGAACGGAT GTTTATCGCT AATGCAACAG GTTGTAGCTC
3351    GATCTGGGGT GCCAGCGCTC CGTCGATGCC ATACAAGACC AACAGGCTGG
3401    GACAGGGTCC AGCTTGGGGG AATTCCCTAT TCGAGGATGC TGCAGAGTAC
3451    GGGTTCGGAA TGAACATGAG TATGTTTGCG CGTAGAACTC ATCTCGCGGA
3501    TCTTGCTGCT AAAGCTCTCG AGTCTGATGC TTCTGGAGAT GTCAAGGAAG
3551    CATTGCAGGG TTGGCTCGCT GGGAAAAACG ACCCGATTAA GTCTAAAGAA
3601    TACGGGGATA AGTTGAAGAA ACTTCTAGCT GGTCAAAAGG ACGGGTTGTT
3651    GGGACAAATT GCAGCAATGT CAGACCTTTA CACGAAGAAA AGTGTTTGGA
3701    TCTTTGGTGG CGATGGATGG GCGTATGATA TTGGTTATGG TGGCCTTGAT
3751    CACGTCCTCG CAAGCGGCGA AGATGTGAAC GTGTTTGTGA TGGATACTGA
3801    AGTTTACTCC AACACCGGTG GACAATCCTC AAAAGCAACA CCAACCGGGG
3851    CCGTGGCTAA ATTCGCGGCT GCCGGCAAAA GGACTGGAAA AAAGGATCTG
3901    GCCAGAATGG TTATGACTTA TGGATACGTA TATGTAGCTA CAGTATCAAT
3951    GGGCTATAGC AAACAGCAAT TTCTTAAAGT CCTCAAGGAA GCTGAGAGCT
4001    TCCCAGGTCC TTCACTTGTT ATCGCCTACG CGACATGTAT CAATCAAGGT
4051    TTACGAAAGG GAATGGGGAA AAGCCAAGAT GTGATGAACA CCGCTGTTAA
4101    AAGCGGTTAT TGGCCTTTGT TCCGCTATGA TCCTCGTCTT GCGGCCCAAG
4151    GAAAGAATCC GTTTCAGCTA GACTCTAAGG CACCAGACGG TAGTGTTGAG
4201    GAATTTTTGA TGGCTCAGAA TCGATTTGCG GTCCTTGATC GATCGTTCCC
4251    AGAAGATGCC AAGAGGTTGA GGGCGCAAGT TGCACATGAA TTGGATGTTA
4301    GGTTTAAGGA GTTAGAACAC ATGGCGGCTA CAAATATCTT CGAGTCCTTC
4351    GCTCCTGCTG GAGGCAAAGC TGACGGTTCA GTAGATTTTG GAGAAGGCGC
4401    AGAGTTTTGT ACTAGAGATG ACACACCGAT GATGGCCAGA CCAGATAGTG
4451    GCGAAGCATG CGACCAAAAT AGAGCAGGAA CGTCTGAGCA GCAAGGAGAT
4501    TTGTCGAAGA GGACCAAGAA ATGAGGCGCG CCTGAGTAAT TCTGATATTA
4551    GAGGGAGCAT TAATGTGTTG TTGTGATGTG GTTTATATGG GGAAATTAAA
4601    TAAATGATGT ATGTACCTCT TGCCTATGTA GGTTTGTGTG TTTTGTTTTG
4651    TTGTCTAGCT TTGGTTATTA AGTAGTAGGG ACGTTCGTTC GTGTCTCAAA
4701    AAAAGGGGTA CTACCACTCT GTAGTGTATA TGGATGCTGG AAATCAATGT
4751    GTTTTGTATT TGTTCACCTC CATTGTTGAA TTCAATGTCA AATGTGTTTT
4801    GCGTTGGTTA TGTGTAAAAT TACTATCTTT CTCGTCCGAT GATCAAAGTT
4851    TTAAGCAACA AAACCAAGGG TGAAATTTAA ACTGTGCTTT GTTGAAGATT
4901    CTTTTATCAT ATTGAAAATC AAATTACTAG CAGCAGATTT TACCTAGCAT
4951    GAAATTTTAT CAACAGTACA GCACTCACTA ACCAAGTTCC AAACTAAGAT
5001    GCGCCATTAA CATCAGCCAA TAGGCATTTT CAGCAAAAGC TTGTACGTAG
5051    TGTTTATCTT TGTTGCTTTT CTGAACAATT TATTTACTAT GTAAATATAT
5101    TATCAATGTT TAATCTATTT TAATTTGCAC ATGAATTTTC ATTTTATTTT
5151    TACTTTACAA AACAAATAAA TATATATGCA AAAAAATTTA CAAACGATGC
5201    ACGGGTTACA AACTAATTTC ATTAAATGCT AATGCAGATT TTGTGAAGTA
5251    AAACTCCAAT TATGATGAAA AATACCACCA ACACCACCTG CGAAACTGTA
5301    TCCCAACTGT CCTTAATAAA AATGTTAAAA AGTATATTAT TCTCATTTGT
5351    CTGTCATAAT TTATGTACCC CACTTTAATT TTTCTGATGT ACTAAACCGA
5401    GGGCAAACTG AAACCTGTTC CTCATGCAAA GCCCCTACTC ACCATGTATC
5451    ATGTACGTGT CATCACCCAA CAACTCCACT TTTGCTATAT AACAACACCC
5501    CCGTCACACT CTCCCTCTCT AACACACACC CCACTAACAA TTCCTTCACT
5551    TGCAGCACTG TTGCATCATC ATCTTCATTG CAAAACCCTA AACTTCACCT
5601    TCAACCGCGG CCGCAGATCT AAAATGGCTT CTATGATATC CTCTTCCGCT
5651    GTGACAACAG TCAGCCGTGC CTCTAGGGGG CAATCCGCCG CAGTGGCTCC
5701    ATTCGGCGGC CTCAAATCCA TGACTGGATT CCCAGTGAAG AAGGTCAACA
5751    CTGACATTAC TTCCATTACA AGCAATGGTG GAAGAGTAAA GTGCATGCAG
5801    GTGTGGCCTC CAATTGGAAA GAAGAAGTTT GAGACTCTTT CCTATTTGCC
5851    ACCATTGACG AGAGATTCTA GAGTGCTCAG CCAGCAATCC ATCCAGAAGG
```

FIG. 26C DNA sequence of pMBXS994 (Cont'd)

```
5901   TTCTCGTGGC TAACCGTGGT GAGATTGCTA TTCGTATCTT TAGAGCGTGT
5951   ACCGAGTTGA ACATCCGAAC TGTCGCTGTT TATAGTAAAG AAGATTCTGG
6001   ATCATACCAC AGATACAAAG CTGACGAGGC CTACTTGGTT GGTGAAGGTA
6051   AGAAGCCTAT TGACGCTTAT CTTGATATAG AGGGCATCAT TGATATTGCC
6101   AAGAGAAACA AAGTTGATGC AATTCATCCG GGATACGGTT TTCTATCAGA
6151   AAACATTCAC TTTGCACGAC GATGTGAAGA AGAGGGAATC GTGTTCATCG
6201   GACCTAAAAG CGAACACTTG GATATGTTTG GGGACAAGGT TAAGGCAAGG
6251   GAACAAGCAG AGAAGGCAGG AATTCCAGTG ATACCTGGAT CGGATGGGCC
6301   TGCTGAAACT CTTGAAGCTG TCGAACAATT CGGCCAGGCT AACGGATACC
6351   CAATCATCAT TAAGGCTTCT TTAGGTGGTG GGGGAAGGGG GATGAGAATC
6401   GTGCGATCCG AATCTGAGGT AAAAGAGGCT TATGAACGTG CTAAATCGGA
6451   AGCTAAAGCG GCCTTTGGGA ACGATGAAGT CTATGTCGAG AAACTAATCG
6501   AGAATCCCAA GCACATCGAG GTTCAAGTGA TTGGTGATAA GCAAGGTAAC
6551   GTTGTTCACC TTTTCGAGAG AGATTGTTCT GTTCAACGTA GACACCAAAA
6601   AGTGATAGAA GTAGCTCCAT CGGTATCGTT GAGCCCAGAA CTAAGGGACC
6651   AGATATGCGA GGCTGCTGTC GCGCTTGCAA AGAATGTCAA CTATATCAAT
6701   GCAGGCACTG TCGAATTCTT GGTAGCCAAT AATGAGTTTT ACTTCATTGA
6751   GGTCAACCCT AGAGTTCAAG TTGAGCATAC CATTACCGAA ATGATCACTG
6801   GGGTGGATAT CGTACAGACT CAGATCCTCG TTGCTCAAGG CCATTCCCTT
6851   CATTCCAAGA AGGTGAATAT TCCAGAGCAA AAGGATATCT TTACAATTGG
6901   TTATGCGATT CAATCACGAG TTACCACAGA AGATCCACAA AATGACTTCA
6951   TGCCAGATAC GGGAAAGATA ATGGCATACC GTTCTGGTGG CGGATTTGGT
7001   GTTCGATTAG ACACAGGTAA TAGTTTTCAG GGAGCTGTGA TAACGCCATA
7051   CTATGATTCT TTATTGGTTA AGTTGAGTAC TTGGGCTCTC ACTTTCGAGC
7101   AAGCCGCAGC GAAAATGGTC AGAAACCTTC AGGAGTTCAG AATTAGAGGT
7151   ATTAAGACGA ACATTCCATT CTTAGAGAAC GTTGCTAAAC ATGAGAAGTT
7201   TCTGACAGGA CAATATGATA CAAGTTTCAT AGACACTACA CCTGAACTCT
7251   TTAACTTCCC TAAACAAAAA GACAGAGGTA CGAAAATGTT GACATATATC
7301   GGAAACGTGA CAGTTAATGG GTTCCCAGGT ATCGGTAAGA AAGAAAAGCC
7351   GGCCTTTGAT AAACCCCTTG GTGTTAAAGT GGATGTGGAT CAACAACCTG
7401   CTAGGGGCAC TAAGCAAATC CTTGATGAAA AGGGTGCAGA GGGACTGGCA
7451   AATTGGGTTA AAGAGCAGAA ATCAGTTCTT CTGACAGATA CCACATTTCG
7501   TGATGCTCAT CAATCATTAC TAGCAACAAG AATTAGATCA CACGATCTGA
7551   AAAAGATCGC TAATCCAACC GCTGCTCTTT GGCCGGAACT CTTCTCTATG
7601   GAAATGTGGG GTGGGGCCAC ATTCGATGTC GCGTACCGTT TTCTAAAAGA
7651   AGATCCTTGG AAGCGTCTGG AAGATTTGAG AAAAGAGGTG CCCAATACCC
7701   TGTTCCAGAT GCTTTTGCGT TCTAGCAATG CCGTCGGATA TACCAATTAT
7751   CCTGACAATG TGATCAAAGA ATTCGTAAAA CAGTCCGCTC AATCTGGTAT
7801   CGACGTTTTT AGGATTTTCG ATTCACTTAA TTGGGTAAAA GGTATGACGT
7851   TAGCGATTGA TGCTGTACGT GATACTGGAA AGGTTGCAGA GGCCGCCATT
7901   TGCTACACTG GAGACATTTT GGATAAGAAT AGAACTAAAT ACGACTTGGC
7951   TTATTACACT TCCATGGCAA AAGAACTTGA GGCTGCCGGT GCACATATTC
8001   TGGGGATAAA GGATATGGCC GGTTTGCTCA AACCGCAGGC AGCATATGAG
8051   TTGGTTTCAG CCCTTAAAGA AACTATTGAC ATACCCGTTC ATCTGCACAC
8101   GCATGACACG TCGGGCAATG GAATCTATAT GTATGCAAAG GCTGTCGAGG
8151   CTGGCGTGGA TATCATTGAT GTCGCTGTAA GCTCTATGGC TGGACTTACA
8201   TCCCAGCCAT CAGCCTCTGG ATTCTATCAT GCTATGGAAG GTAACGATCG
8251   TAGACCCGAA ATGAATGTCC AAGGGGTCGA ATTACTGTCA CAGTACTGGG
8301   AGAGTGTGCG TAAGTATTAC TCAGAGTTTG AGAGCGGTAT GAAGAGTCCC
8351   CATACCGAGA TTTATGAGCA CGAGATGCCT GGTGGACAAT ACTCTAACTT
8401   GCAACAGCAA GCGAAGGGGG TTGGTTTGGG AGATAGGTGG AACGAAGTGA
8451   AAGAAATGTA TAGACGTGTC AACGACATGT TTGGTGATAT TGTGAAAGTA
8501   ACTCCTAGTT CTAAGGTAGT TGGAGACATG GCACTGTACA TGGTTCAGAA
8551   TAACCTTACT GAAAAGGATG TTTACGAGAA GGGGGAGTCA CTTGACTTCC
8601   CTGATTCAGT GGTTGAACTG TTCAAGGGAA ATATCGGTCA ACCGCATGGG
8651   GGATTTCCAG AAAAACTACA GAAACTGATA CTAAAGGGAC AGGAGCCAAT
8701   TACTGTTCGA CCAGGAGAGC TCTTGGAGCC GGTTTCTTTT GAGGCTATCA
8751   AGCAAGAATT CAAAGAACAA CATAACCTTG AAATTTCTGA TCAGGACGCG
8801   GTTGCTTACG CACTTTATCC AAAGGTCTTT ACTGATTACG TGAAAACCAC
```

FIG. 26D DNA sequence of pMBXS994 (Cont'd)

```
8851   AGAGTCTTAT GGTGATATAA GTGTGCTAGA TACACCAACA TTTTTCTATG
8901   GCATGACTCT TGGAGAAGAG ATTGAAGTGG AAATAGAAAG GGGAAAAACA
8951   CTCATTGTTA AACTGATATC TATCGGAGAG CCTCAACCTG ATGCTACAAG
9001   GGTAGTGTAC TTTGAATTGA ATGGACAACC TAGAGAAGTA GTGATTAAAG
9051   ATGAGTCAAT AAAGTCAAGC GTGCAGGAGA GGCTAAAGGC AGATAGAACC
9101   AATCCGTCGC ACATTGCAGC TTCTATGCCT GGCACCGTCA TAAAAGTCCT
9151   CGCTGAAGCT GGTACTAAAG TCAACAAAGG TGACCATCTT ATGATCAACG
9201   AAGCAATGAA GATGGAAACT ACGGTTCAGG CACCTTTCAG TGGAACAATC
9251   AAGCAGGTTC ATGTTAAGAA TGGCGAGCCT ATCCAGACTG GTGACTTGCT
9301   TTTGGAGATT GAAAAGGCCT GAGTCGACGC GATCGCGCGG CCGCTGAGTA
9351   ATTCTGATAT TAGAGGGAGC ATTAATGTGT TGTTGTGATG TGGTTTATAT
9401   GGGGAAATTA AATAAATGAT GTATGTACCT CTTGCCTATG TAGGTTTGTG
9451   TGTTTTGTTT TGTTGTCTAG CTTTGGTTAT TAAGTAGTAG GGACGTTCGT
9501   TCGTGTCTCA AAAAAAGGGG TACTACCACT CTGTAGTGTA TATGGATGCT
9551   GGAAATCAAT GTGTTTTGTA TTTGTTCACC TCCATTGTTG AATTCAATGT
9601   CAAATGTGTT TTGCGTTGGT TATGTGTAAA ATTACTATCT TTCTCGTCCG
9651   ATGATCAAAG TTTTAAGCAA CAAAACCAAG GGTGAAATTT AAACTGTGCT
9701   TTGTTGAAGA TTCTTTTATC ATATTGAAAA TCAAATTACT AGCAGCAGAT
9751   TTTACCTAGC ATGAAATTTT ATCAACAGTA CAGCACTCAC TAACCAAGTT
9801   CCAAACTAAG ATGCGCCATT AACATCAGCC AATAGGCATT TTCAGCAAGT
9851   TTAAACTACG TAGTGTTTAT CTTTGTTGCT TTTCTGAACA ATTTATTTAC
9901   TATGTAAATA TATTATCAAT GTTTAATCTA TTTTAATTTG CACATGAATT
9951   TTCATTTTAT TTTTACTTTA CAAAACAAAT AAATATATAT GCAAAAAAAT
10001  TTACAAACGA TGCACGGGTT ACAAACTAAT TTCATTAAAT GCTAATGCAG
10051  ATTTTGTGAA GTAAAACTCC AATTATGATG AAAAATACCA CCAACACCAC
10101  CTGCGAAACT GTATCCCAAC TGTCCTTAAT AAAAATGTTA AAAAGTATAT
10151  TATTCTCATT TGTCTGTCAT AATTTATGTA CCCCACTTTA ATTTTTCTGA
10201  TGTACTAAAC CGAGGGCAAA CTGAAACCTG TTCCTCATGC AAAGCCCCTA
10251  CTCACCATGT ATCATGTACG TGTCATCACC CAACAACTCC ACTTTTGCTA
10301  TATAACAACA CCCCCGTCAC ACTCTCCCTC TCTAACACAC ACCCCACTAA
10351  CAATTCCTTC ACTTGCAGCA CTGTTGCATC ATCATCTTCA TTGCAAAACC
10401  CTAAACTTCA CCTTCAACCG CGGCCGCTCG CGAAAAATGG CTTCTATGAT
10451  ATCCTCTTCC GCTGTGACAA CAGTCAGCCG TGCCTCTAGG GGGCAATCCG
10501  CCGCAGTGGC TCCATTCGGC GGCCTCAAAT CCATGACTGG ATTCCCAGTG
10551  AAGAAGGTCA ACACTGACAT TACTTCCATT ACAAGCAATG GTGGAAGAGT
10601  AAAGTGCATG CAGGTGTGGC CTCCAATTGG AAAGAAGAAG TTTGAGACTC
10651  TTTCCTATTT GCCACCATTG ACGAGAGATT CTAGAGTGAA CATACACGAG
10701  TACCAAGCAA AAGAGTTGCT CAAGACCTAT GGAGTGCCGG TCCCAGACGG
10751  AGCGGTAGCT TATAGTGATG CTCAAGCGGC TTCCGTCGCT GAAGAGATTG
10801  GTGGCTCTAG ATGGGTTGTA AAGGCGCAGA TACACGCTGG TGGAAGGGGA
10851  AAGGCAGGTG GTGTGAAGGT GGCCCATAGC ATTGAAGAGG TTCGTCAGTA
10901  CGCTGATGCG ATGCTTGGGT CCCATCTCGT TACACATCAA ACAGGGCCTG
10951  GTGGTTCATT AGTTCAACGT TTGTGGGTGG AGCAAGCATC ACATATCAAG
11001  AAAGAGTATT ATCTGGGATT TGTTATTGAT AGAGGTAACC AAAGAATTAC
11051  CTTAATTGCT TCTTCTGAAG GGGGAATGGA GATAGAAGAG GTTGCTAAAG
11101  AGACACCAGA AAAGATCGTC AAAGAGGTTG TAGACCCTGC AATCGGATTG
11151  CTTGATTTTC AGTGTAGAAA GGTTGCAACT GCAATAGGAC TTAAGGGAAA
11201  GCTTATGCCC CAGGCAGTTA GACTTATGAA GGCTATCTAT AGGTGTATGC
11251  GAGATAAGGA TGCTCTCCAG GCAGAGATCA ATCCTTTGGC AATAGTAGGT
11301  GAAAGTGACG AGTCGCTCAT GGTTCTTGAT GCTAAATTCA ATTTTGATGA
11351  CAATGCTCTT TACAGACAAC GAACAATTAC TGAAATGAGG GATCTCGCAG
11401  AAGAAGATCC TAAAGAAGTC GAAGCTTCTG GACACGGATT GAATTACATC
11451  GCCCTCGATG GGAACATCGG TTGTATTGTG AATGGAGCTG GTCTTGCTAT
11501  GGCCAGCCTG GATGCCATCA CTCTACATGG CGGTCGTCCA GCTAACTTCT
11551  TAGATGTCGG CGGTGGGGCT TCTCCTGAAA AGGTTACGAA TGCGTGCAGA
11601  ATTGTTTTGG AAGATCCGAA CGTCCGTTGT ATACTGGTGA ACATTTTTGC
11651  CGGAATTAAC AGGTGCGATT GGATTGCAAA AGGACTTATT CAAGCCTGCG
11701  ACTCACTACA GATTAAAGTT CCACTGATCG TTCGATTGGC AGGCACTAAT
11751  GTAGATGAAG GCAGGAAAAT CCTAGCGGAG TCGGGTTTAA GTTTCATAAC
```

FIG. 26E DNA sequence of pMBXS994 (Cont'd)

```
11801 GGCAGAGAAT TTGGACGACG CGGCTGCTAA AGCCGTGGCT ATCGTGAAAG
11851 GGTGAACGCG TTGAGTAATT CTGATATTAG AGGGAGCATT AATGTGTTGT
11901 TGTGATGTGG TTTATATGGG GAAATTAAAT AAATGATGTA TGTACCTCTT
11951 GCCTATGTAG GTTTGTGTGT TTTGTTTTGT TGTCTAGCTT TGGTTATTAA
12001 GTAGTAGGGA CGTTCGTTCG TGTCTCAAAA AAAGGGGTAC TACCACTCTG
12051 TAGTGTATAT GGATGCTGGA AATCAATGTG TTTTGTATTT GTTCACCTCC
12101 ATTGTTGAAT TCAATGTCAA ATGTGTTTTG CGTTGGTTAT GTGTAAAATT
12151 ACTATCTTTC TCGTCCGATG ATCAAAGTTT TAAGCAACAA AACCAAGGGT
12201 GAAATTTAAA CTGTGCTTTG TTGAAGATTC TTTTATCATA TTGAAAATCA
12251 AATTACTAGC AGCAGATTTT ACCTAGCATG AAATTTTATC AACAGTACAG
12301 CACTCACTAA CCAAGTTCCA AACTAAGATG CGCCATTAAC ATCAGCCAAT
12351 AGGCATTTTC AGCAATGTAC ATACGTAGTG TTTATCTTTG TTGCTTTTCT
12401 GAACAATTTA TTTACTATGT AAATATATTA TCAATGTTTA ATCTATTTTA
12451 ATTTGCACAT GAATTTTCAT TTTATTTTTA CTTTACAAAA CAAATAAATA
12501 TATATGCAAA AAAATTTACA AACGATGCAC GGGTTACAAA CTAATTTCAT
12551 TAAATGCTAA TGCAGATTTT GTGAAGTAAA ACTCCAATTA TGATGAAAAA
12601 TACCACCAAC ACCACCTGCG AAACTGTATC CCAACTGTCC TTAATAAAAA
12651 TGTTAAAAAG TATATTATTC TCATTTGTCT GTCATAATTT ATGTACCCCA
12701 CTTTAATTTT TCTGATGTAC TAAACCGAGG GCAAACTGAA ACCTGTTCCT
12751 CATGCAAAGC CCCTACTCAC CATGTATCAT GTACGTGTCA TCACCCAACA
12801 ACTCCACTTT TGCTATATAA CAACACCCCC GTCACACTCT CCCTCTCTAA
12851 CACACACCCC ACTAACAATT CCTTCACTTG CAGCACTGTT GCATCATCAT
12901 CTTCATTGCA AAACCCTAAA CTTCACCTTC AACCGCGGCC GCGACGTCAA
12951 AATGGCTTCT ATGATATCCT CTTCCGCTGT GACAACAGTC AGCCGTGCCT
13001 CTAGGGGGCA ATCCGCCGCA GTGGCTCCAT TCGGCGGCCT CAAATCCATG
13051 ACTGGATTCC CAGTGAAGAA GGTCAACACT GACATTACTT CCATTACAAG
13101 CAATGGTGGA AGAGTAAAGT GCATGCAGGT GTGGCCTCCA ATTGGAAAGA
13151 AGAAGTTTGA GACTCTTTCC TATTTGCCAC CATTGACGAG AGATTCTAGA
13201 GTCTCGGTTT TCGTGAATAA ACATTCCAAG GTCATCTTTC AAGGCTTTAC
13251 CGGGGAGCAT GCTACATTTC ACGCAAAAGA TGCAATGCGA ATGGGCACAA
13301 GGGTTGTCGG TGGCGTTACT CCTGGAAAGG GTGGGACTAG ACATCCAGAT
13351 CCTGAGCTCG CTCATCTTCC GGTATTCGAT ACCGTTGCCG AAGCCGTTGC
13401 TGCTACAGGA GCTGATGTAT CAGCTGTGTT TGTCCCACCC CCTTTCAATG
13451 CAGACGCACT TATGGAAGCA ATTGATGCCG GTATTAGAGT GGCTGTCACT
13501 ATAGCGGATG GAATTCCTGT GCATGACATG ATCAGATTGC AAAGGTATAG
13551 AGTAGGAAAG GACTCTATTG TTATCGGGCC TAACACACCA GGAATCATAA
13601 CGCCTGGTGA GTGTAAAGTG GGTATCATGC CGAGTCACAT ATACAAGAAG
13651 GGAAACGTGG GTATAGTGAG TCGATCAGGA ACATTGAATT ACGAGGCGAC
13701 GGAACAAATG GCTGCGCTAG GCTTAGGGAT TACTACTTCT GTTGGAATTG
13751 GTGGTGATCC TATAAACGGC ACTGACTTTG TGACTGTTCT CCGTGCATTC
13801 GAGGCTGATC CAGAAACGGA AATTGTAGTT ATGATCGGAG AAATAGGTGG
13851 ACCGCAGGAA GTTGCCGCAG CTAGATGGGC AAAAGAGAAT ATGACCAAAC
13901 CAGTTATTGG GTTCGTAGCT GGTTTAGCAG CCCCCACAGG GCGTAGGATG
13951 GGACACGCAG GTGCTATTAT CAGCTCTGAG GCTGATACCG CTGGAGCTAA
14001 GATGGATGCC ATGGAAGCTC TTGGTCTGTA TGTCGCTAGG AACCCAGCGC
14051 AAATCGGACA GACAGTTTTG CGTGCGGCAC AGGAGCATGG AATTAGATTT
14101 TGAGGGCCCG TTAACTGAGT AATTCTGATA TTAGAGGGAG CATTAATGTG
14151 TTGTTGTGAT GTGGTTTATA TGGGGAAATT AAATAAATGA TGTATGTACC
14201 TCTTGCCTAT GTAGGTTTGT GTGTTTTGTT TTGTTGTCTA GCTTTGGTTA
14251 TTAAGTAGTA GGGACGTTCG TTCGTGTCTC AAAAAAAGGG GTACTACCAC
14301 TCTGTAGTGT ATATGGATGC TGGAAATCAA TGTGTTTTGT ATTTGTTCAC
14351 CTCCATTGTT GAATTCAATG TCAAATGTGT TTTGCGTTGG TTATGTGTAA
14401 AATTACTATC TTTCTCGTCC GATGATCAAA GTTTTAAGCA ACAAAACCAA
14451 GGGTGAAATT TAAACTGTGC TTTGTTGAAG ATTCTTTTAT CATATTGAAA
14501 ATCAAATTAC TAGCAGCAGA TTTTACCTAG CATGAAATTT TATCAACAGT
14551 ACAGCACTCA CTAACCAAGT TCCAAACTAA GATGCGCCAT TAACATCAGC
14601 CAATAGGCAT TTTCAGCAAG TTTAAACCGG ACCGTACGTA GTGTTTATCT
14651 TTGTTGCTTT TCTGAACAAT TTATTTACTA TGTAAATATA TTATCAATGT
14701 TTAATCTATT TTAATTTGCA CATGAATTTT CATTTTATTT TTACTTTACA
```

FIG. 26F DNA sequence of pMBXS994 (Cont'd)

```
14751  AAACAAATAA ATATATATGC AAAAAAATTT ACAAACGATG CACGGGTTAC
14801  AAACTAATTT CATTAAATGC TAATGCAGAT TTTGTGAAGT AAAACTCCAA
14851  TTATGATGAA AAATACCACC AACACCACCT GCGAAACTGT ATCCCAACTG
14901  TCCTTAATAA AAATGTTAAA AAGTATATTA TTCTCATTTG TCTGTCATAA
14951  TTTATGTACC CCACTTTAAT TTTTCTGATG TACTAAACCG AGGGCAAACT
15001  GAAACCTGTT CCTCATGCAA AGCCCCTACT CACCATGTAT CATGTACGTG
15051  TCATCACCCA ACAACTCCAC TTTTGCTATA TAACAACACC CCCGTCACAC
15101  TCTCCCTCTC TAACACACAC CCCACTAACA ATTCCTTCAC TTGCAGCACT
15151  GTTGCATCAT CATCTTCATT GCAAAACCCT AAACTTCACC TTCAACCGCG
15201  GCCGCCACGT GAAAATGGCT TCTATGATAT CCTCTTCCGC TGTGACAACA
15251  GTCAGCCGTG CCTCTAGGGG GCAATCCGCC GCAGTGGCTC CATTCGGCGG
15301  CCTCAAATCC ATGACTGGAT TCCCAGTGAA GAAGGTCAAC ACTGACATTA
15351  CTTCCATTAC AAGCAATGGT GGAAGAGTAA AGTGCATGCA GGTGTGGCCT
15401  CCAATTGGAA AGAAGAAGTT TGAGACTCTT TCCTATTTGC CACCATTGAC
15451  GAGAGATTCT AGAGTGAGCT TCCGTTTGCA ACCAGCTCCG CCAGCAAGGC
15501  CCAATAGATG TCAACTTTTT GGGCCTGGAT CTCGACCGGC TTTGTTTGAG
15551  AAAATGGCCG CTTCAGCCGC GGACGTTATC AATCTGGATT TAGAGGATAG
15601  TGTTGCCCCA GATGATAAAG CTCAGGCTAG AGCAAATATC ATTGAGGCTA
15651  TAAACGGTCT AGACTGGGGT AGAAAGTATC TCAGTGTTAG AATTAACGGA
15701  CTTGATACGC CTTTCTGGTA TCGAGATGTC GTTGACTTGC TTGAGCAGGC
15751  AGGAGATAGA CTTGATCAAA TCATGATCCC TAAGGTTGGC TGTGCTGCGG
15801  ATGTTTACGC CGTCGATGCT TTGGTAACAG CAATTGAACG TGCTAAAGGG
15851  CGTACTAAGC CTCTATCATT TGAAGTGATA ATAGAGTCTG CAGCTGGTAT
15901  CGCACATGTT GAAGAAATAG CCGCTTCGTC ACCAAGACTC CAAGCCATGT
15951  CTTTGGGTGC AGCCGATTTT GCAGCTTCTA TGGGAATGCA GACTACAGGG
16001  ATTGGTGGAA CGCAAGAGAA CTACTATATG CTCCACGACG GACAAAAGCA
16051  CTGGTCCGAT CCTTGGCATT GGGCTCAGGC TGCAATCGTC GCAGCGTGCA
16101  GAACACATGG GATTTTACCC GTTGACGGCC CGTTCGGTGA CTTCTCTGAT
16151  GACGAAGGAT TCAGGGCACA AGCTCGAAGG TCCGCTACTC TTGGAATGGT
16201  GGGAAAATGG GCCATACATC CAAAGCAAGT GGCTCTCGCT AATGAAGTGT
16251  TTACACCTAG CGAGACTGCA GTAACCGAAG CGAGGGAGAT TTTAGCGGCT
16301  ATGGATGCTG CTAAGGCGAG AGGCGAAGGT GCTACCGTGT ACAAAGGTAG
16351  GCTGGTAGAT ATCGCGTCGA TTAAACAGGC AGAAGTCATT GTTCGTCAGG
16401  CTGAGATGAT TAGTGCATGA ACTAGTTGAG TAATTCTGAT ATTAGAGGGA
16451  GCATTAATGT GTTGTTGTGA TGTGGTTTAT ATGGGGAAAT TAAATAAATG
16501  ATGTATGTAC CTCTTGCCTA TGTAGGTTTG TGTGTTTTGT TTTGTTGTCT
16551  AGCTTTGGTT ATTAAGTAGT AGGGACGTTC GTTCGTGTCT CAAAAAAAGG
16601  GGTACTACCA CTCTGTAGTG TATATGGATG CTGGAAATCA ATGTGTTTTG
16651  TATTTGTTCA CCTCCATTGT TGAATTCAAT GTCAAATGTG TTTTGCGTTG
16701  GTTATGTGTA AAATTACTAT CTTTCTCGTC CGATGATCAA AGTTTTAAGC
16751  AACAAAACCA AGGGTGAAAT TTAAACTGTG CTTTGTTGAA GATTCTTTTA
16801  TCATATTGAA AATCAAATTA CTAGCAGCAG ATTTTACCTA GCATGAAATT
16851  TTATCAACAG TACAGCACTC ACTAACCAAG TTCCAAACTA AGATGCGCCA
16901  TTAACATCAG CCAATAGGCA TTTTCAGCAA GTTTAAACTC CGGATACGTA
16951  GTGTTTATCT TTGTTGCTTT TCTGAACAAT TTATTTACTA TGTAAATATA
17001  TTATCAATGT TTAATCTATT TTAATTTGCA CATGAATTTT CATTTTATTT
17051  TTACTTTACA AAACAAATAA ATATATATGC AAAAAAATTT ACAAACGATG
17101  CACGGGTTAC AAACTAATTT CATTAAATGC TAATGCAGAT TTTGTGAAGT
17151  AAAACTCCAA TTATGATGAA AAATACCACC AACACCACCT GCGAAACTGT
17201  ATCCCAACTG TCCTTAATAA AAATGTTAAA AAGTATATTA TTCTCATTTG
17251  TCTGTCATAA TTTATGTACC CCACTTTAAT TTTTCTGATG TACTAAACCG
17301  AGGGCAAACT GAAACCTGTT CCTCATGCAA AGCCCCTACT CACCATGTAT
17351  CATGTACGTG TCATCACCCA ACAACTCCAC TTTTGCTATA TAACAACACC
17401  CCCGTCACAC TCTCCCTCTC TAACACACAC CCCACTAACA ATTCCTTCAC
17451  TTGCAGCACT GTTGCATCAT CATCTTCATT GCAAAACCCT AAACTTCACC
                  AvrII
                  ~~~~~~~
17501  TTCAACCGCG GCCGCCCTAG GAAAATGGCT TCTATGATAT CCTCTTCCGC
17551  TGTGACAACA GTCAGCCGTG CCTCTAGGGG GCAATCCGCC GCAGTGGCTC
```

FIG. 26G DNA sequence of pMBXS994 (Cont'd)

```
17601     CATTCGGCGG CCTCAAATCC ATGACTGGAT TCCCAGTGAA GAAGGTCAAC
17651     ACTGACATTA CTTCCATTAC AAGCAATGGT GGAAGAGTAA AGTGCATGCA
17701     GGTGTGGCCT CCAATTGGAA AGAAGAAGTT TGAGACTCTT TCCTATTTGC
17751     CACCATTGAC GAGAGATTCT AGAGTTGCAC AGTACCAAGA CGATATCAAG
17801     GCGGTTGCAG GGCTTAAGGA GAATCACGGC TCCGCATGGA ATGCCATCAA
17851     CCCGGAGTAT GCCGCCAGGA TGAGGGCGCA GAACAAGTTC AAGACGGGCC
17901     TTGACATTGC AAAGTATACG GCTAAGATTA TGCGGGCCGA TATGGCAGCC
17951     TACGACGCCG ACAGCTCGAA GTACACACAG AGCCTCGGTT GTTGGCATGG
18001     TTTCATTGGT CAGCAGAAGA TGATCTCAAT CAAGAAACAT TTCAACAGCA
18051     CGGAACGCCG TTACCTCTAC CTTTCTGGCT GGATGGTAGC CGCGCTTAGA
18101     TCCGAGTTTG GCCCCCTACC GGATCAGTCC ATGCACGAAA AGACGAGTGT
18151     CTCCGCACTC ATTCGGGAAC TCTACACTTT TCTGCGCCAA GCGGACGCTA
18201     GGGAGTTGGG GGGCCTGTTT CGGGAGCTTG ACGCGGCCCA AGGCCCAGCT
18251     AAGGCGGCCA TTCAAGCGAA GATCGACAAC CACGTCACTC ATGTGGTCCC
18301     AATCATAGCT GATATCGACG CTGGCTTCGG CAATGCGGAA GCAACATACC
18351     TGTTGGCCAA GCAGTTCATC GAGGCCGGGG CTTGCTGCAT ACAGATAGAG
18401     AACCAGGTTT CTGACGAAAA GCAATGTGGA CATCAAGACG GAAAGGTTAC
18451     CGTGCCCCAC GAGGATTTTC TTGCAAAAAT CCGAGCGATT CGTTATGCGT
18501     TTTTAGAGTT GGGCGTGGAT GACGGTATCA TCGTGGCCAG GACCGATAGT
18551     CTCGGTGCTG GTCTGACAAA GCAAATCGCA GTGACCAATA CGCCTGGAGA
18601     CTTAGGGGAT CAGTACAACA GCTTCCTCGA TTGCGAGGAG CTTAGCGCAG
18651     ATCAGCTCGG AAATGGCGAC GTTATCATCA AGCGTGATGG AAAGCTACTC
18701     CGCCCCAAGC GCCTCCCGTC TAACTTGTTC CAGTTCCGGG CTGGAACTGG
18751     CGAAGCGCGA TGCGTCCTGG ACTGCGTGAC CGCGCTCCAG AACGGCGCCG
18801     ACCTACTCTG GATTGAGACA GAAAAGCCTC ACATAGCTCA AATCGGCGGA
18851     ATGGTATCGG AGATAAGGAA AGTCATACCC AACGCCAAAC TGGTGTACAA
18901     CAACTCTCCG TCGTTCAATT GGACCCTGAA CTTTAGACAG CAAGCATACG
18951     ATGCTATGAA AGCCGCTGGG AAAGACGTGT CAGCATACGA CCGCGCCCAG
19001     CTTATGTCCG TGGAGTACGA CCAAACGGAA CTGGCTAAGC TGGCTGATGA
19051     GAAAATCAGA ACATTCCAGG CCGACGCCTC AAGGGAGGCC GGGATCTTCC
19101     ATCACTTGAT TACCTTACCA ACATATCACA CTGCGGCCCT GTCAACCGAC
19151     AATTTGGCTA AGGAGTACTT CGGAGATCAG GGGATGCTCG GTTATGTCGC
19201     GGGCGTTCAG AGGAAGGAGA TCCGACAGGG CATCGCATGT GTCAAGCACC
19251     AAAACATGAG CGGGAGTGAC ATCGGGGATG ATCATAAAGA GTATTTCTCC
19301     GGCGAAGCCG CGCTGAAGGC CGCCGGCAAA GACAACACTA TGAATCAATT
           XmaI
          ~~~~~~~
19351     CTGACCCGGG TGAGTAATTC TGATATTAGA GGGAGCATTA ATGTGTTGTT
19401     GTGATGTGGT TTATATGGGG AAATTAAATA AATGATGTAT GTACCTCTTG
19451     CCTATGTAGG TTTGTGTGTT TTGTTTTGTT GTCTAGCTTT GGTTATTAAG
19501     TAGTAGGGAC GTTCGTTCGT GTCTCAAAAA AAGGGGTACT ACCACTCTGT
19551     AGTGTATATG GATGCTGGAA ATCAATGTGT TTTGTATTTG TTCACCTCCA
19601     TTGTTGAATT CAATGTCAAA TGTGTTTTGC GTTGGTTATG TGTAAAATTA
19651     CTATCTTTCT CGTCCGATGA TCAAAGTTTT AAGCAACAAA ACCAAGGGTG
19701     AAATTTAAAC TGTGCTTTGT TGAAGATTCT TTTATCATAT TGAAAATCAA
19751     ATTACTAGCA GCAGATTTTA CCTAGCATGA AATTTTATCA ACAGTACAGC
19801     ACTCACTAAC CAAGTTCCAA ACTAAGATGC GCCATTAACA TCAGCCAATA
19851     GGCATTTTCA GCAAGCTCGA GTCACGTAGT GCCTCAGCGT TTAAACGTAC
19901     GTAGTGTTTA TCTTTGTTGC TTTTCTGAAC AATTTATTTA CTATGTAAAT
19951     ATATTATCAA TGTTTAATCT ATTTTAATTT GCACATGAAT TTTCATTTTA
20001     TTTTTACTTT ACAAAACAAA TAAATATATA TGCAAAAAAA TTTACAAACG
20051     ATGCACGGGT TACAAACTAA TTTCATTAAA TGCTAATGCA GATTTTGTGA
20101     AGTAAAACTC CAATTATGAT GAAAAATACC ACCAACACCA CCTGCGAAAC
20151     TGTATCCCAA CTGTCCTTAA TAAAAATGTT AAAAAGTATA TTATTCTCAT
20201     TTGTCTGTCA TAATTTATGT ACCCCACTTT AATTTTTCTG ATGTACTAAA
20251     CCGAGGGCAA ACTGAAACCT GTTCCTCATG CAAAGCCCCT ACTCACCATG
20301     TATCATGTAC GTGTCATCAC CCAACAACTC CACTTTTGCT ATATAACAAC
20351     ACCCCCGTCA CACTCTCCCT CTCTAACACA CACCCCACTA ACAATTCCTT
20401     CACTTGCAGC ACTGTTGCAT CATCATCTTC ATTGCAAAAC CCTAAACTTC
```

FIG. 26H DNA sequence of pMBXS994 (Cont'd)

```
20451    ACCTTCAACC GCGGCCGCTT CGAAAAAATG GCTTCTATGA TATCCTCTTC
20501    CGCTGTGACA ACAGTCAGCC GTGCCTCTAG GGGGCAATCC GCCGCAGTGG
20551    CTCCATTCGG CGGCCTCAAA TCCATGACTG GATTCCCAGT GAAGAAGGTC
20601    AACACTGACA TTACTTCCAT TACAAGCAAT GGTGGAAGAG TAAAGTGCAT
20651    GCAGGTGTGG CCTCCAATTG GAAAGAAGAA GTTTGAGACT CTTTCCTATT
20701    TGCCACCATT GACGAGAGAT TCTAGAGTCA CCGAGCAAGC CACAACGACA
20751    GATGAACTCG CTTTTACTAG GCCATATGGT GAACAGGAAA AGCAAATTCT
20801    TACAGCAGAA GCTGTTGAGT TTTTGACCGA GTTGGTTACT CACTTTACAC
20851    CTCAAAGAAA CAAGTTACTC GCAGCACGTA TCCAGCAGCA ACAAGACATA
20901    GATAATGGTA CACTTCCAGA TTTCATTTCG GAGACTGCAT CTATTCGAGA
20951    TGCCGATTGG AAAATCAGGG GTATCCCCGC AGATTTAGAA GATAGGAGAG
21001    TTGAAATAAC CGGACCTGTA GAAAGAAAAA TGGTCATCAA CGCTCTAAAC
21051    GCCAACGTCA AAGTGTTTAT GGCTGATTTT GAGGACTCGC TAGCACCTGA
21101    TTGGAACAAG GTGATAGATG GCCAGATCAA TTTGAGAGAT GCTGTCAATG
21151    GGACAATCTC CTATACTAAT GAGGCTGGAA AGATTTATCA ACTCAAACCT
21201    AATCCGGCAG TGCTGATTTG TAGGGTTCGT GGATTACACC TGCCTGAAAA
21251    GCATGTTACG TGGCGTGGGG AAGCAATTCC TGGCAGCCTT TTTGACTTCG
21301    CTCTTTACTT TTTCCATAAC TACCAGGCGC TGTTGGCTAA GGGGTCAGGT
21351    CCATATTTCT ATCTTCCGAA AACTCAAAGT TGGCAAGAAG CTGCCTGGTG
21401    GTCTGAGGTG TTCTCCTATG CAGAGGATCG TTTCAATTTA CCACGAGGTA
21451    CGATCAAAGC AACTCTGTTA ATTGAGACAC TCCCGGCTGT GTTTCAAATG
21501    GACGAGATAC TACACGCTCT CAGGGACCAC ATTGTTGGTC TTAATTGCGG
21551    AAGATGGGAC TATATCTTCT CCTACATCAA GACTCTAAAG AACTACCCGG
21601    ATAGAGTTCT GCCTGACCGT CAAGCTGTTA CTATGGATAA ACCATTTCTT
21651    AATGCTTACT CTAGACTCTT GATTAAGACC TGTCATAAGC GTGGAGCCTT
21701    CGCAATGGGC GGAATGGCCG CTTTTATCCC GTCAAAAGAT GAAGAGCACA
21751    ACAATCAGGT TTTGAACAAG GTAAAAGCGG ATAAATCTCT TGAAGCCAAT
21801    AATGGGCATG ATGGCACTTG GATTGCTCAT CCAGGTCTAG CTGATACAGC
21851    GATGGCTGTA TTCAACGACA TCTTGGGTTC AAGAAAGAAT CAACTTGAAG
21901    TGATGAGAGA GCAAGACGCG CCAATAACAG CTGATCAACT TTTGGCGCCA
21951    TGCGATGGTG AACGAACGGA AGAAGGTATG AGAGCCAATA TCCGAGTTGC
22001    TGTGCAGTAC ATAGAGGCTT GGATTTCAGG AAACGGGTGT GTCCCCATTT
22051    ATGGACTCAT GGAAGATGCG GCTACTGCTG AAATTAGCAG GACCTCTATT
22101    TGGCAGTGGA TACATCATCA AAAGACATTA AGCAACGGAA AACCTGTTAC
22151    TAAGGCCCTC TTCAGGCAGA TGCTTGGGGA AGAGATGAAA GTAATTGCGA
22201    GTGAGTTGGG AGAAGAGAGA TTTTCTCAGG GTAGATTTGA TGACGCAGCG
22251    AGGTTGATGG AGCAGATCAC CACCAGTGAC GAGCTCATAG ATTTCTTAAC
22301    GTTGCCTGGA TACCGACTAC TTGCTTGAAT TTAAATGCGG CCGCTGAGTA
22351    ATTCTGATAT TAGAGGGAGC ATTAATGTGT TGTTGTGATG TGGTTTATAT
22401    GGGGAAATTA AATAAATGAT GTATGTACCT CTTGCCTATG TAGGTTTGTG
22451    TGTTTTGTTT TGTTGTCTAG CTTTGGTTAT TAAGTAGTAG GGACGTTCGT
22501    TCGTGTCTCA AAAAAAGGGG TACTACCACT CTGTAGTGTA TATGGATGCT
22551    GGAAATCAAT GTGTTTTGTA TTTGTTCACC TCCATTGTTG AATTCAATGT
22601    CAAATGTGTT TTGCGTTGGT TATGTGTAAA ATTACTATCT TTCTCGTCCG
22651    ATGATCAAAG TTTTAAGCAA CAAAACCAAG GGTGAAATTT AAACTGTGCT
22701    TTGTTGAAGA TTCTTTTATC ATATTGAAAA TCAAATTACT AGCAGCAGAT
22751    TTTACCTAGC ATGAAATTTT ATCAACAGTA CAGCACTCAC TAACCAAGTT
22801    CCAAACTAAG ATGCGCCATT AACATCAGCC AATAGGCATT TTCAGCAAAG
22851    CAAATGAATT CGTAATCATG TCATAGCTGT TTCCTGTGTG AAATTGTTAT
22901    CCGCTCACAA TTCCACACAA CATACGAGCC GGAAGCATAA AGTGTAAAGC
22951    CTGGGGTGCC TAATGAGTGA GCTAACTCAC ATTAATTGCG TTGCGCTCAC
23001    TGCCCGCTTT CCAGTCGGGA AACCTGTCGT GCCAGCTGCA TTAATGAATC
23051    GGCCAACGCG CGGGGAGAGG CGGTTTGCGT ATTGGCTAGA GCAGCTTGCC
23101    AACATGGTGG AGCACGACAC TCTCGTCTAC TCCAAGAATA TCAAAGATAC
23151    AGTCTCAGAA GACCAAAGGG CTATTGAGAC TTTTCAACAA AGGGTAATAT
23201    CGGGAAACCT CCTCGGATTC CATTGCCCAG CTATCTGTCA CTTCATCAAA
23251    AGGACAGTAG AAAAGGAAGG TGGCACCTAC AAATGCCATC ATTGCGATAA
23301    AGGAAAGGCT ATCGTTCAAG ATGCCTCTGC CGACAGTGGT CCCAAAGATG
23351    GACCCCCACC CACGAGGAGC ATCGTGGAAA AAGAAGACGT TCCAACCACG
```

FIG. 26I DNA sequence of pMBXS994 (Cont'd)

```
23401  TCTTCAAAGC AAGTGGATTG ATGTGAACAT GGTGGAGCAC GACACTCTCG
23451  TCTACTCCAA GAATATCAAA GATACAGTCT CAGAAGACCA AAGGGCTATT
23501  GAGACTTTTC AACAAAGGGT AATATCGGGA AACCTCCTCG GATTCCATTG
23551  CCCAGCTATC TGTCACTTCA TCAAAAGGAC AGTAGAAAAG GAAGGTGGCA
23601  CCTACAAATG CCATCATTGC GATAAAGGAA AGGCTATCGT TCAAGATGCC
23651  TCTGCCGACA GTGGTCCCAA AGATGGACCC CCACCCACGA GGAGCATCGT
23701  GGAAAAAGAA GACGTTCCAA CCACGTCTTC AAAGCAAGTG GATTGATGTG
23751  ATATCTCCAC TGACGTAAGG GATGACGCAC AATCCCACTA TCCTTCGCAA
23801  GACCCTTCCT CTATATAAGG AAGTTCATTT CATTTGGAGA GGACACGCTG
23851  AAATCACCAG TCTCTCTCTA CAAATCTATC TCTCTCGAGA AAATGGTGAG
23901  CAAGGGCGAG GAGCTGTTCA CCGGGGTGGT GCCCATCCTG GTCGAGCTGG
23951  ACGGCGACGT AAACGGCCAC AAGTTCAGCG TGTCCGGCGA GGGCGAGGGC
24001  GATGCCACCT ACGGCAAGCT GACCCTGAAG TTCATCTGCA CCACCGGCAA
24051  GCTGCCCGTG CCCTGGCCCA CCCTCGTGAC CACCTTCACC TACGGCGTGC
24101  AGTGCTTCAG CCGCTACCCC GACCACATGA AGCAGCACGA CTTCTTCAAG
24151  TCCGCCATGC CCGAAGGCTA CGTCCAGGAG CGCACCATCT TCTTCAAGGA
24201  CGACGGCAAC TACAAGACCC GCGCCGAGGT GAAGTTCGAG GGCGACACCC
24251  TGGTGAACCG CATCGAGCTG AAGGGCATCG ACTTCAAGGA GGACGGCAAC
24301  ATCCTGGGGC ACAAGCTGGA GTACAACTAC AACAGCCACA ACGTCTATAT
24351  CATGGCCGAC AAGCAGAAGA ACGGCATCAA GGTGAACTTC AAGATCCGCC
24401  ACAACATCGA GGACGGCAGC GTGCAGCTCG CCGACCACTA CCAGCAGAAC
24451  ACCCCCATCG GCGACGGCCC CGTGCTGCTG CCCGACAACC ACTACCTGAG
24501  CACCCAGTCC GCCCTGAGCA AAGACCCCAA CGAGAAGCGC GATCACATGG
24551  TCCTGCTGGA GTTCGTGACC GCCGCCGGGA TCACTCACGG CATGGACGAG
24601  CTGTACAAGT AAGAGCTCGG TCACCTGTCC AACAGTCTCA GGGTTAATGT
24651  CTATGTATCT TAAATAATGT TGTCGGCGAT CGTTCAAACA TTTGGCAATA
24701  AAGTTTCTTA AGATTGAATC CTGTTGCCGG TCTTGCGATG ATTATCATAT
24751  AATTTCTGTT GAATTACGTT AAGCATGTAA TAATTAACAT GTAATGCATG
24801  ACGTTATTTA TGAGATGGGT TTTTATGATT AGAGTCCCGC AATTATACAT
24851  TTAATACGCG ATAGAAAACA AAATATAGCG CGCAAACTAG GATAAATTAT
24901  CGCGCGCGGT GTCATCTATG TTACTAGATC GGGAATTAAA CTATCAGTGT
24951  TTGACAGGAT ATATTGGCGG GTAAACCTAA GAGAAAAGAG CGTTTATTAG
25001  AATAATCGGA TATTTAAAAG GGCGTGAAAA GGTTTATCCG TTCGTCCATT
25051  TGTATGTGCA TGCCAACCAC AGGGTTCCCC TCGGGATCAA AGTACTTTGA
25101  TCCAACCCCT CCGCTGCTAT AGTGCAGTCG GCTTCTGACG TTCAGTGCAG
25151  CCGTCTTCTG AAAACGACAT GTCGCACAAG TCCTAAGTTA CGCGACAGGC
25201  TGCCGCCCTG CCCTTTTCCT GGCGTTTTCT TGTCGCGTGT TTTAGTCGCA
25251  TAAAGTAGAA TACTTGCGAC TAGAACCGGA GACATTACGC CATGAACAAG
25301  AGCGCCGCCG CTGGCCTGCT GGGCTATGCC CGCGTCAGCA CCGACGACCA
25351  GGACTTGACC AACCAACGGG CCGAACTGCA CGCGGCCGGC TGCACCAAGC
25401  TGTTTTCCGA GAAGATCACC GGCACCAGGC GCGACCGCCC GGAGCTGGCC
25451  AGGATGCTTG ACCACCTACG CCCTGGCGAC GTTGTGACAG TGACCAGGCT
25501  AGACCGCCTG GCCCGCAGCA CCCGCGACCT ACTGGACATT GCCGAGCGCA
25551  TCCAGGAGGC CGGCGCGGGC CTGCGTAGCC TGGCAGAGCC GTGGGCCGAC
25601  ACCACCACGC CGGCCGGCCG CATGGTGTTG ACCGTGTTCG CCGGCATTGC
25651  CGAGTTCGAG CGTTCCCTAA TCATCGACCG CACCCGGAGC GGGCGCGAGG
25701  CCGCCAAGGC CCGAGGCGTG AAGTTTGGCC CCCGCCCTAC CCTCACCCCG
25751  GCACAGATCG CGCACGCCCG CGAGCTGATC GACCAGGAAG GCCGCACCGT
25801  GAAAGAGGCG GCTGCACTGC TTGGCGTGCA TCGCTCGACC CTGTACCGCG
25851  CACTTGAGCG CAGCGAGGAA GTGACGCCCA CCGAGGCCAG GCGGCGCGGT
25901  GCCTTCCGTG AGGACGCATT GACCGAGGCC GACGCCCTGG CGGCCGCCGA
25951  GAATGAACGC CAAGAGGAAC AAGCATGAAA CCGCACCAGG ACGGCCAGGA
26001  CGAACCGTTT TTCATTACCG AAGAGATCGA GGCGGAGATG ATCGCGGCCG
26051  GGTACGTGTT CGAGCCGCCC GCGCACGTCT CAACCGTGCG GCTGCATGAA
26101  ATCCTGGCCG GTTTGTCTGA TGCCAAGCTG GCGGCCTGGC CGGCCAGCTT
26151  GGCCGCTGAA GAAACCGAGC GCCGCCGTCT AAAAAGGTGA TGTGTATTTG
26201  AGTAAAACAG CTTGCGTCAT GCGGTCGCTG CGTATATGAT GCGATGAGTA
26251  AATAAACAAA TACGCAAGGG GAACGCATGA AGGTTATCGC TGTACTTAAC
26301  CAGAAAGGCG GGTCAGGCAA GACGACCATC GCAACCCATC TAGCCCGCGC
```

FIG. 26J DNA sequence of pMBXS994 (Cont'd)

```
26351     CCTGCAACTC GCCGGGGCCG ATGTTCTGTT AGTCGATTCC GATCCCCAGG
26401     GCAGTGCCCG CGATTGGGCG GCCGTGCGGG AAGATCAACC GCTAACCGTT
26451     GTCGGCATCG ACCGCCCGAC GATTGACCGC GACGTGAAGG CCATCGGCCG
26501     GCGCGACTTC GTAGTGATCG ACGGAGCGCC CCAGGCGGCG GACTTGGCTG
26551     TGTCCGCGAT CAAGGCAGCC GACTTCGTGC TGATTCCGGT GCAGCCAAGC
26601     CCTTACGACA TATGGGCCAC CGCCGACCTG GTGGAGCTGG TTAAGCAGCG
26651     CATTGAGGTC ACGGATGGAA GGCTACAAGC GGCCTTTGTC GTGTCGCGGG
26701     CGATCAAAGG CACGCGCATC GGCGGTGAGG TTGCCGAGGC GCTGGCCGGG
26751     TACGAGCTGC CCATTCTTGA GTCCCGTATC ACGCAGCGCG TGAGCTACCC
26801     AGGCACTGCC GCCGCCGGCA CAACCGTTCT TGAATCAGAA CCCGAGGGCG
26851     ACGCTGCCCG CGAGGTCCAG GCGCTGGCCG CTGAAATTAA ATCAAAACTC
26901     ATTTGAGTTA ATGAGGTAAA GAGAAAATGA GCAAAAGCAC AAACACGCTA
26951     AGTGCCGGCC GTCCGAGCGC ACGCAGCAGC AAGGCTGCAA CGTTGGCCAG
27001     CCTGGCAGAC ACGCCAGCCA TGAAGCGGGT CAACTTTCAG TTGCCGGCGG
27051     AGGATCACAC CAAGCTGAAG ATGTACGCGG TACGCCAAGG CAAGACCATT
27101     ACCGAGCTGC TATCTGAATA CATCGCGCAG CTACCAGAGT AAATGAGCAA
27151     ATGAATAAAT GAGTAGATGA ATTTTAGCGG CTAAAGGAGG CGGCATGGAA
27201     AATCAAGAAC AACCAGGCAC CGACGCCGTG GAATGCCCCA TGTGTGGAGG
27251     AACGGGCGGT TGGCCAGGCG TAAGCGGCTG GGTTGCCTGC CGGCCCTGCA
27301     ATGGCACTGG AACCCCCAAG CCCGAGGAAT CGGCGTGAGC GGTCGCAAAC
27351     CATCCGGCCC GGTACAAATC GGCGCGGCGC TGGGTGATGA CCTGGTGGAG
27401     AAGTTGAAGG CCGCGCAGGC CGCCCAGCGG CAACGCATCG AGGCAGAAGC
27451     ACGCCCCGGT GAATCGTGGC AAGCGGCCGC TGATCGAATC CGCAAAGAAT
27501     CCCGGCAACC GCCGGCAGCC GGTGCGCCGT CGATTAGGAA GCCGCCCAAG
27551     GGCGACGAGC AACCAGATTT TTTCGTTCCG ATGCTCTATG ACGTGGGCAC
27601     CCGCGATAGT CGCAGCATCA TGGACGTGGC CGTTTTCCGT CTGTCGAAGC
27651     GTGACCGACG AGCTGGCGAG GTGATCCGCT ACGAGCTTCC AGACGGGCAC
27701     GTAGAGGTTT CCGCAGGGCC GGCCGGCATG GCCAGTGTGT GGGATTACGA
27751     CCTGGTACTG ATGGCGGTTT CCCATCTAAC CGAATCCATG AACCGATACC
27801     GGGAAGGGAA GGGAGACAAG CCCGGCCGCG TGTTCCGTCC ACACGTTGCG
27851     GACGTACTCA AGTTCTGCCG GCGAGCCGAT GGCGGAAAGC AGAAAGACGA
27901     CCTGGTAGAA ACCTGCATTC GGTTAAACAC CACGCACGTT GCCATGCAGC
27951     GTACGAAGAA GGCCAAGAAC GGCCGCCTGG TGACGGTATC CGAGGGTGAA
28001     GCCTTGATTA GCCGCTACAA GATCGTAAAG AGCGAAACCG GGCGGCCGGA
28051     GTACATCGAG ATCGAGCTAG CTGATTGGAT GTACCGCGAG ATCACAGAAG
28101     GCAAGAACCC GGACGTGCTG ACGGTTCACC CCGATTACTT TTTGATCGAT
28151     CCCGGCATCG GCCGTTTTCT CTACCGCCTG GCACGCCGCG CCGCAGGCAA
28201     GGCAGAAGCC AGATGGTTGT TCAAGACGAT CTACGAACGC AGTGGCAGCG
28251     CCGGAGAGTT CAAGAAGTTC TGTTTCACCG TGCGCAAGCT GATCGGGTCA
28301     AATGACCTGC CGGAGTACGA TTTGAAGGAG GAGGCGGGGC AGGCTGGCCC
28351     GATCCTAGTC ATGCGCTACC GCAACCTGAT CGAGGGCGAA GCATCCGCCG
28401     GTTCCTAATG TACGGAGCAG ATGCTAGGGC AAATTGCCCT AGCAGGGGAA
28451     AAAGGTCGAA AAGGTCTCTT TCCTGTGGAT AGCACGTACA TTGGGAACCC
28501     AAAGCCGTAC ATTGGGAACC GGAACCCGTA CATTGGGAAC CCAAAGCCGT
28551     ACATTGGGAA CCGGTCACAC ATGTAAGTGA CTGATATAAA AGAGAAAAAA
28601     GGCGATTTTT CCGCCTAAAA CTCTTTAAAA CTTATTAAAA CTCTTAAAAC
28651     CCGCCTGGCC TGTGCATAAC TGTCTGGCCA GCGCACAGCC GAAGAGCTGC
28701     AAAAAGCGCC TACCCTTCGG TCGCTGCGCT CCCTACGCCC CGCCGCTTCG
28751     CGTCGGCCTA TCGCGGCCGC TGGCCGCTCA AAAATGGCTG GCCTACGGCC
28801     AGGCAATCTA CCAGGGCGCG GACAAGCCGC GCCGTCGCCA CTCGACCGCC
28851     GGCGCCCACA TCAAGGCACC CTGCCTCGCG CGTTTCGGTG ATGACGGTGA
28901     AAACCTCTGA CACATGCAGC TCCCGGAGAC GGTCACAGCT TGTCTGTAAG
28951     CGGATGCCGG GAGCAGACAA GCCCGTCAGG GCGCGTCAGC GGGTGTTGGC
29001     GGGTGTCGGG GCGCAGCCAT GACCCAGTCA CGTAGCGATA GCGGAGTGTA
29051     TACTGGCTTA ACTATGCGGC ATCAGAGCAG ATTGTACTGA GAGTGCACCA
29101     TATGCGGTGT GAAATACCGC ACAGATGCGT AAGGAGAAAA TACCGCATCA
29151     GGCGCTCTTC CGCTTCCTCG CTCACTGACT CGCTGCGCTC GGTCGTTCGG
29201     CTGCGGCGAG CGGTATCAGC TCACTCAAAG GCGGTAATAC GGTTATCCAC
29251     AGAATCAGGG GATAACGCAG GAAAGAACAT GTGAGCAAAA GGCCAGCAAA
```

FIG. 26K DNA sequence of pMBXS994 (Cont'd)

```
29301  AGGCCAGGAA CCGTAAAAAG GCCGCGTTGC TGGCGTTTTT CCATAGGCTC
29351  CGCCCCCCTG ACGAGCATCA CAAAAATCGA CGCTCAAGTC AGAGGTGGCG
29401  AAACCCGACA GGACTATAAA GATACCAGGC GTTTCCCCCT GGAAGCTCCC
29451  TCGTGCGCTC TCCTGTTCCG ACCCTGCCGC TTACCGGATA CCTGTCCGCC
29501  TTTCTCCCTT CGGGAAGCGT GGCGCTTTCT CATAGCTCAC GCTGTAGGTA
29551  TCTCAGTTCG GTGTAGGTCG TTCGCTCCAA GCTGGGCTGT GTGCACGAAC
29601  CCCCCGTTCA GCCCGACCGC TGCGCCTTAT CCGGTAACTA TCGTCTTGAG
29651  TCCAACCCGG TAAGACACGA CTTATCGCCA CTGGCAGCAG CCACTGGTAA
29701  CAGGATTAGC AGAGCGAGGT ATGTAGGCGG TGCTACAGAG TTCTTGAAGT
29751  GGTGGCCTAA CTACGGCTAC ACTAGAAGGA CAGTATTTGG TATCTGCGCT
29801  CTGCTGAAGC CAGTTACCTT CGGAAAAAGA GTTGGTAGCT CTTGATCCGG
29851  CAAACAAACC ACCGCTGGTA GCGGTGGTTT TTTTGTTTGC AAGCAGCAGA
29901  TTACGCGCAG AAAAAAAGGA TCTCAAGAAG ATCCTTTGAT CTTTTCTACG
29951  GGGTCTGACG CTCAGTGGAA CGAAAACTCA CGTTAAGGGA TTTTGGTCAT
30001  GCATTCTAGG TACTAAAACA ATTCATCCAG TAAAATATAA TATTTTATTT
30051  TCTCCCAATC AGGCTTGATC CCCAGTAAGT CAAAAAATAG CTCGACATAC
30101  TGTTCTTCCC CGATATCCTC CCTGATCGAC CGGACGCAGA AGGCAATGTC
30151  ATACCACTTG TCCGCCCTGC CGCTTCTCCC AAGATCAATA AAGCCACTTA
30201  CTTTGCCATC TTTCACAAAG ATGTTGCTGT CTCCCAGGTC GCCGTGGGAA
30251  AAGACAAGTT CCTCTTCGGG CTTTTCCGTC TTTAAAAAAT CATACAGCTC
30301  GCGCGGATCT TTAAATGGAG TGTCTTCTTC CCAGTTTTCG CAATCCACAT
30351  CGGCCAGATC GTTATTCAGT AAGTAATCCA ATTCGGCTAA GCGGCTGTCT
30401  AAGCTATTCG TATAGGGACA ATCCGATATG TCGATGGAGT GAAAGAGCCT
30451  GATGCACTCC GCATACAGCT CGATAATCTT TTCAGGGCTT TGTTCATCTT
30501  CATACTCTTC CGAGCAAAGG ACGCCATCGG CCTCACTCAT GAGCAGATTG
30551  CTCCAGCCAT CATGCCGTTC AAAGTGCAGG ACCTTTGGAA CAGGCAGCTT
30601  TCCTTCCAGC CATAGCATCA TGTCCTTTTC CCGTTCCACA TCATAGGTGG
30651  TCCCTTTATA CCGGCTGTCC GTCATTTTTA AATATAGGTT TTCATTTTCT
30701  CCCACCAGCT TATATACCTT AGCAGGAGAC ATTCCTTCCG TATCTTTTAC
30751  GCAGCGGTAT TTTTCGATCA GTTTTTTCAA TTCCGGTGAT ATTCTCATTT
30801  TAGCCATTTA TTATTTCCTT CCTCTTTTCT ACAGTATTTA AAGATACCCC
30851  AAGAAGCTAA TTATAACAAG ACGAACTCCA ATTCACTGTT CCTTGCATTC
30901  TAAAACCTTA AATACCAGAA AACAGCTTTT TCAAAGTTGT TTTCAAAGTT
30951  GGCGTATAAC ATAGTATCGA CGGAGCCGAT TTTGAAACCG CGGTGATCAC
31001  AGGCAGCAAC GCTCTGTCAT CGTTACAATC AACATGCTAC CCTCCGCGAG
31051  ATCATCCGTG TTTCAAACCC GGCAGCTTAG TTGCCGTTCT TCCGAATAGC
31101  ATCGGTAACA TGAGCAAAGT CTGCCGCCTT ACAACGGCTC TCCCGCTGAC
31151  GCCGTCCCGG ACTGATGGGC TGCCTGTATC GAGTGGTGAT TTTGTGCCGA
31201  GCTGCCGGTC GGGGAGCTGT TGGCTGGCTG GTGGCAGGAT ATATTGTGGT
31251  GTAAACAAAT TGACGCTTAG ACAACTTAAT AACACATTGC GGACGTTTTT
31301  AATGTACTGA ATTAACGCCG AATTAATT
```

PLANTS WITH ENHANCED YIELD AND METHODS OF CONSTRUCTION

CROSS-REFERENCE TO RELATED APPLICATIONS

This application is a continuation of U.S. application Ser. No. 15/565,086, filed Oct. 6, 2017, which is the U.S. National Stage of International Application No. PCT/US2016/026767, filed Apr. 8, 2016, which claims the benefit of U.S. Provisional Application Nos. 62/144,727, filed on Apr. 8, 2015, 62/145,757, filed on Apr. 10, 2015 and 62/190,281, filed on Jul. 9, 2015, all of which are hereby incorporated by reference.

GOVERNMENT SUPPORT

This invention was made in part with government support under Grant Number DE-AR0000201 from the United States DOE, ARPA-e PETRO program. The government has certain rights in this invention.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "YTEN-60322US4-Sequence-Listing_ST25," created Sep. 24, 2021, file size of 241,666 bytes, is hereby incorporated by reference.

BACKGROUND OF THE INVENTION

The world faces a major challenge in the next 35 years to meet the increased demands for food production to feed a growing global population which is expected to reach 9 billion by the year 2050 (*Food and Agriculture Organization of the United Nations* (2009), *How to Feed the World in* 2050, (website: www.fao.org/fileadmin/templates/wsfs/docs/expert_paper/How_to_Feed_the_World_in_2050.pdf). The added population in combination with increased demand for improved diet, in particular increased animal protein, linked to improving living standards in developing countries requires food output to increase by up to 70% in this time period. The added population and concomitant land use changes for new living space and infrastructure, alternative uses for crops such as biofuels and biobased products and changing weather patterns makes achieving this a very challenging goal. Crop productivity is limited by numerous factors, one factor being the relative inefficiency of photochemical conversion of light energy to fixed carbon during photosynthesis and another the loss of fixed carbon by photorespiration and/or other metabolic pathways having enzymes catalyzing decarboxylation reactions. The invention can be applied to any crop however it is particularly useful for major agricultural crops used for animal feed or for direct human consumption. These crops including corn, wheat, rice, barley, oats, millet, sorghum, cassava, sugar beets, potatoes and oilseeds such as Brassica, soybean, sunflower, safflower, camelina, that are primarily grown and harvested for seed production. Current crop production relies primarily on crop species that were bred by conventional means for improved seed yield which was improved by continuous incremental changes over many years. Over this period any step changes in yield were typically enabled by new technologies such as the advent of nitrogen fertilizers, dwarf wheat varieties, dwarf rice, hybrids such as corn with "hybrid vigor', and more recently improved agronomic practices such as increased density of seed planting enabled largely by transgenic input traits including herbicide resistance and pesticide resistance. Thus, there is a need for transgenic plants with enhanced carbon capture systems to improve crop yield and/or seed yield. Given the inherent complexity of plant metabolism and the fact that plants have evolved to balance inputs with growth and reproduction, it is highly likely that achieving step changes in crop yield will require new technology approaches. One such new technology with the potential to enable step changes in crop yield is based on the science of metabolic engineering.

Over the last twenty years metabolic engineering primarily of microbial systems to improve and/or introduce entirely new metabolic pathways to increase carbon utilization or make entirely new products based on multiple enzymatic steps has advanced enormously. This technology has already demonstrated some success in plants. There are multiple known existing prokaryotic carbon fixation pathways (Fuchs, G., *Alternative Pathways of Carbon Dioxide Fixation: Insights into the Early Evolution of Life*? Annual Review of Microbiology, 2011, 65, 631; Bar-Even, A., E. Noor, and R. Milo, *A survey of carbon fixation pathways through a quantitative lens*. J Exp Bot, 2012, 63, 2325) as well as synthetic pathways based primarily on prokaryotic enzymes (Mainguet, S. E., L. S. Gronenberg, S. S. Wong, and J. C. Liao, *A reverse glyoxylate shunt to build a non-native route from C4 to C2 in Escherichia coli*. Metab Eng, 2013, 19, 116; US 2014/0150135; WO2014210587, Bar-Even, A., E. Noor, N. E. Lewis, and R. Milo, *Design and analysis of synthetic carbon fixation pathways*. Proc Natl Acad Sci USA, 2010, 107, 8889) that may be applicable for supplementing or replacing the Calvin Benson cycle in land plants. It is however very uncertain that engineering of these novel carbon fixation pathways into land plants can be successfully accomplished as noted by Bar-Even, A., E. Noor, N. E. Lewis, and R. Milo, *Design and analysis of synthetic carbon fixation pathways*. Proc Natl Acad Sci USA, 2010, 107, 8889) in the abstract of their publication: "Although implementing such alternative cycles presents daunting challenges related to expression levels, activity, stability, localization, and regulation, we believe our findings suggest exciting avenues of exploration-". This is in part due to the extreme environments in which the microbes having these pathways exist such that the microbial enzymes available may not function in plants or function well within the temperature range at which plants can be grown. Other challenging factors include the tightly controlled balance of metabolic intermediates, the availability of enzyme cofactors such as the types and levels of redox cofactors and energy in the form of ATP and subcellular compartmentation in plant cells and tissues all add additional complexity. Furthermore, the normal development of plants from seed to mature plant to seed production and senescence and the shifting flow of plant metabolism in different plant tissues represents a further challenge to successfully using microbial carbon fixation systems to enhance crop yield or the yield of specific crop targets such as seed in particular.

SUMMARY OF THE INVENTION

The present disclosure relates to methods of using novel metabolic pathways having enzymes catalyzing carboxylation reactions and/or enzymes using NADPH or NADH as a cofactor to enhance the yield of desirable crop traits including increased biomass yield, increased seed yield, increased oil content in seed, increased protein content in seed, increased starch content in seed, or increased sucrose content in stalks or seed. These modifications can be combined with other traits including herbicide resistance, pest resistance, nitrogen use efficiency, heat tolerance, drought tolerance and water use efficiency or industrial traits such as polyhydroxyalkanoate polymers or modified oil compositions. The invention is particularly relevant to reducing economic costs to farmers and increasing food production.

Disclosed herein are transgenic plants and seeds of transgenic plants selected on the basis of having a higher yield in comparison with a corresponding plant that is not expressing the heterologous enzyme(s). The metabolic pathways and enzymatic steps, which are the subject of the disclosed invention are shown in FIGS. 1-2.

In a first embodiment of the disclosed invention, the transgenic plant comprises one or more transgenes encoding two, three, four, five, six, seven, eight or more enzymes selected from the group: an oxygen tolerant pyruvate oxidoreductase (Por); pyruvate carboxylase (Pyc); malate synthase (AceB), malate dehydrogenase (Mdh); malate thiokinase (SucC and SucD), malyl-CoA Lyase (Mcl) and isocitrate lyase (Icl) wherein the transgenic plant is selected on the basis of having a higher yield in comparison with a corresponding plant that is not expressing the heterologous enzyme(s).

In a second embodiment of the disclosed invention, the transgenic plant comprises one or more transgenes encoding an oxygen tolerant pyruvate oxidoreductase (Por) and a pyruvate carboxylase (Pyc) wherein the transgenic plant is selected on the basis of having a higher yield in comparison with a corresponding plant that is not expressing the heterologous enzyme(s).

In a third embodiment of the disclosed invention, the transgenic plant comprises two or more transgenes encoding an oxygen tolerant pyruvate oxidoreductase (Por), a pyruvate carboxylase (Pyc), and a malate synthase (AceB), wherein the transgenic plant is selected on the basis of having a higher yield in comparison with a corresponding plant that is not expressing the heterologous enzyme(s).

In a fourth embodiment of the disclosed invention, the transgenic plant comprises five or more transgenes encoding an oxygen tolerant pyruvate oxidoreductase (Por), a pyruvate carboxylase (Pyc), a malate synthase (AceB), malate thiokinase (SucC, SucD), and a malyl-CoA Lyase (Mcl), wherein the transgenic plant is selected on the basis of having a higher yield in comparison with a corresponding plant that is not expressing the heterologous enzyme(s).

In a fifth embodiment of the disclosed invention, the transgenic plant comprises six or more transgenes encoding an oxygen tolerant pyruvate oxidoreductase (Por), a pyruvate carboxylase (Pyc), a malate synthase (AceB), malate thiokinase (SucC, SucD), a malyl-CoA Lyase (Mcl), and a malate dehydrogenase (Mdh), wherein the transgenic plant is selected on the basis of having a higher yield in comparison with a corresponding plant that is not expressing the heterologous enzyme(s).

In a sixth embodiment of the disclosed invention, the transgenic plant comprises seven or more transgenes encoding an oxygen tolerant pyruvate oxidoreductase (Por), a pyruvate carboxylase (Pyc), a malate synthase (AceB), malate thiokinase (SucC, SucD), a Malyl-CoA Lyase (Mcl), a malate dehydrogenase (Mdh), and an isocitrate lyase (Icl), wherein the transgenic plant is selected on the basis of having a higher yield in comparison with a corresponding plant that is not expressing the heterologous enzyme(s).

In a seventh embodiment of the disclosed invention, the transgenic plant comprises two or more transgenes encoding an oxygen tolerant pyruvate oxidoreductase (Por), a malate synthase (AceB), and one or more transgenes encoding a pyruvate carboxylase (Pyc), malate thiokinase (SucC, SucD), a Malyl-CoA Lyase (Mcl), a malate dehydrogenase (Mdh), and an isocitrate lyase (Icl), wherein the transgenic plant is selected on the basis of having a higher yield in comparison with a corresponding plant that is not expressing the heterologous enzyme(s).

In an eighth embodiment of the disclosed invention, the transgenic plant of embodiments one through seven further comprises an additional one or more transgenes encoding one or more additional enzymes selected from the group: NADP-malate dehydrogenase (NADP-Mdh); fumarate hydratase (FumC); NADH-dependent fumarate reductase (FRDg); aconitase hydratase 1 (AcnA); ATP-citrate lyase A-1 (AclA-1); and ATP-citrate lyase subunit B2 (AclB-2), wherein the transgenic plant is selected on the basis of having a higher yield in comparison with a corresponding plant that is not expressing the heterologous enzyme(s).

In a ninth embodiment of the disclosed invention, the transgenic plant of embodiments one through seven further comprises an additional one or more transgenes encoding an NADP-malate dehydrogenase (NADP-Mdh) enzyme or the transgenes used in embodiments one through seven are expressed in a plant which has been modified through precise genome engineering to increase the expression of an existing plant gene encoding NADP-malate dehydrogenase (NADP-Mdh) enzyme activity.

In a tenth embodiment of the disclosed invention, the transgenic plant comprises one or more transgenes encoding an NADP-malate dehydrogenase (NADP-Mdh) enzyme or is a plant which has been modified through precise genome engineering to increase the expression of an existing plant gene encoding NADP-malate dehydrogenase (NADP-Mdh) enzyme activity wherein the transgenic plant or plant is selected on the basis of having a higher yield in comparison with a corresponding plant that is not expressing the heterologous enzyme(s).

In a first aspect of embodiments one through ten, the heterologous enzymes expressed from the transgenes are targeted to the plastids of the plant wherein the transgenic plant is selected on the basis of having a higher yield in comparison with a corresponding plant that is not expressing the heterologous enzyme(s).

In a second aspect of embodiments one through ten, the expression of the transgene(s) is under the control of one or more seed specific promoter(s) and the heterologous enzymes expressed from the transgenes are targeted to the plastids of the plant wherein the transgenic plant is selected on the basis of having a higher seed yield in comparison with a corresponding plant that is not expressing the heterologous enzyme(s).

In an aspect of embodiments one through ten including the first and second aspects, the transgenic plant is selected on the basis of having a yield increase of at least 5%, at least 10%, at least 15%, at least 20%, at least 25%, at least 30%, at least 35%, at least 40%, at least 60%, or at least 80%, at least 90%, at least 100% at least 120% or higher in comparison with a corresponding plant that is not expressing the heterologous enzyme(s).

In an aspect of embodiments one through ten including the first and second aspects, the transgenic plant is selected on the basis of having a seed yield increase at least 5%, at least 10%, at least 15%, at least 20%, at least 30%, at least 40%, at least 50% or higher in comparison with a corresponding plant that is not expressing the heterologous enzyme(s). In an embodiment, the transgenic plant has a seed oil content at least 1%, at least 3%, at least 5%, at least 10%, at least 15%, at least 20%, or at least 25% or higher than the oil content of a wild type plant of the same species.

In an additional embodiment of the invention, the transgenic plants of all of the previous embodiments and aspects include additional transgenes encoding a bicarbonate transporter localized to the chloroplast membrane to increase the level of bicarbonate and/or carbon dioxide available for use by carbon fixation enzymes within the disclosed metabolic pathways.

In an embodiment, a method of producing a transformed plant having enhanced yield comprises transforming a plant cell with the disclosed transgenes; growing a plant from the plant cell until the plant produces seed; and selecting seeds from a plant in which yield is enhanced in comparison with a corresponding plant that is not expressing the heterologous enzyme(s) is disclosed. In an additional embodiment describe methods and genetic constructs are described that minimize the number of transgenes, or transgenes plus modifications to the expression of genes present naturally in the plant, to achieve the yield change outcomes.

In an embodiment methods, metabolic pathways, enzymes, and crops for enhancing the yield of food crops to support the future needs of the growing world population are disclosed.

In an embodiment the transgenic plants of all of the previous embodiments and aspects include additional transgenes encoding input traits such as herbicide or pesticide tolerance, insect resistance, drought tolerance, stress tolerance, nitrogen and water use efficiency or additional enzymes or traits to further increase yield. For example, the disclosed constructs may also contain expression cassettes for one or more transgenes encoding enzymes or other proteins for enhancing the availability of substrates for the disclosed metabolic pathways and enzymes. These include for example enzymes capable of increasing photosynthesis, increasing carbon flow through the Calvin cycle in photosynthesis, and/or increasing regeneration of ribulose 1,5-bisphosphate, the acceptor molecule in the Calvin cycle that upon fixation of $CO_2$ is converted to two molecules of 3-phosphoglycerate, the key intermediate for acetyl-CoA production.

Candidate enzymes include but are not limited to sedoheptulose 1,7-bisphosphatase (SBPase, EC 3.1.3.37), fructose 1,6-bisphosphatase (FBPase, EC 3.1.3.11), a bi-functional enzyme encoding both SBPase and FBPase activities, transketolase (EC 2.2.1.1), and aldolase (EC 4.1.2.13). SBPase, transketolase, and aldolase activities have been shown to have an impact on the control of carbon fixed by the Calvin cycle (Raines, 2003, *Photosynthesis Research,* 75, 1-10) which could be attributed to an increase in ribulose 1,5-bisphosphate regenerative capacity. Such enzymes have been introduced into plants to enhance the flux of carbon to acetyl-CoA (U.S. Pat. Appl. Publ. (2012), US 2012/0060413), a key intermediate in the disclosed pathways (FIGS. 1-2, 12, 14, and 18). Vectors expressing transcription factors, such as those described in patent application WO 2014/100289, can be combined with the vectors described in the invention, including vectors pMBXS1022, pMBXS1023, pMBXS919, pMBXS1056, pMBXS1057, pMBXS1058, pMBXS1059 and pMBXS1060, to further enhance yield.

Transgenes encoding proteins involved in the transport of bicarbonate in cyanobacterial and algal systems can be added to increase the availability of $CO_2$ for the Calvin cycle and for the carboxylation enzymes present in the metabolic pathways disclosed herein. Suitable bicarbonate transporter genes can be obtained from cyanobacteria and algal species. A novel bicarbonate transporter from *Chlamydomonas reinhardtii* (CCP1) that significantly increases plant yield has recently been described (pending PCT Application No. PCT/US2014/072347, "Plants with enhanced photosynthesis and methods of manufacture thereof", incorporated herein by reference in its entirety, and in U.S. Provisional Patent Application No. 62/291,341, "Transgenic land plants comprising a bicarbonate transporter protein of an edible eukaryotic algae")) and would be particularly useful for the purposes of the disclosed invention. An example embodiment of a suitable bicarbonate transporter transgene is the bicarbonate transporter from *Chlamydomonas reinhardtii* (CCP1) of SEQ ID NO: 6 (NCBI Genbank NCBI Reference Sequence: XM_001692145.1, *Chlamydomonas reinhardtii* strain CC-503 cw92 mt+, available at website: www.ncbi.nlm.nih.gov/nuccore/XM_001692145.1) that encodes a protein of SEQ ID NO: 7 (Low-CO2-inducible chloroplast envelope protein, available at Source: website: www.uniprot.org/uniprot/A8IT08). SEQ ID NO: 6 is shown in FIG. 24; SEQ ID NO: 7 is shown in FIG. 25.

Other suitable examples of bicarbonate transporter genes are provided in TABLE 11 and TABLE 12, below.

The transgenic plants of embodiments 1-10 may have additional transgenes that provide resistance to one or more herbicides selected from, but not limited to, the following group: glyphosate, 2,4-D, 2,4-D choline, Liberty Link, Dicamba, glufosinate, mesotrione, isoxaflutole, tembotrione, pyroxasulfone, fluthiacet-methyl, atrazine, triazines, metolachlor, imazethapyr, fomesafen, metribuzin, and bicyclopyrone.

Vectors expressing genes encoding enzymes to metabolize glyoxylate in the plastid, including plastid targeted glyoxylate carboligase and/or plastid targeted tartronic semialdehyde reductase, can be combined with the vectors described in the invention to further enhance the efficiency of the yield traits disclosed in this invention. Glyoxylate is a key intermediate in the disclosed pathways (FIG. 1) as well as a key product in the disclosed minimum gene sets to increase seed yield (FIGS. 1, 14, and 18). Plastid targeted glyoxylate carboligase would convert glyoxylate to tartronic semialdehyde and plastid targeted tartronic semialdehyde reductase would convert tartronic semialdehyde to glycerate. Both of these metabolites may be more readily metabolized within the plastid. Previous researchers have shown that heterologous expression of plastid targeted glyoxylate dehydrogenase (also known as glyoxylate reductase), glyoxylate carboligase, and tartronic semialdehyde reductase to convert glyoxylate formed during photorespiration to glycerate increases photosynthesis and biomass production in *Arabidopsis thaliana* (Kebeish, R. 2007, 25, 593-599). Synthetic $CO_2$ fixation pathways to produce glyoxylate in plants have also been described (US 2014/0150135) and can be combined with the enzyme systems described herein Alternatively, endogenous plastid localized glyoxylate reductase activity can be increased through promoter replacement, precise genome engineering, or heterologous expression of the transgene to increase the conversion of glyoxylate to glycolate. Previous researchers have suggested that cytosolic and plastid localized glyoxylate reductases in *Arabidopsis* detoxify the glyoxylate and/or contribute to redox balance (Allan et al., 2009, Biochem. J., 423, 15-22).

In an embodiment, transgenic plants are generated which express the gene and enzyme combinations disclosed herein and are grown through a number of planting cycles to generate homozygous lines and screened for increased seed yield and/or increased seed oil content and those lines having significantly higher seed yield and/or increased seed oil content are selected.

In a method embodiments, metabolic pathways, enzymes and crops for enhancing the yield of food crops to support the future needs of the growing world population are disclosed.

The disclosed invention describes the in planta expression of combinations of transgenes encoding multiple enzymes in complex metabolic pathways resulting in step changes in crop yield. An exemplary seed crop was engineered to increase its yield. Unexpected step changes in yield have been obtained by engineering seed specific expression of novel combinations of enzymes to increase carbon fixation. Furthermore, the targeting of this yield increase to the harvested product of interest was demonstrated in the embodiment of the oilseed crop, where the product of interest is the seed.

Herein there is described the introduction of multiple transgenes, encoding novel metabolic pathways having enzymes catalyzing carboxylation reactions and/or enzymes using NADPH or NADH as a cofactor, into crops, screening the resulting transgenic crop lines produced for increased yield and selecting those transgenic lines having higher yield. In particular, by using plant promoters active in the developing seed and targeting each of the enzymes introduced by the transgenes to the plastids in the plant cells step changes had been demonstrated in seed yield and increased oil content. Although described and demonstrated with large numbers of transgenes, it will be obvious to those skilled in the art that it is routine experimentation to define the minimum gene sets essential to achieve the yield change outcomes demonstrated and provide the simplest system possible to facilitate regulatory approval for large scale planting.

BRIEF DESCRIPTION OF THE DRAWINGS

FIGS. 19A-J, collectively, represent the DNA sequence of pMBXS918 (SEQ ID NO: 1).

FIGS. 20A-J, collectively, represent the DNA sequence of pMBXS919 (SEQ ID NO: 2).

FIGS. 21A-M, collectively, represent the DNA Sequence of pMBXS1022 (SEQ ID NO: 3).

FIGS. 22A-K, collectively, represent the DNA Sequence of pMBXS1023 (SEQ ID NO: 4).

FIGS. 23A-J, collectively, represent the DNA sequence of pMBXS1024 (SEQ ID NO: 5).

FIG. 24 represents the DNA Sequence of the bicarbonate transporter gene of *Chlamydomonas reinhardtii* strain CC-503 cw92 mt+, NCBI Reference Sequence: XM_001692145.1 (SEQ ID NO: 6).

FIG. 25 represents Protein sequence of Low-0O2-inducible chloroplast envelope protein CCP1 of *Chlamydomonas reinhardtii* (SEQ ID NO: 7).

FIGS. 26A-K, collectively, describe the DNA sequence of pMBXS994 (SEQ ID NO: 8).

DETAILED DESCRIPTION OF THE INVENTION

Figure 1:
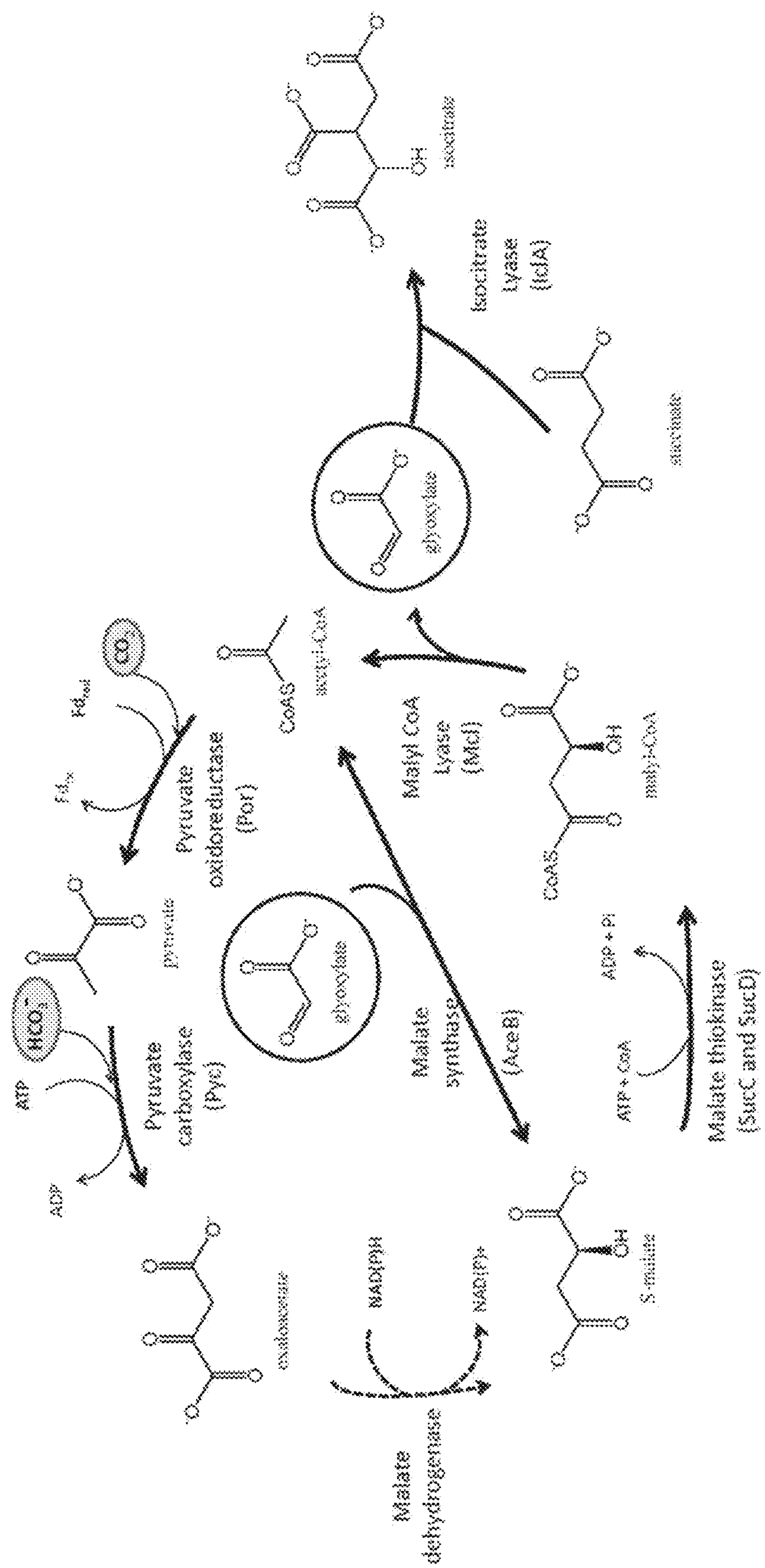
FIG. 1: Metabolic pathways and enzymes expressed from the genes encoded in the plant transformation vectors pMBXS994, pMBXS1022, pMBXS1023, and pMBXS1024. Plasmids pMBXS994 and pMBXS1022 contain seed specific expression cassettes for the genes por, pyc, sucC, sucD, mcl, iclA, and aceB. Plasmid pMBXS1023 contains seed specific expression cassettes for the genes por, pyc, sucC, sucD, mcl, and iclA. Plasmid pMBXS1024 contains seed specific expression cassettes for the genes pyc, sucC, sucD, mcl, iclA, and aceB. Abbreviations are as follows: por, pyruvate oxidoreductase; pyc, pyruvate carboxylase; aceB, malate synthase; sucC and sucD, malate thiokinase; mcl, malyl CoA lyase; iclA, isocitrate lyase. Endogenous plastid malate dehydrogenase activity is shown in dotted lines. Co-expression of *M. capsulatus* sucC and sucD in recombinant *E. coli* was recently shown to provide malate thiokinase activity (Mainguet et al., Metab Eng, 2013, 19, 116).

A description of example embodiments of the invention follows.

Definitions

Plants and Plant Species Suitable for Practicing the Disclosed Invention:

For the purposes of the invention, “plant” refers to all genera and species of higher and lower plants of the Plant Kingdom. The term includes the mature plants, seeds, shoots and seedlings, and parts, propagation material, plant organ tissue, protoplasts, callus and other cultures, for example cell cultures, derived from them, and all other species of groups of plant cells giving functional or structural units. Mature plants refers to plants at any developmental stage beyond the seedling. Seedling refers to a young, immatureplant at an early developmental stage.

“Plant” encompasses all annual and perennial monocotyledonous or dicotyledonous plants and includes by way of example, but not by limitation, those of the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Populus, Camelina, Beta, Solanum, and Carthamus.

Preferred plants are those from the following plant families: Amaranthaceae, Asteraceae, Brassicaceae, Carophyllaceae, Chenopodiaceae, Compositae, Cruciferae, Cucurbitaceae, Euphorbiaceae, Fabaceae, Labiatae, Leguminosae, Papilionoideae, Liliaceae, Linaceae, Malvaceae, Poaceae, Rosaceae, Rubiaceae, Saxifragaceae, Scrophulariaceae, Solanaceae, Sterculiaceae, Tetragoniaceae, Theaceae, Umbelliferae.

The invention can particularly be applied advantageously to monocotyledonous or dicotyledonous plant organisms. Preferred dicotyledonous plants are selected in particular from the dicotyledonous crop plants such as, for example, Asteraceae such as sunflower, tagetes or calendula and others; Compositae, especially the genus Lactuca, very particularly the species sativa (lettuce) and others; Cruciferae, particularly the genus Brassica, very particularly the species napus (oilseed rape), campestris (beet), oleracea cv Tastie (cabbage), oleracea cv Snowball Y (cauliflower) and oleracea cv Emperor (broccoli) and other cabbages; and the genus Arabidopsis, very particularly the species thaliana, and cress or canola and others; Cucurbitaceae such as melon, pumpkin/squash or zucchini and others; Leguminosae, particularly the genus Glycine, very particularly the species max (soybean), soya, and alfalfa, pea, beans or peanut and others; Rubiaceae, preferably the subclass Lamiidae such as, for example Coffea arabica or Coffea liberica (coffee bush) and others; Solanaceae, particularly the genus Lycopersicon, very particularly the species esculentum (tomato), the genus Solanum, very particularly the species tuberosum (potato) and melongena (aubergine) and the genus Capsicum, very particularly the genus annuum (pepper) and tobacco or paprika and others; Sterculiaceae, preferably the subclass Dilleniidae such as, for example, Theobroma cacao (cacao bush) and others; Theaceae, preferably the subclass Dilleniidae such as, for example, Camellia sinensis or Thea sinensis (tea shrub) and others; Umbelliferae, particularly the genus Daucus (very particularly the species carota (carrot)) and Apium (very particularly the species graveolens dulce (celery)) and others; and linseed, cotton, hemp, flax, cucumber, spinach, carrot, sugar beet and the various tree, nut and grapevine species, in particular banana and kiwi fruit. Preferred monocotyledonous plants include maize, rice, wheat, sugarcane, sorghum, oats and barley.

In some cases preferred crops are used for food production for animals, humans or both.

In some cases, the entire crop is used, for example by animal consumption directly in the field, or harvested after the growing season and used or processed in which case it is desirable to increase the yield of the entire plant biomass. In this case, the transgenes should be expressed in the green tissue of the plant using for example constitutive or leaf-specific promoters and the enzymes encoded by the transgenes to the plastids, in particular the chloroplasts of the plants. Examples of these types of crops include forage crops such as hay, alfalfa, silage corn etc.

In other cases the seed is the most valuable part of the plant harvested and the plant stems, stalks leaves etc. are left in the field. Examples of this include the majority of the major food crops including maize (corn), wheat, oats, barley, soybean, millet, sorghum, potato, pulses, beans, tomatoes, oilseeds, etc. In the case of plants used for the harvesting of seed, it is desirable to increase the yield of the seed without necessarily increasing the yield of the other parts of the plant to maximize the use of agronomic inputs such as fertilizer, water etc. for the production of the seed. This can be achieved as described in the disclosed invention by using seed specific or silique specific promoters to control the expression of the transgenes in the developing seed and targeting the enzymes expressed from the transgenes to the plastid of the seed using plastid targeting signals as is well known in the art.

Of particular interest for transformation are plants, which are oilseed plants. In oilseed plants of interest the oil is accumulated in the seed and can account for greater than 10%, greater than 15%, greater than 18%, greater than 25%, greater than 35%, greater than 50% by weight of the weight of dry seed. Oil crops encompass by way of example: Borago officinalis (borage); Camelina (false flax); Brassica species such as *B. campestris, B. napus, B. rapa, B. carinata* (mustard, oilseed rape or turnip rape); Cannabis sativa (hemp); Carthamus tinctorius (safflower); Cocos nucifera (coconut); Crambe abyssinica (crambe); Cuphea species (Cuphea species yield fatty acids of medium chain length, in particular for industrial applications); Elaeis guinensis (African oil palm); Elaeis oleifera (American oil palm); Glycine max (soybean); Gossypium hirsutum (American cotton); Gossypium barbadense (Egyptian cotton); Gossypium herbaceum (Asian cotton); Helianthus annuus (sunflower); Jatropha curcas (jatropha); Linum usitatissimum (linseed or flax); Oenothera biennis (evening primrose); Olea europaea (olive); Oryza sativa (rice); Ricinus communis (castor); Sesamum indicum (sesame); Thlaspi caerulescens (pennycress); Triticum species (wheat); Zea mays (maize), and various nut species such as, for example, walnut or almond.

Camelina species, commonly known as false flax, are native to Mediterranean regions of Europe and Asia and seem to be particularly adapted to cold semiarid climate zones (steppes and prairies). The species Camelina sativa was historically cultivated as an oilseed crop to produce vegetable oil and animal feed. It has been introduced to the high plain regions of Canada and parts of the United States as an industrial oilseed crop. In addition to being useful as an industrial oilseed crop, Camelina is a very useful model system for developing new tools and transgenic approaches to enhancing the yield of crops in general and for enhancing the yield of seed and seed oil in particular. Demonstrated transgene encoded enzyme combinations and improvements in Camelina can then be deployed in major oilseed crops including Brassica species including *B. napus* (canola), *B. rapa, B. juncea, B. carinata*, crambe, soybean, sunflower, safflower, oil palm, flax, cotton. The disclosed invention can be used to increase the yield of any crop.

Figure 2:
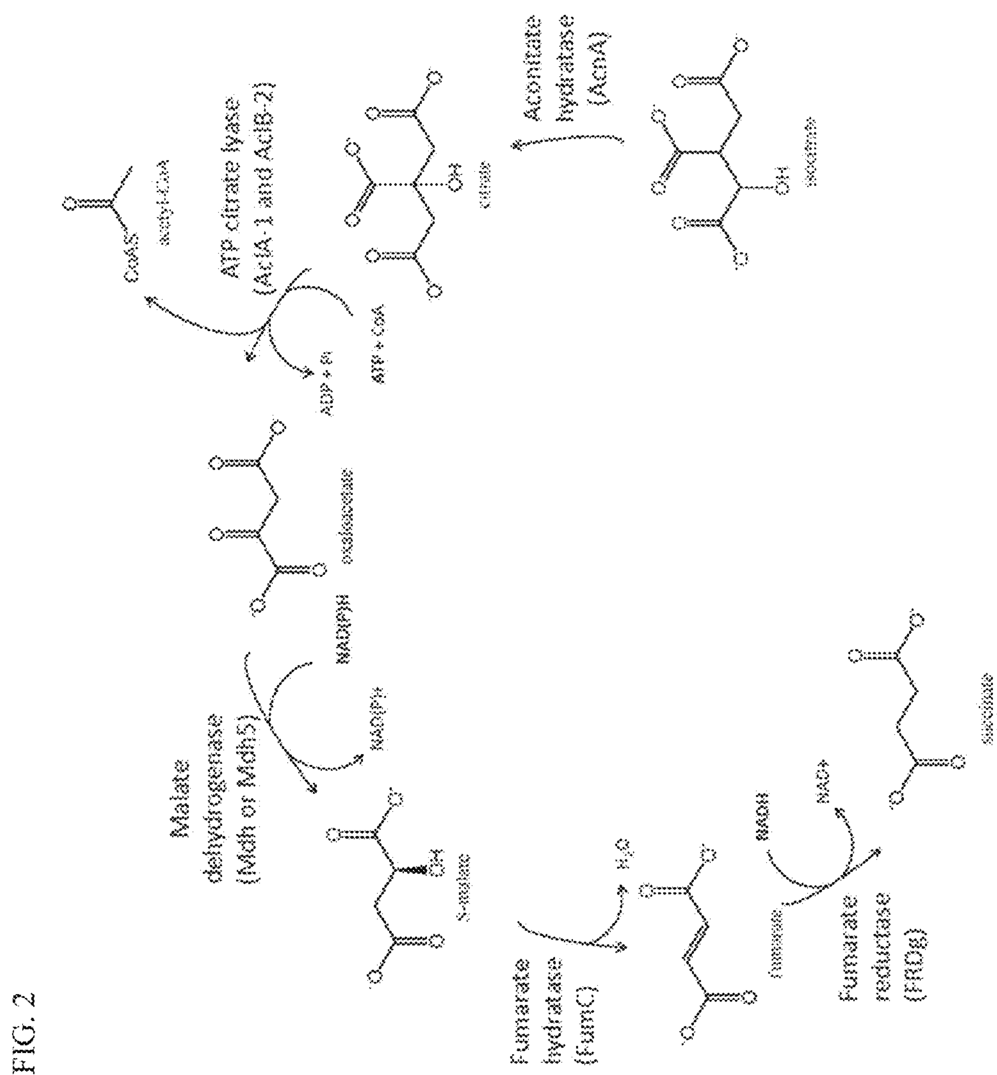
FIG. 2: Metabolic pathways and enzymes expressed from the genes encoded in the plant transformation vectors pMBXS919 and pMBXS918. Plasmid pMBXS919 contains seed specific expression cassettes for the genes MDH5, fumC, FRDg, acnA, aclA-1, and aclB-2. Plasmid pMBXS918 contains seed specific expression cassettes for the genes mdh, fumC, FRDg, acnA, aclA-1, and aclB-2. Gene abbreviations are as follows: mdh, NAD specific malate dehydrogenase from *E. coli*; MDH5, NADP specific malate dehydrogenase from *C. reinhardtii*; fumC, fumarate hydratase class II; FRDg, fumarate reductase; acnA, aconitase; aclA-1, subunit of ATP-citrate lyase; aclB-2, subunit of ATP-citrate lyase.
Figure 3:
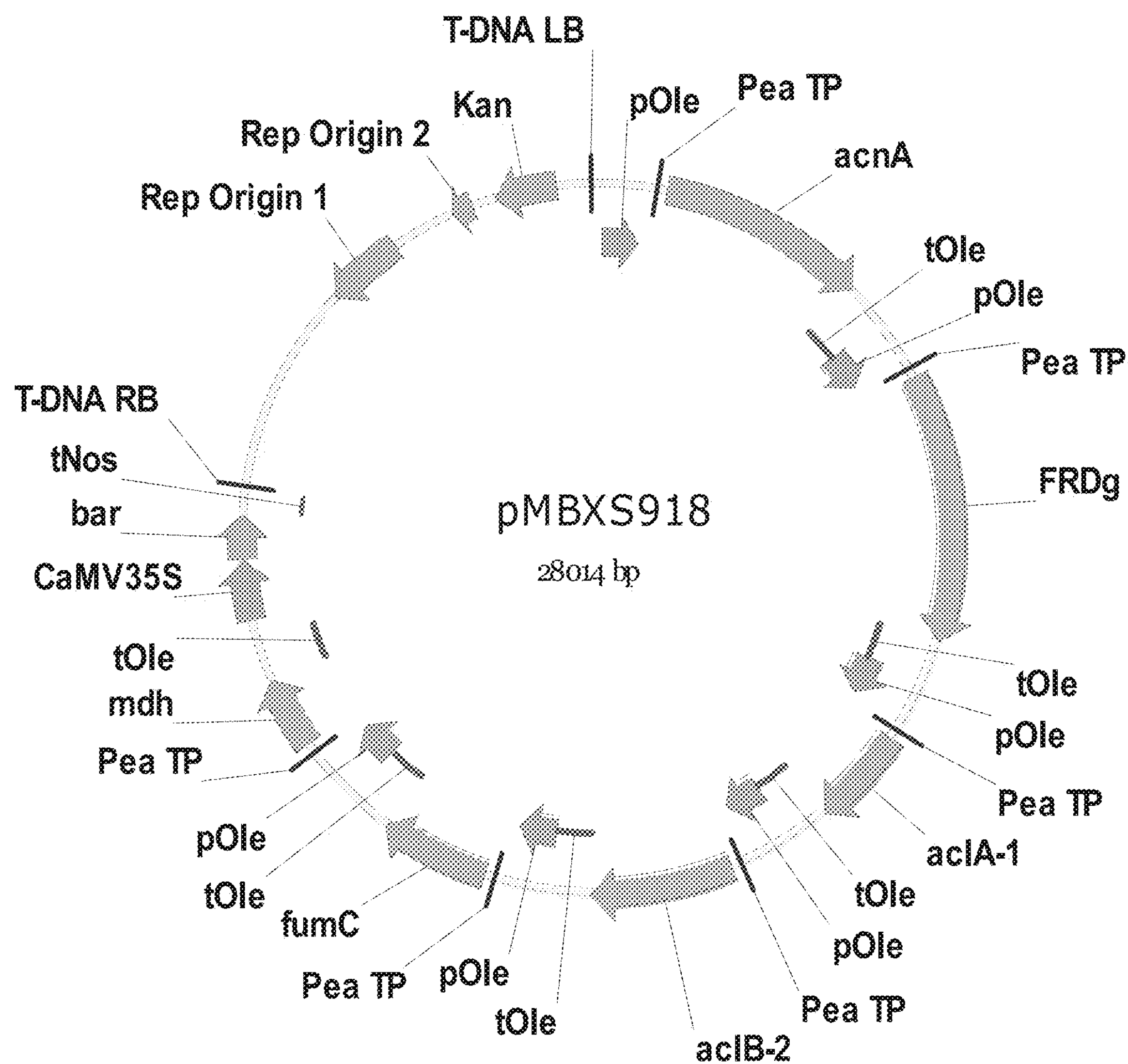
FIG. 3: Plasmid map of vector pMBXS918. Plasmid pMBXS918 contains seed specific expression cassettes, driven by the promoter from the soya bean oleosin isoform A gene (abbreviated pOle), for expression of plastid targeted mdh, fumC, FRDg, acnA, aclA-1, and aclB-2. An expression cassette for the bar gene, driven by the CaMV35S promoter, imparts transgenic plants resistance to the herbicide bialophos.
Figure 4:
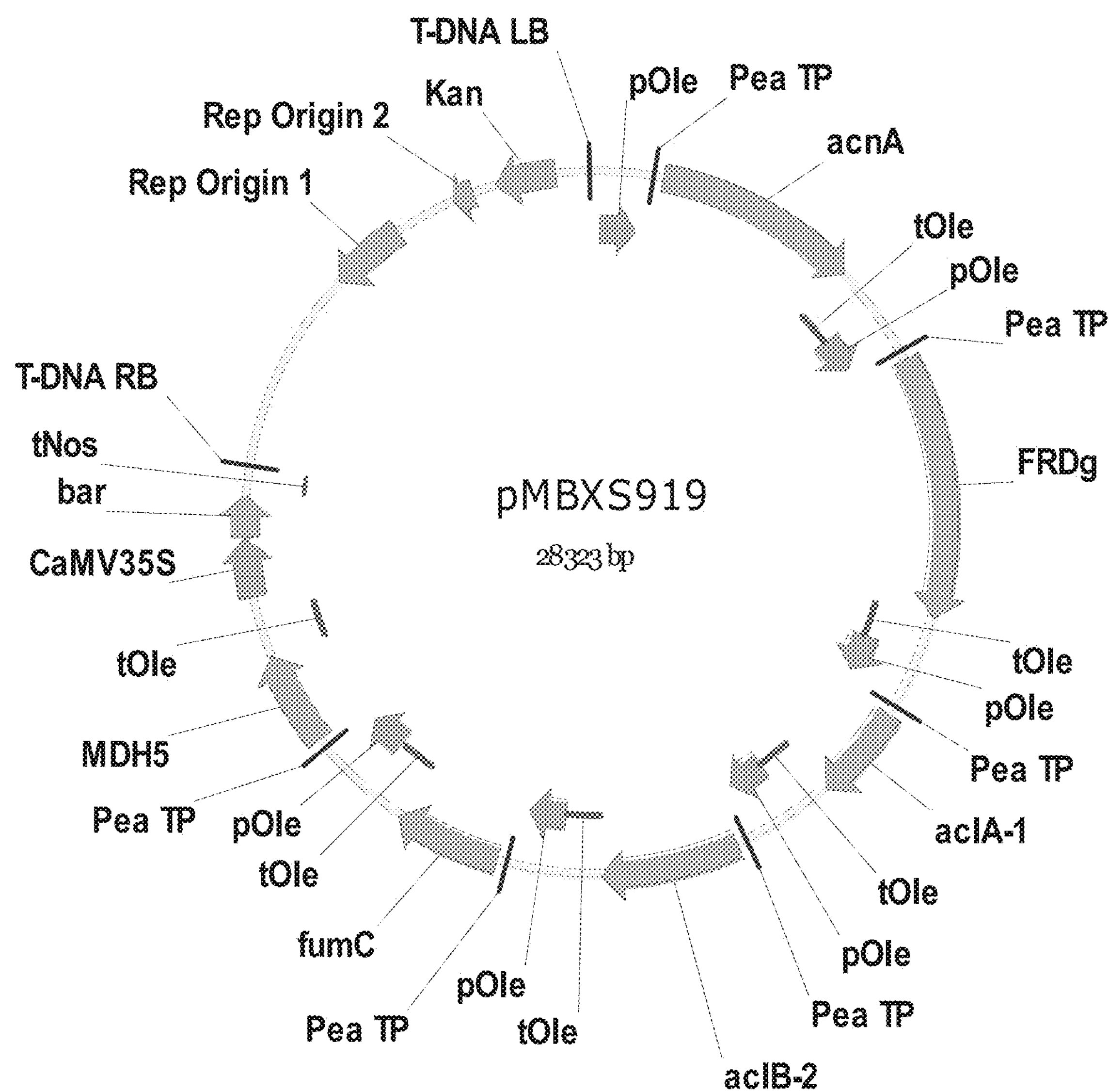
FIG. 4: Plasmid map of pMBXS919. Plasmid pMBXS919 contains seed specific expression cassettes, driven by the promoter from the soya bean oleosin isoform A gene, for expression of plastid targeted MDH5, fumC, FRDg, acnA, aclA-1, and aclB-2. An expression cassette for the bar gene, driven by the CaMV35S promoter, imparts transgenic plants resistance to the herbicide bialophos.
Figure 5:
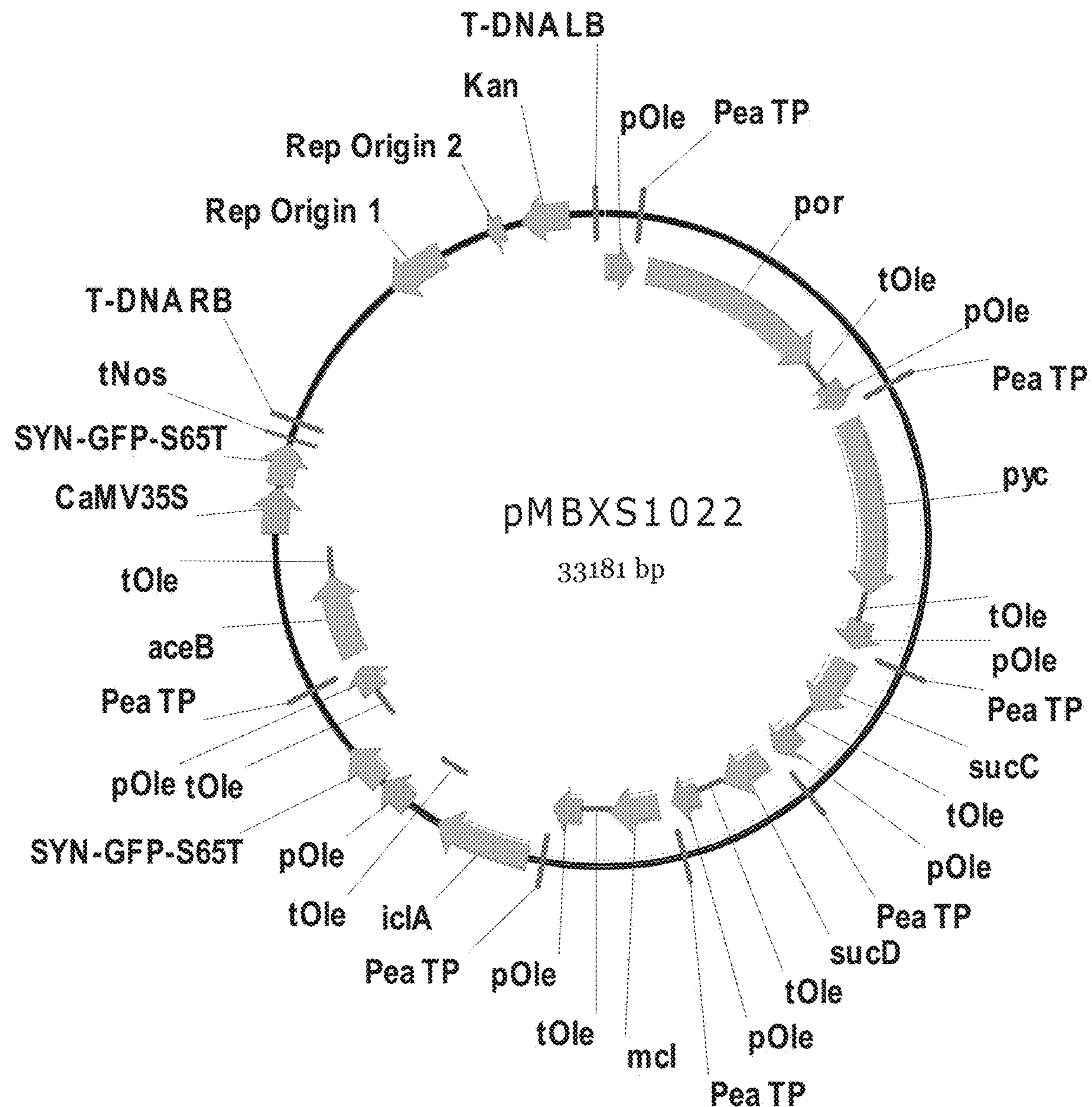
FIG. 5: Plasmid map of vector pMBXS1022. Plasmid pMBXS1022 contains seed specific expression cassettes, driven by the promoter from the soya bean oleosin isoform A gene, for expression of plastid targeted por, sucC, sucD, mcl, iclA, pyc, and aceB. Expression cassettes for the gene encoding green fluorescent protein (GFP), driven by either the CaMV35S or soya bean oleosin promoters, allows detection of transgenic seeds by fluorescent microscopy. Plasmid pMBXS994 is equivalent to pMBXS1022 except that it does not contain the seed specific expression cassette for GFP.
Figure 6:
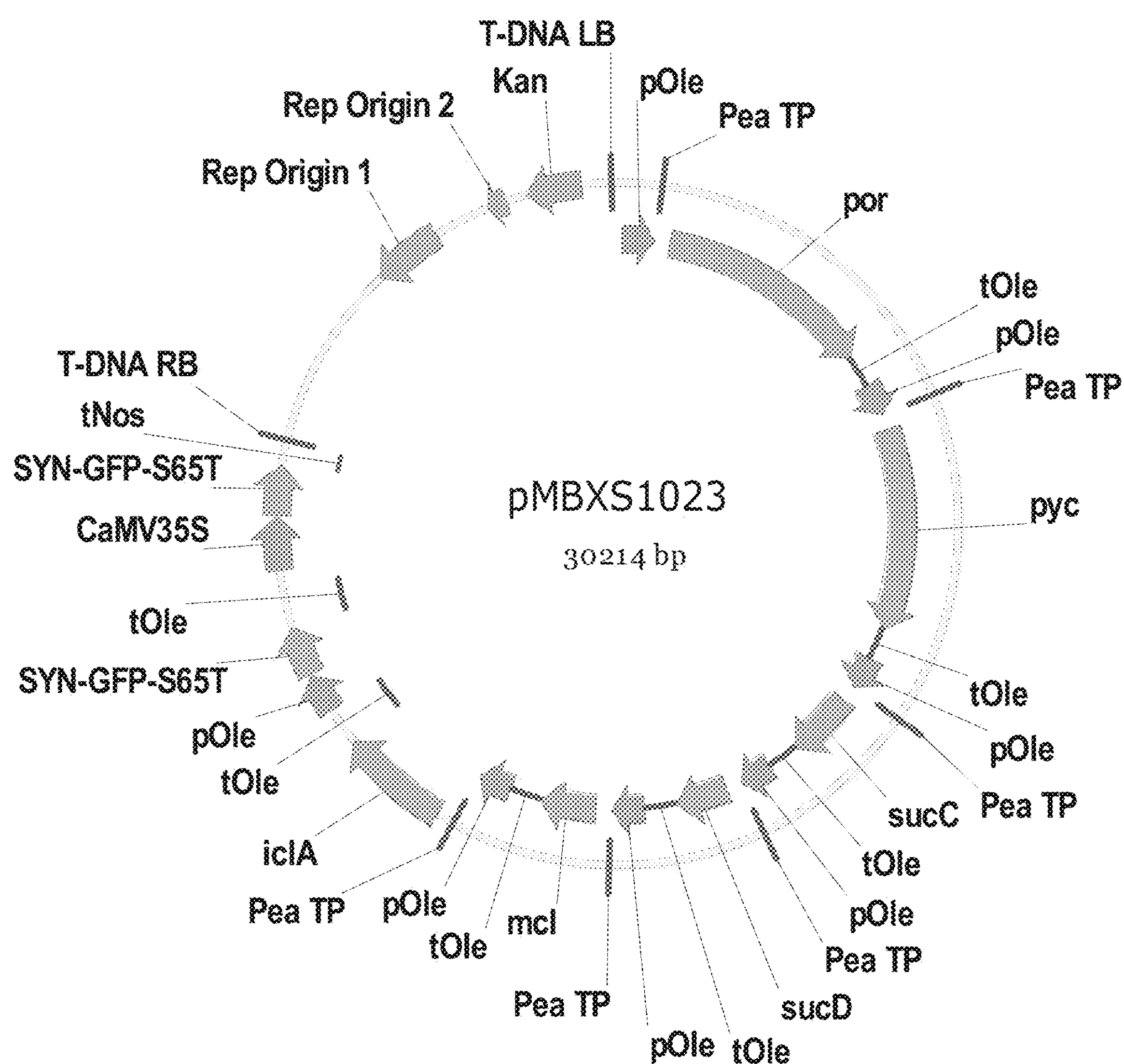
FIG. 6: Plasmid map of vector pMBXS1023. Plasmid pMBXS1023 contains seed specific expression cassettes, driven by the promoter from the soya bean oleosin isoform A gene, for expression of plastid targeted por, sucC, sucD, mcl, iclA, and pyc. Expression cassettes for the gene encoding GFP, driven by either the CaMV35S or soybean oleosin promoters, allows detection of transgenic seeds by fluorescent microscopy.
Figure 7:
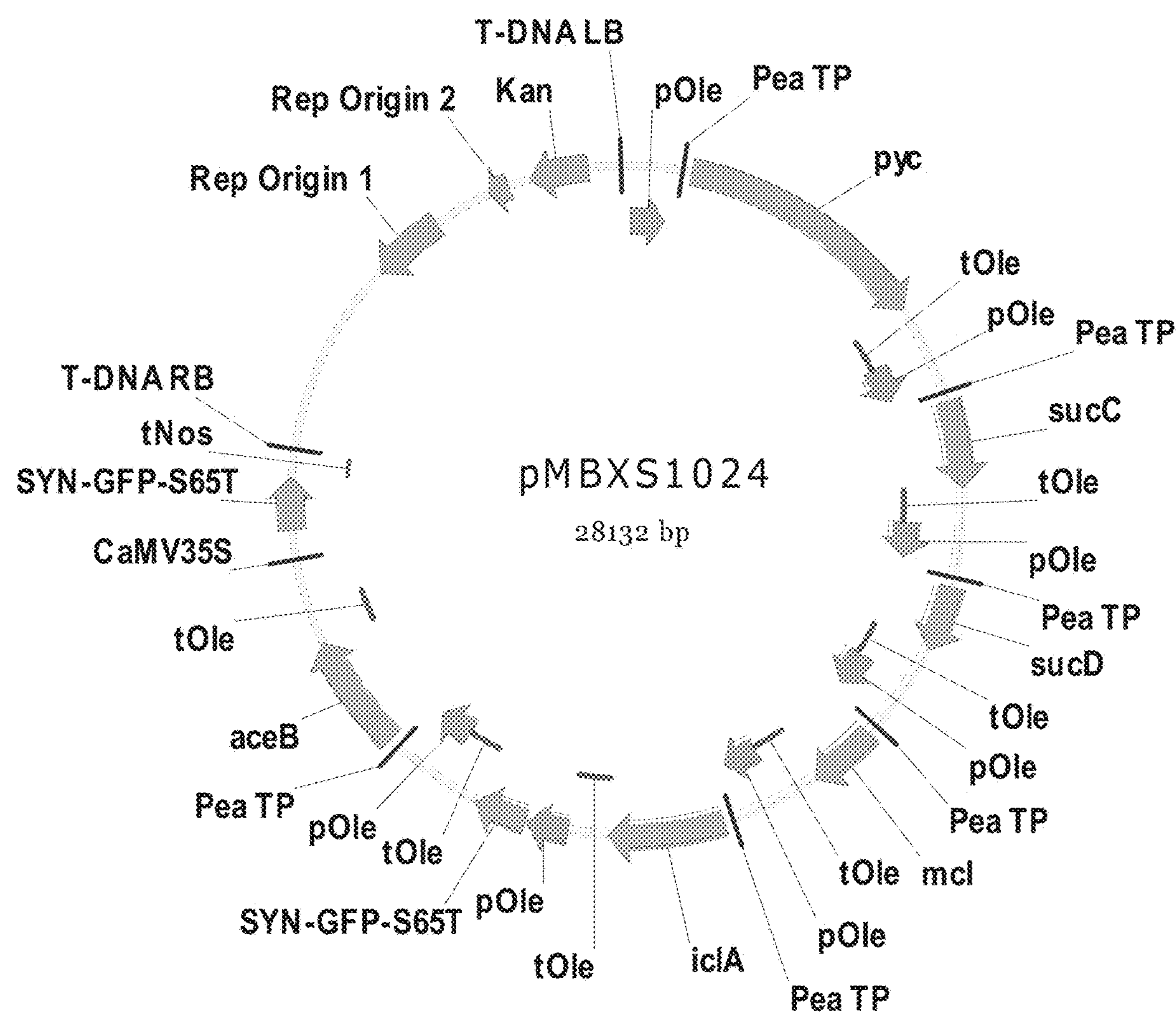
FIG. 7: Plasmid map of vector pMBXS1024. Plasmid pMBXS1024 contains seed specific expression cassettes, driven by the promoter from the soya bean oleosin isoform A gene, for expression of plastid targeted sucC, sucD, mcl, iclA, aceB, and pyc. Expression cassettes for the gene encoding GFP, driven by either the CaMV35S or soybean oleosin promoters, are included.

Metabolic Enzymes and Genes Encoding them Useful for Practicing the Invention Metabolic pathways and the enzymes useful for practicing the disclosed invention are illustrated in FIG. 1 and FIG. 2 which show the enzymatic reactions catalyzed by these enzymes. A list of exemplary enzymes and genes encoding them are shown in TABLE 1.

TABLE 1

Metabolic enzymes and genes useful for practicing the invention.

| Enzyme | EC number | Gene | Source | Accession | Alternate genes |
|---|---|---|---|---|---|
| Pyruvate oxidoreductase | EC 1.2.7.1 | por | *Desulfovibrio africanus* | Y09702 | *Desulfomicrobium baculatum*, WP_015773255, 67% amino acid homology to *D. africanus* POR<br>*Desulfovibrio vulgaris*, WP_012612979, 67% amino acid homology to *D. africanus* POR<br>*Clostridium acetobutylicum* DSM 1731, AEI34679.1, 53% amino acid homology to *D. africanus* POR |
| Malate thiokinase[1] | EC 6.2.1.9 | sucC | *Methylococcus capsulatus* | WP_010960994 | *Methylohalobius crimeensis*, WP_022948601.1, 76% amino acid homology to *M. capsulatus* sucC<br>*Desmospora* sp. 8437, WP_009708795.1, 60% amino acid homology to *M. capsulatus* sucC |
| Malate thiokinase[1] | EC 6.2.1.9 | sucD | *Methylococcus capsulatus* | WP_010960995.1 | *Burkholderia sacchari*, WP_035525486.1, 60% amino acid homology to *M. capsulatus* sucD<br>*Ferrovum myxofaciens*, WP_031597727.1, 60% amino acid homology to *M. capsulatus* sucD |
| Malyl-CoA Lyase | EC 4.1.3.24 | mcl | *Rhodobacter sphaeroides* | WP_011336971.1 | *Rodovulum* sp. NI22, WP_037207860.1, 91% amino acid homology to *R. sphaeroides* mcl<br>*Roseobacter* sp. GAI101, WP_008227028.1, 89% homology to *R. sphaeroides* mcl |
| Isocitrate lyase | EC 4.1.3.1 | iclA | *Cupriavidus necator* | WP_013957076.1 | *Ralstonia pickettii*, WP_022539987.1, 99% amino acid homology to iclA from *C. necator*<br>*Burkholderia ubonensis* MSMB22, 97% amino acid homology to iclA from *C. necator* |
| Pyruvate carboxylase | EC 6.4.1.1 | pyc | *Bacillus subtilis* | WP_003244778 | *Salinibacillus aidingensis*, WP_044156008.1, 98% amino acid homology homology to *B. subtilis* pyc |

TABLE 1-continued

Metabolic enzymes and genes useful for practicing the invention.

| Enzyme | EC number | Gene | Source | Accession | Alternate genes |
| --- | --- | --- | --- | --- | --- |
| | | | | | *Bacillus pumilus*, WP_041084951.1, 84% amino acid homology homology to *B. subtilis* pyc |
| Malate synthase | EC 2.3.3.9 | aceB | *Escherichia coli* | EGI07962.1 | *Shigella flexneri*, WP_039061102.1, 99% amino acid homology to *E. coli* aceB *Citrobacter youngae*, WP_032940912.1, 92% amino acid homology to *E. coli* aceB |
| Malate dehydrogenase (NAD specific) | EC 1.1.1.37 | mdh | *Escherichia coli* | EFJ62433.1 | *Shigella flexneri*, WP_039060497.1, 99% amino acid homology to *E. coli* mdh *Citrobacter rodentium*, WP_012908482, 96% amino acid homology to *E. coli* mdh |
| Malate dehydrogenase (NADP specific) | EC 1.1.1.37 | MDH 5 | *Chlamydomonas reinhardtii* | XP_001696786.1 | *Dunaliella salina*, ABY61960.1, 76% homology to *C. reinhardtii* MDH5 *Monoraphidium neglectum*, KIZ07165.1, 80% homology to *C. reinhardtii* MDH5 *Sorghum bicolor*, P17606 *Zea mays*, P15719 *Medicago sativa*, O48902.1 |
| Fumarate hydratase class II | EC 4.2.1.2 | fumC | *Escherichia coli* | WP_032187409 | *Shigella flexneri*, WP_0001099068.1, 99% homology to *E. coli* fumC *Citrobacter koseri*, CDZ83504.1, 94% homology to *E. coli* fumC |
| Fumarate reductase | EC 1.3.1.6 | FRDg | *Trypanosoma brucei* | AAN40014.1 | *Trypanosoma brucei gambiense* DAL972, CBH10991.1, 84% homology to FRDg of *T. brucei* *Strigomonas culicis*,, EPY23130.1, 66% homology to *T. brucei* FRDg |
| Aconitate hydratase | EC 4.2.1.3 | acnA | *Escherichia coli* | WP_045149543 | *Shigella flexneri*, WP_000099511.1, 99% homology to *E. coli* acnA *Citrobacter koseri*, CDZ83277.1, 93% homology to *E. coli* acnA |
| ATP-citrate lyase | EC 2.3.3.8 | aclA-1 | *Arabidopsis thaliana* | NP_172537.1 | *Arabidopsis lyrata* subsp. *lyrata*, XP_002889824.1, 98% homology to *A. thaliana* aclA-1 *Brassica napus*, CDY70177.1, 95% homology to *A. thaliana* aclA-1 |
| ATP-citrate lyase | EC 2.3.3.8 | aclB-2 | *Arabidopsis thaliana* | NP_199757 | *Brassica napus*, CDY00032.1, 99% homology to *A.* thaliana aclB-2 *Arabidopsis lyrata* subsp. *lyrata*, XP 002863984.1, 99% homology to *A. thaliana* aclB-2 |

[1]The *Methylococcus capsulatus* malate thiokinase (or malate-CoA ligase) was originally annotated as sucC and sucD encoding succinyl-CoA synthetase. Co-expression of *M. capsulatus* sucC and sucD in recombinant *E. coli* was recently shown to provide malate thiokinase activity (Mainguet et al., Metab Eng, 2013, 19, 116).

It is well known in the art that alternative genes encoding these metabolic enzymes can be identified based on nucleotide and or protein sequence homology and either isolated from their species of origin or constructed by DNA synthesis techniques. Metabolic enzyme includes metabolic enzymes homologous to the enzymes listed in TABLE 1 so long as the metabolic enzyme can catalyze the same enzymatic reaction shown in either FIG. 1 or FIG. 2. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog" meaning a polynucleotide or polypeptide that is the functional equivalent of a polynucleotide or polypeptide in another species, and "paralog" meaning a functionally similar sequence when considered within the same species. Paralogs present in the same species or orthologs of the gene in other species can readily be identified without undue experimentation, by molecular biological techniques well known in the art.

As used herein, "percent homology" of two amino acid sequences or of two nucleic acid sequences is determined using the algorithm of Karlin and Altschul (1990) *Proc. Natl. Acad. Sci., U.S.A.* 87: 2264-2268. Such an algorithm is incorporated into the NBLAST and XBLAST programs of Altschul et al. (1990) *J. Mol. Biol.* 215: 403-410. BLAST nucleotide searches are performed with the NBLAST program, score=100, word length 12, to obtain nucleotide sequences homologous to a nucleic acid molecule of the invention. BLAST protein searches are performed with the XBLAST program, score=50, word length=3, to obtain amino acid sequences homologous to a reference polypeptide. To obtain gapped alignments for comparison purposes, Gapped BLAST is utilized as described in Altschul et al. (1997) *Nucleic Acids Res.* 25: 3389-3402. When utilizing BLAST and Gapped BLAST programs, the default parameters are typically used. (See website: www.ncbi.nlm.nih.gov)

In addition, polynucleotides that are substantially identical to a polynucleotide encoding any of the metabolic enzymes listed in TABLE 1 are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically at least about 110 nucleotides. Typically, homologous sequences can be confirmed by hybridization, wherein hybridization under stringent conditions. Using the stringent hybridization [i.e., washing the nucleic acid fragments twice where each wash is at room temperature for 30 minutes with 2×sodium chloride and sodium citrate buffer (2×SSC buffer; 300 mM sodium chloride and 30 mM sodium citrate, pH 7.0) and 0.1% sodium dodecyl sulfate (SDS); followed by washing one time at 50° C. for 30 minutes with 2×SCC and 0.1% SDS; and then washing two times where each wash is at room temperature for 10 minutes with 2×SSC], homologous sequences can be identified comprising at most about 25 to about 30% base pair mismatches, or about 15 to about 25% base pair mismatches, or about 5 to about 15% base pair mismatches.

The term metabolic enzymes includes polynucleotides that encode the enzyme activities listed in TABLE 1 including polypeptides or full-length proteins that contain substitutions, insertions, or deletions into the polypeptide backbone. Related polypeptides are aligned with the metabolic enzymes listed in TABLE 1 by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. Metabolic enzymes and homologous polypeptides are preferably greater than or equal to about 75%, preferably greater than or equal to about 80%, more preferably greater than or equal to about 90% or most preferably greater than or equal to about 95% identical.

A homologous polypeptide may be produced, for example, by conventional site-directed mutagenesis of polynucleotides (which is one avenue for routinely identifying residues of the molecule that are functionally important or not), by random mutation, by chemical synthesis, or by chemical or enzymatic cleavage of the polypeptides. In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

In some cases, for example the pyruvate oxidoreductase enzyme it is desirable to use an enzyme which retains its enzymatic activity in the presence of oxygen for example, from *D. africanus* (Pieulle, L., V. Magro, and E. C. Hatchikian, *Isolation and analysis of the gene encoding the pyruvate-ferredoxin oxidoreductase of Desulfovibrio africanus, production of the recombinant enzyme in Escherichia coli, and effect of carboxy-terminal deletions on its stability.* J Bacteriol, 1997, 179, 5684; Vita, N., E. C. Hatchikian, M. Nouailler, A. Dolla, and L. Pieulle, *Disulfide Bond-Dependent Mechanism of Protection against Oxidative Stress in Pyruvate-Ferredoxin Oxidoreductase of Anaerobic Desulfovibrio Bacteria.* Biochemistry, 2008, 47, 957). Preferably the metabolic enzymes and the genes encoding them are not obtained from mammalian, specifically human species, or from organisms which are known pathogens.

Methods for Producing Transgenic Plants

Unless otherwise indicated, the disclosure encompasses all conventional techniques of plant transformation, plant breeding, microbiology, cell biology and recombinant DNA, which are within the skill of the art. See, e.g., Sambrook and Russell, *Molecular Cloning: A Laboratory Manual,* 3rd edition, 2001; *Current Protocols in Molecular Biology*, F. M. Ausubel et al. eds., 1987; *Plant Breeding: Principles and Prospects*, M. D. Hayward et al., 1993; *Current Protocols in Protein Science*, Coligan et al., eds., 1995, (John Wiley & Sons, Inc.); the series *Methods in Enzymology* (Academic Press, Inc.): PCR 2: *A Practical Approach*, M. J. MacPherson, B. D. Hames and G. R. Taylor eds., 1995.

Unless otherwise noted, technical terms are used according to conventional usage. Definitions of common terms in molecular biology may be found in Lewin, *Genes VII,* 2001 (Oxford University Press), *The Encyclopedia of Molecular Biology*, Kendrew et al., eds., 1999 (Wiley-Interscience) and *Molecular Biology and Biotechnology, a Comprehensive Desk Reference*, Robert A. Meyers, ed., 1995 (VCH Publishers, Inc), *Current Protocols In Molecular Biology*, F. M. Ausubel et al., eds., 1987 (Green Publishing), Sambrook and Russell, *Molecular Cloning: A Laboratory Manual,* 3rd edition, 2001.

A number of terms used herein are defined and clarified in the following section. As used herein, a "vector" is a replicon, such as a plasmid, phage, or cosmid, into which another DNA segment may be inserted so as to bring about the replication of the inserted segment. The vectors described herein can be expression vectors. As used herein, an "expression vector" is a vector that includes one or more expression control sequences. As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest. As used herein, "transformed" and "transfected" encompass the introduction of a nucleic acid (e.g., a vector) into a cell by a number of techniques known in the art.

"Plasmids" are designated by a lower case "p" preceded and/or followed by capital letters and/or numbers.

The term "plant" is used in its broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that is largely differentiated into a structure that is present at any stage of a plant's development. Such structures include, but are not limited to, a fruit, shoot, stem, leaf, flower petal, etc.

The term "plant tissue" includes differentiated and undifferentiated tissues of plants including those present in roots, shoots, leaves, inflorescences, anthers, pollen, ovaries, seeds and tumors, as well as cells in culture (e.g., single cells, protoplasts, embryos, callus, etc.). Plant tissue may be in planta, in organ culture, tissue culture, or cell culture.

The term "plant part" as used herein refers to a plant structure, a plant organ, a plant tissue or a plant cell.

A "non-naturally occurring plant" refers to a plant that does not occur in nature without human intervention. Non-naturally occurring plants include transgenic plants and plants created through genetic engineering.

The term "plant cell" refers to a structural and physiological unit of a plant, comprising a protoplast and a cell wall. The plant cell may be in the form of an isolated single cell or a cultured cell, or as a part of a higher organized unit such as, for example, a plant tissue, a plant organ, or a whole plant.

The term plastid refers to a subcellular organelle of the plant and includes chloroplasts and plastids in developing seed. The term "plant cell culture" refers to cultures of plant units such as, for example, protoplasts, cells and cell clusters in a liquid medium or on a solid medium, cells in plant tissues and organs, microspores and pollen, pollen tubes, anthers, ovules, embryo sacs, zygotes and embryos at various stages of development. The term "plant material" refers to leaves, stems, roots, inflorescences and flowers or flower parts, fruits, pollen, anthers, egg cells, zygotes, seeds, cuttings, cell or tissue cultures, or any other part or product of a plant.

A "plant organ" refers to a distinct and visibly structured and differentiated part of a plant, such as a root, stem, leaf, flower bud, inflorescence, spikelet, floret, seed or embryo.

The term "non-transgenic plant" refers to a plant that has not been genetically engineered with heterologous nucleic acids. These non-transgenic plants can be the test or control plant when comparisons are made, including wild-type plants.

A "corresponding non-transgenic plant" refers to the plant prior to the introduction of heterologous nucleic acids. This plant can be the test plant or control plant, including wild type plants.

A "trait' refers to morphological, physiological, biochemical and physical characteristics or other distinguishing feature of a plant or a plant part or a cell or plant material. The term "trait modification" refers to a detectable change in a characteristic of a plant or a plant part or a plant cell induced by the expression of a polynucleotide or a polypeptide of the invention compared to a plant not expressing them, such as a wild type plant. Some trait modifications can be evaluated quantitatively, such as content of different metabolites, proteins, pigments, lignin, vitamins, starch, sucrose, glucose, fatty acids and other storage compounds, seed size and number, organ size and weight, total plant biomass, yield of seed and yield of genetically engineered products.

Physical plant characteristics that can be modified include cell development (such as the number of trichomes), fruit and seed size and number, yields and size of plant parts such as stems, leaves and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ identity, organ shape or size. The ability to improve plant yield, plant seed yield, and plant seed oil content would be of great economic advantage to farmers worldwide and would allow for increased food production necessary to meet the demands of the growing global population.

Methods and Transgenic Plants, Plant Tissue, Seed and Plant Cell of the Invention Described herein are methods of producing a transgenic plant, plant tissue, seed, or plant cell, wherein said plant, plant tissue, seed or plant cell comprises incorporated in the genome of said plant, plant tissue, seed, or plant cell: one or more polynucleotides encoding one or more transgenes encoding metabolic pathway enzymes, heterologous to the plant with DNA sequences to enable their expression or in the case of a metabolic enzyme native to that plant its increased expression or the cellular location of that enzyme. In some cases alternative regulatory sequences, homologous or heterologous to the plant can be inserted in front of a native plant gene to alter the expression of a plant enzyme and/or alter the cellular location in which the plant enzyme is functionally active. The term transgene refers to a recombinant polynucleotide or nucleic acid that comprises a coding sequence encoding a protein or RNA molecule. The transgenes encoding the specific enzymes illustrated in FIG. 1 and FIG. 2 are operatively linked to the regulatory elements necessary for expression in the plant and in some cases, targeting of the expressed enzymes to subcellular organelles such as the plastid, and inserted into a vector adapted for expression in a plant cell as illustrated in FIGS. 3, 4, 5, 6, and 7. Suitable vectors for plant expression include T-DNA vectors. Alternatively, DNA fragments containing the transgene and the necessary regulatory elements for expression of the transgene can be excised from a plasmid and delivered to the plant cell using microprojectile bombardment-mediated methods. "Operatively linked" refers to a juxtaposition wherein the components so described are in a relationship permitting them to function in their intended manner. Combinations of heterologous and homologous enzymes shown in FIGS. 1 and 2 and listed in TABLE 1 are also suitable for practicing the invention. For example, plants express a Malate dehydrogenase enzyme in plastids of developing seeds (Beeler, S., H. C. Liu, M. Stadler, T. Schreier, S. Eicke, W. L. Lue, E. Truernit, S. C. Zeeman, J. Chen, and O. Kotting, *Plastidial NAD-dependent malate dehydrogenase is critical for embryo development and heterotrophic metabolism in Arabidopsis*. Plant Physiol, 2014, 164, 1175).

It was found that incorporation of combinations of genes encoding subsets of the metabolic enzymes listed in TABLE 1 increased the yield of the plant as determined by measuring the weight of the transgenic plant or measuring the weight of the seed produced by the transgenic plant and comparing it to a transgenic plant or plant seed containing vector sequences without the transgenes encoding the metabolic enzymes. For example, increases in the yield of seed up to two times or higher than plants not having the metabolic enzymes expressed are shown in the examples herein. In some cases, in addition to the increase in seed yield, the oil content of those seed are measurably higher.

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in *Gene Transfer to Plants,* 1995, Potrykus et al., eds., Springer-Verlag Berlin Heidelberg New York, *Transgenic Plants: A Production System for Industrial and Pharmaceutical Proteins,* 1996, Owen et al., eds., John Wiley & Sons Ltd. England, and *Methods in Plant Molecular Biology: A Laboratory Course Manual,* 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof. (See, for example, U.S. Pat. No. 5,639,949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. (See, for example, U.S. Pat. No. 5,639,949). Alternatively, DNA fragments containing the transgene and the necessary regulatory elements for expression of the transgene can be excised from a plasmid and delivered to the plant cell using microprojectile bombardment-mediated methods.

Engineered mini-chromosomes can also be used to express one or more genes in plant cells. Cloned telomeric repeats introduced into cells may truncate the distal portion of a chromosome by the formation of a new telomere at the integration site. Using this method, a vector for gene transfer can be prepared by trimming off the arms of a natural plant chromosome and adding an insertion site for large inserts (Yu et al., 2006, Proc. Natl. Acad. Sci. USA 103: 17331-17336; Yu et al., 2007, Proc. Natl. Acad. Sci. USA 104: 8924-8929).

An alternative approach to chromosome engineering in plants involves in vivo assembly of autonomous plant mini-chromosomes (Carlson et al., 2007, PLoS Genet. 3: 1965-74). Plant cells can be transformed with centromeric sequences and screened for plants that have assembled autonomous chromosomes de novo. Useful constructs combine a selectable marker gene with genomic DNA fragments containing centromeric satellite and retroelement sequences and/or other repeats.

Another approach useful to the described invention is Engineered Trait Loci ("ETL") technology (U.S. Pat. No. 6,077,697; US 2006/0143732). This system targets DNA to a heterochromatic region of plant chromosomes, such as the pericentric heterochromatin, in the short arm of acrocentric chromosomes. Targeting sequences may include ribosomal DNA (rDNA) or lambda phage DNA. The pericentric rDNA region supports stable insertion, low recombination, and high levels of gene expression. This technology is also useful for stacking of multiple traits in a plant (US 2006/0246586).

Zinc-finger nucleases (ZFNs) are also useful for practicing the invention in that they allow double strand DNA cleavage at specific sites in plant chromosomes such that targeted gene insertion or deletion can be performed (Shukla et al., 2009, Nature 459: 437-441; Townsend et al., 2009, *Nature* 459: 442-445).

The CRISPR/Cas9 system (Sander, J. D. and Joung, J. K., Nature Biotechnology, published online Mar. 2, 2014; doi; 10.1038/nbt.2842) is particularly useful for editing plant genomes to modulate the expression of homologous genes encoding enzymes, for example the NADP-specific malate dehydrogenase enzyme found naturally in the plant cell plastids useful for practicing the disclosed invention. Several examples of the use of this technology to edit the genomes of plants have now been reported (Belhaj et al. Plant Methods 2013, 9:39).

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (Townsend et al., U.S. Pat. No. 5,563,055; Zhao et al. WO US98/01268), direct gene transfer (Paszkowski et al. (1984) EMBO J. 3:2717-2722), and ballistic particle acceleration (see, for example, Sanford et al., U.S. Pat. No. 4,945,050; Tomes et al. (1995) *Plant Cell, Tissue, and Organ Culture: Fundamental Methods*, ed. Gamborg and Phillips (Springer-Verlag, Berlin); and McCabe et al. *Biotechnology* 6:923-926 (1988)). Also see Weissinger et al. *Ann. Rev. Genet.* 22:421-477 (1988); Sanford et al. Particulate Science and Technology 5:27-37 (1987) (onion); Christou et al. *Plant Physiol.* 87:671-674 (1988) (soybean); McCabe et al. (1988) BioTechnology 6:923-926 (soybean); Finer and McMullen *In Vitro Cell Dev. Biol.* 27P:175-182 (1991) (soybean); Singh et al. *Theor. Appl. Genet.* 96:319-324 (1998)(soybean); Dafta et al. (1990) *Biotechnology* 8:736-740 (rice); Klein et al. *Proc. Natl. Acad. Sci*. USA 85:4305-4309 (1988) (maize); Klein et al. *Biotechnology* 6:559-563 (1988) (maize); Tomes, U.S. Pat. No. 5,240,855; Buising et al., U.S. Pat. Nos. 5,322,783 and 5,324,646; Tomes et al. (1995) in Plant Cell, Tissue, and Organ Culture: Fundamental Methods, ed. Gamborg (Springer-Verlag, Berlin) (maize); Klein et al. Plant Physiol. 91:440-444 (1988) (maize); Fromm et al. *Biotechnology* 8:833-839 (1990) (maize); Hooykaas-Van Slogteren et al. *Nature* 311:763-764 (1984); Bowen et al., U.S. Pat. No. 5,736,369 (cereals); Bytebier et al. *Proc. Natl. Acad. Sci. USA* 84:5345-5349 (1987) (Liliaceae); De Wet et al. in The Experimental Manipulation of Ovule Tissues, ed. Chapman et al. (Longman, N.Y.), pp. 197-209 (1985) (pollen); Kaeppler et al. *Plant Cell Reports* 9:415-418 (1990) and Kaeppler et al. *Theor. Appl. Genet.* 84:560-566 (1992) (whisker-mediated transformation); D'Halluin et al. *Plant Cell* 4:1495-1505 (1992) (electroporation); Li et al. *Plant Cell Reports* 12:250-255 (1993) and Christou and Ford Annals of Botany 75:407-413 (1995) (rice); Osjoda et al. *Nature Biotechnology* 14:745-750 (1996) (maize via *Agrobacterium tumefaciens*); all of which are herein incorporated by reference in their entirety. References for protoplast transformation and/or gene gun for Agrisoma technology are described in WO 2010/037209. Methods for transforming plant protoplasts are available including transformation using polyethylene glycol (PEG), electroporation, and calcium phosphate precipitation (see for example Potrykus et al., 1985, Mol. Gen. Genet., 199, 183-188; Potrykus et al., 1985, Plant Molecular Biology Reporter, 3, 117-128), Methods for plant regeneration from protoplasts have also been described [Evans et al., in Handbook of Plant Cell Culture, Vol 1, (Macmillan Publishing Co., New York, 1983); Vasil, I K in Cell Culture and Somatic Cell Genetics (Academic, Orlando, 1984)].

Methods for transformation of plastids such as chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation may be accomplished by transactivation of a silent plastid-borne transgene by tissue-preferred expression of a nuclear-encoded and plastid-directed RNA polymerase (McBride et al., *Proc. Natl. Acad. Sci. USA,* 1994,91:7301-7305) or by use of an integrase, such as the phiC31 phage site-specific integrase, to target the gene insertion to a previously inserted phage attachment site (Lutz et al., *Plant J,* 2004, 37, 906-13). Plastid transformation vectors can be designed such that the transgenes are expressed from a promoter sequence that has been inserted with the transgene during the plastid transformation process or, alternatively, from an endogenous plastidial promoter such that an extension of an existing plastidial operon is achieved (Herz et al., *Transgenic Research,* 2005, 14, 969-982). An alternative method for plastid transformation as described in WO 2010/061186 wherein RNA produced in the nucleus of a plant cell can be targeted to the plastid genome can also be used to practice the disclosed invention. Inducible gene expression from the plastid genome using a synthetic riboswitch has also been reported (Verhounig et al. (2010), Proc Natl Acad Sci USA 107: 6204-6209). Methods for designing plastid transformation vectors are described by Lutz et al. (Lutz et al., *Plant Physiol,* 2007, 145, 1201-10).

Recombinase technologies which are useful for producing the disclosed transgenic plants include the cre-lox, FLP/FRT and Gin systems. Methods by which these technologies can be used for the purpose described herein are described for example in (U.S. Pat. No. 5,527,695; Dale And Ow, 1991, *Proc. Natl. Acad. Sci. USA* 88: 10558-10562; Medberry et al., 1995, *Nucleic Acids Res.* 23: 485-490).

Transformation protocols as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, *Plant Cell Rep.* 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Procedures for in planta transformation can be simple. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable Arabidopsis transformants can be obtained by several in planta methods including vacuum infiltration (Clough & Bent, 1998, *The Plant J.* 16: 735-743), transformation of germinating seeds (Feldmann & Marks, 1987, *Mol. Gen. Genet.* 208: 1-9), floral dip (Clough and Bent, 1998, *Plant J.* 16: 735-743), and floral spray (Chung et al., 2000, *Transgenic Res.* 9: 471-476). Other plants that have successfully been transformed by in planta methods include rapeseed and radish (vacuum infiltration, Ian and Hong, 2001, *Transgenic Res.,* 10: 363-371; Desfeux et al., 2000, *Plant Physiol.* 123: 895-904), *Medicago truncatula* (vacuum infiltration, Trieu et al., 2000, *Plant J.* 22: 531-541), camelina (floral dip, WO/2009/117555 to Nguyen et al.), and wheat (floral dip, Zale et al., 2009, *Plant Cell Rep.* 28: 903-913). In planta methods have also been used for transformation of germ cells in maize (pollen, Wang et al. 2001, *Acta Botanica Sin.,* 43, 275-279; Zhang et al., 2005, *Euphytica,* 144, 11-22; pistils, *Chumakov et al.* 2006, *Russian J. Genetics,* 42, 893-897; Mamontova et al. 2010, *Russian J. Genetics,* 46, 501-504) and *Sorghum* (pollen, Wang et al. 2007, *Biotechnol. Appl. Biochem.,* 48, 79-83).

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location.

The cells that have been transformed may be grown into plants in accordance with conventional techniques. See, for example, McCormick et al. *Plant Cell Reports* 5:81-84 (1986). These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

In some scenarios, it may be advantageous to insert a multi-gene pathway into the plant by crossing of lines containing portions of the pathway to produce hybrid plants in which the entire pathway has been reconstructed. This is especially the case when high levels of product in a seed compromises the ability of the seed to germinate or the resulting seedling to survive under normal soil growth conditions. Hybrid lines can be created by crossing a line containing one or more genes with a line containing the other gene(s) needed to complete a biosynthetic pathway. Use of lines that possess cytoplasmic male sterility (Esser, K. et al., 2006, Progress in Botany, Springer Berlin Heidelberg. 67, 31-52) with the appropriate maintainer and restorer lines allows these hybrid lines to be produced efficiently. Cytoplasmic male sterility systems are already available for some Brassicaceae species (Esser, K. et al., 2006, Progress in Botany, Springer Berlin Heidelberg. 67, 31-52). These Brassicaceae species can be used as gene sources to produce cytoplasmic male sterility systems for other oilseeds of interest such as Camelina.

Transgenic plants can be produced using conventional techniques to express any genes of interest in plants or plant cells (*Methods in Molecular Biology,* 2005, vol. 286, Transgenic Plants: Methods and Protocols, Pena L., ed., Humana Press, Inc. Totowa, NJ; Shyamkumar Barampuram and Zhanyuan J. Zhang, Recent Advances in Plant Transformation, in James A. Birchler (ed.), *Plant Chromosome Engineering: Methods and Protocols*, Methods in Molecular Biology, vol. 701, Springer Science+Business Media). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole fertile plants. Detailed description of transformation techniques are within the knowledge of those skilled in the art.

Plant promoters can be selected to control the expression of the transgene in different plant tissues or organelles for all of which methods are known to those skilled in the art (Gasser & Fraley, 1989, *Science* 244: 1293-1299). In one embodiment, promoters are selected from those of eukaryotic or synthetic origin that are known to yield high levels of expression in plants and algae. In a preferred embodiment, promoters are selected from those that are known to provide high levels of expression in monocots.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize 1n2-2 promoter, which is activated by benzenesulfonamide herbicide safeners, the maize GST promoter, which is activated by hydrophobic electrophilic compounds that are used as pre-emergent herbicides, and the tobacco PR-1 promoter which is activated by salicylic acid. Other chemical-regulated promoters include steroid-responsive promoters [see, for example, the glucocorticoid-inducible promoter (Schena et al., 1991, *Proc. Natl. Acad. Sci. USA* 88: 10421-10425; McNellis et al., 1998, *Plant J.* 14 :247-257) and tetracycline-inducible and tetracycline-repressible promoters (see, for example, Gatz et al., 1991, *Mol. Gen. Genet.* 227: 229-237; U.S. Pat. Nos. 5,814,618 and 5,789,156, herein incorporated by reference in their entirety).

A three-component osmotically inducible expression system suitable for plant metabolic engineering has recently been reported (Feng et al., 2011, *PLoS ONE* 6: 1-9).

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

"Tissue-preferred" promoters can be used to target gene expression within a particular tissue. Compared to chemically inducible systems, developmentally and spatially regulated stimuli are less dependent on penetration of external factors into plant sells. Tissue-preferred promoters include those described by Van Ex et al., 2009, *Plant Cell Rep.* 28: 1509-1520; Yamamoto et al., 1997, *Plant J.* 12: 255-265;

Kawamata et al., 1997, *Plant Cell Physiol.* 38: 792-803; Hansen et al., 1997, *Mol. Gen. Genet.* 254: 337-343; Russell et al., 199), *Transgenic Res.* 6: 157-168; Rinehart et al., 1996, *Plant Physiol* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Differ.* 20: 181-196, Orozco et al., 1993, *Plant Mol. Biol.* 23: 1129-1138; Matsuoka et al., 1993, *Proc. Natl. Acad. Sci. USA* 90: 9586-9590, and Guevara-Garcia et al., 1993, *Plant J.* 4: 495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al., 1989, *BioEssays* 10: 108-113, herein incorporated by reference. Such seed-preferred promoters include, but are not limited to, Cim1 (cytokinin-induced message), cZ19B1 (maize 19 kDa zein), milps (myo-inositol-1-phosphate synthase), and ce1A (cellulose synthase). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1. The stage specific developmental promoter of the late embryogenesis abundant protein gene LEA has successfully been used to drive a recombination system for excision-mediated expression of a lethal gene at late embryogenesis stages in the seed terminator technology (U.S. Pat. No. 5,723,765 to Oliver et al.).

Leaf-specific promoters are known in the art. See, for example, WO/2011/041499 and U.S. Patent No 2011/0179511 A1 to Thilmony et al.; Yamamoto et al., 1997, *Plant J.* 12: 255-265; Kwon et al., 1994, *Plant Physiol.* 105: 357-367; Yamamoto et al., 1994, *Plant Cell Physiol.* 35: 773-778; Gotor et al., 1993, *Plant J.* 3: 509-518; Orozco et al., 1993, *Plant Mol. Biol.* 23: 1129-1138, and Matsuoka et al., 1993, *Proc. Natl. Acad. Sci. USA* 90: 9586-9590.

Certain embodiments use transgenic plants or plant cells having multi-gene expression constructs harboring more than one promoter. The promoters can be the same or different.

Any of the described promoters can be used to control the expression of one or more of the genes of the invention, their homologs and/or orthologs as well as any other genes of interest in a defined spatiotemporal manner.

Nucleic acid sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra. The following is a description of various components of typical expression cassettes.

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

The coding sequence of the selected gene may be genetically engineered by altering the coding sequence for optimal expression in the crop species of interest. Methods for modifying coding sequences to achieve optimal expression in a particular crop species are well known (Perlak et al., 1991, *Proc. Natl. Acad. Sci. USA* 88: 3324 and Koziel et al., 1993, *Biotechnology* 11: 194-200).

Individual plants within a population of transgenic plants that express a recombinant gene(s) may have different levels of gene expression. The variable gene expression is due to multiple factors including multiple copies of the recombinant gene, chromatin effects, and gene suppression. Accordingly, a phenotype of the transgenic plant may be measured as a percentage of individual plants within a population. The yield of a plant can be measured simply by weighing. The yield of seed from a plant can also be determined by weighing.

The present inventors have transformed plants with recombinant DNA molecules that encode heterologous metabolic enzymes in the nuclear genome. The expressed recombinant metabolic enzymes are transported into the plastid compartments of the plant cells. Transgenic plants and plant cells expressing the recombinant metabolic enzymes are selected on the basis of having higher yield of total biomass or seed compared to wild type plants of the same species not comprising the recombinant metabolic enzymes. The transgenic plants also show increased seed yield compared to wild type plants of the same species not comprising the recombinant heterologous enzymes. In some cases the transgenic plants show increased seed yield and higher oil content as compared to wild type plants of the same species not comprising the recombinant heterologous enzymes.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A transgenic plant can be produced by selection of transformed seeds or by selection of transformed plant cells and subsequent regeneration.

In one embodiment, the transgenic plants are grown (e.g., on soil) and harvested. In one embodiment, above ground tissue is harvested separately from below ground tissue. Suitable above ground tissues include shoots, stems, leaves, flowers, grain, and seed. Exemplary below ground tissues include tubers, roots, and root hairs. In one embodiment, whole plants are harvested and the above ground tissue is subsequently separated from the below ground tissue.

Selectable Markers

Genetic constructs may encode a selectable marker to enable selection of transformation events. There are many methods that have been described for the selection of transformed plants [for review see (Miki et al., *Journal of*

*Biotechnology,* 2004, 107, 193-232) and references incorporated within]. Selectable marker genes that have been used extensively in plants include the neomycin phosphotransferase gene nptII (U.S. Pat. Nos. 5,034,322, 5,530,196), hygromycin resistance gene (U.S. Pat. No. 5,668,298, Waldron et al., (1985), *Plant Mol Biol,* 5:103-108; Zhijian et al., (1995), *Plant Sci,* 108:219-227), the bar gene encoding resistance to phosphinothricin (U.S. Pat. No. 5,276,268), the expression of aminoglycoside 3"-adenyltransferase (aadA) to confer spectinomycin resistance (U.S. Pat. No. 5,073, 675), the use of inhibition resistant 5-enolpyruvyl-3-phosphoshikimate synthetase (U.S. Pat. No. 4,535,060) and methods for producing glyphosate tolerant plants (U.S. Pat. Nos. 5,463,175; 7,045,684). Other suitable selectable markers include, but are not limited to, genes encoding resistance to chloramphenicol (Herrera Estrella et al., (1983), *EMBO J,* 2:987-992), methotrexate (Herrera Estrella et al., (1983), *Nature,* 303:209-213; Meijer et al, (1991), *Plant Mol Biol,* 16:807-820); streptomycin (Jones et al., (1987), *Mol Gen Genet,* 210:86-91); bleomycin (Hille et al., (1990), *Plant Mol Biol,* 7:171-176) ; sulfonamide (Guerineau et al., (1990), *Plant Mol Biol,* 15:127-136); bromoxynil (Stalker et al., (1988), *Science,* 242:419-423); glyphosate (Shaw et al., (1986), *Science,* 233:478-481); phosphinothricin (DeBlock et al., (1987), *EMBO J,* 6:2513-2518).

Methods of plant selection that do not use antibiotics or herbicides as a selective agent have been previously described and include expression of glucosamine-6-phosphate deaminase to inactive glucosamine in plant selection medium (U.S. Pat. No. 6,444,878) and a positive/negative system that utilizes D-amino acids (Erikson et al., *Nat Biotechnol,* 2004, 22, 455-8). European Patent Publication No. EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of transgenic plants.

Methods for positive selection using sorbitol dehydrogenase to convert sorbitol to fructose for plant growth have also been described (WO 2010/102293). Screenable marker genes include the beta-glucuronidase gene (Jefferson et al., 1987, *EMBO J.* 6: 3901-3907; U.S. Pat. No. 5,268,463) and native or modified green fluorescent protein gene (Cubitt et al., 1995, *Trends Biochem. Sci.* 20: 448-455; Pan et al., 1996, *Plant Physiol.* 112: 893-900).

Transformation events can also be selected through visualization of fluorescent proteins such as the fluorescent proteins from the nonbioluminescent Anthozoa species which include DsRed, a red fluorescent protein from the *Discosoma* genus of coral (Matz et al. (1999), Nat Biotechnol 17: 969-73). An improved version of the DsRed protein has been developed (Bevis and Glick (2002), Nat Biotech 20: 83-87) for reducing aggregation of the protein.

Visual selection can also be performed with the yellow fluorescent proteins (YFP) including the variant with accelerated maturation of the signal (Nagai, T. et al. (2002), Nat Biotech 20: 87-90), the blue fluorescent protein, the cyan fluorescent protein, and the green fluorescent protein (Sheen et al. (1995), Plant J 8: 777-84; Davis and Vierstra (1998), Plant Molecular Biology 36: 521-528). A summary of fluorescent proteins can be found in Tzfira et al. (Tzfira et al. (2005), Plant Molecular Biology 57: 503-516) and Verkhusha and Lukyanov (Verkhusha, V. V. and K. A. Lukyanov (2004),Nat Biotech 22: 289-296) whose references are incorporated in entirety. Improved versions of many of the fluorescent proteins have been made for various applications. Use of the improved versions of these proteins or the use of combinations of these proteins for selection of transformants will be obvious to those skilled in the art.

For plastid transformation constructs, a preferred selectable marker is the spectinomycin-resistant allele of the plastid 16S ribosomal RNA gene (Staub J M, Maliga P, *Plant Cell* 4: 39-45 (1992); Svab Z, Hajdukiewicz P, Maliga P, *Proc. Natl. Acad. Sci. USA* 87: 8526-8530 (1990)). Selectable markers that have since been successfully used in plastid transformation include the bacterial aadA gene that encodes aminoglycoside 3'-adenyltransferase (AadA) conferring spectinomycin and streptomycin resistance (Svab et al., *Proc. Natl. Acad. Sci. USA,* 1993, 90, 913-917), nptII that encodes aminoglycoside phosphotransferase for selection on kanamycin (Carrer H, Hockenberry T N, Svab Z, Maliga P., *Mol. Gen. Genet.* 241: 49-56 (1993); Lutz K A, et al., *Plant J.* 37: 906-913 (2004); Lutz K A, et al., *Plant Physiol.* 145: 1201-1210 (2007)), aphA6, another aminoglycoside phosphotransferase (Huang F-C, et al, *Mol. Genet. Genomics* 268: 19-27 (2002)), and chloramphenicol acetyltransferase (Li, W., et al. (2010), Plant Mol Biol, DOI 10.1007/s11103-010-9678-4). Another selection scheme has been reported that uses a chimeric betaine aldehyde dehydrogenase gene (BADH) capable of converting toxic betaine aldehyde to nontoxic glycine betaine (Daniell H, et al., *Curr. Genet.* 39: 109-116 (2001)).

Plastid Targeting Signals

Plastid targeting sequences are known in the art and include the chloroplast small subunit of ribulose-1,5-bisphosphate carboxylase (Rubisco) (de Castro Silva Filho et al. *Plant Mol. Biol.* 30:769-780 (1996); Schnell et al. *J. Biol. Chem.* 266(5):3335-3342 (1991)); 5-(enolpyruvyl)shikimate-3-phosphate synthase (EPSPS) (Archer et al. *J. Bioenerg. Biomemb.* 22(6):789-810 (1990)); tryptophan synthase (Zhao et al. *J. Biol. Chem.* 270(11):6081-6087 (1995)); plastocyanin (Lawrence et al. *J. Biol. Chem.* 272(33):20357-20363 (1997)); chorismate synthase (Schmidt et al. J. Biol. Chem. 268(36):27447-27457 (1993)); and the light harvesting chlorophyll a/b binding protein (LHBP) (Lamppa et al. *J. Biol. Chem.* 263:14996-14999 (1988)). See also Von Heijne et al. *Plant Mol. Biol. Rep.* 9:104-126 (1991); Clark et al. *J. Biol. Chem.* 264:17544-17550 (1989); Della-Cioppa et al. *Plant Physiol.* 84:965-968 (1987); Romer et al. *Biochem. Biophys. Res. Commun.* 196:1414-1421 (1993); and Shah et al. *Science* 233:478-481 (1986). Alternative plastid targeting signals have also been described in the following: US 2008/0263728; Miras, S. et al. (2002), J Biol Chem 277(49): 47770-8; Miras, S. et al. (2007), J Biol Chem 282: 29482-29492.

Herbicide Resistance and Insect Tolerance

The engineered plants for increased yield may have stacked input traits that include herbicide resistance and insect tolerance, for example a plant that is tolerant to the herbicide glyphosate and that produces the *Bacillus thuringiensis* (BT) toxin. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the genetically engineered plant (Suh, et al., J. M Plant Mol. Biol. 1993, 22, 195-205). BT toxin is a protein that is lethal to many insects providing the plant that produces it protection against pests (Barton, et al. Plant Physiol. 1987, 85, 1103-1109). Other useful herbicide tolerance traits include but are not limited to tolerance to Dicamba by expression of the dicamba monoxygenase gene (Behrens et al, 2007, Science, 316, 1185), tolerance to 2,4-D and 2,4-D choline by expression of a bacterial aad-1 gene that encodes for an aryloxyalkanoate dioxygenase enzyme (Wright et al., Proceedings of the National Academy of Sciences, 2010, 107, 20240), glufosinate tolerance by expression of the bialophos resistance gene (bar) or the pat gene encoding the enzyme phosphinotricin acetyl transferase (Droge et al., Planta, 1992, 187, 142), as well as genes encoding a modified 4-hydroxyphenylpyruvate dioxygenase (HPPD) that provides tolerance to the herbicides mesotrione, isoxaflutole, and tembotrione. (Siehl et al., Plant Physiol, 2014, 166, 1162).

The invention is further illustrated by the following non-limiting examples. Any variations in the exemplified compositions and methods that occur to the skilled artisan are intended to fall within the scope of the present invention.

EXAMPLES

Example 1

Construction of Metabolic Enzyme Expression Vectors pMBXS918, pMBXS919, pMBXS994, pMBXS1022, pMBXS1023, and pMBXS1024

Plasmids pMBXS918, pMBXS919, pMBXS994, pMBXS1022, pMBXS1023, and pMBXS1024, are derivatives of pCAMBIA binary vectors (Centre for Application of Molecular Biology to International Agriculture, Canberra, Australia) and were constructed using conventional molecular biology and cloning techniques. The transgenes encoded by these plasmids are listed in TABLE 2. The enzyme activities, substrates, and metabolic pathways are shown in FIGS. 1 and 2.

Maps illustrating the metabolic enzyme encoding genes and plant expression elements for directing their expression in plants in the plasmid vectors pMBXS918, pMBXS919, pMBXS1022, pMBXS1023, and pMBXS1024 are shown in FIGS. 3-7. Plasmid vectors pMBXS1022 and pMBXS994 have the same metabolic enzymes but differ in the expression of green fluorescent protein (GFP) for visual selection of transformants. pMBXS1022 has two expression cassettes for GFP, one seed specific and one constitutive, whereas pMBXS994 has only a constitutive expression cassette for GFP.

To construct gene expression cassettes for metabolic pathway enzymes, a DNA sequence encoding a plastid signal peptide was fused to the N-terminus of each gene to direct the encoded protein to the plastid. The plastid signal peptide consisted of DNA encoding the signal peptide from the ribulose-1,5-bisphosphatase carboxylase (Rubisco) small subunit from Pisum sativum, including the first 24 amino acids of the mature protein (Cashmore, *Nuclear genes encoding the small subunit of ribulose-*1,5-*bisphosphate carboxylase*, in *Genetic Engineering of Plants*, T. Kosuge, Meredith, C. P. & Hollaender, A., Editor. 1983, Plenum: New York. p. 29). A three amino acid linker containing an Xba I restriction site allowed direct fusion of the desired transgene to the plastid signal peptide (Kourtz et al., 2005, Plant Biotechnol. J., 2005, 3, 435). Each plastid targeting signal modified gene was placed between the seed specific promoter and corresponding 3'-termination sequence from the soya bean oleosin isoform A gene (Rowley and Herman, Biochim. Biophys. Acta, 1997, 1345, 1) to form the seed specific expression cassettes. Seed specific expression cassettes were cloned into pCAMBIA vectors using conventional cloning techniques. The nucleotide sequence of the complete vectors pMBXS918, pMBXS919, pMBXS1022, pMBXS1023, and pMBXS1024 are shown in FIGS. 19-23.

TABLE 2

Summary of constructs for transformation into Camelina.[1]

| Enzyme | Gene | pMBXS918 | pMBXS919 | pMBXS994 | pMBXS1022 | pMBXS1023 | pMBXS1024 |
|---|---|---|---|---|---|---|---|
| Malate dehydrogenase (NADH) | mdh | + | | | | | |
| Malate dehydrogenase (NADPH) | Mdh5 | | + | | | | |
| Fumarate hydratase | fumC | + | + | | | | |
| Fumarate reductase | FRDg | + | + | | | | |
| Aconitase | acnA | + | + | | | | |
| ATP-citrate lyase subunit | ac1A-1 | + | + | | | | |
| ATP citrate lyase subunit | ac1B-2 | + | + | | | | |
| Pyruvate oxidoreductase | Por | | | + | + | + | |
| Succinyl-CoA synthetase subunit | sucC | | | + | + | + | + |
| Succinyl-CoA synthetase subunit | sucD | | | + | + | + | + |
| Malyl-CoA lyase | mcl | | | + | + | + | + |
| Isocitrate lyase | ic1A | | | + | + | + | + |
| Pyruvate carboxylase | pyc | | | + | + | + | + |
| Malate synthase | aceB | | | + | + | | + |
| Phosphinothricin acetyl transferase | bar | + | + | | | | |

TABLE 2-continued

| Summary of constructs for transformation into Camelina.[1] | | | | | | | |
|---|---|---|---|---|---|---|---|
| Enzyme | Gene | pMBXS918 | pMBXS919 | pMBXS994 | pMBXS1022 | pMBXS1023 | pMBXS1024 |
| Green fluorescent protein | GFP (with 35S promoter) | | + | + | + | + | |
| | GFP (with pOle) | | | + | + | + | |

[1]Co-expression of *M. capsulatus* sucC and sucD in recombinant *E. coli* was recently shown to provide malate thiokinase activity (Mainguet et al., Metab Eng, 2013, 19, 116). The malate dehydrogenases in vectors pMBXS918 and pMBXS919 differ with respect to cofactor specificity, NADH for pMBXS918 and NADPH for pMBXS919.

Example 2

Generation of Camelina Nuclear Transformants Expressing Metabolic Enzymes to Increase Yield In preparation for plant transformation experiments, seeds of *Camelina sativa* germplasm 10CS0043 (abbreviated WT43, obtained from Agriculture and Agri-Food Canada) were sown directly into 4 inch pots filled with soil in the greenhouse. Growth conditions were maintained at 24° C. during the day and 18° C. during the night. Plants were grown until flowering. Plants with a number of unopened flower buds were used in 'floral dip' transformations.

*Agrobacterium* strain GV3101 (pMP90) was transformed with the construct of interest using electroporation. A single colony of GV3101 (pMP90) containing the construct of interest was obtained from a freshly streaked plate and was inoculated into 5 mL LB medium. After overnight growth at 28° C., 2 mL of culture was transferred to a 500-mL flask containing 300 mL of LB and incubated overnight at 28° C. Cells were pelleted by centrifugation (6,000 rpm, 20 min), and diluted to an OD600 of ~0.8 with infiltration medium containing 5% sucrose and 0.05% (v/v) Silwet-L77 (Lehle Seeds, Round Rock, TX, USA). Camelina plants were transformed by "floral dip" using transformation constructs as follows. Pots containing plants at the flowering stage were placed inside a 460 mm height vacuum desiccator (Bel-Art, Pequannock, NJ, USA). Inflorescences were immersed into the *Agrobacterium* inoculum contained in a 500-ml beaker. A vacuum (85 kPa) was applied and held for 5 min. Plants were removed from the desiccator and were covered with plastic bags in the dark for 24 h at room temperature. Plants were removed from the bags and returned to normal growth conditions within the greenhouse for seed formation.

To identify Camelina seeds expressing GFP, fully mature seeds were harvested from transformed plants and dried for 2 days in an oven with mechanical convection set at 22° C. GFP expressing seeds were visualized by fluorescent microscopy using a Nikon AZ100 microscope with a eGFP filter (Excitation bandpass 470/40, Emission Bandpass 525/50). For plasmids pMBXS919 and pMBXS918, the presence of a bar gene on the T-DNA allowed selection of transformants by spraying a solution of 400 mg/L of the herbicide Liberty (active ingredient 15% glufosinate-ammonium).

Example 3

Screening of Transgenic Plants and Identification of Plants with Higher Yield Transgenic plant lines produced using the different plasmid vectors and vector combinations are shown in TABLE 3 together with the analysis of the yield of the T2 generation seed from each line.

TABLE 3

T2 Seed yield in lines of Camelina transformed with one genetic construct to enhance yield.

| Line | Transformed Plasmids | seed yield (g) | % compared to vector control |
|---|---|---|---|
| Wild-type [1] | | 3.02 ± 1.36 | 87% |
| JS11[2] | pMBXS012[3] | 3.49 ± 1.30 | 100% |
| 14-1721 | pMBXS918 | 3.60 | 103% |
| 14-1722 | pMBXS918 | 2.94 | 84% |
| 14-1645 | pMBXS919 | 7.20 | 206% |
| 14-1646 | pMBXS919 | 3.23 | 92% |
| 14-1686 | pMBXS919 | 4.47 | 128% |
| 14-1621 | pMBXS994 | 6.42 | 184% |
| 14-1635 | pMBXS1022 | 6.36 | 182% |
| 14-1636 | pMBXS1022 | 6.72 | 192% |

1 Wild-type seed yield values are an average of 5 plants.

[2]JS11 seed yield values are an average of 18 plants.

[3]Vector control containing the bar gene.

Seed weight yield was determined by harvesting all of the mature seeds from a plant and drying them in an oven with mechanical convection set at 22° C. for two days. The weight of the entire harvested seed was recorded. Total seed oil content and oil fatty acid profile were determined using published procedures for preparation of fatty acid methyl esters (Li et al., Phytochemistry, 67, 904) with some modifications. Briefly, 25-30 mg of mature seeds were placed in 13×100 mm screw-cap test tubes. To each tube, 1.5 mL of 2.5% (v/v) sulfuric acid in methanol (w/0.01% w/v BHT), 400 μL toluene, and 500 μg of a triheptadecanoin (Nu-Chek Prep, Elysian, MN) solution (10 mg/mL in toluene) as internal standard were added. Tubes were purged with nitrogen, capped, and heated at 90° C. for 1 h. Upon cooling, 1 mL of 1 M sodium chloride and 1 mL of heptane were added to each tube. Following mixing and centrifugation, the heptane layer containing fatty acid methyl esters was analyzed with an Agilent 7890A gas chromatograph with a 30 m×0.25 mm (inner diameter) INNOWax column (Agilent) and flame ionization detection. The oven temperature was programmed from 185° C. (1 min hold) to 235° C. (1 min hold) at a rate of 10° C./min (11 min total run time), and the front inlet pressure was 35.8 psi of He. The oil content (% of seed weight) was determined by comparison of the detector response from seed-derived fatty acid methyl esters relative to methyl heptadecanoate from the triheptadecanoin internal standard. Transgenic lines produced with either of plasmids pMBXS994 or pMBXS1022 not only had significantly higher seed yield but in addition the seed oil content was increased by up to 25% as compared to the control plants.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. The modifier "about" used in connection with a quantity is inclusive of the stated value and has the meaning dictated by the context (e.g., includes the degree of error associated with measurement of the particular quantity).

Example 4

Alternate Combinations of Metabolic Enzymes to Increase Seed Yield Obtained by Co-Transformation of Plasmids Two single colonies of GV3101 (pMP90), each carrying a specific construct required for co-transformation, were obtained from freshly streaked plates and inoculated into two separate vials containing 5 mL LB medium. After overnight growth at 28° C., 2 mL of culture of each construct was transferred to separate 500-mL flask containing 300 mL of LB and incubated overnight at 28° C. Cells were pelleted by centrifugation (4,000 rpm, 20 min), and diluted to an OD600 of ~0.8 with infiltration medium containing 5% sucrose. The cultures, each carrying a specific construct, were mixed 1:1 by volume and 0.05% (v/v) Silwet-L77 (Lehle Seeds, Round Rock, TX, USA) was added. Camelina plants were transformed by "floral dip" using transformation constructs as described above.

To identify co-transformed lines, GFP expressing seeds were visualized by fluorescent microscopy using a Nikon AZ100 microscope with an eGFP filter (Excitation bandpass 470/40, Emission Bandpass 525/50) and planted in soil. The presence of the bar gene on the T-DNA of pMBXS918 or pMBXS919 constructs allowed selection of co-transformants by spraying a solution of 400 mg/L of the herbicide Liberty (active ingredient 15% glufosinate-ammonium) on plantlets obtained from GFP expressing seeds.

Co-transformations of select plasmid combinations were performed and transgenic plants isolated. T1 plants were grown in a greenhouse to produce T2 seed. Seed yield from select lines is shown in TABLE 4.

TABLE 4

T2 seed yield in co-transformed lines of Camelina.

| Line | Transformed Plasmids | seed yield (g) | % compared to vector control |
|---|---|---|---|
| Wild-type [1] | | 3.02 ± 1.36 | 87% |
| JS11[2] | pMBXO12[3] | 3.49 ± 1.30 | 100% |
| 14-1685 | pMBXS919/ pMBXS994 | 7.70 | 220% |
| 14-1724 | pMBXS919/ pMBXS1022 | 3.79 | 108% |
| 14-1704 | pMBXS919/ pMBXS1023 | 2.93 | 84% |
| 14-1749 | pMBXS918/ pMBXS1024 | 4.26 | 122% |
| 14-1745 | pMBXS919/ pMBXS1024 | 3.00 | 86% |

[1] Wild-type seed yield values are an average of 5 plants.
[2] JS11 seed yield values are an average of 18 plants.
[3] Vector control containing the bar and gfp gene T2 seeds were sown and eight individual T2 plants from lines transformed with constructs for high yield were grown in the greenhouse in a randomized complete block design. T3 seed was harvested and seed weight was recorded for the individual plants. Average T3 seed yield was calculated from 8 T2 plants per line and compared to yield data of 7 plants containing empty vector pMBXO12 (TABLE 5).

Multiple individual plants within a line showed significantly increased yield. The highest seed yield was obtained with a plant from line 15-0406 that was co-transformed with plasmids pMBXS919 and pMBXS1024. The seed yield of this plant was 276% of the average of the vector control line JS11 and produced 13.63 grams of seed from a single plant under greenhouse growth conditions.

TABLE 5

T3 seed yield in co-transformed lines of Camelina.

| Line | Generation | Parental line | Transformed Plasmids | seed yield (g) per plant | % compared to vector control |
|---|---|---|---|---|---|
| JS11 (bar containing vector control)[1] | T3 plants producing T4 seed | — | pMBXO12 | 4.94 ± 0.94 | 100% |
| 15-0382 | T2 plants producing T3 seed | 14-1704 | pMBXS919, pMBXS1023 | 12.90 | 261% |
| 15-0383 | | | | 3.88 | 79% |
| 15-0384 | | | | 6.23 | 126% |
| 15-0385 | | | | 3.72 | 75% |
| 15-0386 | | | | 10.25 | 207% |
| 15-0387 | | | | 3.28 | 66% |
| 15-0388 | | | | 4.00 | 81% |
| 15-0389 | | | | 7.97 | 161% |
| Average value of 8 plants from this event = 6.53 ± 3.55 | | | | | |
| 15-0390 | T2 plants producing T3 seed | 14-1724 | pMBXS919, pMBXS1022 | 3.04 | 62% |
| 15-0391 | | | | 3.21 | 65% |
| 15-0392 | | | | 3.82 | 77% |
| 15-0393 | | | | 3.97 | 80% |
| 15-0394 | | | | 5.06 | 102% |
| 15-0395 | | | | 5.64 | 114% |
| 15-0396 | | | | 4.77 | 97% |
| 15-0397 | | | | 5.32 | 108% |
| Average value of 8 plants from this event = 4.35 ± 0.98 | | | | | |
| 15-0398 | T2 plants producing T3 seed | 14-1905 | pMBXS919, pMBXS1022 | 10.33 | 209% |
| 150-399 | | | | 3.95 | 80% |
| 15-0400 | | | | 8.25 | 167% |
| 15-0401 | | | | 3.94 | 80% |
| 15-0402 | | | | 8.2 | 166% |
| 15-0403 | | | | 6.55 | 133% |

TABLE 5-continued

| T3 seed yield in co-transformed lines of Camelina. | | | | | |
|---|---|---|---|---|---|
| Line | Generation | Parental line | Transformed Plasmids | seed yield (g) per plant | % compared to vector control |
| 15-0404 | | | | 3.79 | 77% |
| 15-0405 | | | | 8.72 | 177% |
| Average value of 8 plants from this event = 6.72 ± 2.55 | | | | | |
| 15-0406 | T2 plants producing T3 seed | 14-1745 | pMBXS919, pMBXS1024 | 13.63 | 276% |
| 15-0407 | | | | 2.32 | 47% |
| 15-0408 | | | | 6.37 | 129% |
| 15-0409 | | | | 5.05 | 102% |
| 15-0410 | | | | 7.15 | 145% |
| 15-0411 | | | | 1.85 | 37% |
| 15-0412 | | | | 3.87 | 78% |
| 15-0413 | | | | 5.98 | 121% |
| Average value of 8 plants from this event = 5.78 ± 3.69 | | | | | |

[1]JS11 seed yield values are an average of 7 plants.

The weight of 100 seeds from the highest yielding co-transformed lines within TABLE 5 was determined. Seeds from these lines were larger as determined by the increase in 100 seed weight (TABLE 6). The largest seeds were from a plant co-transformed with pMBXS919/p1024 which contained an average 100 seed weight of 141.53 mg, significantly higher (132%) than the control line JS11 that contained an average 100 seed weight of 106.64 mg. The T3 seed yield and 100 seed weight were used to estimate the total number of seeds per plant. Results from these calculations show that the highest yielding plants produced both heavier seeds and more seeds per plant. The approach and methods described in this example can be used to screen for and select the highest yielding lines for commercial production.

TABLE 6

| Average 100 T3 seed weight produced from highest yielding T2 plants from co-transformed lines. | | | | | | |
|---|---|---|---|---|---|---|
| Plant ID | Constructs | $T_3$ seed yield of highest producing $T_2$ plant (g) | Average seed weight of 100 seeds (mg)[1] | % compared to control | Calculated total # of seeds produced per plant | % compared to control |
| 15-0417_JS11 | p1V1BX0122 | 5.97 | 106.64 ± 2.71 | 100 | 5598 | 100 |
| 15-0406_LX03 | p1V1BXS919/pMBXS1024 | 13.63 | 141.53 ± 3.57 | 132 | 9631 | 172 |
| 15-0398_LG08 | p1V1BXS919/pMBXS1022 | 10.33 | 139.11 ± 2.69 | 130 | 7426 | 133 |
| 15-0382_LU03 | p1V1BXS919/pMBXS1023 | 12.9 | 136.88 ± 1.14 | 128 | 9424 | 168 |

[1]3 replicates of 100 seeds were weighed from a plant that produced highest seed yield in that line.

[2]bar and gfp gene containing vector control.

The length and width of individual seeds from the highest yielding control line (JS11) and the highest yielding transgenic lines were also measured (TABLE 7) showing a small increase in seed size.

TABLE 7

Average seed length and width of seed harvested from select lines co-transformed with plasmids to increase yield[1].

| Plant ID | Constructs | Seed length (mm) | % compared to control | Seed width | % compared to control |
|---|---|---|---|---|---|
| 15-0417_ JS11 | pMBXO12[2] | 1.86 ± 0.15 | 100 | 1.04 ± 0.12 | 100 |
| 15-0406_ LX03 | pMBXS919/ pMBXS1024 | 2.04 ± 0.09 | 110 | 1.19 ± 0.11 | 114 |
| 15-0398_ LG08 | pMBXS919/ pMBXS1022 | 2.14 ± 0.14 | 115 | 1.08 ± 0.12 | 104 |
| 15-0382_ LU03 | pMBXS919/ pMBXS1023 | 2.10 ± 0.11 | 113 | 1.07 ± 0.09 | 103 |

[1]Each data set is the average and standard deviation of approximately 100 seeds. Image J software was used to calculate seed size.
[2]bar gene containing vector control.

Example 5

Oil and Protein Content of Seed Harvested from Co-Transformed Lines

Figure 8:
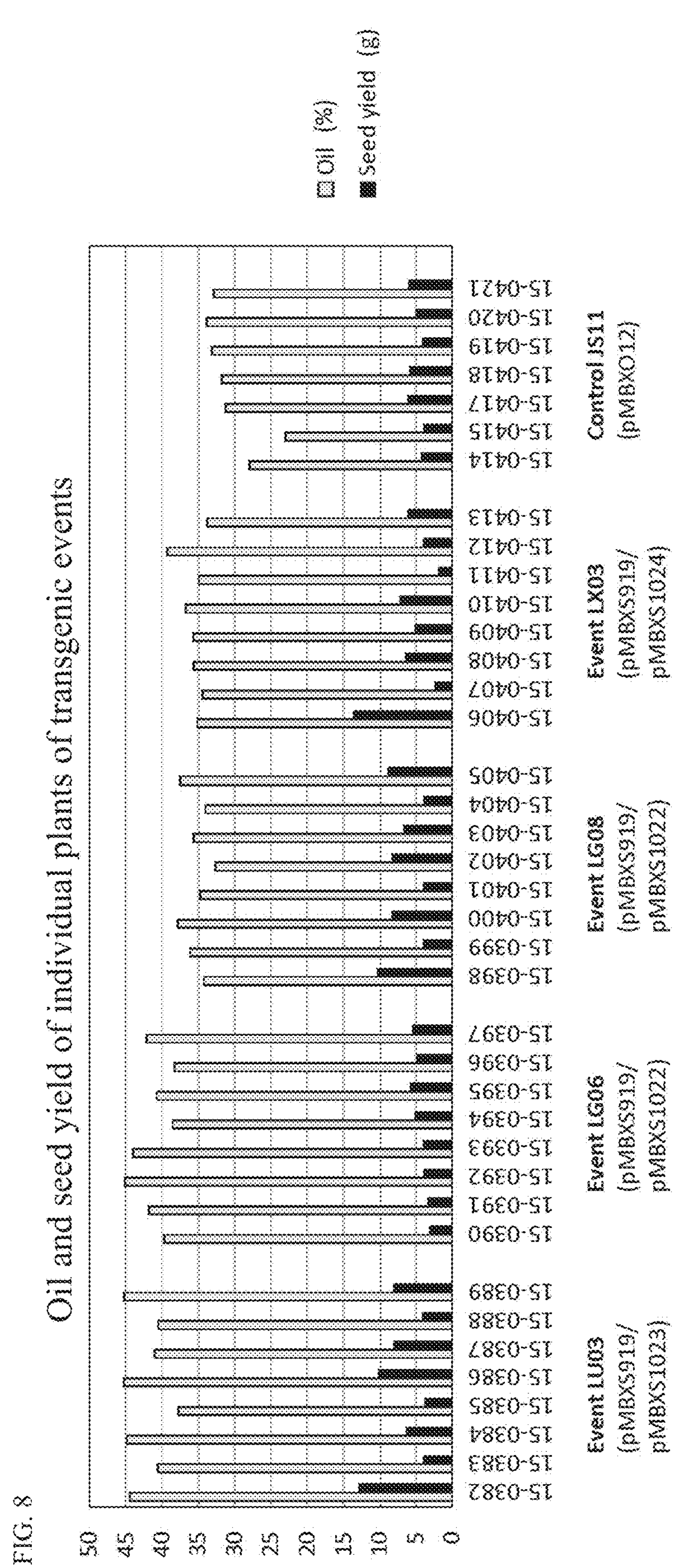
FIG. 8: Seed oil content (% seed weight) and seed yield per plant (grams) in co-transformed lines.
Figure 9:
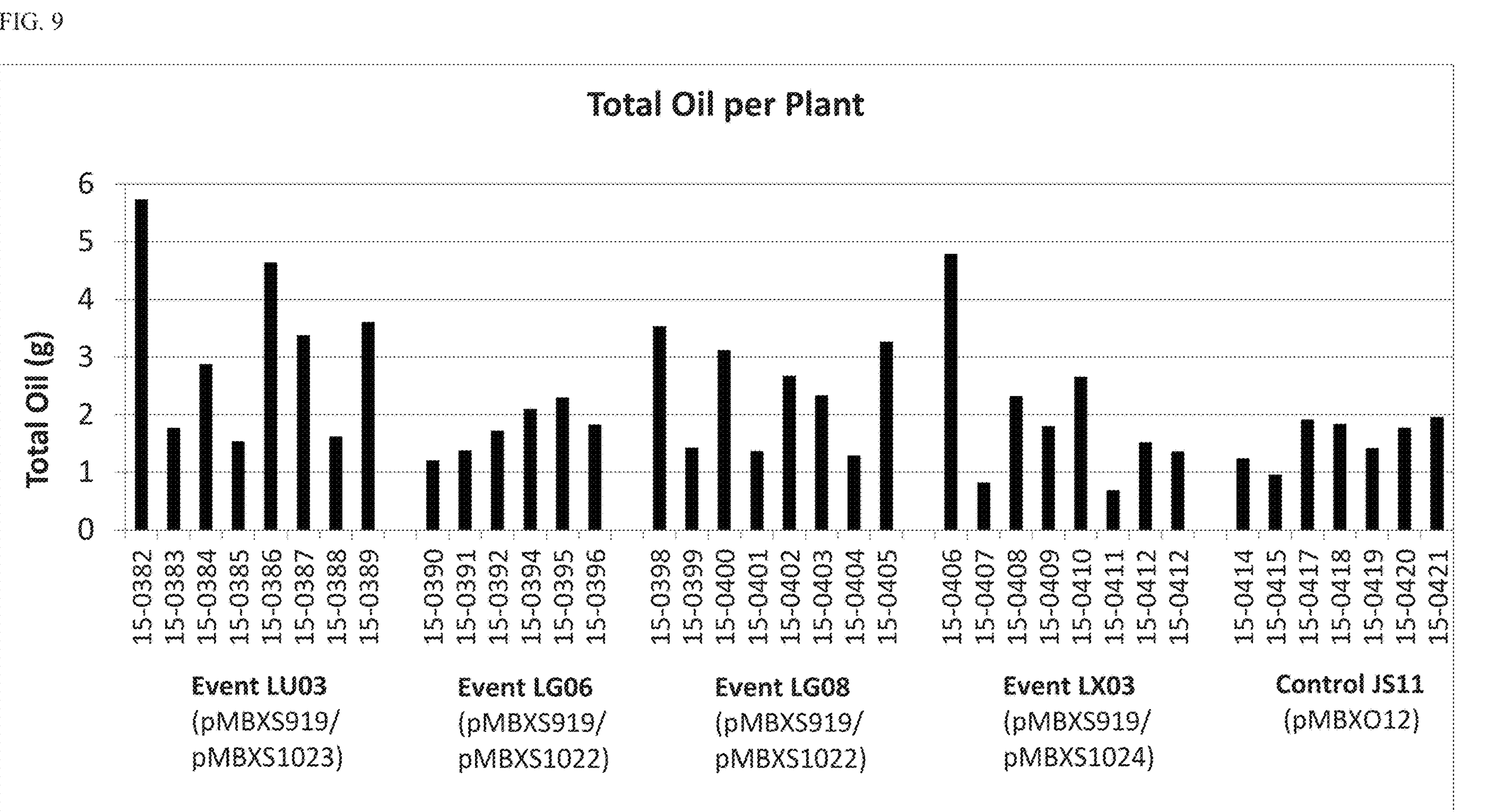
FIG. 9: Total oil (grams) per plant in co-transformed lines.

The oil content of lines was measured for each of the plants described in TABLE 5 using the procedures described earlier. The oil content of replicate plants from an individual event is shown in FIG. 8. The total oil per plant, calculated by multiplying the % oil content of the seed with the seed yield per plant, is shown in FIG. 9. Substantial increases in total oil content per plant were observed in some lines, with the highest value obtained with plant 15-0382 (FIG. 9).

Figure 10:
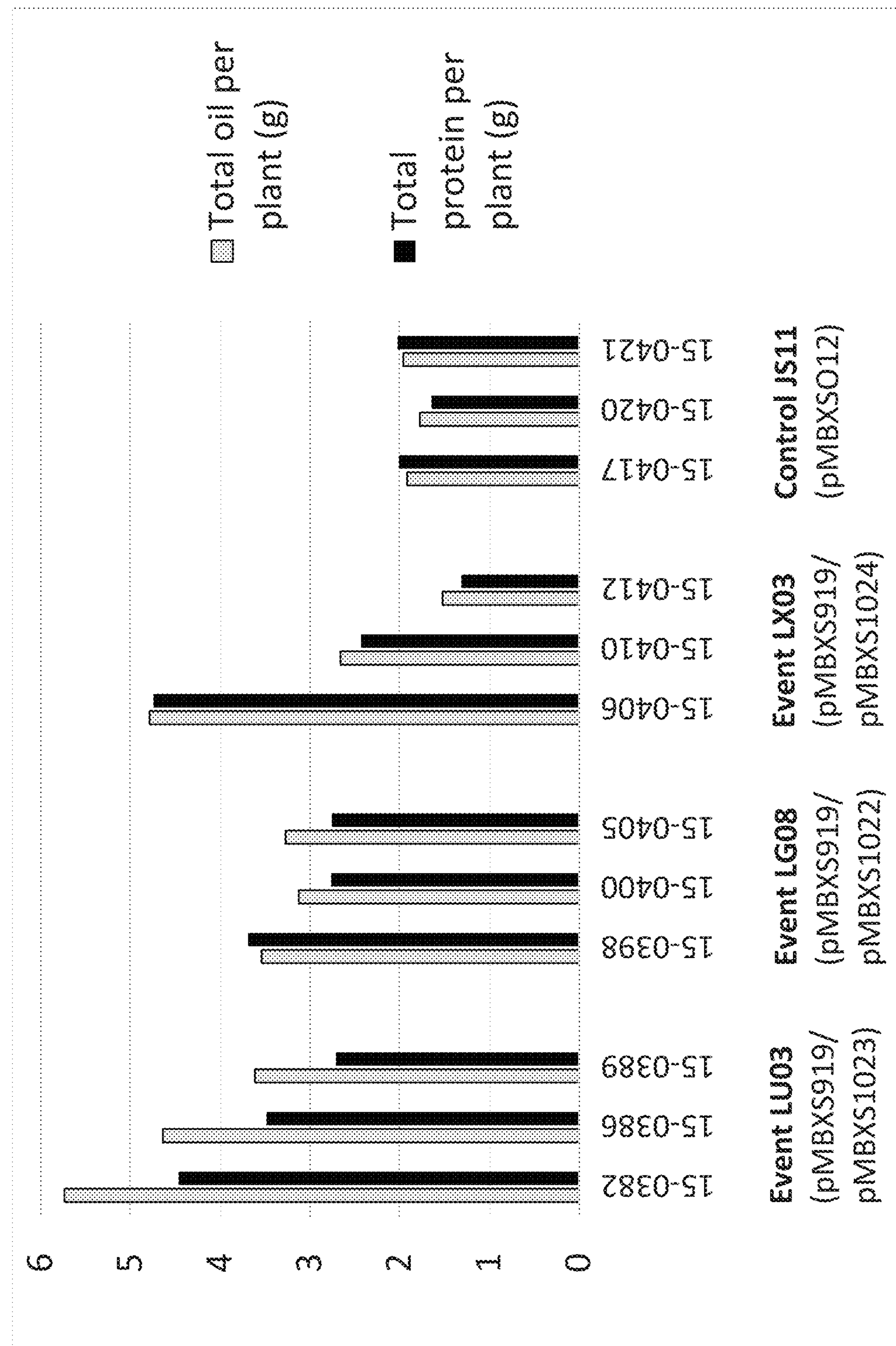
FIG. 10: Total oil (grams) per total seed harvested per plant and total protein (grams) per total seed harvested per plant in select high oil producing co-transformed lines.

Protein content in bulk Camelina seeds was measured using the American Oil Chemists Society (AOCS, Urbana, IL, USA) Ba 4e-93 method (Generic Combustion Method for Determination of Crude Protein). Select lines were chosen based on their total oil content per plant (FIG. 9). Seed protein content (% seed weight) remained relatively stable despite the increases in seed oil content (% seed weight) (TABLE 8). The higher seed yield for many of the lines (TABLE 5) translated into more total protein per plant (FIG. 10).

TABLE 8

Protein content in seed harvested from the highest oil producing co-transformed lines of Camelina.

| Line | Generation | Parental line | Transformed Plasmids | Oil content (% seed weight) | Protein content (% seed weight) |
|---|---|---|---|---|---|
| JS11[1] | T3 plants producing T4 seed | — | pMBXO12 | 28.6 ± 1.4 | 33.8 ± 0.6% |
| 15-0382 | T2 plants producing T3 seed | 14-1704 | pMBXS919, pMBXS1023 | 44.5 | 34.6 |
| 15-0386 | | | | 45.3 | 34.0 |
| 15-0389 | | | | 45.3 | 34.0 |
| 15-0398 | T2 plants producing T3 seed | 14-1905 | pMBXS919, pMBXS1022 | 34.3 | 35.7 |
| 15-0400 | | | | 37.9 | 33.5 |
| 150-405 | | | | 37.5 | 31.6 |
| 15-0406 | T2 plants producing T3 seed | 14-1745 | pMBXS919, pMBXS1024 | 35.1 | 34.8 |
| 15-0410 | | | | 37.2 | 34.0 |
| 15-0412 | | | | 39.3 | 33.9 |

[1]bar containing vector control

Example 6

Minimum Gene Sets Encoding Metabolic Enzymes to Increase Seed Yield

It is well known in the art that it is desirable for plant breeding and regulatory approval purposes to reduce the number of transgenes in a line for commercial development to the minimum set while still achieving the desired outcome, which in the case of this invention is higher plant yield and/or higher plant seed yield and/or higher seed oil content. Having unequivocally demonstrated the achievement of significantly higher yield in the transgenic plants containing the different sets of metabolic enzymes alone and in combination, it is routine to now proceed to determine the optimum yield increase with the minimum set of genes. For this reason a series of additional plasmid vectors are constructed encoding the metabolic enzyme combinations as shown in TABLE 9. By transforming camelina as described above and determining the change in seed yield as compared to a vector control and to the highest yielding lines in TABLES 3-5, it will be routine experimentation to achieve the desired outcome. Alternate combinations of transgenes that can be used to improve seed and/or seed oil yield are listed in TABLE 9.

TABLE 9

Alternate combinations of metabolic enzymes to increase seed yield.

| Transgenes | Enzymes | Result of combined reactions |
|---|---|---|
| por and pyc | Pyruvate oxidoreductase and pyruvate carboxylase | Conversion of acetyl-CoA to oxaloacetate with the fixation of 1 molecule of $HCO_3^-$ and 1 molecule of $CO_2$ |
| por | Pyruvate oxidoreductase | Conversion of acetyl-CoA to pyruvate with the fixation of 1 molecule of $CO_2$ |
| pyc | pyruvate carboxylase | Conversion of pyruvate to oxaloacetate with the fixation of 1 molecule of $HCO_3^-$ |
| por, pyc, sucC, sucD, and mcl in combination with endogenous malate dehydrogenase activity | Pyruvate oxidoreductase, pyruvate carboxylase, malate thiokinase, malyl-CoA lyase, endogenous malate dehydrogenase activity | Cycle that fixes 1 molecule of $HCO_3^-$ and 1 molecule of $CO_2$ and produces glyoxylate |
| por, pyc, aceB in combination with endogenous malate dehydrogenase activity | Pyruvate oxidoreductase, pyruvate carboxylase, malate synthase, endogenous malate dehydrogenase activity | Cycle that fixes 1 molecule of $HCO_3^-$ and 1 molecule of $CO_2$ and produces glyoxylate |
| pyc, sucC, sucD, and mcl in combination with endogenous malate dehydrogenase activity | Pyruvate carboxylase, malate thiokinase, malyl-CoA lyase, endogenous malate dehydrogenase activity | Conversion of pyruvate to acetyl-CoA and glyoxylate with fixation of 1 molecule of $HCO_3^-$ |
| pyc and aceB in combination with endogenous malate dehydrogenase activity | Pyruvate carboxylase, malate synthase, and endogenous malate dehydrogenase activity | Conversion of pyruvate to acetyl-CoA and glyoxylate with fixation of 1 molecule of $HCO_3^-$ |
| MDH5 | NADP specific malate dehydrogenase | Inter-conversion of oxaloacetate and malate, balance of redox |
| aclA-1, aclB-2, MDH5, fumC, FRDg | ATP citrate lyase, malate dehydrogenase, fumarate hydratase, fumarate reductase | Conversion of citrate to acetyl-CoA and succinate |
| MDH5, fumC, FRDg | malate dehydrogenase, fumarate hydratase, fumarate reductase | Conversion of oxaloacetate to succinate |
| fumC, FRDg | fumarate hydratase, fumarate reductase | Conversion of malate to succinate |

In a preferred embodiment, genes sets in plasmids pMBXS1056, pMBXS1057, pMBXS1058, pMBXS1059, and pMBXS1060 are transformed into Camelina (TABLE 10). In one embodiment, a recA− strain of *Agrobacterium*, such as AGL1 [Lazo, G et al., *Biotechnology* 9, 963-967 (1991)], is used to increase plasmid stability during the cultivation of the *Agrobacterium* stock for transformation.

TABLE 10

Transformation constructs for delivering enhanced yield expressing a reduced number of transgenes.

| Enzyme | Gene | pMBXS1056 | pMBXS1057 | pMBXS1058 | pMBXS1059 | pMBXS1060 |
|---|---|---|---|---|---|---|
| Malate dehydrogenase (NADH) | mdh | | | | | |
| Malate dehydrogenase (NADPH) | Mdh5 | | | | + | + |
| Fumarate hydratase | fumC | | | | | |
| Fumarate reductase | FRDg | | | | | |
| Aconitase | acnA | | | | | |
| ATP-citrate lyase subunit | ac1A-1 | | | | | |
| ATP citrate lyase subunit | ac1B-2 | | | | | |
| Pyruvate oxidoreductase | Por | + | + | + | + | + |
| Succinyl-CoA synthetase subunit | sucC | | + | | | + |
| Succinyl-CoA synthetase subunit | sucD | | + | | | + |
| Malyl-CoA lyase | mcl | | + | | + | + |
| Isocitrate lyase | ic1A | | | | | |
| Pyruvate carboxylase | pyc | + | + | + | + | + |
| Malate synthase | aceB | | | + | + | |
| Phosphinothricin acetyl transferase | bar | | | | | |
| Green fluorescent protein | GFP (with 35S promoter) | + | + | + | + | + |
| | GFP (with pOle) | + | + | + | + | + |

Co-expression of *M. capsulatus* sucC and sucD in recombinant *E. coli* was recently shown to provide malate thiokinase activity (Mainguet et al., Metab Eng, 2013, 19, 116).

Figure 11:
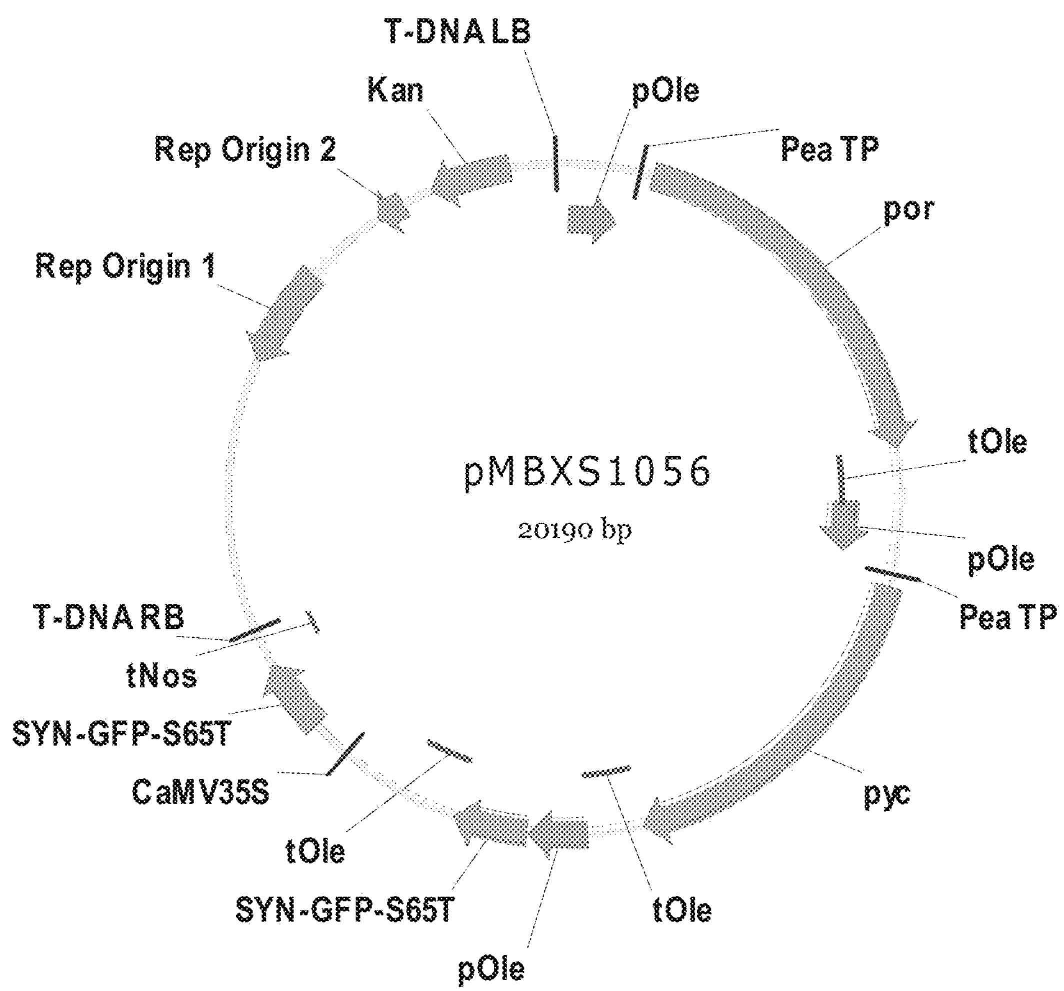
FIG. 11: Plasmid map of vector pMBXS1056.
Figure 12:
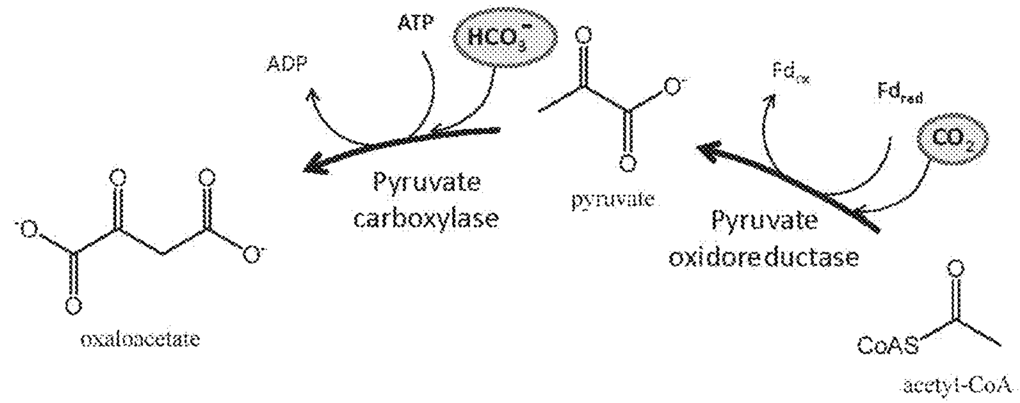
FIG. 12: Metabolic pathways for conversion of 1 $CO_2$, 1 $HCO_3^-$, and 1 acetyl-CoA to 1 oxaloacetate are shown in (a) and (b). In the presence of endogenous plant malate dehydrogenase activity (b), oxaloacetate can be converted to S-malate.
Figure 12:
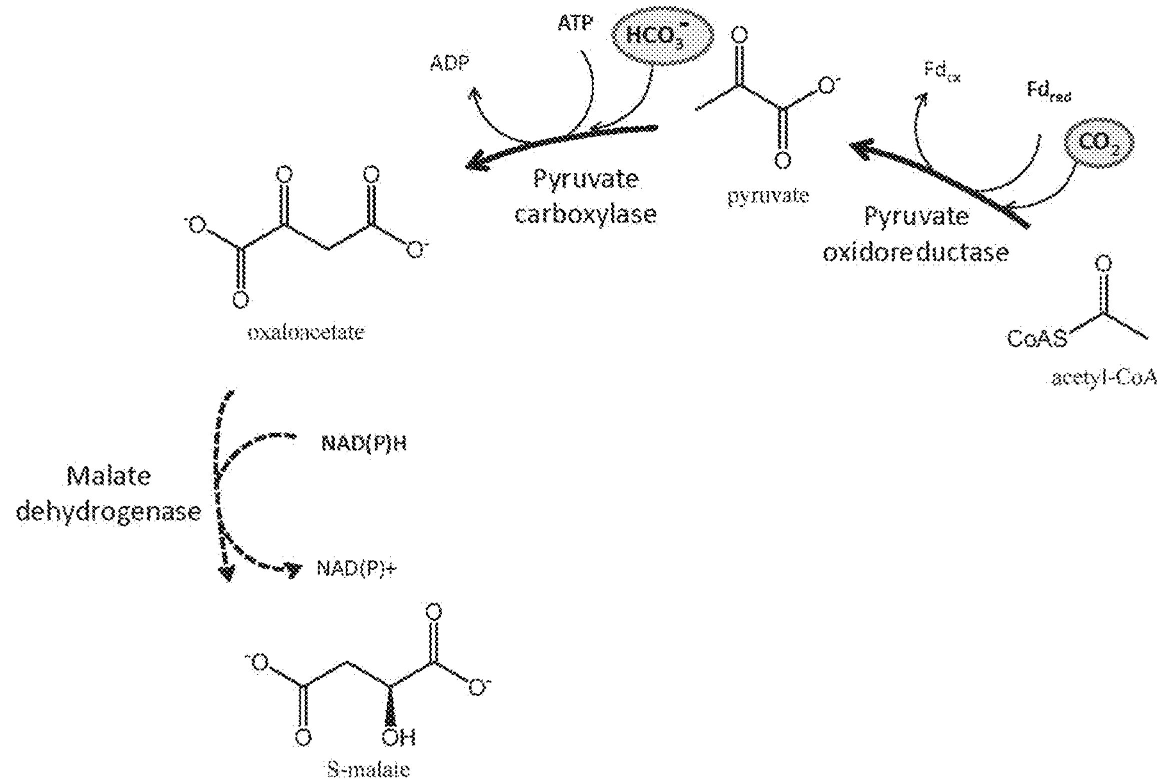

Vector pMBXS1056 (FIG. 11) contains expression cassettes for pyruvate carboxylase (Pyc) and pyruvate oxidoreductase (Por) to enable conversion of 1 molecule of CO2, 1 molecule of HCO3−, and 1 acetyl-CoA to 1 molecule of oxaloacetate (FIG. 12(*a*)). In the presence of endogenous plant malate dehydrogenase activity (FIG. 12(*b*)), oxaloacetate can be converted to S-malate. This plasmid was transformed into *Agrobacterium* strain GV3101 (pMP90) and used to vacuum infiltrate Camelina. Transgenic T1 seeds were identified by their GFP fluorescence. T1 seeds of 40 lines were planted in soil in a greenhouse to produce T2 seeds.

Figure 13:
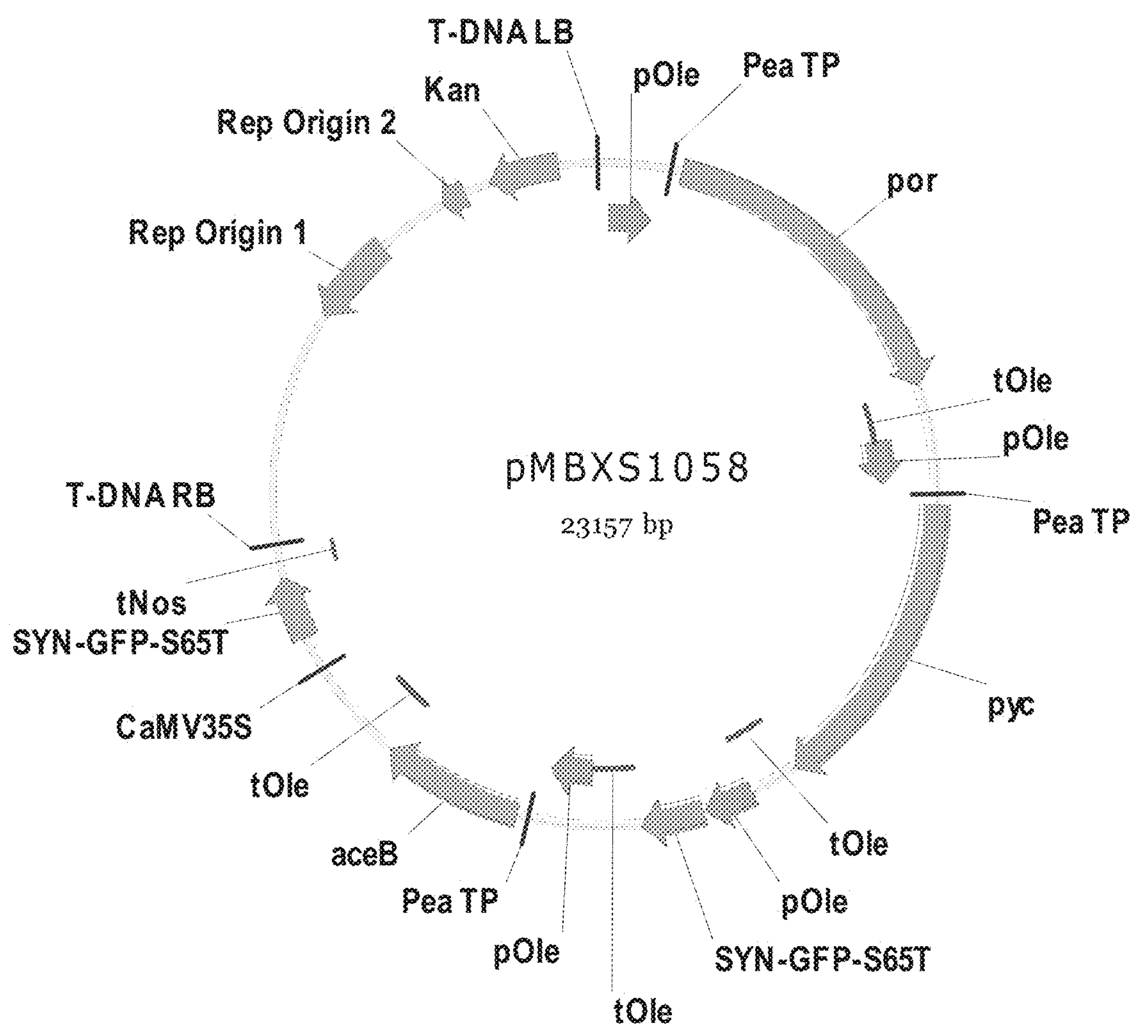
FIG. 13: Plasmid map of vector pMBXS1058.
Figure 14:
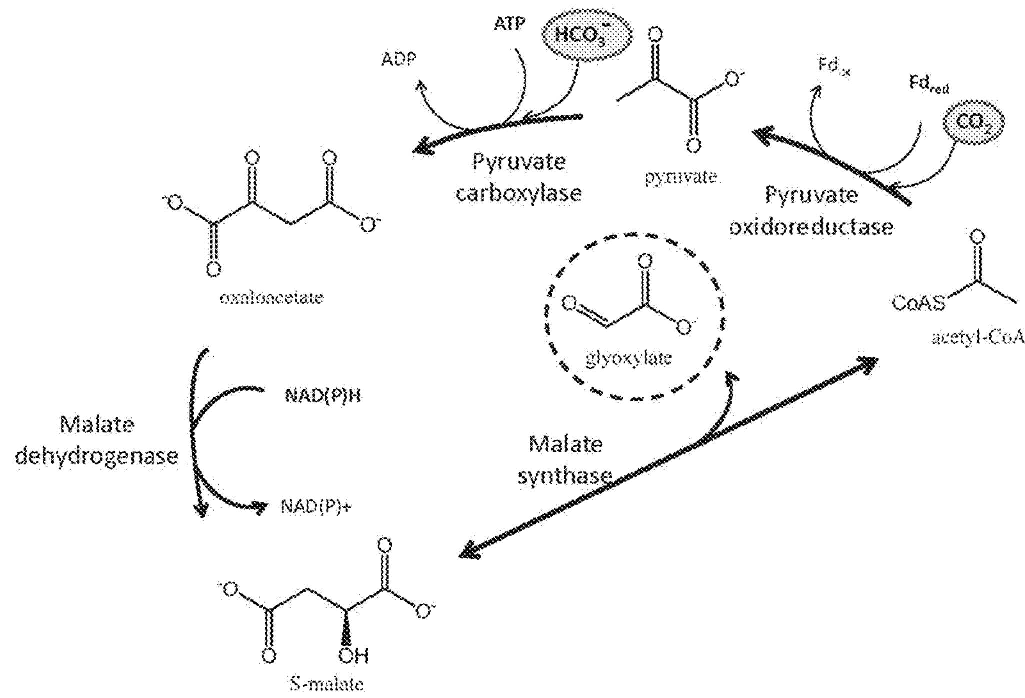
FIG. 14: Metabolic pathways for converting 1 $CO_2$ and 1 $HCO_3^-$ to 1 glyoxylate. Malate dehydrogenase can either be an endogenous plant enzyme activity or encoded by a transgene.
Figure 14:
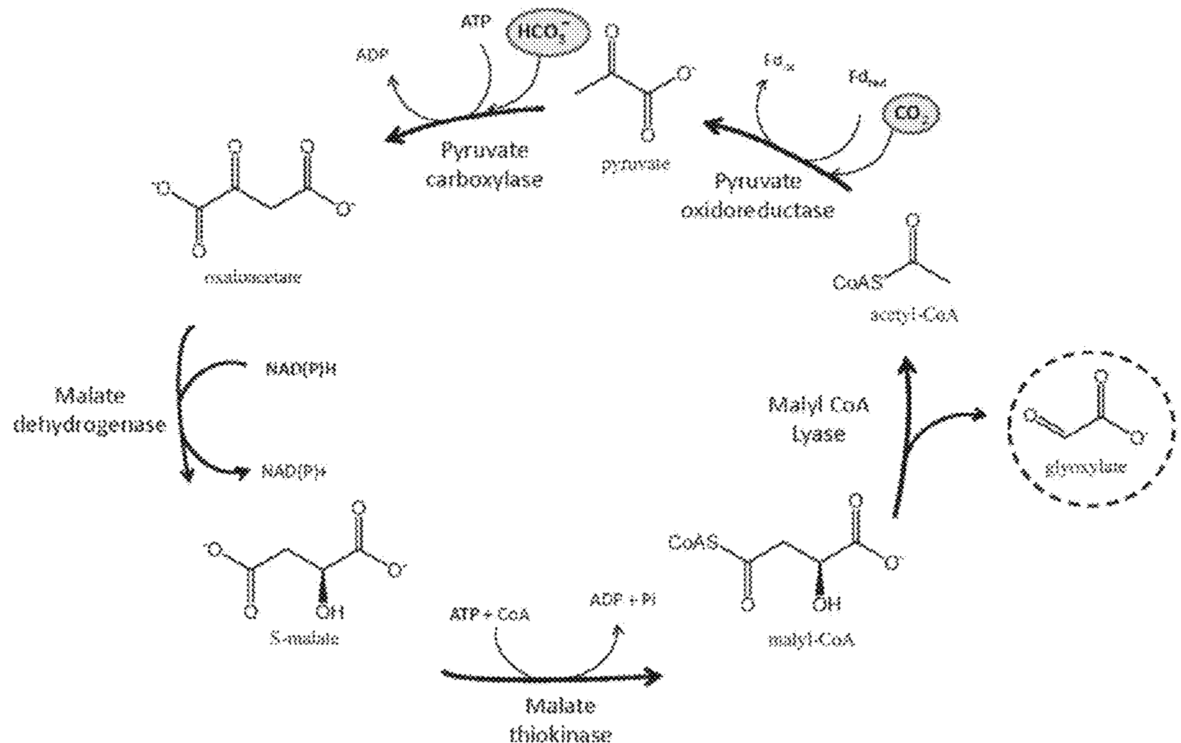

Construct pMBXS1058 (FIG. 13) contains expression cassettes for pyruvate carboxylase (Pyc), pyruvate oxidoreductase (Por), and malate synthase (AceB). In the presence of endogenous plant malate dehydrogenase activity, this construct is designed to enable the conversion of 1 molecule of $CO_2$ and 1 molecule of $HCO_3^-$ to 1 molecule of glyoxylate (FIG. 14(*a*)). This plasmid was transformed into Agrobacterium strain GV3101 (pMP90) and used to vacuum infiltrate Camelina. Transgenic T1 seeds were identified by their GFP fluorescence. T1 seeds of 59 lines were planted in soil in a greenhouse to produce T2 seeds.

Figure 15:
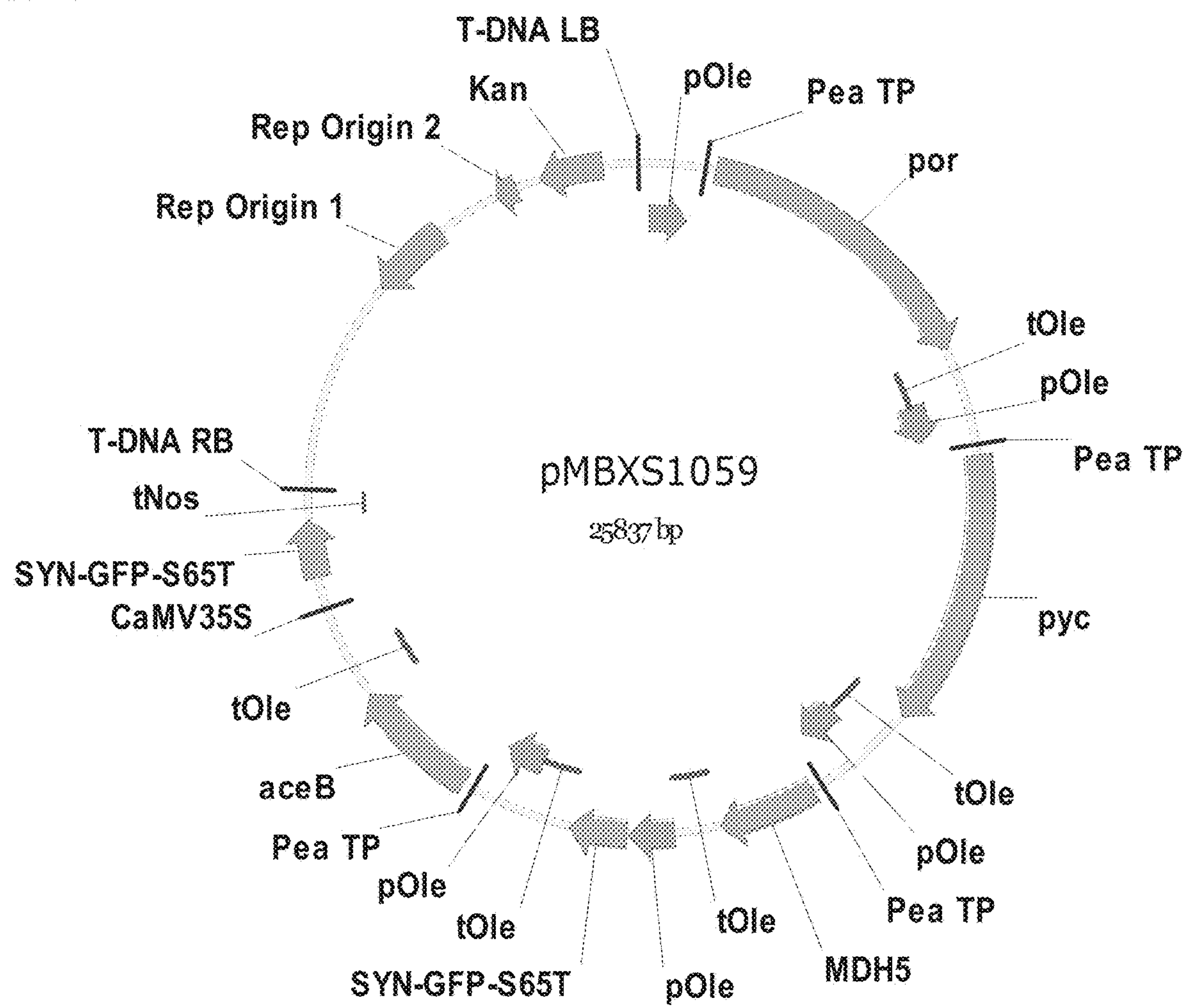
FIG. 15: Plasmid map of vector pMBXS1059.

Construct pMBXS1059 (FIG. 15) contains expression cassettes for pyruvate oxidoreductase (Por), pyruvate carboxylase (Pyc), malate dehydrogenase (Mdh5), and malate synthase (AceB). This construct is designed to enable the conversion of 1 molecule of $CO_2$ and 1 molecule of $HCO_3^-$ to 1 molecule of glyoxylate (FIG. 14(*a*)). This plasmid was transformed into Agrobacterium strain GV3101 (pMP90) and used to vacuum infiltrate Camelina. Transgenic T1 seeds were identified by their GFP fluorescence. T1 seeds of 21 lines were planted in soil in a greenhouse to produce T2 seed.

Figure 16:
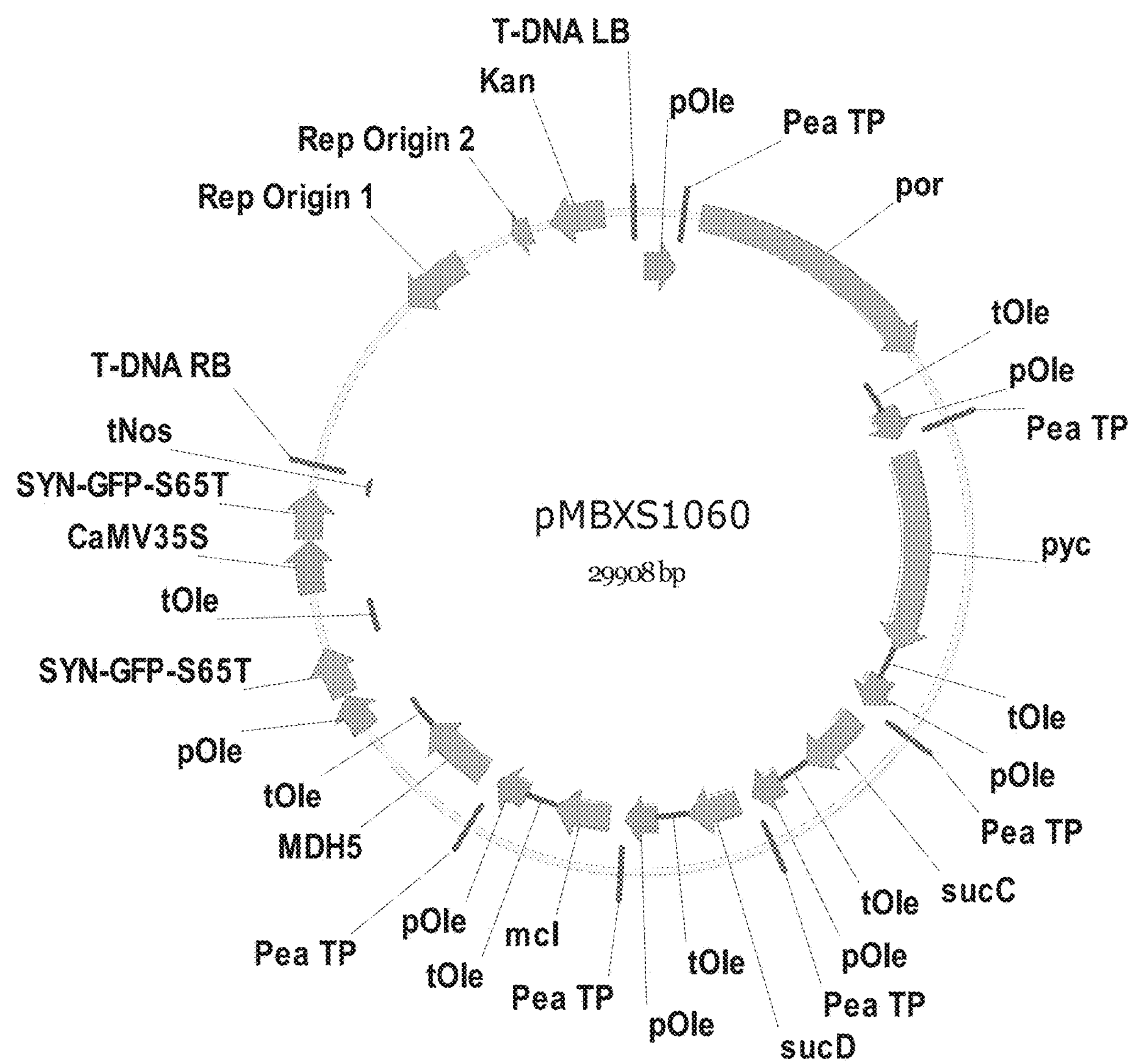
FIG. 16: Plasmid map of vector pMBXS1060.

Construct pMBXS1060 (FIG. 16) contains expression cassettes for pyruvate oxidoreductase (Por), pyruvate carboxylase (Pyc), malate dehydrogenase (Mdh5), malate thiokinase (SucC and SucD), and malyl-CoA lyase (Mcl). This construct is designed to enable the conversion of 1 molecule of $CO_2$ and 1 molecule of $HCO_3^-$ to 1 molecule of glyoxylate (FIG. 14(*b*)). This plasmid was transformed into *Agrobacterium* strain AGL1 and used to vacuum infiltrate Camelina. Transgenic T1 seeds were identified by their GFP fluorescence.

Figure 17:
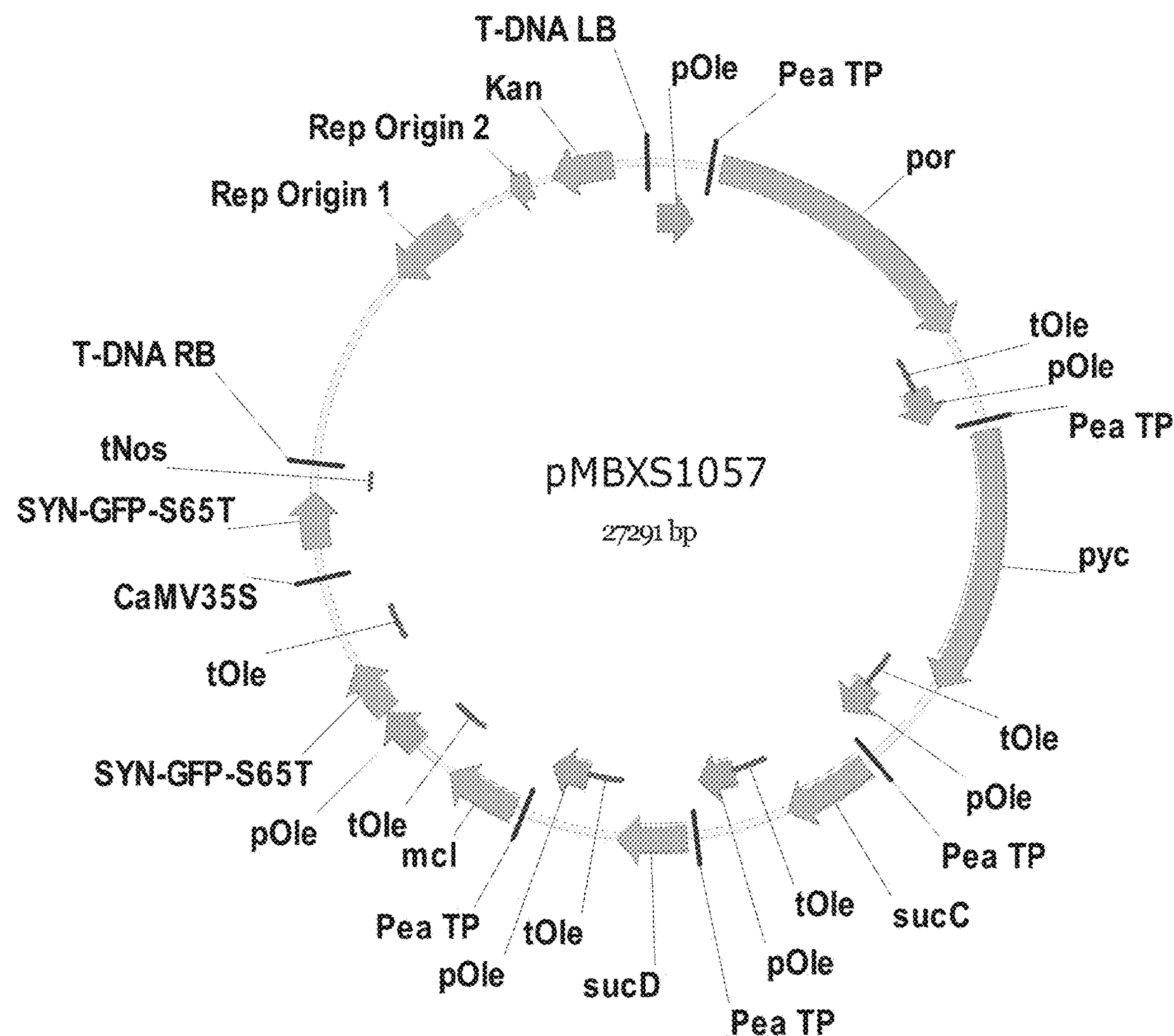
FIG. 17: Plasmid map of vector pMBXS1057.

Construct pMBXS1057 (FIG. 17) contains expression cassettes for pyruvate oxidoreductase (Por), pyruvate carboxylase (Pyc), malate thiokinase (SucC and SucD), and malyl-CoA lyase (Mcl). In the presence of endogenous plant malate dehydrogenase activity, this construct is designed to enable the conversion of 1 molecule of $CO_2$ and 1 molecule of $HCO_3^-$ to 1 molecule of glyoxylate (FIG. 14(*b*)). This plasmid was transformed into *Agrobacterium* strain GV3101 (pMP90) and used to vacuum infiltrate Camelina. Transgenic T1 seeds were identified by their GFP fluorescence. T1 seeds of 50 lines were planted in soil in a greenhouse to produce T2 seed.

Figure 18:
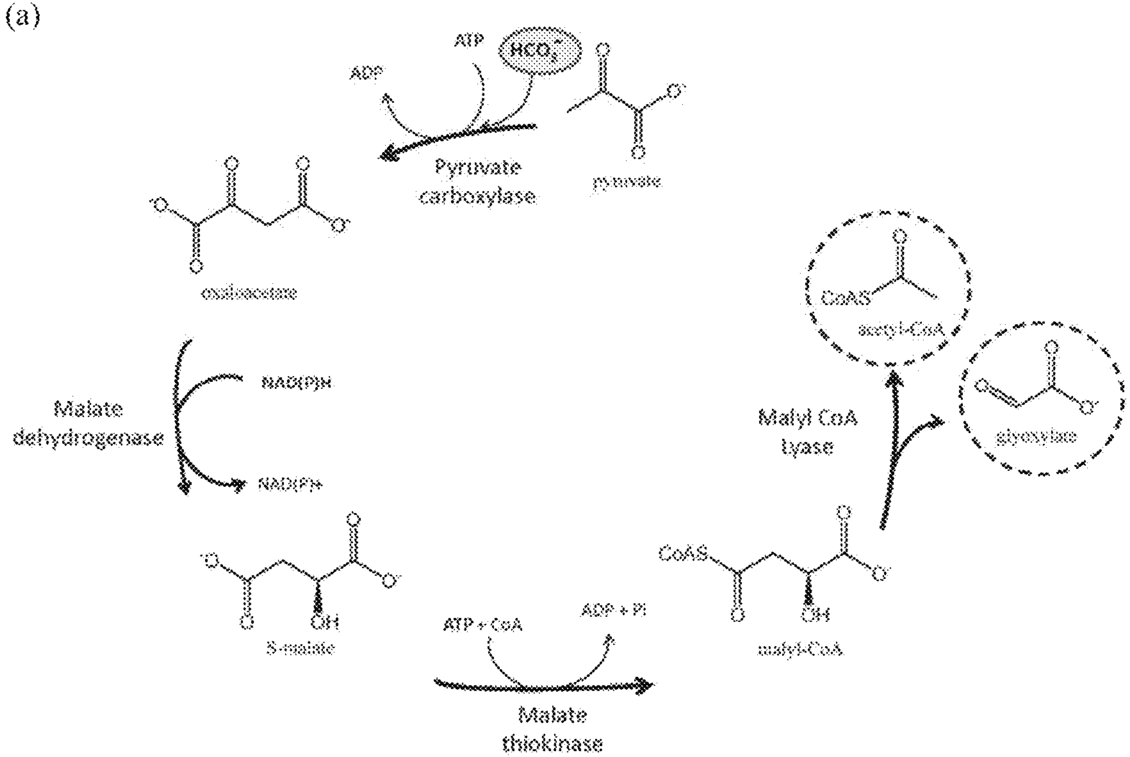
FIG. 18: Metabolic pathways for converting 1 pyruvate and 1 $HCO_3^-$ into 1 acetyl-CoA and 1 glyoxylate. Enzymes to enable conversion are selected from (a) pyruvate carboxylase, malate dehydrogenase, malate thiokinase, and malyl-CoA lyase or (b) pyruvate carboxylase, malate dehydrogenase, and malate synthase. Malate dehydrogenase can be supplied by either an endogenous plant enzyme activity or a transgene encoded activity.
Figure 18:
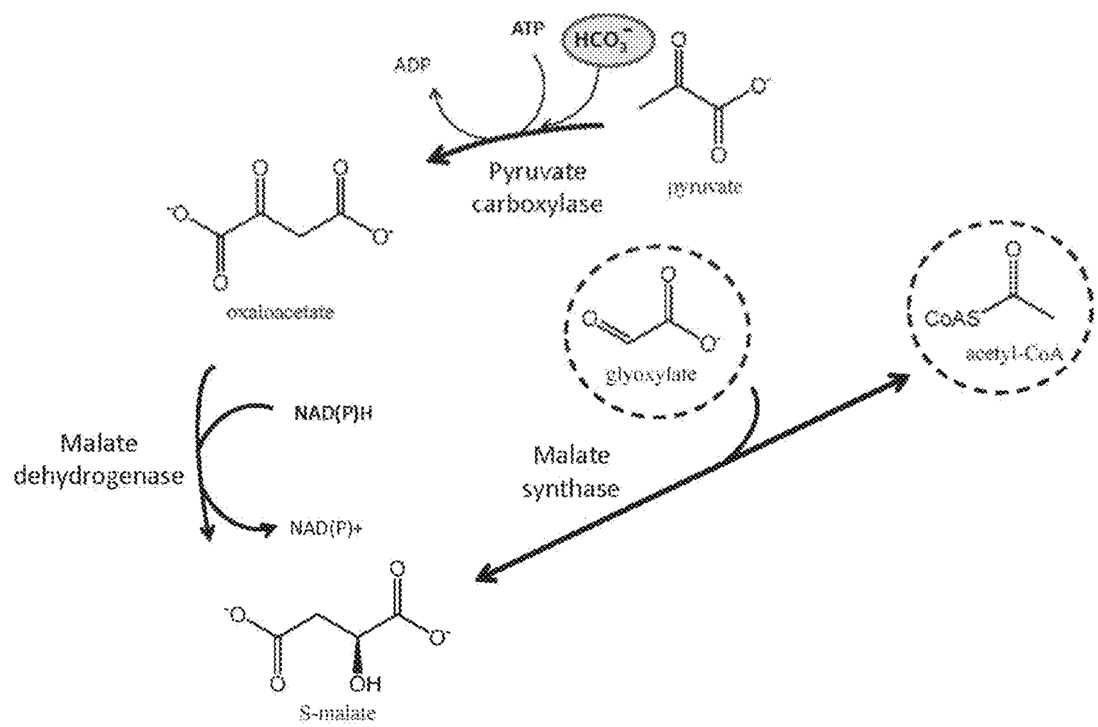

Alternative constructs can be constructed to convert 1 molecule of pyruvate and 1 molecule of $HCO_3^-$ to 1 molecule of acetyl-CoA and 1 molecule of glyoxylate as shown in FIG. 18. These constructs can contain either endogenous or transgene encoded malate dehydrogenase activity.

Example 7

Co-Expression of Yield Enhancing Genes with a Nucleotide Sequence Encoding a Bicarbonate Transporter Operably Linked to a Seed Specific Promoter Examples 1-6 describe novel sets of transgenes to increase seed and/or seed oil yield. These methods can be further enhanced by co-expression of a bicarbonate transporter localized to the chloroplast envelope since diffusion of $CO_2$ across plastid membranes is considered to be a significant limiting factor of photosynthesis (Tholen & Zhu, 2011, Plant Physiol. 156, 90-105). The bicarbonate transporter would increase the supply of bicarbonate ($HCO_3^-$) available to pyruvate carboxylase and, in the presence of a carbonic anhydrase as well as increase the supply of $CO_2$ to the pyruvate oxidoreductase reactions described in Examples 1-6. Carbonic anhydrases are known to be present in chloroplasts to allow the interconversion of bicarbonate and carbon dioxide as shown below:

$$[CO_2+H_2O\longleftrightarrow HCO_3^-+H^+]$$

Bicarbonate transporters from cyanobacteria can be modified with a targeting signal to direct the protein to the chloroplast envelope.

In a preferred embodiment, bicarbonate transporters from green algae that possess chloroplasts and whose bicarbonate transporters already localize to a chloroplast envelope can be used.

In another embodiment, the bicarbonate transporter is encoded by the CCP1 gene [Accession No. XM_001692145.1] (SEQ ID NO: 6) as described in WO2015103074, incorporated herein by reference in its entirety.

In yet another embodiment, the bicarbonate transporter is expressed under a seed specific or constitutive promoter.

In an alternative embodiment, the bicarbonate transporter is expressed under a seed specific or constitutive promoter and does not localize to the plastid, such as the CCP1 gene [Accession No. XM_001692145.1] (SEQ ID NO: 6) as described in U.S. Provisional Patent Application No. 62/291,341.

An expression cassette including a seed specific promoter sequence operably linked to a heterologous nucleotide sequence encoding a bicarbonate transporter can be co-transformed with constructs selected from those described in Examples 1-6. In the case of a cyanobacterial bicarbonate transporter, the transgene nucleotide sequence is modified with a sequence that will direct the bicarbonate transporter to the plastid envelope.

Example 8

Enhancing Yield in Other Crops

Constructs described in Examples 1-7 can be transformed into other crops to increase seed yield.

Transformation of *Brassica napus, Brassica carinata*, and *Brassica juncea.*

Transformation of *Brassica carinata*

*Brassica carinata* can be transformed using a previously described floral dip method (Shiv et al., 2008, Journal of Plant Biochemistry and Biotechnology 17, 1-4). Briefly constructs of interest are transformed into *Agrobacterium* strain GV3101 and cells are grown in liquid medium. Cells are harvested and resuspended in a transformation medium consisting of ½ MS salts, 5% sucrose, and 0.05% Silwet L-77. Brassica carinata plants are grown in a greenhouse until inflorescences develop and approximately 25% of their flowers are opened. Plasmids used for transformation of *Brassica carinata* are modified to encode the biapholos resistance selectable marker. Plants are submerged in a prepared solution of *Agrobacterium* containing the modified pMBXS1022, pMBXS919, or a mixture of *Agrobacterium* strains containing pMBXS1022 and pMBXS919, for approximately 1 minute, and covered for 24 hours. Plants are returned to the greenhouse and allowed to set seed. Transformed seeds are screened by picking DsRed seeds under the appropriate wavelength of light as described above. Transgenic lines are screened and transgenic lines having increased plant yield and/or increased seed yield and/or increased seed oil content are selected.

Transformation of *Brassica napus*

*Brassica* seeds are surface sterilized in 10% commercial bleach (Javex, Colgate-Palmolive) for 30 min with gentle shaking. The seeds are washed three times in sterile distilled water and placed in germination medium comprising Murashige-Skoog (MS) salts and vitamins, 3% (w/v) sucrose and 0.7% (w/v) phytagar, pH 5.8 at a density of 20 per plate and maintained at 24° C. and a 16 h light/8 h dark photoperiod at a light intensity of 60-80 $\mu Em^{-2}s^{-1}$ for 4-5 days.

Construct pMBXS1023 is modified to add the neomycin transferase (nptII) selectable marker. Constructs pMBXS919 or pMBXS1023 are introduced into *Agrobacterium tumefaciens* strain EHA101 (Hood et. al., 1986, J. Bacteriol. 168: 1291-1301) by electroporation. Prior to transformation of cotyledonary petioles, single colonies of strain EHA101 harboring each construct are grown in 5 ml of minimal medium supplemented with appropriate antibiotics for 48 hr at 28° C. One ml of bacterial suspension was pelleted by centrifugation for 1 min in a microfuge. The pellet was resuspended in 1 ml minimal medium.

For transformation, cotyledons are excised from 4 or in some cases 5 day old seedlings so that they included ~2 mm of petiole at the base. Individual cotyledons with the cut surface of their petioles are immersed in diluted bacterial suspension for 1 s and immediately embedded to a depth of ~2 mm in co-cultivation medium, MS medium with 3% (w/v) sucrose and 0.7% phytagar and enriched with 20 μM benzyladenine. For co-transformation of pMBXS1023 and pMBXS919 constructs, the bacterial suspension for immersion contains a mixture of two Agrobacterium strains containing either pMBXS1023 or pMBXS919. The inoculated cotyledons are plated at a density of 10 per plate and incubated under the same growth conditions for 48 h. After co-cultivation, the cotyledons are transferred to regeneration medium comprising MS medium supplemented with 3% sucrose, 20 μM benzyladenine, 0.7% (w/v) phytagar, pH 5.8, 300 mg/L timentin, 20 mg/L Kanamycin and 2.5 mg/L Glufosinate ammonium. After 2-3 weeks regenerant shoots obtained are cut and maintained on "shoot elongation" medium (MS medium containing, 3% sucrose, 300 mg/L timentin, 0.7% (w/v) phytagar, 300 mg/L timentin, 20 mg/L kanamycin and 2.5 mg/L Glufosinate ammonium, pH 5.8) in Magenta jars. The elongated shoots are transferred to "rooting" medium comprising MS medium, 3% sucrose, 2 mg/L indole butyric acid, 0.7% phytagar, 500 mg/L carbenicillin, 20 mg/L kanamycin and 5 mg/L Glufosinate ammonium. After roots emerge, plantlets are transferred to potting mix (Redi Earth, W. R. Grace and Co.). The plants are maintained in a misting chamber (75% relative humidity) under the same growth conditions. Plants are allowed to self pollinate to produce seeds. T1 plantlets are screened by germinating seeds on kanamycin-supplemented medium and subsequently spraying a solution of 400 mg/L of the herbicide Liberty as described above.

*Brassica napus* can also be transformed using the floral dip procedure described by Shiv et al. (Shiv et al., 2008, *Journal of Plant Biochemistry and Biotechnology* 17, 1-4) as described above for *Brassica carinata*. Transgenic lines are screened and transgenic lines having increased plant yield and/or increased seed yield and/or increased seed oil content are selected.

Transformation of *Brassica juncea*

*Brassica juncea* can be transformed using hypocotyl explants according to the methods described by Barfield and Pua (Barfield and Pua, Plant Cell Reports, 10, 308-314) or Pandian et al. (Pandian, et al., 2006, *Plant Molecular Biology Reporter* 24: 103a-103i) as follows:

*B. juncea* seeds are sterilized 2 min in 70% (v/v) ethanol and washed for 20 min in 25% commercial bleach (10 g/L hypochlorite). Seeds are rinsed 3× in sterile water. Surface-sterilized seeds are plated on germination medium (1×MS salts, 1×MS vitamins, 30 g/L sucrose, 500 mg/L MES. pH 5.5) and kept in the cold room for 2 days. Seeds are incubated for 4-6 days at 24° C. under low light (20 μm $m^{-1}s^{-1}$). Hypocotyl segments are excised and rinsed in 50 mL of callus induction medium (1×MS salts, 1×B5 vitamins, 30 g/L sucrose, 500 mg/L MES, 1.0 mg/L 2,4-D, 1.0 mg/L kinetin pH 5.8) for 30 min without agitation. This procedure is repeated but with agitation on orbital shaker (~140 g) for 48 h at 24° C. in low light (10 μm $m^{-1}s^{-1}$).

*Agrobacterium* can be prepared as follows: Cells of *Agrobacterium* strain AGL1 (Lazo, G. et al. (1991), *Biotechnology,* 9: 963-967) containing pMBXS1023 or pMBXS919 are grown in 5 mL of LB medium with appropriate antibiotic at 28° C. for 2 days. The 5 mL culture is transferred to 250 mL flask with 45 mL of LB and cultured for 4 h at 28° C. Cells are pelleted and resuspended in BM medium (1×MS salts, 1×B5 vitamins, 30 g/L sucrose, 500 mg/L MES, pH 5.8). The optical density at 600 nm is adjusted to 0.2 with BM medium and used for inoculation.

Explants are co-cultivated with Agrobacterium containing pMBXS1023, pMBXS919, or a mixture of pMBXS1023 and pMBXS919, for 20 min after which time the *Agrobacterium* suspension is removed. Hypocotyl explants are washed once in callus induction medium after which cocultivation proceeds for 48 h with gentle shaking on orbital shaker. After several washes in CIM, explants are transferred to selective shoot-inducing medium (500 mg/L AgNO2, 0.4 mg/L zeatin riboside, 2.0 mg/L benzylamino purine, 0.01 mg/L GA, 200 mg/L Timentin, appropriate selection agent and 8 g/L agar added to basal medium) plates for regeneration at 24° C. Root formation is induced on root-inducing medium (0.5×MS salts, 0.5×B5 vitamins, 10 g/L sucrose, 500 mg/L MES, 0.1 mg/L indole-3-butyric acid, 200 mg/L Timentin, appropriate selection agent and 8 g/L agar, pH 5.8).

Plantlets are removed from agar, gently washed, and transferred to potting soil in pots. Plants are grown in a humid environment for a week and then transferred to the greenhouse. Transgenic lines are screened and transgenic lines having increased plant yield and/or increased seed yield and/or increased seed oil content are selected.

*Agrobacterium*-Mediated Transformation of Maize

The binary vectors provided in the invention can be used for Agrobacterium-mediated transformation of maize following a previously described procedure (Frame et al., 2006, *Agrobacterium* Protocols Wang K., ed., Vol. 1, pp 185-199, Humana Press). For maize transformation, the visual GFP marker described in pMBXS1023 can be changed to a selectable marker that imparts resistance to glyphosate, such as the CP4 gene.

Plant material: Plants grown in a greenhouse are used as an explant source. Ears are harvested 9-13 d after pollination and surface sterilized with 80% ethanol.

Explant isolation, infection and co-cultivation: Immature zygotic embryos (1.2-2.0 mm) are aseptically dissected from individual kernels and incubated in *A. tumefaciens* strain EHA101 culture (grown in 5 ml N6 medium supplemented with 100 μM acetosyringone for stimulation of the bacterial vir genes for 2-5 h prior to transformation) at room temperature for 5 min. The infected embryos are transferred scutellum side up on to a co-cultivation medium (N6 agar-solidified medium containing 300 mg/l cysteine, 5 μM silver nitrate and 100 μM acetosyringone) and incubated at 20° C., in the dark for 3 d. Embryos are transferred to N6 resting medium containing 100 mg/l cefotaxime, 100 mg/l vancomycin and 5 μM silver nitrate and incubated at 28° C., in the dark for 7 d.

Callus selection: All embryos are transferred on to the first selection medium (the resting medium described above supplemented with 1.5 mg/l bialaphos for selection of pMBXS919 and glyphosate for selection of pMBXS1023) and incubated at 28° C., in the dark for 2 weeks followed by subculture on a selection medium containing glyphosate and 3 mg/l bialaphos. Proliferating pieces of callus are propagated and maintained by subculture on the same medium every 2 weeks.

Plant regeneration and selection: Herbicide resistant embryogenic callus lines are transferred on to regeneration medium I (MS basal medium supplemented with 60 g/l sucrose, glyphosate, 1.5 mg/l bialaphos and mg/l cefotaxime and solidified with 3 g/l Gelrite) and incubated at 25° C., in the dark for 2 to 3 weeks. Mature embryos formed during this period are transferred on to regeneration medium II (the same as regeneration medium I with 3 mg/l bialaphos) for germination in the light (25° C., 80-100 $\mu E/m^2/s$ light intensity, 16/8 -h photoperiod). Regenerated plants are ready for transfer to soil within 10-14 days. Transgenic lines are screened and transgenic lines having increased plant yield and/or increased seed yield are selected.

*Agrobacterium*-Mediated Transformation of Sorghum

The vectors provided in the invention can be used for sorghum transformation following a previously described procedure (Zhao, 2006, *Agrobacterium Protocols* Wang K., ed., Vol. 1, pp 233-244, Humana Press). For sorghum transformation, the visual GFP marker described in pMBXS1023 can be changed to a selectable marker that imparts resistance to phosphinothricin (PPT), such as the pat gene encoding phosphinotricin acetyl transferase. For biomass sorghum or energy sorghum, seed specific promoters in pMBXS1023 and pMBXS919 should be replaced with promoters active in biomass, such as the cab-m5 promoter of the chlorophyll a/b-binding protein in maize (Sullivan et al,. Mol Gen Genet, 1989, 215, 431; Becker et al., Plant Mol Biol, 1992, 20, 49).

Plant material: Plants grown under greenhouse, growth chamber or field conditions are used as an explant source. Immature panicles are harvested 9-12 d post pollination and individual kernels are surface sterilized with 50% bleach for 30 min followed by three washes with sterile distilled water.

Explant isolation, infection and co-cultivation: Immature zygotic embryos (1-1.5 mm) are aseptically dissected from individual kernels and incubated in A. tumefaciens strain LBA4404 suspension in PHI-I liquid medium (MS basal medium supplemented with 1 g/l casamino acids, 1.5 mg/l 2,4-D, 68.5 g/l sucrose, 36 g/l glucose and 100 μM acetosyringone) at room temperature for 5 min. The infected embryos are transferred with embryonic axis down on to a co-cultivation PHI-T medium (agar-solidified modified PHI-I medium containing 2.0 mg/l 2,4-D, 20 g/l sucrose, 10 g/l glucose, 0.5 g/l MES, 0.7 g/l proline, 10 mg/l ascorbic acid and 100 μM acetosyringone) and incubated at 25° C., in the dark for 3 d. For resting, embryos are transferred to the same medium (without acetosyringone) supplemented with 100 mg/l carbenicillin and incubated at 28° C., in the dark for 4 d.

Callus selection: Embryos are transferred on to the first selection medium PHI-U (PHI-T medium described above supplemented with 1.5 mg/l 2,4-D, 100 mg/l carbenicillin and 5 mg/l PPT without glucose and acetosyringone) and incubated at 28° C., in the dark for 2 weeks followed by subculture on a selection medium containing 10 mg/l PPT. Proliferating pieces of callus are propagated and maintained by subculture on the same medium every 2 weeks for the remainder of the callus selection process of 10 weeks.

Plant regeneration and selection: Herbicide-resistant callus is transferred on to regeneration medium I (PHI-U medium supplemented with 0.5 mg/l kinetin) and incubated at 28° C., in the dark for 2 to 3 weeks for callus growth and embryo development. Cultures are transferred on to regeneration medium II (MS basal medium with 0.5 mg/l zeatin, 700 mg/l proline, 60 g/l sucrose and 100 mg/l carbenicillin) for shoot formation (28° C., in the dark). After 2-3 weeks, shoots are transferred on to a rooting medium (regeneration II medium supplemented with 20 g/l sucrose, 0.5 mg/l NAA and 0.5 mg/l IBA) and grown at 25° C., 270 $\mu E/m^2/s$ light intensity with a 16/8-h photoperiod. When the regenerated plants are 8-10 cm tall, they can be transferred to soil and grown under greenhouse conditions. Transgenic lines are screened and transgenic lines having increased plant yield and/or increased seed yield are selected.

*Agrobacterium*-Mediated Transformation of Barley

The vectors pMBXS1023 and/or pMBXS919 provided in the invention can be used for transformation of barley as described by Tingay et al., 1997, Plant J. 11: 1369-1376. For barley transformation, the visual GFP marker described in pMBXS1023 can be changed to a selectable marker that imparts resistance to hygromycin, such as the hygromycin phosphotransferase gene.

Plant material: Plants of the spring cultivar Golden Promise are grown under greenhouse or growth chamber conditions at 18° C. with a 16/8 hours photoperiod. Spikes are harvested when the zygotic embryos are 1.5-2.5 mm in length. Developing caryopses are sterilized with sodium hypochlorite (15% w/v chlorine) for 10 min and rinsed four times with sterile water.

Explant Isolation, Infection and Co-Cultivation:

Immature zygotic embryos are aseptically dissected from individual kernels and after removal of the embryonic axes are placed scutellum side up on a callus induction medium (Gelrite-solidified MS basal medium containing 30 g/l maltose, 1.0 g/l casein hydrolysate, 0.69 g/l proline and 2.5 mg/L dicamba. Embryos are incubated at 24° C. in the dark during subsequent culture. One day after isolation, the embryos are incubated in A. tumefaciens strain AGL1 culture (grown from a single colony in MG/L medium) followed by a transfer on to the medium described above.

Callus Selection:

After co-cultivation for 2-3 d, embryos are transferred on to the callus induction medium supplemented with 50 mg/L hygromycin, 3 mg/l bialaphos and 150 mg/l Timentin. Cultures are selected for about 2 months with transfers to a fresh selection medium every 2 weeks.

Plant Regeneration and Selection:

Bialaphos and hygromycin-resistant embryogenic callus lines are transferred to a Phytagel-solidified regeneration medium containing 1 mg/l BA, 50 mg/L hygromycin, and 3 mg/l bialaphos for selection of transgenic plants and grown at 24° C. under fluorescent lights with a 16/8 h photoperiod. For root development, regenerated plants are transferred to a hormone-free callus induction medium supplemented with 50 mg/L hygromycin and 1 mg/l bialaphos. After development of a root system, plants are transferred to soil and grown in a greenhouse or a growth chamber under the conditions described above. Transgenic lines are screened and transgenic lines having increased plant yield and/or increased seed yield are selected.

*Agrobacterium*-Mediated Transformation of Rice

The binary vectors provided in the invention can be used for *Agrobacterium*-mediated transformation of rice following a previously described procedure (Herve and Kayano, 2006, *Agrobacterium Protocols* Wang K., ed., Vol. 1, pp 213-222, Humana Press). For transformation of rice, the visual GFP marker described in pMBXS1023 can be changed to a selectable marker such as hygromycin appropriate for rice transformation.

Plant material: Mature seeds from japonica rice varieties grown in a greenhouse are used as an explant source.

Culture transformation and selection: Dehusked seeds are surface sterilized with 70% ethanol for 1 min and 3% sodium hypochlorite for 30 min followed by six washes with sterile distilled water. Seeds are plated embryo side up on an induction medium (Gelrite-solidified N6 basal medium supplemented with 300 mg/l casamino acids, 2.88 g/l proline, 30 g/l sucrose and 2 mg/l 2,4-D) and incubated at 32° C., under continuous light for 5 d. Germinated seeds with swelling of the scutellum are infected with *A. tumefaciens* strain LBA4404 (culture from 3-d-old plates resuspended in N6 medium supplemented with 100 μM acetosyringone, 68.5 g/l sucrose and 36 g/l glucose) at room temperature for 2 min followed by transfer on to a co-cultivation medium (N6 Gelrite-solidified medium containing 300 mg/l casamino acids, 30 g/l sucrose, 10 g/l glucose, 2 mg/l 2,4-D and 100 μM acetosyringone) and incubation at 25° C., in the dark for 3 d.

For selection of transformed embryogenic tissues, whole seedlings washed with 250 mg/l cephotaxine are transferred on to N6 agar-solidified medium containing 300 mg/l casamino acids, 2.88 g/l proline, 30 g/l sucrose, 2 mg/l 2,4-D, 100 mg/l cefotaxime, 100 mg/l vancomycin and 35 mg/l G418 disulfate). Cultures are incubated at 32° C., under continuous light for 2-3 weeks.

Plant regeneration and selection: Resistant proliferating calluses are transferred on to agar-solidified N6 medium containing 300 mg/l casamino acids, 500 mg/l proline, 30 g/l sucrose, 1 mg/l NAA, 5 mg/l ABA, 2 mg/l kinetin, 100 mg/l cefotaxime, 100 mg/l vancomycin and 20 mg/l G418 disulfate. After one week of growth at 32° C., under continuous light, the surviving calluses are transferred on to MS medium (solidified with 10 g/l agarose) supplemented with 2 g/l casamino acids, 30 g/l sucrose, 30 g/l sorbitol, 0.02 mg/l NAA, 2 mg/l kinetin, 100 mg/l cefotaxime, 100 mg/l vancomycin and 20 mg/l G418 disulfate and incubated under the same conditions for another week followed by a transfer on to the same medium with 7 g/l agarose. After 2 weeks, the emerging shoots are transferred on to Gelrite-solidified MS hormone-free medium containing 30 g/l sucrose and grown under continuous light for 1-2 weeks to promote shoot and root development. When the regenerated plants are 8-10 cm tall, they can be transferred to soil and grown under greenhouse conditions. After about 10-16 weeks, transgenic seeds are harvested.

Indica rice varieties are transformed with *Agrobacterium* following a similar procedure (Datta and Datta, 2006, *Agrobacterium Protocols* Wang K., ed., Vol. 1, pp 201-212, Humana Press).

Following transformation transgenic lines are screened and plants having increased plant yield and/or increased seed yield are selected.

Microprojectile Bombardment-Mediated Transformation of Sugarcane

For transformation of sugarcane the visual GFP marker described in pMBXS1023 can be changed to a selectable marker appropriate for sugarcane transformation, such as the npt gene. Transformation of sugarcane via biolistics follows a previously described protocol (Taparia et al., 2012, *In Vitro Cell. Dev. Biol.* 48: 15-22))

Plant material: Greenhouse-grown plants with 6-8 visible nodes are used as an explant source. Tops are collected and surface sterilized with 70% ethanol. The outermost leaves are removed under aseptic conditions and immature leaf whorl cross sections (about 2 mm) are cut from the region 1-10 cm above the apical node.

Culture initiation, transformation and selection: The isolated leaf sections are cultured on MS basal media supplemented with 20 g/l sucrose, 1.86 mg/l p-chlorophenoxyacetic acid (CPA), 1.86 mg/l NAA and 0.09 mg/l BA at 28° C., under 30 μmol/m$^2$/s light intensity and a 16/8-h photoperiod for 7 d. Embryogenic cultures are subcultured to fresh medium and used for transformation.

For microprojectile bombardment, leaf disks are plated on the culture initiation medium supplemented with 0.4 M sorbitol 4 hours before gene transfer. Plasmid DNA (200 ng) containing plasmids pMBXS919 and/or pMBXS1023, modified to contain the appropriate selectable marker gene, is precipitated onto 1.8 mg gold particles (0.6 μm) following a previously described procedure (Altpeter and Sandhu, 2010, *Genetic transformation—biolistics,* Davey & Anthony eds., pp 217-237, Wiley, Hoboken). The DNA (10 ng per shot) is delivered to the explants by a PDS-100 Biolistic particle delivery system (Biorad) using 1100-psi rupture disk, 26.5 mmHg chamber vacuum and a shelf distance of 6 cm. pressure). The bombarded explants are transferred to the culture initiation medium described above and incubated for 4 days.

For selection, cultures are transferred on to the initiation medium supplemented with 30 mg/l geneticin and incubated for 10 d followed by another selection cycle under the same conditions.

Plant regeneration and selection: Cultures are transferred on to the selection medium described above without CPA and grown at 28° C., under 100 μmol/m$^2$/s light intensity with a 16/8-h photoperiod. Leaf disks with small shoots (about 0.5 cm) are plated on a hormone-free medium with 30 mg/l geneticin for shoot growth and root development. Prior to transfer to soil, roots of regenerated plants can be dipped into a commercially available root promoting powder. Transgenic lines are screened and transgenic lines having increased plant yield and/or increased sugar production are selected.

Transformation of Wheat by Microprojectile Bombardment

The gene constructs provided in the invention can be used for wheat transformation by microprojectile bombardment following a previously described protocol (Weeks et al., 1993, *Plant Physiol* 102: 1077-1084). For transformation of wheat, the visual GFP marker described in pMBXS1023 can be changed to a selectable marker appropriate for wheat transformation, such as the hygromycin phosphotransferase (hph) and phosphomannose isomerase (pmi) genes imparting resistance to hygromycin and mannose, respectively.

Plant material: Plants from the spring wheat cultivar Bobwhite are grown at 18-20° C. day and 14-16° C. night temperatures under a 16 h photoperiod. Spikes are collected 10-12 weeks after sowing (12-16 days post anthesis). Individual caryopses at the early-medium milk stage are sterilized with 70% ethanol for 5 min and 20% sodium hypochlorite for 15 min followed by three washes with sterile water.

Culture initiation, transformation and selection: Immature zygotic embryos (0.5-1.5 mm) are dissected under aseptic conditions, placed scutellum side up on a culture induction medium (Phytagel-solidified MS medium containing 20 g/l sucrose and 1.5 mg/l 2,4-D) and incubated at 27° C., in the light (43 μmol/m$^2$/s) for 3-5 d.

For microprojectile bombardment, embryo-derived calluses are plated on the culture initiation medium supplemented with 0.4 M sorbitol 4 hours before gene transfer. Plasmid DNA containing pMBXS919 and/or pMBXS1023 and the marker gene bar and hpt is precipitated onto 0.6-μm gold particles and delivered to the explants as described for sugarcane.

The bombarded explants are transferred to callus selection medium (the culture initiation medium described above containing 1-2 mg/l bialaphos and 25 mg/L hygromycin and subcultured every 2 weeks.

Plant regeneration and selection: After one-two selection cycles, cultures are transferred on to MS regeneration medium supplemented with 25 mg/L hygromycin, and 2 mg/l bialaphos. For root formation, the resulting antibiotic and herbicide-resistant shoots are transferred to hormone-free half-strength MS medium. Plants with well-developed roots are transferred to soil and acclimated to lower humidity at 21° C. with a 16-h photoperiod (300 μmol/m$^2$/s) for about 2 weeks prior to transfer to a greenhouse. Transgenic lines are screened and transgenic lines having increased plant yield and/or increased seed yield are selected.

*Agrobacterium*-Mediated Transformation of Soybean

For transformation of soybean, the visual GFP marker described in pMBXS1023 can be changed to a selectable marker appropriate for soybean transformation, such as a gene imparting resistance to hygromycin. *Agrobacterium*-mediated transformation of soybean following a previously described procedure (Ko et al., 2006, *Agrobacterium Protocols* Wang K., ed., Vol. 1, pp 397-405, Humana Press).

Plant material: Immature seeds from soybean plants grown under greenhouse or field conditions are used as an explant source. Young pods are harvested and surface sterilized with 70% 2-propanol for 30 sec and 25% Clorox for 20 min followed by three washes with sterile distilled water.

Culture transformation and selection: Under aseptic conditions, immature seeds are removed from the pods and the cotyledons are separated from the seed coat followed by incubation in *A. tumefaciens* culture (grown from a single colony at 28° C., overnight) in co-cultivation medium (MS salts and B5 vitamins) supplemented with 30 g/l sucrose, 40 mg/l 2,4-D and 40 mg/l acetosyringone for 60 min. Infected explants are plated abaxial side up on agar-solidified co-cultivation medium and incubated at 25° C., in the dark for 4 d.

For selection of transformed tissues, cotyledons washed with 500 mg/l cephotaxine are placed abaxial side up on a medium for induction of somatic embryo formation (Gelrite-solidified MS medium containing 30 g/l sucrose, 40 mg/l 2,4-D, 500 mg/l cefotaxime, 3 mg/L glufosinate and 10 mg/l hygromycin) and incubated at 25° C., under a 23-h photoperiod (10-20 μE/m$^2$/s) for 2 weeks. After another two weeks of growth under the same conditions in the presence of 6 mg/L glufosinate and 25 mg/l hygromycin, the antibiotic-resistant somatic embryos are transferred on MS medium for embryo maturation supplemented with 60 g/l maltose, 500 mg/l cefotaxime, 3 mg/L glufosinate, and 10 mg/l hygromycin and grown under the same conditions for 8 weeks with 2-week subculture intervals.

Plant regeneration and selection: The resulting cotyledonary stage embryos are desiccated at 25° C., under a 23-h photoperiod (60-80 μE/m$^2$/s) for 5-7 d followed by culture on MS regeneration medium containing 30 g/l sucrose and 500 mg/l cefotaxime for 4-6 weeks for shoot and root development. When the plants are 5-10 cm tall, they are transferred to soil and grown in a greenhouse after acclimatization for 7 d. Transgenic lines are screened and plants having increased plant yield or seed yield and/or oil content are selected.

Microprojectile Bombardment-Mediated Transformation of Soybean

The genes in constructs pMBXS919 or pMBXS1023 can be co-bombarded with hygromycin resistance gene via biolistics into embryogenic cultures of soybean to obtain transgenic plants. The transformation, selection, and plant regeneration protocols were described previously (Santarém E R, J J Finer, 1999. In Vitro Cellular and Developmental Biology—Plant 35:451-455.)

Plant material: Immature zygotic embryos are isolated from developing pods from plants grown under greenhouse conditions or field. The cotyledons are excised and plated on MS salts and B5 vitamins, 6% sucrose, 40 mg/l 2,4-D, (pH 7.0) and 0.2% Gelrite for 3-4 weeks at 27° C. under a 16-h photoperiod (30 μE/m$^2$/s) to induce somatic embryos.

Transformation and selection: Bright green, globular, proliferative embryos are transferred to MS salts and B5 vitamins, 3% sucrose, 5 mM asparagine, 20 mg/l 2,4-D (pH 5.7) and 0.2% Gelrite and are subcultured every 2-3 weeks. Embryogenic tissues are subcultured 3-5 days prior to bombardment on the same media. For bombardment, clusters of embryogenic tissues are placed in the center of 90 mm Petri dishes containing the media and co-bombarded, using bombardment apparatus, with a fragment containing genes in constructs pMBXS919 or pMBXS1023 and a fragment with the hygromycin gene precipitated on gold particles.

For selection, after one week all tissues are transferred to MS salts with B5 vitamins, 3% sucrose, 5 mM asparagine, 20 mg/l 2,4-D, 15 mg/L Hygromycin (pH 5.7) and 0.2% Gelrite for 3-4 weeks. All resistant tissues are selected and transferred to fresh media until embryos are cream-colored and ready for desiccation.

Embryo maturation and germination: Clones are regenerated by first placing embryos on MS salts with B5 vitamins, 6% Maltose (pH 5.7), 0.2% Gelrite and 0.5% activated charcoal for 3-4 weeks. Embryos are desiccated in a dry Petri dish sealed with parafilm and placed on the shelf for 2-5 days and germinated on growth regulator-free MS medium. Plants are transferred to soil after optimum root and shoot formation.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

TABLE 11

DNA and protein sequences showing significant similarity to *Chlamydomonas reinhardtii* CCP1 determined from a tBLASTN search of Genbank using accession number XM_001692145 for C.r. CCP1 protein.

| Accession Numbers\| Description | E Value |
|---|---|
| *Chlamydomonas reinhardtii* | |
| ref\|XM 001692145.1\| *Chlamydomonas reinhardtii* strain CC-503 | 0 |
| gb\|U75345.1\| CRU75345 *Chlamydomonas reinhardtii* envelope prote . . . | 0 |
| ref\|XM 001692236.1\| *Chlamydomonas reinhardtii* strain CC-503 c . . . | 0 |
| gb\|U75346.1\| CRU75346 *Chlamydomonas reinhardtii* envelope prote . . . | 0 |
| ref\|XM 001691276.1\| *Chlamydomonas reinhardtii* strain CC-503 | 6.00E−29 |
| ref\|XM 001703524.1\| *Chlamydomonas reinhardtii* | 2.00E−21 |
| ref\|XM 001696176.1\| *Chlamydomonas reinhardtii* strain CC-503 | 1.00E−13 |
| Other Algae | |
| ref\|XM 002951197.1\| *Volvox carteri f. nagariensis* | 0 |
| ref\|XM 005707055.1\| *Galdieria sulphuraria* | 9.00E−44 |
| ref\|XM_002180092.1\| *Phaeodactylum tricornutum* CCAP 1055/1 | 1.00E−36 |
| ref\|XM 005650930.1\| *Coccomyxa subellipsoidea* C-169 | 3.00E−36 |
| ref\|XM_005846489.1\| *Chlorella variabilis* | 8.00E−35 |
| ref\|XM_005715654.1\| *Chondrus crispus* | 3.00E−31 |
| ref\|XM_005852157.1\| *Chlorella variabilis* | 2.00E−30 |
| ref\|XM_005835528.1\| *Guillardia theta* CCMP2712 | 2.00E−29 |

TABLE 11-continued

DNA and protein sequences showing significant similarity to *Chlamydomonas reinhardtii* CCP1 determined from a tBLASTN search of Genbank using accession number XM_001692145 for C.r. CCP1 protein.

| Accession Numbers\| Description | E Value |
|---|---|
| ref\|XM_001416612.1\| *Ostreococcus lucimarinus* CCE9901 | 5.00E−29 |
| ref\|XM_005648666.1\| *Coccomyxa subellipsoidea* C-169 | 7.00E−29 |
| ref\|XM 005713259.1\| *Chondrus crispus Putative* | 1.00E−28 |
| ref\|XM_002290899.1\| *Thalassiosira pseudonana* CCMP1335 | 5.00E−28 |
| ref\|XM_003062315.1\| *Micromonas pusilla* CCMP1545 | 9.00E−28 |
| ref\|XM_002501234.1\| *Micromonas* sp. RCC299 | 2.00E−27 |
| ref\|XM_003078113.1\| *Ostreococcus tauri* | 2.00E−27 |
| ref\|XM_002287074.1\| *Thalassiosira pseudonana* CCMP1335 | 3.00E−27 |
| gb\|CP000583.1\| *Ostreococcus lucimarinus* CCE9901 | 5.00E−27 |
| gb\|CP001325.1\| *Micromonas* sp. RCC299 | 8.00E−27 |
| ref\|XM 005761119.1\| *Emiliania huxleyi* CCMP1516 | 2.00E−26 |
| ref\|XM_005770260.1\| *Emiliania huxleyi* CCMP1516 | 2.00E−26 |
| ref\|XM_005782860.1\| *Emiliania huxleyi* CCMP1516 | 4.00E−26 |
| ref\|XM 005780967.1\| *Emiliania huxleyi* CCMP1516 | 9.00E−26 |
| ref\|XM_002505238.1\| *Micromonas* sp. RCC299 | 3.00E−24 |
| gb\|GU554694.1\| uncultured dinoflagellate | 1.00E−23 |
| ref\|XM_005645863.1\| *Coccomyxa subellipsoidea* C-169 | 1.00E−23 |
| gb\|CP001330.1\| *Micromonas* sp. RCC299 | 3.00E−23 |
| ref\|XM_005821628.1\| *Guillardia theta* CCMP2712 | 1.00E−22 |
| ref\|XM_005839321.1\| *Guillardia theta* CCMP2712 | 1.00E−22 |
| ref\|XM_002181059 .1\| *Phaeodactylum tricornutum* CCAP 1055/1 | 3.00E−22 |
| ref\|XM_005843001.1\| *Chlorella variabilis* | 3.00E−22 |
| ref\|XM_005820122.1\| *Guillardia theta* CCMP2712 | 4.00E−22 |
| ref\|\|XM_002507318.1\| *Micromonas* sp. RCC299 | 4.00E−21 |
| ref\|XM_002186292.1\| *Phaeodactylum tricornutum* CCAP 1055/1 | 1.00E−20 |
| ref\|XM_005855105.1\| *Nannochloropsis gaditana* CCMP526 | 5.00E−20 |
| ref\|XM_005650392.1\| *Coccomyxa subellipsoidea* C-169 | 2.00E−19 |
| gb\|HQ199284.1\| *Karlodinium micrum* | 2.00E−19 |
| ref\|XM_002292980.1\| *Thalassiosira pseudonana* CCMP1335 | 2.00E−18 |
| ref\|XM_002178459.1\| *Phaeodactylum tricornutum* CCAP 1055/1 | 1.00E−17 |
| ref\|XM 005834754.1\| *Guillardia theta* CCMP2712 | 3.00E−17 |
| ref\|XM 002288920.1\| *Thalassiosira pseudonana* CCMP1335 | 3.00E−17 |
| ref\|XM 001421091.1\| *Ostreococcus lucimarinus* CCE9901 | 3.00E−17 |
| ref\|XM 001422789.1\| *Ostreococcus lucimarinus* CCE9901 | 3.00E−17 |
| ref\|XM 002292865.1\| *Thalassiosira pseudonana* CCMP1335 | 4.00E−17 |
| gb\|CP000601.1\| *Ostreococcus lucimarinus* CCE9901 | 2.00E−16 |
| gb\|CP000593.1\| *Ostreococcus lucimarinus* CCE9901 | 2.00E−16 |
| ref\|XM 003075149.1\| *Ostreococcus tauri* | 6.00E−16 |
| ref\|XM 001416252.1\| *Ostreococcus lucimarinus* CCE9901 | 1.00E−15 |
| ref\|XM 002295407.1\| *Thalassiosira pseudonana* CCMP1335 | 1.00E−15 |
| ref\|XM 002292854.1\| *Thalassiosira pseudonana* CCMP1335 | 1.00E−15 |
| ref\|XM 002179955.1\| *Phaeodactylum tricornutum* CCAP 1055/1 | 2.00E−15 |
| gb\|CP000582.1\| *Ostreococcus lucimarinus* CCE9901 | 2.00E−15 |
| ref\|XM 005705684.1\| *Galdieria sulphuraria* | 6.00E−15 |
| ref\|XM 002502386.1\| *Micromonas* sp. RCC299 | 7.00E−15 |
| ref\|XM 005538709.1\| *Cyanidioschyzon merolae* strain 10D | 7.00E−15 |
| ref\|XM 003060288.1\| *Micromonas pusilla* CCMP1545 | 1.00E−14 |
| ref\|XM 002287700.1\| *Thalassiosira pseudonana* CCMP1335 | 1.00E−14 |
| ref\|XM 005706410.1\| *Galdieria sulphuraria* | 1.00E−14 |
| ref\|XM 002501612.1\| *Micromonas* sp. RCC299 | 1.00E−14 |
| ref\|XM 002957505.1\| *Volvox carteri f. nagariensis* | 1.00E−14 |
| ref\|XM 001416306.1\| *Ostreococcus lucimarinus* CCE9901 | 2.00E−14 |
| ref\|XM 005705667.1\| *Galdieria sulphuraria* | 2.00E−14 |
| ref\|XM 002952252.1\| *Volvox carteri f. nagariensis* | 2.00E−14 |
| ref\|XM 002184902.1\| *Phaeodactylum tricornutum* CCAP 1055/1 | 3.00E−14 |
| ref\|XM 003082660.1\| *Ostreococcus tauri* | 3.00E−14 |
| dbj\|AP006501.2\| *Cyanidioschyzon merolae* strain 10D | 4.00E−14 |
| gb\|CP001326.1\| *Micromonas* sp. RCC299 | 6.00E−14 |
| ref\|XM_005833520.1\| *Guillardia theta* CCMP2712 hypothetical | 7.00E−14 |
| ref\|XM_002181779.1\| *Phaeodactylum tricornutum* CCAP 1055/1 | 9.00E−14 |
| ref\|XM 002183511.1\| *Phaeodactylum tricornutum* CCAP 1055/1 | 9.00E−14 |
| ref\|XM 005645399.1\| *Coccomyxa subellipsoidea* C-169 | 2.00E−13 |
| ref\|XM 005645636.1\| *Coccomyxa subellipsoidea* C-169 | 2.00E−13 |
| ref\|XM 005712871.1\| *Chondrus crispus* | 3.00E−13 |
| ref\|XM 002294126.1\| *Thalassiosira pseudonana* CCMP1335 | 3.00E−13 |
| ref\|XM 002945774.1\| *Volvox carteri f. nagariensis* | 4.00E−13 |
| ref\|XM 001696541.1\| *Chlamydomonas reinhardtii* | 4.00E−13 |
| ref\|XM 005830601.1\| *Guillardia theta* CCMP2712 | 5.00E−13 |
| ref\|XM 002286219.1\| *Thalassiosira pseudonana* CCMP1335 | 5.00E−13 |
| ref\|XM 005704882.1\| *Galdieria sulphuraria* | 6.00E−13 |
| ref\|XM 005703227.1\| *Galdieria sulphuraria* | 7.00E−13 |
| ref\|XM 005851446.1\| *Chlorella variabilis* | 9.00E−13 |
| emb\|FO082276.1\| *Bathycoccus prasinos* | 2.00E−12 |
| ref\|XM 003057854.1\| *Micromonas pusilla* CCMP1545 | 2.00E−12 |

TABLE 11-continued

DNA and protein sequences showing significant similarity to *Chlamydomonas reinhardtii* CCP1 determined from a tBLASTN search of Genbank using accession number XM_001692145 for C.r. CCP1 protein.

| Accession Numbers\| Description | E Value |
|---|---|
| ref\|XM 005829724.1\| *Guillardia theta* CCMP2712 | 2.00E−12 |
| ref\|XM 001692202.1\| *Chlamydomonas reinhardtii* strain CC-503 | 3.00E−12 |
| ref\|XM 002952755.1\| *Volvox carteri f. nagariensis* | 4.00E−12 |
| ref\|XM 002290151.1\| *Thalassiosira pseudonana* CCMP1335 | 4.00E−12 |
| ref\|XM 003080464.1\| *Ostreococcus tauri* | 4.00E−12 |
| ref\|XM 001698874.1\| *Chlamydomonas reinhardtii* | 5.00E−12 |
| ref\|XM 005702733.1\| *Galdieria sulphuraria* | 5.00E−12 |
| ref\|XM 005649150.1\| *Coccomyxa subellipsoidea* C-169 | 7.00E−12 |
| ref\|XM 005702730.1\| *Galdieria sulphuraria* | 7.00E−12 |
| ref\|XM 001418979.1\| *Ostreococcus lucimarinus* CCE9901 | 9.00E−12 |
| ref\|XM 005836140.1\| *Guillardia theta* CCMP2712 | 9.00E−12 |
| Diatoms | |
| ref\|XM_002180092.1\| *Phaeodactylum tricomutum* CCAP 1055/1 | 1.00E−37 |
| ref\|XM_002290899.1\| *Thalassiosira pseudonana* CCMP1335 | 5.00E−29 |
| ref\|XM_002287074.1\| *Thalassiosira pseudonana* CCMP1335 | 3.00E−28 |
| ref\|XM_002181059.1\| *Phaeodactylum tricomutum* CCAP 1055/1 | 3.00E−23 |
| ref\|XM_002186292.1\| *Phaeodactylum tricomutum* CCAP 1055/1 | 1.00E−21 |
| ref\|XM_002292980.1\| *Thalassiosira pseudonana* CCMP1335 | 2.00E−19 |
| ref\|XM_002178459.1\| *Phaeodactylum tricomutum* CCAP 1055/1 | 2.00E−18 |
| ref\|XM_002288920.1\| *Thalassiosira pseudonana* CCMP1335 | 3.00E−18 |
| ref\|XM_002292865.1\| *Thalassiosira pseudonana* CCMP1335 | 4.00E−18 |
| ref\|XM_002295407.1\| *Thalassiosira pseudonana* CCMP1335 | 1.00E−16 |
| ref\|XM_002292854.1\| *Thalassiosira pseudonana* CCMP1335 | 1.00E−16 |
| ref\|XM_002179955.1\| *Phaeodactylum tricomutum* CCAP 1055/1 | 2.00E−16 |
| ref\|XM_002287700.1\| *Thalassiosira pseudonana* CCMP1335 | 1.00E−15 |
| ref\|XM_002184902.1\| *Phaeodactylum tricomutum* CCAP 1055/1 | 3.00E−15 |
| ref\|XM_002179954.1\| *Phaeodactylum tricomutum* CCAP 1055/1 | 3.00E−15 |
| ref\|XM_002181779.1\| *Phaeodactylum tricomutum* CCAP 1055/1 | 9.00E−15 |
| ref\|XM_002183511.1\| *Phaeodactylum tricomutum* CCAP 1055/1 | 1.00E−14 |
| ref\|XM_002294126.1\| *Thalassiosira pseudonana* CCMP1335 | 3.00E−14 |
| ref\|XM 002286219.1\| *Thalassiosira pseudonana* CCMP1335 | 5.00E−14 |
| ref\|XM 002184448.1\| *Phaeodactylum tricomutum* CCAP 1055/1 | 1.00E−13 |
| gb\|AC151917.1\| *Phaeodactylum tricomutum* clone JGIAHOK-13P1, | 3.00E−13 |
| ref\|XM 002290151.1\| *Thalassiosira pseudonana* CCMP1335 | 4.00E−13 |
| ref\|XM 002185993.1\| *Phaeodactylum tricomutum* CCAP 1055/1 | 1.00E−12 |
| gb\|CP001142.1\| *Phaeodactylum tricomutum* CCAP 1055/1 | 1.00E−12 |
| ref\|XM 002287767.1\| *Thalassiosira pseudonana* CCMP1335 | 1.00E−12 |
| ref\|XM 002288448.1\| *Thalassiosira pseudonana* CCMP1335 | 6.00E−12 |
| ref\|XM 002185105.1\| *Phaeodactylum tricomutum* CCAP 1055/1 | 3.00E−11 |
| ref\|XM 002289746.1\| *Thalassiosira pseudonana* CCMP1335 | 6.00E−11 |
| ref\|XM 002287949.1\| *Thalassiosira pseudonana* CCMP1335 | 8.00E−11 |
| ref\|XM 002292598.1\| *Thalassiosira pseudonana* CCMP1335 | 2.00E−10 |
| ref\|XM 002181188.1\| *Phaeodactylum tricomutum* CCAP 1055/1 | 3.00E−10 |
| ref\|XM 002185854.1\| *Phaeodactylum tricomutum* CCAP 1055/1 | 6.00E−10 |

TABLE 12

Proteins with homology to *Chlamydomonas reinhardtii* CCP1 in edible algae.

| | Necleotide | | Homology to CCP1 | | | | | |
|---|---|---|---|---|---|---|---|---|
| | Accession (and SEQ ID NO of | Number of amino | Consensus positions | Identity Positions | Program | | | |
| Organism | corresponding protein) | acids | (%) | (%) | Motif Finder[a] | | ProSite[b] | |
| *Chlamydomonas reinhardtii* | XM_001692145.1 | 358 | 100 | 100 | Mitochondrial carrier protein | 3 predicted motifs sparming amino acids 28-119; 129-235; & 245-334 | Solute carrier protein[c] | 3 predicted motifs spanning amino acids 22-118; 131-231;& 246-333 |
| *Chlorella sorokiniana* | GAPD01006726.1 | 354[d] | 72.8 | 59.9 | Mitochondrial carrier protein | 3 predicted motifs spanning amino acids 25-117; 128-228; & 243-329 | Solute carrier protein[c] | 3 predicted motifs spanning amino acids 20-116; 131-227; & 238-325 |

TABLE 12-continued

Proteins with homology to *Chlamydomonas reinhardtii* CCP1 in edible algae.

| Organism | Necleotide Accession (and SEQ ID NO of corresponding protein) | Number of amino acids | Homology to CCP1 Consensus positions (%) | Homology to CCP1 Identity Positions (%) | Program Motif Finder[a] | | Program ProSite[b] | |
|---|---|---|---|---|---|---|---|---|
| *Chlorella* variabilis | XM_005846489.1 | 303 | 42.5 | 25.8 | Mitochondrial carrier protein | 3 predicted motifs spanning amino acids 25-117; 128-228; & 243-329 | Solute carrier protein[c] | 3 predicted motifs spanning amino acids 3-86; 96-200; & 212-300 |
| *Chlorella variabilis* | XM_005852157.1 | 323 | 40.3 | 25.2 | Mitochondrial carrier protein | 3 predicted motifs spanning amino acids 4-88; 97-199; & 121-301 | Solute carrier protein[c] | 3 predicted motifs spanning amino acids 25-112; 124-218; & 230-319 |
| *Chlorella variabilis* | XM_005843001.1 | 323 | 39.3 | 24.7 | Mitochondrial carrier protein | 3 predicted motifs spanning amino acids 26-115; 125-221; & 229-322 | Solute carrier protein[c] | 3 predicted motifs spanning amino acids 8-92; 101-189; & 221-308 |
| *Chondrus crispus* | XM_005712871.1 | 328 | 34.7 | 20.3 | Mitochondrial carrier protein | 3 predicted motifs spanning amino acids 9-90; 108-187; & 225-307 | Solute carrier protein[c] | 3 predicted motifs spanning amino acids 39-128; 135-227; & 238-324 |
| *Chlorella variabilis* | XM_005851446.1 | 306 | 35.8 | 21.7 | Mitochondrial carrier protein | 3 predicted motifs spanning amino acids 11-101; 112-206; & 213-299 | Solute carrier protein[c] | 3 predicted motifs spanning amino acids 11-100; 112-203; & 212-298 |
| *Chondrus crispus* | XM_005715654.1 | 233 | 35.2 | 22.9 | Mitochondrial carrier protein | 3 predicted motifs spanning amino acids 3-40; 47-132; & 141-231 | Solute carrier protein[c] | 3 predicted motifs spanning amino acids 1-37; 47-131; & 142-229 |
| *Chondrus crispus* | XM_005713259.1 | 194 | 29.9 | 18.4 | Mitochondrial carrier protein | 2 predicted motifs spanning amino acids 7-93 & 102-191 | Solute carrier protein[c] | 2 predicted motifs spanning amino acids 8-92 & 103-190 |

[a]website: www.genome.jp/tools/motif/

[b]website: prosite.expasy.org/

[c]Predicted as one of several substrate carrier proteins involved in energy transfer in the inner mitochondrial membrane (website: prosite.expasy.org/cgi-bin/prosite/nicedoc.pl?PS50920)

[d]sequence from first methionine of deposited transcribed mRNA sequence to first stop codon

What is claimed is:

1. A transgenic plant comprising two or more heterologous enzymes, each heterologous enzyme encoded by a transgene, wherein:
   - the two or more heterologous enzymes comprise a pyruvate carboxylase (Pyc) and a malate synthase (AceB); and
   - the transgenic plant has one or more increased properties selected from seed yield or seed oil content compared to a plant of the same species not comprising the one or more heterologous enzymes.

2. The transgenic plant according to claim 1, wherein the transgene encoding each of the one or more heterologous enzymes comprises a nucleotide sequence encoding a plastid signal peptide directing the one or more heterologous enzymes to the plastids of the transgenic plant.

3. The transgenic plant according to claim 1, wherein the transgene encoding each of the one or more heterologous enzymes is expressed from a seed specific promoter.

4. The transgenic plant according to claim 1, wherein the transgenic plant was produced from camelina, a *Brassica* species, *Brassica napus, Brassica rapa, Brassica juncea, Brassica carinata, crambe*, soybean, sunflower, safflower, oil palm, flax, or cotton.

5. The transgenic plant according to claim 1, wherein the transgenic plant was produced from camelina.

6. The transgenic plant of claim 1, wherein the transgenic plant has the one or more properties increased by at least 15% compared to a plant of the same species not comprising the one or more heterologous enzymes.

7. The transgenic plant of claim 1, wherein the transgenic plant has the one or more properties increased by at least 20% compared to a plant of the same species not comprising the one or more heterologous enzymes.

8. The transgenic plant of claim 1, wherein the transgenic plant has the one or more properties increased by at least 25% compared to a plant of the same species not comprising the one or more heterologous enzymes.

9. The transgenic plant of claim 1, wherein the transgenic plant has the one or more properties increased by at least 30% compared to a plant of the same species not comprising the one or more heterologous enzymes.

10. The transgenic plant of claim 1, wherein the transgenic plant has the one or more properties increased by at least 40% compared to a plant of the same species not comprising the one or more heterologous enzymes.

11. The transgenic plant of claim 1, wherein the transgenic plant has the one or more properties increased from 50% to 300% compared to a plant of the same species not comprising the one or more heterologous enzymes.

12. The transgenic plant according to claim 1, wherein the transgenic plant further comprises a heterologous bicarbonate transporter transgene that includes a nucleotide sequence encoding a plastid signal peptide directing the heterologous bicarbonate transporter to plastids of the transgenic plant.

13. The transgenic plant according to claim 1, wherein the transgenic plant further comprises, as a transgene, a *Chlamydomonas reinhardtii* CCP1 gene having the sequence of SEQ ID NO: 6.

14. The transgenic plant according to claim 1, wherein the pyruvate carboxylase comprises pyruvate carboxylase of *Bacillus subtilis* encoded by nucleotides 5879-9319 of SEQ ID NO: 3.

15. The transgenic plant according to claim 1, wherein the pyruvate carboxylase comprises one or more of pyruvate carboxylase of *Bacillus subtilis*, pyruvate carboxylase of *Salinibacillus aidingensis*, or pyruvate carboxylase of *Bacillus pumilus*.

16. A method for making and selecting a transgenic plant having an increase in at least one property selected from seed yield or seed oil content compared to a wild type plant, the method comprising:
   - providing one or more transgenic plants according to claim 1;
   - growing the one or more transgenic plants in soil;
   - measuring the at least one property of the one or more transgenic plants; and
   - selecting the one or more transgenic plants that have an increase in the at least one property compared to a wild type control plant of the same species.

* * * * *

SEQUENCE LISTING

```
<160> NUMBER OF SEQ ID NOS: 8

<210> SEQ ID NO 1
<211> LENGTH: 28014
<212> TYPE: DNA
<213> ORGANISM: Artificial Sequence
<220> FEATURE:
<223> OTHER INFORMATION: Synthetic construct plasmid pMBXS918

<400> SEQUENCE: 1

ctagggtacg tagtgtttat ctttgttgct tttctgaaca atttatttac tatgtaaata      60

tattatcaat gtttaatcta ttttaatttg cacatgaatt ttcattttat ttttacttta     120

caaaacaaat aaatatatat gcaaaaaaat ttacaaacga tgcacgggtt acaaactaat     180

ttcattaaat gctaatgcag attttgtgaa gtaaaactcc aattatgatg aaaaatacca     240

ccaacaccac ctgcgaaact gtatcccaac tgtccttaat aaaaatgtta aaaagtatat     300

tattctcatt tgtctgtcat aatttatgta ccccacttta atttttctga tgtactaaac     360

cgagggcaaa ctgaaacctg ttcctcatgc aaagccccta ctcaccatgt atcatgtacg     420
```

```
tgtcatcacc caacaactcc acttttgcta tataacaaca cccccgtcac actctccctc    480
tctaacacac accccactaa caattccttc acttgcagca ctgttgcatc atcatcttca    540
ttgcaaaacc ctaaacttca ccttcaaccg gatccaaaat ggcttctatg atatcctctt    600
ccgctgtgac aacagtcagc cgtgcctcta gggggcaatc cgccgcagtg gctccattcg    660
gcggcctcaa atccatgact ggattcccag tgaagaaggt caacactgac attacttcca    720
ttacaagcaa tggtggaaga gtaaagtgca tgcaggtgtg gcctccaatt ggaaagaaga    780
agtttgagac tctttcctat ttgccaccat tgacgagaga ttctagagtt tcgagcacac    840
tgagagaagc atcaaaagat acgttgcaag caaaggataa aacatatcat tactactctt    900
tacctctcgc tgctaagtct ctaggagaca taactcgttt gccgaagtcc ttgaaggtat    960
tactcgaaaa cctattaagg tggcaagacg gaaatagcgt tacagaagaa gatattcacg   1020
ctcttgcggg atggttgaag aatgcacacg cagatcgaga gattgcatat agacctgcta   1080
gagtgttgat gcaagatttc accggtgttc cggctgtcgt tgatttagcg gctatgaggg   1140
aagcagtgaa gaggttgggt ggggatactg ccaaagtgaa ccctcttagt cccgttgatc   1200
ttgttataga tcattcagtc actgttgaca ggtttggaga tgatgaggca tttgaagaga   1260
acgtgcgtct ggaaatggaa cgtaaccatg agagatatgt ctttcttaag tgggggaaac   1320
aagcgttttc tcgtttctcc gttgttccgc ctggtaccgg aatctgtcat caggtcaatc   1380
ttgagtatct cggaaaagca gtctggtccg agcttcagga tggtgagtgg attgcctacc   1440
cagatacact tgttggcacg gattcccata ctacaatgat caatggactg gggggttttgg   1500
gctggggagt aggtgggatc gaggctgaag ctgctatgct agggcaaccg gtgtcaatgc   1560
tcattcctga tgtcgtgggt tttaagctca ctggaaaact tcgagaggga attaccgcta   1620
ccgatctggt actcacagtt acccaaatgc ttagaaaaca tggtgtagtg ggaaatttg   1680
ttgaattcta cggtgacgga cttgatagtc tgccgctcgc cgaccgtgct actattgcca   1740
atatgtcgcc agagtatggt gcgacatgtg gcttcttccc aattgatgcg gttacgctgg   1800
attacatgcg tttatctggt cgatctgagg atcaagttga gttggttgag aagtatgcga   1860
aggcacaggg tatgtggaga aatccaggag atgaacctat ctttacttct actttggagt   1920
tagacatgaa tgatgttgag gctagcttgg ctgggcctaa gcgtccacaa gatagggttg   1980
ctcttccaga tgtgccgaaa gcctttgcag cttcaaacga attagaagtc aacgcgaccc   2040
ataaagacag acaaccagtt gactatgtaa tgaacggtca tcaataccag cttcctgatg   2100
gcgctgttgt tatcgcggca ataacttctt gcaccaatac gagtaatcca agtgtactaa   2160
tggccgctgg actcctggcc aagaaggctg tgactcttgg tcttaagcga cagccttggg   2220
ttaaggcatc actggctccc ggtagcaaag tcgtgagcga ttatcttgct aaagcgaaac   2280
tcacgccata cttggacgaa ctgggtttca atctcgttgg atatggatgc acaacctgta   2340
tcggaaactc tggccctttta cctgatccca ttgaaacagc tataaagaag agtgatctta   2400
ctgtgggcgc tgtcctaagt ggaaacagaa atttcgaggg aagaatacac cctctcgtta   2460
aaacaaattg gttagcttct cccccattag ttgtggccta tgctttggcc gggaatatga   2520
acattaacct tgcttcagag ccgattggac acgatcgtaa aggggaccct gtgtatttga   2580
aagacatctg gccatccgca caagaaatag ctcgtgcggt tgaacaagtg tctacagaaa   2640
tgttccgaaa agagtatgcc gaggtttttg aaggtactgc tgagtggaag ggtataaacg   2700
ttacaaggtc tgacacgtat ggttggcaag aagattctac ttacatcagg cttagtccat   2760
tctttgatga gatgcaggca actcctgccc cagtagagga catccacgga gctagaattc   2820
```

```
tggcaatgct aggagattct gttactaccg atcacatttc cccagctggc tcgattaagc   2880
ccgattcacc agctggaagg tacttgcaag gtaggggcgt tgagagaaag gactttaact   2940
catacggttc gcgtagaggc aaccacgaag taatgatgag gggcacgttc gcaaatatcc   3000
gaatcagaaa tgaaatggtg ccaggcgtgg aagggggaat gacaagacat ttgcctgact   3060
cagatgtcgt ttcgatttac gatgctgcaa tgagatacaa acaggagcag acacctctag   3120
cagtcatagc tggtaaagaa tatggaagtg gtagctctag ggattgggcg gctaaaggac   3180
cgagacttct cggtatcagg gtggtgattg cggaatcatt cgagagaatc catagaagca   3240
atctcatagg gatgggaata ttgcctttag agtttccaca gggagtgacg cgaaagactt   3300
tgggacttac cggtgaagaa aagattgaca ttggtgatct ccagaattta cagcctggtg   3360
caactgtccc tgttaccctc acaagagccg acgggtccca agaggtggtc ccgtgtcgat   3420
gcagaatcga cacagcaacg gaattgactt actatcagaa cgatggaata ctgcattacg   3480
tgatccgtaa catgcttaaa tgaggcgcgc ctgagtaatt ctgatattag agggagcatt   3540
aatgtgttgt tgtgatgtgg tttatatggg gaaattaaat aaatgatgta tgtacctctt   3600
gcctatgtag gtttgtgtgt tttgttttgt tgtctagctt tggttattaa gtagtaggga   3660
cgttcgttcg tgtctcaaaa aaaggggtac taccactctg tagtgtatat ggatgctgga   3720
aatcaatgtg ttttgtattt gttcacctcc attgttgaat tcaatgtcaa atgtgttttg   3780
cgttggttat gtgtaaaatt actatctttc tcgtccgatg atcaaagttt taagcaacaa   3840
aaccaagggt gaaatttaaa ctgtgctttg ttgaagattc ttttatcata ttgaaaatca   3900
aattactagc agcagatttt acctagcatg aaattttatc aacagtacag cactcactaa   3960
ccaagttcca aactaagatg cgccattaac atcagccaat aggcattttc agcaaaagct   4020
tgtacgtagt gtttatcttt gttgcttttc tgaacaattt atttactatg taaatatatt   4080
atcaatgttt aatctatttt aatttgcaca tgaattttca ttttattttt actttacaaa   4140
acaaataaat atatatgcaa aaaaatttac aaacgatgca cgggttacaa actaatttca   4200
ttaaatgcta atgcagattt tgtgaagtaa aactccaatt atgatgaaaa ataccaccaa   4260
caccacctgc gaaactgtat cccaactgtc cttaataaaa atgttaaaaa gtatattatt   4320
ctcatttgtc tgtcataatt tatgtacccc actttaattt ttctgatgta ctaaaccgag   4380
ggcaaactga aacctgttcc tcatgcaaag cccctactca ccatgtatca tgtacgtgtc   4440
atcacccaac aactccactt ttgctatata acaacacccc cgtcacactc tccctctcta   4500
acacacaccc cactaacaat tccttcactt gcagcactgt tgcatcatca tcttcattgc   4560
aaaaccctaa acttcacctt caaccgcggc cgcagatcta aaatggcttc tatgatatcc   4620
tcttccgctg tgacaacagt cagccgtgcc tctagggggc aatccgccgc agtggctcca   4680
ttcggcggcc tcaaatccat gactggattc ccagtgaaga aggtcaacac tgacattact   4740
tccattacaa gcaatggtgg aagagtaaag tgcatgcagg tgtggcctcc aattggaaag   4800
aagaagtttg agactctttc ctatttgcca ccattgacga gagattctag agtggttgac   4860
ggaaggtcat cagcttcgat cgtggcagtc gatcctgaaa gggctgcaag ggagagagat   4920
gctgcagcca gggcgcttct ccaagattcc cctttgcata ctacgatgca gtatgcaact   4980
tctggacttg aacttaccgt accgtatgct cttaaggttg tggcatctgc ggatacgttt   5040
gaccgtgcta aagaagtcgc agacgaggtt ctgagatgtg cttggcagct tgctgatact   5100
gttctaaatt cgtttaatcc taactcagaa gtcagtcttg ttgggagact tccagtgggg   5160
```

-continued

```
cagaaacacc aaatgtctgc gcctctcaaa agagtgatgg cttgttgtca gagggtatac   5220
aactcttcag caggatgctt cgatccttcc actgctccag ttgcaaaggc cttaagagag   5280
attgccttgg gtaaagagag aaataacgca tgtttggaag ccctcaccca agcgtgcact   5340
cttccaaact catttgtcat tgattttgaa gctggtacca ttagtagaaa gcatgaacat   5400
gcgagtttag accttggtgg agtatctaag ggttacatag tagattacgt tatagataac   5460
ataaacgcag ctggtttcca gaacgttttc ttcgactggg gcggtgattg cagggcttct   5520
gggatgaacg caagaaatac accgtgggtt gttgggatca ctagaccgcc atctcttgac   5580
atgcttccta acccacccaa agaggcttca tatatctcgg ttatttccct cgacaatgaa   5640
gcattagcga catctggtga ttacgagaat ttgatttaca ccgcagacga taagccgttg   5700
acgtgcacat atgactggaa aggtaaagaa ctaatgaagc ctagccaaag taacatagcc   5760
caagtgtctg taaaatgcta ctctgctatg tatgctgacg ccctcgcaac cgcttgtttt   5820
atcaagcgag atccagctaa ggtaagacaa cttctagacg gatggcgtta tgttcgtgat   5880
actgtgcgag attatcgagt ctatgtaaga gagaatgaaa gagtggcaaa aatgtttgag   5940
atcgccacgg aagatgctga gatgagaaag agaagaataa gtaatacgct tccagcccga   6000
gtgatcgttg ttggtggcgg cttggcaggg ctatctgcgg cgatcgaggc ggctggttgt   6060
ggggcacagg ttgttctaat ggagaaagaa gccaagttag gcggtaacag tgctaaggca   6120
accagcggga taaatggatg ggtactaga gcacaggcaa aagcctcaat cgttgatggt   6180
ggtaaatact ttgaacgaga tacatataag tcaggaattg gcggaaatac tgatccagca   6240
cttgttaaga cactcagcat gaagagtgcg gatgccattg ggtggctgac ttcgctcggt   6300
gtgcctctta ctgtcttatc tcaattaggt ggacactcac gtaagagaac acacagggca   6360
cctgataaga aggatggaac gccactacct attggattca ctattatgaa aactctcgaa   6420
gatcatgttc gtggaaactt atctggacga attacaatta tggaaaattg ttcggttaca   6480
tcactgcttt ccgaaactaa agagcgtcct gatgggacca aacaaattcg tgtcacgggt   6540
gttgagttca cccaggctgg tagcgggaaa actacaatct tagctgatgc cgttatctta   6600
gctacaggtg ggttttctaa tgacaaaacc gcggattccc ttttgaggga acacgcaccg   6660
catttggtca acttccccac cacaaacggg ccttgggcta ctggagatgg agttaaactt   6720
gcacagagac ttggtgctca acttgtagat atggataaag ttcagttaca tccgacagga   6780
ctcataaacc ctaaagatcc agcaaacccg acaaagttct taggacctga ggccttgcgt   6840
ggcagcggtg gtgtgctgct gaacaagcaa ggcaagagat ttgtgaatga actagaccta   6900
cgttctgttg tgagtaaggc tattatggaa caaggtgctg agtacccagg ttctggcggc   6960
tcgatgttcg cttactgcgt tcttaacgcc gcagctcaaa agctatttgg agtatcatcc   7020
catgagttct actggaaaaa gatgggtctt ttcgtcaaag ctgacactat gagggatctg   7080
gctgctctta tcggttgtcc tgtcgagtct gtgcaacaga cattggaaga atatgagaga   7140
ctgtctattt cccagagatc atgcccaata accaggaagt cggtttaccc ttgtgtctta   7200
ggaactaagg gtccgtatta cgttgctttt gtgacacctt caatccacta tactatgggt   7260
ggttgcttga tttcccctag tgcagaaatt caaatgaaaa acacctcatc gagagcacct   7320
ttatcacatt ccaatcccat cctgggttta ttcggagctg gtgaggtaac tggcggtgtc   7380
cacggtggca ataggcttgg gggcaattcc cttctggaat gtgtggtttt cggaaggatt   7440
gcaggtgacc gagcttccac tatattgcaa agaaaatcca gtgcgctgtc tttcaaggtg   7500
tggactacag ttgttcttag agaggtgcgt gagggcggag tgtacggcgc tggttctagg   7560
```

```
gttctaagat ttaaccttcc tggagcactt caacgttccg ggctatcttt aggacagttt   7620

atcgctatac gaggggattg ggatggacag caacttattg gttactattc tccaattact   7680

ctcccagatg acctcggaat gatagacatt cttgctagat cagacaaagg cacactcagg   7740

gagtggattt ctgctctgga gccaggtgat gccgtggaaa tgaaagcgtg cggcggtctt   7800

gtaattgaac gtagactttc agataagcat tttgtgttta tggggcacat catcaataag   7860

ctatgtttga tcgccggtgg gactggcgtt gcgcccatgt tgcagattat caaggcggca   7920

tttatgaagc cctttataga tacgctggag agtgtgcatt tgatctatgc tgcagaggat   7980

gtaacggagc ttacatatcg tgaagttctg gaagaacgac gaagggaatc gagaggtaaa   8040

ttcaagaaaa ctttcgttct taataggcca ccccctttgt ggactgacgg cgtcgggttc   8100

atagatcgag ggatacttac aaatcatgtc caacccccat ccgataatct tttggtggcc   8160

atttgtggac cgcccgttat gcagcgtata gtgaaggcta cactgaaaac tttgggatat   8220

aacatgaact tggttagaac ggtagacgag actgaacctt caggtagcag taagatttga   8280

gcgatcgcgc ggccgctgag taattctgat attagaggga gcattaatgt gttgttgtga   8340

tgtggtttat atggggaaat taaataaatg atgtatgtac ctcttgccta tgtaggtttg   8400

tgtgttttgt tttgttgtct agctttggtt attaagtagt agggacgttc gttcgtgtct   8460

caaaaaaagg ggtactacca ctctgtagtg tatatggatg ctggaaatca atgtgttttg   8520

tatttgttca cctccattgt tgaattcaat gtcaaatgtg ttttgcgttg gttatgtgta   8580

aaattactat ctttctcgtc cgatgatcaa agttttaagc aacaaaacca agggtgaaat   8640

ttaaactgtg ctttgttgaa gattctttta tcatattgaa aatcaaatta ctagcagcag   8700

attttaccta gcatgaaatt ttatcaacag tacagcactc actaaccaag ttccaaacta   8760

agatgcgcca ttaacatcag ccaataggca ttttcagcaa gtttaaacta cgtagtgttt   8820

atctttgttg cttttctgaa caatttattt actatgtaaa tatattatca atgtttaatc   8880

tattttaatt tgcacatgaa ttttcatttt atttttactt tacaaaacaa ataaatatat   8940

atgcaaaaaa atttacaaac gatgcacggg ttacaaacta atttcattaa atgctaatgc   9000

agattttgtg aagtaaaact ccaattatga tgaaaaatac caccaacacc acctgcgaaa   9060

ctgtatccca actgtcctta ataaaaatgt taaaaagtat attattctca tttgtctgtc   9120

ataatttatg taccccactt taatttttct gatgtactaa accgagggca aactgaaacc   9180

tgttcctcat gcaaagcccc tactcaccat gtatcatgta cgtgtcatca cccaacaact   9240

ccacttttgc tatataacaa cacccccgtc acactctccc tctctaacac acaccccact   9300

aacaattcct tcacttgcag cactgttgca tcatcatctt cattgcaaaa ccctaaactt   9360

caccttcaac cgcggccgct cgcgaaaaat ggcttctatg atatcctctt ccgctgtgac   9420

aacagtcagc cgtgcctcta gggggcaatc cgccgcagtg gctccattcg gcggcctcaa   9480

atccatgact ggattcccag tgaagaaggt caacactgac attacttcca ttacaagcaa   9540

tggtggaaga gtaaagtgca tgcaggtgtg gcctccaatt ggaaagaaga agtttgagac   9600

tctttcctat ttgccaccat tgacgagaga ttctagagtg gctaggaaga agatccgtga   9660

atatgactct aaaaggcttg tcaaagaaca tttcaagagg cttagtggaa aagaactccc   9720

tattaggtct gtgcagatta acgaaacaac tgatcttaac gaattggttg agaaagagcc   9780

ttggttgagc agtgaaaagt tagtcgtgaa gccagacatg ttgtttggaa aacgtggaaa   9840

atcaggactt gtcgctctca aactggactt tgctgatgtc gcaacgtttg ttaaagagag   9900
```

```
actaggtaaa gaggttgaga tgtcaggatg taaaggaccc ataacgacct ttattgttga   9960
accattcgtt ccacataacg aagaatacta ccttaatgta gtgtcggata gattaggatg  10020
ctccatatca ttctccgagt gtggcgggat cgagattgaa gagaactggg ataaggtcaa  10080
aacaatcttt ttgccaaccg gtgcttcgct gacacctgag atttgtgctc cccttgttgc  10140
tacacttcca cttgagatta aggcagaaat agaagagttc atcaaggtta tctttactct  10200
gttccaagat ttagatttca cttttctcga aatgaatccg tttactttag tcgatggttc  10260
tccgtatcct ttggatatgc gaggtgagct ggatgacaca gcggctttta agaacttcaa  10320
gaagtgggga gatattgagt tcccattgcc gtttggccgt gttatgtctc caactgaatc  10380
cttcatacac ggactcgatg aaaagaccag tgcatctctc aagtttaccg ttctaaatcc  10440
taagggtaga atctggacta tggtagctgg gggtggagcc tctgtaatct acgctgatac  10500
tgttggtgat cttggctatg ctagcgaatt agggaactat gcggagtaca gcggtgcacc  10560
taaagaggac gaggtactcc aatatgcccg agtggtgatt gattgtgcta cggcaaatcc  10620
tgacggaaag tcaagagccc ttgtgattgg gggtggtata gcaaatttca cagacgttgc  10680
agcgactttc aatggtatca ttagagcctt gaaagagaaa gaggccaaac taaaggctgc  10740
gagaatgcac atttttgttc gtagaggtgg ccctaattac cagaagggtt tggctaaaat  10800
gcgagctttg ggagatgata taggcgtgcc tatcgaagtt tatggacctg aagcaacgat  10860
gaccgggatc tgcaaagaag caatacaata cattacagct gcagcgtgaa cgcgttgagt  10920
aattctgata ttagagggag cattaatgtg ttgttgtgat gtggtttata tggggaaatt  10980
aaataaatga tgtatgtacc tcttgcctat gtaggtttgt gtgttttgtt ttgttgtcta  11040
gctttggtta ttaagtagta gggacgttcg ttcgtgtctc aaaaaaaggg gtactaccac  11100
tctgtagtgt atatggatgc tggaaatcaa tgtgttttgt atttgttcac ctccattgtt  11160
gaattcaatg tcaaatgtgt tttgcgttgg ttatgtgtaa aattactatc tttctcgtcc  11220
gatgatcaaa gttttaagca acaaaaccaa gggtgaaatt taaactgtgc tttgttgaag  11280
attcttttat catattgaaa atcaaattac tagcagcaga ttttacctag catgaaattt  11340
tatcaacagt acagcactca ctaaccaagt tccaaactaa gatgcgccat taacatcagc  11400
caataggcat tttcagcaat gtacatacgt agtgtttatc tttgttgctt ttctgaacaa  11460
tttatttact atgtaaatat attatcaatg tttaatctat tttaatttgc acatgaattt  11520
tcattttatt tttactttac aaaacaaata aatatatatg caaaaaaatt tacaaacgat  11580
gcacgggtta caaactaatt tcattaaatg ctaatgcaga ttttgtgaag taaaactcca  11640
attatgatga aaaataccac caacaccacc tgcgaaactg tatcccaact gtccttaata  11700
aaaatgttaa aaagtatatt attctcattt gtctgtcata atttatgtac cccactttaa  11760
tttttctgat gtactaaacc gagggcaaac tgaaacctgt tcctcatgca aagcccctac  11820
tcaccatgta tcatgtacgt gtcatcaccc aacaactcca cttttgctat ataacaacac  11880
ccccgtcaca ctctccctct ctaacacaca ccccactaac aattccttca cttgcagcac  11940
tgttgcatca tcatcttcat tgcaaaaccc taaacttcac cttcaaccgc ggccgcgacg  12000
tcaaaatggc ttctatgata tcctcttccg ctgtgacaac agtcagccgt gcctctaggg  12060
ggcaatccgc cgcagtggct ccattcggcg gcctcaaatc catgactgga ttcccagtga  12120
agaaggtcaa cactgacatt acttccatta caagcaatgg tggaagagta aagtgcatgc  12180
aggtgtggcc tccaattgga aagaagaagt ttgagactct ttcctatttg ccaccattga  12240
cgagagattc tagagttgct accggccaac tcttttcccg aacaacgcaa gctctattct  12300
```

```
acaactataa acaacttcca gttcaaagaa tgttagattt cgatttctta tgcggaagag  12360
aaacaccatc agtggctgga attatcaatc cagggtccga gggatttcag aaattgtttt  12420
tcggtcaaga agagatagct attccagtcc atgcggccat agaagcagct tgtgccgccc  12480
accccactgc tgatgttttc atcaactttg cttcgttcag gagtgcggct gcaagttcga  12540
tggcagctct caagcaacct acaatcaagg tcgtagcaat aatcgcagag ggagtcccag  12600
aatctgacac caagcaactc atcgcttatg cccgagcgaa caataaagtg gttataggtc  12660
ctgctactgt gggcggaatt caggctggag cttttaagat tggtgacact gcggggacca  12720
ttgataacat tatccaatgc aagctgtatc gtccgggtag tgtcggattt gtttccaagt  12780
ctggtgggat gtctaatgag atgtataaca ctgtagcaag agtaactgat ggcatttatg  12840
aggggatagc aattgggggt gacgttttcc ccggttcaac tttatccgat catatcctga  12900
gatttaacaa tatcccgcaa atcaagatga tggttgtact aggagagctt gggggacgtg  12960
acgagtattc acttgttgaa gctctgaaag agggtaaagt caataaacct gttgtcgctt  13020
gggtgtcagg cacctgtgca agactcttca aaagcgaggt ccagtttggt cacgcaggag  13080
cgaagagcgg tggagagatg gagtctgcac aagctaaaaa ccaggcgttg atagatgcag  13140
gcgcaattgt tccaacatct tttgaagcct tggagagcgc gatcaaagaa acttttgaga  13200
aacttgtcga agaaggtaag gtttcgccga ttaaagaagt aatcccacct cagatccctg  13260
aggatctaaa ttccgcaatt aagtctggaa aggtgagggc tccaacgcat atcatatcga  13320
cgatttctga tgatagaggg gaagagccgt gctacgcagg tgttcctatg tctagcataa  13380
ttgagcaagg ttacggagtg ggagatgtca tttcattgtt atggttcaaa cgtagtctcc  13440
cgaggtattg taccaaattc attgagattt gcataatgct ttgtgcggat catggaccct  13500
gtgtatctgg tgctcataat actatcgtta ctgccagagc tggaaaagat ttggtgtcta  13560
gtctcgtttc aggcttattg acaataggtc ctcgattcgg tggggccatc gacgacgctg  13620
ccaggtactt taaggatgca tgtgacagaa acctcacacc atatgaattt gtggaaggca  13680
tgaaaaagaa gggcattaga gtgcctggaa ttggtcatcg tattaagtca agggataata  13740
gagacaagag agttgaactt ttacagaagt ttgctcgaag taatttccct agcgttaagt  13800
acatggaata cgcggttact gttgaaacgt acacattgtc taaggctaat aacttggtgc  13860
ttaatgttga tggtgctata ggttcattat tcttggatct acttgcaggt tctggaatgt  13920
tcacaaagca ggaaatcgac gagatagtgc aaattggata cctgaacgga ctatttgtgt  13980
tggctaggtc aatagggctt atcggacaca cgtttgatca gaaacgtctt aaacagcctc  14040
tctaccgaca cccttgggaa gatgttctgt ataccaaatg agttaactga gtaattctga  14100
tattagaggg agcattaatg tgttgttgtg atgtggttta tatggggaaa ttaaataaat  14160
gatgtatgta cctcttgcct atgtaggttt gtgtgttttg ttttgttgtc tagctttggt  14220
tattaagtag tagggacgtt cgttcgtgtc tcaaaaaaag ggtactacc actctgtagt  14280
gtatatggat gctggaaatc aatgtgtttt gtatttgttc acctccattg ttgaattcaa  14340
tgtcaaatgt gttttgcgtt ggttatgtgt aaaattacta tctttctcgt ccgatgatca  14400
aagttttaag caacaaaacc aagggtgaaa tttaaactgt gctttgttga agattctttt  14460
atcatattga aaatcaaatt actagcagca gattttacct agcatgaaat tttatcaaca  14520
gtacagcact cactaaccaa gttccaaact aagatgcgcc attaacatca gccaataggc  14580
attttcagca agtttaaacc ggaccgtacg tagtgtttat ctttgttgct tttctgaaca  14640
```

-continued

```
atttatttac tatgtaaata tattatcaat gtttaatcta ttttaatttg cacatgaatt  14700
ttcattttat ttttacttta caaaacaaat aaatatatat gcaaaaaaat ttacaaacga  14760
tgcacgggtt acaaactaat ttcattaaat gctaatgcag attttgtgaa gtaaaactcc  14820
aattatgatg aaaaatacca ccaacaccac ctgcgaaact gtatcccaac tgtccttaat  14880
aaaaatgtta aaaagtatat tattctcatt tgtctgtcat aatttatgta ccccacttta  14940
atttttctga tgtactaaac cgagggcaaa ctgaaacctg ttcctcatgc aaagccccta  15000
ctcaccatgt atcatgtacg tgtcatcacc caacaactcc acttttgcta tataacaaca  15060
cccccgtcac actctccctc tctaacacac accccactaa caattccttc acttgcagca  15120
ctgttgcatc atcatcttca ttgcaaaacc ctaaacttca ccttcaaccg cggccgccac  15180
gtgaaaatgg cttctatgat atcctcttcc gctgtgacaa cagtcagccg tgcctctagg  15240
gggcaatccg ccgcagtggc tccattcggc ggcctcaaat ccatgactgg attcccagtg  15300
aagaaggtca acactgacat tacttccatt acaagcaatg gtggaagagt aaagtgcatg  15360
caggtgtggc ctccaattgg aaagaagaag tttgagactc tttcctattt gccaccattg  15420
acgagagatt ctagagtgaa tactgttcgt tcagagaaag actctatggg ggctatagac  15480
gtgcctgctg ataagttatg gggagcccag actcaacgta gcctggagca ctttaggata  15540
tcgactgaga agatgcctac gtccttgatt catgcccttg ctctcactaa gagagcagca  15600
gcaaaagtta atgaggatct cggccttttta tccgaagaga aagcatctgc catacgacag  15660
gccgctgatg aagtgttggc gggtcagcat gatgatgagt tcccattagc tatctggcag  15720
acaggctctg gtactcaatc caacatgaac atgaatgagg tgctagcaaa cagggcctca  15780
gagcttttag gtggggtcag gggaatggaa cgaaaggttc atcccaacga tgacgtaaac  15840
aagtcacaat cgagtaatga tgtgttccca actgctatgc acgttgcagc tctgcttgcg  15900
ttgagaaagc aacttattcc acaactcaaa actctcaccc aaacattgaa tgaaaagtca  15960
agggcctttg cagatatcgt gaagatcgga cgaacacatc ttcaggacgc tacaccactg  16020
acgttgggac aagagatttc tggatgggtt gctatgttgg aacataactt gaaacatatc  16080
gagtatagtt tacctcatgt tgcagaacta gcattgggtg gtacagcagt cggtaccggc  16140
ctcaacacac atcctgaata cgctagacgt gtagctgatg aacttgccgt tattacctgc  16200
gctccgttcg ttacggctcc taataagttt gaagctcttg ctacttgtga tgctctagtc  16260
caagctcatg gtgcactaaa gggacttgcg gcatctttaa tgaagattgc aaatgatgtc  16320
cgttggctag caagcggacc aagatgtgga ataggcgaaa tttccatccc tgagaacgag  16380
cccggatcat ctattatgcc gggtaaagtt aatccaacgc agtgtgaagc cttgaccatg  16440
ctttgctgcc aggtaatggg aaacgatgtg gccatcaata tgggtggtgc gagtggaaac  16500
tttgagctga atgtctttag accgatggtt atccacaact ttcttcagag tgtaaggctt  16560
ctcgccgacg ggatggagtc attcaataaa cactgtgcgg ttggcataga gccaaacaga  16620
gaacgtatca atcaacttct caatgaatct ctaatgttgg ttactgctct caacacccac  16680
attgggtacg acaaagctgc tgaaattgct aaaaaggcgc acaaagaagg tttaacactg  16740
aaagcggcag ctctcgctct cggttatctg tctgaagctg agttcgattc gtgggtcaga  16800
cctgaacaaa tggtgggaag catgaaggct gggagatgaa ctagttgagt aattctgata  16860
ttagagggag cattaatgtg ttgttgtgat gtggtttata tggggaaatt aaataaatga  16920
tgtatgtacc tcttgcctat gtaggtttgt gtgttttgtt ttgttgtcta gctttggtta  16980
ttaagtagta gggacgttcg ttcgtgtctc aaaaaaaggg gtactaccac tctgtagtgt  17040
```

```
atatggatgc tggaaatcaa tgtgttttgt atttgttcac ctccattgtt gaattcaatg  17100
tcaaatgtgt tttgcgttgg ttatgtgtaa aattactatc tttctcgtcc gatgatcaaa  17160
gttttaagca acaaaaccaa gggtgaaatt taaactgtgc tttgttgaag attcttttat  17220
catattgaaa atcaaattac tagcagcaga ttttacctag catgaaattt tatcaacagt  17280
acagcactca ctaaccaagt tccaaactaa gatgcgccat taacatcagc caataggcat  17340
tttcagcaag tttaaactcc ggattaatta agtcgacggg cccgtttaaa ccacgtagtg  17400
cctcagcgtt taaacgtacg tagtgtttat ctttgttgct tttctgaaca atttatttac  17460
tatgtaaata tattatcaat gtttaatcta ttttaatttg cacatgaatt ttcattttat  17520
ttttacttta caaaacaaat aaatatatat gcaaaaaaat ttacaaacga tgcacgggtt  17580
acaaactaat ttcattaaat gctaatgcag attttgtgaa gtaaaactcc aattatgatg  17640
aaaaatacca ccaacaccac ctgcgaaact gtatcccaac tgtccttaat aaaaatgtta  17700
aaaagtatat tattctcatt tgtctgtcat aatttatgta ccccacttta attttctga  17760
tgtactaaac cgagggcaaa ctgaaacctg ttcctcatgc aaagccccta ctcaccatgt  17820
atcatgtacg tgtcatcacc caacaactcc acttttgcta tataacaaca cccccgtcac  17880
actctccctc tctaacacac accccactaa caattccttc acttgcagca ctgttgcatc  17940
atcatcttca ttgcaaaacc ctaaacttca ccttcaaccg cggccgcttc gaaaaaatgg  18000
cttctatgat atcctcttcc gctgtgacaa cagtcagccg tgcctctagg gggcaatccg  18060
ccgcagtggc tccattcggc ggcctcaaat ccatgactgg attcccagtg aagaaggtca  18120
acactgacat tacttccatt acaagcaatg gtggaagagt aaagtgcatg caggtgtggc  18180
ctccaattgg aaagaagaag tttgagactc tttcctattt gccaccattg acgagagatt  18240
ctagagtgaa agttgcagtt cttggagcag caggtggaat tggacaggct ttggctctct  18300
tgcttaaaac tcaactaccc agtggatctg agttatcatt gtacgatatt gccccagtaa  18360
cccctggggt ggcagttgat ctctcccata tccccacagc tgttaagatt aagggattca  18420
gcggtgagga tgctacacct gctttggaag gcgcagatgt ggttctcatt tcggcaggcg  18480
tggcaagaaa gccaggtatg gataggtctg atctctttaa cgtcaatgct gggatagtca  18540
agaacttggt acaacaagtc gctaagacct gccctaaggc ctgtattggt atcataacga  18600
atccggttaa tacaacagtt gctattgcgg cagaggttct caaaaaggcg ggagtttacg  18660
acaagaataa actatttggc gtaactactc ttgatatcat acgtagtaat acgttcgtag  18720
ccgaactcaa agggaagcaa cctggtgagg tagaagtgcc agttattggt gggcactcag  18780
gagtcactat cctgcctctt cttagtcagg ttccaggtgt gagctttacc gagcaagaag  18840
tcgcggatct tacaaagaga atccaaaacg cgggaactga agttgttgag gctaaagctg  18900
gtggtgggtc ggccacgctg tctatgggac aagccgcagc ccgttttggc ctttcacttg  18960
tgcgagcttt gcagggagag caaggggttg tcgaatgtgc atatgtggaa ggtgacggtc  19020
agtatgctag gttcttctct cagccgttgt tacttggcaa aaatggagtt gaagagagaa  19080
aatctatcgg taccttatcc gcgtttgagc agaacgctct agagggaatg ctggacactt  19140
taaagaaaga catagctctg ggagaagaat tcgtgaacaa atgaatttaa atgcggccgc  19200
tgagtaattc tgatattaga gggagcatta atgtgttgtt gtgatgtggt ttatatgggg  19260
aaattaaata aatgatgtat gtacctcttg cctatgtagg tttgtgtgtt ttgttttgtt  19320
gtctagcttt ggttattaag tagtagggac gttcgttcgt gtctcaaaaa aaggggtact  19380
```

-continued

```
accactctgt agtgtatatg gatgctggaa atcaatgtgt tttgtatttg ttcacctcca  19440
ttgttgaatt caatgtcaaa tgtgttttgc gttggttatg tgtaaaatta ctatctttct  19500
cgtccgatga tcaaagtttt aagcaacaaa accaagggtg aaatttaaac tgtgctttgt  19560
tgaagattct tttatcatat tgaaaatcaa attactagca gcagatttta cctagcatga  19620
aattttatca acagtacagc actcactaac caagttccaa actaagatgc gccattaaca  19680
tcagccaata ggcattttca gcaaagcaaa tgaattcgta atcatgtcat agctgtttcc  19740
tgtgtgaaat tgttatccgc tcacaattcc acacaacata cgagccggaa gcataaagtg  19800
taaagcctgg ggtgcctaat gagtgagcta actcacatta attgcgttgc gctcactgcc  19860
cgctttccag tcgggaaacc tgtcgtgcca gctgcattaa tgaatcggcc aacgcgcggg  19920
gagaggcggt ttgcgtattg gctagagcag cttgccaaca tggtggagca cgacactctc  19980
gtctactcca agaatatcaa agatacagtc tcagaagacc aaagggctat tgagactttt  20040
caacaaaggg taatatcggg aaacctcctc ggattccatt gcccagctat ctgtcacttc  20100
atcaaaagga cagtagaaaa ggaaggtggc acctacaaat gccatcattg cgataaagga  20160
aaggctatcg ttcaagatgc ctctgccgac agtggtccca aagatggacc cccacccacg  20220
aggagcatcg tggaaaaaga agacgttcca accacgtctt caaagcaagt ggattgatgt  20280
gaacatggtg gagcacgaca ctctcgtcta ctccaagaat atcaaagata cagtctcaga  20340
agaccaaagg gctattgaga cttttcaaca aagggtaata tcgggaaacc tcctcggatt  20400
ccattgccca gctatctgtc acttcatcaa aaggacagta gaaaaggaag gtggcaccta  20460
caaatgccat cattgcgata aaggaaaggc tatcgttcaa gatgcctctg ccgacagtgg  20520
tcccaaagat ggacccccac ccacgaggag catcgtggaa aaagaagacg ttccaaccac  20580
gtcttcaaag caagtggatt gatgtgatat ctccactgac gtaagggatg acgcacaatc  20640
ccactatcct tcgcaagacc cttcctctat ataaggaagt tcatttcatt tggagaggac  20700
acgctgaaat caccagtctc tctctacaaa tctatctctc tcgagatgag cccagaacga  20760
cgcccggccg acatccgccg tgccaccgag gcggacatgc cggcggtctg caccatcgtc  20820
aaccactaca tcgagacaag cacggtcaac ttccgtaccg agccgcagga accgcaggag  20880
tggacggacg acctcgtccg tctgcgggag cgctatccct ggctcgtcgc cgaggtggac  20940
ggcgaggtcg ccggcatcgc ctacgcgggc ccctggaagg cacgcaacgc ctacgactgg  21000
acggccgagt cgaccgtgta cgtctccccc cgccaccagc ggacgggact gggctccacg  21060
ctctacaccc acctgctgaa gtccctggag gcacagggct tcaagagcgt ggtcgctgtc  21120
atcgggctgc ccaacgaccc gagcgtgcgc atgcacgagg cgctcggata tgccccccgc  21180
ggcatgctgc gggcggccgg cttcaagcac gggaactggc atgacgtggg tttctggcag  21240
ctggacttca gcctgccggt accgccccgt ccggtcctgc ccgtcaccga gatttgagag  21300
ctcggtcacc tgtccaacag tctcagggtt aatgtctatg tatcttaaat aatgttgtcg  21360
gcgatcgttc aaacatttgg caataaagtt tcttaagatt gaatcctgtt gccggtcttg  21420
cgatgattat catataattt ctgttgaatt acgttaagca tgtaataatt aacatgtaat  21480
gcatgacgtt atttatgaga tgggttttta tgattagagt cccgcaatta tacatttaat  21540
acgcgataga aaacaaaata tagcgcgcaa actaggataa attatcgcgc gcggtgtcat  21600
ctatgttact agatcgggaa ttaaactatc agtgtttgac aggatatatt ggcgggtaaa  21660
cctaagagaa aagagcgttt attagaataa tcggatattt aaaagggcgt gaaaaggttt  21720
atccgttcgt ccatttgtat gtgcatgcca accacagggt tcccctcggg atcaaagtac  21780
```

```
tttgatccaa cccctccgct gctatagtgc agtcggcttc tgacgttcag tgcagccgtc  21840
ttctgaaaac gacatgtcgc acaagtccta agttacgcga caggctgccg ccctgccctt  21900
ttcctggcgt tttcttgtcg cgtgttttag tcgcataaag tagaatactt gcgactagaa  21960
ccggagacat tacgccatga acaagagcgc cgccgctggc ctgctgggct atgcccgcgt  22020
cagcaccgac gaccaggact tgaccaacca acgggccgaa ctgcacgcgg ccggctgcac  22080
caagctgttt tccgagaaga tcaccggcac caggcgcgac cgcccggagc tggccaggat  22140
gcttgaccac ctacgccctg gcgacgttgt gacagtgacc aggctagacc gcctggcccg  22200
cagcacccgc gacctactgg acattgccga gcgcatccag gaggccggcg cgggcctgcg  22260
tagcctggca gagccgtggg ccgacaccac cacgccggcc ggccgcatgg tgttgaccgt  22320
gttcgccggc attgccgagt tcgagcgttc cctaatcatc gaccgcaccc ggagcgggcg  22380
cgaggccgcc aaggcccgag gcgtgaagtt tggcccccgc cctaccctca ccccggcaca  22440
gatcgcgcac gcccgcgagc tgatcgacca ggaaggccgc accgtgaaag aggcggctgc  22500
actgcttggc gtgcatcgct cgaccctgta ccgcgcactt gagcgcagcg aggaagtgac  22560
gcccaccgag gccaggcggc gcggtgcctt ccgtgaggac gcattgaccg aggccgacgc  22620
cctggcggcc gccgagaatg aacgccaaga ggaacaagca tgaaaccgca ccaggacggc  22680
caggacgaac cgtttttcat taccgaagag atcgaggcgg agatgatcgc ggccgggtac  22740
gtgttcgagc cgcccgcgca cgtctcaacc gtgcggctgc atgaaatcct ggccggtttg  22800
tctgatgcca agctggcggc ctggccggcc agcttggccg ctgaagaaac cgagcgccgc  22860
cgtctaaaaa ggtgatgtgt atttgagtaa aacagcttgc gtcatgcggt cgctgcgtat  22920
atgatgcgat gagtaaataa acaaatacgc aaggggaacg catgaaggtt atcgctgtac  22980
ttaaccagaa aggcgggtca ggcaagacga ccatcgcaac ccatctagcc cgcgccctgc  23040
aactcgccgg ggccgatgtt ctgttagtcg attccgatcc ccagggcagt gcccgcgatt  23100
gggcggccgt gcgggaagat caaccgctaa ccgttgtcgg catcgaccgc ccgacgattg  23160
accgcgacgt gaaggccatc ggccggcgcg acttcgtagt gatcgacgga gcgccccagg  23220
cggcggactt ggctgtgtcc gcgatcaagg cagccgactt cgtgctgatt ccggtgcagc  23280
caagccctta cgacatatgg gccaccgccg acctggtgga gctggttaag cagcgcattg  23340
aggtcacgga tggaaggcta caagcggcct ttgtcgtgtc gcgggcgatc aaaggcacgc  23400
gcatcggcgg tgaggttgcc gaggcgctgg ccgggtacga gctgcccatt cttgagtccc  23460
gtatcacgca gcgcgtgagc tacccaggca ctgccgccgc cggcacaacc gttcttgaat  23520
cagaacccga gggcgacgct gcccgcgagg tccaggcgct ggccgctgaa attaaatcaa  23580
aactcatttg agttaatgag gtaaagagaa aatgagcaaa agcacaaaca cgctaagtgc  23640
cggccgtccg agcgcacgca gcagcaaggc tgcaacgttg gccagcctgg cagacacgcc  23700
agccatgaag cgggtcaact ttcagttgcc ggcggaggat cacaccaagc tgaagatgta  23760
cgcggtacgc caaggcaaga ccattaccga gctgctatct gaatacatcg cgcagctacc  23820
agagtaaatg agcaaatgaa taaatgagta gatgaatttt agcggctaaa ggaggcggca  23880
tggaaaatca agaacaacca ggcaccgacg ccgtggaatg ccccatgtgt ggaggaacgg  23940
gcggttggcc aggcgtaagc ggctgggttg cctgccggcc ctgcaatggc actggaaccc  24000
ccaagcccga ggaatcggcg tgagcggtcg caaaccatcc ggcccggtac aaatcggcgc  24060
ggcgctgggt gatgacctgg tggagaagtt gaaggccgcg caggccgccc agcggcaacg  24120
```

-continued

```
catcgaggca gaagcacgcc ccggtgaatc gtggcaagcg gccgctgatc gaatccgcaa  24180
agaatcccgg caaccgccgg cagccggtgc gccgtcgatt aggaagccgc ccaagggcga  24240
cgagcaacca gattttttcg ttccgatgct ctatgacgtg ggcacccgcg atagtcgcag  24300
catcatggac gtggccgttt tccgtctgtc gaagcgtgac cgacgagctg gcgaggtgat  24360
ccgctacgag cttccagacg ggcacgtaga ggtttccgca gggccggccg gcatggccag  24420
tgtgtgggat tacgacctgg tactgatggc ggtttcccat ctaaccgaat ccatgaaccg  24480
ataccgggaa gggaagggag acaagcccgg ccgcgtgttc cgtccacacg ttgcggacgt  24540
actcaagttc tgccggcgag ccgatggcgg aaagcagaaa gacgacctgg tagaaacctg  24600
cattcggtta aacaccacgc acgttgccat gcagcgtacg aagaaggcca agaacggccg  24660
cctggtgacg gtatccgagg gtgaagcctt gattagccgc tacaagatcg taaagagcga  24720
aaccgggcgg ccggagtaca tcgagatcga gctagctgat tggatgtacc gcgagatcac  24780
agaaggcaag aacccggacg tgctgacggt tcaccccgat tactttttga tcgatcccgg  24840
catcggccgt tttctctacc gcctggcacg ccgcgccgca ggcaaggcag aagccagatg  24900
gttgttcaag acgatctacg aacgcagtgg cagcgccgga gagttcaaga agttctgttt  24960
caccgtgcgc aagctgatcg ggtcaaatga cctgccggag tacgatttga aggaggaggc  25020
ggggcaggct ggcccgatcc tagtcatgcg ctaccgcaac ctgatcgagg gcgaagcatc  25080
cgccggttcc taatgtacgg agcagatgct agggcaaatt gccctagcag gggaaaaagg  25140
tcgaaaaggt ctctttcctg tggatagcac gtacattggg aacccaaagc cgtacattgg  25200
gaaccggaac ccgtacattg ggaacccaaa gccgtacatt gggaaccggt cacacatgta  25260
agtgactgat ataaaagaga aaaaaggcga tttttccgcc taaaactctt taaaacttat  25320
taaaactctt aaaacccgcc tggcctgtgc ataactgtct ggccagcgca cagccgaaga  25380
gctgcaaaaa gcgcctaccc ttcggtcgct gcgctcccta cgccccgccg cttcgcgtcg  25440
gcctatcgcg gccgctggcc gctcaaaaat ggctggccta cggccaggca atctaccagg  25500
gcgcggacaa gccgcgccgt cgccactcga ccgccggcgc ccacatcaag gcaccctgcc  25560
tcgcgcgttt cggtgatgac ggtgaaaacc tctgacacat gcagctcccg gagacggtca  25620
cagcttgtct gtaagcggat gccgggagca gacaagcccg tcagggcgcg tcagcgggtg  25680
ttggcgggtg tcggggcgca gccatgaccc agtcacgtag cgatagcgga gtgtatactg  25740
gcttaactat gcggcatcag agcagattgt actgagagtg caccatatgc ggtgtgaaat  25800
accgcacaga tgcgtaagga gaaaataccg catcaggcgc tcttccgctt cctcgctcac  25860
tgactcgctg cgctcggtcg ttcggctgcg gcgagcggta tcagctcact caaaggcggt  25920
aatacggtta tccacagaat caggggataa cgcaggaaag aacatgtgag caaaaggcca  25980
gcaaaaggcc aggaaccgta aaaaggccgc gttgctggcg tttttccata ggctccgccc  26040
ccctgacgag catcacaaaa atcgacgctc aagtcagagg tggcgaaacc cgacaggact  26100
ataaagatac caggcgtttc cccctggaag ctccctcgtg cgctctcctg ttccgaccct  26160
gccgcttacc ggatacctgt ccgcctttct cccttcggga agcgtggcgc tttctcatag  26220
ctcacgctgt aggtatctca gttcggtgta ggtcgttcgc tccaagctgg gctgtgtgca  26280
cgaacccccc gttcagcccg accgctgcgc cttatccggt aactatcgtc ttgagtccaa  26340
cccggtaaga cacgacttat cgccactggc agcagccact ggtaacagga ttagcagagc  26400
gaggtatgta ggcggtgcta cagagttctt gaagtggtgg cctaactacg gctacactag  26460
aaggacagta tttggtatct gcgctctgct gaagccagtt accttcggaa aaagagttgg  26520
```

```
tagctcttga tccggcaaac aaaccaccgc tggtagcggt ggtttttttg tttgcaagca  26580

gcagattacg cgcagaaaaa aaggatctca agaagatcct ttgatctttt ctacggggtc  26640

tgacgctcag tggaacgaaa actcacgtta agggattttg gtcatgcatt ctaggtacta  26700

aaacaattca tccagtaaaa tataatattt tattttctcc caatcaggct tgatccccag  26760

taagtcaaaa aatagctcga catactgttc ttccccgata tcctccctga tcgaccggac  26820

gcagaaggca atgtcatacc acttgtccgc cctgccgctt ctcccaagat caataaagcc  26880

acttactttg ccatctttca caaagatgtt gctgtctccc aggtcgccgt gggaaaagac  26940

aagttcctct tcgggctttt ccgtctttaa aaaatcatac agctcgcgcg gatctttaaa  27000

tggagtgtct tcttcccagt tttcgcaatc cacatcggcc agatcgttat tcagtaagta  27060

atccaattcg gctaagcggc tgtctaagct attcgtatag ggacaatccg atatgtcgat  27120

ggagtgaaag agcctgatgc actccgcata cagctcgata atcttttcag ggctttgttc  27180

atcttcatac tcttccgagc aaaggacgcc atcggcctca ctcatgagca gattgctcca  27240

gccatcatgc cgttcaaagt gcaggacctt tggaacaggc agctttcctt ccagccatag  27300

catcatgtcc ttttcccgtt ccacatcata ggtggtccct ttataccggc tgtccgtcat  27360

ttttaaatat aggttttcat ttctcccac cagcttatat accttagcag gagacattcc  27420

ttccgtatct tttacgcagc ggtatttttc gatcagtttt ttcaattccg gtgatattct  27480

cattttagcc atttattatt tccttcctct tttctacagt atttaaagat accccaagaa  27540

gctaattata acaagacgaa ctccaattca ctgttccttg cattctaaaa ccttaaatac  27600

cagaaaacag ctttttcaaa gttgttttca aagttggcgt ataacatagt atcgacggag  27660

ccgattttga aaccgcggtg atcacaggca gcaacgctct gtcatcgtta caatcaacat  27720

gctaccctcc gcgagatcat ccgtgtttca aacccggcag cttagttgcc gttcttccga  27780

atagcatcgg taacatgagc aaagtctgcc gccttacaac ggctctcccg ctgacgccgt  27840

cccggactga tgggctgcct gtatcgagtg gtgattttgt gccgagctgc cggtcgggga  27900

gctgttggct ggctggtggc aggatatatt gtggtgtaaa caaattgacg cttagacaac  27960

ttaataacac attgcggacg tttttaatgt actgaattaa cgccgaatta attc        28014
```

```
<210> SEQ ID NO 2
<211> LENGTH: 28323
<212> TYPE: DNA
<213> ORGANISM: Artificial Sequence
<220> FEATURE:
<223> OTHER INFORMATION: Synthetic construct plasmid pMBXS919

<400> SEQUENCE: 2

ctagggtacg tagtgtttat ctttgttgct tttctgaaca atttatttac tatgtaaata     60

tattatcaat gtttaatcta ttttaatttg cacatgaatt ttcattttat ttttacttta    120

caaaacaaat aaatatatat gcaaaaaaat ttacaaacga tgcacgggtt acaaactaat    180

ttcattaaat gctaatgcag attttgtgaa gtaaaactcc aattatgatg aaaaatacca    240

ccaacaccac ctgcgaaact gtatcccaac tgtccttaat aaaaatgtta aaaagtatat    300

tattctcatt tgtctgtcat aatttatgta ccccacttta atttttctga tgtactaaac    360

cgagggcaaa ctgaaacctg ttcctcatgc aaagccccta ctcaccatgt atcatgtacg    420

tgtcatcacc caacaactcc acttttgcta tataacaaca cccccgtcac actctccctc    480

tctaacacac accccactaa caattccttc acttgcagca ctgttgcatc atcatcttca    540
```

```
ttgcaaaacc ctaaacttca ccttcaaccg gatccaaaat ggcttctatg atatcctctt    600
ccgctgtgac aacagtcagc cgtgcctcta gggggcaatc cgccgcagtg gctccattcg    660
gcggcctcaa atccatgact ggattcccag tgaagaaggt caacactgac attacttcca    720
ttacaagcaa tggtggaaga gtaaagtgca tgcaggtgtg gcctccaatt ggaaagaaga    780
agtttgagac tctttcctat ttgccaccat tgacgagaga ttctagagtt tcgagcacac    840
tgagagaagc atcaaaagat acgttgcaag caaaggataa aacatatcat tactactctt    900
tacctctcgc tgctaagtct ctaggagaca taactcgttt gccgaagtcc ttgaaggtat    960
tactcgaaaa cctattaagg tggcaagacg gaaatagcgt tacagaagaa gatattcacg   1020
ctcttgcggg atggttgaag aatgcacacg cagatcgaga gattgcatat agacctgcta   1080
gagtgttgat gcaagatttc accggtgttc cggctgtcgt tgatttagcg gctatgaggg   1140
aagcagtgaa gaggttgggt ggggatactg ccaaagtgaa ccctcttagt cccgttgatc   1200
ttgttataga tcattcagtc actgttgaca ggtttggaga tgatgaggca tttgaagaga   1260
acgtgcgtct ggaaatggaa cgtaaccatg agagatatgt ctttcttaag tgggggaaac   1320
aagcgttttc tcgtttctcc gttgttccgc ctggtaccgg aatctgtcat caggtcaatc   1380
ttgagtatct cggaaaagca gtctggtccg agcttcagga tggtgagtgg attgcctacc   1440
cagatacact tgttggcacg gattcccata ctacaatgat caatggactg gggtttttgg   1500
gctggggagt aggtgggatc gaggctgaag ctgctatgct agggcaaccg gtgtcaatgc   1560
tcattcctga tgtcgtgggt tttaagctca ctggaaaact tcgagaggga attaccgcta   1620
ccgatctggt actcacagtt acccaaatgc ttagaaaaca tggtgtagtg ggaaatttg    1680
ttgaattcta cggtgacgga cttgatagtc tgccgctcgc cgaccgtgct actattgcca   1740
atatgtcgcc agagtatggt gcgacatgtg gcttcttccc aattgatgcg gttacgctgg   1800
attacatgcg tttatctggt cgatctgagg atcaagttga gttggttgag aagtatgcga   1860
aggcacaggg tatgtggaga aatccaggag atgaacctat ctttacttct actttggagt   1920
tagacatgaa tgatgttgag gctagcttgg ctgggcctaa gcgtccacaa gatagggttg   1980
ctcttccaga tgtgccgaaa gcctttgcag cttcaaacga attagaagtc aacgcgaccc   2040
ataaagacag acaaccagtt gactatgtaa tgaacggtca tcaataccag cttcctgatg   2100
gcgctgttgt tatcgcggca ataacttctt gcaccaatac gagtaatcca agtgtactaa   2160
tggccgctgg actcctggcc aagaaggctg tgactcttgg tcttaagcga cagccttggg   2220
ttaaggcatc actggctccc ggtagcaaag tcgtgagcga ttatcttgct aaagcgaaac   2280
tcacgccata cttggacgaa ctgggtttca atctcgttgg atatggatgc acaacctgta   2340
tcggaaactc tggcccttta cctgatccca ttgaaacagc tataaagaag agtgatctta   2400
ctgtgggcgc tgtcctaagt ggaaacagaa atttcgaggg aagaatacac cctctcgtta   2460
aaacaaattg gttagcttct cccccattag ttgtggccta tgctttggcc gggaatatga   2520
acattaacct tgcttcagag ccgattggac acgatcgtaa aggggaccct gtgtatttga   2580
aagacatctg gccatccgca caagaaatag ctcgtgcggt tgaacaagtg tctacagaaa   2640
tgttccgaaa agagtatgcc gaggtttttg aaggtactgc tgagtggaag ggtataaacg   2700
ttacaaggtc tgacacgtat ggttggcaag aagattctac ttacatcagg cttagtccat   2760
tctttgatga gatgcaggca actcctgccc cagtagagga catccacgga gctagaattc   2820
tggcaatgct aggagattct gttactaccg atcacatttc cccagctggc tcgattaagc   2880
ccgattcacc agctggaagg tacttgcaag gtaggggcgt tgagagaaag gactttaact   2940
```

```
catacggttc gcgtagaggc aaccacgaag taatgatgag ggcacgttc gcaaatatcc 3000
gaatcagaaa tgaaatggtg ccaggcgtgg aagggggaat gacaagacat ttgcctgact 3060
cagatgtcgt ttcgatttac gatgctgcaa tgagatacaa acaggagcag acacctctag 3120
cagtcatagc tggtaaagaa tatggaagtg gtagctctag ggattgggcg gctaaaggac 3180
cgagacttct cggtatcagg gtggtgattg cggaatcatt cgagagaatc catagaagca 3240
atctcatagg gatgggaata ttgcctttag agtttccaca gggagtgacg cgaaagactt 3300
tgggacttac cggtgaagaa aagattgaca ttggtgatct ccagaattta cagcctggtg 3360
caactgtccc tgttaccctc acaagagccg acgggtccca agaggtggtc ccgtgtcgat 3420
gcagaatcga cacagcaacg gaattgactt actatcagaa cgatggaata ctgcattacg 3480
tgatccgtaa catgcttaaa tgaggcgcgc ctgagtaatt ctgatattag agggagcatt 3540
aatgtgttgt tgtgatgtgg tttatatggg gaaattaaat aaatgatgta tgtacctctt 3600
gcctatgtag gtttgtgtgt tttgttttgt tgtctagctt tggttattaa gtagtaggga 3660
cgttcgttcg tgtctcaaaa aaaggggtac taccactctg tagtgtatat ggatgctgga 3720
aatcaatgtg ttttgtattt gttcacctcc attgttgaat tcaatgtcaa atgtgttttg 3780
cgttggttat gtgtaaaatt actatctttc tcgtccgatg atcaaagttt taagcaacaa 3840
aaccaagggt gaaatttaaa ctgtgctttg ttgaagattc ttttatcata ttgaaaatca 3900
aattactagc agcagatttt acctagcatg aaattttatc aacagtacag cactcactaa 3960
ccaagttcca aactaagatg cgccattaac atcagccaat aggcattttc agcaaaagct 4020
tgtacgtagt gtttatcttt gttgcttttc tgaacaattt atttactatg taaatatatt 4080
atcaatgttt aatctatttt aatttgcaca tgaattttca ttttattttt actttacaaa 4140
acaaataaat atatatgcaa aaaaatttac aaacgatgca cgggttacaa actaatttca 4200
ttaaatgcta atgcagattt tgtgaagtaa aactccaatt atgatgaaaa ataccaccaa 4260
caccacctgc gaaactgtat cccaactgtc cttaataaaa atgttaaaaa gtatattatt 4320
ctcatttgtc tgtcataatt tatgtacccc actttaattt ttctgatgta ctaaaccgag 4380
ggcaaactga aacctgttcc tcatgcaaag cccctactca ccatgtatca tgtacgtgtc 4440
atcacccaac aactccactt ttgctatata acaacacccc cgtcacactc tccctctcta 4500
acacacaccc cactaacaat tccttcactt gcagcactgt tgcatcatca tcttcattgc 4560
aaaaccctaa acttcacctt caaccgcggc cgcagatcta aaatggcttc tatgatatcc 4620
tcttccgctg tgacaacagt cagccgtgcc tctagggggc aatccgccgc agtggctcca 4680
ttcggcggcc tcaaatccat gactggattc ccagtgaaga aggtcaacac tgacattact 4740
tccattacaa gcaatggtgg aagagtaaag tgcatgcagg tgtggcctcc aattggaaag 4800
aagaagtttg agactctttc ctatttgcca ccattgacga gagattctag agtggttgac 4860
ggaaggtcat cagcttcgat cgtggcagtc gatcctgaaa gggctgcaag ggagagagat 4920
gctgcagcca gggcgcttct ccaagattcc cctttgcata ctacgatgca gtatgcaact 4980
tctggacttg aacttaccgt accgtatgct cttaaggttg tggcatctgc ggatacgttt 5040
gaccgtgcta aagaagtcgc agacgaggtt ctgagatgtg cttggcagct tgctgatact 5100
gttctaaatt cgtttaatcc taactcagaa gtcagtcttg ttgggagact tccagtgggg 5160
cagaaacacc aaatgtctgc gcctctcaaa agagtgatgg cttgttgtca gagggtatac 5220
aactcttcag caggatgctt cgatccttcc actgctccag ttgcaaaggc cttaagagag 5280
```

```
attgccttgg gtaaagagag aaataacgca tgtttggaag ccctcaccca agcgtgcact   5340
cttccaaact catttgtcat tgattttgaa gctggtacca ttagtagaaa gcatgaacat   5400
gcgagtttag accttggtgg agtatctaag ggttacatag tagattacgt tatagataac   5460
ataaacgcag ctggtttcca gaacgttttc ttcgactggg gcggtgattg cagggcttct   5520
gggatgaacg caagaaatac accgtgggtt gttgggatca ctagaccgcc atctcttgac   5580
atgcttccta acccacccaa agaggcttca tatatctcgg ttatttccct cgacaatgaa   5640
gcattagcga catctggtga ttacgagaat ttgatttaca ccgcagacga taagccgttg   5700
acgtgcacat atgactggaa aggtaaagaa ctaatgaagc ctagccaaag taacatagcc   5760
caagtgtctg taaaatgcta ctctgctatg tatgctgacg ccctcgcaac cgcttgtttt   5820
atcaagcgag atccagctaa ggtaagacaa cttctagacg gatggcgtta tgttcgtgat   5880
actgtgcgag attatcgagt ctatgtaaga gagaatgaaa gagtggcaaa aatgtttgag   5940
atcgccacgg aagatgctga gatgagaaag agaagaataa gtaatacgct tccagcccga   6000
gtgatcgttg ttggtggcgg cttggcaggg ctatctgcgg cgatcgaggc ggctggttgt   6060
ggggcacagg ttgttctaat ggagaaagaa gccaagttag gcggtaacag tgctaaggca   6120
accagcggga taaatggatg ggtactaga gcacaggcaa aagcctcaat cgttgatggt   6180
ggtaaatact ttgaacgaga tacatataag tcaggaattg gcggaaatac tgatccagca   6240
cttgttaaga cactcagcat gaagagtgcg gatgccattg ggtggctgac ttcgctcggt   6300
gtgcctctta ctgtcttatc tcaattaggt ggacactcac gtaagagaac acacagggca   6360
cctgataaga aggatggaac gccactacct attggattca ctattatgaa aactctcgaa   6420
gatcatgttc gtggaaactt atctggacga attacaatta tggaaaattg ttcggttaca   6480
tcactgcttt ccgaaactaa agagcgtcct gatgggacca aacaaattcg tgtcacgggt   6540
gttgagttca cccaggctgg tagcgggaaa actacaatct tagctgatgc cgttatctta   6600
gctacaggtg ggttttctaa tgacaaaacc gcggattccc ttttgaggga acacgcaccg   6660
catttggtca acttccccac cacaaacggg ccttgggcta ctggagatgg agttaaactt   6720
gcacagagac ttggtgctca acttgtagat atggataaag ttcagttaca tccgacagga   6780
ctcataaacc ctaaagatcc agcaaacccg acaaagttct taggacctga ggccttgcgt   6840
ggcagcggtg gtgtgctgct gaacaagcaa ggcaagagat ttgtgaatga actagaccta   6900
cgttctgttg tgagtaaggc tattatggaa caaggtgctg agtacccagg ttctggcggc   6960
tcgatgttcg cttactgcgt tcttaacgcc gcagctcaaa agctatttgg agtatcatcc   7020
catgagttct actggaaaaa gatgggtctt ttcgtcaaag ctgacactat gagggatctg   7080
gctgctctta tcggttgtcc tgtcgagtct gtgcaacaga cattggaaga atatgagaga   7140
ctgtctattt cccagagatc atgcccaata accaggaagt cggtttaccc ttgtgtctta   7200
ggaactaagg gtccgtatta cgttgctttt gtgacacctt caatccacta tactatgggt   7260
ggttgcttga tttcccctag tgcagaaatt caaatgaaaa acacctcatc gagagcacct   7320
ttatcacatt ccaatcccat cctgggttta ttcggagctg gtgaggtaac tggcggtgtc   7380
cacggtggca ataggcttgg gggcaattcc cttctggaat gtgtggtttt cggaaggatt   7440
gcaggtgacc gagcttccac tatattgcaa agaaaatcca gtgcgctgtc tttcaaggtg   7500
tggactacag ttgttcttag agaggtgcgt gagggcggag tgtacggcgc tggttctagg   7560
gttctaagat ttaaccttcc tggagcactt caacgttccg ggctatcttt aggacagttt   7620
atcgctatac gaggggattg ggatggacag caacttattg gttactattc tccaattact   7680
```

```
ctcccagatg acctcggaat gatagacatt cttgctagat cagacaaagg cacactcagg   7740
gagtggattt ctgctctgga gccaggtgat gccgtggaaa tgaaagcgtg cggcggtctt   7800
gtaattgaac gtagactttc agataagcat tttgtgttta tggggcacat catcaataag   7860
ctatgtttga tcgccggtgg gactggcgtt gcgcccatgt tgcagattat caaggcggca   7920
tttatgaagc cctttataga tacgctggag agtgtgcatt tgatctatgc tgcagaggat   7980
gtaacggagc ttacatatcg tgaagttctg gaagaacgac gaagggaatc gagaggtaaa   8040
ttcaagaaaa ctttcgttct taataggcca ccccctttgt ggactgacgg cgtcgggttc   8100
atagatcgag ggatacttac aaatcatgtc caaccccat ccgataatct tttggtggcc   8160
atttgtggac cgcccgttat gcagcgtata gtgaaggcta cactgaaaac tttgggatat   8220
aacatgaact tggttagaac ggtagacgag actgaacctt caggtagcag taagatttga   8280
gcgatcgcgc ggccgctgag taattctgat attagaggga gcattaatgt gttgttgtga   8340
tgtggtttat atggggaaat taaataaatg atgtatgtac ctcttgccta tgtaggtttg   8400
tgtgttttgt tttgttgtct agctttggtt attaagtagt agggacgttc gttcgtgtct   8460
caaaaaaagg ggtactacca ctctgtagtg tatatggatg ctggaaatca atgtgttttg   8520
tatttgttca cctccattgt tgaattcaat gtcaaatgtg ttttgcgttg gttatgtgta   8580
aaattactat ctttctcgtc cgatgatcaa agttttaagc aacaaaacca agggtgaaat   8640
ttaaactgtg ctttgttgaa gattctttta tcatattgaa aatcaaatta ctagcagcag   8700
attttaccta gcatgaaatt ttatcaacag tacagcactc actaaccaag ttccaaacta   8760
agatgcgcca ttaacatcag ccaataggca ttttcagcaa gtttaaacta cgtagtgttt   8820
atctttgttg cttttctgaa caatttattt actatgtaaa tatattatca atgtttaatc   8880
tattttaatt tgcacatgaa ttttcatttt atttttactt tacaaaacaa ataaatatat   8940
atgcaaaaaa atttacaaac gatgcacggg ttacaaacta atttcattaa atgctaatgc   9000
agattttgtg aagtaaaact ccaattatga tgaaaaatac caccaacacc acctgcgaaa   9060
ctgtatccca actgtcctta ataaaaatgt taaaaagtat attattctca tttgtctgtc   9120
ataatttatg taccccactt taatttttct gatgtactaa accgagggca aactgaaacc   9180
tgttcctcat gcaaagcccc tactcaccat gtatcatgta cgtgtcatca cccaacaact   9240
ccacttttgc tatataacaa cacccccgtc acactctccc tctctaacac acaccccact   9300
aacaattcct tcacttgcag cactgttgca tcatcatctt cattgcaaaa ccctaaactt   9360
caccttcaac cgcggccgct cgcgaaaaat ggcttctatg atatcctctt ccgctgtgac   9420
aacagtcagc cgtgcctcta gggggcaatc cgccgcagtg gctccattcg gcggcctcaa   9480
atccatgact ggattcccag tgaagaaggt caacactgac attacttcca ttacaagcaa   9540
tggtggaaga gtaaagtgca tgcaggtgtg gcctccaatt ggaaagaaga agtttgagac   9600
tctttcctat ttgccaccat tgacgagaga ttctagagtg gctaggaaga agatccgtga   9660
atatgactct aaaaggcttg tcaaagaaca tttcaagagg cttagtggaa aagaactccc   9720
tattaggtct gtgcagatta acgaaacaac tgatcttaac gaattggttg agaaagagcc   9780
ttggttgagc agtgaaaagt tagtcgtgaa gccagacatg ttgtttggaa aacgtggaaa   9840
atcaggactt gtcgctctca aactggactt tgctgatgtc gcaacgtttg ttaaagagag   9900
actaggtaaa gaggttgaga tgtcaggatg taaaggaccc ataacgacct ttattgttga   9960
accattcgtt ccacataacg aagaatacta ccttaatgta gtgtcggata gattaggatg  10020
```

```
ctccatatca ttctccgagt gtggcgggat cgagattgaa gagaactggg ataaggtcaa  10080
aacaatcttt ttgccaaccg gtgcttcgct gacacctgag atttgtgctc cccttgttgc  10140
tacacttcca cttgagatta aggcagaaat agaagagttc atcaaggtta tctttactct  10200
gttccaagat ttagatttca cttttctcga aatgaatccg tttactttag tcgatggttc  10260
tccgtatcct ttggatatgc gaggtgagct ggatgacaca gcggctttta agaacttcaa  10320
gaagtgggga gatattgagt tcccattgcc gtttggccgt gttatgtctc caactgaatc  10380
cttcatacac ggactcgatg aaaagaccag tgcatctctc aagtttaccg ttctaaatcc  10440
taagggtaga atctggacta tggtagctgg gggtggagcc tctgtaatct acgctgatac  10500
tgttggtgat cttggctatg ctagcgaatt agggaactat gcggagtaca gcggtgcacc  10560
taaagaggac gaggtactcc aatatgcccg agtggtgatt gattgtgcta cggcaaatcc  10620
tgacggaaag tcaagagccc ttgtgattgg gggtggtata gcaaatttca cagacgttgc  10680
agcgactttc aatggtatca ttagagcctt gaaagagaaa gaggccaaac taaaggctgc  10740
gagaatgcac atttttgttc gtagaggtgg ccctaattac cagaagggtt tggctaaaat  10800
gcgagctttg ggagatgata taggcgtgcc tatcgaagtt tatggacctg aagcaacgat  10860
gaccgggatc tgcaaagaag caatacaata cattacagct gcagcgtgaa cgcgttgagt  10920
aattctgata ttagagggag cattaatgtg ttgttgtgat gtggtttata tggggaaatt  10980
aaataaatga tgtatgtacc tcttgcctat gtaggtttgt gtgttttgtt ttgttgtcta  11040
gctttggtta ttaagtagta gggacgttcg ttcgtgtctc aaaaaaaggg gtactaccac  11100
tctgtagtgt atatggatgc tggaaatcaa tgtgttttgt atttgttcac ctccattgtt  11160
gaattcaatg tcaaatgtgt tttgcgttgg ttatgtgtaa aattactatc tttctcgtcc  11220
gatgatcaaa gttttaagca acaaaaccaa gggtgaaatt taaactgtgc tttgttgaag  11280
attcttttat catattgaaa atcaaattac tagcagcaga ttttacctag catgaaattt  11340
tatcaacagt acagcactca ctaaccaagt tccaaactaa gatgcgccat taacatcagc  11400
caataggcat tttcagcaat gtacatacgt agtgtttatc tttgttgctt ttctgaacaa  11460
tttatttact atgtaaatat attatcaatg tttaatctat tttaatttgc acatgaattt  11520
tcattttatt tttactttac aaaacaaata aatatatatg caaaaaaatt tacaaacgat  11580
gcacgggtta caaactaatt tcattaaatg ctaatgcaga ttttgtgaag taaaactcca  11640
attatgatga aaaataccac caacaccacc tgcgaaactg tatcccaact gtccttaata  11700
aaaatgttaa aaagtatatt attctcattt gtctgtcata atttatgtac cccactttaa  11760
tttttctgat gtactaaacc gagggcaaac tgaaacctgt tcctcatgca aagcccctac  11820
tcaccatgta tcatgtacgt gtcatcaccc aacaactcca cttttgctat ataacaacac  11880
ccccgtcaca ctctccctct ctaacacaca ccccactaac aattccttca cttgcagcac  11940
tgttgcatca tcatcttcat tgcaaaaccc taaacttcac cttcaaccgc ggccgcgacg  12000
tcaaaatggc ttctatgata tcctcttccg ctgtgacaac agtcagccgt gcctctaggg  12060
ggcaatccgc cgcagtggct ccattcggcg gcctcaaatc catgactgga ttcccagtga  12120
agaaggtcaa cactgacatt acttccatta caagcaatgg tggaagagta aagtgcatgc  12180
aggtgtggcc tccaattgga aagaagaagt ttgagactct ttcctatttg ccaccattga  12240
cgagagattc tagagttgct accggccaac tcttttcccg aacaacgcaa gctctattct  12300
acaactataa acaacttcca gttcaaagaa tgttagattt cgatttctta tgcggaagag  12360
aaacaccatc agtggctgga attatcaatc cagggtccga gggatttcag aaattgtttt  12420
```

```
tcggtcaaga agagatagct attccagtcc atgcggccat agaagcagct tgtgccgccc  12480
accccactgc tgatgttttc atcaactttg cttcgttcag gagtgcggct gcaagttcga  12540
tggcagctct caagcaacct acaatcaagg tcgtagcaat aatcgcagag ggagtcccag  12600
aatctgacac caagcaactc atcgcttatg cccgagcgaa caataaagtg gttataggtc  12660
ctgctactgt gggcggaatt caggctggag cttttaagat tggtgacact gcggggacca  12720
ttgataacat tatccaatgc aagctgtatc gtccgggtag tgtcggattt gtttccaagt  12780
ctggtgggat gtctaatgag atgtataaca ctgtagcaag agtaactgat ggcatttatg  12840
aggggatagc aattgggggt gacgttttcc ccggttcaac tttatccgat catatcctga  12900
gatttaacaa tatcccgcaa atcaagatga tggttgtact aggagagctt gggggacgtg  12960
acgagtattc acttgttgaa gctctgaaag agggtaaagt caataaacct gttgtcgctt  13020
gggtgtcagg cacctgtgca agactcttca aaagcgaggt ccagtttggt cacgcaggag  13080
cgaagagcgg tggagagatg gagtctgcac aagctaaaaa ccaggcgttg atagatgcag  13140
gcgcaattgt tccaacatct tttgaagcct tggagagcgc gatcaaagaa acttttgaga  13200
aacttgtcga agaaggtaag gtttcgccga ttaaagaagt aatcccacct cagatccctg  13260
aggatctaaa ttccgcaatt aagtctggaa aggtgagggc tccaacgcat atcatatcga  13320
cgatttctga tgatagaggg gaagagccgt gctacgcagg tgttcctatg tctagcataa  13380
ttgagcaagg ttacggagtg ggagatgtca tttcattgtt atggttcaaa cgtagtctcc  13440
cgaggtattg taccaaattc attgagattt gcataatgct ttgtgcggat catggaccct  13500
gtgtatctgg tgctcataat actatcgtta ctgccagagc tggaaaagat ttggtgtcta  13560
gtctcgtttc aggcttattg acaataggtc ctcgattcgg tggggccatc gacgacgctg  13620
ccaggtactt taaggatgca tgtgacagaa acctcacacc atatgaattt gtggaaggca  13680
tgaaaaagaa gggcattaga gtgcctggaa ttggtcatcg tattaagtca agggataata  13740
gagacaagag agttgaactt ttacagaagt ttgctcgaag taatttccct agcgttaagt  13800
acatggaata cgcggttact gttgaaacgt acacattgtc taaggctaat aacttggtgc  13860
ttaatgttga tggtgctata ggttcattat tcttggatct acttgcaggt tctggaatgt  13920
tcacaaagca ggaaatcgac gagatagtgc aaattggata cctgaacgga ctatttgtgt  13980
tggctaggtc aatagggctt atcggacaca cgtttgatca gaaacgtctt aaacagcctc  14040
tctaccgaca cccttgggaa gatgttctgt ataccaaatg agttaactga gtaattctga  14100
tattagaggg agcattaatg tgttgttgtg atgtggttta tatggggaaa ttaaataaat  14160
gatgtatgta cctcttgcct atgtaggttt gtgtgttttg ttttgttgtc tagctttggt  14220
tattaagtag tagggacgtt cgttcgtgtc tcaaaaaaag gggtactacc actctgtagt  14280
gtatatggat gctggaaatc aatgtgtttt gtatttgttc acctccattg ttgaattcaa  14340
tgtcaaatgt gttttgcgtt ggttatgtgt aaaattacta tctttctcgt ccgatgatca  14400
aagttttaag caacaaaacc aagggtgaaa tttaaactgt gctttgttga agattctttt  14460
atcatattga aaatcaaatt actagcagca gattttacct agcatgaaat tttatcaaca  14520
gtacagcact cactaaccaa gttccaaact aagatgcgcc attaacatca gccaataggc  14580
attttcagca agtttaaacc ggaccgtacg tagtgtttat ctttgttgct tttctgaaca  14640
atttatttac tatgtaaata tattatcaat gtttaatcta ttttaatttg cacatgaatt  14700
ttcattttat ttttacttta caaaacaaat aaatatatat gcaaaaaaat ttacaaacga  14760
```

```
tgcacgggtt acaaactaat ttcattaaat gctaatgcag attttgtgaa gtaaaactcc  14820
aattatgatg aaaaatacca ccaacaccac ctgcgaaact gtatcccaac tgtccttaat  14880
aaaaatgtta aaaagtatat tattctcatt tgtctgtcat aatttatgta ccccacttta  14940
atttttctga tgtactaaac cgagggcaaa ctgaaacctg ttcctcatgc aaagccccta  15000
ctcaccatgt atcatgtacg tgtcatcacc caacaactcc acttttgcta tataacaaca  15060
cccccgtcac actctccctc tctaacacac accccactaa caattccttc acttgcagca  15120
ctgttgcatc atcatcttca ttgcaaaacc ctaaacttca ccttcaaccg cggccgccac  15180
gtgaaaatgg cttctatgat atcctcttcc gctgtgacaa cagtcagccg tgcctctagg  15240
gggcaatccg ccgcagtggc tccattcggc ggcctcaaat ccatgactgg attcccagtg  15300
aagaaggtca acactgacat tacttccatt acaagcaatg gtggaagagt aaagtgcatg  15360
caggtgtggc ctccaattgg aaagaagaag tttgagactc tttcctattt gccaccattg  15420
acgagagatt ctagagtgaa tactgttcgt tcagagaaag actctatggg ggctatagac  15480
gtgcctgctg ataagttatg gggagcccag actcaacgta gcctggagca ctttaggata  15540
tcgactgaga agatgcctac gtccttgatt catgcccttg ctctcactaa gagagcagca  15600
gcaaaagtta atgaggatct cggccttttta tccgaagaga aagcatctgc catacgacag  15660
gccgctgatg aagtgttggc gggtcagcat gatgatgagt tcccattagc tatctggcag  15720
acaggctctg gtactcaatc caacatgaac atgaatgagg tgctagcaaa cagggcctca  15780
gagcttttag gtggggtcag gggaatggaa cgaaaggttc atcccaacga tgacgtaaac  15840
aagtcacaat cgagtaatga tgtgttccca actgctatgc acgttgcagc tctgcttgcg  15900
ttgagaaagc aacttattcc acaactcaaa actctcaccc aaacattgaa tgaaaagtca  15960
agggcctttg cagatatcgt gaagatcgga cgaacacatc ttcaggacgc tacaccactg  16020
acgttgggac aagagatttc tggatgggtt gctatgttgg aacataactt gaaacatatc  16080
gagtatagtt tacctcatgt tgcagaacta gcattgggtg gtacagcagt cggtaccggc  16140
ctcaacacac atcctgaata cgctagacgt gtagctgatg aacttgccgt tattacctgc  16200
gctccgttcg ttacggctcc taataagttt gaagctcttg ctacttgtga tgctctagtc  16260
caagctcatg gtgcactaaa gggacttgcg gcatctttaa tgaagattgc aaatgatgtc  16320
cgttggctag caagcggacc aagatgtgga ataggcgaaa tttccatccc tgagaacgag  16380
cccggatcat ctattatgcc gggtaaagtt aatccaacgc agtgtgaagc cttgaccatg  16440
ctttgctgcc aggtaatggg aaacgatgtg gccatcaata tgggtggtgc gagtggaaac  16500
tttgagctga atgtctttag accgatggtt atccacaact ttcttcagag tgtaaggctt  16560
ctcgccgacg ggatggagtc attcaataaa cactgtgcgg ttggcataga gccaaacaga  16620
gaacgtatca atcaacttct caatgaatct ctaatgttgg ttactgctct caacacccac  16680
attgggtacg acaaagctgc tgaaattgct aaaaaggcgc acaaagaagg tttaacactg  16740
aaagcggcag ctctcgctct cggttatctg tctgaagctg agttcgattc gtgggtcaga  16800
cctgaacaaa tggtgggaag catgaaggct gggagatgaa ctagttgagt aattctgata  16860
ttagagggag cattaatgtg ttgttgtgat gtggtttata tggggaaatt aaataaatga  16920
tgtatgtacc tcttgcctat gtaggtttgt gtgttttgtt ttgttgtcta gctttggtta  16980
ttaagtagta gggacgttcg ttcgtgtctc aaaaaaaggg gtactaccac tctgtagtgt  17040
atatggatgc tggaaatcaa tgtgttttgt atttgttcac ctccattgtt gaattcaatg  17100
tcaaatgtgt tttgcgttgg ttatgtgtaa aattactatc tttctcgtcc gatgatcaaa  17160
```

```
gttttaagca acaaaaccaa gggtgaaatt taaactgtgc tttgttgaag attcttttat  17220
catattgaaa atcaaattac tagcagcaga ttttacctag catgaaattt tatcaacagt  17280
acagcactca ctaaccaagt tccaaactaa gatgcgccat taacatcagc caataggcat  17340
tttcagcaag tttaaactcc ggattaatta agtcgacggg cccgtttaaa ccacgtagtg  17400
cctcagcgtt taaacgtacg tagtgtttat ctttgttgct tttctgaaca atttatttac  17460
tatgtaaata tattatcaat gtttaatcta ttttaatttg cacatgaatt ttcattttat  17520
ttttacttta caaaacaaat aaatatatat gcaaaaaaat ttacaaacga tgcacgggtt  17580
acaaactaat ttcattaaat gctaatgcag attttgtgaa gtaaaactcc aattatgatg  17640
aaaaatacca ccaacaccac ctgcgaaact gtatcccaac tgtccttaat aaaaatgtta  17700
aaaagtatat tattctcatt tgtctgtcat aatttatgta ccccacttta atttttctga  17760
tgtactaaac cgagggcaaa ctgaaacctg ttcctcatgc aaagccccta ctcaccatgt  17820
atcatgtacg tgtcatcacc caacaactcc acttttgcta tataacaaca cccccgtcac  17880
actctccctc tctaacacac accccactaa caattccttc acttgcagca ctgttgcatc  17940
atcatcttca ttgcaaaacc ctaaacttca ccttcaaccg cggccgcttc gaaaaaatgg  18000
cttctatgat atcctcttcc gctgtgacaa cagtcagccg tgcctctagg gggcaatccg  18060
ccgcagtggc tccattcggc ggcctcaaat ccatgactgg attcccagtg aagaaggtca  18120
acactgacat tacttccatt acaagcaatg gtggaagagt aaagtgcatg caggtgtggc  18180
ctccaattgg aaagaagaag tttgagactc tttcctattt gccaccattg acgagagatt  18240
ctagagttgc attgaacatg aaacagcaac aagcaggtct ttcccgtaaa gccgctaggt  18300
ctgtatcttc tagagcacct gtagttgtgc gtgctgttgc tgctcccgtc gcacctgcgg  18360
cagaggctga agccaaaaag gcttatggag ttttcagact ctcatatgac acgcaaaatg  18420
aagatgcatc acttacaagg tcatggaaaa agactgttaa ggttgctgtc actggcgcat  18480
caggtaatat cgccaaccat ctcttattca tgttggcatc cggtgaagtg tatggaaagg  18540
atcaacctat cgcattgcaa ctgctcggat cggagaggtc gaaagaagct ctagagggcg  18600
tagctatgga gctggaagat agcttgtacc cacttttgcg tgaggtcagc attggtacag  18660
acccatacga ggtttttggc gatgccgatt gggcgctaat gataggagcc aagccaagag  18720
gtccaggaat ggaacgagct gacttacttc agcagaatgg tgagattttt caggtgcaag  18780
ggagagcact aaatgagtca gcatcgagaa actgcaaggt gctcgtagtg ggaaatcctt  18840
gtaatacgaa cgctctcatt gctatggaaa atgctccaaa catcccacga aagaactttc  18900
acgcccttac tcgtttagat gaaaaccgtg ctaaatgtca attggctcta aaatctggaa  18960
agttctacac cagtgtctct cgaatggcga tatggggtaa ccatagcact acacaggttc  19020
ctgactttgt gaatgcaagg ataggtggac ttcctgcgcc ggatgttatt agggacatga  19080
aatggtttag ggaagagttc acacctaagg tcgcgctgag aggtggtgcc cttatcaaaa  19140
agtggggcag atccagtgcg gcatccacag cggtttctgt ggcagatgct atcagagctt  19200
tagtagtgcc cactgcgcca ggggattgtt ttagtaccgg agttattagc gatggcaatc  19260
cttacggagt tcgtgaagga ttgattttca gttttccgtg cagaagtaag gggggacggag  19320
attatgagat ttgtgataac ttcattgttg acgaatggct tcgagctaag atcagggcct  19380
ctgaagatga gttacagaaa gaaaaagagt gcgtgtctca ccttataggg atgatgggtg  19440
gaagttgtgc tctcagaggg gcagaggata ccacggtccc tggtgaaaat tgaatttaaa  19500
```

```
tgcggccgct gagtaattct gatattagag ggagcattaa tgtgttgttg tgatgtggtt  19560
tatatgggga aattaaataa atgatgtatg tacctcttgc ctatgtaggt ttgtgtgttt  19620
tgttttgttg tctagctttg gttattaagt agtagggacg ttcgttcgtg tctcaaaaaa  19680
aggggtacta ccactctgta gtgtatatgg atgctggaaa tcaatgtgtt ttgtatttgt  19740
tcacctccat tgttgaattc aatgtcaaat gtgttttgcg ttggttatgt gtaaaattac  19800
tatctttctc gtccgatgat caaagtttta agcaacaaaa ccaagggtga aatttaaact  19860
gtgctttgtt gaagattctt ttatcatatt gaaaatcaaa ttactagcag cagattttac  19920
ctagcatgaa attttatcaa cagtacagca ctcactaacc aagttccaaa ctaagatgcg  19980
ccattaacat cagccaatag gcattttcag caaagcaaat gaattcgtaa tcatgtcata  20040
gctgtttcct gtgtgaaatt gttatccgct cacaattcca cacaacatac gagccggaag  20100
cataaagtgt aaagcctggg gtgcctaatg agtgagctaa ctcacattaa ttgcgttgcg  20160
ctcactgccc gctttccagt cgggaaacct gtcgtgccag ctgcattaat gaatcggcca  20220
acgcgcgggg agaggcggtt tgcgtattgg ctagagcagc ttgccaacat ggtggagcac  20280
gacactctcg tctactccaa gaatatcaaa gatacagtct cagaagacca aagggctatt  20340
gagacttttc aacaaagggt aatatcggga aacctcctcg gattccattg cccagctatc  20400
tgtcacttca tcaaaaggac agtagaaaag gaaggtggca cctacaaatg ccatcattgc  20460
gataaaggaa aggctatcgt tcaagatgcc tctgccgaca gtggtcccaa agatggaccc  20520
ccacccacga ggagcatcgt ggaaaaagaa gacgttccaa ccacgtcttc aaagcaagtg  20580
gattgatgtg aacatggtgg agcacgacac tctcgtctac tccaagaata tcaaagatac  20640
agtctcagaa gaccaaaggg ctattgagac ttttcaacaa agggtaatat cgggaaacct  20700
cctcggattc cattgcccag ctatctgtca cttcatcaaa aggacagtag aaaaggaagg  20760
tggcacctac aaatgccatc attgcgataa aggaaaggct atcgttcaag atgcctctgc  20820
cgacagtggt cccaaagatg gacccccacc cacgaggagc atcgtggaaa aagaagacgt  20880
tccaaccacg tcttcaaagc aagtggattg atgtgatatc tccactgacg taagggatga  20940
cgcacaatcc cactatcctt cgcaagaccc ttcctctata taaggaagtt catttcattt  21000
ggagaggaca cgctgaaatc accagtctct ctctacaaat ctatctctct cgagatgagc  21060
ccagaacgac gcccggccga catccgccgt gccaccgagg cggacatgcc ggcggtctgc  21120
accatcgtca accactacat cgagacaagc acggtcaact tccgtaccga gccgcaggaa  21180
ccgcaggagt ggacggacga cctcgtccgt ctgcgggagc gctatccctg gctcgtcgcc  21240
gaggtggacg gcgaggtcgc cggcatcgcc tacgcgggcc cctggaaggc acgcaacgcc  21300
tacgactgga cggccgagtc gaccgtgtac gtctcccccc gccaccagcg gacgggactg  21360
ggctccacgc tctacaccca cctgctgaag tccctggagg cacagggctt caagagcgtg  21420
gtcgctgtca tcgggctgcc caacgacccg agcgtgcgca tgcacgaggc gctcggatat  21480
gccccccgcg gcatgctgcg ggcggccggc ttcaagcacg ggaactggca tgacgtgggt  21540
ttctggcagc tggacttcag cctgccggta ccgccccgtc cggtcctgcc cgtcaccgag  21600
atttgagagc tcggtcacct gtccaacagt ctcagggtta atgtctatgt atcttaaata  21660
atgttgtcgg cgatcgttca aacatttggc aataaagttt cttaagattg aatcctgttg  21720
ccggtcttgc gatgattatc atataatttc tgttgaatta cgttaagcat gtaataatta  21780
acatgtaatg catgacgtta tttatgagat gggtttttat gattagagtc ccgcaattat  21840
acatttaata cgcgatagaa aacaaaatat agcgcgcaaa ctaggataaa ttatcgcgcg  21900
```

```
cggtgtcatc tatgttacta gatcgggaat taaactatca gtgtttgaca ggatatattg  21960
gcgggtaaac ctaagagaaa agagcgttta ttagaataat cggatattta aaagggcgtg  22020
aaaaggttta tccgttcgtc catttgtatg tgcatgccaa ccacagggtt cccctcggga  22080
tcaaagtact ttgatccaac ccctccgctg ctatagtgca gtcggcttct gacgttcagt  22140
gcagccgtct tctgaaaacg acatgtcgca caagtcctaa gttacgcgac aggctgccgc  22200
cctgcccttt tcctggcgtt ttcttgtcgc gtgttttagt cgcataaagt agaatacttg  22260
cgactagaac cggagacatt acgccatgaa caagagcgcc gccgctggcc tgctgggcta  22320
tgcccgcgtc agcaccgacg accaggactt gaccaaccaa cgggccgaac tgcacgcggc  22380
cggctgcacc aagctgtttt ccgagaagat caccggcacc aggcgcgacc gcccggagct  22440
ggccaggatg cttgaccacc tacgccctgg cgacgttgtg acagtgacca ggctagaccg  22500
cctggcccgc agcacccgcg acctactgga cattgccgag cgcatccagg aggccggcgc  22560
gggcctgcgt agcctggcag agccgtgggc cgacaccacc acgccggccg gccgcatggt  22620
gttgaccgtg ttcgccggca ttgccgagtt cgagcgttcc ctaatcatcg accgcacccg  22680
gagcgggcgc gaggccgcca aggcccgagg cgtgaagttt ggcccccgcc ctaccctcac  22740
cccggcacag atcgcgcacg cccgcgagct gatcgaccag gaaggccgca ccgtgaaaga  22800
ggcggctgca ctgcttggcg tgcatcgctc gaccctgtac cgcgcacttg agcgcagcga  22860
ggaagtgacg cccaccgagg ccaggcggcg cggtgccttc cgtgaggacg cattgaccga  22920
ggccgacgcc ctggcggccg ccgagaatga acgccaagag gaacaagcat gaaaccgcac  22980
caggacggcc aggacgaacc gtttttcatt accgaagaga tcgaggcgga gatgatcgcg  23040
gccgggtacg tgttcgagcc gcccgcgcac gtctcaaccg tgcggctgca tgaaatcctg  23100
gccggtttgt ctgatgccaa gctggcggcc tggccggcca gcttggccgc tgaagaaacc  23160
gagcgccgcc gtctaaaaag gtgatgtgta tttgagtaaa acagcttgcg tcatgcggtc  23220
gctgcgtata tgatgcgatg agtaaataaa caaatacgca aggggaacgc atgaaggtta  23280
tcgctgtact taaccagaaa ggcgggtcag gcaagacgac catcgcaacc catctagccc  23340
gcgccctgca actcgccggg gccgatgttc tgttagtcga ttccgatccc cagggcagtg  23400
cccgcgattg ggcggccgtg cgggaagatc aaccgctaac cgttgtcggc atcgaccgcc  23460
cgacgattga ccgcgacgtg aaggccatcg gccggcgcga cttcgtagtg atcgacggag  23520
cgccccaggc ggcggacttg gctgtgtccg cgatcaaggc agccgacttc gtgctgattc  23580
cggtgcagcc aagcccttac gacatatggg ccaccgccga cctggtggag ctggttaagc  23640
agcgcattga ggtcacggat ggaaggctac aagcggcctt tgtcgtgtcg cgggcgatca  23700
aaggcacgcg catcggcggt gaggttgccg aggcgctggc cgggtacgag ctgcccattc  23760
ttgagtcccg tatcacgcag cgcgtgagct acccaggcac tgccgccgcc ggcacaaccg  23820
ttcttgaatc agaacccgag ggcgacgctg cccgcgaggt ccaggcgctg gccgctgaaa  23880
ttaaatcaaa actcatttga gttaatgagg taaagagaaa atgagcaaaa gcacaaacac  23940
gctaagtgcc ggccgtccga gcgcacgcag cagcaaggct gcaacgttgg ccagcctggc  24000
agacacgcca gccatgaagc gggtcaactt tcagttgccg gcggaggatc acaccaagct  24060
gaagatgtac gcggtacgcc aaggcaagac cattaccgag ctgctatctg aatacatcgc  24120
gcagctacca gagtaaatga gcaaatgaat aaatgagtag atgaatttta gcggctaaag  24180
gaggcggcat ggaaaatcaa gaacaaccag gcaccgacgc cgtggaatgc cccatgtgtg  24240
```

-continued

```
gaggaacggg cggttggcca ggcgtaagcg gctgggttgc ctgccggccc tgcaatggca  24300
ctggaacccc caagcccgag gaatcggcgt gagcggtcgc aaaccatccg gcccggtaca  24360
aatcggcgcg gcgctgggtg atgacctggt ggagaagttg aaggccgcgc aggccgccca  24420
gcggcaacgc atcgaggcag aagcacgccc cggtgaatcg tggcaagcgg ccgctgatcg  24480
aatccgcaaa gaatcccggc aaccgccggc agccggtgcg ccgtcgatta ggaagccgcc  24540
caagggcgac gagcaaccag atttttttcgt tccgatgctc tatgacgtgg gcacccgcga  24600
tagtcgcagc atcatggacg tggccgtttt ccgtctgtcg aagcgtgacc gacgagctgg  24660
cgaggtgatc cgctacgagc ttccagacgg gcacgtagag gtttccgcag ggccggccgg  24720
catggccagt gtgtgggatt acgacctggt actgatggcg gtttcccatc taaccgaatc  24780
catgaaccga taccgggaag ggaagggaga caagcccggc cgcgtgttcc gtccacacgt  24840
tgcggacgta ctcaagttct gccggcgagc cgatggcgga aagcagaaag acgacctggt  24900
agaaacctgc attcggttaa acaccacgca cgttgccatg cagcgtacga agaaggccaa  24960
gaacggccgc ctggtgacgg tatccgaggg tgaagccttg attagccgct acaagatcgt  25020
aaagagcgaa accgggcggc cggagtacat cgagatcgag ctagctgatt ggatgtaccg  25080
cgagatcaca gaaggcaaga acccggacgt gctgacggtt caccccgatt actttttgat  25140
cgatcccggc atcggccgtt ttctctaccg cctggcacgc cgcgccgcag gcaaggcaga  25200
agccagatgg ttgttcaaga cgatctacga acgcagtggc agcgccggag agttcaagaa  25260
gttctgtttc accgtgcgca agctgatcgg gtcaaatgac ctgccggagt acgatttgaa  25320
ggaggaggcg gggcaggctg gcccgatcct agtcatgcgc taccgcaacc tgatcgaggg  25380
cgaagcatcc gccggttcct aatgtacgga gcagatgcta gggcaaattg ccctagcagg  25440
ggaaaaaggt cgaaaaggtc tctttcctgt ggatagcacg tacattggga acccaaagcc  25500
gtacattggg aaccggaacc cgtacattgg gaacccaaag ccgtacattg ggaaccggtc  25560
acacatgtaa gtgactgata taaaagagaa aaaaggcgat ttttccgcct aaaactcttt  25620
aaaacttatt aaaactctta aaacccgcct ggcctgtgca taactgtctg gccagcgcac  25680
agccgaagag ctgcaaaaag cgcctaccct tcggtcgctg cgctccctac gccccgccgc  25740
ttcgcgtcgg cctatcgcgg ccgctggccg ctcaaaaatg gctggcctac ggccaggcaa  25800
tctaccaggg cgcggacaag ccgcgccgtc gccactcgac cgccggcgcc cacatcaagg  25860
caccctgcct cgcgcgtttc ggtgatgacg gtgaaaacct ctgacacatg cagctcccgg  25920
agacggtcac agcttgtctg taagcggatg ccgggagcag acaagcccgt cagggcgcgt  25980
cagcgggtgt tggcgggtgt cggggcgcag ccatgaccca gtcacgtagc gatagcggag  26040
tgtatactgg cttaactatg cggcatcaga gcagattgta ctgagagtgc accatatgcg  26100
gtgtgaaata ccgcacagat gcgtaaggag aaaataccgc atcaggcgct cttccgcttc  26160
ctcgctcact gactcgctgc gctcggtcgt tcggctgcgg cgagcggtat cagctcactc  26220
aaaggcggta atacggttat ccacagaatc aggggataac gcaggaaaga acatgtgagc  26280
aaaaggccag caaaaggcca ggaaccgtaa aaaggccgcg ttgctggcgt ttttccatag  26340
gctccgcccc cctgacgagc atcacaaaaa tcgacgctca agtcagaggt ggcgaaaccc  26400
gacaggacta taaagatacc aggcgtttcc ccctggaagc tccctcgtgc gctctcctgt  26460
tccgaccctg ccgcttaccg gatacctgtc cgcctttctc ccttcgggaa gcgtggcgct  26520
ttctcatagc tcacgctgta ggtatctcag ttcggtgtag gtcgttcgct ccaagctggg  26580
ctgtgtgcac gaaccccccg ttcagcccga ccgctgcgcc ttatccggta actatcgtct  26640
```

```
tgagtccaac ccggtaagac acgacttatc gccactggca gcagccactg gtaacaggat  26700

tagcagagcg aggtatgtag gcggtgctac agagttcttg aagtggtggc ctaactacgg  26760

ctacactaga aggacagtat ttggtatctg cgctctgctg aagccagtta ccttcggaaa  26820

aagagttggt agctcttgat ccggcaaaca aaccaccgct ggtagcggtg gtttttttgt  26880

ttgcaagcag cagattacgc gcagaaaaaa aggatctcaa gaagatcctt tgatcttttc  26940

tacggggtct gacgctcagt ggaacgaaaa ctcacgttaa gggattttgg tcatgcattc  27000

taggtactaa aacaattcat ccagtaaaat ataatatttt attttctccc aatcaggctt  27060

gatccccagt aagtcaaaaa atagctcgac atactgttct tccccgatat cctccctgat  27120

cgaccggacg cagaaggcaa tgtcatacca cttgtccgcc ctgccgcttc tcccaagatc  27180

aataaagcca cttactttgc catctttcac aaagatgttg ctgtctccca ggtcgccgtg  27240

ggaaaagaca agttcctctt cgggcttttc cgtctttaaa aaatcataca gctcgcgcgg  27300

atctttaaat ggagtgtctt cttcccagtt ttcgcaatcc acatcggcca gatcgttatt  27360

cagtaagtaa tccaattcgg ctaagcggct gtctaagcta ttcgtatagg gacaatccga  27420

tatgtcgatg gagtgaaaga gcctgatgca ctccgcatac agctcgataa tcttttcagg  27480

gctttgttca tcttcatact cttccgagca aaggacgcca tcggcctcac tcatgagcag  27540

attgctccag ccatcatgcc gttcaaagtg caggaccttt ggaacaggca gctttccttc  27600

cagccatagc atcatgtcct ttcccgttc cacatcatag gtggtccctt tataccggct  27660

gtccgtcatt tttaaatata ggttttcatt ttctcccacc agcttatata ccttagcagg  27720

agacattcct tccgtatctt ttacgcagcg gtatttttcg atcagttttt tcaattccgg  27780

tgatattctc attttagcca tttattattt ccttcctctt ttctacagta tttaaagata  27840

ccccaagaag ctaattataa caagacgaac tccaattcac tgttccttgc attctaaaac  27900

cttaaatacc agaaaacagc tttttcaaag ttgttttcaa agttggcgta taacatagta  27960

tcgacggagc cgattttgaa accgcggtga tcacaggcag caacgctctg tcatcgttac  28020

aatcaacatg ctaccctccg cgagatcatc cgtgtttcaa acccggcagc ttagttgccg  28080

ttcttccgaa tagcatcggt aacatgagca aagtctgccg ccttacaacg gctctcccgc  28140

tgacgccgtc ccggactgat gggctgcctg tatcgagtgg tgattttgtg ccgagctgcc  28200

ggtcggggag ctgttggctg gctggtggca ggatatattg tggtgtaaac aaattgacgc  28260

ttagacaact taataacaca ttgcggacgt ttttaatgta ctgaattaac gccgaattaa  28320

ttc                                                                28323
```

<210> SEQ ID NO 3
<211> LENGTH: 33181
<212> TYPE: DNA
<213> ORGANISM: Artificial Sequence
<220> FEATURE:
<223> OTHER INFORMATION: Synthetic construct plasmid pMBXS1022

<400> SEQUENCE: 3

```
aaggtacgta gtgtttatct ttgttgcttt tctgaacaat ttatttacta tgtaaatata     60

ttatcaatgt ttaatctatt ttaatttgca catgaatttt cattttattt ttactttaca    120

aaacaaataa atatatatgc aaaaaaattt acaaacgatg cacgggttac aaactaattt    180

cattaaatgc taatgcagat tttgtgaagt aaaactccaa ttatgatgaa aaataccacc    240

aacaccacct gcgaaactgt atcccaactg tccttaataa aaatgttaaa aagtatatta    300
```

```
ttctcatttg tctgtcataa tttatgtacc ccactttaat ttttctgatg tactaaaccg    360

agggcaaact gaaacctgtt cctcatgcaa agcccctact caccatgtat catgtacgtg    420

tcatcaccca acaactccac ttttgctata taacaacacc cccgtcacac tctccctctc    480

taacacacac cccactaaca attccttcac ttgcagcact gttgcatcat catcttcatt    540

gcaaaaccct aaacttcacc ttcaaccgga tccaaaatgg cttctatgat atcctcttcc    600

gctgtgacaa cagtcagccg tgcctctagg gggcaatccg ccgcagtggc tccattcggc    660

ggcctcaaat ccatgactgg attcccagtg aagaaggtca acactgacat tacttccatt    720

acaagcaatg gtggaagagt aaagtgcatg caggtgtggc ctccaattgg aaagaagaag    780

tttgagactc tttcctattt gccaccattg acgagagatt ctagagttgg gaaaaagatg    840

atgactactg atgggaatac tgcaaccgct cacgtagctt atgcgatgtc agaagttgca    900

gctatctacc caatcacgcc gtccagtaca atgggagagg aagctgatga ctgggcagca    960

cagggaagaa agaatatctt cggtcaaacg cttacgatta gggagatgca atcggaagcc   1020

ggagcagcgg gtgccgtaca tggagctctt gcagctggcg ccttaactac cacctttacg   1080

gcttctcaag gactactctt gatgatccct aacatgtaca agatatcagg agaattgctt   1140

cctggagtct ttcatgtcac tgctagagct attgccgccc acgccctttc aatctttggt   1200

gatcatcagg atatatatgc agcgaggcag acagggttcg ctatgcttgc ttcaagctcg   1260

gtgcaagaag cacatgacat ggctttagtt gcccaccttg ccgccatcga atctaacgtc   1320

cctttcatgc atttcttcga cgggtttcgc acgtcacacg aaattcaaaa gattgaagtt   1380

ctcgattatg cagatatggc atccttagtg aatcagaaag ctctcgcaga gttccgtgct   1440

aaatctatga atccagagca tccacatgtt cgtggtactg ctcaaaaccc tgacatatat   1500

ttccagggaa gagaggcagc aaacccgtat tacttgaaag ttcctgggat tgtagcagag   1560

tatatgcaaa aagttgcaag tctaacaggg agatcgtaca agctgttcga ctatgttgga   1620

gctcctgatg ctgagcgtgt cattgtttct atgggttcca gttgcgagac aatcgaagaa   1680

gtgatcaatc acctcgctgc taagggagaa aagattggtt tgattaaggt ccgattatac   1740

cgtccatttg tatctgaagc tttctttgct gcgttaccgg catctgctaa ggttattaca   1800

gttctggata gaactaagga gcccggagct cctggcgacc ctttgtacct tgatgtctgt   1860

tcagcattcg tcgaaagggg agaagctatg cccaaaatcc tcgcaggccg ctatgggctc   1920

ggatctaagg agttttcacc cgctatggtt aaatctgttt atgataacat gagtggtgct   1980

aagaagaacc attttaccgt tggtatagag gacgatgtca cgggaacatc tctgccggtt   2040

gataatgcgt ttgctgatac aacccctaaa ggaactatcc agtgtcagtt ctggggtttg   2100

ggtgcagatg gtactgtcgg ggcgaataag caggctatca aaatcatagg agataacact   2160

gatctattcg ctcaaggtta cttttcatac gactctaaga aaagtggtgg tataactatc   2220

agtcacttgc gatttggaga aaagccaata caatctacct atttggtgaa ccgggctgac   2280

tacgttgctt gtcataaccc tgcctatgtt ggtatatacg atattttaga gggtatcaaa   2340

gatgggggca catttgtcct caattctccc tggtcgagtc ttgaagatat ggataaacat   2400

cttccaagcg ggattaagag aaccatagcg aataagaagc ttaagtttta caacattgat   2460

gcggtgaaaa tagcaacaga tgttggtttg ggcggcagaa ttaacatgat aatgcagacc   2520

gcattcttca aactagctgg tgtactccct ttcgagaagg cagtggatct cctcaaaaag   2580

tctattcata aagcctatgg aaagaaggga gagaagatcg tgaaaatgaa tactgacgca   2640

gtagatcaag cagttacgag ccttcaagag ttcaagtacc cagactcatg gaaggatgct   2700
```

```
ccagcagaga caaaagctga gccaatgaca aacgagttct tcaaaaatgt tgtcaagcct   2760
atcctcactc aacaaggcga taaattaccg gtttccgctt ttgaagccga tggacgtttt   2820
ccactgggaa cttctcagtt tgagaaacgc ggagtggcta ttaacgttcc tcagtgggta   2880
cctgaaaatt gcatccaatg caatcaatgc gcttttgtgt gcccgcattc cgcgatactt   2940
cctgttttgg ctaaagagga agagttagtc ggagcgcctg ccaacttcac cgctttggaa   3000
gcgaaaggaa aagaattgaa aggttacaaa ttcagaattc agattaacac tctcgactgc   3060
atgggctgcg gaaattgtgc cgacatatgt cctcccaaag aaaaggcttt agtgatgcag   3120
ccactggaca ctcagaggga tgcccaagtg ccaaatttgg agtatgcagc cagaattcca   3180
gtgaagtccg aggttcttcc gcgggattct ctcaaaggat cacaattcca agaaccactg   3240
atggagtttt caggcgcatg tagtggatgt ggtgaaacac cttacgtacg tgtgattact   3300
cagttatttg gagaacggat gtttatcgct aatgcaacag gttgtagctc gatctggggt   3360
gccagcgctc cgtcgatgcc atacaagacc aacaggctgg gacagggtcc agcttggggg   3420
aattccctat tcgaggatgc tgcagagtac gggttcggaa tgaacatgag tatgtttgcg   3480
cgtagaactc atctcgcgga tcttgctgct aaagctctcg agtctgatgc ttctggagat   3540
gtcaaggaag cattgcaggg ttggctcgct gggaaaaacg acccgattaa gtctaaagaa   3600
tacggggata agttgaagaa acttctagct ggtcaaaagg acgggttgtt gggacaaatt   3660
gcagcaatgt cagaccttta cacgaagaaa agtgtttgga tctttggtgg cgatggatgg   3720
gcgtatgata ttggttatgg tggccttgat cacgtcctcg caagcggcga agatgtgaac   3780
gtgtttgtga tggatactga agtttactcc aacaccggtg gacaatcctc aaaagcaaca   3840
ccaaccgggg ccgtggctaa attcgcggct gccggcaaaa ggactggaaa aaaggatctg   3900
gccagaatgg ttatgactta tggatacgta tatgtagcta cagtatcaat gggctatagc   3960
aaacagcaat ttcttaaagt cctcaaggaa gctgagagct tcccaggtcc ttcacttgtt   4020
atcgcctacg cgacatgtat caatcaaggt ttacgaaagg gaatggggaa aagccaagat   4080
gtgatgaaca ccgctgttaa aagcggttat tggcctttgt tccgctatga tcctcgtctt   4140
gcggcccaag gaaagaatcc gtttcagcta gactctaagg caccagacgg tagtgttgag   4200
gaatttttga tggctcagaa tcgatttgcg gtccttgatc gatcgttccc agaagatgcc   4260
aagaggttga gggcgcaagt tgcacatgaa ttggatgtta ggtttaagga gttagaacac   4320
atggcggcta caaatatctt cgagtccttc gctcctgctg gaggcaaagc tgacggttca   4380
gtagattttg gagaaggcgc agagttttgt actagagatg acacaccgat gatggccaga   4440
ccagatagtg gcgaagcatg cgaccaaaat agagcaggaa cgtctgagca gcaaggagat   4500
ttgtcgaaga ggaccaagaa atgaggcgcg cctgagtaat tctgatatta gagggagcat   4560
taatgtgttg ttgtgatgtg gtttatatgg ggaaattaaa taaatgatgt atgtacctct   4620
tgcctatgta ggtttgtgtg ttttgttttg ttgtctagct ttggttatta agtagtaggg   4680
acgttcgttc gtgtctcaaa aaaaggggta ctaccactct gtagtgtata tggatgctgg   4740
aaatcaatgt gttttgtatt tgttcacctc cattgttgaa ttcaatgtca aatgtgtttt   4800
gcgttggtta tgtgtaaaat tactatcttt ctcgtccgat gatcaaagtt ttaagcaaca   4860
aaaccaaggg tgaaatttaa actgtgcttt gttgaagatt cttttatcat attgaaaatc   4920
aaattactag cagcagattt tacctagcat gaaattttat caacagtaca gcactcacta   4980
accaagttcc aaactaagat gcgccattaa catcagccaa taggcatttt cagcaaaagc   5040
```

-continued ttgtacgtag tgtttatctt tgttgctttt ctgaacaatt tatttactat gtaaatatat 5100
tatcaatgtt taatctattt taatttgcac atgaattttc attttatttt tactttacaa 5160
aacaaataaa tatatatgca aaaaaattta caaacgatgc acgggttaca aactaatttc 5220
attaaatgct aatgcagatt ttgtgaagta aaactccaat tatgatgaaa aataccacca 5280
acaccacctg cgaaactgta tcccaactgt ccttaataaa aatgttaaaa agtatattat 5340
tctcatttgt ctgtcataat ttatgtaccc cactttaatt tttctgatgt actaaaccga 5400
gggcaaactg aaacctgttc ctcatgcaaa gcccctactc accatgtatc atgtacgtgt 5460
catcacccaa caactccact tttgctatat aacaacaccc ccgtcacact ctccctctct 5520
aacacacacc ccactaacaa ttccttcact tgcagcactg ttgcatcatc atcttcattg 5580
caaaacccta aacttcacct tcaaccgcgg ccgcagatct aaaatggctt ctatgatatc 5640
ctcttccgct gtgacaacag tcagccgtgc ctctaggggg caatccgccg cagtggctcc 5700
attcggcggc ctcaaatcca tgactggatt cccagtgaag aaggtcaaca ctgacattac 5760
ttccattaca agcaatggtg gaagagtaaa gtgcatgcag gtgtggcctc caattggaaa 5820
gaagaagttt gagactcttt cctatttgcc accattgacg agagattcta gagtgctcag 5880
ccagcaatcc atccagaagg ttctcgtggc taaccgtggt gagattgcta ttcgtatctt 5940
tagagcgtgt accgagttga acatccgaac tgtcgctgtt tatagtaaag aagattctgg 6000
atcataccac agatacaaag ctgacgaggc ctacttggtt ggtgaaggta agaagcctat 6060
tgacgcttat cttgatatag agggcatcat tgatattgcc aagagaaaca aagttgatgc 6120
aattcatccg ggatacggtt ttctatcaga aaacattcac tttgcacgac gatgtgaaga 6180
agagggaatc gtgttcatcg gacctaaaag cgaacacttg gatatgtttg gggacaaggt 6240
taaggcaagg gaacaagcag agaaggcagg aattccagtg atacctggat cggatgggcc 6300
tgctgaaact cttgaagctg tcgaacaatt cggccaggct aacggatacc caatcatcat 6360
taaggcttct ttaggtggtg gggaaggggg gatgagaatc gtgcgatccg aatctgaggt 6420
aaaagaggct tatgaacgtg ctaaatcgga agctaaagcg gcctttggga acgatgaagt 6480
ctatgtcgag aaactaatcg agaatcccaa gcacatcgag gttcaagtga ttggtgataa 6540
gcaaggtaac gttgttcacc ttttcgagag agattgttct gttcaacgta gacaccaaaa 6600
agtgatagaa gtagctccat cggtatcgtt gagcccagaa ctaagggacc agatatgcga 6660
ggctgctgtc gcgcttgcaa agaatgtcaa ctatatcaat gcaggcactg tcgaattctt 6720
ggtagccaat aatgagtttt acttcattga ggtcaaccct agagttcaag ttgagcatac 6780
cattaccgaa atgatcactg ggtggatat cgtacagact cagatcctcg ttgctcaagg 6840
ccattccctt cattccaaga aggtgaatat tccagagcaa aaggatatct ttacaattgg 6900
ttatgcgatt caatcacgag ttaccacaga agatccacaa aatgacttca tgccagatac 6960
gggaaagata atggcatacc gttctggtgg cggatttggt gttcgattag acacaggtaa 7020
tagttttcag ggagctgtga taacgccata ctatgattct ttattggtta agttgagtac 7080
ttgggctctc actttcgagc aagccgcagc gaaaatggtc agaaaccttc aggagttcag 7140
aattagaggt attaagacga acattccatt cttagagaac gttgctaaac atgagaagtt 7200
tctgacagga caatatgata caagtttcat agacactaca cctgaactct ttaacttccc 7260
taaacaaaaa gacagaggta cgaaaatgtt gacatatatc ggaaacgtga cagttaatgg 7320
gttcccaggt atcggtaaga aagaaaagcc ggcctttgat aaaccccttg gtgttaaagt 7380
ggatgtggat caacaacctg ctaggggcac taagcaaatc cttgatgaaa agggtgcaga 7440

```
gggactggca aattgggtta aagagcagaa atcagttctt ctgacagata ccacatttcg   7500
tgatgctcat caatcattac tagcaacaag aattagatca cacgatctga aaaagatcgc   7560
taatccaacc gctgctcttt ggccggaact cttctctatg gaaatgtggg gtggggccac   7620
attcgatgtc gcgtaccgtt ttctaaaaga agatccttgg aagcgtctgg aagatttgag   7680
aaaagaggtg cccaataccc tgttccagat gcttttgcgt tctagcaatg ccgtcggata   7740
taccaattat cctgacaatg tgatcaaaga attcgtaaaa cagtccgctc aatctggtat   7800
cgacgttttt aggatttcg attcacttaa ttgggtaaaa ggtatgacgt tagcgattga   7860
tgctgtacgt gatactggaa aggttgcaga ggccgccatt tgctacactg gagacatttt   7920
ggataagaat agaactaaat acgacttggc ttattacact tccatggcaa aagaacttga   7980
ggctgccggt gcacatattc tggggataaa ggatatggcc ggtttgctca aaccgcaggc   8040
agcatatgag ttggtttcag cccttaaaga aactattgac atacccgttc atctgcacac   8100
gcatgacacg tcgggcaatg gaatctatat gtatgcaaag gctgtcgagg ctggcgtgga   8160
tatcattgat gtcgctgtaa gctctatggc tggacttaca tcccagccat cagcctctgg   8220
attctatcat gctatggaag gtaacgatcg tagacccgaa atgaatgtcc aaggggtcga   8280
attactgtca cagtactggg agagtgtgcg taagtattac tcagagtttg agagcggtat   8340
gaagagtccc cataccgaga tttatgagca cgagatgcct ggtggacaat actctaactt   8400
gcaacagcaa gcgaaggggg ttggtttggg agataggtgg aacgaagtga aagaaatgta   8460
tagacgtgtc aacgacatgt ttggtgatat tgtgaaagta actcctagtt ctaaggtagt   8520
tggagacatg gcactgtaca tggttcagaa taaccttact gaaaaggatg tttacgagaa   8580
gggggagtca cttgacttcc ctgattcagt ggttgaactg ttcaagggaa atatcggtca   8640
accgcatggg ggatttccag aaaaactaca gaaactgata ctaaagggac aggagccaat   8700
tactgttcga ccaggagagc tcttggagcc ggtttctttt gaggctatca agcaagaatt   8760
caaagaacaa cataaccttg aaatttctga tcaggacgcg gttgcttacg cactttatcc   8820
aaaggtcttt actgattacg tgaaaaccac agagtcttat ggtgatataa gtgtgctaga   8880
tacaccaaca tttttctatg gcatgactct tggagaagag attgaagtgg aaatagaaag   8940
gggaaaaaca ctcattgtta aactgatatc tatcggagag cctcaacctg atgctacaag   9000
ggtagtgtac tttgaattga atggacaacc tagagaagta gtgattaaag atgagtcaat   9060
aaagtcaagc gtgcaggaga ggctaaaggc agatagaacc aatccgtcgc acattgcagc   9120
ttctatgcct ggcaccgtca taaaagtcct cgctgaagct ggtactaaag tcaacaaagg   9180
tgaccatctt atgatcaacg aagcaatgaa gatggaaact acggttcagg cacctttcag   9240
tggaacaatc aagcaggttc atgttaagaa tggcgagcct atccagactg gtgacttgct   9300
tttggagatt gaaaaggcct gagtcgacgc gatcgcgcgg ccgctgagta attctgatat   9360
tagagggagc attaatgtgt tgttgtgatg tggtttatat ggggaaatta aataaatgat   9420
gtatgtacct cttgcctatg taggtttgtg tgttttgttt tgttgtctag ctttggttat   9480
taagtagtag ggacgttcgt tcgtgtctca aaaaaagggg tactaccact ctgtagtgta   9540
tatggatgct ggaaatcaat gtgttttgta tttgttcacc tccattgttg aattcaatgt   9600
caaatgtgtt ttgcgttggt tatgtgtaaa attactatct ttctcgtccg atgatcaaag   9660
ttttaagcaa caaaaccaag ggtgaaattt aaactgtgct ttgttgaaga ttcttttatc   9720
atattgaaaa tcaaattact agcagcagat tttacctagc atgaaatttt atcaacagta   9780
```

```
cagcactcac taaccaagtt ccaaactaag atgcgccatt aacatcagcc aataggcatt   9840
ttcagcaagt ttaaactacg tagtgtttat ctttgttgct tttctgaaca atttatttac   9900
tatgtaaata tattatcaat gtttaatcta ttttaatttg cacatgaatt ttcattttat   9960
ttttacttta caaaacaaat aaatatatat gcaaaaaaat ttacaaacga tgcacgggtt  10020
acaaactaat ttcattaaat gctaatgcag attttgtgaa gtaaaactcc aattatgatg  10080
aaaaatacca ccaacaccac ctgcgaaact gtatcccaac tgtccttaat aaaaatgtta  10140
aaaagtatat tattctcatt tgtctgtcat aatttatgta ccccacttta atttttctga  10200
tgtactaaac cgagggcaaa ctgaaacctg ttcctcatgc aaagccccta ctcaccatgt  10260
atcatgtacg tgtcatcacc caacaactcc actttgcta tataacaaca cccccgtcac  10320
actctccctc tctaacacac accccactaa caattccttc acttgcagca ctgttgcatc  10380
atcatcttca ttgcaaaacc ctaaacttca ccttcaaccg cggccgctcg cgaaaaatgg  10440
cttctatgat atcctcttcc gctgtgacaa cagtcagccg tgcctctagg gggcaatccg  10500
ccgcagtggc tccattcggc ggcctcaaat ccatgactgg attcccagtg aagaaggtca  10560
acactgacat tacttccatt acaagcaatg gtggaagagt aaagtgcatg caggtgtggc  10620
ctccaattgg aaagaagaag tttgagactc tttcctattt gccaccattg acgagagatt  10680
ctagagtgaa catacacgag taccaagcaa aagagttgct caagacctat ggagtgccgg  10740
tcccagacgg agcggtagct tatagtgatg ctcaagcggc ttccgtcgct gaagagattg  10800
gtggctctag atgggttgta aaggcgcaga tacacgctgg tggaagggga aaggcaggtg  10860
gtgtgaaggt ggcccatagc attgaagagg ttcgtcagta cgctgatgcg atgcttgggt  10920
cccatctcgt tacacatcaa acagggcctg gtggttcatt agttcaacgt ttgtgggtgg  10980
agcaagcatc acatatcaag aaagagtatt atctgggatt tgttattgat agaggtaacc  11040
aaagaattac cttaattgct tcttctgaag gggaatggga gatagaagag gttgctaaag  11100
agacaccaga aaagatcgtc aaagaggttg tagaccctgc aatcggattg cttgattttc  11160
agtgtagaaa ggttgcaact gcaataggac ttaagggaaa gcttatgccc caggcagtta  11220
gacttatgaa ggctatctat aggtgtatgc gagataagga tgctctccag gcagagatca  11280
atcctttggc aatagtaggt gaaagtgacg agtcgctcat ggttcttgat gctaaattca  11340
attttgatga caatgctctt tacagacaac gaacaattac tgaaatgagg gatctcgcag  11400
aagaagatcc taaagaagtc gaagcttctg gacacggatt gaattacatc gccctcgatg  11460
ggaacatcgg ttgtattgtg aatggagctg gtcttgctat ggccagcctg gatgccatca  11520
ctctacatgg cggtcgtcca gctaacttct tagatgtcgg cggtggggct tctcctgaaa  11580
aggttacgaa tgcgtgcaga attgttttgg aagatccgaa cgtccgttgt atactggtga  11640
acatttttgc cggaattaac aggtgcgatt ggattgcaaa aggacttatt caagcctgcg  11700
actcactaca gattaaagtt ccactgatcg ttcgattggc aggcactaat gtagatgaag  11760
gcaggaaaat cctagcggag tcgggtttaa gtttcataac ggcagagaat ttggacgacg  11820
cggctgctaa agccgtggct atcgtgaaag ggtgaacgcg ttgagtaatt ctgatattag  11880
agggagcatt aatgtgttgt tgtgatgtgg tttatatggg gaaattaaat aaatgatgta  11940
tgtacctctt gcctatgtag gtttgtgtgt tttgttttgt tgtctagctt tggttattaa  12000
gtagtaggga cgttcgttcg tgtctcaaaa aaaggggtac taccactctg tagtgtatat  12060
ggatgctgga aatcaatgtg ttttgtattt gttcacctcc attgttgaat tcaatgtcaa  12120
atgtgttttg cgttggttat gtgtaaaatt actatctttc tcgtccgatg atcaaagttt  12180
```

```
taagcaacaa aaccaagggt gaaatttaaa ctgtgctttg ttgaagattc ttttatcata  12240
ttgaaaatca aattactagc agcagatttt acctagcatg aaattttatc aacagtacag  12300
cactcactaa ccaagttcca aactaagatg cgccattaac atcagccaat aggcattttc  12360
agcaatgtac atacgtagtg tttatctttg ttgcttttct gaacaattta tttactatgt  12420
aaatatatta tcaatgttta atctatttta atttgcacat gaattttcat tttattttta  12480
ctttacaaaa caaataaata tatatgcaaa aaaatttaca aacgatgcac gggttacaaa  12540
ctaatttcat taaatgctaa tgcagatttt gtgaagtaaa actccaatta tgatgaaaaa  12600
taccaccaac accacctgcg aaactgtatc ccaactgtcc ttaataaaaa tgttaaaaag  12660
tatattattc tcatttgtct gtcataattt atgtacccca ctttaatttt tctgatgtac  12720
taaaccgagg gcaaactgaa acctgttcct catgcaaagc cctactcac catgtatcat  12780
gtacgtgtca tcacccaaca actccacttt tgctatataa caacaccccc gtcacactct  12840
ccctctctaa cacacacccc actaacaatt ccttcacttg cagcactgtt gcatcatcat  12900
cttcattgca aaaccctaaa cttcaccttc aaccgcggcc gcgacgtcaa aatggcttct  12960
atgatatcct cttccgctgt gacaacagtc agccgtgcct ctagggggca atccgccgca  13020
gtggctccat tcggcggcct caaatccatg actggattcc cagtgaagaa ggtcaacact  13080
gacattactt ccattacaag caatggtgga agagtaaagt gcatgcaggt gtggcctcca  13140
attggaaaga agaagtttga gactctttcc tatttgccac cattgacgag agattctaga  13200
gtctcggttt tcgtgaataa acattccaag gtcatctttc aaggctttac cggggagcat  13260
gctacatttc acgcaaaaga tgcaatgcga atgggcacaa gggttgtcgg tggcgttact  13320
cctggaaagg gtgggactag acatccagat cctgagctcg ctcatcttcc ggtattcgat  13380
accgttgccg aagccgttgc tgctacagga gctgatgtat cagctgtgtt tgtcccaccc  13440
cctttcaatg cagacgcact tatggaagca attgatgccg gtattagagt ggctgtcact  13500
atagcggatg gaattcctgt gcatgacatg atcagattgc aaaggtatag agtaggaaag  13560
gactctattg ttatcgggcc taacacacca ggaatcataa cgcctggtga gtgtaaagtg  13620
ggtatcatgc cgagtcacat atacaagaag ggaaacgtgg gtatagtgag tcgatcagga  13680
acattgaatt acgaggcgac ggaacaaatg gctgcgctag gcttagggat tactacttct  13740
gttggaattg gtggtgatcc tataaacggc actgactttg tgactgttct ccgtgcattc  13800
gaggctgatc cagaaacgga aattgtagtt atgatcggag aaataggtgg accgcaggaa  13860
gttgccgcag ctagatgggc aaaagagaat atgaccaaac cagttattgg gttcgtagct  13920
ggtttagcag cccccacagg gcgtaggatg ggacacgcag gtgctattat cagctctgag  13980
gctgataccg ctggagctaa gatggatgcc atggaagctc ttggtctgta tgtcgctagg  14040
aacccagcgc aaatcggaca gacagttttg cgtgcggcac aggagcatgg aattagattt  14100
tgagggcccg ttaactgagt aattctgata ttagagggag cattaatgtg ttgttgtgat  14160
gtggtttata tggggaaatt aaataaatga tgtatgtacc tcttgcctat gtaggtttgt  14220
gtgttttgtt ttgttgtcta gctttggtta ttaagtagta gggacgttcg ttcgtgtctc  14280
aaaaaaaggg gtactaccac tctgtagtgt atatggatgc tggaaatcaa tgtgttttgt  14340
atttgttcac ctccattgtt gaattcaatg tcaaatgtgt tttgcgttgg ttatgtgtaa  14400
aattactatc tttctcgtcc gatgatcaaa gttttaagca acaaaaccaa gggtgaaatt  14460
taaactgtgc tttgttgaag attcttttat catattgaaa atcaaattac tagcagcaga  14520
```

```
ttttacctag catgaaattt tatcaacagt acagcactca ctaaccaagt tccaaactaa  14580
gatgcgccat taacatcagc caataggcat tttcagcaag tttaaaccgg accgtacgta  14640
gtgtttatct ttgttgcttt tctgaacaat ttatttacta tgtaaatata ttatcaatgt  14700
ttaatctatt ttaatttgca catgaatttt cattttattt ttactttaca aaacaaataa  14760
atatatatgc aaaaaaattt acaaacgatg cacgggttac aaactaattt cattaaatgc  14820
taatgcagat tttgtgaagt aaaactccaa ttatgatgaa aaataccacc aacaccacct  14880
gcgaaactgt atcccaactg tccttaataa aaatgttaaa aagtatatta ttctcatttg  14940
tctgtcataa tttatgtacc ccactttaat ttttctgatg tactaaaccg agggcaaact  15000
gaaacctgtt cctcatgcaa agcccctact caccatgtat catgtacgtg tcatcaccca  15060
acaactccac ttttgctata taacaacacc cccgtcacac tctccctctc taacacacac  15120
cccactaaca attccttcac ttgcagcact gttgcatcat catcttcatt gcaaaaccct  15180
aaacttcacc ttcaaccgcg gccgccacgt gaaaatggct tctatgatat cctcttccgc  15240
tgtgacaaca gtcagccgtg cctctagggg gcaatccgcc gcagtggctc cattcggcgg  15300
cctcaaatcc atgactggat tcccagtgaa gaaggtcaac actgacatta cttccattac  15360
aagcaatggt ggaagagtaa agtgcatgca ggtgtggcct ccaattggaa agaagaagtt  15420
tgagactctt tcctatttgc caccattgac gagagattct agagtgagct tccgtttgca  15480
accagctccg ccagcaaggc ccaatagatg tcaacttttt gggcctggat ctcgaccggc  15540
tttgtttgag aaaatggccg cttcagccgc ggacgttatc aatctggatt tagaggatag  15600
tgttgcccca gatgataaag ctcaggctag agcaaatatc attgaggcta taaacggtct  15660
agactggggt agaaagtatc tcagtgttag aattaacgga cttgatacgc ctttctggta  15720
tcgagatgtc gttgacttgc ttgagcaggc aggagataga cttgatcaaa tcatgatccc  15780
taaggttggc tgtgctgcgg atgtttacgc cgtcgatgct ttggtaacag caattgaacg  15840
tgctaaaggg cgtactaagc ctctatcatt tgaagtgata atagagtctg cagctggtat  15900
cgcacatgtt gaagaaatag ccgcttcgtc accaagactc caagccatgt ctttgggtgc  15960
agccgatttt gcagcttcta tgggaatgca gactacaggg attggtggaa cgcaagagaa  16020
ctactatatg ctccacgacg gacaaaagca ctggtccgat ccttggcatt gggctcaggc  16080
tgcaatcgtc gcagcgtgca gaacacatgg gattttaccc gttgacggcc cgttcggtga  16140
cttctctgat gacgaaggat tcagggcaca agctcgaagg tccgctactc ttggaatggt  16200
gggaaaatgg gccatacatc caaagcaagt ggctctcgct aatgaagtgt ttacacctag  16260
cgagactgca gtaaccgaag cgagggagat tttagcggct atggatgctg ctaaggcgag  16320
aggcgaaggt gctaccgtgt acaaaggtag gctggtagat atcgcgtcga ttaaacaggc  16380
agaagtcatt gttcgtcagg ctgagatgat tagtgcatga actagttgag taattctgat  16440
attagaggga gcattaatgt gttgttgtga tgtggtttat atggggaaat taaataaatg  16500
atgtatgtac ctcttgccta tgtaggtttg tgtgttttgt tttgttgtct agctttggtt  16560
attaagtagt agggacgttc gttcgtgtct caaaaaaagg ggtactacca ctctgtagtg  16620
tatatggatg ctggaaatca atgtgttttg tatttgttca cctccattgt tgaattcaat  16680
gtcaaatgtg ttttgcgttg gttatgtgta aaattactat ctttctcgtc cgatgatcaa  16740
agttttaagc aacaaaacca agggtgaaat ttaaactgtg ctttgttgaa gattctttta  16800
tcatattgaa aatcaaatta ctagcagcag attttaccta gcatgaaatt ttatcaacag  16860
tacagcactc actaaccaag ttccaaacta agatgcgcca ttaacatcag ccaataggca  16920
```

```
ttttcagcaa gtttaaactc cggatacgta gtgtttatct ttgttgcttt tctgaacaat  16980
ttatttacta tgtaaatata ttatcaatgt ttaatctatt ttaatttgca catgaatttt  17040
cattttattt ttactttaca aaacaaataa atatatatgc aaaaaaattt acaaacgatg  17100
cacgggttac aaactaattt cattaaatgc taatgcagat tttgtgaagt aaaactccaa  17160
ttatgatgaa aaataccacc aacaccacct gcgaaactgt atcccaactg tccttaataa  17220
aaatgttaaa aagtatatta ttctcatttg tctgtcataa tttatgtacc ccactttaat  17280
ttttctgatg tactaaaccg agggcaaact gaaacctgtt cctcatgcaa agcccctact  17340
caccatgtat catgtacgtg tcatcaccca acaactccac ttttgctata taacaacacc  17400
cccgtcacac tctccctctc taacacacac cccactaaca attccttcac ttgcagcact  17460
gttgcatcat catcttcatt gcaaaaccct aaacttcacc ttcaaccgcg gccgccctag  17520
gaaaatggct tctatgatat cctcttccgc tgtgacaaca gtcagccgtg cctctagggg  17580
gcaatccgcc gcagtggctc cattcggcgg cctcaaatcc atgactggat tcccagtgaa  17640
gaaggtcaac actgacatta cttccattac aagcaatggt ggaagagtaa agtgcatgca  17700
ggtgtggcct ccaattggaa agaagaagtt tgagactctt tcctatttgc caccattgac  17760
gagagattct agagttgcac agtaccaaga cgatatcaag gcggttgcag ggcttaagga  17820
gaatcacggc tccgcatgga atgccatcaa cccggagtat gccgccagga tgagggcgca  17880
gaacaagttc aagacgggcc ttgacattgc aaagtatacg gctaagatta tgcgggccga  17940
tatggcagcc tacgacgccg acagctcgaa gtacacacag agcctcggtt gttggcatgg  18000
tttcattggt cagcagaaga tgatctcaat caagaaacat ttcaacagca cggaacgccg  18060
ttacctctac ctttctggct ggatggtagc cgcgcttaga tccgagtttg gccccctacc  18120
ggatcagtcc atgcacgaaa agacgagtgt ctccgcactc attcgggaac tctacacttt  18180
tctgcgccaa gcggacgcta gggagttggg gggcctgttt cgggagcttg acgcggccca  18240
aggcccagct aaggcggcca ttcaagcgaa gatcgacaac cacgtcactc atgtggtccc  18300
aatcatagct gatatcgacg ctggcttcgg caatgcggaa gcaacatacc tgttggccaa  18360
gcagttcatc gaggccgggg cttgctgcat acagatagag aaccaggttt ctgacgaaaa  18420
gcaatgtgga catcaagacg gaaaggttac cgtgccccac gaggattttc ttgcaaaaat  18480
ccgagcgatt cgttatgcgt ttttagagtt gggcgtggat gacggtatca tcgtggccag  18540
gaccgatagt ctcggtgctg gtctgacaaa gcaaatcgca gtgaccaata cgcctggaga  18600
cttaggggat cagtacaaca gcttcctcga ttgcgaggag cttagcgcag atcagctcgg  18660
aaatggcgac gttatcatca agcgtgatgg aaagctactc cgccccaagc gcctcccgtc  18720
taacttgttc cagttccggg ctggaactgg cgaagcgcga tgcgtcctgg actgcgtgac  18780
cgcgctccag aacggcgccg acctactctg gattgagaca gaaaagcctc acatagctca  18840
aatcggcgga atggtatcgg agataaggaa agtcataccc aacgccaaac tggtgtacaa  18900
caactctccg tcgttcaatt ggaccctgaa ctttagacag caagcatacg atgctatgaa  18960
agccgctggg aaagacgtgt cagcatacga ccgcgcccag cttatgtccg tggagtacga  19020
ccaaacggaa ctggctaagc tggctgatga gaaaatcaga acattccagg ccgacgcctc  19080
aagggaggcc gggatcttcc atcacttgat taccttacca acatatcaca ctgcggccct  19140
gtcaaccgac aatttggcta aggagtactt cggagatcag gggatgctcg gttatgtcgc  19200
gggcgttcag aggaaggaga tccgacaggg catcgcatgt gtcaagcacc aaaacatgag  19260
```

-continued

```
cgggagtgac atcggggatg atcataaaga gtatttctcc ggcgaagccg cgctgaaggc  19320
cgccggcaaa gacaacacta tgaatcaatt ctgacccggg tgagtaattc tgatattaga  19380
gggagcatta atgtgttgtt gtgatgtggt ttatatgggg aaattaaata aatgatgtat  19440
gtacctcttg cctatgtagg tttgtgtgtt ttgttttgtt gtctagcttt ggttattaag  19500
tagtagggac gttcgttcgt gtctcaaaaa aaggggtact accactctgt agtgtatatg  19560
gatgctggaa atcaatgtgt tttgtatttg ttcacctcca ttgttgaatt caatgtcaaa  19620
tgtgttttgc gttggttatg tgtaaaatta ctatctttct cgtccgatga tcaaagtttt  19680
aagcaacaaa accaagggtg aaatttaaac tgtgctttgt tgaagattct tttatcatat  19740
tgaaaatcaa attactagca gcagatttta cctagcatga aattttatca acagtacagc  19800
actcactaac caagttccaa actaagatgc gccattaaca tcagccaata ggcattttca  19860
gcaagctcga gtcacgtagt ggtacgtagt gtttatcttt gttgcttttc tgaacaattt  19920
atttactatg taaatatatt atcaatgttt aatctatttt aatttgcaca tgaattttca  19980
ttttattttt actttacaaa acaaataaat atatatgcaa aaaaatttac aaacgatgca  20040
cgggttacaa actaatttca ttaaatgcta atgcagattt tgtgaagtaa aactccaatt  20100
atgatgaaaa ataccaccaa caccacctgc gaaactgtat cccaactgtc cttaataaaa  20160
atgttaaaaa gtatattatt ctcatttgtc tgtcataatt tatgtacccc actttaattt  20220
ttctgatgta ctaaaccgag ggcaaactga aacctgttcc tcatgcaaag cccctactca  20280
ccatgtatca tgtacgtgtc atcacccaac aactccactt ttgctatata acaacacccc  20340
cgtcacactc tccctctcta acacacaccc cactaacaat tccttcactt gcagcactgt  20400
tgcatcatca tcttcattgc aaaaccctaa acttcacctt caaccgcggc cgcttcgaag  20460
gatccaaaat ggtgagcaag ggcgaggagc tgttcaccgg ggtggtgccc atcctggtcg  20520
agctggacgg cgacgtaaac ggccacaagt tcagcgtgtc cggcgagggc gagggcgatg  20580
ccacctacgg caagctgacc ctgaagttca tctgcaccac cggcaagctg cccgtgccct  20640
ggcccaccct cgtgaccacc ttcacctacg gcgtgcagtg cttcagccgc taccccgacc  20700
acatgaagca gcacgacttc ttcaagtccg ccatgcccga aggctacgtc caggagcgca  20760
ccatcttctt caaggacgac ggcaactaca agacccgcgc cgaggtgaag ttcgagggcg  20820
acaccctggt gaaccgcatc gagctgaagg gcatcgactt caaggaggac ggcaacatcc  20880
tggggcacaa gctggagtac aactacaaca gccacaacgt ctatatcatg gccgacaagc  20940
agaagaacgg catcaaggtg aacttcaaga tccgccacaa catcgaggac ggcagcgtgc  21000
agctcgccga ccactaccag cagaacaccc ccatcggcga cggccccgtg ctgctgcccg  21060
acaaccacta cctgagcacc cagtccgccc tgagcaaaga ccccaacgag aagcgcgatc  21120
acatggtcct gctggagttc gtgaccgccg ccgggatcac tcacggcatg gacgagctgt  21180
acaagtaaag cggccgcccg ggctgcagtt cgaaatttaa atgcggccgc tgagtaattc  21240
tgatattaga gggagcatta atgtgttgtt gtgatgtggt ttatatgggg aaattaaata  21300
aatgatgtat gtacctcttg cctatgtagg tttgtgtgtt ttgttttgtt gtctagcttt  21360
ggttattaag tagtagggac gttcgttcgt gtctcaaaaa aaggggtact accactctgt  21420
agtgtatatg gatgctggaa atcaatgtgt tttgtatttg ttcacctcca ttgttgaatt  21480
caatgtcaaa tgtgttttgc gttggttatg tgtaaaatta ctatctttct cgtccgatga  21540
tcaaagtttt aagcaacaaa accaagggtg aaatttaaac tgtgctttgt tgaagattct  21600
tttatcatat tgaaaatcaa attactagca gcagatttta cctagcatga aattttatca  21660
```

```
acagtacagc actcactaac caagttccaa actaagatgc gccattaaca tcagccaata  21720
ggcattttca gcaacctcag cgtttaaacg tacgtagtgt ttatctttgt tgcttttctg  21780
aacaatttat ttactatgta aatatattat caatgtttaa tctattttaa tttgcacatg  21840
aattttcatt ttatttttac tttacaaaac aaataaatat atatgcaaaa aaatttacaa  21900
acgatgcacg ggttacaaac taatttcatt aaatgctaat gcagattttg tgaagtaaaa  21960
ctccaattat gatgaaaaat accaccaaca ccacctgcga aactgtatcc caactgtcct  22020
taataaaaat gttaaaaagt atattattct catttgtctg tcataattta tgtaccccac  22080
tttaattttt ctgatgtact aaaccgaggg caaactgaaa cctgttcctc atgcaaagcc  22140
cctactcacc atgtatcatg tacgtgtcat cacccaacaa ctccactttt gctatataac  22200
aacacccccg tcacactctc cctctctaac acacacccca ctaacaattc cttcacttgc  22260
agcactgttg catcatcatc ttcattgcaa aaccctaaac ttcaccttca accgcggccg  22320
cttcgaaaaa atggcttcta tgatatcctc ttccgctgtg acaacagtca gccgtgcctc  22380
tagggggcaa tccgccgcag tggctccatt cggcggcctc aaatccatga ctggattccc  22440
agtgaagaag gtcaacactg acattacttc cattacaagc aatggtggaa gagtaaagtg  22500
catgcaggtg tggcctccaa ttggaaagaa gaagtttgag actctttcct atttgccacc  22560
attgacgaga gattctagag tcaccgagca agccacaacg acagatgaac tcgcttttac  22620
taggccatat ggtgaacagg aaaagcaaat tcttacagca gaagctgttg agtttttgac  22680
cgagttggtt actcacttta cacctcaaag aaacaagtta ctcgcagcac gtatccagca  22740
gcaacaagac atagataatg gtacacttcc agatttcatt tcggagactg catctattcg  22800
agatgccgat tggaaaatca ggggtatccc cgcagattta gaagatagga gagttgaaat  22860
aaccggacct gtagaaagaa aaatggtcat caacgctcta aacgccaacg tcaaagtgtt  22920
tatggctgat tttgaggact cgctagcacc tgattggaac aaggtgatag atggccagat  22980
caatttgaga gatgctgtca atgggacaat ctcctatact aatgaggctg gaaagattta  23040
tcaactcaaa cctaatccgg cagtgctgat ttgtagggtt cgtggattac acctgcctga  23100
aaagcatgtt acgtggcgtg gggaagcaat tcctggcagc ctttttgact tcgctcttta  23160
ctttttccat aactaccagg cgctgttggc taaggggtca ggtccatatt tctatcttcc  23220
gaaaactcaa agttggcaag aagctgcctg gtggtctgag gtgttctcct atgcagagga  23280
tcgtttcaat ttaccacgag gtacgatcaa agcaactctg ttaattgaga cactcccggc  23340
tgtgtttcaa atggacgaga tactacacgc tctcagggac cacattgttg gtcttaattg  23400
cggaagatgg gactatatct tctcctacat caagactcta aagaactacc cggatagagt  23460
tctgcctgac cgtcaagctg ttactatgga taaaccattt cttaatgctt actctagact  23520
cttgattaag acctgtcata agcgtggagc cttcgcaatg ggcggaatgg ccgcttttat  23580
cccgtcaaaa gatgaagagc acaacaatca ggttttgaac aaggtaaaag cggataaatc  23640
tcttgaagcc aataatgggc atgatggcac ttggattgct catccaggtc tagctgatac  23700
agcgatggct gtattcaacg acatcttggg ttcaagaaag aatcaacttg aagtgatgag  23760
agagcaagac gcgccaataa cagctgatca acttttggcg ccatgcgatg gtgaacgaac  23820
ggaagaaggt atgagagcca atatccgagt tgctgtgcag tacatagagg cttggatttc  23880
aggaaacggg tgtgtcccca tttatggact catggaagat gcggctactg ctgaaattag  23940
caggacctct atttggcagt ggatacatca tcaaaagaca ttaagcaacg gaaaacctgt  24000
```

```
tactaaggcc ctcttcaggc agatgcttgg ggaagagatg aaagtaattg cgagtgagtt  24060
gggagaagag agattttctc agggtagatt tgatgacgca gcgaggttga tggagcagat  24120
caccaccagt gacgagctca tagatttctt aacgttgcct ggataccgac tacttgcttg  24180
aatttaaatg cggccgctga gtaattctga tattagaggg agcattaatg tgttgttgtg  24240
atgtggttta tatggggaaa ttaaataaat gatgtatgta cctcttgcct atgtaggttt  24300
gtgtgttttg ttttgttgtc tagctttggt tattaagtag tagggacgtt cgttcgtgtc  24360
tcaaaaaaag gggtactacc actctgtagt gtatatggat gctggaaatc aatgtgtttt  24420
gtatttgttc acctccattg ttgaattcaa tgtcaaatgt gttttgcgtt ggttatgtgt  24480
aaaattacta tctttctcgt ccgatgatca aagttttaag caacaaaacc aagggtgaaa  24540
tttaaactgt gctttgttga agattctttt atcatattga aatcaaatt actagcagca  24600
gattttacct agcatgaaat tttatcaaca gtacagcact cactaaccaa gttccaaact  24660
aagatgcgcc attaacatca gccaataggc attttcagca aagcaaatga attcgtaatc  24720
atgtcatagc tgtttcctgt gtgaaattgt tatccgctca caattccaca caacatacga  24780
gccggaagca taaagtgtaa agcctggggt gcctaatgag tgagctaact cacattaatt  24840
gcgttgcgct cactgcccgc tttccagtcg ggaaacctgt cgtgccagct gcattaatga  24900
atcggccaac gcgcggggag aggcggtttg cgtattggct agagcagctt gccaacatgg  24960
tggagcacga cactctcgtc tactccaaga atatcaaaga tacagtctca gaagaccaaa  25020
gggctattga gacttttcaa caaagggtaa tatcgggaaa cctcctcgga ttccattgcc  25080
cagctatctg tcacttcatc aaaaggacag tagaaaagga aggtggcacc tacaaatgcc  25140
atcattgcga taaaggaaag gctatcgttc aagatgcctc tgccgacagt ggtcccaaag  25200
atggaccccc acccacgagg agcatcgtgg aaaaagaaga cgttccaacc acgtcttcaa  25260
agcaagtgga ttgatgtgaa catggtggag cacgacactc tcgtctactc caagaatatc  25320
aaagatacag tctcagaaga ccaaagggct attgagactt ttcaacaaag ggtaatatcg  25380
ggaaacctcc tcggattcca ttgcccagct atctgtcact tcatcaaaag gacagtagaa  25440
aaggaaggtg gcacctacaa atgccatcat tgcgataaag gaaaggctat cgttcaagat  25500
gcctctgccg acagtggtcc caaagatgga cccccaccca cgaggagcat cgtggaaaaa  25560
gaagacgttc caaccacgtc ttcaaagcaa gtggattgat gtgatatctc cactgacgta  25620
agggatgacg cacaatccca ctatccttcg caagaccctt cctctatata aggaagttca  25680
tttcatttgg agaggacacg ctgaaatcac cagtctctct ctacaaatct atctctctcg  25740
agaaaatggt gagcaagggc gaggagctgt tcaccggggt ggtgcccatc ctggtcgagc  25800
tggacggcga cgtaaacggc cacaagttca gcgtgtccgg cgagggcgag ggcgatgcca  25860
cctacggcaa gctgaccctg aagttcatct gcaccaccgg caagctgccc gtgccctggc  25920
ccaccctcgt gaccaccttc acctacggcg tgcagtgctt cagccgctac cccgaccaca  25980
tgaagcagca cgacttcttc aagtccgcca tgcccgaagg ctacgtccag gagcgcacca  26040
tcttcttcaa ggacgacggc aactacaaga cccgcgccga ggtgaagttc gagggcgaca  26100
ccctggtgaa ccgcatcgag ctgaagggca tcgacttcaa ggaggacggc aacatcctgg  26160
ggcacaagct ggagtacaac tacaacagcc acaacgtcta tatcatggcc gacaagcaga  26220
agaacggcat caaggtgaac ttcaagatcc gccacaacat cgaggacggc agcgtgcagc  26280
tcgccgacca ctaccagcag aacaccccca tcggcgacgg ccccgtgctg ctgcccgaca  26340
accactacct gagcacccag tccgccctga gcaaagaccc caacgagaag cgcgatcaca  26400
```

```
tggtcctgct ggagttcgtg accgccgccg ggatcactca cggcatggac gagctgtaca  26460
agtaagagct cggtcacctg tccaacagtc tcagggttaa tgtctatgta tcttaaataa  26520
tgttgtcggc gatcgttcaa acatttggca ataaagtttc ttaagattga atcctgttgc  26580
cggtcttgcg atgattatca tataatttct gttgaattac gttaagcatg taataattaa  26640
catgtaatgc atgacgttat ttatgagatg ggtttttatg attagagtcc cgcaattata  26700
catttaatac gcgatagaaa acaaaatata gcgcgcaaac taggataaat tatcgcgcgc  26760
ggtgtcatct atgttactag atcgggaatt aaactatcag tgtttgacag gatatattgg  26820
cgggtaaacc taagagaaaa gagcgtttat tagaataatc ggatatttaa aagggcgtga  26880
aaaggtttat ccgttcgtcc atttgtatgt gcatgccaac cacagggttc ccctcgggat  26940
caaagtactt tgatccaacc cctccgctgc tatagtgcag tcggcttctg acgttcagtg  27000
cagccgtctt ctgaaaacga catgtcgcac aagtcctaag ttacgcgaca ggctgccgcc  27060
ctgccctttt cctggcgttt tcttgtcgcg tgttttagtc gcataaagta gaatacttgc  27120
gactagaacc ggagacatta cgccatgaac aagagcgccg ccgctggcct gctgggctat  27180
gcccgcgtca gcaccgacga ccaggacttg accaaccaac gggccgaact gcacgcggcc  27240
ggctgcacca agctgttttc cgagaagatc accggcacca ggcgcgaccg cccggagctg  27300
gccaggatgc ttgaccacct acgccctggc gacgttgtga cagtgaccag gctagaccgc  27360
ctggcccgca gcacccgcga cctactggac attgccgagc gcatccagga ggccggcgcg  27420
ggcctgcgta gcctggcaga gccgtgggcc gacaccacca cgccggccgg ccgcatggtg  27480
ttgaccgtgt tcgccggcat tgccgagttc gagcgttccc taatcatcga ccgcacccgg  27540
agcgggcgcg aggccgccaa ggcccgaggc gtgaagtttg gcccccgccc taccctcacc  27600
ccggcacaga tcgcgcacgc ccgcgagctg atcgaccagg aaggccgcac cgtgaaagag  27660
gcggctgcac tgcttggcgt gcatcgctcg accctgtacc gcgcacttga gcgcagcgag  27720
gaagtgacgc ccaccgaggc caggcggcgc ggtgccttcc gtgaggacgc attgaccgag  27780
gccgacgccc tggcggccgc cgagaatgaa cgccaagagg aacaagcatg aaaccgcacc  27840
aggacggcca ggacgaaccg tttttcatta ccgaagagat cgaggcggag atgatcgcgg  27900
ccgggtacgt gttcgagccg cccgcgcacg tctcaaccgt gcggctgcat gaaatcctgg  27960
ccggtttgtc tgatgccaag ctggcggcct ggccggccag cttggccgct gaagaaaccg  28020
agcgccgccg tctaaaaagg tgatgtgtat ttgagtaaaa cagcttgcgt catgcggtcg  28080
ctgcgtatat gatgcgatga gtaaataaac aaatacgcaa ggggaacgca tgaaggttat  28140
cgctgtactt aaccagaaag gcgggtcagg caagacgacc atcgcaaccc atctagcccg  28200
cgccctgcaa ctcgccgggg ccgatgttct gttagtcgat tccgatcccc agggcagtgc  28260
ccgcgattgg gcggccgtgc gggaagatca accgctaacc gttgtcggca tcgaccgccc  28320
gacgattgac cgcgacgtga aggccatcgg ccggcgcgac ttcgtagtga tcgacggagc  28380
gccccaggcg gcggacttgg ctgtgtccgc gatcaaggca gccgacttcg tgctgattcc  28440
ggtgcagcca agcccttacg acatatgggc caccgccgac ctggtggagc tggttaagca  28500
gcgcattgag gtcacggatg gaaggctaca agcggccttt gtcgtgtcgc gggcgatcaa  28560
aggcacgcgc atcggcggtg aggttgccga ggcgctggcc gggtacgagc tgcccattct  28620
tgagtcccgt atcacgcagc gcgtgagcta cccaggcact gccgccgccg gcacaaccgt  28680
tcttgaatca gaacccgagg gcgacgctgc ccgcgaggtc caggcgctgg ccgctgaaat  28740
```

```
taaatcaaaa ctcatttgag ttaatgaggt aaagagaaaa tgagcaaaag cacaaacacg 28800
ctaagtgccg gccgtccgag cgcacgcagc agcaaggctg caacgttggc cagcctggca 28860
gacacgccag ccatgaagcg ggtcaacttt cagttgccgg cggaggatca caccaagctg 28920
aagatgtacg cggtacgcca aggcaagacc attaccgagc tgctatctga atacatcgcg 28980
cagctaccag agtaaatgag caaatgaata aatgagtaga tgaattttag cggctaaagg 29040
aggcggcatg gaaaatcaag aacaaccagg caccgacgcc gtggaatgcc ccatgtgtgg 29100
aggaacgggc ggttggccag gcgtaagcgg ctgggttgcc tgccggccct gcaatggcac 29160
tggaaccccc aagcccgagg aatcggcgtg agcggtcgca aaccatccgg cccggtacaa 29220
atcggcgcgg cgctgggtga tgacctggtg gagaagttga aggccgcgca ggccgcccag 29280
cggcaacgca tcgaggcaga agcacgcccc ggtgaatcgt ggcaagcggc cgctgatcga 29340
atccgcaaag aatcccggca accgccggca gccggtgcgc cgtcgattag gaagccgccc 29400
aagggcgacg agcaaccaga tttttcgtt ccgatgctct atgacgtggg cacccgcgat 29460
agtcgcagca tcatggacgt ggccgttttc cgtctgtcga agcgtgaccg acgagctggc 29520
gaggtgatcc gctacgagct tccagacggg cacgtagagg tttccgcagg gccggccggc 29580
atggccagtg tgtgggatta cgacctggta ctgatggcgg tttcccatct aaccgaatcc 29640
atgaaccgat accgggaagg gaagggagac aagcccggcc gcgtgttccg tccacacgtt 29700
gcggacgtac tcaagttctg ccggcgagcc gatggcggaa agcagaaaga cgacctggta 29760
gaaacctgca ttcggttaaa caccacgcac gttgccatgc agcgtacgaa gaaggccaag 29820
aacggccgcc tggtgacggt atccgagggt gaagccttga ttagccgcta caagatcgta 29880
aagagcgaaa ccgggcggcc ggagtacatc gagatcgagc tagctgattg gatgtaccgc 29940
gagatcacag aaggcaagaa cccggacgtg ctgacggttc accccgatta ctttttgatc 30000
gatcccggca tcggccgttt tctctaccgc ctggcacgcc gcgccgcagg caaggcagaa 30060
gccagatggt tgttcaagac gatctacgaa cgcagtggca gcgccggaga gttcaagaag 30120
ttctgtttca ccgtgcgcaa gctgatcggg tcaaatgacc tgccggagta cgatttgaag 30180
gaggaggcgg ggcaggctgg cccgatccta gtcatgcgct accgcaacct gatcgagggc 30240
gaagcatccg ccggttccta atgtacggag cagatgctag ggcaaattgc cctagcaggg 30300
gaaaaaggtc gaaaaggtct ctttcctgtg gatagcacgt acattgggaa cccaaagccg 30360
tacattggga accggaaccc gtacattggg aacccaaagc cgtacattgg gaaccggtca 30420
cacatgtaag tgactgatat aaaagagaaa aaaggcgatt tttccgccta aaactcttta 30480
aaacttatta aaactcttaa aacccgcctg gcctgtgcat aactgtctgg ccagcgcaca 30540
gccgaagagc tgcaaaaagc gcctaccctt cggtcgctgc gctccctacg ccccgccgct 30600
tcgcgtcggc ctatcgcggc cgctggccgc tcaaaaatgg ctggcctacg gccaggcaat 30660
ctaccagggc gcggacaagc cgcgccgtcg ccactcgacc gccggcgccc acatcaaggc 30720
accctgcctc gcgcgtttcg gtgatgacgg tgaaaacctc tgacacatgc agctcccgga 30780
gacggtcaca gcttgtctgt aagcggatgc cgggagcaga caagcccgtc agggcgcgtc 30840
agcgggtgtt ggcgggtgtc ggggcgcagc catgacccag tcacgtagcg atagcggagt 30900
gtatactggc ttaactatgc ggcatcagag cagattgtac tgagagtgca ccatatgcgg 30960
tgtgaaatac cgcacagatg cgtaaggaga aaataccgca tcaggcgctc ttccgcttcc 31020
tcgctcactg actcgctgcg ctcggtcgtt cggctgcggc gagcggtatc agctcactca 31080
aaggcggtaa tacggttatc cacagaatca ggggataacg caggaaagaa catgtgagca 31140
```

```
aaaggccagc aaaaggccag gaaccgtaaa aaggccgcgt tgctggcgtt tttccatagg  31200
ctccgccccc ctgacgagca tcacaaaaat cgacgctcaa gtcagaggtg gcgaaacccg  31260
acaggactat aaagatacca ggcgtttccc cctggaagct ccctcgtgcg ctctcctgtt  31320
ccgaccctgc cgcttaccgg atacctgtcc gcctttctcc cttcgggaag cgtggcgctt  31380
tctcatagct cacgctgtag gtatctcagt tcggtgtagg tcgttcgctc caagctgggc  31440
tgtgtgcacg aaccccccgt tcagcccgac cgctgcgcct tatccggtaa ctatcgtctt  31500
gagtccaacc cggtaagaca cgacttatcg ccactggcag cagccactgg taacaggatt  31560
agcagagcga ggtatgtagg cggtgctaca gagttcttga agtggtggcc taactacggc  31620
tacactagaa ggacagtatt tggtatctgc gctctgctga agccagttac cttcggaaaa  31680
agagttggta gctcttgatc cggcaaacaa accaccgctg gtagcggtgg tttttttgtt  31740
tgcaagcagc agattacgcg cagaaaaaaa ggatctcaag aagatccttt gatcttttct  31800
acggggtctg acgctcagtg gaacgaaaac tcacgttaag ggattttggt catgcattct  31860
aggtactaaa acaattcatc cagtaaaata taatatttta ttttctccca atcaggcttg  31920
atccccagta agtcaaaaaa tagctcgaca tactgttctt ccccgatatc ctccctgatc  31980
gaccggacgc agaaggcaat gtcataccac ttgtccgccc tgccgcttct cccaagatca  32040
ataaagccac ttactttgcc atctttcaca aagatgttgc tgtctcccag gtcgccgtgg  32100
gaaaagacaa gttcctcttc gggcttttcc gtctttaaaa aatcatacag ctcgcgcgga  32160
tctttaaatg gagtgtcttc ttcccagttt tcgcaatcca catcggccag atcgttattc  32220
agtaagtaat ccaattcggc taagcggctg tctaagctat tcgtataggg acaatccgat  32280
atgtcgatgg agtgaaagag cctgatgcac tccgcataca gctcgataat cttttcaggg  32340
ctttgttcat cttcatactc ttccgagcaa aggacgccat cggcctcact catgagcaga  32400
ttgctccagc catcatgccg ttcaaagtgc aggacctttg gaacaggcag ctttccttcc  32460
agccatagca tcatgtcctt ttcccgttcc acatcatagg tggtcccttt ataccggctg  32520
tccgtcattt ttaaatatag gttttcattt tctcccacca gcttatatac cttagcagga  32580
gacattcctt ccgtatcttt tacgcagcgg tatttttcga tcagtttttt caattccggt  32640
gatattctca ttttagccat ttattatttc cttcctcttt tctacagtat ttaaagatac  32700
cccaagaagc taattataac aagacgaact ccaattcact gttccttgca ttctaaaacc  32760
ttaaatacca gaaaacagct tttcaaagt tgttttcaaa gttggcgtat aacatagtat  32820
cgacggagcc gattttgaaa ccgcggtgat cacaggcagc aacgctctgt catcgttaca  32880
atcaacatgc taccctccgc gagatcatcc gtgtttcaaa cccggcagct tagttgccgt  32940
tcttccgaat agcatcggta acatgagcaa agtctgccgc cttacaacgg ctctcccgct  33000
gacgccgtcc cggactgatg ggctgcctgt atcgagtggt gattttgtgc cgagctgccg  33060
gtcggggagc tgttggctgg ctggtggcag gatatattgt ggtgtaaaca aattgacgct  33120
tagacaactt aataacacat tgcggacgtt tttaatgtac tgaattaacg ccgaattaat  33180
t                                                                  33181
```

<210> SEQ ID NO 4
<211> LENGTH: 30214
<212> TYPE: DNA
<213> ORGANISM: Artificial Sequence
<220> FEATURE:
<223> OTHER INFORMATION: Synthetic construct plasmid pMBXS1023

<400> SEQUENCE: 4

```
aaggtacgta gtgtttatct ttgttgcttt tctgaacaat ttatttacta tgtaaatata     60
ttatcaatgt ttaatctatt ttaatttgca catgaatttt cattttattt ttactttaca    120
aaacaaataa atatatatgc aaaaaaattt acaaacgatg cacgggttac aaactaattt    180
cattaaatgc taatgcagat tttgtgaagt aaaactccaa ttatgatgaa aaataccacc    240
aacaccacct gcgaaactgt atcccaactg tccttaataa aaatgttaaa aagtatatta    300
ttctcatttg tctgtcataa tttatgtacc ccactttaat ttttctgatg tactaaaccg    360
agggcaaact gaaacctgtt cctcatgcaa agcccctact caccatgtat catgtacgtg    420
tcatcaccca acaactccac ttttgctata taacaacacc cccgtcacac tctccctctc    480
taacacacac cccactaaca attccttcac ttgcagcact gttgcatcat catcttcatt    540
gcaaaaccct aaacttcacc ttcaaccgga tccaaaatgg cttctatgat atcctcttcc    600
gctgtgacaa cagtcagccg tgcctctagg gggcaatccg ccgcagtggc tccattcggc    660
ggcctcaaat ccatgactgg attcccagtg aagaaggtca acactgacat tacttccatt    720
acaagcaatg gtggaagagt aaagtgcatg caggtgtggc ctccaattgg aaagaagaag    780
tttgagactc tttcctattt gccaccattg acgagagatt ctagagttgg gaaaaagatg    840
atgactactg atgggaatac tgcaaccgct cacgtagctt atgcgatgtc agaagttgca    900
gctatctacc caatcacgcc gtccagtaca atgggagagg aagctgatga ctgggcagca    960
cagggaagaa agaatatctt cggtcaaacg cttacgatta gggagatgca atcggaagcc   1020
ggagcagcgg gtgccgtaca tggagctctt gcagctggcg ccttaactac cacctttacg   1080
gcttctcaag gactactctt gatgatccct aacatgtaca agatatcagg agaattgctt   1140
cctggagtct ttcatgtcac tgctagagct attgccgccc acgccctttc aatctttggt   1200
gatcatcagg atatatatgc agcgaggcag acagggttcg ctatgcttgc ttcaagctcg   1260
gtgcaagaag cacatgacat ggctttagtt gcccaccttg ccgccatcga atctaacgtc   1320
cctttcatgc atttcttcga cggtttcgc acgtcacacg aaattcaaaa gattgaagtt    1380
ctcgattatg cagatatggc atccttagtg aatcagaaag ctctcgcaga gttccgtgct   1440
aaatctatga atccagagca tccacatgtt cgtggtactg ctcaaaaccc tgacatatat   1500
ttccagggaa gagaggcagc aaacccgtat tacttgaaag ttcctgggat tgtagcagag   1560
tatatgcaaa aagttgcaag tctaacaggg agatcgtaca agctgttcga ctatgttgga   1620
gctcctgatg ctgagcgtgt cattgtttct atgggttcca gttgcgagac aatcgaagaa   1680
gtgatcaatc acctcgctgc taagggagaa aagattggtt tgattaaggt ccgattatac   1740
cgtccatttg tatctgaagc tttctttgct gcgttaccgg catctgctaa ggttattaca   1800
gttctggata gaactaagga gcccggagct cctggcgacc ctttgtacct tgatgtctgt   1860
tcagcattcg tcgaaagggg agaagctatg cccaaaatcc tcgcaggccg ctatgggctc   1920
ggatctaagg agttttcacc cgctatggtt aaatctgttt atgataacat gagtggtgct   1980
aagaagaacc attttaccgt tggtatagag gacgatgtca cgggaacatc tctgccggtt   2040
gataatgcgt ttgctgatac aacccctaaa ggaactatcc agtgtcagtt ctggggtttg   2100
ggtgcagatg gtactgtcgg ggcgaataag caggctatca aaatcatagg agataacact   2160
gatctattcg ctcaaggtta cttttcatac gactctaaga aaagtggtgg tataactatc   2220
agtcacttgc gatttggaga aaagccaata caatctacct atttggtgaa ccgggctgac   2280
tacgttgctt gtcataaccc tgcctatgtt ggtatatacg atattttaga gggtatcaaa   2340
```

```
gatgggggca catttgtcct caattctccc tggtcgagtc ttgaagatat ggataaacat   2400
cttccaagcg ggattaagag aaccatagcg aataagaagc ttaagtttta caacattgat   2460
gcggtgaaaa tagcaacaga tgttggtttg ggcggcagaa ttaacatgat aatgcagacc   2520
gcattcttca aactagctgg tgtactccct ttcgagaagg cagtggatct cctcaaaaag   2580
tctattcata aagcctatgg aaagaaggga gagaagatcg tgaaaatgaa tactgacgca   2640
gtagatcaag cagttacgag ccttcaagag ttcaagtacc cagactcatg gaaggatgct   2700
ccagcagaga caaaagctga gccaatgaca aacgagttct tcaaaaatgt tgtcaagcct   2760
atcctcactc aacaaggcga taaattaccg gtttccgctt ttgaagccga tggacgtttt   2820
ccactgggaa cttctcagtt tgagaaacgc ggagtggcta ttaacgttcc tcagtgggta   2880
cctgaaaatt gcatccaatg caatcaatgc gcttttgtgt gcccgcattc cgcgatactt   2940
cctgttttgg ctaaagagga agagttagtc ggagcgcctg ccaacttcac cgctttggaa   3000
gcgaaaggaa aagaattgaa aggttacaaa ttcagaattc agattaacac tctcgactgc   3060
atgggctgcg gaaattgtgc cgacatatgt cctcccaaag aaaaggcttt agtgatgcag   3120
ccactggaca ctcagaggga tgcccaagtg ccaaatttgg agtatgcagc cagaattcca   3180
gtgaagtccg aggttcttcc gcgggattct ctcaaaggat cacaattcca agaaccactg   3240
atggagtttt caggcgcatg tagtggatgt ggtgaaacac cttacgtacg tgtgattact   3300
cagttatttg gagaacggat gtttatcgct aatgcaacag gttgtagctc gatctggggt   3360
gccagcgctc cgtcgatgcc atacaagacc aacaggctgg gacagggtcc agcttggggg   3420
aattccctat tcgaggatgc tgcagagtac gggttcggaa tgaacatgag tatgtttgcg   3480
cgtagaactc atctcgcgga tcttgctgct aaagctctcg agtctgatgc ttctggagat   3540
gtcaaggaag cattgcaggg ttggctcgct gggaaaaacg acccgattaa gtctaaagaa   3600
tacggggata agttgaagaa acttctagct ggtcaaaagg acgggttgtt gggacaaatt   3660
gcagcaatgt cagaccttta cacgaagaaa agtgtttgga tctttggtgg cgatggatgg   3720
gcgtatgata ttggttatgg tggccttgat cacgtcctcg caagcggcga agatgtgaac   3780
gtgtttgtga tggatactga agtttactcc aacaccggtg gacaatcctc aaaagcaaca   3840
ccaaccgggg ccgtggctaa attcgcggct gccggcaaaa ggactggaaa aaaggatctg   3900
gccagaatgg ttatgactta tggatacgta tatgtagcta cagtatcaat gggctatagc   3960
aaacagcaat ttcttaaagt cctcaaggaa gctgagagct tcccaggtcc ttcacttgtt   4020
atcgcctacg cgacatgtat caatcaaggt ttacgaaagg gaatggggaa aagccaagat   4080
gtgatgaaca ccgctgttaa aagcggttat tggcctttgt tccgctatga tcctcgtctt   4140
gcggcccaag gaaagaatcc gtttcagcta gactctaagg caccagacgg tagtgttgag   4200
gaatttttga tggctcagaa tcgatttgcg gtccttgatc gatcgttccc agaagatgcc   4260
aagaggttga gggcgcaagt tgcacatgaa ttggatgtta ggtttaagga gttagaacac   4320
atggcggcta caaatatctt cgagtccttc gctcctgctg gaggcaaagc tgacggttca   4380
gtagattttg gagaaggcgc agagttttgt actagagatg acacaccgat gatggccaga   4440
ccagatagtg gcgaagcatg cgaccaaaat agagcaggaa cgtctgagca gcaaggagat   4500
ttgtcgaaga ggaccaagaa atgaggcgcg cctgagtaat tctgatatta gagggagcat   4560
taatgtgttg ttgtgatgtg gtttatatgg ggaaattaaa taaatgatgt atgtacctct   4620
tgcctatgta ggtttgtgtg ttttgttttg ttgtctagct ttggttatta agtagtaggg   4680
```

```
acgttcgttc gtgtctcaaa aaaaggggta ctaccactct gtagtgtata tggatgctgg   4740
aaatcaatgt gttttgtatt tgttcacctc cattgttgaa ttcaatgtca aatgtgtttt   4800
gcgttggtta tgtgtaaaat tactatcttt ctcgtccgat gatcaaagtt ttaagcaaca   4860
aaaccaaggg tgaaatttaa actgtgcttt gttgaagatt cttttatcat attgaaaatc   4920
aaattactag cagcagattt tacctagcat gaaattttat caacagtaca gcactcacta   4980
accaagttcc aaactaagat gcgccattaa catcagccaa taggcatttt cagcaaaagc   5040
ttgtacgtag tgtttatctt tgttgctttt ctgaacaatt tatttactat gtaaatatat   5100
tatcaatgtt taatctattt taatttgcac atgaattttc attttatttt tactttacaa   5160
aacaaataaa tatatatgca aaaaaattta caaacgatgc acgggttaca aactaatttc   5220
attaaatgct aatgcagatt ttgtgaagta aaactccaat tatgatgaaa aataccacca   5280
acaccacctg cgaaactgta tcccaactgt ccttaataaa aatgttaaaa agtatattat   5340
tctcatttgt ctgtcataat ttatgtaccc cactttaatt tttctgatgt actaaaccga   5400
gggcaaactg aaacctgttc ctcatgcaaa gcccctactc accatgtatc atgtacgtgt   5460
catcacccaa caactccact tttgctatat aacaacaccc ccgtcacact ctccctctct   5520
aacacacacc ccactaacaa ttccttcact tgcagcactg ttgcatcatc atcttcattg   5580
caaaacccta aacttcacct tcaaccgcgg ccgcagatct aaaatggctt ctatgatatc   5640
ctcttccgct gtgacaacag tcagccgtgc ctctaggggg caatccgccg cagtggctcc   5700
attcggcggc ctcaaatcca tgactggatt cccagtgaag aaggtcaaca ctgacattac   5760
ttccattaca agcaatggtg gaagagtaaa gtgcatgcag gtgtggcctc caattggaaa   5820
gaagaagttt gagactcttt cctatttgcc accattgacg agagattcta gagtgctcag   5880
ccagcaatcc atccagaagg ttctcgtggc taaccgtggt gagattgcta ttcgtatctt   5940
tagagcgtgt accgagttga acatccgaac tgtcgctgtt tatagtaaag aagattctgg   6000
atcataccac agatacaaag ctgacgaggc ctacttggtt ggtgaaggta agaagcctat   6060
tgacgcttat cttgatatag agggcatcat tgatattgcc aagagaaaca aagttgatgc   6120
aattcatccg ggatacggtt ttctatcaga aaacattcac tttgcacgac gatgtgaaga   6180
agagggaatc gtgttcatcg gacctaaaag cgaacacttg gatatgtttg gggacaaggt   6240
taaggcaagg gaacaagcag agaaggcagg aattccagtg atacctggat cggatgggcc   6300
tgctgaaact cttgaagctg tcgaacaatt cggccaggct aacggatacc caatcatcat   6360
taaggcttct ttaggtggtg ggggaagggg gatgagaatc gtgcgatccg aatctgaggt   6420
aaaagaggct tatgaacgtg ctaaatcgga agctaaagcg gcctttggga acgatgaagt   6480
ctatgtcgag aaactaatcg agaatcccaa gcacatcgag gttcaagtga ttggtgataa   6540
gcaaggtaac gttgttcacc ttttcgagag agattgttct gttcaacgta gacaccaaaa   6600
agtgatagaa gtagctccat cggtatcgtt gagcccagaa ctaagggacc agatatgcga   6660
ggctgctgtc gcgcttgcaa agaatgtcaa ctatatcaat gcaggcactg tcgaattctt   6720
ggtagccaat aatgagtttt acttcattga ggtcaaccct agagttcaag ttgagcatac   6780
cattaccgaa atgatcactg ggtggatat cgtacagact cagatcctcg ttgctcaagg   6840
ccattccctt cattccaaga aggtgaatat tccagagcaa aaggatatct ttacaattgg   6900
ttatgcgatt caatcacgag ttaccacaga agatccacaa aatgacttca tgccagatac   6960
gggaaagata atggcatacc gttctggtgg cggatttggt gttcgattag acacaggtaa   7020
tagttttcag ggagctgtga taacgccata ctatgattct ttattggtta agttgagtac   7080
```

```
ttgggctctc actttcgagc aagccgcagc gaaaatggtc agaaaccttc aggagttcag   7140
aattagaggt attaagacga acattccatt cttagagaac gttgctaaac atgagaagtt   7200
tctgacagga caatatgata caagtttcat agacactaca cctgaactct ttaacttccc   7260
taaacaaaaa gacagaggta cgaaaatgtt gacatatatc ggaaacgtga cagttaatgg   7320
gttcccaggt atcggtaaga aagaaaagcc ggcctttgat aaaccccttg gtgttaaagt   7380
ggatgtggat caacaacctg ctaggggcac taagcaaatc cttgatgaaa agggtgcaga   7440
gggactggca aattgggtta aagagcagaa atcagttctt ctgacagata ccacatttcg   7500
tgatgctcat caatcattac tagcaacaag aattagatca cacgatctga aaaagatcgc   7560
taatccaacc gctgctcttt ggccggaact cttctctatg gaaatgtggg gtggggccac   7620
attcgatgtc gcgtaccgtt ttctaaaaga agatccttgg aagcgtctgg aagatttgag   7680
aaaagaggtg cccaataccc tgttccagat gcttttgcgt tctagcaatg ccgtcggata   7740
taccaattat cctgacaatg tgatcaaaga attcgtaaaa cagtccgctc aatctggtat   7800
cgacgttttt aggattttcg attcacttaa ttgggtaaaa ggtatgacgt tagcgattga   7860
tgctgtacgt gatactggaa aggttgcaga ggccgccatt tgctacactg gagacatttt   7920
ggataagaat agaactaaat acgacttggc ttattacact tccatggcaa aagaacttga   7980
ggctgccggt gcacatattc tggggataaa ggatatggcc ggtttgctca aaccgcaggc   8040
agcatatgag ttggtttcag cccttaaaga aactattgac atacccgttc atctgcacac   8100
gcatgacacg tcgggcaatg gaatctatat gtatgcaaag gctgtcgagg ctggcgtgga   8160
tatcattgat gtcgctgtaa gctctatggc tggacttaca tcccagccat cagcctctgg   8220
attctatcat gctatggaag gtaacgatcg tagacccgaa atgaatgtcc aaggggtcga   8280
attactgtca cagtactggg agagtgtgcg taagtattac tcagagtttg agagcggtat   8340
gaagagtccc cataccgaga tttatgagca cgagatgcct ggtggacaat actctaactt   8400
gcaacagcaa gcgaaggggg ttggtttggg agataggtgg aacgaagtga aagaaatgta   8460
tagacgtgtc aacgacatgt ttggtgatat tgtgaaagta actcctagtt ctaaggtagt   8520
tggagacatg gcactgtaca tggttcagaa taaccttact gaaaaggatg tttacgagaa   8580
gggggagtca cttgacttcc ctgattcagt ggttgaactg ttcaagggaa atatcggtca   8640
accgcatggg ggatttccag aaaaactaca gaaactgata ctaaagggac aggagccaat   8700
tactgttcga ccaggagagc tcttggagcc ggtttctttt gaggctatca agcaagaatt   8760
caaagaacaa cataaccttg aaatttctga tcaggacgcg gttgcttacg cactttatcc   8820
aaaggtcttt actgattacg tgaaaaccac agagtcttat ggtgatataa gtgtgctaga   8880
tacaccaaca tttttctatg gcatgactct tggagaagag attgaagtgg aaatagaaag   8940
gggaaaaaca ctcattgtta aactgatatc tatcggagag cctcaacctg atgctacaag   9000
ggtagtgtac tttgaattga atggacaacc tagagaagta gtgattaaag atgagtcaat   9060
aaagtcaagc gtgcaggaga ggctaaaggc agatagaacc aatccgtcgc acattgcagc   9120
ttctatgcct ggcaccgtca taaaagtcct cgctgaagct ggtactaaag tcaacaaagg   9180
tgaccatctt atgatcaacg aagcaatgaa gatggaaact acggttcagg cacctttcag   9240
tggaacaatc aagcaggttc atgttaagaa tggcgagcct atccagactg gtgacttgct   9300
tttggagatt gaaaaggcct gagtcgacgc gatcgcgcgg ccgctgagta attctgatat   9360
tagagggagc attaatgtgt tgttgtgatg tggtttatat ggggaaatta aataaatgat   9420
```

```
gtatgtacct cttgcctatg taggtttgtg tgttttgttt tgttgtctag ctttggttat   9480
taagtagtag ggacgttcgt tcgtgtctca aaaaaagggg tactaccact ctgtagtgta   9540
tatggatgct ggaaatcaat gtgttttgta tttgttcacc tccattgttg aattcaatgt   9600
caaatgtgtt ttgcgttggt tatgtgtaaa attactatct ttctcgtccg atgatcaaag   9660
ttttaagcaa caaaaccaag ggtgaaattt aaactgtgct ttgttgaaga ttcttttatc   9720
atattgaaaa tcaaattact agcagcagat tttacctagc atgaaatttt atcaacagta   9780
cagcactcac taaccaagtt ccaaactaag atgcgccatt aacatcagcc aataggcatt   9840
ttcagcaagt ttaaactacg tagtgtttat ctttgttgct tttctgaaca atttatttac   9900
tatgtaaata tattatcaat gtttaatcta ttttaatttg cacatgaatt ttcattttat   9960
ttttacttta caaaacaaat aaatatatat gcaaaaaaat ttacaaacga tgcacgggtt  10020
acaaactaat ttcattaaat gctaatgcag attttgtgaa gtaaaactcc aattatgatg  10080
aaaaatacca ccaacaccac ctgcgaaact gtatcccaac tgtccttaat aaaaatgtta  10140
aaaagtatat tattctcatt tgtctgtcat aatttatgta ccccacttta atttttctga  10200
tgtactaaac cgagggcaaa ctgaaacctg ttcctcatgc aaagccccta ctcaccatgt  10260
atcatgtacg tgtcatcacc caacaactcc actttgcta tataacaaca cccccgtcac  10320
actctccctc tctaacacac accccactaa caattccttc acttgcagca ctgttgcatc  10380
atcatcttca ttgcaaaacc ctaaacttca ccttcaaccg cggccgctcg cgaaaaatgg  10440
cttctatgat atcctcttcc gctgtgacaa cagtcagccg tgcctctagg gggcaatccg  10500
ccgcagtggc tccattcggc ggcctcaaat ccatgactgg attcccagtg aagaaggtca  10560
acactgacat tacttccatt acaagcaatg gtggaagagt aaagtgcatg caggtgtggc  10620
ctccaattgg aaagaagaag tttgagactc tttcctattt gccaccattg acgagagatt  10680
ctagagtgaa catacacgag taccaagcaa aagagttgct caagacctat ggagtgccgg  10740
tcccagacgg agcggtagct tatagtgatg ctcaagcggc ttccgtcgct gaagagattg  10800
gtggctctag atgggttgta aaggcgcaga tacacgctgg tggaagggga aaggcaggtg  10860
gtgtgaaggt ggcccatagc attgaagagg ttcgtcagta cgctgatgcg atgcttgggt  10920
cccatctcgt tacacatcaa acagggcctg gtggttcatt agttcaacgt ttgtgggtgg  10980
agcaagcatc acatatcaag aaagagtatt atctgggatt tgttattgat agaggtaacc  11040
aaagaattac cttaattgct tcttctgaag ggggaatgga gatagaagag gttgctaaag  11100
agacaccaga aaagatcgtc aaagaggttg tagaccctgc aatcggattg cttgattttc  11160
agtgtagaaa ggttgcaact gcaataggac ttaagggaaa gcttatgccc caggcagtta  11220
gacttatgaa ggctatctat aggtgtatgc gagataagga tgctctccag gcagagatca  11280
atcctttggc aatagtaggt gaaagtgacg agtcgctcat ggttcttgat gctaaattca  11340
attttgatga caatgctctt tacagacaac gaacaattac tgaaatgagg gatctcgcag  11400
aagaagatcc taaagaagtc gaagcttctg gacacggatt gaattacatc gccctcgatg  11460
ggaacatcgg ttgtattgtg aatggagctg gtcttgctat ggccagcctg gatgccatca  11520
ctctacatgg cggtcgtcca gctaacttct tagatgtcgg cggtggggct tctcctgaaa  11580
aggttacgaa tgcgtgcaga attgttttgg aagatccgaa cgtccgttgt atactggtga  11640
acatttttgc cggaattaac aggtgcgatt ggattgcaaa aggacttatt caagcctgcg  11700
actcactaca gattaaagtt ccactgatcg ttcgattggc aggcactaat gtagatgaag  11760
gcaggaaaat cctagcggag tcgggtttaa gtttcataac ggcagagaat ttggacgacg  11820
```

```
cggctgctaa agccgtggct atcgtgaaag ggtgaacgcg ttgagtaatt ctgatattag  11880
agggagcatt aatgtgttgt tgtgatgtgg tttatatggg gaaattaaat aaatgatgta  11940
tgtacctctt gcctatgtag gtttgtgtgt tttgttttgt tgtctagctt tggttattaa  12000
gtagtaggga cgttcgttcg tgtctcaaaa aaaggggtac taccactctg tagtgtatat  12060
ggatgctgga aatcaatgtg ttttgtattt gttcacctcc attgttgaat tcaatgtcaa  12120
atgtgttttg cgttggttat gtgtaaaatt actatctttc tcgtccgatg atcaaagttt  12180
taagcaacaa aaccaagggt gaaatttaaa ctgtgctttg ttgaagattc ttttatcata  12240
ttgaaaatca aattactagc agcagatttt acctagcatg aaatttttatc aacagtacag  12300
cactcactaa ccaagttcca aactaagatg cgccattaac atcagccaat aggcattttc  12360
agcaatgtac atacgtagtg tttatctttg ttgcttttct gaacaattta tttactatgt  12420
aaatatatta tcaatgttta atctatttta atttgcacat gaattttcat tttattttta  12480
ctttacaaaa caaataaata tatatgcaaa aaaatttaca aacgatgcac gggttacaaa  12540
ctaatttcat taaatgctaa tgcagatttt gtgaagtaaa actccaatta tgatgaaaaa  12600
taccaccaac accacctgcg aaactgtatc ccaactgtcc ttaataaaaa tgttaaaaag  12660
tatattattc tcatttgtct gtcataattt atgtacccca ctttaatttt tctgatgtac  12720
taaaccgagg gcaaactgaa acctgttcct catgcaaagc ccctactcac catgtatcat  12780
gtacgtgtca tcacccaaca actccacttt tgctatataa caacaccccc gtcacactct  12840
ccctctctaa cacacacccc actaacaatt ccttcacttg cagcactgtt gcatcatcat  12900
cttcattgca aaaccctaaa cttcaccttc aaccgcggcc gcgacgtcaa aatggcttct  12960
atgatatcct cttccgctgt gacaacagtc agccgtgcct ctagggggca atccgccgca  13020
gtggctccat tcggcggcct caaatccatg actggattcc cagtgaagaa ggtcaacact  13080
gacattactt ccattacaag caatggtgga agagtaaagt gcatgcaggt gtggcctcca  13140
attggaaaga agaagtttga gactctttcc tatttgccac cattgacgag agattctaga  13200
gtctcggttt tcgtgaataa acattccaag gtcatctttc aaggctttac cggggagcat  13260
gctacatttc acgcaaaaga tgcaatgcga atgggcacaa gggttgtcgg tggcgttact  13320
cctggaaagg gtgggactag acatccagat cctgagctcg ctcatcttcc ggtattcgat  13380
accgttgccg aagccgttgc tgctacagga gctgatgtat cagctgtgtt tgtcccaccc  13440
cctttcaatg cagacgcact tatggaagca attgatgccg gtattagagt ggctgtcact  13500
atagcggatg gaattcctgt gcatgacatg atcagattgc aaaggtatag agtaggaaag  13560
gactctattg ttatcgggcc taacacacca ggaatcataa cgcctggtga gtgtaaagtg  13620
ggtatcatgc cgagtcacat atacaagaag ggaaacgtgg gtatagtgag tcgatcagga  13680
acattgaatt acgaggcgac ggaacaaatg gctgcgctag gcttagggat tactacttct  13740
gttggaattg gtggtgatcc tataaacggc actgactttg tgactgttct ccgtgcattc  13800
gaggctgatc cagaaacgga aattgtagtt atgatcggag aaataggtgg accgcaggaa  13860
gttgccgcag ctagatgggc aaaagagaat atgaccaaac cagttattgg gttcgtagct  13920
ggtttagcag cccccacagg gcgtaggatg ggacacgcag gtgctattat cagctctgag  13980
gctgataccg ctggagctaa gatggatgcc atggaagctc ttggtctgta tgtcgctagg  14040
aacccagcgc aaatcggaca gacagttttg cgtgcggcac aggagcatgg aattagattt  14100
tgagggcccg ttaactgagt aattctgata ttagagggag cattaatgtg ttgttgtgat  14160
```

```
gtggtttata tggggaaatt aaataaatga tgtatgtacc tcttgcctat gtaggtttgt  14220
gtgttttgtt ttgttgtcta gctttggtta ttaagtagta gggacgttcg ttcgtgtctc  14280
aaaaaaaggg gtactaccac tctgtagtgt atatggatgc tggaaatcaa tgtgttttgt  14340
atttgttcac ctccattgtt gaattcaatg tcaaatgtgt tttgcgttgg ttatgtgtaa  14400
aattactatc tttctcgtcc gatgatcaaa gttttaagca acaaaaccaa gggtgaaatt  14460
taaactgtgc tttgttgaag attcttttat catattgaaa atcaaattac tagcagcaga  14520
ttttacctag catgaaattt tatcaacagt acagcactca ctaaccaagt tccaaactaa  14580
gatgcgccat taacatcagc caataggcat tttcagcaag tttaaaccgg accgtacgta  14640
gtgtttatct ttgttgcttt tctgaacaat ttatttacta tgtaaatata ttatcaatgt  14700
ttaatctatt ttaatttgca catgaatttt cattttattt ttactttaca aaacaaataa  14760
atatatatgc aaaaaaattt acaaacgatg cacgggttac aaactaattt cattaaatgc  14820
taatgcagat tttgtgaagt aaaactccaa ttatgatgaa aaataccacc aacaccacct  14880
gcgaaactgt atcccaactg tccttaataa aaatgttaaa aagtatatta ttctcatttg  14940
tctgtcataa tttatgtacc ccactttaat ttttctgatg tactaaaccg agggcaaact  15000
gaaacctgtt cctcatgcaa agcccctact caccatgtat catgtacgtg tcatcaccca  15060
acaactccac ttttgctata taacaacacc cccgtcacac tctccctctc taacacacac  15120
cccactaaca attccttcac ttgcagcact gttgcatcat catcttcatt gcaaaaccct  15180
aaacttcacc ttcaaccgcg gccgccacgt gaaaatggct tctatgatat cctcttccgc  15240
tgtgacaaca gtcagccgtg cctctagggg gcaatccgcc gcagtggctc cattcggcgg  15300
cctcaaatcc atgactggat tcccagtgaa gaaggtcaac actgacatta cttccattac  15360
aagcaatggt ggaagagtaa agtgcatgca ggtgtggcct ccaattggaa agaagaagtt  15420
tgagactctt tcctatttgc caccattgac gagagattct agagtgagct tccgtttgca  15480
accagctccg ccagcaaggc ccaatagatg tcaacttttt gggcctggat ctcgaccggc  15540
tttgtttgag aaaatggccg cttcagccgc ggacgttatc aatctggatt tagaggatag  15600
tgttgcccca gatgataaag ctcaggctag agcaaatatc attgaggcta taaacggtct  15660
agactggggt agaaagtatc tcagtgttag aattaacgga cttgatacgc ctttctggta  15720
tcgagatgtc gttgacttgc ttgagcaggc aggagataga cttgatcaaa tcatgatccc  15780
taaggttggc tgtgctgcgg atgtttacgc cgtcgatgct ttggtaacag caattgaacg  15840
tgctaaaggg cgtactaagc ctctatcatt tgaagtgata atagagtctg cagctggtat  15900
cgcacatgtt gaagaaatag ccgcttcgtc accaagactc caagccatgt ctttgggtgc  15960
agccgatttt gcagcttcta tggaatgca gactacaggg attggtggaa cgcaagagaa  16020
ctactatatg ctccacgacg gacaaaagca ctggtccgat ccttggcatt gggctcaggc  16080
tgcaatcgtc gcagcgtgca gaacacatgg gattttaccc gttgacggcc cgttcggtga  16140
cttctctgat gacgaaggat tcagggcaca agctcgaagg tccgctactc ttggaatggt  16200
gggaaaatgg gccatacatc caaagcaagt ggctctcgct aatgaagtgt ttacacctag  16260
cgagactgca gtaaccgaag cgagggagat tttagcggct atggatgctg ctaaggcgag  16320
aggcgaaggt gctaccgtgt acaaaggtag gctggtagat atcgcgtcga ttaaacaggc  16380
agaagtcatt gttcgtcagg ctgagatgat tagtgcatga actagttgag taattctgat  16440
attagaggga gcattaatgt gttgttgtga tgtggtttat atggggaaat taaataaatg  16500
atgtatgtac ctcttgccta tgtaggtttg tgtgttttgt tttgttgtct agctttggtt  16560
```

```
attaagtagt agggacgttc gttcgtgtct caaaaaaagg ggtactacca ctctgtagtg  16620
tatatggatg ctggaaatca atgtgttttg tatttgttca cctccattgt tgaattcaat  16680
gtcaaatgtg ttttgcgttg gttatgtgta aaattactat ctttctcgtc cgatgatcaa  16740
agttttaagc aacaaaacca agggtgaaat ttaaactgtg ctttgttgaa gattctttta  16800
tcatattgaa aatcaaatta ctagcagcag attttaccta gcatgaaatt ttatcaacag  16860
tacagcactc actaaccaag ttccaaacta agatgcgcca ttaacatcag ccaataggca  16920
ttttcagcaa gtttaaactc cggatacgta gtgtttatct ttgttgcttt tctgaacaat  16980
ttatttacta tgtaaatata ttatcaatgt ttaatctatt ttaatttgca catgaatttt  17040
cattttattt ttactttaca aaacaaataa atatatatgc aaaaaaattt acaaacgatg  17100
cacgggttac aaactaattt cattaaatgc taatgcagat tttgtgaagt aaaactccaa  17160
ttatgatgaa aaataccacc aacaccacct gcgaaactgt atcccaactg tccttaataa  17220
aaatgttaaa aagtatatta ttctcatttg tctgtcataa tttatgtacc ccactttaat  17280
ttttctgatg tactaaaccg agggcaaact gaaacctgtt cctcatgcaa agcccctact  17340
caccatgtat catgtacgtg tcatcaccca acaactccac ttttgctata taacaacacc  17400
cccgtcacac tctccctctc taacacacac cccactaaca attccttcac ttgcagcact  17460
gttgcatcat catcttcatt gcaaaaccct aaacttcacc ttcaaccgcg gccgccctag  17520
gaaaatggct tctatgatat cctcttccgc tgtgacaaca gtcagccgtg cctctagggg  17580
gcaatccgcc gcagtggctc cattcggcgg cctcaaatcc atgactggat tcccagtgaa  17640
gaaggtcaac actgacatta cttccattac aagcaatggt ggaagagtaa agtgcatgca  17700
ggtgtggcct ccaattggaa agaagaagtt tgagactctt tcctatttgc caccattgac  17760
gagagattct agagttgcac agtaccaaga cgatatcaag gcggttgcag ggcttaagga  17820
gaatcacggc tccgcatgga atgccatcaa cccggagtat gccgccagga tgagggcgca  17880
gaacaagttc aagacgggcc ttgacattgc aaagtatacg gctaagatta tgcgggccga  17940
tatggcagcc tacgacgccg acagctcgaa gtacacacag agcctcggtt gttggcatgg  18000
tttcattggt cagcagaaga tgatctcaat caagaaacat ttcaacagca cggaacgccg  18060
ttacctctac ctttctggct ggatggtagc cgcgcttaga tccgagtttg gccccctacc  18120
ggatcagtcc atgcacgaaa agacgagtgt ctccgcactc attcgggaac tctacacttt  18180
tctgcgccaa gcggacgcta gggagttggg gggcctgttt cgggagcttg acgcggccca  18240
aggcccagct aaggcggcca ttcaagcgaa gatcgacaac cacgtcactc atgtggtccc  18300
aatcatagct gatatcgacg ctggcttcgg caatgcggaa gcaacatacc tgttggccaa  18360
gcagttcatc gaggccgggg cttgctgcat acagatagag aaccaggttt ctgacgaaaa  18420
gcaatgtgga catcaagacg gaaaggttac cgtgccccac gaggattttc ttgcaaaaat  18480
ccgagcgatt cgttatgcgt ttttagagtt gggcgtggat gacggtatca tcgtggccag  18540
gaccgatagt ctcggtgctg gtctgacaaa gcaaatcgca gtgaccaata cgcctggaga  18600
cttaggggat cagtacaaca gcttcctcga ttgcgaggag cttagcgcag atcagctcgg  18660
aaatggcgac gttatcatca agcgtgatgg aaagctactc cgccccaagc gcctcccgtc  18720
taacttgttc cagttccggg ctggaactgg cgaagcgcga tgcgtcctgg actgcgtgac  18780
cgcgctccag aacggcgccg acctactctg gattgagaca gaaaagcctc acatagctca  18840
aatcggcgga atggtatcgg agataaggaa agtcataccc aacgccaaac tggtgtacaa  18900
```

```
caactctccg tcgttcaatt ggaccctgaa ctttagacag caagcatacg atgctatgaa  18960
agccgctggg aaagacgtgt cagcatacga ccgcgcccag cttatgtccg tggagtacga  19020
ccaaacggaa ctggctaagc tggctgatga gaaaatcaga acattccagg ccgacgcctc  19080
aagggaggcc gggatcttcc atcacttgat taccttacca acatatcaca ctgcggccct  19140
gtcaaccgac aatttggcta aggagtactt cggagatcag gggatgctcg gttatgtcgc  19200
gggcgttcag aggaaggaga tccgacaggg catcgcatgt gtcaagcacc aaaacatgag  19260
cgggagtgac atcggggatg atcataaaga gtatttctcc ggcgaagccg cgctgaaggc  19320
cgccggcaaa gacaacacta tgaatcaatt ctgacccggg tgagtaattc tgatattaga  19380
gggagcatta atgtgttgtt gtgatgtggt ttatatgggg aaattaaata aatgatgtat  19440
gtacctcttg cctatgtagg tttgtgtgtt ttgttttgtt gtctagcttt ggttattaag  19500
tagtagggac gttcgttcgt gtctcaaaaa aaggggtact accactctgt agtgtatatg  19560
gatgctggaa atcaatgtgt tttgtatttg ttcacctcca ttgttgaatt caatgtcaaa  19620
tgtgttttgc gttggttatg tgtaaaatta ctatctttct cgtccgatga tcaaagtttt  19680
aagcaacaaa accaagggtg aaatttaaac tgtgctttgt tgaagattct tttatcatat  19740
tgaaaatcaa attactagca gcagatttta cctagcatga aattttatca acagtacagc  19800
actcactaac caagttccaa actaagatgc gccattaaca tcagccaata ggcattttca  19860
gcaagctcga gtcacgtagt ggtacgtagt gtttatcttt gttgcttttc tgaacaattt  19920
atttactatg taaatatatt atcaatgttt aatctatttt aatttgcaca tgaattttca  19980
ttttattttt actttacaaa acaaataaat atatatgcaa aaaaatttac aaacgatgca  20040
cgggttacaa actaatttca ttaaatgcta atgcagattt tgtgaagtaa aactccaatt  20100
atgatgaaaa ataccaccaa caccacctgc gaaactgtat cccaactgtc cttaataaaa  20160
atgttaaaaa gtatattatt ctcatttgtc tgtcataatt tatgtacccc actttaattt  20220
ttctgatgta ctaaaccgag ggcaaactga aacctgttcc tcatgcaaag cccctactca  20280
ccatgtatca tgtacgtgtc atcacccaac aactccactt ttgctatata acaacacccc  20340
cgtcacactc tccctctcta acacacaccc cactaacaat tccttcactt gcagcactgt  20400
tgcatcatca tcttcattgc aaaaccctaa acttcacctt caaccgcggc cgcttcgaag  20460
gatccaaaat ggtgagcaag ggcgaggagc tgttcaccgg ggtggtgccc atcctggtcg  20520
agctggacgg cgacgtaaac ggccacaagt tcagcgtgtc cggcgagggc gagggcgatg  20580
ccacctacgg caagctgacc ctgaagttca tctgcaccac cggcaagctg cccgtgccct  20640
ggcccaccct cgtgaccacc ttcacctacg gcgtgcagtg cttcagccgc taccccgacc  20700
acatgaagca gcacgacttc ttcaagtccg ccatgcccga aggctacgtc caggagcgca  20760
ccatcttctt caaggacgac ggcaactaca agacccgcgc cgaggtgaag ttcgagggcg  20820
acaccctggt gaaccgcatc gagctgaagg gcatcgactt caaggaggac ggcaacatcc  20880
tggggcacaa gctggagtac aactacaaca gccacaacgt ctatatcatg gccgacaagc  20940
agaagaacgg catcaaggtg aacttcaaga tccgccacaa catcgaggac ggcagcgtgc  21000
agctcgccga ccactaccag cagaacaccc ccatcggcga cggccccgtg ctgctgcccg  21060
acaaccacta cctgagcacc cagtccgccc tgagcaaaga ccccaacgag aagcgcgatc  21120
acatggtcct gctggagttc gtgaccgccg ccgggatcac tcacggcatg gacgagctgt  21180
acaagtaaag cggccgcccg ggctgcagtt cgaaatttaa atgcggccgc tgagtaattc  21240
tgatattaga gggagcatta atgtgttgtt gtgatgtggt ttatatgggg aaattaaata  21300
```

-continued

```
aatgatgtat gtacctcttg cctatgtagg tttgtgtgtt ttgttttgtt gtctagcttt  21360
ggttattaag tagtagggac gttcgttcgt gtctcaaaaa aaggggtact accactctgt  21420
agtgtatatg gatgctggaa atcaatgtgt tttgtatttg ttcacctcca ttgttgaatt  21480
caatgtcaaa tgtgttttgc gttggttatg tgtaaaatta ctatctttct cgtccgatga  21540
tcaaagtttt aagcaacaaa accaagggtg aaatttaaac tgtgctttgt tgaagattct  21600
tttatcatat tgaaaatcaa attactagca gcagatttta cctagcatga aattttatca  21660
acagtacagc actcactaac caagttccaa actaagatgc gccattaaca tcagccaata  21720
ggcattttca gcaaagcaaa tgaattcgta atcatgtcat agctgtttcc tgtgtgaaat  21780
tgttatccgc tcacaattcc acacaacata cgagccggaa gcataaagtg taaagcctgg  21840
ggtgcctaat gagtgagcta actcacatta attgcgttgc gctcactgcc cgctttccag  21900
tcgggaaacc tgtcgtgcca gctgcattaa tgaatcggcc aacgcgcggg gagaggcggt  21960
ttgcgtattg gctagagcag cttgccaaca tggtggagca cgacactctc gtctactcca  22020
agaatatcaa agatacagtc tcagaagacc aaagggctat tgagactttt caacaaaggg  22080
taatatcggg aaacctcctc ggattccatt gcccagctat ctgtcacttc atcaaaagga  22140
cagtagaaaa ggaaggtggc acctacaaat gccatcattg cgataaagga aaggctatcg  22200
ttcaagatgc ctctgccgac agtggtccca aagatggacc cccacccacg aggagcatcg  22260
tggaaaaaga agacgttcca accacgtctt caaagcaagt ggattgatgt gaacatggtg  22320
gagcacgaca ctctcgtcta ctccaagaat atcaaagata cagtctcaga agaccaaagg  22380
gctattgaga cttttcaaca aagggtaata tcgggaaacc tcctcggatt ccattgccca  22440
gctatctgtc acttcatcaa aaggacagta gaaaaggaag gtggcaccta caaatgccat  22500
cattgcgata aaggaaaggc tatcgttcaa gatgcctctg ccgacagtgg tcccaaagat  22560
ggacccccac ccacgaggag catcgtggaa aaagaagacg ttccaaccac gtcttcaaag  22620
caagtggatt gatgtgatat ctccactgac gtaagggatg acgcacaatc ccactatcct  22680
tcgcaagacc cttcctctat ataaggaagt tcatttcatt tggagaggac acgctgaaat  22740
caccagtctc tctctacaaa tctatctctc tcgagaaaat ggtgagcaag ggcgaggagc  22800
tgttcaccgg ggtggtgccc atcctggtcg agctggacgg cgacgtaaac ggccacaagt  22860
tcagcgtgtc cggcgagggc gagggcgatg ccacctacgg caagctgacc ctgaagttca  22920
tctgcaccac cggcaagctg cccgtgccct ggcccaccct cgtgaccacc ttcacctacg  22980
gcgtgcagtg cttcagccgc taccccgacc acatgaagca gcacgacttc ttcaagtccg  23040
ccatgcccga aggctacgtc caggagcgca ccatcttctt caaggacgac ggcaactaca  23100
agacccgcgc cgaggtgaag ttcgagggcg acaccctggt gaaccgcatc gagctgaagg  23160
gcatcgactt caaggaggac ggcaacatcc tggggcacaa gctggagtac aactacaaca  23220
gccacaacgt ctatatcatg gccgacaagc agaagaacgg catcaaggtg aacttcaaga  23280
tccgccacaa catcgaggac ggcagcgtgc agctcgccga ccactaccag cagaacaccc  23340
ccatcggcga cggccccgtg ctgctgcccg acaaccacta cctgagcacc cagtccgccc  23400
tgagcaaaga ccccaacgag aagcgcgatc acatggtcct gctggagttc gtgaccgccg  23460
ccgggatcac tcacggcatg gacgagctgt acaagtaaga gctcggtcac ctgtccaaca  23520
gtctcagggt taatgtctat gtatcttaaa taatgttgtc ggcgatcgtt caaacatttg  23580
gcaataaagt ttcttaagat tgaatcctgt tgccggtctt gcgatgatta tcatataatt  23640
```

```
tctgttgaat tacgttaagc atgtaataat taacatgtaa tgcatgacgt tatttatgag  23700
atgggttttt atgattagag tcccgcaatt atacatttaa tacgcgatag aaaacaaaat  23760
atagcgcgca aactaggata aattatcgcg cgcggtgtca tctatgttac tagatcggga  23820
attaaactat cagtgtttga caggatatat tggcgggtaa acctaagaga aaagagcgtt  23880
tattagaata atcggatatt taaaagggcg tgaaaaggtt tatccgttcg tccatttgta  23940
tgtgcatgcc aaccacaggg ttcccctcgg gatcaaagta ctttgatcca acccctccgc  24000
tgctatagtg cagtcggctt ctgacgttca gtgcagccgt cttctgaaaa cgacatgtcg  24060
cacaagtcct aagttacgcg acaggctgcc gccctgccct tttcctggcg ttttcttgtc  24120
gcgtgtttta gtcgcataaa gtagaatact tgcgactaga accggagaca ttacgccatg  24180
aacaagagcg ccgccgctgg cctgctgggc tatgcccgcg tcagcaccga cgaccaggac  24240
ttgaccaacc aacgggccga actgcacgcg gccggctgca ccaagctgtt ttccgagaag  24300
atcaccggca ccaggcgcga ccgcccggag ctggccagga tgcttgacca cctacgccct  24360
ggcgacgttg tgacagtgac caggctagac cgcctggccc gcagcacccg cgacctactg  24420
gacattgccg agcgcatcca ggaggccggc gcgggcctgc gtagcctggc agagccgtgg  24480
gccgacacca ccacgccggc cggccgcatg gtgttgaccg tgttcgccgg cattgccgag  24540
ttcgagcgtt ccctaatcat cgaccgcacc cggagcgggc gcgaggccgc caaggcccga  24600
ggcgtgaagt ttggcccccg ccctaccctc accccggcac agatcgcgca cgcccgcgag  24660
ctgatcgacc aggaaggccg caccgtgaaa gaggcggctg cactgcttgg cgtgcatcgc  24720
tcgaccctgt accgcgcact tgagcgcagc gaggaagtga cgcccaccga ggccaggcgg  24780
cgcggtgcct tccgtgagga cgcattgacc gaggccgacg ccctggcggc cgccgagaat  24840
gaacgccaag aggaacaagc atgaaaccgc accaggacgg ccaggacgaa ccgtttttca  24900
ttaccgaaga gatcgaggcg gagatgatcg cggccgggta cgtgttcgag ccgcccgcgc  24960
acgtctcaac cgtgcggctg catgaaatcc tggccggttt gtctgatgcc aagctggcgg  25020
cctggccggc cagcttggcc gctgaagaaa ccgagcgccg ccgtctaaaa aggtgatgtg  25080
tatttgagta aaacagcttg cgtcatgcgg tcgctgcgta tatgatgcga tgagtaaata  25140
aacaaatacg caaggggaac gcatgaaggt tatcgctgta cttaaccaga aaggcgggtc  25200
aggcaagacg accatcgcaa cccatctagc ccgcgccctg caactcgccg gggccgatgt  25260
tctgttagtc gattccgatc cccagggcag tgcccgcgat tgggcggccg tgcgggaaga  25320
tcaaccgcta accgttgtcg gcatcgaccg cccgacgatt gaccgcgacg tgaaggccat  25380
cggccggcgc gacttcgtag tgatcgacgg agcgccccag gcggcggact tggctgtgtc  25440
cgcgatcaag gcagccgact tcgtgctgat tccggtgcag ccaagccctt acgacatatg  25500
ggccaccgcc gacctggtgg agctggttaa gcagcgcatt gaggtcacgg atggaaggct  25560
acaagcggcc tttgtcgtgt cgcgggcgat caaaggcacg cgcatcggcg gtgaggttgc  25620
cgaggcgctg gccgggtacg agctgcccat tcttgagtcc cgtatcacgc agcgcgtgag  25680
ctacccaggc actgccgccg ccggcacaac cgttcttgaa tcagaacccg agggcgacgc  25740
tgcccgcgag gtccaggcgc tggccgctga aattaaatca aaactcattt gagttaatga  25800
ggtaaagaga aaatgagcaa aagcacaaac acgctaagtg ccggccgtcc gagcgcacgc  25860
agcagcaagg ctgcaacgtt ggccagcctg gcagacacgc cagccatgaa gcgggtcaac  25920
tttcagttgc cggcggagga tcacaccaag ctgaagatgt acgcggtacg ccaaggcaag  25980
accattaccg agctgctatc tgaatacatc gcgcagctac cagagtaaat gagcaaatga  26040
```

```
ataaatgagt agatgaattt tagcggctaa aggaggcggc atggaaaatc aagaacaacc  26100
aggcaccgac gccgtggaat gccccatgtg tggaggaacg ggcggttggc caggcgtaag  26160
cggctgggtt gcctgccggc cctgcaatgg cactggaacc cccaagcccg aggaatcggc  26220
gtgagcggtc gcaaaccatc cggcccggta caaatcggcg cggcgctggg tgatgacctg  26280
gtggagaagt tgaaggccgc gcaggccgcc cagcggcaac gcatcgaggc agaagcacgc  26340
cccggtgaat cgtggcaagc ggccgctgat cgaatccgca aagaatcccg gcaaccgccg  26400
gcagccggtg cgccgtcgat taggaagccg cccaagggcg acgagcaacc agattttttc  26460
gttccgatgc tctatgacgt gggcacccgc gatagtcgca gcatcatgga cgtggccgtt  26520
ttccgtctgt cgaagcgtga ccgacgagct ggcgaggtga tccgctacga gcttccagac  26580
gggcacgtag aggtttccgc agggccggcc ggcatggcca gtgtgtggga ttacgacctg  26640
gtactgatgg cggtttccca tctaaccgaa tccatgaacc gataccggga agggaaggga  26700
gacaagcccg gccgcgtgtt ccgtccacac gttgcggacg tactcaagtt ctgccggcga  26760
gccgatggcg gaaagcagaa agacgacctg gtagaaacct gcattcggtt aaacaccacg  26820
cacgttgcca tgcagcgtac gaagaaggcc aagaacggcc gcctggtgac ggtatccgag  26880
ggtgaagcct tgattagccg ctacaagatc gtaaagagcg aaaccgggcg gccggagtac  26940
atcgagatcg agctagctga ttggatgtac cgcgagatca cagaaggcaa gaacccggac  27000
gtgctgacgg ttcaccccga ttactttttg atcgatcccg gcatcggccg ttttctctac  27060
cgcctggcac gccgcgccgc aggcaaggca gaagccagat ggttgttcaa gacgatctac  27120
gaacgcagtg gcagcgccgg agagttcaag aagttctgtt tcaccgtgcg caagctgatc  27180
gggtcaaatg acctgccgga gtacgatttg aaggaggagg cggggcaggc tggcccgatc  27240
ctagtcatgc gctaccgcaa cctgatcgag ggcgaagcat ccgccggttc ctaatgtacg  27300
gagcagatgc tagggcaaat tgccctagca ggggaaaaag gtcgaaaagg tctctttcct  27360
gtggatagca cgtacattgg gaacccaaag ccgtacattg ggaaccggaa cccgtacatt  27420
gggaacccaa agccgtacat tgggaaccgg tcacacatgt aagtgactga tataaaagag  27480
aaaaaaggcg atttttccgc ctaaaactct ttaaaactta ttaaaactct taaaacccgc  27540
ctggcctgtg cataactgtc tggccagcgc acagccgaag agctgcaaaa agcgcctacc  27600
cttcggtcgc tgcgctccct acgccccgcc gcttcgcgtc ggcctatcgc ggccgctggc  27660
cgctcaaaaa tggctggcct acggccaggc aatctaccag ggcgcggaca agccgcgccg  27720
tcgccactcg accgccggcg cccacatcaa ggcaccctgc ctcgcgcgtt tcggtgatga  27780
cggtgaaaac ctctgacaca tgcagctccc ggagacggtc acagcttgtc tgtaagcgga  27840
tgccgggagc agacaagccc gtcagggcgc gtcagcgggt gttggcgggt gtcggggcgc  27900
agccatgacc cagtcacgta gcgatagcgg agtgtatact ggcttaacta tgcggcatca  27960
gagcagattg tactgagagt gcaccatatg cggtgtgaaa taccgcacag atgcgtaagg  28020
agaaaatacc gcatcaggcg ctcttccgct tcctcgctca ctgactcgct gcgctcggtc  28080
gttcggctgc ggcgagcggt atcagctcac tcaaaggcgg taatacggtt atccacagaa  28140
tcaggggata acgcaggaaa gaacatgtga gcaaaaggcc agcaaaaggc caggaaccgt  28200
aaaaaggccg cgttgctggc gtttttccat aggctccgcc cccctgacga gcatcacaaa  28260
aatcgacgct caagtcagag gtggcgaaac ccgacaggac tataaagata ccaggcgttt  28320
ccccctggaa gctccctcgt gcgctctcct gttccgaccc tgccgcttac cggatacctg  28380
```

```
tccgcctttc tcccttcggg aagcgtggcg ctttctcata gctcacgctg taggtatctc  28440
agttcggtgt aggtcgttcg ctccaagctg ggctgtgtgc acgaaccccc cgttcagccc  28500
gaccgctgcg ccttatccgg taactatcgt cttgagtcca acccggtaag acacgactta  28560
tcgccactgg cagcagccac tggtaacagg attagcagag cgaggtatgt aggcggtgct  28620
acagagttct tgaagtggtg gcctaactac ggctacacta gaaggacagt atttggtatc  28680
tgcgctctgc tgaagccagt taccttcgga aaaagagttg gtagctcttg atccggcaaa  28740
caaaccaccg ctggtagcgg tggttttttt gtttgcaagc agcagattac gcgcagaaaa  28800
aaaggatctc aagaagatcc tttgatcttt tctacggggt ctgacgctca gtggaacgaa  28860
aactcacgtt aagggatttt ggtcatgcat tctaggtact aaaacaattc atccagtaaa  28920
atataatatt ttattttctc ccaatcaggc ttgatcccca gtaagtcaaa aaatagctcg  28980
acatactgtt cttccccgat atcctccctg atcgaccgga cgcagaaggc aatgtcatac  29040
cacttgtccg ccctgccgct tctcccaaga tcaataaagc cacttacttt gccatctttc  29100
acaaagatgt tgctgtctcc caggtcgccg tgggaaaaga caagttcctc ttcgggcttt  29160
tccgtcttta aaaaatcata cagctcgcgc ggatctttaa atggagtgtc ttcttcccag  29220
ttttcgcaat ccacatcggc cagatcgtta ttcagtaagt aatccaattc ggctaagcgg  29280
ctgtctaagc tattcgtata gggacaatcc gatatgtcga tggagtgaaa gagcctgatg  29340
cactccgcat acagctcgat aatcttttca gggctttgtt catcttcata ctcttccgag  29400
caaaggacgc catcggcctc actcatgagc agattgctcc agccatcatg ccgttcaaag  29460
tgcaggacct ttggaacagg cagctttcct tccagccata gcatcatgtc cttttcccgt  29520
tccacatcat aggtggtccc tttataccgg ctgtccgtca tttttaaata taggttttca  29580
ttttctccca ccagcttata taccttagca ggagacattc cttccgtatc ttttacgcag  29640
cggtattttt cgatcagttt tttcaattcc ggtgatattc tcattttagc catttattat  29700
ttccttcctc ttttctacag tatttaaaga taccccaaga agctaattat aacaagacga  29760
actccaattc actgttcctt gcattctaaa accttaaata ccagaaaaca gctttttcaa  29820
agttgttttc aaagttggcg tataacatag tatcgacgga gccgattttg aaaccgcggt  29880
gatcacaggc agcaacgctc tgtcatcgtt acaatcaaca tgctaccctc cgcgagatca  29940
tccgtgtttc aaacccggca gcttagttgc cgttcttccg aatagcatcg gtaacatgag  30000
caaagtctgc cgccttacaa cggctctccc gctgacgccg tcccggactg atgggctgcc  30060
tgtatcgagt ggtgattttg tgccgagctg ccggtcgggg agctgttggc tggctggtgg  30120
caggatatat tgtggtgtaa acaaattgac gcttagacaa cttaataaca cattgcggac  30180
gtttttaatg tactgaatta acgccgaatt aatt                              30214
```

<210> SEQ ID NO 5
<211> LENGTH: 28132
<212> TYPE: DNA
<213> ORGANISM: Artificial Sequence
<220> FEATURE:
<223> OTHER INFORMATION: Synthetic construct plasmid pMBXS1024

<400> SEQUENCE: 5

```
gtagtgttta tctttgttgc ttttctgaac aatttattta ctatgtaaat atattatcaa     60
tgtttaatct attttaattt gcacatgaat tttcatttta tttttacttt acaaaacaaa    120
taaatatata tgcaaaaaaa tttacaaacg atgcacgggt tacaaactaa tttcattaaa    180
tgctaatgca gattttgtga agtaaaactc caattatgat gaaaaatacc accaacacca    240
```

```
cctgcgaaac tgtatcccaa ctgtccttaa taaaaatgtt aaaaagtata ttattctcat    300
ttgtctgtca taatttatgt accccacttt aatttttctg atgtactaaa ccgagggcaa    360
actgaaacct gttcctcatg caaagcccct actcaccatg tatcatgtac gtgtcatcac    420
ccaacaactc cacttttgct atataacaac acccccgtca cactctccct ctctaacaca    480
caccccacta acaattcctt cacttgcagc actgttgcat catcatcttc attgcaaaac    540
cctaaacttc accttcaacc gcggccgcag atctaaaatg gcttctatga tatcctcttc    600
cgctgtgaca acagtcagcc gtgcctctag ggggcaatcc gccgcagtgg ctccattcgg    660
cggcctcaaa tccatgactg gattcccagt gaagaaggtc aacactgaca ttacttccat    720
tacaagcaat ggtggaagag taaagtgcat gcaggtgtgg cctccaattg gaaagaagaa    780
gtttgagact ctttcctatt tgccaccatt gacgagagat tctagagtgc tcagccagca    840
atccatccag aaggttctcg tggctaaccg tggtgagatt gctattcgta tctttagagc    900
gtgtaccgag ttgaacatcc gaactgtcgc tgtttatagt aaagaagatt ctggatcata    960
ccacagatac aaagctgacg aggcctactt ggttggtgaa ggtaagaagc ctattgacgc   1020
ttatcttgat atagagggca tcattgatat tgccaagaga aacaaagttg atgcaattca   1080
tccgggatac ggtttttctat cagaaaacat tcactttgca cgacgatgtg aagaagaggg   1140
aatcgtgttc atcggaccta aagcgaaca cttggatatg tttggggaca aggttaaggc   1200
aagggaacaa gcagagaagg caggaattcc agtgatacct ggatcggatg ggcctgctga   1260
aactcttgaa gctgtcgaac aattcggcca ggctaacgga tacccaatca tcattaaggc   1320
ttctttaggt ggtgggggaa gggggatgag aatcgtgcga tccgaatctg aggtaaaaga   1380
ggcttatgaa cgtgctaaat cggaagctaa agcggccttt gggaacgatg aagtctatgt   1440
cgagaaacta atcgagaatc ccaagcacat cgaggttcaa gtgattggtg ataagcaagg   1500
taacgttgtt cacctttcg agagagattg ttctgttcaa cgtagacacc aaaaagtgat   1560
agaagtagct ccatcggtat cgttgagccc agaactaagg gaccagatat gcgaggctgc   1620
tgtcgcgctt gcaaagaatg tcaactatat caatgcaggc actgtcgaat tcttggtagc   1680
caataatgag ttttacttca ttgaggtcaa ccctagagtt caagttgagc ataccattac   1740
cgaaatgatc actggggtgg atatcgtaca gactcagatc ctcgttgctc aaggccattc   1800
ccttcattcc aagaaggtga atattccaga gcaaaaggat atctttacaa ttggttatgc   1860
gattcaatca cgagttacca cagaagatcc acaaaatgac ttcatgccag atacgggaaa   1920
gataatggca taccgttctg gtggcggatt tggtgttcga ttagacacag gtaatagttt   1980
tcagggagct gtgataacgc catactatga ttctttattg gttaagttga gtacttgggc   2040
tctcactttc gagcaagccg cagcgaaaat ggtcagaaac cttcaggagt tcagaattag   2100
aggtattaag acgaacattc cattcttaga gaacgttgct aaacatgaga agtttctgac   2160
aggacaatat gatacaagtt tcatagacac tacacctgaa ctctttaact tccctaaaca   2220
aaaagacaga ggtacgaaaa tgttgacata tatcggaaac gtgacagtta atgggttccc   2280
aggtatcggt aagaaagaaa agccggcctt tgataaaccc cttggtgtta aagtggatgt   2340
ggatcaacaa cctgctaggg gcactaagca aatccttgat gaaaagggtg cagagggact   2400
ggcaaattgg gttaaagagc agaaatcagt tcttctgaca gataccacat ttcgtgatgc   2460
tcatcaatca ttactagcaa caagaattag atcacacgat ctgaaaaaga tcgctaatcc   2520
aaccgctgct ctttggccgg aactcttctc tatggaaatg tggggtgggg ccacattcga   2580
```

```
tgtcgcgtac cgttttctaa aagaagatcc ttggaagcgt ctggaagatt tgagaaaaga   2640

ggtgcccaat accctgttcc agatgctttt gcgttctagc aatgccgtcg gatataccaa   2700

ttatcctgac aatgtgatca aagaattcgt aaaacagtcc gctcaatctg gtatcgacgt   2760

ttttaggatt ttcgattcac ttaattgggt aaaaggtatg acgttagcga ttgatgctgt   2820

acgtgatact ggaaaggttg cagaggccgc catttgctac actggagaca ttttggataa   2880

gaatagaact aaatacgact tggcttatta cacttccatg gcaaaagaac ttgaggctgc   2940

cggtgcacat attctgggga taaaggatat ggccggtttg ctcaaaccgc aggcagcata   3000

tgagttggtt tcagccctta aagaaactat tgacataccc gttcatctgc acacgcatga   3060

cacgtcgggc aatggaatct atatgtatgc aaaggctgtc gaggctggcg tggatatcat   3120

tgatgtcgct gtaagctcta tggctggact tacatcccag ccatcagcct ctggattcta   3180

tcatgctatg gaaggtaacg atcgtagacc cgaaatgaat gtccaagggg tcgaattact   3240

gtcacagtac tgggagagtg tgcgtaagta ttactcagag tttgagagcg gtatgaagag   3300

tccccatacc gagatttatg agcacgagat gcctggtgga caatactcta acttgcaaca   3360

gcaagcgaag gggggttggtt tgggagatag gtggaacgaa gtgaaagaaa tgtatagacg   3420

tgtcaacgac atgtttggtg atattgtgaa agtaactcct agttctaagg tagttggaga   3480

catggcactg tacatggttc agaataacct tactgaaaag gatgtttacg agaaggggga   3540

gtcacttgac ttccctgatt cagtggttga actgttcaag ggaaatatcg gtcaaccgca   3600

tgggggattt ccagaaaaac tacagaaact gatactaaag ggacaggagc caattactgt   3660

tcgaccagga gagctcttgg agccggtttc ttttgaggct atcaagcaag aattcaaaga   3720

acaacataac cttgaaattt ctgatcagga cgcggttgct tacgcacttt atccaaaggt   3780

ctttactgat tacgtgaaaa ccacagagtc ttatggtgat ataagtgtgc tagatacacc   3840

aacatttttc tatggcatga ctcttggaga agagattgaa gtggaaatag aaaggggaaa   3900

aacactcatt gttaaactga tatctatcgg agagcctcaa cctgatgcta caagggtagt   3960

gtactttgaa ttgaatggac aacctagaga agtagtgatt aaagatgagt caataaagtc   4020

aagcgtgcag gagaggctaa aggcagatag aaccaatccg tcgcacattg cagcttctat   4080

gcctggcacc gtcataaaag tcctcgctga agctggtact aaagtcaaca aaggtgacca   4140

tcttatgatc aacgaagcaa tgaagatgga aactacggtt caggcacctt tcagtggaac   4200

aatcaagcag gttcatgtta agaatggcga gcctatccag actggtgact tgcttttgga   4260

gattgaaaag gcctgagtcg acgcgatcgc gcggccgctg agtaattctg atattagagg   4320

gagcattaat gtgttgttgt gatgtggttt atatggggaa attaaataaa tgatgtatgt   4380

acctcttgcc tatgtaggtt tgtgtgtttt gttttgttgt ctagctttgg ttattaagta   4440

gtagggacgt tcgttcgtgt ctcaaaaaaa ggggtactac cactctgtag tgtatatgga   4500

tgctggaaat caatgtgttt tgtatttgtt cacctccatt gttgaattca atgtcaaatg   4560

tgttttgcgt tggttatgtg taaaattact atctttctcg tccgatgatc aaagttttaa   4620

gcaacaaaac caagggtgaa atttaaactg tgctttgttg aagattcttt tatcatattg   4680

aaaatcaaat tactagcagc agattttacc tagcatgaaa ttttatcaac agtacagcac   4740

tcactaacca agttccaaac taagatgcgc cattaacatc agccaatagg cattttcagc   4800

aagtttaaac tacgtagtgt ttatctttgt tgcttttctg aacaatttat ttactatgta   4860

aatatattat caatgtttaa tctattttaa tttgcacatg aattttcatt ttatttttac   4920

tttacaaaac aaataaatat atatgcaaaa aaatttacaa acgatgcacg ggttacaaac   4980
```

```
taatttcatt aaatgctaat gcagattttg tgaagtaaaa ctccaattat gatgaaaaat   5040
accaccaaca ccacctgcga aactgtatcc caactgtcct taataaaaat gttaaaaagt   5100
atattattct catttgtctg tcataattta tgtaccccac tttaattttt ctgatgtact   5160
aaaccgaggg caaactgaaa cctgttcctc atgcaaagcc cctactcacc atgtatcatg   5220
tacgtgtcat cacccaacaa ctccactttt gctatataac aacacccccg tcacactctc   5280
cctctctaac acacacccca ctaacaattc cttcacttgc agcactgttg catcatcatc   5340
ttcattgcaa aaccctaaac ttcaccttca accgcggccg ctcgcgaaaa atggcttcta   5400
tgatatcctc ttccgctgtg acaacagtca gccgtgcctc tagggggcaa tccgccgcag   5460
tggctccatt cggcggcctc aaatccatga ctggattccc agtgaagaag gtcaacactg   5520
acattacttc cattacaagc aatggtggaa gagtaaagtg catgcaggtg tggcctccaa   5580
ttggaaagaa gaagtttgag actctttcct atttgccacc attgacgaga gattctagag   5640
tgaacataca cgagtaccaa gcaaaagagt tgctcaagac ctatggagtg ccggtcccag   5700
acggagcggt agcttatagt gatgctcaag cggcttccgt cgctgaagag attggtggct   5760
ctagatgggt tgtaaaggcg cagatacacg ctggtggaag gggaaaggca ggtggtgtga   5820
aggtggccca tagcattgaa gaggttcgtc agtacgctga tgcgatgctt gggtcccatc   5880
tcgttacaca tcaaacaggg cctggtggtt cattagttca acgtttgtgg gtggagcaag   5940
catcacatat caagaaagag tattatctgg gatttgttat tgatagaggt aaccaaagaa   6000
ttaccttaat tgcttcttct gaagggggaa tggagataga agaggttgct aaagagacac   6060
cagaaaagat cgtcaaagag gttgtagacc ctgcaatcgg attgcttgat tttcagtgta   6120
gaaaggttgc aactgcaata ggacttaagg gaaagcttat gccccaggca gttagactta   6180
tgaaggctat ctataggtgt atgcgagata aggatgctct ccaggcagag atcaatcctt   6240
tggcaatagt aggtgaaagt gacgagtcgc tcatggttct tgatgctaaa ttcaattttg   6300
atgacaatgc tctttacaga caacgaacaa ttactgaaat gagggatctc gcagaagaag   6360
atcctaaaga agtcgaagct tctggacacg gattgaatta catcgccctc gatgggaaca   6420
tcggttgtat tgtgaatgga gctggtcttg ctatggccag cctggatgcc atcactctac   6480
atggcggtcg tccagctaac ttcttagatg tcggcggtgg ggcttctcct gaaaaggtta   6540
cgaatgcgtg cagaattgtt ttggaagatc cgaacgtccg ttgtatactg gtgaacattt   6600
ttgccggaat taacaggtgc gattggattg caaaaggact tattcaagcc tgcgactcac   6660
tacagattaa agttccactg atcgttcgat tggcaggcac taatgtagat gaaggcagga   6720
aaatcctagc ggagtcgggt ttaagtttca taacggcaga gaatttggac gacgcggctg   6780
ctaaagccgt ggctatcgtg aaagggtgaa cgcgttgagt aattctgata ttagagggag   6840
cattaatgtg ttgttgtgat gtggtttata tggggaaatt aaataaatga tgtatgtacc   6900
tcttgcctat gtaggtttgt gtgttttgtt ttgttgtcta gctttggtta ttaagtagta   6960
gggacgttcg ttcgtgtctc aaaaaaaggg gtactaccac tctgtagtgt atatggatgc   7020
tggaaatcaa tgtgttttgt atttgttcac ctccattgtt gaattcaatg tcaaatgtgt   7080
tttgcgttgg ttatgtgtaa aattactatc tttctcgtcc gatgatcaaa gttttaagca   7140
acaaaaccaa gggtgaaatt taaactgtgc tttgttgaag attcttttat catattgaaa   7200
atcaaattac tagcagcaga ttttacctag catgaaattt tatcaacagt acagcactca   7260
ctaaccaagt tccaaactaa gatgcgccat taacatcagc caataggcat tttcagcaat   7320
```

-continued

```
gtacatacgt agtgtttatc tttgttgctt ttctgaacaa tttatttact atgtaaatat   7380
attatcaatg tttaatctat tttaatttgc acatgaattt tcattttatt tttactttac   7440
aaaacaaata aatatatatg caaaaaaatt tacaaacgat gcacgggtta caaactaatt   7500
tcattaaatg ctaatgcaga ttttgtgaag taaaactcca attatgatga aaaataccac   7560
caacaccacc tgcgaaactg tatcccaact gtccttaata aaaatgttaa aaagtatatt   7620
attctcattt gtctgtcata atttatgtac cccactttaa tttttctgat gtactaaacc   7680
gagggcaaac tgaaacctgt tcctcatgca aagcccctac tcaccatgta tcatgtacgt   7740
gtcatcaccc aacaactcca cttttgctat ataacaacac ccccgtcaca ctctccctct   7800
ctaacacaca ccccactaac aattccttca cttgcagcac tgttgcatca tcatcttcat   7860
tgcaaaaccc taaacttcac cttcaaccgc ggccgcgacg tcaaaatggc ttctatgata   7920
tcctcttccg ctgtgacaac agtcagccgt gcctctaggg ggcaatccgc cgcagtggct   7980
ccattcggcg gcctcaaatc catgactgga ttcccagtga agaaggtcaa cactgacatt   8040
acttccatta caagcaatgg tggaagagta aagtgcatgc aggtgtggcc tccaattgga   8100
aagaagaagt ttgagactct ttcctatttg ccaccattga cgagagattc tagagtctcg   8160
gttttcgtga ataaacattc caaggtcatc tttcaaggct ttaccgggga gcatgctaca   8220
tttcacgcaa aagatgcaat gcgaatgggc acaagggttg tcggtggcgt tactcctgga   8280
aagggtggga ctagacatcc agatcctgag ctcgctcatc ttccggtatt cgataccgtt   8340
gccgaagccg ttgctgctac aggagctgat gtatcagctg tgtttgtccc acccccttc    8400
aatgcagacg cacttatgga agcaattgat gccggtatta gagtggctgt cactatagcg   8460
gatggaattc ctgtgcatga catgatcaga ttgcaaaggt atagagtagg aaaggactct   8520
attgttatcg ggcctaacac accaggaatc ataacgcctg gtgagtgtaa agtgggtatc   8580
atgccgagtc acatatacaa gaagggaaac gtgggtatag tgagtcgatc aggaacattg   8640
aattacgagg cgacggaaca aatggctgcg ctaggcttag ggattactac ttctgttgga   8700
attggtggtg atcctataaa cggcactgac tttgtgactg ttctccgtgc attcgaggct   8760
gatccagaaa cggaaattgt agttatgatc ggagaaatag gtggaccgca ggaagttgcc   8820
gcagctagat gggcaaaaga gaatatgacc aaaccagtta ttgggttcgt agctggttta   8880
gcagcccccca cagggcgtag gatgggacac gcaggtgcta ttatcagctc tgaggctgat   8940
accgctggag ctaagatgga tgccatggaa gctcttggtc tgtatgtcgc taggaaccca   9000
gcgcaaatcg gacagacagt tttgcgtgcg gcacaggagc atggaattag attttgaggg   9060
cccgttaact gagtaattct gatattagag ggagcattaa tgtgttgttg tgatgtggtt   9120
tatatgggga aattaaataa atgatgtatg tacctcttgc ctatgtaggt ttgtgtgttt   9180
tgttttgttg tctagctttg gttattaagt agtagggacg ttcgttcgtg tctcaaaaaa   9240
aggggtacta ccactctgta gtgtatatgg atgctggaaa tcaatgtgtt ttgtatttgt   9300
tcacctccat tgttgaattc aatgtcaaat gtgttttgcg ttggttatgt gtaaaattac   9360
tatctttctc gtccgatgat caaagtttta agcaacaaaa ccaagggtga aatttaaact   9420
gtgctttgtt gaagattctt ttatcatatt gaaaatcaaa ttactagcag cagattttac   9480
ctagcatgaa attttatcaa cagtacagca ctcactaacc aagttccaaa ctaagatgcg   9540
ccattaacat cagccaatag gcattttcag caagtttaaa ccggaccgta cgtagtgttt   9600
atctttgttg cttttctgaa caatttattt actatgtaaa tatattatca atgtttaatc   9660
tattttaatt tgcacatgaa ttttcatttt atttttactt tacaaaacaa ataaatatat   9720
```

```
atgcaaaaaa atttacaaac gatgcacggg ttacaaacta atttcattaa atgctaatgc   9780
agattttgtg aagtaaaact ccaattatga tgaaaaatac caccaacacc acctgcgaaa   9840
ctgtatccca actgtcctta ataaaaatgt taaaaagtat attattctca tttgtctgtc   9900
ataatttatg taccccactt taatttttct gatgtactaa accgagggca aactgaaacc   9960
tgttcctcat gcaaagcccc tactcaccat gtatcatgta cgtgtcatca cccaacaact  10020
ccacttttgc tatataacaa cacccccgtc acactctccc tctctaacac acaccccact  10080
aacaattcct tcacttgcag cactgttgca tcatcatctt cattgcaaaa ccctaaactt  10140
caccttcaac cgcggccgcc acgtgaaaat ggcttctatg atatcctctt ccgctgtgac  10200
aacagtcagc cgtgcctcta gggggcaatc cgccgcagtg gctccattcg gcggcctcaa  10260
atccatgact ggattcccag tgaagaaggt caacactgac attacttcca ttacaagcaa  10320
tggtggaaga gtaaagtgca tgcaggtgtg gcctccaatt ggaaagaaga agtttgagac  10380
tctttcctat ttgccaccat tgacgagaga ttctagagtg agcttccgtt tgcaaccagc  10440
tccgccagca aggcccaata gatgtcaact ttttgggcct ggatctcgac cggctttgtt  10500
tgagaaaatg gccgcttcag ccgcggacgt tatcaatctg gatttagagg atagtgttgc  10560
cccagatgat aaagctcagg ctagagcaaa tatcattgag gctataaacg gtctagactg  10620
gggtagaaag tatctcagtg ttagaattaa cggacttgat acgcctttct ggtatcgaga  10680
tgtcgttgac ttgcttgagc aggcaggaga tagacttgat caaatcatga tccctaaggt  10740
tggctgtgct gcggatgttt acgccgtcga tgctttggta acagcaattg aacgtgctaa  10800
agggcgtact aagcctctat catttgaagt gataatagag tctgcagctg gtatcgcaca  10860
tgttgaagaa atagccgctt cgtcaccaag actccaagcc atgtctttgg gtgcagccga  10920
ttttgcagct tctatgggaa tgcagactac agggattggt ggaacgcaag agaactacta  10980
tatgctccac gacggacaaa agcactggtc cgatccttgg cattgggctc aggctgcaat  11040
cgtcgcagcg tgcagaacac atgggatttt acccgttgac ggcccgttcg gtgacttctc  11100
tgatgacgaa ggattcaggg cacaagctcg aaggtccgct actcttggaa tggtgggaaa  11160
atgggccata catccaaagc aagtggctct cgctaatgaa gtgtttacac ctagcgagac  11220
tgcagtaacc gaagcgaggg agattttagc ggctatggat gctgctaagg cgagaggcga  11280
aggtgctacc gtgtacaaag gtaggctggt agatatcgcg tcgattaaac aggcagaagt  11340
cattgttcgt caggctgaga tgattagtgc atgaactagt tgagtaattc tgatattaga  11400
gggagcatta atgtgttgtt gtgatgtggt ttatatgggg aaattaaata aatgatgtat  11460
gtacctcttg cctatgtagg tttgtgtgtt ttgttttgtt gtctagcttt ggttattaag  11520
tagtagggac gttcgttcgt gtctcaaaaa aaggggtact accactctgt agtgtatatg  11580
gatgctggaa atcaatgtgt tttgtatttg ttcacctcca ttgttgaatt caatgtcaaa  11640
tgtgttttgc gttggttatg tgtaaaatta ctatctttct cgtccgatga tcaaagtttt  11700
aagcaacaaa accaagggtg aaatttaaac tgtgctttgt tgaagattct tttatcatat  11760
tgaaaatcaa attactagca gcagatttta cctagcatga aattttatca acagtacagc  11820
actcactaac caagttccaa actaagatgc gccattaaca tcagccaata ggcattttca  11880
gcaagtttaa actccggata cgtagtgttt atctttgttg cttttctgaa caatttattt  11940
actatgtaaa tatattatca atgtttaatc tattttaatt tgcacatgaa ttttcatttt  12000
atttttactt tacaaaacaa ataaatatat atgcaaaaaa atttacaaac gatgcacggg  12060
```

```
ttacaaacta atttcattaa atgctaatgc agattttgtg aagtaaaact ccaattatga  12120
tgaaaaatac caccaacacc acctgcgaaa ctgtatccca actgtcctta ataaaaatgt  12180
taaaaagtat attattctca tttgtctgtc ataatttatg taccccactt taatttttct  12240
gatgtactaa accgagggca aactgaaacc tgttcctcat gcaaagcccc tactcaccat  12300
gtatcatgta cgtgtcatca cccaacaact ccacttttgc tatataacaa cacccccgtc  12360
acactctccc tctctaacac acaccccact aacaattcct tcacttgcag cactgttgca  12420
tcatcatctt cattgcaaaa ccctaaactt caccttcaac cgcggccgcc ctaggaaaat  12480
ggcttctatg atatcctctt ccgctgtgac aacagtcagc cgtgcctcta gggggcaatc  12540
cgccgcagtg gctccattcg gcggcctcaa atccatgact ggattcccag tgaagaaggt  12600
caacactgac attacttcca ttacaagcaa tggtggaaga gtaaagtgca tgcaggtgtg  12660
gcctccaatt ggaaagaaga agtttgagac tctttcctat ttgccaccat tgacgagaga  12720
ttctagagtt gcacagtacc aagacgatat caaggcggtt gcagggctta aggagaatca  12780
cggctccgca tggaatgcca tcaacccgga gtatgccgcc aggatgaggg cgcagaacaa  12840
gttcaagacg ggccttgaca ttgcaaagta tacggctaag attatgcggg ccgatatggc  12900
agcctacgac gccgacagct cgaagtacac acagagcctc ggttgttggc atggtttcat  12960
tggtcagcag aagatgatct caatcaagaa acatttcaac agcacggaac gccgttacct  13020
ctacctttct ggctggatgg tagccgcgct tagatccgag tttggccccc taccggatca  13080
gtccatgcac gaaaagacga gtgtctccgc actcattcgg gaactctaca cttttctgcg  13140
ccaagcggac gctagggagt tggggggcct gtttcgggag cttgacgcgg cccaaggccc  13200
agctaaggcg gccattcaag cgaagatcga caaccacgtc actcatgtgg tcccaatcat  13260
agctgatatc gacgctggct tcggcaatgc ggaagcaaca tacctgttgg ccaagcagtt  13320
catcgaggcc ggggcttgct gcatacagat agagaaccag gtttctgacg aaaagcaatg  13380
tggacatcaa gacggaaagg ttaccgtgcc ccacgaggat tttcttgcaa aaatccgagc  13440
gattcgttat gcgtttttag agttgggcgt ggatgacggt atcatcgtgg ccaggaccga  13500
tagtctcggt gctggtctga caaagcaaat cgcagtgacc aatacgcctg gagacttagg  13560
ggatcagtac aacagcttcc tcgattgcga ggagcttagc gcagatcagc tcggaaatgg  13620
cgacgttatc atcaagcgtg atggaaagct actccgcccc aagcgcctcc cgtctaactt  13680
gttccagttc cgggctggaa ctggcgaagc gcgatgcgtc ctggactgcg tgaccgcgct  13740
ccagaacggc gccgacctac tctggattga gacagaaaag cctcacatag ctcaaatcgg  13800
cggaatggta tcggagataa ggaaagtcat acccaacgcc aaactggtgt acaacaactc  13860
tccgtcgttc aattggaccc tgaactttag acagcaagca tacgatgcta tgaaagccgc  13920
tgggaaagac gtgtcagcat acgaccgcgc ccagcttatg tccgtggagt acgaccaaac  13980
ggaactggct aagctggctg atgagaaaat cagaacattc caggccgacg cctcaaggga  14040
ggccgggatc ttccatcact tgattacctt accaacatat cacactgcgg ccctgtcaac  14100
cgacaatttg gctaaggagt acttcggaga tcaggggatg ctcggttatg tcgcgggcgt  14160
tcagaggaag gagatccgac agggcatcgc atgtgtcaag caccaaaaca tgagcgggag  14220
tgacatcggg gatgatcata aagagtattt ctccggcgaa gccgcgctga aggccgccgg  14280
caaagacaac actatgaatc aattctgacc cgggtgagta attctgatat tagagggagc  14340
attaatgtgt tgttgtgatg tggtttatat ggggaaatta aataaatgat gtatgtacct  14400
cttgcctatg taggtttgtg tgttttgttt tgttgtctag ctttggttat taagtagtag  14460
```

```
ggacgttcgt tcgtgtctca aaaaaagggg tactaccact ctgtagtgta tatggatgct  14520
ggaaatcaat gtgttttgta tttgttcacc tccattgttg aattcaatgt caaatgtgtt  14580
ttgcgttggt tatgtgtaaa attactatct ttctcgtccg atgatcaaag ttttaagcaa  14640
caaaaccaag ggtgaaattt aaactgtgct ttgttgaaga ttcttttatc atattgaaaa  14700
tcaaattact agcagcagat tttacctagc atgaaatttt atcaacagta cagcactcac  14760
taaccaagtt ccaaactaag atgcgccatt aacatcagcc aataggcatt ttcagcaagc  14820
tcgagtcacg tagtggtacg tagtgtttat ctttgttgct tttctgaaca atttatttac  14880
tatgtaaata tattatcaat gtttaatcta ttttaatttg cacatgaatt ttcattttat  14940
ttttacttta caaaacaaat aaatatatat gcaaaaaaat ttacaaacga tgcacgggtt  15000
acaaactaat ttcattaaat gctaatgcag attttgtgaa gtaaaactcc aattatgatg  15060
aaaaatacca ccaacaccac ctgcgaaact gtatcccaac tgtccttaat aaaaatgtta  15120
aaaagtatat tattctcatt tgtctgtcat aatttatgta ccccacttta atttttctga  15180
tgtactaaac cgagggcaaa ctgaaacctg ttcctcatgc aaagccccta ctcaccatgt  15240
atcatgtacg tgtcatcacc caacaactcc acttttgcta tataacaaca cccccgtcac  15300
actctccctc tctaacacac accccactaa caattccttc acttgcagca ctgttgcatc  15360
atcatcttca ttgcaaaacc ctaaacttca ccttcaaccg cggccgcttc gaaggatcca  15420
aaatggtgag caagggcgag gagctgttca ccggggtggt gcccatcctg gtcgagctgg  15480
acggcgacgt aaacggccac aagttcagcg tgtccggcga gggcgagggc gatgccacct  15540
acggcaagct gaccctgaag ttcatctgca ccaccggcaa gctgcccgtg ccctggccca  15600
ccctcgtgac caccttcacc tacggcgtgc agtgcttcag ccgctacccc gaccacatga  15660
agcagcacga cttcttcaag tccgccatgc ccgaaggcta cgtccaggag cgcaccatct  15720
tcttcaagga cgacggcaac tacaagaccc gcgccgaggt gaagttcgag ggcgacaccc  15780
tggtgaaccg catcgagctg aagggcatcg acttcaagga ggacggcaac atcctggggc  15840
acaagctgga gtacaactac aacagccaca acgtctatat catggccgac aagcagaaga  15900
acggcatcaa ggtgaacttc aagatccgcc acaacatcga ggacggcagc gtgcagctcg  15960
ccgaccacta ccagcagaac acccccatcg gcgacggccc cgtgctgctg cccgacaacc  16020
actacctgag cacccagtcc gccctgagca aagaccccaa cgagaagcgc gatcacatgg  16080
tcctgctgga gttcgtgacc gccgccggga tcactcacgg catggacgag ctgtacaagt  16140
aaagcggccg cccgggctgc agttcgaaat ttaaatgcgg ccgctgagta attctgatat  16200
tagagggagc attaatgtgt tgttgtgatg tggtttatat ggggaaatta aataaatgat  16260
gtatgtacct cttgcctatg taggtttgtg tgttttgttt tgttgtctag ctttggttat  16320
taagtagtag ggacgttcgt tcgtgtctca aaaaaagggg tactaccact ctgtagtgta  16380
tatggatgct ggaaatcaat gtgttttgta tttgttcacc tccattgttg aattcaatgt  16440
caaatgtgtt ttgcgttggt tatgtgtaaa attactatct ttctcgtccg atgatcaaag  16500
ttttaagcaa caaaaccaag ggtgaaattt aaactgtgct ttgttgaaga ttcttttatc  16560
atattgaaaa tcaaattact agcagcagat tttacctagc atgaaatttt atcaacagta  16620
cagcactcac taaccaagtt ccaaactaag atgcgccatt aacatcagcc aataggcatt  16680
ttcagcaacc tcagcgttta aacgtacgta gtgtttatct ttgttgcttt tctgaacaat  16740
ttatttacta tgtaaatata ttatcaatgt ttaatctatt ttaatttgca catgaatttt  16800
```

```
cattttattt ttactttaca aaacaaataa atatatatgc aaaaaaattt acaaacgatg  16860
cacgggttac aaactaattt cattaaatgc taatgcagat tttgtgaagt aaaactccaa  16920
ttatgatgaa aaataccacc aacaccacct gcgaaactgt atcccaactg tccttaataa  16980
aaatgttaaa aagtatatta ttctcatttg tctgtcataa tttatgtacc ccactttaat  17040
ttttctgatg tactaaaccg agggcaaact gaaacctgtt cctcatgcaa agcccctact  17100
caccatgtat catgtacgtg tcatcaccca acaactccac ttttgctata taacaacacc  17160
cccgtcacac tctccctctc taacacacac cccactaaca attccttcac ttgcagcact  17220
gttgcatcat catcttcatt gcaaaaccct aaacttcacc ttcaaccgcg gccgcttcga  17280
aaaaatggct tctatgatat cctcttccgc tgtgacaaca gtcagccgtg cctctagggg  17340
gcaatccgcc gcagtggctc cattcggcgg cctcaaatcc atgactggat tcccagtgaa  17400
gaaggtcaac actgacatta cttccattac aagcaatggt ggaagagtaa agtgcatgca  17460
ggtgtggcct ccaattggaa agaagaagtt tgagactctt tcctatttgc caccattgac  17520
gagagattct agagtcaccg agcaagccac aacgacagat gaactcgctt ttactaggcc  17580
atatggtgaa caggaaaagc aaattcttac agcagaagct gttgagtttt tgaccgagtt  17640
ggttactcac tttacacctc aaagaaacaa gttactcgca gcacgtatcc agcagcaaca  17700
agacatagat aatggtacac ttccagattt catttcggag actgcatcta ttcgagatgc  17760
cgattggaaa atcaggggta tccccgcaga tttagaagat aggagagttg aaataaccgg  17820
acctgtagaa agaaaaatgg tcatcaacgc tctaaacgcc aacgtcaaag tgtttatggc  17880
tgattttgag gactcgctag cacctgattg gaacaaggtg atagatggcc agatcaattt  17940
gagagatgct gtcaatggga caatctccta tactaatgag gctggaaaga tttatcaact  18000
caaacctaat ccggcagtgc tgatttgtag ggttcgtgga ttacacctgc ctgaaaagca  18060
tgttacgtgg cgtggggaag caattcctgg cagccttttt gacttcgctc tttacttttt  18120
ccataactac caggcgctgt tggctaaggg gtcaggtcca tatttctatc ttccgaaaac  18180
tcaaagttgg caagaagctg cctggtggtc tgaggtgttc tcctatgcag aggatcgttt  18240
caatttacca cgaggtacga tcaaagcaac tctgttaatt gagacactcc cggctgtgtt  18300
tcaaatggac gagatactac acgctctcag ggaccacatt gttggtctta attgcggaag  18360
atgggactat atcttctcct acatcaagac tctaaagaac tacccggata gagttctgcc  18420
tgaccgtcaa gctgttacta tggataaacc atttcttaat gcttactcta gactcttgat  18480
taagacctgt cataagcgtg gagccttcgc aatgggcgga atggccgctt ttatcccgtc  18540
aaaagatgaa gagcacaaca atcaggtttt gaacaaggta aaagcggata aatctcttga  18600
agccaataat gggcatgatg gcacttggat tgctcatcca ggtctagctg atacagcgat  18660
ggctgtattc aacgacatct tgggttcaag aaagaatcaa cttgaagtga tgagagagca  18720
agacgcgcca ataacagctg atcaactttt ggcgccatgc gatggtgaac gaacggaaga  18780
aggtatgaga gccaatatcc gagttgctgt gcagtacata gaggcttgga tttcaggaaa  18840
cgggtgtgtc cccatttatg gactcatgga agatgcggct actgctgaaa ttagcaggac  18900
ctctatttgg cagtggatac atcatcaaaa gacattaagc aacggaaaac ctgttactaa  18960
ggccctcttc aggcagatgc ttggggaaga gatgaaagta attgcgagtg agttgggaga  19020
agagagattt tctcagggta gatttgatga cgcagcgagg ttgatggagc agatcaccac  19080
cagtgacgag ctcatagatt tcttaacgtt gcctggatac cgactacttg cttgaattta  19140
aatgcggccg ctgagtaatt ctgatattag agggagcatt aatgtgttgt tgtgatgtgg  19200
```

```
tttatatggg gaaattaaat aaatgatgta tgtacctctt gcctatgtag gtttgtgtgt  19260
tttgttttgt tgtctagctt tggttattaa gtagtaggga cgttcgttcg tgtctcaaaa  19320
aaaggggtac taccactctg tagtgtatat ggatgctgga aatcaatgtg ttttgtattt  19380
gttcacctcc attgttgaat tcaatgtcaa atgtgttttg cgttggttat gtgtaaaatt  19440
actatctttc tcgtccgatg atcaaagttt taagcaacaa aaccaagggt gaaatttaaa  19500
ctgtgctttg ttgaagattc ttttatcata ttgaaaatca aattactagc agcagatttt  19560
acctagcatg aaattttatc aacagtacag cactcactaa ccaagttcca aactaagatg  19620
cgccattaac atcagccaat aggcattttc agcaaagcaa atgaattcgt aatcatgtca  19680
tagctgtttc ctgtgtgaaa ttgttatccg ctcacaattc cacacaacat acgagccgga  19740
agcataaagt gtaaagcctg gggtgcctaa tgagtgagct aactcacatt aattgcgttg  19800
cgctcactgc ccgctttcca gtcgggaaac ctgtcgtgcc agctgcatta atgaatcggc  19860
caacgcgcgg ggagaggcgg tttgcgtatt ggctagagca gcttgccaac atggtggagc  19920
acgacactct cgtctactcc aagaatatca aagatacagt ctcagaagac caaagggcta  19980
ttgagacttt tcaacaaagg gtaatatcgg gaaacctcct cggattccat tgcccagcta  20040
tctgtcactt catcaaaagg acagtagaaa aggaaggtgg cacctacaaa tgccatcatt  20100
gcgataaagg aaaggctatc gttcaagatg cctctgccga cagtggtccc aaagatggac  20160
ccccacccac gaggagcatc gtggaaaaag aagacgttcc aaccacgtct tcaaagcaag  20220
tggattgatg tgaacatggt ggagcacgac actctcgtct actccaagaa tatcaaagat  20280
acagtctcag aagaccaaag ggctattgag acttttcaac aaagggtaat atcgggaaac  20340
ctcctcggat tccattgccc agctatctgt cacttcatca aaaggacagt agaaaaggaa  20400
ggtggcacct acaaatgcca tcattgcgat aaaggaaagg ctatcgttca agatgcctct  20460
gccgacagtg gtcccaaaga tggaccccca cccacgagga gcatcgtgga aaaagaagac  20520
gttccaacca cgtcttcaaa gcaagtggat tgatgtgata tctccactga cgtaagggat  20580
gacgcacaat cccactatcc ttcgcaagac ccttcctcta tataaggaag ttcatttcat  20640
ttggagagga cacgctgaaa tcaccagtct ctctctacaa atctatctct ctcgagaaaa  20700
tggtgagcaa gggcgaggag ctgttcaccg gggtggtgcc catcctggtc gagctggacg  20760
gcgacgtaaa cggccacaag ttcagcgtgt ccggcgaggg cgagggcgat gccacctacg  20820
gcaagctgac cctgaagttc atctgcacca ccggcaagct gcccgtgccc tggcccaccc  20880
tcgtgaccac cttcacctac ggcgtgcagt gcttcagccg ctaccccgac cacatgaagc  20940
agcacgactt cttcaagtcc gccatgcccg aaggctacgt ccaggagcgc accatcttct  21000
tcaaggacga cggcaactac aagacccgcg ccgaggtgaa gttcgagggc gacaccctgg  21060
tgaaccgcat cgagctgaag ggcatcgact tcaaggagga cggcaacatc ctggggcaca  21120
agctggagta caactacaac agccacaacg tctatatcat ggccgacaag cagaagaacg  21180
gcatcaaggt gaacttcaag atccgccaca acatcgagga cggcagcgtg cagctcgccg  21240
accactacca gcagaacacc cccatcggcg acggccccgt gctgctgccc gacaaccact  21300
acctgagcac ccagtccgcc ctgagcaaag accccaacga gaagcgcgat cacatggtcc  21360
tgctggagtt cgtgaccgcc gccgggatca ctcacggcat ggacgagctg tacaagtaag  21420
agctcggtca cctgtccaac agtctcaggg ttaatgtcta tgtatcttaa ataatgttgt  21480
cggcgatcgt tcaaacattt ggcaataaag tttcttaaga ttgaatcctg ttgccggtct  21540
```

```
tgcgatgatt atcatataat ttctgttgaa ttacgttaag catgtaataa ttaacatgta  21600
atgcatgacg ttatttatga gatgggtttt tatgattaga gtcccgcaat tatacattta  21660
atacgcgata gaaaacaaaa tatagcgcgc aaactaggat aaattatcgc gcgcggtgtc  21720
atctatgtta ctagatcggg aattaaacta tcagtgtttg acaggatata ttggcgggta  21780
aacctaagag aaaagagcgt ttattagaat aatcggatat ttaaaagggc gtgaaaaggt  21840
ttatccgttc gtccatttgt atgtgcatgc caaccacagg gttcccctcg ggatcaaagt  21900
actttgatcc aacccctccg ctgctatagt gcagtcggct tctgacgttc agtgcagccg  21960
tcttctgaaa acgacatgtc gcacaagtcc taagttacgc gacaggctgc cgccctgccc  22020
ttttcctggc gttttcttgt cgcgtgtttt agtcgcataa agtagaatac ttgcgactag  22080
aaccggagac attacgccat gaacaagagc gccgccgctg gcctgctggg ctatgcccgc  22140
gtcagcaccg acgaccagga cttgaccaac caacgggccg aactgcacgc ggccggctgc  22200
accaagctgt tttccgagaa gatcaccggc accaggcgcg accgcccgga gctggccagg  22260
atgcttgacc acctacgccc tggcgacgtt gtgacagtga ccaggctaga ccgcctggcc  22320
cgcagcaccc gcgacctact ggacattgcc gagcgcatcc aggaggccgg cgcgggcctg  22380
cgtagcctgg cagagccgtg ggccgacacc accacgccgg ccggccgcat ggtgttgacc  22440
gtgttcgccg gcattgccga gttcgagcgt tccctaatca tcgaccgcac ccggagcggg  22500
cgcgaggccg ccaaggcccg aggcgtgaag tttggccccc gccctaccct caccccggca  22560
cagatcgcgc acgcccgcga gctgatcgac caggaaggcc gcaccgtgaa agaggcggct  22620
gcactgcttg gcgtgcatcg ctcgaccctg taccgcgcac ttgagcgcag cgaggaagtg  22680
acgcccaccg aggccaggcg gcgcggtgcc ttccgtgagg acgcattgac cgaggccgac  22740
gccctggcgg ccgccgagaa tgaacgccaa gaggaacaag catgaaaccg caccaggacg  22800
gccaggacga accgtttttc attaccgaag agatcgaggc ggagatgatc gcggccgggt  22860
acgtgttcga gccgcccgcg cacgtctcaa ccgtgcggct gcatgaaatc ctggccggtt  22920
tgtctgatgc caagctggcg gcctggccgg ccagcttggc cgctgaagaa accgagcgcc  22980
gccgtctaaa aaggtgatgt gtatttgagt aaaacagctt gcgtcatgcg gtcgctgcgt  23040
atatgatgcg atgagtaaat aaacaaatac gcaaggggaa cgcatgaagg ttatcgctgt  23100
acttaaccag aaaggcgggt caggcaagac gaccatcgca acccatctag cccgcgccct  23160
gcaactcgcc ggggccgatg ttctgttagt cgattccgat ccccagggca gtgcccgcga  23220
ttgggcggcc gtgcgggaag atcaaccgct aaccgttgtc ggcatcgacc gcccgacgat  23280
tgaccgcgac gtgaaggcca tcggccggcg cgacttcgta gtgatcgacg gagcgcccca  23340
ggcggcggac ttggctgtgt ccgcgatcaa ggcagccgac ttcgtgctga ttccggtgca  23400
gccaagccct tacgacatat gggccaccgc cgacctggtg gagctggtta agcagcgcat  23460
tgaggtcacg gatggaaggc tacaagcggc ctttgtcgtg tcgcgggcga tcaaaggcac  23520
gcgcatcggc ggtgaggttg ccgaggcgct ggccgggtac gagctgccca ttcttgagtc  23580
ccgtatcacg cagcgcgtga gctacccagg cactgccgcc gccggcacaa ccgttcttga  23640
atcagaaccc gagggcgacg ctgcccgcga ggtccaggcg ctggccgctg aaattaaatc  23700
aaaactcatt tgagttaatg aggtaaagag aaaatgagca aaagcacaaa cacgctaagt  23760
gccggccgtc cgagcgcacg cagcagcaag gctgcaacgt tggccagcct ggcagacacg  23820
ccagccatga agcgggtcaa ctttcagttg ccggcggagg atcacaccaa gctgaagatg  23880
tacgcggtac gccaaggcaa gaccattacc gagctgctat ctgaatacat cgcgcagcta  23940
```

```
ccagagtaaa tgagcaaatg aataaatgag tagatgaatt ttagcggcta aaggaggcgg  24000
catggaaaat caagaacaac caggcaccga cgccgtggaa tgccccatgt gtggaggaac  24060
gggcggttgg ccaggcgtaa gcggctgggt tgcctgccgg ccctgcaatg gcactggaac  24120
ccccaagccc gaggaatcgg cgtgagcggt cgcaaaccat ccggcccggt acaaatcggc  24180
gcggcgctgg gtgatgacct ggtggagaag ttgaaggccg cgcaggccgc ccagcggcaa  24240
cgcatcgagg cagaagcacg ccccggtgaa tcgtggcaag cggccgctga tcgaatccgc  24300
aaagaatccc ggcaaccgcc ggcagccggt gcgccgtcga ttaggaagcc gcccaagggc  24360
gacgagcaac cagatttttt cgttccgatg ctctatgacg tgggcacccg cgatagtcgc  24420
agcatcatgg acgtggccgt tttccgtctg tcgaagcgtg accgacgagc tggcgaggtg  24480
atccgctacg agcttccaga cgggcacgta gaggtttccg cagggccggc cggcatggcc  24540
agtgtgtggg attacgacct ggtactgatg gcggtttccc atctaaccga atccatgaac  24600
cgataccggg aagggaaggg agacaagccc ggccgcgtgt tccgtccaca cgttgcggac  24660
gtactcaagt tctgccggcg agccgatggc ggaaagcaga aagacgacct ggtagaaacc  24720
tgcattcggt taaacaccac gcacgttgcc atgcagcgta cgaagaaggc caagaacggc  24780
cgcctggtga cggtatccga gggtgaagcc ttgattagcc gctacaagat cgtaaagagc  24840
gaaaccgggc ggccggagta catcgagatc gagctagctg attggatgta ccgcgagatc  24900
acagaaggca agaacccgga cgtgctgacg gttcaccccg attacttttt gatcgatccc  24960
ggcatcggcc gttttctcta ccgcctggca cgccgcgccg caggcaaggc agaagccaga  25020
tggttgttca agacgatcta cgaacgcagt ggcagcgccg gagagttcaa gaagttctgt  25080
ttcaccgtgc gcaagctgat cgggtcaaat gacctgccgg agtacgattt gaaggaggag  25140
gcggggcagg ctggcccgat cctagtcatg cgctaccgca acctgatcga gggcgaagca  25200
tccgccggtt cctaatgtac ggagcagatg ctagggcaaa ttgccctagc aggggaaaaa  25260
ggtcgaaaag gtctctttcc tgtggatagc acgtacattg ggaacccaaa gccgtacatt  25320
gggaaccgga acccgtacat tgggaaccca aagccgtaca ttgggaaccg gtcacacatg  25380
taagtgactg atataaaaga gaaaaaaggc gatttttccg cctaaaactc tttaaaactt  25440
attaaaactc ttaaaacccg cctggcctgt gcataactgt ctggccagcg cacagccgaa  25500
gagctgcaaa aagcgcctac ccttcggtcg ctgcgctccc tacgccccgc cgcttcgcgt  25560
cggcctatcg cggccgctgg ccgctcaaaa atggctggcc tacggccagg caatctacca  25620
gggcgcggac aagccgcgcc gtcgccactc gaccgccggc gcccacatca aggcaccctg  25680
cctcgcgcgt ttcggtgatg acggtgaaaa cctctgacac atgcagctcc cggagacggt  25740
cacagcttgt ctgtaagcgg atgccgggag cagacaagcc cgtcagggcg cgtcagcggg  25800
tgttggcggg tgtcggggcg cagccatgac ccagtcacgt agcgatagcg gagtgtatac  25860
tggcttaact atgcggcatc agagcagatt gtactgagag tgcaccatat gcggtgtgaa  25920
ataccgcaca gatgcgtaag gagaaaatac cgcatcaggc gctcttccgc ttcctcgctc  25980
actgactcgc tgcgctcggt cgttcggctg cggcgagcgg tatcagctca ctcaaaggcg  26040
gtaatacggt tatccacaga atcaggggat aacgcaggaa agaacatgtg agcaaaaggc  26100
cagcaaaagg ccaggaaccg taaaaaggcc gcgttgctgg cgtttttcca taggctccgc  26160
ccccctgacg agcatcacaa aaatcgacgc tcaagtcaga ggtggcgaaa cccgacagga  26220
ctataaagat accaggcgtt tccccctgga agctccctcg tgcgctctcc tgttccgacc  26280
```

ctgccgctta ccggatacct gtccgccttt ctcccttcgg gaagcgtggc gctttctcat 26340
agctcacgct gtaggtatct cagttcggtg taggtcgttc gctccaagct gggctgtgtg 26400
cacgaacccc ccgttcagcc cgaccgctgc gccttatccg gtaactatcg tcttgagtcc 26460
aacccggtaa gacacgactt atcgccactg gcagcagcca ctggtaacag gattagcaga 26520
gcgaggtatg taggcggtgc tacagagttc ttgaagtggt ggcctaacta cggctacact 26580
agaaggacag tatttggtat ctgcgctctg ctgaagccag ttaccttcgg aaaaagagtt 26640
ggtagctctt gatccggcaa acaaaccacc gctggtagcg gtggtttttt tgtttgcaag 26700
cagcagatta cgcgcagaaa aaaaggatct caagaagatc ctttgatctt ttctacgggg 26760
tctgacgctc agtggaacga aaactcacgt taagggattt tggtcatgca ttctaggtac 26820
taaaacaatt catccagtaa aatataatat tttattttct cccaatcagg cttgatcccc 26880
agtaagtcaa aaaatagctc gacatactgt tcttccccga tatcctccct gatcgaccgg 26940
acgcagaagg caatgtcata ccacttgtcc gccctgccgc ttctcccaag atcaataaag 27000
ccacttactt tgccatcttt cacaaagatg ttgctgtctc ccaggtcgcc gtgggaaaag 27060
acaagttcct cttcgggctt ttccgtcttt aaaaaatcat acagctcgcg cggatcttta 27120
aatggagtgt cttcttccca gttttcgcaa tccacatcgg ccagatcgtt attcagtaag 27180
taatccaatt cggctaagcg gctgtctaag ctattcgtat agggacaatc cgatatgtcg 27240
atggagtgaa agagcctgat gcactccgca tacagctcga taatcttttc agggctttgt 27300
tcatcttcat actcttccga gcaaaggacg ccatcggcct cactcatgag cagattgctc 27360
cagccatcat gccgttcaaa gtgcaggacc tttggaacag gcagctttcc ttccagccat 27420
agcatcatgt ccttttcccg ttccacatca taggtggtcc ctttataccg gctgtccgtc 27480
atttttaaat ataggttttc attttctccc accagcttat ataccttagc aggagacatt 27540
ccttccgtat cttttacgca gcggtatttt tcgatcagtt ttttcaattc cggtgatatt 27600
ctcattttag ccatttatta tttccttcct cttttctaca gtatttaaag ataccccaag 27660
aagctaatta taacaagacg aactccaatt cactgttcct tgcattctaa aaccttaaat 27720
accagaaaac agctttttca aagttgtttt caaagttggc gtataacata gtatcgacgg 27780
agccgatttt gaaaccgcgg tgatcacagg cagcaacgct ctgtcatcgt tacaatcaac 27840
atgctaccct ccgcgagatc atccgtgttt caaacccggc agcttagttg ccgttcttcc 27900
gaatagcatc ggtaacatga gcaaagtctg ccgccttaca acggctctcc cgctgacgcc 27960
gtcccggact gatgggctgc ctgtatcgag tggtgatttt gtgccgagct gccggtcggg 28020
gagctgttgg ctggctggtg gcaggatata ttgtggtgta aacaaattga cgcttagaca 28080
acttaataac acattgcgga cgtttttaat gtactgaatt aacgccgaat ta 28132

<210> SEQ ID NO 6
<211> LENGTH: 2008
<212> TYPE: DNA
<213> ORGANISM: Chlamydomonas reinhardtii

<400> SEQUENCE: 6
cataacttca aagcctaaac gtctattcct cgtgccaagg cactttctcc ggaagcgcac 60
ccacctctcc gcgccgctcg ccttcacgcg tgctctcagc tcaacaccac tgtaactcag 120
gccttgacgg gcttgtttta tcaaaaccag caagaatgtc atccgacgct atgactatca 180
acgagtcgct gatggaggtg gagcacactc ccgccgtcca caagcgcatt ctggatatcc 240
tgcccggcat ttcaggcggt gtggcccgtg tcatgatcgg ccagcccttt gacaccatca 300

```
aggtgcggct gcaagtgctg ggtcagggca ctgccctggc ggccaagctg ccgccgtcgg    360
aggtgtacaa ggactcgatg gactgcatcc gcaagatgat caagagcgag ggcccgctgt    420
ccttctacaa gggcaccgtc gcgcccctgg tcggcaacat ggtcctgctg ggcatccact    480
tccccgtctt ctcggccgtg cgaaagcagc tggagggtga tgaccactac tccaacttct    540
cccacgccaa cgtcctgctg tcgggcgcgg ctgccggtgc cgccggttct ctgatctctg    600
cccccgtgga gctggtccgc accaagatgc agatgcagcg ccgcgccgct ctggctggca    660
cggtggccgc cggcgccgcc gcctcggctg gcgccgagga gttctacaag ggctcgctgg    720
actgcttcaa gcaggtcatg tccaagcacg gcatcaaggg cctgtaccgt ggtttcacct    780
ccaccatcct gcgtgacatg cagggctacg cctggttctt cctgggctac gaggccactg    840
tcaaccactt cctgcagaac gccggccccg gtgtgcacac caaggccgac ctcaactacc    900
tgcaggtcat ggccgccggc gtggtggcgg gcttcggcct gtggggctcc atgttcccca    960
tcgacaccat caagtccaag ctgcaggccg actccttcgc caagccccag tactcgtcca   1020
cgatggactg cctcaagaag gtgctggcga gcgagggcca ggcgggtctg tggcgcggct   1080
tctccgccgc catgtaccgc gccatccccg tcaacgccgg catcttcctg gcggtggagg   1140
gcacgcgcca gggcatcaag tggtacgagg agaacgtgga gcacatctac ggcggcgtga   1200
tcggccccgc cacgcccacc gccgcgcagt aaatgtggcc gcggctgcgg ctacgtgctt   1260
gagcgcccgc gtgtgctcta tctagctgct gcaacagctg ctgttgcgca cgcggcgcaa   1320
ggcgcaacct cctggcatga caacatggct caaaaggtgt cacgtgtgtg tgtgtgtgtg   1380
tatgtttgtg tgtgcgtgtg gagagtctgg cataggtaga tgtggtcgtt agctttctgc   1440
ttcgttcccc atcgtgaggc gcatacatgc ggcaacaagc cagtggatgc actctgggca   1500
gaacgtgcgt gtgtgctcgt ttttcctagc ttagtggtgg cagcagcggc aacagaaaga   1560
ggtaggcaga agcaggagcg gtcgagggaa caggacagct gctgaataca aaggcgtcag   1620
acctgaacgt aattttgtgc gggcaccata ccccgcttac ggtccaaggg catgatgcct   1680
ttttgatgca cacatcaccc ctccccgcgc atgtatgtta aatgatgatt ttgactgctg   1740
tttttgagag cggaacaagg ggaactgcag tactggctcg gacatgagag gagaggccgg   1800
cgagagaggc tcatgacaaa aagtggaatg ggcttgcaga tgtatatagc agggcaaact   1860
ggcaaaagga gcgatacctt tcgtaagcac agggctgagg tgcatggtcg tggaaggtca   1920
cgggagttga gccgctacac cggctgtcag tgctggtctg tttctccatc gggaaacgcg   1980
ggtcaatatg taatcgtgat gggtttca                                       2008
```

<210> SEQ ID NO 7
<211> LENGTH: 358
<212> TYPE: PRT
<213> ORGANISM: Chlamydomonas reinhardtii

<400> SEQUENCE: 7

```
Met Ser Ser Asp Ala Met Thr Ile Asn Glu Ser Leu Met Glu Val Glu
1               5                   10                  15

His Thr Pro Ala Val His Lys Arg Ile Leu Asp Ile Leu Pro Gly Ile
            20                  25                  30

Ser Gly Gly Val Ala Arg Val Met Ile Gly Gln Pro Phe Asp Thr Ile
        35                  40                  45

Lys Val Arg Leu Gln Val Leu Gly Gln Gly Thr Ala Leu Ala Ala Lys
    50                  55                  60
```

```
Leu Pro Pro Ser Glu Val Tyr Lys Asp Ser Met Asp Cys Ile Arg Lys
65                  70                  75                  80

Met Ile Lys Ser Glu Gly Pro Leu Ser Phe Tyr Lys Gly Thr Val Ala
                85                  90                  95

Pro Leu Val Gly Asn Met Val Leu Leu Gly Ile His Phe Pro Val Phe
            100                 105                 110

Ser Ala Val Arg Lys Gln Leu Glu Gly Asp Asp His Tyr Ser Asn Phe
        115                 120                 125

Ser His Ala Asn Val Leu Leu Ser Gly Ala Ala Ala Gly Ala Ala Gly
    130                 135                 140

Ser Leu Ile Ser Ala Pro Val Glu Leu Val Arg Thr Lys Met Gln Met
145                 150                 155                 160

Gln Arg Arg Ala Ala Leu Ala Gly Thr Val Ala Ala Gly Ala Ala Ala
                165                 170                 175

Ser Ala Gly Ala Glu Glu Phe Tyr Lys Gly Ser Leu Asp Cys Phe Lys
            180                 185                 190

Gln Val Met Ser Lys His Gly Ile Lys Gly Leu Tyr Arg Gly Phe Thr
        195                 200                 205

Ser Thr Ile Leu Arg Asp Met Gln Gly Tyr Ala Trp Phe Phe Leu Gly
    210                 215                 220

Tyr Glu Ala Thr Val Asn His Phe Leu Gln Asn Ala Gly Pro Gly Val
225                 230                 235                 240

His Thr Lys Ala Asp Leu Asn Tyr Leu Gln Val Met Ala Ala Gly Val
                245                 250                 255

Val Ala Gly Phe Gly Leu Trp Gly Ser Met Phe Pro Ile Asp Thr Ile
            260                 265                 270

Lys Ser Lys Leu Gln Ala Asp Ser Phe Ala Lys Pro Gln Tyr Ser Ser
        275                 280                 285

Thr Met Asp Cys Leu Lys Lys Val Leu Ala Ser Glu Gly Gln Ala Gly
    290                 295                 300

Leu Trp Arg Gly Phe Ser Ala Ala Met Tyr Arg Ala Ile Pro Val Asn
305                 310                 315                 320

Ala Gly Ile Phe Leu Ala Val Glu Gly Thr Arg Gln Gly Ile Lys Trp
                325                 330                 335

Tyr Glu Glu Asn Val Glu His Ile Tyr Gly Gly Val Ile Gly Pro Ala
            340                 345                 350

Thr Pro Thr Ala Ala Gln
        355
```

<210> SEQ ID NO 8
<211> LENGTH: 31328
<212> TYPE: DNA
<213> ORGANISM: Artificial Sequence
<220> FEATURE:
<223> OTHER INFORMATION: Synthetic construct plasmid pMBXS994

<400> SEQUENCE: 8

```
aaggtacgta gtgtttatct ttgttgcttt tctgaacaat ttatttacta tgtaaatata      60

ttatcaatgt ttaatctatt ttaatttgca catgaatttt cattttattt ttactttaca     120

aaacaaataa atatatatgc aaaaaaattt acaaacgatg cacgggttac aaactaattt     180

cattaaatgc taatgcagat tttgtgaagt aaaactccaa ttatgatgaa aaataccacc     240

aacaccacct gcgaaactgt atcccaactg tccttaataa aaatgttaaa aagtatatta     300

ttctcatttg tctgtcataa tttatgtacc ccactttaat tttctgatg tactaaaccg     360
```

```
agggcaaact gaaacctgtt cctcatgcaa agcccctact caccatgtat catgtacgtg    420
tcatcaccca acaactccac ttttgctata taacaacacc cccgtcacac tctccctctc    480
taacacacac cccactaaca attccttcac ttgcagcact gttgcatcat catcttcatt    540
gcaaaaccct aaacttcacc ttcaaccgga tccaaaatgg cttctatgat atcctcttcc    600
gctgtgacaa cagtcagccg tgcctctagg gggcaatccg ccgcagtggc tccattcggc    660
ggcctcaaat ccatgactgg attcccagtg aagaaggtca acactgacat tacttccatt    720
acaagcaatg gtggaagagt aaagtgcatg caggtgtggc ctccaattgg aaagaagaag    780
tttgagactc tttcctattt gccaccattg acgagagatt ctagagttgg gaaaaagatg    840
atgactactg atgggaatac tgcaaccgct cacgtagctt atgcgatgtc agaagttgca    900
gctatctacc caatcacgcc gtccagtaca atgggagagg aagctgatga ctgggcagca    960
cagggaagaa agaatatctt cggtcaaacg cttacgatta gggagatgca atcggaagcc   1020
ggagcagcgg gtgccgtaca tggagctctt gcagctggcg ccttaactac cacctttacg   1080
gcttctcaag gactactctt gatgatccct aacatgtaca agatatcagg agaattgctt   1140
cctggagtct ttcatgtcac tgctagagct attgccgccc acgccctttc aatctttggt   1200
gatcatcagg atatatatgc agcgaggcag acagggttcg ctatgcttgc ttcaagctcg   1260
gtgcaagaag cacatgacat ggctttagtt gcccaccttg ccgccatcga atctaacgtc   1320
cctttcatgc atttcttcga cggqtttcgc acgtcacacg aaattcaaaa gattgaagtt   1380
ctcgattatg cagatatggc atccttagtg aatcagaaag ctctcgcaga gttccgtgct   1440
aaatctatga atccagagca tccacatgtt cgtggtactg ctcaaaaccc tgacatatat   1500
ttccagggaa gagaggcagc aaacccgtat tacttgaaag ttcctgggat tgtagcagag   1560
tatatgcaaa aagttgcaag tctaacaggg agatcgtaca agctgttcga ctatgttgga   1620
gctcctgatg ctgagcgtgt cattgtttct atgggttcca gttgcgagac aatcgaagaa   1680
gtgatcaatc acctcgctgc taagggagaa aagattggtt tgattaaggt ccgattatac   1740
cgtccatttg tatctgaagc tttctttgct gcgttaccgg catctgctaa ggttattaca   1800
gttctggata gaactaagga gcccggagct cctggcgacc ctttgtacct tgatgtctgt   1860
tcagcattcg tcgaaagggg agaagctatg cccaaaatcc tcgcaggccg ctatgggctc   1920
ggatctaagg agttttcacc cgctatggtt aaatctgttt atgataacat gagtggtgct   1980
aagaagaacc attttaccgt tggtatagag gacgatgtca cgggaacatc tctgccggtt   2040
gataatgcgt ttgctgatac aacccctaaa ggaactatcc agtgtcagtt ctggggtttg   2100
ggtgcagatg gtactgtcgg ggcgaataag caggctatca aaatcatagg agataacact   2160
gatctattcg ctcaaggtta cttttcatac gactctaaga aagtggtggt tataactatc   2220
agtcacttgc gatttggaga aaagccaata caatctacct atttggtgaa ccgggctgac   2280
tacgttgctt gtcataaccc tgcctatgtt ggtatatacg atattttaga gggtatcaaa   2340
gatgggggca catttgtcct caattctccc tggtcgagtc ttgaagatat ggataaacat   2400
cttccaagcg ggattaagag aaccatagcg aataagaagc ttaagtttta caacattgat   2460
gcggtgaaaa tagcaacaga tgttggtttg ggcggcagaa ttaacatgat aatgcagacc   2520
gcattcttca aactagctgg tgtactccct ttcgagaagg cagtggatct cctcaaaaag   2580
tctattcata aagcctatgg aaagaaggga gagaagatcg tgaaaatgaa tactgacgca   2640
gtagatcaag cagttacgag ccttcaagag ttcaagtacc cagactcatg gaaggatgct   2700
ccagcagaga caaaagctga gccaatgaca aacgagttct tcaaaaatgt tgtcaagcct   2760
```

```
atcctcactc aacaaggcga taaattaccg gtttccgctt ttgaagccga tggacgtttt   2820
ccactgggaa cttctcagtt tgagaaacgc ggagtggcta ttaacgttcc tcagtgggta   2880
cctgaaaatt gcatccaatg caatcaatgc gcttttgtgt gcccgcattc cgcgatactt   2940
cctgttttgg ctaaagagga agagttagtc ggagcgcctg ccaacttcac cgctttggaa   3000
gcgaaaggaa aagaattgaa aggttacaaa ttcagaattc agattaacac tctcgactgc   3060
atgggctgcg gaaattgtgc cgacatatgt cctcccaaag aaaaggcttt agtgatgcag   3120
ccactggaca ctcagaggga tgcccaagtg ccaaatttgg agtatgcagc cagaattcca   3180
gtgaagtccg aggttcttcc gcgggattct ctcaaaggat cacaattcca agaaccactg   3240
atggagtttt caggcgcatg tagtggatgt ggtgaaacac cttacgtacg tgtgattact   3300
cagttatttg gagaacggat gtttatcgct aatgcaacag gttgtagctc gatctggggt   3360
gccagcgctc cgtcgatgcc atacaagacc aacaggctgg gacagggtcc agcttggggg   3420
aattccctat tcgaggatgc tgcagagtac gggttcggaa tgaacatgag tatgtttgcg   3480
cgtagaactc atctcgcgga tcttgctgct aaagctctcg agtctgatgc ttctggagat   3540
gtcaaggaag cattgcaggg ttggctcgct gggaaaaacg acccgattaa gtctaaagaa   3600
tacggggata agttgaagaa acttctagct ggtcaaaagg acgggttgtt gggacaaatt   3660
gcagcaatgt cagaccttta cacgaagaaa agtgtttgga tctttggtgg cgatggatgg   3720
gcgtatgata ttggttatgg tggccttgat cacgtcctcg caagcggcga agatgtgaac   3780
gtgtttgtga tggatactga agtttactcc aacaccggtg gacaatcctc aaaagcaaca   3840
ccaaccgggg ccgtggctaa attcgcggct gccggcaaaa ggactggaaa aaaggatctg   3900
gccagaatgg ttatgactta tggatacgta tatgtagcta cagtatcaat gggctatagc   3960
aaacagcaat ttcttaaagt cctcaaggaa gctgagagct tcccaggtcc ttcacttgtt   4020
atcgcctacg cgacatgtat caatcaaggt ttacgaaagg gaatggggaa aagccaagat   4080
gtgatgaaca ccgctgttaa aagcggttat tggcctttgt tccgctatga tcctcgtctt   4140
gcggcccaag gaaagaatcc gtttcagcta gactctaagg caccagacgg tagtgttgag   4200
gaatttttga tggctcagaa tcgatttgcg gtccttgatc gatcgttccc agaagatgcc   4260
aagaggttga gggcgcaagt tgcacatgaa ttggatgtta ggtttaagga gttagaacac   4320
atggcggcta caaatatctt cgagtccttc gctcctgctg gaggcaaagc tgacggttca   4380
gtagattttg gagaaggcgc agagttttgt actagagatg acacaccgat gatggccaga   4440
ccagatagtg gcgaagcatg cgaccaaaat agagcaggaa cgtctgagca gcaaggagat   4500
ttgtcgaaga ggaccaagaa atgaggcgcg cctgagtaat tctgatatta gagggagcat   4560
taatgtgttg ttgtgatgtg gtttatatgg ggaaattaaa taaatgatgt atgtacctct   4620
tgcctatgta ggtttgtgtg ttttgttttg ttgtctagct ttggttatta agtagtaggg   4680
acgttcgttc gtgtctcaaa aaaaggggta ctaccactct gtagtgtata tggatgctgg   4740
aaatcaatgt gttttgtatt tgttcacctc cattgttgaa ttcaatgtca aatgtgtttt   4800
gcgttggtta tgtgtaaaat tactatcttt ctcgtccgat gatcaaagtt ttaagcaaca   4860
aaaccaaggg tgaaatttaa actgtgcttt gttgaagatt cttttatcat attgaaaatc   4920
aaattactag cagcagattt tacctagcat gaaattttat caacagtaca gcactcacta   4980
accaagttcc aaactaagat gcgccattaa catcagccaa taggcatttt cagcaaaagc   5040
ttgtacgtag tgtttatctt tgttgctttt ctgaacaatt tatttactat gtaaatatat   5100
```

```
tatcaatgtt taatctattt taatttgcac atgaattttc attttatttt tactttacaa   5160
aacaaataaa tatatatgca aaaaaattta caaacgatgc acgggttaca aactaatttc   5220
attaaatgct aatgcagatt ttgtgaagta aaactccaat tatgatgaaa aataccacca   5280
acaccacctg cgaaactgta tcccaactgt ccttaataaa aatgttaaaa agtatattat   5340
tctcatttgt ctgtcataat ttatgtaccc cactttaatt tttctgatgt actaaaccga   5400
gggcaaactg aaacctgttc ctcatgcaaa gcccctactc accatgtatc atgtacgtgt   5460
catcacccaa caactccact tttgctatat aacaacaccc ccgtcacact ctccctctct   5520
aacacacacc ccactaacaa ttccttcact tgcagcactg ttgcatcatc atcttcattg   5580
caaaacccta aacttcacct tcaaccgcgg ccgcagatct aaaatggctt ctatgatatc   5640
ctcttccgct gtgacaacag tcagccgtgc ctctaggggg caatccgccg cagtggctcc   5700
attcggcggc ctcaaatcca tgactggatt cccagtgaag aaggtcaaca ctgacattac   5760
ttccattaca agcaatggtg gaagagtaaa gtgcatgcag gtgtggcctc caattggaaa   5820
gaagaagttt gagactcttt cctatttgcc accattgacg agagattcta gagtgctcag   5880
ccagcaatcc atccagaagg ttctcgtggc taaccgtggt gagattgcta ttcgtatctt   5940
tagagcgtgt accgagttga acatccgaac tgtcgctgtt tatagtaaag aagattctgg   6000
atcataccac agatacaaag ctgacgaggc ctacttggtt ggtgaaggta agaagcctat   6060
tgacgcttat cttgatatag agggcatcat tgatattgcc aagagaaaca aagttgatgc   6120
aattcatccg ggatacggtt ttctatcaga aaacattcac tttgcacgac gatgtgaaga   6180
agagggaatc gtgttcatcg gacctaaaag cgaacacttg gatatgtttg gggacaaggt   6240
taaggcaagg gaacaagcag agaaggcagg aattccagtg atacctggat cggatgggcc   6300
tgctgaaact cttgaagctg tcgaacaatt cggccaggct aacggatacc caatcatcat   6360
taaggcttct ttaggtggtg gggggaaggggg gatgagaatc gtgcgatccg aatctgaggt   6420
aaaagaggct tatgaacgtg ctaaatcgga agctaaagcg gcctttggga acgatgaagt   6480
ctatgtcgag aaactaatcg agaatcccaa gcacatcgag gttcaagtga ttggtgataa   6540
gcaaggtaac gttgttcacc ttttcgagag agattgttct gttcaacgta gacaccaaaa   6600
agtgatagaa gtagctccat cggtatcgtt gagcccagaa ctaagggacc agatatgcga   6660
ggctgctgtc gcgcttgcaa agaatgtcaa ctatatcaat gcaggcactg tcgaattctt   6720
ggtagccaat aatgagtttt acttcattga ggtcaaccct agagttcaag ttgagcatac   6780
cattaccgaa atgatcactg ggtggatat cgtacagact cagatcctcg ttgctcaagg   6840
ccattccctt cattccaaga aggtgaatat tccagagcaa aaggatatct ttacaattgg   6900
ttatgcgatt caatcacgag ttaccacaga agatccacaa aatgacttca tgccagatac   6960
gggaaagata atggcatacc gttctggtgg cggatttggt gttcgattag acacaggtaa   7020
tagttttcag ggagctgtga taacgccata ctatgattct ttattggtta agttgagtac   7080
ttgggctctc actttcgagc aagccgcagc gaaaatggtc agaaaccttc aggagttcag   7140
aattagaggt attaagacga acattccatt cttagagaac gttgctaaac atgagaagtt   7200
tctgacagga caatatgata caagtttcat agacactaca cctgaactct ttaacttccc   7260
taaacaaaaa gacagaggta cgaaaatgtt gacatatatc ggaaacgtga cagttaatgg   7320
gttcccaggt atcggtaaga aagaaaagcc ggcctttgat aaaccccttg gtgttaaagt   7380
ggatgtggat caacaacctg ctaggggcac taagcaaatc cttgatgaaa agggtgcaga   7440
gggactggca aattgggtta aagagcagaa atcagttctt ctgacagata ccacatttcg   7500
```

-continued

```
tgatgctcat caatcattac tagcaacaag aattagatca cacgatctga aaaagatcgc   7560
taatccaacc gctgctcttt ggccggaact cttctctatg gaaatgtggg gtggggccac   7620
attcgatgtc gcgtaccgtt ttctaaaaga agatccttgg aagcgtctgg aagatttgag   7680
aaaagaggtg cccaataccc tgttccagat gcttttgcgt tctagcaatg ccgtcggata   7740
taccaattat cctgacaatg tgatcaaaga attcgtaaaa cagtccgctc aatctggtat   7800
cgacgttttt aggattttcg attcacttaa ttgggtaaaa ggtatgacgt tagcgattga   7860
tgctgtacgt gatactggaa aggttgcaga ggccgccatt tgctacactg gagacatttt   7920
ggataagaat agaactaaat acgacttggc ttattacact tccatggcaa aagaacttga   7980
ggctgccggt gcacatattc tggggataaa ggatatggcc ggtttgctca aaccgcaggc   8040
agcatatgag ttggtttcag cccttaaaga aactattgac atacccgttc atctgcacac   8100
gcatgacacg tcgggcaatg gaatctatat gtatgcaaag gctgtcgagg ctggcgtgga   8160
tatcattgat gtcgctgtaa gctctatggc tggacttaca tcccagccat cagcctctgg   8220
attctatcat gctatggaag gtaacgatcg tagacccgaa atgaatgtcc aaggggtcga   8280
attactgtca cagtactggg agagtgtgcg taagtattac tcagagtttg agagcggtat   8340
gaagagtccc cataccgaga tttatgagca cgagatgcct ggtggacaat actctaactt   8400
gcaacagcaa gcgaaggggg ttggtttggg agataggtgg aacgaagtga aagaaatgta   8460
tagacgtgtc aacgacatgt ttggtgatat tgtgaaagta actcctagtt ctaaggtagt   8520
tggagacatg gcactgtaca tggttcagaa taaccttact gaaaaggatg tttacgagaa   8580
gggggagtca cttgacttcc ctgattcagt ggttgaactg ttcaagggaa atatcggtca   8640
accgcatggg ggatttccag aaaaactaca gaaactgata ctaaagggac aggagccaat   8700
tactgttcga ccaggagagc tcttggagcc ggtttctttt gaggctatca agcaagaatt   8760
caaagaacaa cataaccttg aaatttctga tcaggacgcg gttgcttacg cactttatcc   8820
aaaggtcttt actgattacg tgaaaaccac agagtcttat ggtgatataa gtgtgctaga   8880
tacaccaaca tttttctatg gcatgactct tggagaagag attgaagtgg aaatagaaag   8940
gggaaaaaca ctcattgtta aactgatatc tatcggagag cctcaacctg atgctacaag   9000
ggtagtgtac tttgaattga atggacaacc tagagaagta gtgattaaag atgagtcaat   9060
aaagtcaagc gtgcaggaga ggctaaaggc agatagaacc aatccgtcgc acattgcagc   9120
ttctatgcct ggcaccgtca taaaagtcct cgctgaagct ggtactaaag tcaacaaagg   9180
tgaccatctt atgatcaacg aagcaatgaa gatggaaact acggttcagg cacctttcag   9240
tggaacaatc aagcaggttc atgttaagaa tggcgagcct atccagactg gtgacttgct   9300
tttggagatt gaaaaggcct gagtcgacgc gatcgcgcgg ccgctgagta attctgatat   9360
tagagggagc attaatgtgt tgttgtgatg tggtttatat ggggaaatta aataaatgat   9420
gtatgtacct cttgcctatg taggtttgtg tgttttgttt tgttgtctag ctttggttat   9480
taagtagtag ggacgttcgt tcgtgtctca aaaaaagggg tactaccact ctgtagtgta   9540
tatggatgct ggaaatcaat gtgttttgta tttgttcacc tccattgttg aattcaatgt   9600
caaatgtgtt ttgcgttggt tatgtgtaaa attactatct ttctcgtccg atgatcaaag   9660
ttttaagcaa caaaaccaag ggtgaaattt aaactgtgct ttgttgaaga ttcttttatc   9720
atattgaaaa tcaaattact agcagcagat tttacctagc atgaaatttt atcaacagta   9780
cagcactcac taaccaagtt ccaaactaag atgcgccatt aacatcagcc aataggcatt   9840
```

-continued

```
ttcagcaagt ttaaactacg tagtgtttat ctttgttgct tttctgaaca atttatttac   9900
tatgtaaata tattatcaat gtttaatcta ttttaatttg cacatgaatt ttcattttat   9960
ttttacttta caaaacaaat aaatatatat gcaaaaaaat ttacaaacga tgcacgggtt  10020
acaaactaat ttcattaaat gctaatgcag attttgtgaa gtaaaactcc aattatgatg  10080
aaaaatacca ccaacaccac ctgcgaaact gtatcccaac tgtccttaat aaaaatgtta  10140
aaaagtatat tattctcatt tgtctgtcat aatttatgta ccccacttta atttttctga  10200
tgtactaaac cgagggcaaa ctgaaacctg ttcctcatgc aaagccccta ctcaccatgt  10260
atcatgtacg tgtcatcacc caacaactcc acttttgcta tataacaaca cccccgtcac  10320
actctccctc tctaacacac accccactaa caattccttc acttgcagca ctgttgcatc  10380
atcatcttca ttgcaaaacc ctaaacttca ccttcaaccg cggccgctcg cgaaaaatgg  10440
cttctatgat atcctcttcc gctgtgacaa cagtcagccg tgcctctagg gggcaatccg  10500
ccgcagtggc tccattcggc ggcctcaaat ccatgactgg attcccagtg aagaaggtca  10560
acactgacat tacttccatt acaagcaatg gtggaagagt aaagtgcatg caggtgtggc  10620
ctccaattgg aaagaagaag tttgagactc tttcctattt gccaccattg acgagagatt  10680
ctagagtgaa catacacgag taccaagcaa aagagttgct caagacctat ggagtgccgg  10740
tcccagacgg agcggtagct tatagtgatg ctcaagcggc ttccgtcgct gaagagattg  10800
gtggctctag atgggttgta aaggcgcaga tacacgctgg tggaagggga aaggcaggtg  10860
gtgtgaaggt ggcccatagc attgaagagg ttcgtcagta cgctgatgcg atgcttgggt  10920
cccatctcgt tacacatcaa acagggcctg gtggttcatt agttcaacgt ttgtgggtgg  10980
agcaagcatc acatatcaag aaagagtatt atctgggatt tgttattgat agaggtaacc  11040
aaagaattac cttaattgct tcttctgaag gggggaatgga gatagaagag gttgctaaag  11100
agacaccaga aaagatcgtc aaagaggttg tagaccctgc aatcggattg cttgattttc  11160
agtgtagaaa ggttgcaact gcaataggac ttaagggaaa gcttatgccc caggcagtta  11220
gacttatgaa ggctatctat aggtgtatgc gagataagga tgctctccag gcagagatca  11280
atcctttggc aatagtaggt gaaagtgacg agtcgctcat ggttcttgat gctaaattca  11340
attttgatga caatgctctt tacagacaac gaacaattac tgaaatgagg gatctcgcag  11400
aagaagatcc taaagaagtc gaagcttctg gacacggatt gaattacatc gccctcgatg  11460
ggaacatcgg ttgtattgtg aatggagctg gtcttgctat ggccagcctg gatgccatca  11520
ctctacatgg cggtcgtcca gctaacttct tagatgtcgg cggtggggct tctcctgaaa  11580
aggttacgaa tgcgtgcaga attgttttgg aagatccgaa cgtccgttgt atactggtga  11640
acatttttgc cggaattaac aggtgcgatt ggattgcaaa aggacttatt caagcctgcg  11700
actcactaca gattaaagtt ccactgatcg ttcgattggc aggcactaat gtagatgaag  11760
gcaggaaaat cctagcggag tcgggtttaa gtttcataac ggcagagaat ttggacgacg  11820
cggctgctaa agccgtggct atcgtgaaag ggtgaacgcg ttgagtaatt ctgatattag  11880
agggagcatt aatgtgttgt tgtgatgtgg tttatatggg gaaattaaat aaatgatgta  11940
tgtacctctt gcctatgtag gtttgtgtgt tttgttttgt tgtctagctt tggttattaa  12000
gtagtaggga cgttcgttcg tgtctcaaaa aaaggggtac taccactctg tagtgtatat  12060
ggatgctgga aatcaatgtg ttttgtattt gttcacctcc attgttgaat tcaatgtcaa  12120
atgtgttttg cgttggttat gtgtaaaatt actatctttc tcgtccgatg atcaaagttt  12180
taagcaacaa aaccaagggt gaaatttaaa ctgtgctttg ttgaagattc ttttatcata  12240
```

```
ttgaaaatca aattactagc agcagatttt acctagcatg aaattttatc aacagtacag  12300
cactcactaa ccaagttcca aactaagatg cgccattaac atcagccaat aggcattttc  12360
agcaatgtac atacgtagtg tttatctttg ttgcttttct gaacaattta tttactatgt  12420
aaatatatta tcaatgttta atctatttta atttgcacat gaattttcat tttattttta  12480
ctttacaaaa caaataaata tatatgcaaa aaaatttaca aacgatgcac gggttacaaa  12540
ctaatttcat taaatgctaa tgcagatttt gtgaagtaaa actccaatta tgatgaaaaa  12600
taccaccaac accacctgcg aaactgtatc ccaactgtcc ttaataaaaa tgttaaaaag  12660
tatattattc tcatttgtct gtcataattt atgtacccca ctttaatttt tctgatgtac  12720
taaaccgagg gcaaactgaa acctgttcct catgcaaagc ccctactcac catgtatcat  12780
gtacgtgtca tcacccaaca actccacttt tgctatataa caacaccccc gtcacactct  12840
ccctctctaa cacacacccc actaacaatt ccttcacttg cagcactgtt gcatcatcat  12900
cttcattgca aaaccctaaa cttcaccttc aaccgcggcc gcgacgtcaa aatggcttct  12960
atgatatcct cttccgctgt gacaacagtc agccgtgcct ctagggggca atccgccgca  13020
gtggctccat tcggcggcct caaatccatg actggattcc cagtgaagaa ggtcaacact  13080
gacattactt ccattacaag caatggtgga agagtaaagt gcatgcaggt gtggcctcca  13140
attggaaaga agaagtttga gactctttcc tatttgccac cattgacgag agattctaga  13200
gtctcggttt tcgtgaataa acattccaag gtcatctttc aaggctttac cggggagcat  13260
gctacatttc acgcaaaaga tgcaatgcga atgggcacaa gggttgtcgg tggcgttact  13320
cctggaaagg gtgggactag acatccagat cctgagctcg ctcatcttcc ggtattcgat  13380
accgttgccg aagccgttgc tgctacagga gctgatgtat cagctgtgtt tgtcccaccc  13440
cctttcaatg cagacgcact tatggaagca attgatgccg gtattagagt ggctgtcact  13500
atagcggatg gaattcctgt gcatgacatg atcagattgc aaaggtatag agtaggaaag  13560
gactctattg ttatcgggcc taacacacca ggaatcataa cgcctggtga gtgtaaagtg  13620
ggtatcatgc cgagtcacat atacaagaag ggaaacgtgg gtatagtgag tcgatcagga  13680
acattgaatt acgaggcgac ggaacaaatg gctgcgctag gcttagggat tactacttct  13740
gttggaattg gtggtgatcc tataaacggc actgactttg tgactgttct ccgtgcattc  13800
gaggctgatc cagaaacgga aattgtagtt atgatcggag aaataggtgg accgcaggaa  13860
gttgccgcag ctagatgggc aaaagagaat atgaccaaac cagttattgg gttcgtagct  13920
ggtttagcag cccccacagg gcgtaggatg ggacacgcag gtgctattat cagctctgag  13980
gctgataccg ctggagctaa gatggatgcc atggaagctc ttggtctgta tgtcgctagg  14040
aacccagcgc aaatcggaca gacagttttg cgtgcggcac aggagcatgg aattagattt  14100
tgagggcccg ttaactgagt aattctgata ttagagggag cattaatgtg ttgttgtgat  14160
gtggtttata tggggaaatt aaataaatga tgtatgtacc tcttgcctat gtaggtttgt  14220
gtgttttgtt ttgttgtcta gctttggtta ttaagtagta gggacgttcg ttcgtgtctc  14280
aaaaaaaggg gtactaccac tctgtagtgt atatggatgc tggaaatcaa tgtgttttgt  14340
atttgttcac ctccattgtt gaattcaatg tcaaatgtgt tttgcgttgg ttatgtgtaa  14400
aattactatc tttctcgtcc gatgatcaaa gttttaagca acaaaaccaa gggtgaaatt  14460
taaactgtgc tttgttgaag attcttttat catattgaaa atcaaattac tagcagcaga  14520
ttttacctag catgaaattt tatcaacagt acagcactca ctaaccaagt tccaaactaa  14580
```

```
gatgcgccat taacatcagc caataggcat tttcagcaag tttaaaccgg accgtacgta  14640
gtgtttatct ttgttgcttt tctgaacaat ttatttacta tgtaaatata ttatcaatgt  14700
ttaatctatt ttaatttgca catgaatttt cattttattt ttactttaca aaacaaataa  14760
atatatatgc aaaaaaattt acaaacgatg cacgggttac aaactaattt cattaaatgc  14820
taatgcagat tttgtgaagt aaaactccaa ttatgatgaa aaataccacc aacaccacct  14880
gcgaaactgt atcccaactg tccttaataa aaatgttaaa aagtatatta ttctcatttg  14940
tctgtcataa tttatgtacc ccactttaat ttttctgatg tactaaaccg agggcaaact  15000
gaaacctgtt cctcatgcaa agcccctact caccatgtat catgtacgtg tcatcaccca  15060
acaactccac ttttgctata taacaacacc cccgtcacac tctccctctc taacacacac  15120
cccactaaca attccttcac ttgcagcact gttgcatcat catcttcatt gcaaaaccct  15180
aaacttcacc ttcaaccgcg gccgccacgt gaaaatggct tctatgatat cctcttccgc  15240
tgtgacaaca gtcagccgtg cctctagggg gcaatccgcc gcagtggctc cattcggcgg  15300
cctcaaatcc atgactggat tcccagtgaa gaaggtcaac actgacatta cttccattac  15360
aagcaatggt ggaagagtaa agtgcatgca ggtgtggcct ccaattggaa agaagaagtt  15420
tgagactctt tcctatttgc caccattgac gagagattct agagtgagct tccgtttgca  15480
accagctccg ccagcaaggc ccaatagatg tcaacttttt gggcctggat ctcgaccggc  15540
tttgtttgag aaaatggccg cttcagccgc ggacgttatc aatctggatt tagaggatag  15600
tgttgcccca gatgataaag ctcaggctag agcaaatatc attgaggcta taaacggtct  15660
agactggggt agaaagtatc tcagtgttag aattaacgga cttgatacgc ctttctggta  15720
tcgagatgtc gttgacttgc ttgagcaggc aggagataga cttgatcaaa tcatgatccc  15780
taaggttggc tgtgctgcgg atgtttacgc cgtcgatgct ttggtaacag caattgaacg  15840
tgctaaaggg cgtactaagc ctctatcatt tgaagtgata atagagtctg cagctggtat  15900
cgcacatgtt gaagaaatag ccgcttcgtc accaagactc caagccatgt ctttgggtgc  15960
agccgatttt gcagcttcta tgggaatgca gactacaggg attggtggaa cgcaagagaa  16020
ctactatatg ctccacgacg gacaaaagca ctggtccgat ccttggcatt gggctcaggc  16080
tgcaatcgtc gcagcgtgca gaacacatgg gattttaccc gttgacggcc cgttcggtga  16140
cttctctgat gacgaaggat tcagggcaca agctcgaagg tccgctactc ttggaatggt  16200
gggaaaatgg gccatacatc caaagcaagt ggctctcgct aatgaagtgt ttacacctag  16260
cgagactgca gtaaccgaag cgagggagat tttagcggct atggatgctg ctaaggcgag  16320
aggcgaaggt gctaccgtgt acaaaggtag gctggtagat atcgcgtcga ttaaacaggc  16380
agaagtcatt gttcgtcagg ctgagatgat tagtgcatga actagttgag taattctgat  16440
attagaggga gcattaatgt gttgttgtga tgtggtttat atggggaaat taaataaatg  16500
atgtatgtac ctcttgccta tgtaggtttg tgtgttttgt tttgttgtct agctttggtt  16560
attaagtagt agggacgttc gttcgtgtct caaaaaaagg ggtactacca ctctgtagtg  16620
tatatggatg ctggaaatca atgtgttttg tatttgttca cctccattgt tgaattcaat  16680
gtcaaatgtg ttttgcgttg gttatgtgta aaattactat ctttctcgtc cgatgatcaa  16740
agttttaagc aacaaaacca agggtgaaat ttaaactgtg ctttgttgaa gattctttta  16800
tcatattgaa aatcaaatta ctagcagcag attttaccta gcatgaaatt ttatcaacag  16860
tacagcactc actaaccaag ttccaaacta agatgcgcca ttaacatcag ccaataggca  16920
ttttcagcaa gtttaaactc cggatacgta gtgtttatct ttgttgcttt tctgaacaat  16980
```

```
ttatttacta tgtaaatata ttatcaatgt ttaatctatt ttaatttgca catgaatttt  17040
cattttattt ttactttaca aaacaaataa atatatatgc aaaaaaattt acaaacgatg  17100
cacgggttac aaactaattt cattaaatgc taatgcagat tttgtgaagt aaaactccaa  17160
ttatgatgaa aaataccacc aacaccacct gcgaaactgt atcccaactg tccttaataa  17220
aaatgttaaa aagtatatta ttctcatttg tctgtcataa tttatgtacc ccactttaat  17280
ttttctgatg tactaaaccg agggcaaact gaaacctgtt cctcatgcaa agcccctact  17340
caccatgtat catgtacgtg tcatcaccca acaactccac ttttgctata taacaacacc  17400
cccgtcacac tctccctctc taacacacac cccactaaca attccttcac ttgcagcact  17460
gttgcatcat catcttcatt gcaaaaccct aaacttcacc ttcaaccgcg gccgccctag  17520
gaaaatggct tctatgatat cctcttccgc tgtgacaaca gtcagccgtg cctctagggg  17580
gcaatccgcc gcagtggctc cattcggcgg cctcaaatcc atgactggat tcccagtgaa  17640
gaaggtcaac actgacatta cttccattac aagcaatggt ggaagagtaa agtgcatgca  17700
ggtgtggcct ccaattggaa agaagaagtt tgagactctt tcctatttgc caccattgac  17760
gagagattct agagttgcac agtaccaaga cgatatcaag gcggttgcag ggcttaagga  17820
gaatcacggc tccgcatgga atgccatcaa cccggagtat gccgccagga tgagggcgca  17880
gaacaagttc aagacgggcc ttgacattgc aaagtatacg gctaagatta tgcgggccga  17940
tatggcagcc tacgacgccg acagctcgaa gtacacacag agcctcggtt gttggcatgg  18000
tttcattggt cagcagaaga tgatctcaat caagaaacat ttcaacagca cggaacgccg  18060
ttacctctac ctttctggct ggatggtagc cgcgcttaga tccgagtttg gccccctacc  18120
ggatcagtcc atgcacgaaa agacgagtgt ctccgcactc attcgggaac tctacacttt  18180
tctgcgccaa gcggacgcta gggagttggg gggcctgttt cgggagcttg acgcggccca  18240
aggcccagct aaggcggcca ttcaagcgaa gatcgacaac cacgtcactc atgtggtccc  18300
aatcatagct gatatcgacg ctggcttcgg caatgcggaa gcaacatacc tgttggccaa  18360
gcagttcatc gaggccgggg cttgctgcat acagatagag aaccaggttt ctgacgaaaa  18420
gcaatgtgga catcaagacg gaaaggttac cgtgccccac gaggattttc ttgcaaaaat  18480
ccgagcgatt cgttatgcgt ttttagagtt gggcgtggat gacggtatca tcgtggccag  18540
gaccgatagt ctcggtgctg gtctgacaaa gcaaatcgca gtgaccaata cgcctggaga  18600
cttaggggat cagtacaaca gcttcctcga ttgcgaggag cttagcgcag atcagctcgg  18660
aaatggcgac gttatcatca agcgtgatgg aaagctactc cgccccaagc gcctcccgtc  18720
taacttgttc cagttccggg ctggaactgg cgaagcgcga tgcgtcctgg actgcgtgac  18780
cgcgctccag aacggcgccg acctactctg gattgagaca gaaaagcctc acatagctca  18840
aatcggcgga atggtatcgg agataaggaa agtcataccc aacgccaaac tggtgtacaa  18900
caactctccg tcgttcaatt ggaccctgaa ctttagacag caagcatacg atgctatgaa  18960
agccgctggg aaagacgtgt cagcatacga ccgcgcccag cttatgtccg tggagtacga  19020
ccaaacggaa ctggctaagc tggctgatga gaaaatcaga acattccagg ccgacgcctc  19080
aagggaggcc gggatcttcc atcacttgat taccttacca acatatcaca ctgcggccct  19140
gtcaaccgac aatttggcta aggagtactt cggagatcag gggatgctcg gttatgtcgc  19200
gggcgttcag aggaaggaga tccgacaggg catcgcatgt gtcaagcacc aaaacatgag  19260
cgggagtgac atcggggatg atcataaaga gtatttctcc ggcgaagccg cgctgaaggc  19320
```

```
cgccggcaaa gacaacacta tgaatcaatt ctgacccggg tgagtaattc tgatattaga  19380
gggagcatta atgtgttgtt gtgatgtggt ttatatgggg aaattaaata aatgatgtat  19440
gtacctcttg cctatgtagg tttgtgtgtt ttgttttgtt gtctagcttt ggttattaag  19500
tagtagggac gttcgttcgt gtctcaaaaa aaggggtact accactctgt agtgtatatg  19560
gatgctggaa atcaatgtgt tttgtatttg ttcacctcca ttgttgaatt caatgtcaaa  19620
tgtgttttgc gttggttatg tgtaaaatta ctatctttct cgtccgatga tcaaagtttt  19680
aagcaacaaa accaagggtg aaatttaaac tgtgctttgt tgaagattct tttatcatat  19740
tgaaaatcaa attactagca gcagatttta cctagcatga aattttatca acagtacagc  19800
actcactaac caagttccaa actaagatgc gccattaaca tcagccaata ggcattttca  19860
gcaagctcga gtcacgtagt gcctcagcgt ttaaacgtac gtagtgttta tctttgttgc  19920
ttttctgaac aatttattta ctatgtaaat atattatcaa tgtttaatct attttaattt  19980
gcacatgaat tttcatttta tttttacttt acaaaacaaa taaatatata tgcaaaaaaa  20040
tttacaaacg atgcacgggt tacaaactaa tttcattaaa tgctaatgca gattttgtga  20100
agtaaaactc caattatgat gaaaaatacc accaacacca cctgcgaaac tgtatcccaa  20160
ctgtccttaa taaaaatgtt aaaaagtata ttattctcat ttgtctgtca taatttatgt  20220
accccacttt aatttttctg atgtactaaa ccgagggcaa actgaaacct gttcctcatg  20280
caaagcccct actcaccatg tatcatgtac gtgtcatcac ccaacaactc cacttttgct  20340
atataacaac acccccgtca cactctccct ctctaacaca caccccacta acaattcctt  20400
cacttgcagc actgttgcat catcatcttc attgcaaaac cctaaacttc accttcaacc  20460
gcggccgctt cgaaaaaatg gcttctatga tatcctcttc cgctgtgaca acagtcagcc  20520
gtgcctctag gggggcaatcc gccgcagtgg ctccattcgg cggcctcaaa tccatgactg  20580
gattcccagt gaagaaggtc aacactgaca ttacttccat tacaagcaat ggtggaagag  20640
taaagtgcat gcaggtgtgg cctccaattg gaaagaagaa gtttgagact ctttcctatt  20700
tgccaccatt gacgagagat tctagagtca ccgagcaagc cacaacgaca gatgaactcg  20760
cttttactag gccatatggt gaacaggaaa agcaaattct tacagcagaa gctgttgagt  20820
ttttgaccga gttggttact cactttacac ctcaaagaaa caagttactc gcagcacgta  20880
tccagcagca acaagacata gataatggta cacttccaga tttcatttcg gagactgcat  20940
ctattcgaga tgccgattgg aaaatcaggg gtatccccgc agatttagaa gataggagag  21000
ttgaaataac cggacctgta gaaagaaaaa tggtcatcaa cgctctaaac gccaacgtca  21060
aagtgtttat ggctgatttt gaggactcgc tagcacctga ttggaacaag gtgatagatg  21120
gccagatcaa tttgagagat gctgtcaatg ggacaatctc ctatactaat gaggctggaa  21180
agatttatca actcaaacct aatccggcag tgctgatttg tagggttcgt ggattacacc  21240
tgcctgaaaa gcatgttacg tggcgtgggg aagcaattcc tggcagcctt tttgacttcg  21300
ctctttactt tttccataac taccaggcgc tgttggctaa ggggtcaggt ccatatttct  21360
atcttccgaa aactcaaagt tggcaagaag ctgcctggtg gtctgaggtg ttctcctatg  21420
cagaggatcg tttcaattta ccacgaggta cgatcaaagc aactctgtta attgagacac  21480
tcccggctgt gtttcaaatg gacgagatac tacacgctct cagggaccac attgttggtc  21540
ttaattgcgg aagatgggac tatatcttct cctacatcaa gactctaaag aactacccgg  21600
atagagttct gcctgaccgt caagctgtta ctatggataa accatttctt aatgcttact  21660
ctagactctt gattaagacc tgtcataagc gtggagcctt cgcaatgggc ggaatggccg  21720
```

```
cttttatccc gtcaaaagat gaagagcaca acaatcaggt tttgaacaag gtaaaagcgg  21780
ataaatctct tgaagccaat aatgggcatg atggcacttg gattgctcat ccaggtctag  21840
ctgatacagc gatggctgta ttcaacgaca tcttgggttc aagaaagaat caacttgaag  21900
tgatgagaga gcaagacgcg ccaataacag ctgatcaact tttggcgcca tgcgatggtg  21960
aacgaacgga agaaggtatg agagccaata tccgagttgc tgtgcagtac atagaggctt  22020
ggatttcagg aaacgggtgt gtccccattt atggactcat ggaagatgcg gctactgctg  22080
aaattagcag gacctctatt tggcagtgga tacatcatca aaagacatta agcaacggaa  22140
aacctgttac taaggccctc ttcaggcaga tgcttgggga agagatgaaa gtaattgcga  22200
gtgagttggg agaagagaga ttttctcagg gtagatttga tgacgcagcg aggttgatgg  22260
agcagatcac caccagtgac gagctcatag atttcttaac gttgcctgga taccgactac  22320
ttgcttgaat ttaaatgcgg ccgctgagta attctgatat tagagggagc attaatgtgt  22380
tgttgtgatg tggtttatat ggggaaatta aataaatgat gtatgtacct cttgcctatg  22440
taggtttgtg tgttttgttt tgttgtctag ctttggttat taagtagtag ggacgttcgt  22500
tcgtgtctca aaaaaagggg tactaccact ctgtagtgta tatggatgct ggaaatcaat  22560
gtgttttgta tttgttcacc tccattgttg aattcaatgt caaatgtgtt ttgcgttggt  22620
tatgtgtaaa attactatct ttctcgtccg atgatcaaag ttttaagcaa caaaaccaag  22680
ggtgaaattt aaactgtgct ttgttgaaga ttcttttatc atattgaaaa tcaaattact  22740
agcagcagat tttacctagc atgaaatttt atcaacagta cagcactcac taaccaagtt  22800
ccaaactaag atgcgccatt aacatcagcc aataggcatt ttcagcaaag caaatgaatt  22860
cgtaatcatg tcatagctgt ttcctgtgtg aaattgttat ccgctcacaa ttccacacaa  22920
catacgagcc ggaagcataa agtgtaaagc ctggggtgcc taatgagtga gctaactcac  22980
attaattgcg ttgcgctcac tgcccgcttt ccagtcggga aacctgtcgt gccagctgca  23040
ttaatgaatc ggccaacgcg cggggagagg cggtttgcgt attggctaga gcagcttgcc  23100
aacatggtgg agcacgacac tctcgtctac tccaagaata tcaaagatac agtctcagaa  23160
gaccaaaggg ctattgagac ttttcaacaa agggtaatat cgggaaacct cctcggattc  23220
cattgcccag ctatctgtca cttcatcaaa aggacagtag aaaaggaagg tggcacctac  23280
aaatgccatc attgcgataa aggaaaggct atcgttcaag atgcctctgc cgacagtggt  23340
cccaaagatg gacccccacc cacgaggagc atcgtggaaa aagaagacgt tccaaccacg  23400
tcttcaaagc aagtggattg atgtgaacat ggtggagcac gacactctcg tctactccaa  23460
gaatatcaaa gatacagtct cagaagacca aagggctatt gagacttttc aacaaagggt  23520
aatatcggga aacctcctcg gattccattg cccagctatc tgtcacttca tcaaaaggac  23580
agtagaaaag gaaggtggca cctacaaatg ccatcattgc gataaaggaa aggctatcgt  23640
tcaagatgcc tctgccgaca gtggtcccaa agatggaccc ccacccacga ggagcatcgt  23700
ggaaaaagaa gacgttccaa ccacgtcttc aaagcaagtg gattgatgtg atatctccac  23760
tgacgtaagg gatgacgcac aatcccacta tccttcgcaa gacccttcct ctatataagg  23820
aagttcattt catttggaga ggacacgctg aaatcaccag tctctctcta caaatctatc  23880
tctctcgaga aaatggtgag caagggcgag gagctgttca ccggggtggt gcccatcctg  23940
gtcgagctgg acggcgacgt aaacggccac aagttcagcg tgtccggcga gggcgagggc  24000
gatgccacct acggcaagct gaccctgaag ttcatctgca ccaccggcaa gctgcccgtg  24060
```

```
ccctggccca ccctcgtgac caccttcacc tacggcgtgc agtgcttcag ccgctacccc  24120
gaccacatga agcagcacga cttcttcaag tccgccatgc ccgaaggcta cgtccaggag  24180
cgcaccatct tcttcaagga cgacggcaac tacaagaccc gcgccgaggt gaagttcgag  24240
ggcgacaccc tggtgaaccg catcgagctg aagggcatcg acttcaagga ggacggcaac  24300
atcctggggc acaagctgga gtacaactac aacagccaca acgtctatat catggccgac  24360
aagcagaaga acggcatcaa ggtgaacttc aagatccgcc acaacatcga ggacggcagc  24420
gtgcagctcg ccgaccacta ccagcagaac acccccatcg gcgacggccc cgtgctgctg  24480
cccgacaacc actacctgag cacccagtcc gccctgagca aagaccccaa cgagaagcgc  24540
gatcacatgg tcctgctgga gttcgtgacc gccgccggga tcactcacgg catggacgag  24600
ctgtacaagt aagagctcgg tcacctgtcc aacagtctca gggttaatgt ctatgtatct  24660
taaataatgt tgtcggcgat cgttcaaaca tttggcaata aagtttctta agattgaatc  24720
ctgttgccgg tcttgcgatg attatcatat aatttctgtt gaattacgtt aagcatgtaa  24780
taattaacat gtaatgcatg acgttattta tgagatgggt ttttatgatt agagtcccgc  24840
aattatacat ttaatacgcg atagaaaaca aaatatagcg cgcaaactag gataaattat  24900
cgcgcgcggt gtcatctatg ttactagatc gggaattaaa ctatcagtgt ttgacaggat  24960
atattggcgg gtaaacctaa gagaaaagag cgtttattag aataatcgga tatttaaaag  25020
ggcgtgaaaa ggtttatccg ttcgtccatt tgtatgtgca tgccaaccac agggttcccc  25080
tcgggatcaa agtactttga tccaacccct ccgctgctat agtgcagtcg gcttctgacg  25140
ttcagtgcag ccgtcttctg aaaacgacat gtcgcacaag tcctaagtta cgcgacaggc  25200
tgccgccctg cccttttcct ggcgttttct tgtcgcgtgt tttagtcgca taaagtagaa  25260
tacttgcgac tagaaccgga gacattacgc catgaacaag agcgccgccg ctggcctgct  25320
gggctatgcc cgcgtcagca ccgacgacca ggacttgacc aaccaacggg ccgaactgca  25380
cgcggccggc tgcaccaagc tgttttccga gaagatcacc ggcaccaggc gcgaccgccc  25440
ggagctggcc aggatgcttg accacctacg ccctggcgac gttgtgacag tgaccaggct  25500
agaccgcctg gcccgcagca cccgcgacct actggacatt gccgagcgca tccaggaggc  25560
cggcgcgggc ctgcgtagcc tggcagagcc gtgggccgac accaccacgc cggccggccg  25620
catggtgttg accgtgttcg ccggcattgc cgagttcgag cgttccctaa tcatcgaccg  25680
cacccggagc gggcgcgagg ccgccaaggc ccgaggcgtg aagtttggcc cccgccctac  25740
cctcaccccg gcacagatcg cgcacgcccg cgagctgatc gaccaggaag gccgcaccgt  25800
gaaagaggcg gctgcactgc ttggcgtgca tcgctcgacc ctgtaccgcg cacttgagcg  25860
cagcgaggaa gtgacgccca ccgaggccag gcggcgcggt gccttccgtg aggacgcatt  25920
gaccgaggcc gacgccctgg cggccgccga gaatgaacgc caagaggaac aagcatgaaa  25980
ccgcaccagg acggccagga cgaaccgttt ttcattaccg aagagatcga ggcggagatg  26040
atcgcggccg ggtacgtgtt cgagccgccc gcgcacgtct caaccgtgcg gctgcatgaa  26100
atcctggccg gtttgtctga tgccaagctg gcggcctggc cggccagctt ggccgctgaa  26160
gaaaccgagc gccgccgtct aaaaaggtga tgtgtatttg agtaaaacag cttgcgtcat  26220
gcggtcgctg cgtatatgat gcgatgagta aataaacaaa tacgcaaggg gaacgcatga  26280
aggttatcgc tgtacttaac cagaaaggcg ggtcaggcaa gacgaccatc gcaacccatc  26340
tagcccgcgc cctgcaactc gccggggccg atgttctgtt agtcgattcc gatccccagg  26400
gcagtgcccg cgattgggcg gccgtgcggg aagatcaacc gctaaccgtt gtcggcatcg  26460
```

```
accgcccgac gattgaccgc gacgtgaagg ccatcggccg gcgcgacttc gtagtgatcg  26520
acggagcgcc ccaggcggcg gacttggctg tgtccgcgat caaggcagcc gacttcgtgc  26580
tgattccggt gcagccaagc ccttacgaca tatgggccac cgccgacctg gtggagctgg  26640
ttaagcagcg cattgaggtc acggatggaa ggctacaagc ggcctttgtc gtgtcgcggg  26700
cgatcaaagg cacgcgcatc ggcggtgagg ttgccgaggc gctggccggg tacgagctgc  26760
ccattcttga gtcccgtatc acgcagcgcg tgagctaccc aggcactgcc gccgccggca  26820
caaccgttct tgaatcagaa cccgagggcg acgctgcccg cgaggtccag gcgctggccg  26880
ctgaaattaa atcaaaactc atttgagtta atgaggtaaa gagaaaatga gcaaaagcac  26940
aaacacgcta agtgccggcc gtccgagcgc acgcagcagc aaggctgcaa cgttggccag  27000
cctggcagac acgccagcca tgaagcgggt caactttcag ttgccggcgg aggatcacac  27060
caagctgaag atgtacgcgg tacgccaagg caagaccatt accgagctgc tatctgaata  27120
catcgcgcag ctaccagagt aaatgagcaa atgaataaat gagtagatga attttagcgg  27180
ctaaaggagg cggcatggaa aatcaagaac aaccaggcac cgacgccgtg gaatgcccca  27240
tgtgtggagg aacgggcggt tggccaggcg taagcggctg ggttgcctgc cggccctgca  27300
atggcactgg aaccccccaag cccgaggaat cggcgtgagc ggtcgcaaac catccggccc  27360
ggtacaaatc ggcgcggcgc tgggtgatga cctggtggag aagttgaagg ccgcgcaggc  27420
cgcccagcgg caacgcatcg aggcagaagc acgccccggt gaatcgtggc aagcggccgc  27480
tgatcgaatc cgcaaagaat cccggcaacc gccggcagcc ggtgcgccgt cgattaggaa  27540
gccgcccaag ggcgacgagc aaccagattt tttcgttccg atgctctatg acgtgggcac  27600
ccgcgatagt cgcagcatca tggacgtggc cgttttccgt ctgtcgaagc gtgaccgacg  27660
agctggcgag gtgatccgct acgagcttcc agacgggcac gtagaggttt ccgcagggcc  27720
ggccggcatg gccagtgtgt gggattacga cctggtactg atggcggttt cccatctaac  27780
cgaatccatg aaccgatacc gggaagggaa gggagacaag cccggccgcg tgttccgtcc  27840
acacgttgcg gacgtactca agttctgccg gcgagccgat ggcggaaagc agaaagacga  27900
cctggtagaa acctgcattc ggttaaacac cacgcacgtt gccatgcagc gtacgaagaa  27960
ggccaagaac ggccgcctgg tgacggtatc cgagggtgaa gccttgatta gccgctacaa  28020
gatcgtaaag agcgaaaccg ggcggccgga gtacatcgag atcgagctag ctgattggat  28080
gtaccgcgag atcacagaag gcaagaaccc ggacgtgctg acggttcacc ccgattactt  28140
tttgatcgat cccggcatcg gccgttttct ctaccgcctg gcacgccgcg ccgcaggcaa  28200
ggcagaagcc agatggttgt tcaagacgat ctacgaacgc agtggcagcg ccggagagtt  28260
caagaagttc tgtttcaccg tgcgcaagct gatcgggtca aatgacctgc cggagtacga  28320
tttgaaggag gaggcggggc aggctggccc gatcctagtc atgcgctacc gcaacctgat  28380
cgagggcgaa gcatccgccg gttcctaatg tacggagcag atgctagggc aaattgccct  28440
agcaggggaa aaaggtcgaa aaggtctctt tcctgtggat agcacgtaca ttgggaaccc  28500
aaagccgtac attgggaacc ggaacccgta cattgggaac ccaaagccgt acattgggaa  28560
ccggtcacac atgtaagtga ctgatataaa agagaaaaaa ggcgattttt ccgcctaaaa  28620
ctctttaaaa cttattaaaa ctcttaaaac ccgcctggcc tgtgcataac tgtctggcca  28680
gcgcacagcc gaagagctgc aaaaagcgcc tacccttcgg tcgctgcgct ccctacgccc  28740
cgccgcttcg cgtcggccta tcgcggccgc tggccgctca aaaatggctg gcctacggcc  28800
```

```
aggcaatcta ccagggcgcg gacaagccgc gccgtcgcca ctcgaccgcc ggcgcccaca  28860
tcaaggcacc ctgcctcgcg cgtttcggtg atgacggtga aaacctctga cacatgcagc  28920
tcccggagac ggtcacagct tgtctgtaag cggatgccgg gagcagacaa gcccgtcagg  28980
gcgcgtcagc gggtgttggc gggtgtcggg gcgcagccat gacccagtca cgtagcgata  29040
gcggagtgta tactggctta actatgcggc atcagagcag attgtactga gagtgcacca  29100
tatgcggtgt gaaataccgc acagatgcgt aaggagaaaa taccgcatca ggcgctcttc  29160
cgcttcctcg ctcactgact cgctgcgctc ggtcgttcgg ctgcggcgag cggtatcagc  29220
tcactcaaag gcggtaatac ggttatccac agaatcaggg gataacgcag gaaagaacat  29280
gtgagcaaaa ggccagcaaa aggccaggaa ccgtaaaaag gccgcgttgc tggcgttttt  29340
ccataggctc cgcccccctg acgagcatca caaaaatcga cgctcaagtc agaggtggcg  29400
aaacccgaca ggactataaa gataccaggc gtttccccct ggaagctccc tcgtgcgctc  29460
tcctgttccg accctgccgc ttaccggata cctgtccgcc tttctccctt cgggaagcgt  29520
ggcgctttct catagctcac gctgtaggta tctcagttcg gtgtaggtcg ttcgctccaa  29580
gctgggctgt gtgcacgaac cccccgttca gcccgaccgc tgcgccttat ccggtaacta  29640
tcgtcttgag tccaacccgg taagacacga cttatcgcca ctggcagcag ccactggtaa  29700
caggattagc agagcgaggt atgtaggcgg tgctacagag ttcttgaagt ggtggcctaa  29760
ctacggctac actagaagga cagtatttgg tatctgcgct ctgctgaagc cagttacctt  29820
cggaaaaaga gttggtagct cttgatccgg caaacaaacc accgctggta gcggtggttt  29880
ttttgtttgc aagcagcaga ttacgcgcag aaaaaaagga tctcaagaag atcctttgat  29940
cttttctacg gggtctgacg ctcagtggaa cgaaaactca cgttaaggga ttttggtcat  30000
gcattctagg tactaaaaca attcatccag taaaatataa tattttattt tctcccaatc  30060
aggcttgatc cccagtaagt caaaaaatag ctcgacatac tgttcttccc cgatatcctc  30120
cctgatcgac cggacgcaga aggcaatgtc ataccacttg tccgccctgc cgcttctccc  30180
aagatcaata aagccactta ctttgccatc tttcacaaag atgttgctgt ctcccaggtc  30240
gccgtgggaa aagacaagtt cctcttcggg cttttccgtc tttaaaaaat catacagctc  30300
gcgcggatct ttaaatggag tgtcttcttc ccagttttcg caatccacat cggccagatc  30360
gttattcagt aagtaatcca attcggctaa gcggctgtct aagctattcg tatagggaca  30420
atccgatatg tcgatggagt gaaagagcct gatgcactcc gcatacagct cgataatctt  30480
ttcagggctt tgttcatctt catactcttc cgagcaaagg acgccatcgg cctcactcat  30540
gagcagattg ctccagccat catgccgttc aaagtgcagg acctttggaa caggcagctt  30600
tccttccagc catagcatca tgtccttttc ccgttccaca tcataggtgg tccctttata  30660
ccggctgtcc gtcattttta aatataggtt ttcattttct cccaccagct tatatacctt  30720
agcaggagac attccttccg tatcttttac gcagcggtat ttttcgatca gtttttttcaa  30780
ttccggtgat attctcattt tagccattta ttatttcctt cctcttttct acagtattta  30840
aagatacccc aagaagctaa ttataacaag acgaactcca attcactgtt ccttgcattc  30900
taaaacctta aataccagaa aacagctttt tcaaagttgt tttcaaagtt ggcgtataac  30960
atagtatcga cggagccgat tttgaaaccg cggtgatcac aggcagcaac gctctgtcat  31020
cgttacaatc aacatgctac cctccgcgag atcatccgtg tttcaaaccc ggcagcttag  31080
ttgccgttct tccgaatagc atcggtaaca tgagcaaagt ctgccgcctt acaacggctc  31140
tcccgctgac gccgtcccgg actgatgggc tgcctgtatc gagtggtgat tttgtgccga  31200
```

-continued

```
gctgccggtc ggggagctgt tggctggctg gtggcaggat atattgtggt gtaaacaaat  31260

tgacgcttag acaacttaat aacacattgc ggacgttttt aatgtactga attaacgccg  31320

aattaatt                                                            31328
```